(12) United States Patent
Ibrahim et al.

(10) Patent No.: US 9,440,969 B2
(45) Date of Patent: Sep. 13, 2016

(54) COMPOUNDS AND METHODS FOR KINASE MODULATION, AND INDICATIONS THEREFOR

(71) Applicant: PLEXXIKON INC., Berkeley, CA (US)

(72) Inventors: Prabha N. Ibrahim, Mountain View, CA (US); Guoxian Wu, Foster City, CA (US); Jack Lin, Hercules, CA (US); Wayne Spevak, Berkeley, CA (US); Hanna Cho, Oakland, CA (US); Todd Ewing, Walnut Creek, CA (US); Chao Zhang, Moraga, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 14/514,232

(22) Filed: Oct. 14, 2014

(65) Prior Publication Data

US 2015/0080372 A1 Mar. 19, 2015

Related U.S. Application Data

(63) Continuation of application No. 12/975,239, filed on Dec. 21, 2010, now abandoned.

(60) Provisional application No. 61/289,930, filed on Dec. 23, 2009, provisional application No. 61/383,318, filed on Sep. 15, 2010.

(51) Int. Cl.
| | |
|---|---|
| *C07D 471/04* | (2006.01) |
| *A61K 31/437* | (2006.01) |
| *C07D 519/00* | (2006.01) |
| *A61K 31/497* | (2006.01) |
| *A61K 31/498* | (2006.01) |
| *A61K 31/506* | (2006.01) |
| *A61K 31/519* | (2006.01) |

(52) U.S. Cl.
CPC ........... *C07D 471/04* (2013.01); *A61K 31/437* (2013.01); *A61K 31/497* (2013.01); *A61K 31/498* (2013.01); *A61K 31/506* (2013.01); *A61K 31/519* (2013.01); *C07D 519/00* (2013.01)

(58) Field of Classification Search
CPC ............. C07D 471/04; A61K 31/437; A61K 31/497; A61K 31/498; A61K 31/506; A61K 31/519
USPC ......... 514/210.21, 249, 255.05, 259.41, 269, 514/274, 300; 544/281, 316, 333, 353, 405; 546/113
See application file for complete search history.

(56) References Cited

U.S. PATENT DOCUMENTS

| | | |
|---|---|---|
| 7,202,266 B2 | 4/2007 | Arnold et al. |
| 7,348,338 B2 | 3/2008 | Arnold et al. |
| 7,476,746 B2 | 1/2009 | Artis et al. |
| 7,491,831 B2 | 2/2009 | Artis et al. |
| 7,498,342 B2 | 3/2009 | Ibrahim et al. |
| 7,504,509 B2 | 3/2009 | Ibrahim et al. |
| 7,517,970 B2 | 4/2009 | West |
| 7,531,568 B2 | 5/2009 | Lin et al. |
| 7,572,806 B2 | 8/2009 | Arnold et al. |
| 7,585,859 B2 | 9/2009 | Ibrahim et al. |
| 7,605,168 B2 | 10/2009 | Ibrahim et al. |
| 7,723,374 B2 | 5/2010 | Artis et al. |
| 7,846,941 B2 | 12/2010 | Ibrahim et al. |
| 7,863,288 B2 | 1/2011 | Ibrahim et al. |
| 7,863,289 B2 | 1/2011 | Spevak et al. |
| 7,872,018 B2 | 1/2011 | Ibrahim et al. |
| 7,893,075 B2 | 2/2011 | Zhang et al. |
| 7,947,708 B2 | 5/2011 | Ibrahim et al. |
| 8,053,463 B2 | 11/2011 | Lin et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |

(Continued)

FOREIGN PATENT DOCUMENTS

| | | |
|---|---|---|
| EP | 2 036 990 | 3/2009 |
| WO | WO-2007/002325 | 1/2007 |

(Continued)

OTHER PUBLICATIONS

Cancer classification NCI SEER training, p. 1-3 (2005).*

(Continued)

*Primary Examiner* — Celia Chang
(74) *Attorney, Agent, or Firm* — Sheppard Mullin Richter & Hampton LLP

(57) ABSTRACT

Compounds and salts thereof, formulations thereof, conjugates thereof, derivatives thereof, forms thereof and uses thereof are described. In certain aspects and embodiments, the described compounds or salts thereof, formulations thereof, conjugates thereof, derivatives thereof, forms thereof are active on each of B-Raf, B-Raf V600E and c-Raf-1 protein kinase. In certain aspects and embodiments, the described compounds are active in inhibiting proliferation of a Ras mutant cell line. Also described are methods of use thereof to treat diseases and conditions, including melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma.

19 Claims, No Drawings

(56) References Cited

U.S. PATENT DOCUMENTS

| | | |
|---|---|---|
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,198,273 B2 | 6/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Zhang et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Ibrahim et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 2004/0077595 A1 | 4/2004 | Cheng et al. |
| 2004/0142864 A1 | 7/2004 | Bremer et al. |
| 2004/0171062 A1 | 9/2004 | Hirth et al. |
| 2005/0048573 A1 | 3/2005 | Artis et al. |
| 2005/0079548 A1 | 4/2005 | Artis et al. |
| 2005/0164300 A1 | 7/2005 | Artis et al. |
| 2005/0170431 A1 | 8/2005 | Ibrahim et al. |
| 2006/0058339 A1 | 3/2006 | Ibrahim et al. |
| 2006/0135540 A1 | 6/2006 | Lin et al. |
| 2006/0160135 A1 | 7/2006 | Wang et al. |
| 2007/0066641 A1 | 3/2007 | Ibrahim et al. |
| 2007/0072904 A1 | 3/2007 | Lin et al. |
| 2008/0221127 A1 | 9/2008 | Lin et al. |
| 2008/0234349 A1 | 9/2008 | Lin et al. |
| 2008/0249137 A1 | 10/2008 | Lin et al. |
| 2010/0190777 A1 | 7/2010 | Wu et al. |
| 2010/0286142 A1 | 11/2010 | Ibrahim et al. |
| 2010/0310659 A1 | 12/2010 | Desai et al. |
| 2011/0092538 A1 | 4/2011 | Spevak et al. |
| 2011/0112127 A1 | 5/2011 | Zhang et al. |
| 2011/0166174 A1 | 7/2011 | Ibrahim et al. |
| 2011/0183988 A1 | 7/2011 | Ibrahim et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0237531 A1 | 9/2013 | Wu et al. |
| 2013/0261117 A1 | 10/2013 | Ibrahim et al. |
| 2013/0274259 A1 | 10/2013 | Zhang et al. |
| 2013/0303534 A1 | 11/2013 | Ibrahim et al. |
| 2014/0037617 A1 | 2/2014 | Zhang et al. |
| 2014/0038948 A1 | 2/2014 | Wu et al. |
| 2014/0045840 A1 | 2/2014 | Zhang et al. |
| 2014/0094611 A1 | 4/2014 | Ibrahim et al. |
| 2014/0128373 A1 | 5/2014 | Ibrahim et al. |
| 2014/0128390 A1 | 5/2014 | Lin et al. |
| 2014/0213554 A1 | 7/2014 | Wu et al. |
| 2014/0243365 A1 | 8/2014 | Zhang et al. |
| 2014/0288070 A1 | 9/2014 | Ibrahim et al. |
| 2014/0303121 A1 | 10/2014 | Zhang et al. |
| 2014/0303187 A1 | 10/2014 | Wu et al. |
| 2014/0357612 A1 | 12/2014 | Zhang et al. |
| 2015/0133400 A1 | 5/2015 | Zhang et al. |
| 2015/0166547 A1 | 6/2015 | Ibrahim et al. |
| 2015/0183793 A1 | 7/2015 | Zhang et al. |

FOREIGN PATENT DOCUMENTS

| | | |
|---|---|---|
| WO | WO-2007/002433 | 1/2007 |
| WO | WO-2007/013896 | 5/2007 |
| WO | WO-2008/079903 | 7/2008 |
| WO | WO-2008/079906 | 7/2008 |
| WO | WO 2010/104945 | 9/2010 |
| WO | WO-2010/111527 | 9/2010 |
| WO | WO-2010/129467 | 11/2010 |
| WO | WO 2010/129567 | 11/2010 |

OTHER PUBLICATIONS

A375, ATCC description p. 1 (2015).*
Ibramhim "preparation of . . . " CA155:123383 (2011).*
Chai et al. "Preparation of substituted . . . " CA156:637855 (2012).*
COLO205, cell line description) p. 1-3 (2015).*
Graczyk et al. "Preparation of 7-azaindole . . . " CA139:307749 (2003).*
Improper Markush, Fed. Reg. v.76(27) p. 7162-7175, slide p. 1, 64-67 (2011).*
Morphy "Selectively nonselective kinase . . . " J. Med. Chem. 53, 1413-1437 (web pub. Oct. 2009).*
International Search Report and Written Opinion for PCT/US2010/061601, dated Sep. 23, 2011.
Extended European Search Report for EP Application 10840075.5 dated May 13, 2013.
Pratilas et al., Hcaplus 2008:670875 "Marker genes showing changes in levels of expression in response to antineoplastic drug thereapy and their use in selection of chemotherapy", 2008.
U.S. Appl. No. 14/733,830, filed Jun. 8, 2015, Zhang et al.
U.S. Appl. No. 14/602,119, filed Jan. 21, 2015, Ibrahim et al.
U.S. Appl. No. 14/637,303, filed Mar. 3, 2015, Lin et al.
U.S. Appl. No. 14/798,167, filed Jul. 13, 2015, Ibrahim et al.
U.S. Appl. No. 14/846,545, filed Sep. 4, 2015, Zhang et al.
U.S. Appl. No. 14/839,668, filed Aug. 28, 2015, Ibrahim.
U.S. Appl. No. 14/850,912, filed Sep. 10, 2015, Shi et al.

* cited by examiner

COMPOUNDS AND METHODS FOR KINASE MODULATION, AND INDICATIONS THEREFOR

RELATED APPLICATIONS

The present application is a continuation of U.S. application Ser. No. 12/975,239, filed Dec. 21, 2010, which claims priority to U.S. Provisional patent application Ser. No. 61/289,930, filed Dec. 23, 2009, entitled "Compounds and Methods for Kinase Modulation, and Indications Therefor" and U.S. Provisional patent application Ser. No. 61/383,318, filed Sep. 15, 2010, entitled "Compounds and Methods for Kinase Modulation, and Indications Therefor" and which hare incorporated herein by reference in their entirety and for all purposes.

FIELD OF THE INVENTION

Disclosed are novel compounds and uses thereof. In certain embodiments disclosed compounds are kinase inhibitors.

SUMMARY OF THE INVENTION

In certain aspects and embodiments disclosed herein, compounds are provided, as well as various salts thereof, formulations thereof, conjugates thereof, derivatives thereof, forms thereof and uses thereof. In some embodiments, compounds are any one of Formulae I-XX as described below. In certain embodiments, the compounds inhibit one or more Raf protein kinases, including one or more of A-Raf, B-Raf, and c-Raf-1, and any mutations thereof. In certain embodiments, the compounds inhibit each of c-Raf-1, B-Raf, and B-Raf V600X protein kinase (where X is an amino acid other than valine, e.g., alanine, arginine, aspartic acid, glycine, lysine or methionine). In certain embodiments, the compounds inhibit a B-Raf V600E mutant protein kinase. In certain embodiments, the compounds inhibit each of c-Raf-1, B-Raf, B-Raf V600X, and B-Raf V600E protein kinase. In certain embodiments, the compounds inhibit each of cRaf-1, B-Raf, and B-Raf V600E protein kinase.

Also contemplated in accordance with the present invention are methods for the use of the compounds in treating diseases and conditions associated with regulation of the activity of one or more Raf protein kinases, including one or more of A-Raf, B-Raf, and c-Raf-1, and any mutations thereof. Thus, the use of compounds for therapeutic methods involving modulation of protein kinases are provided. In certain embodiments, the compounds inhibit the activity on one or more Raf kinases, including A-Raf, B-Raf and/or c-Raf-1, including any mutations thereof. In certain embodiments, the compounds are used for therapeutic methods involving modulation of one or more Raf protein kinases, including treatment of a variety of indications, including, but not limited to, melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain and polycystic kidney disease. In certain embodiments, the compounds are used for therapeutic methods involving modulation of B-Raf V600E mutant protein kinase, including treatment of a variety of indications, including, but not limited to, melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma. In certain embodiments, the compounds are used for therapeutic methods involving modulation of c-Raf-1 protein kinase, including treatment of a variety of indications, including, but not limited to, acute pain, chronic pain and polycystic kidney disease.

In a first aspect, compounds having the structure according to the following Formula I

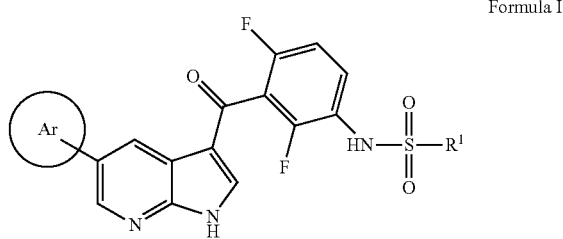

Formula I or a pharmaceutically acceptable salt or a tautomer or a stereoisomer thereof, are provided:

wherein:

$R^1$ is lower alkyl or aryl substituted with one or two members selected from trifluoromethyl, trifluoromethoxy, lower alkyl or halogen (in one embodiment, $R^1$ is lower alkyl or phenyl substituted with one or two members selected from trifluoromethyl, trifluoromethoxy, lower alkyl or halogen; in one embodiment, $R^1$ is methyl, ethyl, n-propyl, 2-trifluoromethyl-phenyl, 3-trifluoromethyl-phenyl, 4-trifluoromethyl-phenyl, 2-fluoro-phenyl, 3-fluoro-phenyl, 4-fluoro-phenyl, 2,3-difluoro-phenyl, 2,4-difluoro-phenyl, 2,6-difluoro-phenyl, 2,5-difluoro-phenyl, 3,4-difluoro-phenyl, 3,5-difluoro-phenyl or 3,6-difluoro-phenyl; in another embodiment, $R^1$ is n-propyl, 4-trifluoromethyl-phenyl, 2-fluoro-phenyl, 3-fluoro-phenyl, or 2,5-difluoro-phenyl; in yet another embodiment, $R^1$ is propyl or 2,5-difluoro-phenyl; in still another embodiment, $R^1$ is phenyl substituted with one to two members independently selected from methyl, ethyl, propyl, butyl, pentyl or isomers thereof);

Ar is selected from the group consisting of bicyclic heteroaryl optionally independently substituted with one or more $R^2$, thiophenyl optionally independently substituted with one or more $R^3$, thiazolyl optionally independently substituted with one or more $R^4$, oxazolyl optionally independently substituted with one or more $R^5$, pyrazolyl optionally independently substituted with one or more $R^6$, pyridyl optionally independently substituted with one or more $R^7$, pyrimidinyl optionally independently substituted with one or more $R^8$, phenyl substituted with one or more $R^9$, and pyrazinyl optionally independently substituted with one or more $R^{10}$;

each $R^2$ is independently selected from the group consisting of —CN, —NO$_2$, —C(O)—$R^{11}$, —S(O)$_2$—$R^{12}$, —O—$R^{13}$, —N($R^{14}$)—$R^{15}$, fluoro, chloro, lower alkyl, lower alkylthio, fluoro substituted lower alkylthio, cycloalkylamino, and heterocycloalkylamino, wherein lower alkyl is optionally independently substituted with one or more fluoro, lower alkoxy, mono-alkylamino, di-alkylamino, cycloalkylamino, or heterocycloalkylamino;

each $R^3$ is independently selected from the group consisting of —CN, —OH, —NH$_2$, —NO$_2$, —C(O)—R$^{11}$, —S(O)$_2$—R$^{12}$, fluoro, chloro, lower alkyl, fluoro substituted lower alkyl, lower alkoxy, fluoro substituted lower alkoxy, lower alkylthio, fluoro substituted lower alkylthio, mono-alkylamino, di-alkylamino, cycloalkyl, heterocycloalkyl, phenyl, and heteroaryl, wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^4$ is independently selected from the group consisting of —CN, —OH, —NH$_2$, —NO$_2$, —C(O)—R$^{11}$, —S(O)$_2$—R$^{12}$, fluoro, chloro, lower alkyl, fluoro substituted lower alkyl, lower alkoxy, fluoro substituted lower alkoxy, lower alkylthio, fluoro substituted lower alkylthio, mono-alkylamino, di-alkylamino, cycloalkyl, heterocycloalkyl, phenyl, and heteroaryl, wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^5$ is independently selected from the group consisting of —CN, —OH, —NH$_2$, —NO$_2$, —C(O)—R$^{11}$, —S(O)$_2$—R$^{12}$, fluoro, chloro, lower alkyl, fluoro substituted lower alkyl, lower alkoxy, fluoro substituted lower alkoxy, lower alkylthio, fluoro substituted lower alkylthio, mono-alkylamino, di-alkylamino, cycloalkyl, heterocycloalkyl, phenyl, and heteroaryl, wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^6$ is independently selected from the group consisting of —CN, —C(O)—R$^{11}$, fluoro, chloro, and lower alkyl, wherein lower alkyl is optionally independently substituted with one or more fluoro, lower alkoxy, mono-alkylamino, di-alkylamino, cycloalkylamino, or heterocycloalkylamino;

each $R^7$ is independently selected from the group consisting of —C(O)—R$^{11}$, —S(O)$_2$—R$^{12}$, —C(O)—N(H)—O—R$^{16}$, —O—R$^{13}$, —N(R$^{14}$)—R$^{15}$, fluoro, chloro, lower alkyl, lower alkylthio, fluoro substituted lower alkylthio, cycloalkyl, heterocycloalkyl, phenyl, and heteroaryl, wherein lower alkyl is optionally independently substituted with one or more fluoro, lower alkoxy, mono-alkylamino, di-alkylamino, cycloalkylamino, and heterocycloalkylamino, and wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^8$ is independently selected from the group consisting of —C(O)—R$^{11}$, —S(O)$_2$—R$^{12}$, —C(O)—N(H)—O—R$^{16}$, —O—R$^{13}$, —N(R$^{14}$)—R$^{15}$, fluoro, chloro, lower alkyl, lower alkylthio, fluoro substituted lower alkylthio, cycloalkyl, heterocycloalkyl, phenyl, and heteroaryl, wherein lower alkyl is optionally independently substituted with one or more fluoro, lower alkoxy, mono-alkylamino, di-alkylamino, cycloalkylamino, or heterocycloalkylamino, and wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^9$ is independently selected from the group consisting of —CN, —NO$_2$, —C(O)—R$^{11}$, —S(O)$_2$—R$^{12}$, —C(O)—N(H)—O—R$^{16}$, —O—R$^{13}$, —N(R$^{14}$)—R$^{15}$, fluoro, chloro, lower alkyl, lower alkylthio, fluoro substituted lower alkylthio, cycloalkyl, heterocycloalkyl, phenyl, and heteroaryl, wherein lower alkyl is optionally independently substituted with one or more fluoro, lower alkoxy, mono-alkylamino, di-alkylamino, cycloalkylamino, or heterocycloalkylamino, and wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^{10}$ is independently selected from the group consisting of —CN, —NO$_2$, —C(O)—R$^{11}$, —S(O)$_2$—R$^{12}$, —C(O)—N(H)—O—R$^{16}$, —O—R$^{13}$, —N(R$^{14}$)—R$^{15}$, fluoro, chloro, lower alkyl, lower alkylthio, fluoro substituted lower alkylthio, cycloalkyl, heterocycloalkyl, phenyl, and heteroaryl, wherein lower alkyl is optionally independently substituted with one or more fluoro, lower alkoxy, mono-alkylamino, di-alkylamino, cycloalkylamino, or heterocycloalkylamino, and wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^{11}$ is independently selected from the group consisting of lower alkyl, —OR$^{13}$, —NH$_2$, mono-alkylamino, di-alkylamino, cycloalkylamino, and heterocycloalkylamino;

each $R^{12}$ is independently selected from the group consisting of —NH$_2$, lower alkyl, mono-alkylamino, di-alkylamino, cycloalkylamino, and heterocycloalkylamino;

each $R^{13}$ is independently hydrogen or lower alkyl optionally substituted with one or more fluoro, or, when $R^{13}$ is $C_{2-6}$, alkyl, $R^{13}$ is optionally independently substituted with lower alkoxy, mono-alkylamino, di-alkylamino, cycloalkylamino, or heterocycloalkylamino; and each $R^{14}$, $R^{15}$ and $R^{16}$ is independently hydrogen, lower alkyl, or cycloalkyl, wherein lower alkyl is optionally substituted with one or more fluoro, or, when $R^{14}$, $R^{15}$ or $R^{16}$ is $C_{2-6}$, alkyl, $R^{14}$, $R^{15}$ and $R^{16}$ are independently substituted with lower alkoxy, mono-alkylamino, di-alkylamino, cycloalkylamino, or heterocycloalkylamino.

In some embodiments of compounds of Formula I, Ar is bicyclic heteroaryl optionally independently substituted with one or more $R^2$ (wherein $R^2$ is one or more of $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$ and $R^{44}$, as appropriate). In some as appropriate). In some embodiments, Ar is selected from Group A as follows:

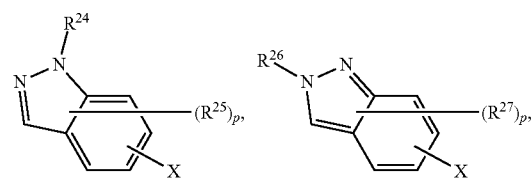

-continued

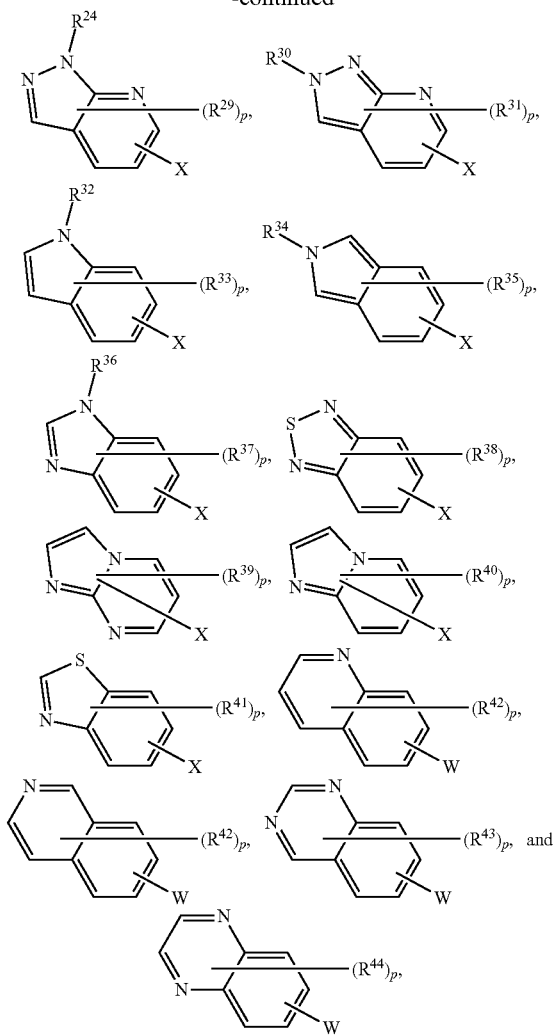

wherein:

W represents the point of attachment to the 5-position of the pyrrolo[2,3-b]pyridine ring of Formula I, wherein W is attached at any available position of the 6-membered phenyl ring portion of Ar;

X represents the point of attachment to the 5-position of the pyrrolo[2,3-b]pyridine ring of Formula I, wherein X is attached at any available position of the 6-membered ring portion of Ar;

Y represents the point of attachment to the 5-position of the pyrrolo[2,3-b]pyridine ring of Formula I, wherein Y is attached at any available position of the bicyclic ring of Ar;

$R^{24}$, $R^{26}$, $R^{28}$, $R^{30}$, $R^{32}$, $R^{34}$, and $R^{36}$ are selected from the group consisting of hydrogen, —C(O)—$R^{45}$, —S(O)$_2$—$R^{46}$, and lower alkyl, wherein lower alkyl is optionally substituted with one or more fluoro, or, when any one of $R^{24}$, $R^{26}$, $R^{28}$, $R^{30}$, $R^{32}$, $R^{34}$, and/or $R^{36}$ is $C_{2-6}$, alkyl, $R^{24}$, $R^{26}$, $R^{28}$, $R^{30}$, $R^{32}$, $R^{34}$, and $R^{36}$ are independently substituted with lower alkoxy, mono-alkylamino, di-alkylamino or cycloalkylamino;

each $R^{25}$, $R^{27}$, $R^{29}$, $R^{31}$, $R^{33}$, $R^{35}$, $R^{37}$, $R^{38}$, $R^{39}$, $R^{40}$, $R^{41}$, $R^{42}$, $R^{43}$, and $R^{44}$, are independently selected from the group consisting of —CN, —C(O)—$R^{45}$, —S(O)$_2$—$R^{46}$, —O—$R^{47}$, —N($R^{48}$)—$R^{49}$, fluoro, chloro, lower alkyl, and cycloalkylamino, and are attached at any available position of the bicyclic ring of Ar, wherein lower alkyl is optionally independently substituted with one or more fluoro, lower alkoxy, mono-alkylamino, di-alkylamino or cycloalkylamino; each $R^{45}$ and $R^{46}$ are independently selected from the group consisting of —O—$R^{47}$, —N($R^{48}$)—$R^{49}$, lower alkyl, mono-alkylamino, di-alkylamino, and cycloalkylamino;

each $R^{47}$ is independently hydrogen or lower alkyl optionally substituted with one or more fluoro, or, when $R^{47}$ is $C_{2-6}$, alkyl, $R^{47}$ is optionally independently substituted with lower alkoxy, mono-alkylamino, di-alkylamino or cycloalkylamino;

each $R^{48}$ and $R^{49}$ are independently selected from the group consisting of hydrogen, lower alkyl, or cycloalkyl, wherein lower alkyl is optionally independently substituted with lower alkoxy, mono-alkylamino, di-alkylamino, or cycloalkylamino; and p is 0, 1, 2 or 3.

In some embodiments of compounds of Formula I, Ar is any one of the bicyclic heteroaryl moieties set forth above in Group A, and $R^1$ is n-propyl.

In some embodiments of compounds of Formula I, Ar is any one of the bicyclic heteroaryl moieties set forth above in Group A, and $R^1$ is 4-trifluoromethyl-phenyl.

In some embodiments of compounds of Formula I, Ar is any one of the bicyclic heteroaryl moieties set forth above in Group A, and $R^1$ is 2-fluoro-phenyl.

In some embodiments of compounds of Formula I, Ar is any one of the bicyclic heteroaryl moieties set forth above in Group A, and $R^1$ is 3-fluoro-phenyl.

In some embodiments of compounds of Formula I, Ar is any one of the bicyclic heteroaryl moieties set forth above in Group A, and $R^1$ is 2,5-difluoro-phenyl.

In some embodiments of compounds of Formula I, Ar is selected from the group consisting of thiophenyl optionally independently substituted with one or more $R^3$, thiazolyl optionally independently substituted with one or more $R^4$, oxazolyl optionally independently substituted with one or more $R^5$, pyrazolyl optionally independently substituted with one or more $R^6$, pyridyl optionally independently substituted with one or more $R^7$, pyrimidinyl optionally independently substituted with one or more $R^8$, phenyl substituted with one or more $R^9$, and pyrazinyl optionally independently substituted with one or more $R^{10}$. In some embodiments, Ar is selected from the group consisting of:

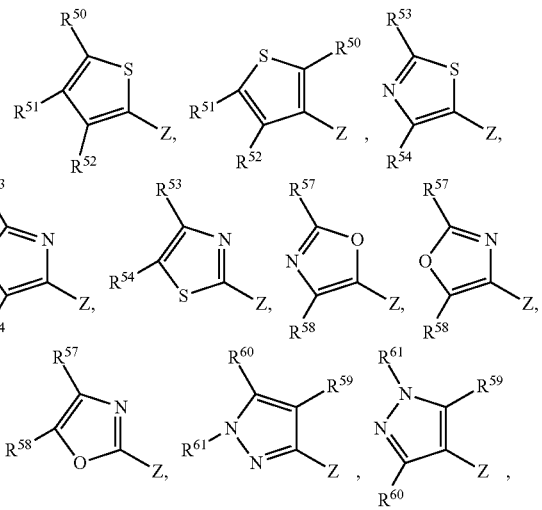

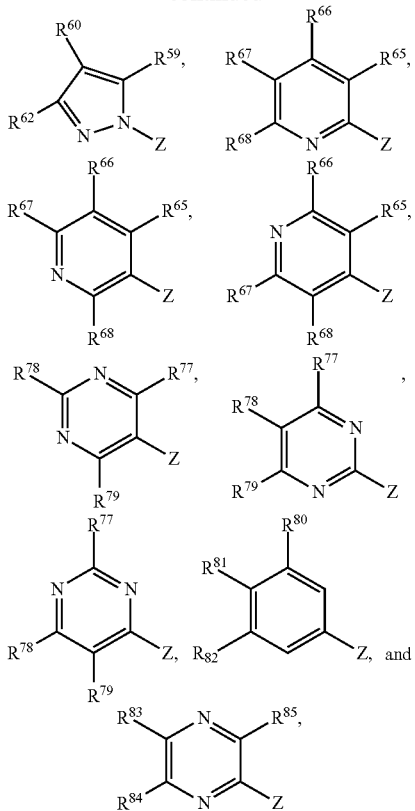

wherein:
Z represents the point of attachment to the 5-position of the pyrrolo[2,3-b]pyridine ring of Formula I;
each $R^{50}$, $R^{51}$ and $R^{52}$ is independently selected from hydrogen or the $R^3$ substituents;
each $R^{53}$ and $R^{54}$ is independently selected from hydrogen or the $R^4$ substituents;
each $R^{57}$ and $R^{58}$ is independently selected from hydrogen or the $R^5$ substituents;
each $R^{59}$, $R^{60}$ and $R^{62}$ is independently selected from hydrogen or the $R^6$ substituents; $R^{61}$ is selected from the group consisting of hydrogen, —C(O)—$R^{45}$, —S(O)$_2$—$R^{46}$, and lower alkyl wherein lower alkyl is optionally independently substituted with one or more fluoro, or, when $R^{59}$, $R^{69}$ and/or $R^{62}$ are $C_{2-6}$, alkyl, $R^{59}$, $R^{69}$ and/or $R^{62}$ are optionally substituted with one or more lower alkoxy, mono-alkylamino, di-alkylamino or cycloalkylamino; wherein each $R^{45}$ and $R^{46}$ is independently selected from the group consisting of —NH$_2$, lower alkyl, mono-alkylamino, di-alkylamino, cycloalkylamino, and heterocycloalkylamino;
each $R^{65}$, $R^{66}$, $R^{67}$ and $R^{68}$ is independently selected from hydrogen or the $R^7$ substituents;
each $R^{77}$, $R^{78}$ and $R^{79}$ is independently selected from hydrogen or the $R^8$ substituents;
each $R^{80}$, $R^{81}$ and $R^{82}$ is independently selected from hydrogen or the $R^9$ substituents, and
each $R^{83}$, $R^{84}$ and $R^{85}$ is independently selected from hydrogen or the $R^{10}$ substituents.

In some embodiments of compounds of Formula I, further to any of the above-mentioned embodiments of Formula I, $R^1$ is n-propyl.

In some embodiments of compounds of Formula I, further to any of the above-mentioned embodiments of Formula I, $R^1$ is 4-trifluoromethyl-phenyl.

In some embodiments of compounds of Formula I, further to any of the above-mentioned embodiments of Formula I, $R^1$ is 2-fluoro-phenyl, 3-fluoro-phenyl or 2,5-difluoro-phenyl. In some embodiments of compounds of Formula I, further to any of the above-mentioned embodiments of Formula I, when $R^1$ is 2-fluoro-phenyl or 2,5-difluoro-phenyl, Ar is not 2-methoxy-pyrimidin-5-yl.

In some embodiments of compounds of Formula I, further to any of the above-mentioned embodiments of Formula I, $R^1$ is 2-fluoro-phenyl.

In some embodiments of compounds of Formula I, further to any of the above-mentioned embodiments of Formula I, $R^1$ is 3-fluoro-phenyl.

In some embodiments of compounds of Formula I, further to any of the above-mentioned embodiments of Formula I, $R^1$ is 2,5-difluoro-phenyl.

In some embodiments of compounds of Formula I, Ar is thiophenyl, providing compounds of Formula II as follows:

Formula II

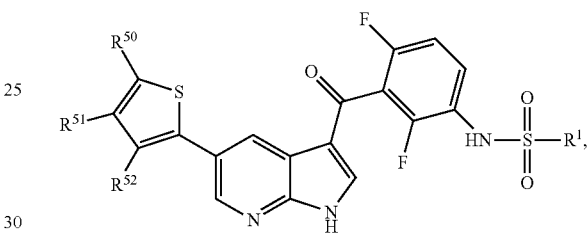

wherein $R^{50}$, $R^{51}$ and $R^{52}$ are independently selected from hydrogen or the $R^3$ substituents. In some embodiments of compounds of Formula II, each $R^3$ is independently CN, —C(O)—$R^{11}$, —S(O)$_2$—$R^{12}$, fluoro, chloro, lower alkyl, fluoro substituted lower alkyl, lower alkoxy, fluoro substituted lower alkoxy, mono-alkylamino, di-alkylamino, cycloalkyl, heterocycloalkyl, phenyl, or heteroaryl, wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is thiophenyl, providing compounds of Formula III as follows:

Formula III

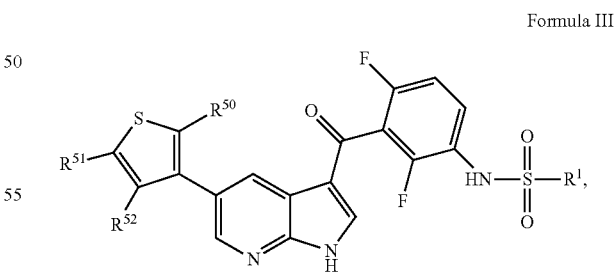

wherein $R^{50}$, $R^{51}$ and $R^{52}$ are independently selected from hydrogen or the $R^3$ substituents. In some embodiments of compounds of Formula III, each $R^3$ is independently —CN, —OH, —NH$_2$, —C(O)—$R^{11}$, —S(O)$_2$—$R^{12}$, fluoro, chloro, lower alkyl, fluoro substituted lower alkyl, lower alkoxy, fluoro substituted lower alkoxy, mono-alkylamino, di-alkylamino, cycloalkyl, heterocycloalkyl, phenyl, or heteroaryl, wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is thiazolyl, providing compounds of Formula IV as follows:

Formula IV

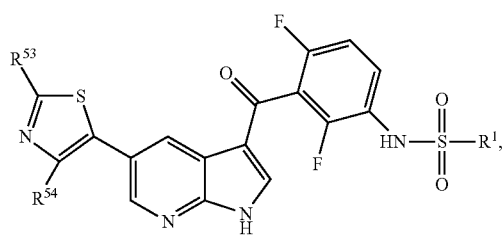

wherein $R^{53}$ and $R^{54}$ are independently selected from hydrogen or the $R^4$ substituents. In some embodiments of compounds of Formula IV, each $R^4$ is independently —CN, —OH, —NH$_2$, —C(O)—$R^{11}$, —S(O)$_2R^{12}$, fluoro, lower alkyl, fluoro substituted lower alkyl, lower alkoxy, fluoro substituted lower alkoxy, mono-alkylamino, di-alkylamino, cycloalkyl, heterocycloalkyl, phenyl, or heteroaryl, wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is thiazolyl, providing compounds of Formula V as follows:

Formula V wherein $R^{53}$ and $R^{54}$ are independently selected from hydrogen or the $R^4$ substituents. In some embodiments of compounds of Formula V, each $R^4$ is independently —C(O)—$R^{11}$, —S(O)$_2$—$R^{12}$, fluoro, lower alkyl, fluoro substituted lower alkyl, lower alkoxy, fluoro substituted lower alkoxy, mono-alkylamino, di-alkylamino, cycloalkyl, heterocycloalkyl, phenyl, or heteroaryl, wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is thiazolyl, providing compounds of Formula VI as follows:

Formula VI

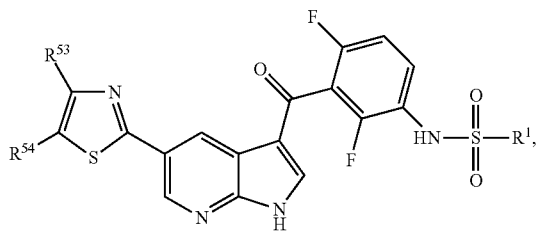

wherein $R^{53}$ and $R^{54}$ are independently selected from hydrogen or the $R^4$ substituents. In some embodiments of compounds of Formula VI, each $R^4$ is independently —C(O)—$R^{11}$, —S(O)$_2$—$R^{12}$, fluoro, lower alkyl, fluoro substituted lower alkyl, lower alkoxy; fluoro substituted lower alkoxy, mono-alkylamino, di-alkylamino, cycloalkyl, heterocycloalkyl, phenyl, or heteroaryl, wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is oxazolyl, providing compounds of Formula VII as follows:

Formula VII wherein $R^{57}$ and $R^{58}$ are independently selected from hydrogen or the $R^5$ substituents. In some embodiments of compounds of Formula VII, each $R^5$ is independently —C(O)—$R^{11}$, —S(O)$_2$—$R^{12}$, fluoro, lower alkyl, fluoro substituted lower alkyl, lower alkoxy, fluoro substituted lower alkoxy, mono-alkylamino, di-alkylamino, cycloalkyl, heterocycloalkyl, phenyl, or heteroaryl, wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is oxazolyl, providing compounds of Formula VIII as follows:

Formula VIII

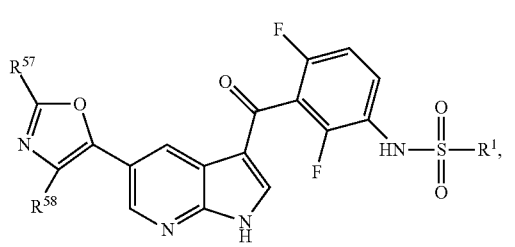

wherein $R^{57}$ and $R^{58}$ are independently selected from hydrogen or the $R^5$ substituents. In some embodiments of compounds of Formula VIII, each $R^5$ is independently —C(O)—$R^{11}$, —S(O)$_2$—$R^{12}$, fluoro, lower alkyl, fluoro substituted lower alkyl, lower alkoxy, fluoro substituted lower alkoxy, mono-alkylamino, di-alkylamino, cycloalkyl, heterocycloalkyl, phenyl, or heteroaryl, wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is oxazolyl, providing compounds of Formula IX as follows:

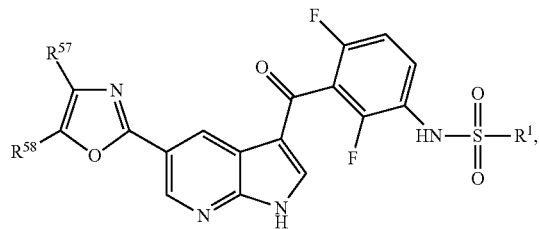

Formula IX wherein $R^{57}$ and $R^{58}$ are independently selected from hydrogen or the $R^5$ substituents. In some embodiments of compounds of Formula IX, each $R^5$ is independently —C(O)—$R^{11}$, —S(O)$_2$—$R^{12}$, fluoro, lower alkyl, fluoro substituted lower alkyl, lower alkoxy, fluoro substituted lower alkoxy, mono-alkylamino, di-alkylamino, cycloalkyl, heterocycloalkyl, phenyl, or heteroaryl, wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is pyrazolyl, providing compounds of Formula X as follows:

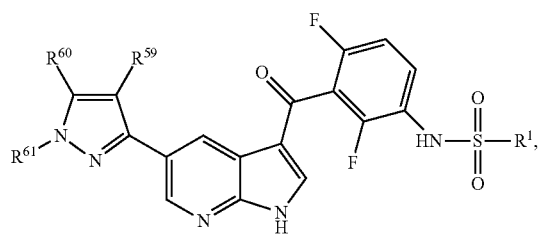

Formula X wherein $R^{59}$, $R^{60}$ and $R^{61}$ are independently selected from hydrogen or the $R^6$ substituents. In some embodiments of compounds of Formula X, each $R^6$ is independently fluoro or lower alkyl, wherein lower alkyl is optionally independently substituted with one or more fluoro, lower alkoxy, mono-alkylamino, di-alkylamino, or cycloalkylamino. $R^1$ is as defined in any of the embodiments above.

In some embodiments of compounds of Formula I, Ar is pyrazolyl, providing compounds of Formula XI as follows:

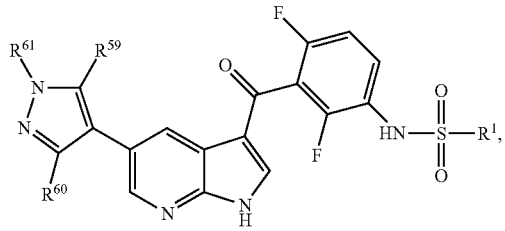

Formula XI wherein $R^{59}$, $R^{60}$ and $R^{61}$ are independently selected from hydrogen or the $R^6$ substituents. In some embodiments of compounds of Formula XI, each $R^6$ is independently fluoro or lower alkyl, wherein lower alkyl is optionally independently substituted with one or more fluoro, lower alkoxy, mono-alkylamino, di-alkylamino, or cycloalkylamino. $R^1$ is as defined in any of the embodiments above.

In some embodiments of compounds of Formula XI, further to any of the above-mentioned embodiments of Formula XI, when $R^{59}$=$R^{61}$ hydrogen, and $R^{60}$ is methyl, $R^1$ is not ethyl, n-propyl, cyclopropyl, n-butyl, isobutyl, p-trifluoromethylphenyl, 3-fluorophenyl, 3-difluoromethoxyphenyl, p-n-propylphenyl or p-isopropylphenyl. In some embodiments of compounds of Formula XI, further to any of the above-mentioned embodiments of Formula XI, when $R^{59}$=$R^{61}$ hydrogen, and $R^{60}$ is isobutyl or 2-morpholinoethyl, $R^1$ is not n-propyl. In some embodiments of compounds of Formula XI, further to any of the above-mentioned embodiments of Formula XI, when $R^{59}$, $R^{60}$, and $R^{61}$ are each methyl, $R^1$ is not n-propyl.

In some embodiments of compounds of Formula I, Ar is pyrazolyl, providing compounds of Formula XII as follows:

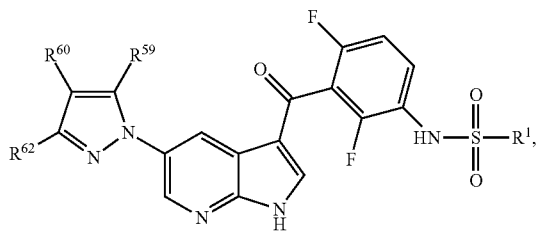

Formula XII wherein $R^{59}$, $R^{60}$ and $R^{62}$ are independently selected from hydrogen or the $R^6$ substituents. In some embodiments of compounds of Formula XII, each $R^6$ is independently fluoro or lower alkyl, wherein lower alkyl is optionally independently substituted with one or more fluoro, lower alkoxy, mono-alkylamino, di-alkylamino, or cycloalkylamino. $R^1$ is as defined in any of the embodiments above.

In some embodiments of compounds of Formula I, Ar is pyridyl, providing compounds of Formula XIII as follows:

Formula XIII

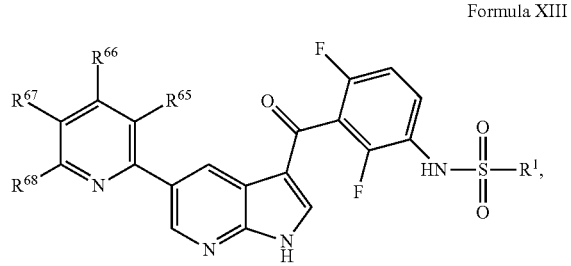

wherein $R^{65}$, $R^{66}$, $R^{67}$ and $R^{68}$ are independently selected from hydrogen or the $R^7$ substituents. In some embodiments of compounds of Formula XIII, each $R^7$ is independently —C(O)—$R^{11}$, —S(O)$_2$—$R^{12}$, —C(O)—N(H)—O—$R^{16}$, —O—$R^{13}$, —N($R^{14}$)—$R^{15}$, fluoro, chloro, lower alkyl, cycloalkyl, heterocycloalkyl, phenyl, or heteroaryl, wherein lower alkyl is optionally independently substituted with one or more fluoro, lower alkoxy, mono-alkylamino, di-alkylamino, cycloalkylamino, or heterocycloalkylamino, and wherein cycloalkyl, heterocycloalkyl, phenyl and heteroaryl are optionally independently substituted with one or more lower alkyl, fluoro substituted lower alkyl, lower alkoxy, or fluoro substituted lower alkoxy.

In some embodiments of compounds of Formula I, Ar is pyridyl, providing compounds of Formula XIV as follows:

Formula XIV

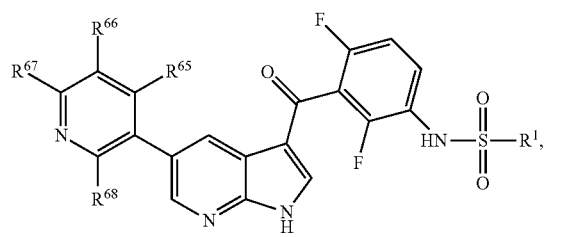

wherein $R^{65}$, $R^{66}$, $R^{67}$ and $R^{68}$ are independently selected from hydrogen or the $R^7$ substituents. In some embodiments of compounds of Formula XIV, each $R^7$ is independently —C(O)—$R^{11}$, —S(O)$_2$—$R^{12}$, —C(O)—N(H)—O—$R^{16}$, —O—$R^{13}$, —N($R^{14}$)—$R^{15}$, fluoro, chloro, lower alkyl, cycloalkyl, heterocycloalkyl, phenyl, or heteroaryl, wherein lower alkyl is optionally independently substituted with one or more fluoro, lower alkoxy, mono-alkylamino, di-alkylamino, cycloalkylamino, or heterocycloalkylamino, and wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is pyridyl, providing compounds of Formula XV as follows:

Formula XV

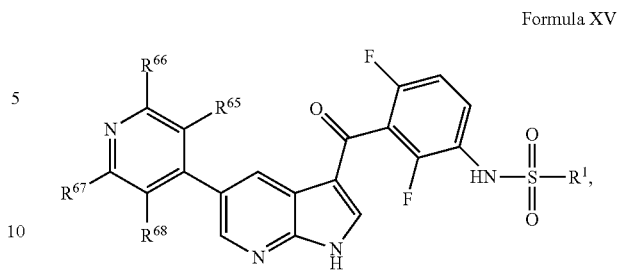

wherein $R^{65}$, $R^{66}$, $R^{67}$ and $R^{68}$ are independently selected from hydrogen or the $R^7$ substituents. In some embodiments of compounds of Formula XV, each $R^7$ is independently —C(O)—$R^{11}$, —S(O)$_2$—$R^{12}$, —C(O)—N(H)—O—$R^{16}$, —O—$R^{13}$, —N($R^{14}$)—$R^{15}$, fluoro, chloro, lower alkyl, cycloalkyl, heterocycloalkyl, phenyl, or heteroaryl, wherein lower alkyl is optionally independently substituted with one or more fluoro, lower alkoxy, mono-alkylamino, di-alkylamino, cycloalkylamino, or heterocycloalkylamino, and wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is pyrimidinyl, providing compounds of Formula XVI as follows:

Formula XVI

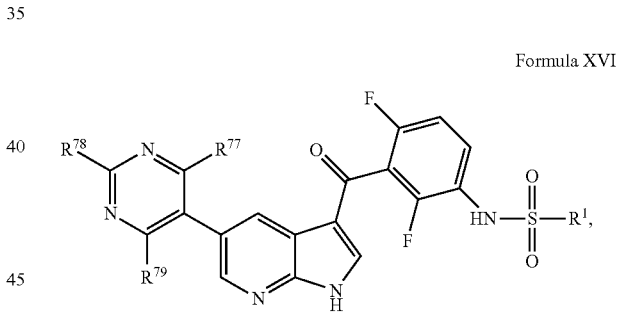

wherein $R^{77}$, $R^{78}$ and $R^{79}$ are independently selected from hydrogen or the $R^8$ substituents. In some embodiments of compounds of Formula XVI, each $R^8$ is independently —C(O)—$R^{11}$, —S(O)$_2$—$R^{12}$, —C(O)—N(H)—O—$R^{16}$, —N($R^{14}$)—$R^{15}$, fluoro, lower alkyl, cycloalkyl, heterocycloalkyl, phenyl, or heteroaryl, wherein lower alkyl is optionally independently substituted with one or more fluoro, lower alkoxy, mono-alkylamino, di-alkylamino, or cycloalkylamino, and wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is pyrimidinyl, providing compounds of Formula XVII as follows:

Formula XVII

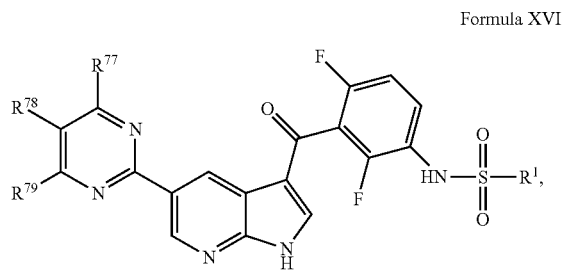

wherein $R^{77}$, $R^{78}$ and $R^{79}$ are independently selected from hydrogen or the $R^8$ substituents. In some embodiments of compounds of Formula XVII, each $R^8$ is independently —C(O)—$R^{11}$, —S(O)$_2$—$R^{12}$, —C(O)—N(H)—O—$R^{16}$, —O—$R^{13}$, —N($R^{14}$)—$R^{15}$, fluoro, lower alkyl, cycloalkyl, heterocycloalkyl, phenyl, or heteroaryl, wherein lower alkyl is optionally independently substituted with one or more fluoro, lower alkoxy, mono-alkylamino, di-alkylamino, or cycloalkylamino, and wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is pyrimidinyl, providing compounds of Formula XVIII as follows:

Formula XVIII

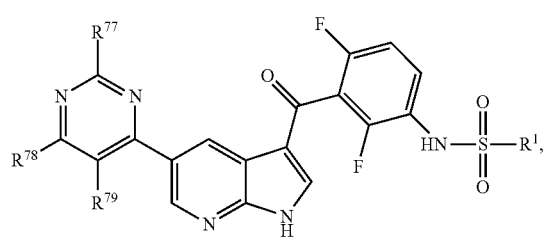

wherein $R^{77}$, $R^{78}$ and $R^{79}$ are independently selected from hydrogen or the $R^8$ substituents. In some embodiments of compounds of Formula XVIII, each $R^8$ is independently —C(O)—$R^{11}$, —S(O)$_2$—$R^{12}$, —C(O)—N(H)—O—$R^{16}$, —O—$R^{13}$, —N($R^{14}$)—$R^{15}$, fluoro, lower alkyl, cycloalkyl, heterocycloalkyl, phenyl, or heteroaryl, wherein lower alkyl is optionally independently substituted with one or more fluoro, lower alkoxy, mono-alkylamino, di-alkylamino, or cycloalkylamino, and wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is phenyl, providing compounds of Formula XIX as follows:

Formula XIX

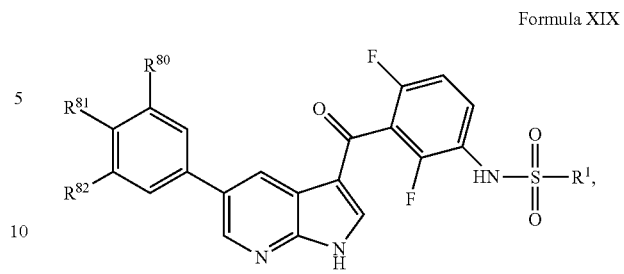

wherein $R^{80}$, $R^{81}$ and $R^{82}$ are independently selected from hydrogen or the $R^9$ substituents. In some embodiments of compounds of Formula XIX, each $R^9$ is independently —C(O)—$R^{11}$, —S(O)$_2$—$R^{12}$, —C(O)—N(H)—O—$R^{16}$, —O—$R^{13}$, —N($R^{14}$)—$R^{15}$, fluoro, lower alkyl, cycloalkyl, heterocycloalkyl, phenyl, or heteroaryl, wherein lower alkyl is optionally independently substituted with one or more fluoro, lower alkoxy, mono-alkylamino, di-alkylamino, or cycloalkylamino, and wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is pyrazinyl, providing compounds of Formula XX as follows:

Formula XX

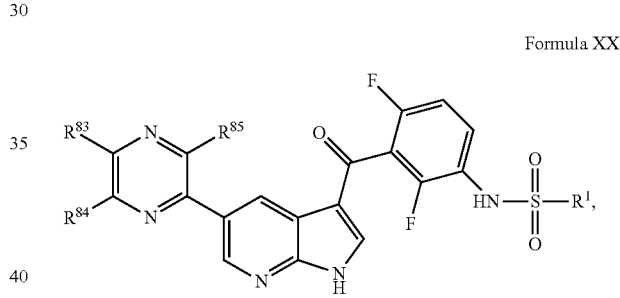

wherein $R^{83}$, $R^{84}$ and $R^{85}$ are independently selected from hydrogen or the $R^{10}$ substituents. In some embodiments of compounds of Formula XX, each $R^{10}$ is independently —C(O)—$R^{11}$, —S(O)$_2$—$R^{12}$, —C(O)—N(H)—O—$R^{16}$, —O—$R^{13}$, —N($R^{14}$)—$R^{15}$, fluoro, lower alkyl, cycloalkyl, heterocycloalkyl, phenyl, or heteroaryl, wherein lower alkyl is optionally independently substituted with one or more fluoro, lower alkoxy, mono-alkylamino, di-alkylamino, or cycloalkylamino, and wherein cycloalkyl, heterocycloalkyl, phenyl and heteroaryl are optionally independently substituted with one or more lower alkyl, fluoro substituted lower alkyl, lower alkoxy, or fluoro substituted lower alkoxy. $R^1$ is as defined in any of the embodiments above.

In some embodiments of compounds of Formula I, Ar is

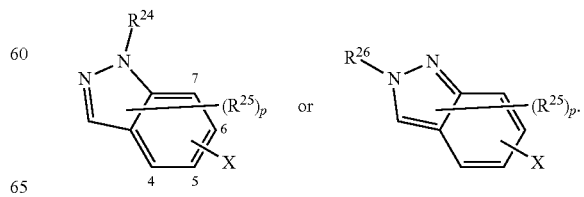

In some embodiments, the subscript p is 0. In some embodiments, $R^{24}$ and $R^{26}$ are each independently H, methyl, ethyl, propyl, methoxycarbonyl, ethylsulfonyl, methylcarbamoyl, acetyl or methylsulfonyl. In one embodiment, X is at the 4-position of the 6-membered benzene ring. In another embodiment, X is at the 5-position of the 6-membered benzene ring. In another embodiment, X is at the 6-position of the 6-membered benzene ring. In another embodiment, X is at the 7-position of the 6-membered benzene ring. All the other variables are as defined in any of the above embodiments.

In some embodiments of compounds of Formula I, Ar is

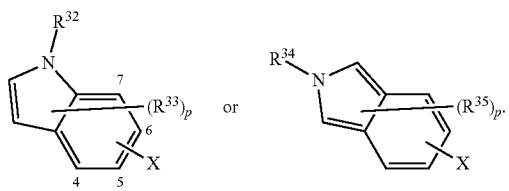

In some embodiments, the subscript p is 0. In some embodiments, $R^{32}$ and $R^{34}$ are each independently H, methyl, ethyl, propyl, methoxycarbonyl, ethylsulfonyl, methylcarbamoyl, acetyl or methylsulfonyl. In one embodiment, X is at the 4-position of the 6-membered benzene ring. In another embodiment, X is at the 5-position of the 6-membered benzene ring. In another embodiment, X is at the 6-position of the 6-membered benzene ring. In another embodiment, X is at the 7-position of the 6-membered benzene ring. All the other variables are as defined in any of the above embodiments.

In some embodiments of compounds of Formula I, Ar is

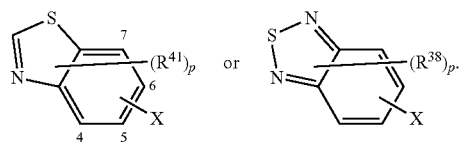

In some embodiments, the subscript p is 0. In one embodiment, X is at the 4-position of the 6-membered benzene ring. In another embodiment, X is at the 5-position of the 6-membered benzene ring. In another embodiment, X is at the 6-position of the 6-membered benzene ring. In another embodiment, X is at the 7-position of the 6-membered benzene ring. All the other variables are as defined in any of the above embodiments.

In some embodiments of compounds of Formula I, Ar is

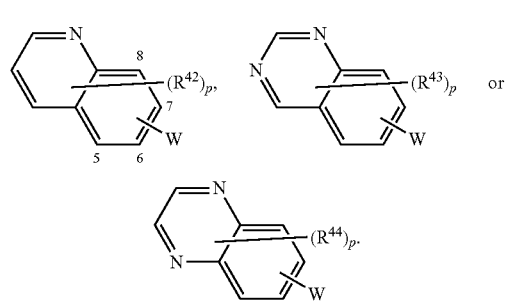

In some embodiments, the subscript p is 0. When Ar is quinolinyl or quinazolinyl, In one embodiment, W is at the 5-position of the 6-membered benzene ring. In another embodiment, W is at the 6-position of the 6-membered benzene ring. In another embodiment, W is at the 7-position of the 6-membered benzene ring. In another embodiment, W is at the 8-position of the 6-membered benzene ring. When Ar is quinoxalinyl, W is at the 5 or 6-position of the 6-membered benzene ring. All the other variables are as defined in any of the above embodiments.

In some embodiments of compounds of Formula I, Ar is

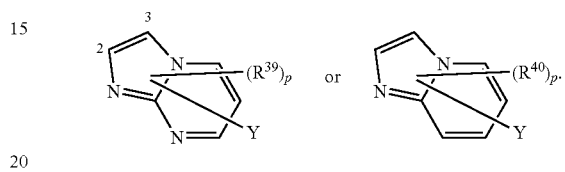

In some embodiments, the subscript p is 0. In one embodiment, y can be at any of the positions on the bicyclic ring. In one embodiment, Y is at the 3-position of the 5-membered imidazole ring. In another embodiment, X is at the 3-position of the 5-membered imidazole ring. All the other variables are as defined in any of the above embodiments.

In some embodiments of compounds of Formula I, Ar is

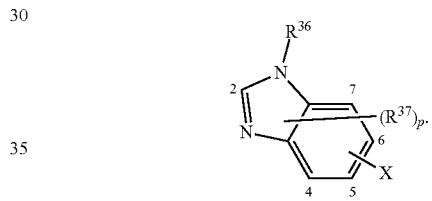

In some embodiments, the subscript p is 0. In some embodiments, $R^{36}$ is H, methyl, ethyl, propyl, methoxycarbonyl, ethylsulfonyl, methylcarbamoyl, acetyl or methylsulfonyl. In another embodiment, X is at the 2-position of the 5-membered imidazole ring. In another embodiment, X is at the 4-position of the 6-membered benzene ring. In another embodiment, X is at the 5-position of the 6-membered benzene ring. In another embodiment, X is at the 6-position of the 6-membered benzene ring. In another embodiment, X is at the 7-position of the 6-membered benzene ring. All the other variables are as defined in any of the above embodiments.

In some embodiments of compounds of Formula I, Ar is

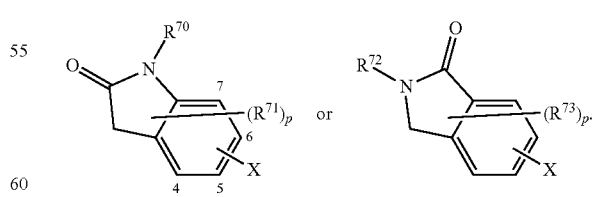

In some embodiments, the subscript p is 0. In some embodiments, $R^{70}$ and $R^{72}$ are each independently H, methyl, ethyl, propyl, methoxycarbonyl, ethylsulfonyl, methylcarbamoyl, acetyl or methylsulfonyl. In one embodiment, X is at the 4-position of the 6-membered benzene ring. In another embodiment, X is at the 5-position of the 6-membered benzene ring. In another embodiment, X is at the 6-position of the 6-membered benzene ring. In another embodiment, X is at the 7-position of the 6-membered benzene ring. All the other variables are as defined in any of the above embodiments.

In some embodiments of compounds of Formula I, Ar is 2-thiazolyl, 4-thiazolyl or 5-thiazolyl, each of which is optionally substituted with from 1 to 2 $R^4$. In other embodiments, Ar is 1-pyrazolyl, 3-pyrazolyl, 4-pyrazolyl or 5-pyrazolyl, each of which is optionally substituted with from 1 to 3 $R^6$. In yet other embodiments, Ar is 2-thiophenyl or 3-thiophenyl, each of which is optionally substituted with from 1 to 3 $R^3$. In still other embodiments, Ar is 2-pyridyl, 3-pyridyl or 4-pyridyl, each of which is optionally substituted with from 1 to 3 $R^7$. In other embodiments, Ar is 2-pyrimidinyl, 3-pyrimidinyl or 4-pyrimidinyl, each of which is optionally substituted with from 1 to 3 $R^8$. In other embodiments, Ar is 2-pyrazinyl, optionally substituted with from 1 to 2 $R^{10}$. In other embodiments, Ar is 2-oxazolyl, 4-oxazolyl or 5-oxazolyl, each of which is optionally substituted with from 1 to 2 $R^5$. In other embodiments, Ar is phenyl, optionally substituted with from 1 to 3 $R^9$. In any of the embodiments of compounds of formula I as described herein, the substituent $R^3$, $R^4$, $R^5$, $R^6$, $R^7$, $R^8$, $R^9$ or $R^{10}$ is selected from —CN, —OH, —NH$_2$, —NO$_2$, —C(O)—$R^{11}$, —S(O)$_2$—$R^{12}$, optionally substituted lower alkyl, optionally substituted lower alkoxy, optionally substituted alkylamino, optionally substituted phenyl or optionally substituted heteroaryl. All the other variables are as defined in any of the above embodiments.

In some embodiments of compounds of Formula I, $R^3$, $R^4$, $R^5$, $R^6$, $R^7$, $R^8$, $R^9$ or $R^{10}$ is selected from 4-piperidinyl, 2-pyrimidinyl, 4-pyrimidinyl, 5-pyrimidinyl, methyl, ethyl, propyl, isopropyl, 1,2,3,4-tetrazol-1-yl, 1,2,3,4-tetrazol-3-yl, 1,2,3,4-tetrazol-5-yl, 4-pyrazolylsulfonyl, 3-pyrazolylsulfonyl, 2-pyridyl, 3-pyridyl, 4-pyridyl, 2-pyrazinyl, carbamoyl, alkylcarbamoyl, alkoxycarbonyl, phenoxycarbonyl, 1-imidazolyl, 2-imidazolyl, 4-imidazolyl, 1-pyrazolyl, 3-pyrazolyl, 4-pyrazolyl, dialkylamino, alkylamino, alkoxy, methoxy, 2-oxo-1-pyrrolidinyl, 2-oxo-4-pyrrolidinyl, 2-oxo-5-pyrrolidinyl, sulfamoyl, alkylsulfamoyl, phenylsulfamoyl, 2-thiazolyl, 4-thiazolyl, 5-thiazolyl, fluoro, chloro, methylsulfonyl, 3-dimethylaminopropoxy, dimethylamino, cyclopropylamino, 2-methoxyethylamino, 2-pyridinyloxy, 3-pyridinyloxy, 4-pyridinyloxy, CF$_3$O—, CN, methylamino, 2-dimethylaminoethylamino, 3-methoxypropylamino, isopropylamino, methoxy, amino, alkoxycarbamoyl, methoxycarbamoyl, formyl, 2-methylaminoethyl, 1,2,4,-oxadiazol-3-yl, 1,2,4,-oxadiazol-5-yl, 1-azetidinyl, 2-azetidinyl or 3-azetidinyl, each of which is optionally substituted with a member selected from a lower alkyl, lower alkoxy, dimethylamino, methylamino, CN, CF$_3$, F, Cl or CF$_3$O. All the other variables are as defined in any of the embodiments described herein.

In some embodiments of compounds of Formula I, Ar is 1H-4-indazolyl, 1H-5-indazolyl, 1H-6-indazolyl, 1H-7-indazolyl, 1,3-benzothiazol-4-yl, 1,3-benzothiazol-5-yl, 1,3-benzothiazol-6-yl, 1,3-benzothiazol-7-yl, imidazo[1,2-a]pyridine-2-yl, imidazo[1,2-a]pyridine-3-yl, imidazo[1,2-a]pyridine-5-yl, imidazo[1,2-a]pyridine-6-yl, imidazo[1,2-a]pyridine-7-yl, imidazo[1,2-a]pyridine-8-yl, imidazo[1,2-a]pyrimidin-5-yl, imidazo[1,2-a]pyrimidin-6-yl, imidazo[1,2-a]pyrimidin-7-yl, imidazo[1,2-a]pyrimidin-8-yl, 1H-indol-5yl, 1H-indol-2yl, 1H-indol-3yl, 1H-indol-4-yl, 1H-indol-6yl, 1H-indol-7yl, 3-methyl-1-H-indol-5-yl, quinazolin-2-yl, quinazolin-4-yl, quinazolin-5-yl, quinazolin-6-yl, quinazolin-7 yl, quinazolin-8-yl, benzimidazol-2-yl, benzimidazol-4-yl, benzimidazol-5-yl, quinolin-2-yl, quinolin-3-yl, quinolin-4-yl, quinolin-5-yl, quinolin-6-yl, quinolin-7-yl, quinolin-8-yl, 1-oxo-isoindolin-4-yl, 1-oxo-isoindolin-5-yl, 1-oxo-isoindolin-6-yl, 1-oxo-isoindolin-7-yl, 2-oxo-indolin-4-yl, 2-oxo-indolin-5-yl, 2-oxo-indolin-6-yl or 2-oxo-indolin-7-yl, each of which is optionally substituted with one to two members selected from methyl, amino, CF$_3$, CF$_3$O, CH$_3$O, acetyl, dimethylamino, fluoro, chloro or methylaminoethyl.

In some embodiments of compounds of Formula I, Ar is 1H-4-indazolyl, 1H-5-indazolyl, 1H-6-indazolyl, 1H-7-indazolyl, 1-methyl-4-indazolyl, 1-methyl-5-indazolyl, 1-methyl-6-indazolyl, 1-methyl-7-indazolyl, 1-acetyl-4-indazolyl, 1-acetyl-5-indazolyl, 1-acetyl-6-indazolyl, 1-acetyl-7-indazolyl, 1-methylsulfonyl-4-indazolyl, 1-methylsulfonyl-5-indazolyl, 1-methylsulfonyl-6-indazolyl, 1-methylsulfonyl-7-indazolyl, 1-methyl-3-amino-6-indazolyl, 1,3-benzothiazol-4-yl, 1,3-benzothiazol-5-yl, 1,3-benzothiazol-6-yl, 1,3-benzothiazol-7-yl, imidazo[1,2-a]pyridine-2-yl, imidazo[1,2-a]pyridine-3-yl, imidazo[1,2-a]pyridine-5-yl, imidazo[1,2-a]pyridine-6-yl, imidazo[1,2-a]pyridine-7-yl, imidazo[1,2-a]pyridine-8-yl, 7-trifluoromethylimidazo[1,2-a]pyrimidin-2-yl, 7-trifluoromethylimidazo[1,2-a]pyrimidin-3-yl, imidazo[1,2-a]pyrimidin-5-yl, imidazo[1,2-a]pyrimidin-6-yl, imidazo[1,2-a]pyrimidin-7-yl, imidazo[1,2-a]pyrimidin-8-yl, 1H-indol-5yl, 1H-indol-2yl, 1H-indol-3yl, 1H-indol-4-yl, 1H-indol-6yl, 1H-indol-7yl, 3-methyl-1-H-indol-5-yl, quinazolin-2-yl, quinazolin-4-yl, quinazolin-5-yl, quinazolin-6-yl, quinazolin-7-yl, quinazolin-8-yl, benzimidazol-2-yl, benzimidazol-4-yl, benzimidazol-5-yl, 1-methyl-2-aminobenzimidazol-5-yl, 1-methyl-2-aminobenzimidazol-4-yl, quinolin-2-yl, quinolin-3-yl, quinolin-4-yl, quinolin-5-yl, quinolin-6-yl, quinolin-7-yl, quinolin-8-yl, 1-oxo-isoindolin-4-yl, 1-oxo-isoindolin-5-yl, 1-oxo-isoindolin-6-yl, 1-oxo-isoindolin-7-yl, 2-oxo-indolin-4-yl, 2-oxo-indolin-5-yl, 2-oxo-indolin-6-yl or 2-oxo-indolin-7-yl.

In various aspects and embodiments, provided are compounds shown in Table I below, and/or pharmaceutically acceptable salts of the compounds shown in Table I.

TABLE I

| Comp # | Structure | Name | MS |
|---|---|---|---|
| P-0001 | 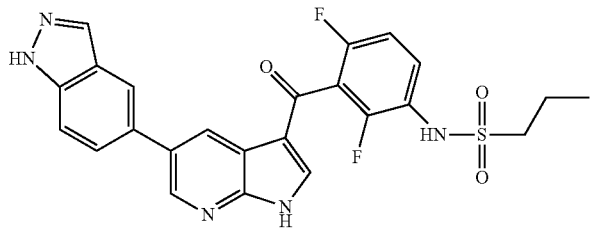 [SMILES: CCCS(=O)(=O)Nc1ccc(F)c(C(=O)c2c[nH]c3ncc(-c4ccc5[nH]ncc5c4)cc23)c1F] | Propane-1-sulfonic acid {2,4-difluoro-3-[5-(1H-indazol-5-yl)-1H-pyrrolo[2,3-b]pyridine-3-carbonyl]-phenyl}-amide | |

TABLE I-continued

| Comp # | Structure | Name | MS |
|---|---|---|---|
| P-0002 | 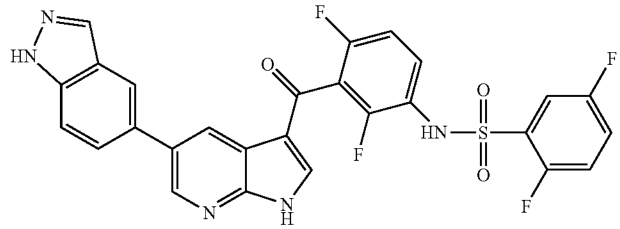 [SMILES: O=C(c1c(F)ccc(NS(=O)(=O)c2cc(F)ccc2F)c1F)c1c[nH]c2ncc(-c3ccc4[nH]ncc4c3)cc12] | N-{2,4-Difluoro-3-[5-(1H-indazol-5-yl)-1H-pyrrolo[2,3-b]pyridine-3-carbonyl]-phenyl}-2,5-difluoro-benzenesulfonamide | |
| P-0003 | 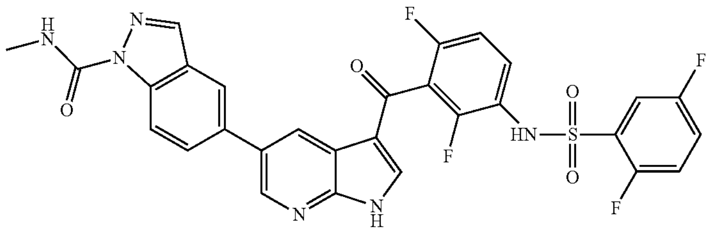 [SMILES: CNC(=O)n1ncc2cc(-c3cnc4[nH]cc(C(=O)c5c(F)ccc(NS(=O)(=O)c6cc(F)ccc6F)c5F)c4c3)ccc21] | 5-{3-[3-(2,5-Difluoro-benzenesulfonylamino)-2,6-difluoro-benzoyl]-1H-pyrrolo[2,3-b]pyridin-5-yl}-indazole-1-carboxylic acid methylamide | |
| P-0004 | 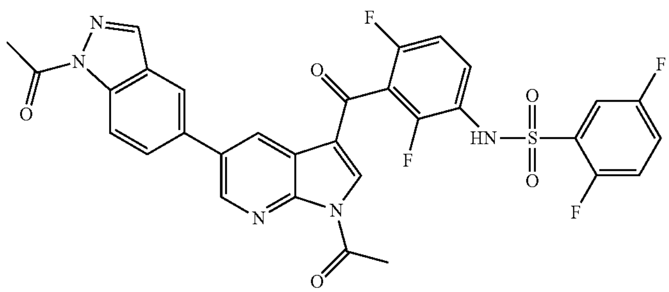 [SMILES: CC(=O)n1cc(C(=O)c2c(F)ccc(NS(=O)(=O)c3cc(F)ccc3F)c2F)c2cc(-c3ccc4c(cnn4C(C)=O)c3)cnc21] | N-{3-[1-Acetyl-5-(1-acetyl-1H-indazol-5-yl)-1H-pyrrolo[2,3-b]pyridine-3-carbonyl]-2,4-difluoro-phenyl}-2,5-difluoro-benzenesulfonamide | 650.0 |
| P-0005 | 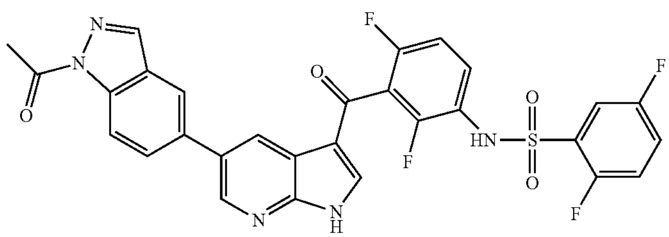 [SMILES: CC(=O)n1ncc2cc(-c3cnc4[nH]cc(C(=O)c5c(F)ccc(NS(=O)(=O)c6cc(F)ccc6F)c5F)c4c3)ccc21] | N-{3-[5-(1-Acetyl-1H-indazol-5-yl)-1H-pyrrolo[2,3-b]pyridine-3-carbonyl]-2,4-difluoro-phenyl}-2,5-difluoro-benzenesulfonamide | 607.8 |
| P-0006 | 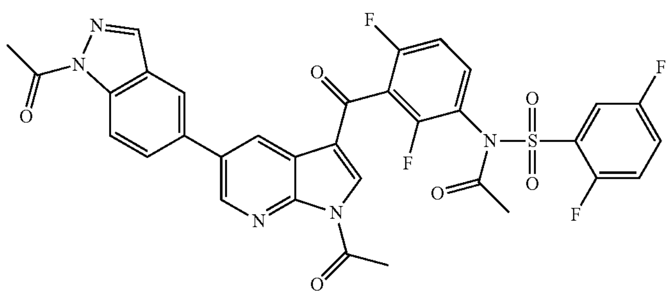 [SMILES: CC(=O)N(c1ccc(F)c(C(=O)c2cn(C(C)=O)c3ncc(-c4ccc5c(cnn5C(C)=O)c4)cc23)c1F)S(=O)(=O)c1cc(F)ccc1F] | N-Acetyl-N-{3-[1-acetyl-5-(1-acetyl-1H-indazol-5-yl)-1H-pyrrolo[2,3-b]pyridine-3-carbonyl]-2,4-difluoro-phenyl}-2,5-difluoro-benzenesulfonamide | 692.0 |
| P-0007 | 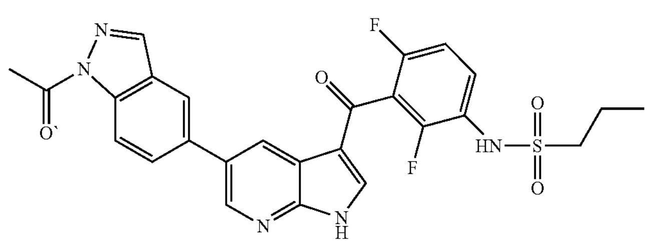 | Propane-1-sulfonic acid {3-[5-(1-acetyl-1H-indazol-5-yl)-1H-pyrrolo[2,3-b]pyridine-3-carbonyl]-2,4-difluoro-phenyl}-amide | |

TABLE I-continued

| Comp # | Structure | Name | MS |
|---|---|---|---|
| P-0008 | 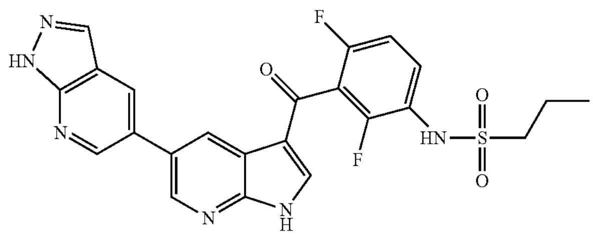 [SMILES: CCCS(=O)(=O)Nc1ccc(F)c(C(=O)c2c[nH]c3ncc(-c4cnc5[nH]ncc5c4)cc23)c1F] | Propane-1-sulfonic acid {2,4-difluoro-3-[5-(1H-pyrazolo[3,4-b]pyridin-5-yl)-1H-pyrrolo[2,3-b]pyridine-3-carbonyl]-phenyl}-amide | |
| P-0009 | 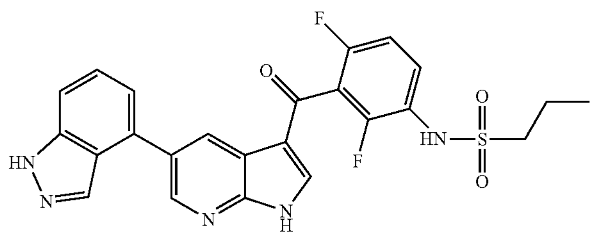 [SMILES: CCCS(=O)(=O)Nc1ccc(F)c(C(=O)c2c[nH]c3ncc(-c4cccc5[nH]ncc45)cc23)c1F] | Propane-1-sulfonic acid {2,4-difluoro-3-[5-(1H-indazol-4-yl)-1H-pyrrolo[2,3-b]pyridine-3-carbonyl]-phenyl}-amide | 496.5 |
| P-0010 | 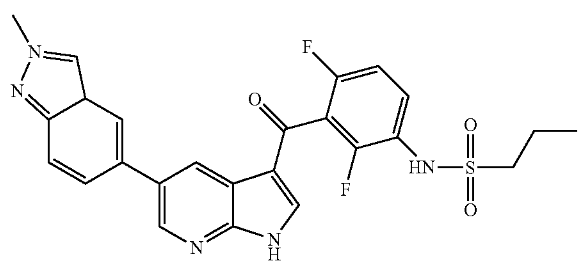 | Propane-1-sulfonic acid {2,4-difluoro-3-[5-(2-methyl-2H-indazol-5-yl)-1H-pyrrolo[2,3-b]pyridine-3-carbonyl]-phenyl}-amide | 510.5 |
| P-0011 | 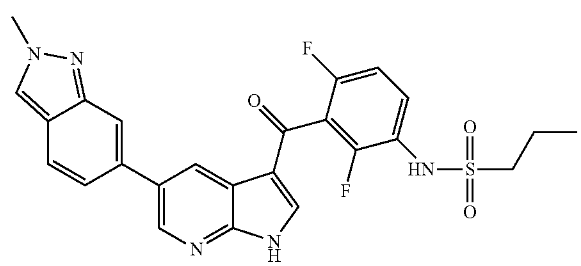 [SMILES: CCCS(=O)(=O)Nc1ccc(F)c(C(=O)c2c[nH]c3ncc(-c4ccc5cn(C)nc5c4)cc23)c1F] | Propane-1-sulfonic acid {2,4-difluoro-3-[5-(2-methyl-2H-indazol-6-yl)-1H-pyrrolo[2,3-b]pyridine-3-carbonyl]-phenyl}-amide | 510.5 |
| P-0012 | 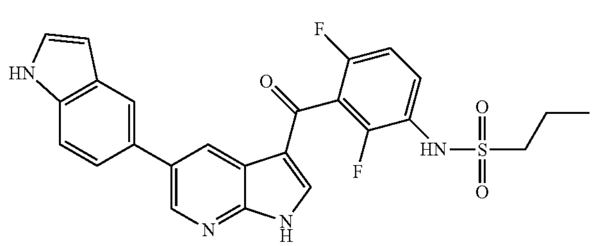 [SMILES: CCCS(=O)(=O)Nc1ccc(F)c(C(=O)c2c[nH]c3ncc(-c4ccc5[nH]ccc5c4)cc23)c1F] | Propane-1-sulfonic acid {2,4-difluoro-3-[5-(1H-indol-5-yl)-1H-pyrrolo[2,3-b]pyridine-3-carbonyl]-phenyl}-amide | 495.5 |
| P-0013 | 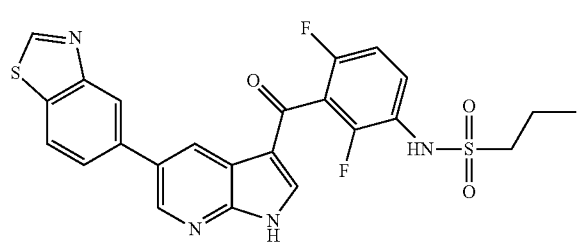 [SMILES: CCCS(=O)(=O)Nc1ccc(F)c(C(=O)c2c[nH]c3ncc(-c4ccc5scnc5c4)cc23)c1F] | Propane-1-sulfonic acid [3-(5-benzothiazol-5-yl-1H-pyrrolo[2,3-b]pyridine-3-carbonyl)-2,4-difluoro-phenyl]-amide | 513.5 |

TABLE I-continued

| Comp # | Structure | Name | MS |
|---|---|---|---|
| P-0014 | 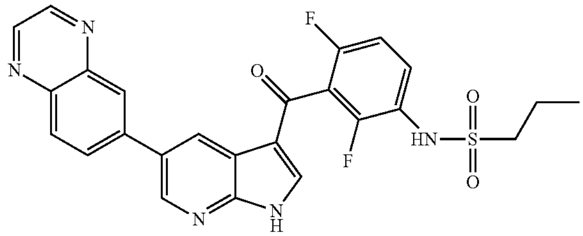 [SMILES: CCCS(=O)(=O)Nc1ccc(F)c(C(=O)c2c[nH]c3ncc(-c4ccc5nccnc5c4)cc23)c1F] | Propane-1-sulfonic acid [2,4-difluoro-3-(5-quinoxalin-6-yl-1H-pyrrolo[2,3-b]pyridine-3-carbonyl)-phenyl]-amide | 508.0 |
| P-0015 | 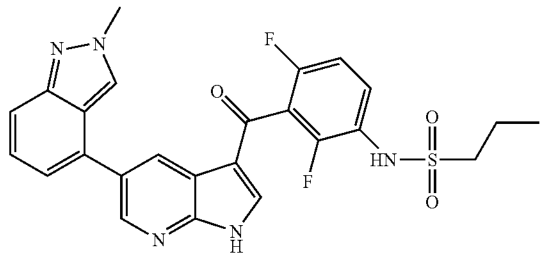 [SMILES: CCCS(=O)(=O)Nc1ccc(F)c(C(=O)c2c[nH]c3ncc(-c4cccc5nn(C)cc45)cc23)c1F] | Propane-1-sulfonic acid {2,4-difluoro-3-[5-(2-methyl-2H-indazol-4-yl)-1H-pyrrolo[2,3-b]pyridine-3-carbonyl]-phenyl}-amide | 510.5 |
| P-0016 | 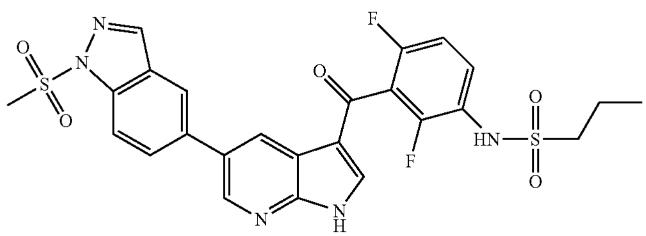 [SMILES: CCCS(=O)(=O)Nc1ccc(F)c(C(=O)c2c[nH]c3ncc(-c4ccc5c(cnn5S(C)(=O)=O)c4)cc23)c1F] | Propane-1-sulfonic acid {2,4-difluoro-3-[5-(1-methanesulfonyl-1H-indazol-5-yl)-1H-pyrrolo[2,3-b]pyridine-3-carbonyl]-phenyl}-amide | 574.5 |
| P-0017 | 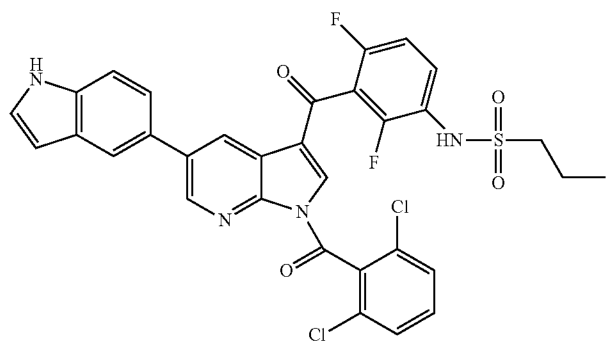 [SMILES: CCCS(=O)(=O)Nc1ccc(F)c(C(=O)c2cn(C(=O)c3c(Cl)cccc3Cl)c3ncc(-c4ccc5[nH]ccc5c4)cc23)c1F] | Propane-1-sulfonic acid {3-[1-(2,6-dichloro-benzoyl)-5-(1H-indol-5-yl)-1H-pyrrolo[2,3-b]pyridine-3-carbonyl]-2,4-difluoro-phenyl}-amide | 669.5 |
| P-0018 | 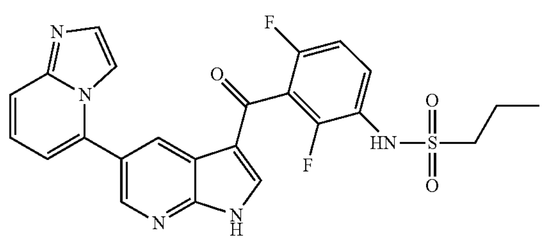 [SMILES: CCCS(=O)(=O)Nc1ccc(F)c(C(=O)c2c[nH]c3ncc(-c4cccc5nccn45)cc23)c1F] | Propane-1-sulfonic acid [2,4-difluoro-3-(5-imidazo[1,2-a]pyridin-5-yl-1H-pyrrolo[2,3-b]pyridine-3-carbonyl)-phenyl]-amide | 495.95 |
| P-0019 | 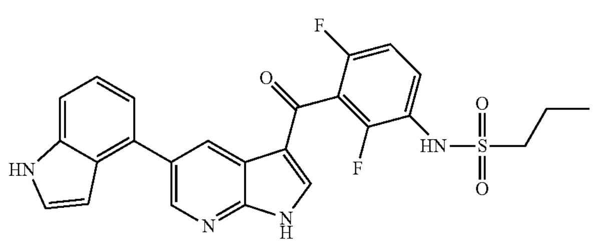 [SMILES: CCCS(=O)(=O)Nc1ccc(F)c(C(=O)c2c[nH]c3ncc(-c4cccc5[nH]ccc45)cc23)c1F] | Propane-1-sulfonic acid {2,4-difluoro-3-[5-(1H-indol-4-yl)-1H-pyrrolo[2,3-b]pyridine-3-carbonyl]-phenyl}-amide | 495.5 |

TABLE I-continued

| Comp # | Structure | Name | MS |
|---|---|---|---|
| P-0020 | 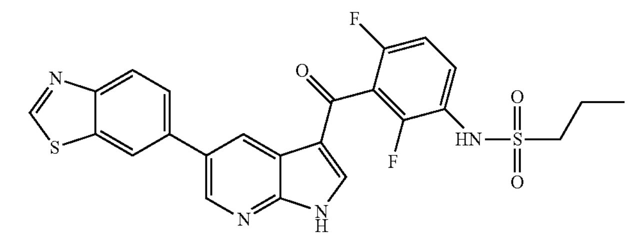 [SMILES: CCCS(=O)(=O)Nc1ccc(F)c(C(=O)c2c[nH]c3ncc(-c4ccc5ncsc5c4)cc23)c1F] | Propane-1-sulfonic acid [3-(5-benzothiazol-6-yl-1H-pyrrolo[2,3-b]pyridine-3-carbonyl)-2,4-difluoro-phenyl]-amide | 513.5 |
| P-0021 | 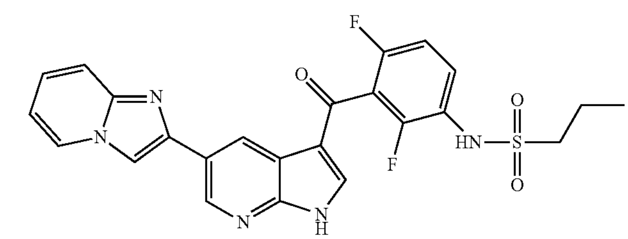 [SMILES: CCCS(=O)(=O)Nc1ccc(F)c(C(=O)c2c[nH]c3ncc(-c4cn5ccccc5n4)cc23)c1F] | Propane-1-sulfonic acid [2,4-difluoro-3-(5-imidazo[1,2-a]pyridin-2-yl-1H-pyrrolo[2,3-b]pyridine-3-carbonyl)-phenyl]-amide | 496.5 |
| P-0022 | 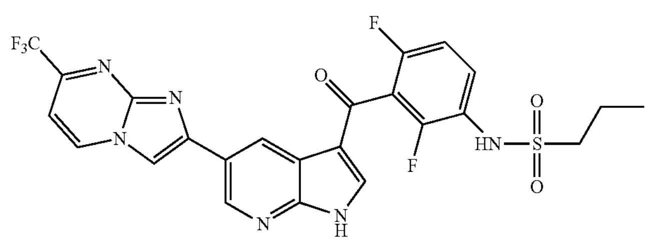 [SMILES: CCCS(=O)(=O)Nc1ccc(F)c(C(=O)c2c[nH]c3ncc(-c4cn5ccc(C(F)(F)F)nc5n4)cc23)c1F] | Propane-1-sulfonic acid {2,4-difluoro-3-[5-(7-trifluoromethyl-imidazo[1,2-a]pyrimidin-2-yl)-1H-pyrrolo[2,3-b]pyridine-3-carbonyl]-phenyl}-amide | 565.5 |
| P-0023 | 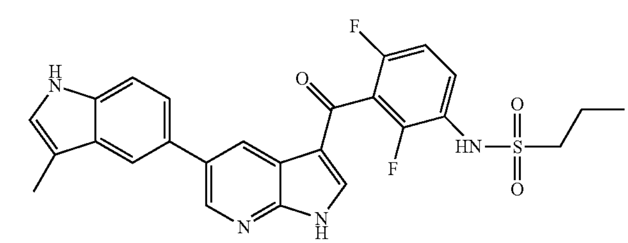 [SMILES: CCCS(=O)(=O)Nc1ccc(F)c(C(=O)c2c[nH]c3ncc(-c4ccc5[nH]cc(C)c5c4)cc23)c1F] | Propane-1-sulfonic acid {2,4-difluoro-3-[5-(3-methyl-1H-indol-5-yl)-1H-pyrrolo[2,3-b]pyridine-3-carbonyl]-phenyl}-amide | 509.5 |
| P-0024 | 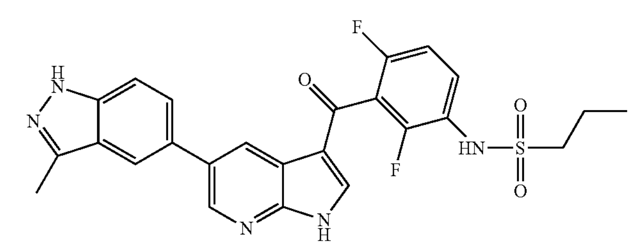 [SMILES: CCCS(=O)(=O)Nc1ccc(F)c(C(=O)c2c[nH]c3ncc(-c4ccc5[nH]nc(C)c5c4)cc23)c1F] | Propane-1-sulfonic acid {2,4-difluoro-3-[5-(3-methyl-1H-indazol-5-yl)-1H-pyrrolo[2,3-b]pyridine-3-carbonyl]-phenyl}-amide | 510.5 |
| P-0025 | 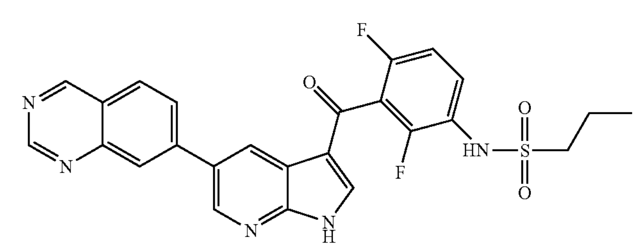 [SMILES: CCCS(=O)(=O)Nc1ccc(F)c(C(=O)c2c[nH]c3ncc(-c4ccc5cncnc5c4)cc23)c1F] | Propane-1-sulfonic acid [2,4-difluoro-3-(5-quinazolin-7-yl-1H-pyrrolo[2,3-b]pyridine-3-carbonyl)-phenyl]-amide | 526.5 |

TABLE I-continued

| Comp # | Structure | Name | MS |
|---|---|---|---|
| P-0026 | 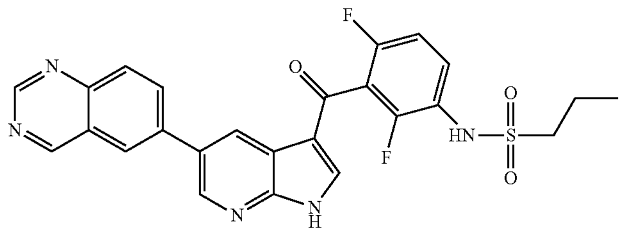 [SMILES: CCCS(=O)(=O)Nc1ccc(F)c(C(=O)c2c[nH]c3ncc(-c4ccc5ncncc5c4)cc23)c1F] | Propane-1-sulfonic acid [2,4-difluoro-3-(5-quinazolin-6-yl-1H-pyrrolo[2,3-b]pyridine-3-carbonyl)-phenyl]-amide | 526.5 |
| P-0027 | 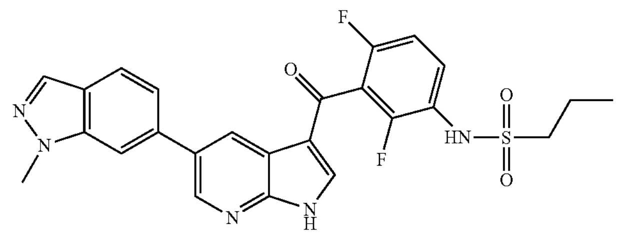 [SMILES: CCCS(=O)(=O)Nc1ccc(F)c(C(=O)c2c[nH]c3ncc(-c4ccc5cnn(C)c5c4)cc23)c1F] | Propane-1-sulfonic acid {2,4-difluoro-3-[5-(1-methyl-1H-indazol-6-yl)-1H-pyrrolo[2,3-b]pyridine-3-carbonyl]-phenyl}-amide | 510.5 |
| P-0028 | 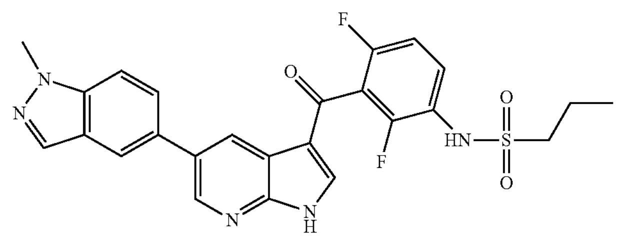 [SMILES: CCCS(=O)(=O)Nc1ccc(F)c(C(=O)c2c[nH]c3ncc(-c4ccc5c(cnn5C)c4)cc23)c1F] | Propane-1-sulfonic acid {2,4-difluoro-3-[5-(1-methyl-1H-indazol-5-yl)-1H-pyrrolo[2,3-b]pyridine-3-carbonyl]-phenyl}-amide | 510.5 |
| P-0029 | 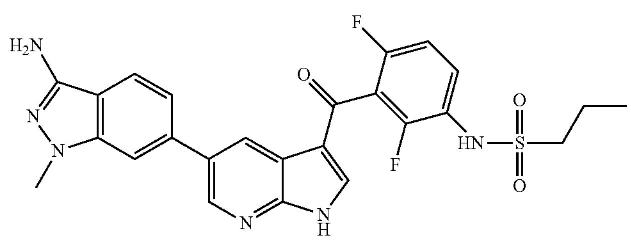 [SMILES: CCCS(=O)(=O)Nc1ccc(F)c(C(=O)c2c[nH]c3ncc(-c4ccc5c(N)nn(C)c5c4)cc23)c1F] | Propane-1-sulfonic acid {3-[5-(3-amino-1-methyl-1H-indazol-6-yl)-1H-pyrrolo[2,3-b]pyridine-3-carbonyl]-2,4-difluoro-phenyl}-amide | |
| P-0030 | 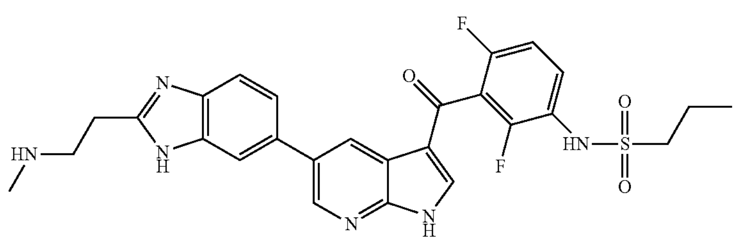 [SMILES: CCCS(=O)(=O)Nc1ccc(F)c(C(=O)c2c[nH]c3ncc(-c4ccc5nc(CCNC)[nH]c5c4)cc23)c1F] | Propane-1-sulfonic acid (2,4-difluoro-3-{5-[2-(2-methylamino-ethyl)-3H-benzoimidazol-5-yl]-1H-pyrrolo[2,3-b]pyridine-3-carbonyl}-phenyl)-amide | |
| P-0031 | 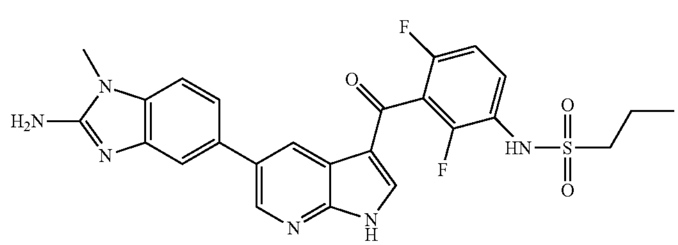 [SMILES: CCCS(=O)(=O)Nc1ccc(F)c(C(=O)c2c[nH]c3ncc(-c4ccc5c(c4)nc(N)n5C)cc23)c1F] | Propane-1-sulfonic acid {3-[5-(2-amino-1-methyl-1H-benzoimidazol-5-yl)-1H-pyrrolo[2,3-b]pyridine-3-carbonyl]-2,4-difluoro-phenyl}-amide | |

TABLE I-continued

| Comp # | Structure | Name | MS |
|---|---|---|---|
| P-0032 | 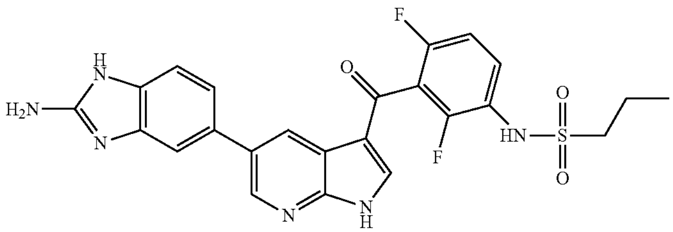 [SMILES: CCCS(=O)(=O)Nc1ccc(F)c(C(=O)c2c[nH]c3ncc(-c4ccc5[nH]c(N)nc5c4)cc23)c1F] | Propane-1-sulfonic acid {3-[5-(2-amino-1H-benzoimidazol-5-yl)-1H-pyrrolo[2,3-b]pyridine-3-carbonyl]-2,4-difluoro-phenyl}-amide | |
| P-0033 | 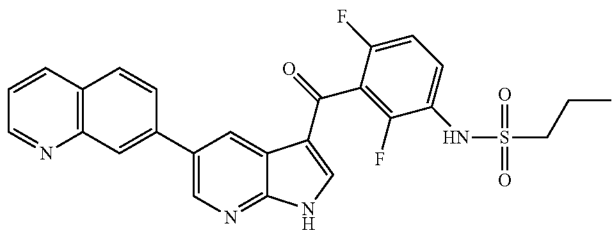 [SMILES: CCCS(=O)(=O)Nc1ccc(F)c(C(=O)c2c[nH]c3ncc(-c4ccc5cccnc5c4)cc23)c1F] | Propane-1-sulfonic acid [2,4-difluoro-3-(5-quinolin-7-yl-1H-pyrrolo[2,3-b]pyridine-3-carbonyl)-phenyl]-amide | 507.0 |
| P-0034 | 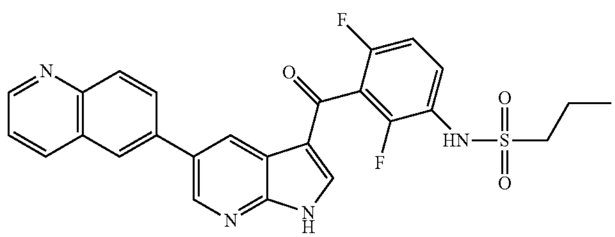 [SMILES: CCCS(=O)(=O)Nc1ccc(F)c(C(=O)c2c[nH]c3ncc(-c4ccc5ncccc5c4)cc23)c1F] | Propane-1-sulfonic acid [2,4-difluoro-3-(5-quinolin-6-yl-1H-pyrrolo[2,3-b]pyridine-3-carbonyl)-phenyl]-amide | 507.0 |
| P-0035 | 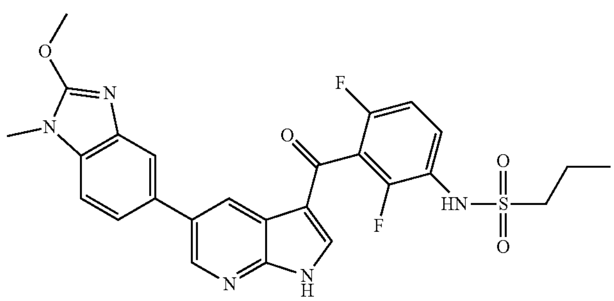 [SMILES: CCCS(=O)(=O)Nc1ccc(F)c(C(=O)c2c[nH]c3ncc(-c4ccc5c(c4)nc(OC)n5C)cc23)c1F] | Propane-1-sulfonic acid {2,4-difluoro-3-[5-(2-methoxy-1-methyl-1H-benzoimidazol-5-yl)-1H-pyrrolo[2,3-b]pyridine-3-carbonyl]-phenyl}-amide | |
| P-0036 | 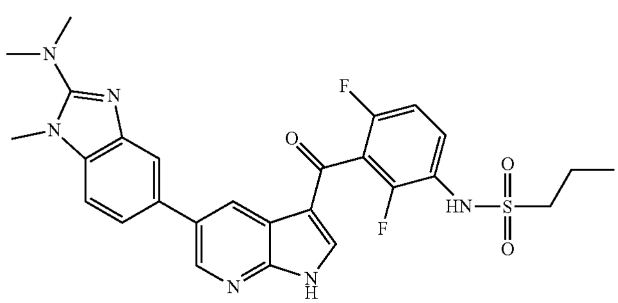 [SMILES: CCCS(=O)(=O)Nc1ccc(F)c(C(=O)c2c[nH]c3ncc(-c4ccc5c(c4)nc(N(C)C)n5C)cc23)c1F] | Propane-1-sulfonic acid {3-[5-(2-dimethylamino-1-methyl-1H-benzoimidazol-5-yl)-1H-pyrrolo[2,3-b]pyridine-3-carbonyl]-2,4-difluoro-phenyl}-amide | |
| P-0037 | 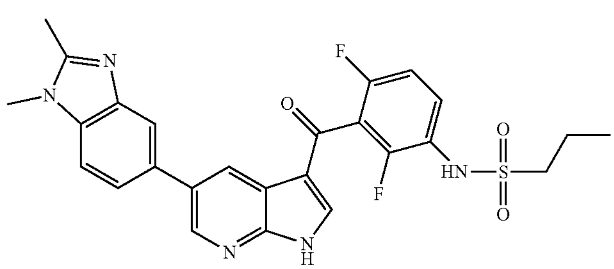 [SMILES: CCCS(=O)(=O)Nc1ccc(F)c(C(=O)c2c[nH]c3ncc(-c4ccc5c(c4)nc(C)n5C)cc23)c1F] | Propane-1-sulfonic acid {3-[5-(1,2-dimethyl-1H-benzoimidazol-5-yl)-1H-pyrrolo[2,3-b]pyridine-3-carbonyl]-2,4-difluoro-phenyl}-amide | |

TABLE I-continued

| Comp # | Structure | Name | MS |
|---|---|---|---|
| P-0038 | 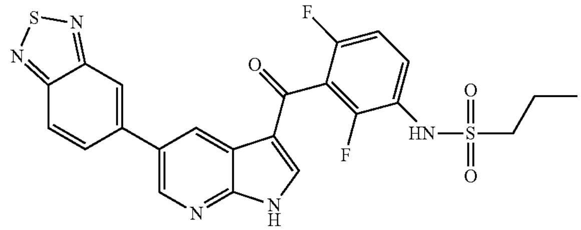 [SMILES: CCCS(=O)(=O)Nc1ccc(F)c(C(=O)c2c[nH]c3ncc(-c4ccc5nsnc5c4)cc23)c1F] | Propane-1-sulfonic acid [3-(5-benzo[1,2,5]thiadiazol-5-yl-1H-pyrrolo[2,3-b]pyridine-3-carbonyl)-2,4-difluoro-phenyl]-amide | 514.0 |
| P-0039 | 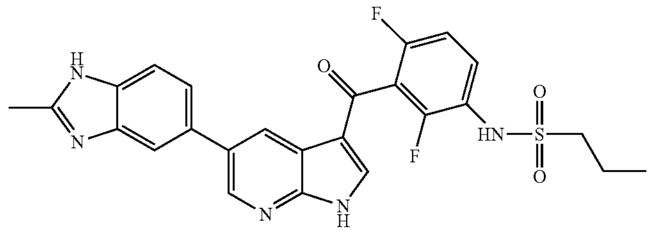 [SMILES: CCCS(=O)(=O)Nc1ccc(F)c(C(=O)c2c[nH]c3ncc(-c4ccc5[nH]c(C)nc5c4)cc23)c1F] | Propane-1-sulfonic acid {2,4-difluoro-3-[5-(2-methyl-1H-benzoimidazol-5-yl)-1H-pyrrolo[2,3-b]pyridine-3-carbonyl]-phenyl}-amide | 510.0 |
| P-1001 | 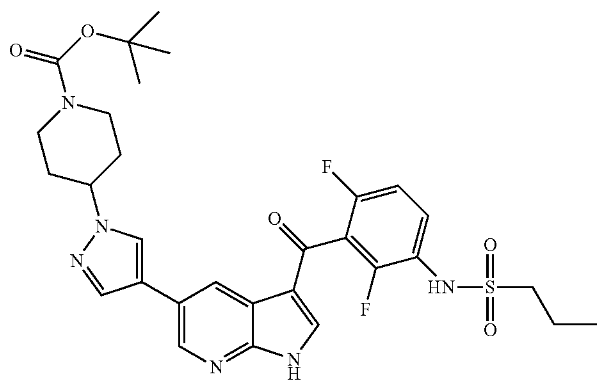 [SMILES: CCCS(=O)(=O)Nc1ccc(F)c(C(=O)c2c[nH]c3ncc(-c4cnn(C5CCN(C(=O)OC(C)(C)C)CC5)c4)cc23)c1F] | 4-(4-{3-[2,6-Difluoro-3-(propane-1-sulfonylamino)-benzoyl]-1H-pyrrolo[2,3-b]pyridin-5-yl}-pyrazol-1-yl)-piperidine-1-carboxylic acid tert-butyl ester | 629.0 |
| P-1002 | 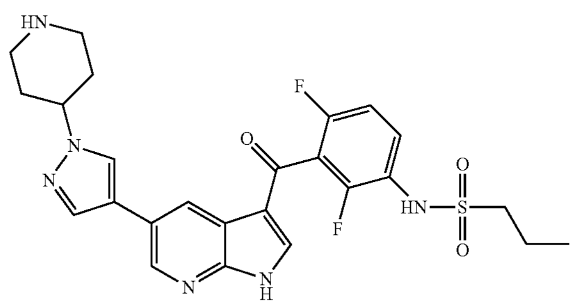 [SMILES: CCCS(=O)(=O)Nc1ccc(F)c(C(=O)c2c[nH]c3ncc(-c4cnn(C5CCNCC5)c4)cc23)c1F] | Propane-1-sulfonic acid {2,4-difluoro-3-[5-(1-piperidin-4-yl-1H-pyrazol-4-yl)-1H-pyrrolo[2,3-b]pyridine-3-carbonyl]-phenyl}-amide | 529.0 |
| P-1003 | 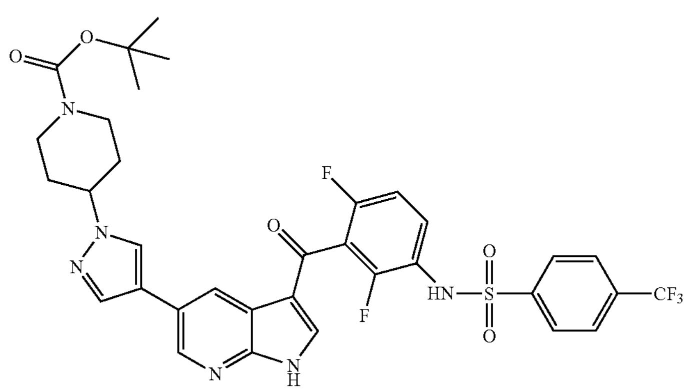 [SMILES: CC(C)(C)OC(=O)N1CCC(n2cc(-c3cnc4[nH]cc(C(=O)c5c(F)ccc(NS(=O)(=O)c6ccc(C(F)(F)F)cc6)c5F)c4c3)cn2)CC1] | 4-(4-{3-[2,6-Difluoro-3-(4-trifluoromethyl-benzenesulfonylamino)-benzoyl]-1H-pyrrolo[2,3-b]pyridin-5-yl}-pyrazol-1-yl)-piperidine-1-carboxylic acid tert-butyl ester | 731.1 |

TABLE I-continued

| Comp # | Name | MS |
|---|---|---|
| P-1004 | N-{2,4-Difluoro-3-[5-(1-piperidin-4-yl-1H-pyrazol-4-yl)-1H-pyrrolo[2,3-b]pyridine-3-carbonyl]-phenyl}-4-trifluoromethyl-benzenesulfonamide | 631.0 |
| P-1005 | Propane-1-sulfonic acid {2,4-difluoro-3-[5-(1-pyrimidin-2-yl-1H-pyrazol-4-yl)-1H-pyrrolo[2,3-b]pyridine-3-carbonyl]-phenyl}-amide | 524.5 |
| P-1006 | Propane-1-sulfonic acid (3-{5-[3,5-dimethyl-1-(1H-tetrazol-5-yl)-1H-pyrazol-4-yl]-1H-pyrrolo[2,3-b]pyridine-3-carbonyl}-2,4-difluoro-phenyl)-amide | 542.5 |
| P-1007 | Propane-1-sulfonic acid (3-{5-[1-(1,3-dimethyl-1H-pyrazole-4-sulfonyl)-3,5-dimethyl-1H-pyrazol-4-yl]-1H-pyrrolo[2,3-b]pyridine-3-carbonyl}-2,4-difluoro-phenyl)-amide | 632.5 |
| P-1008 | Propane-1-sulfonic acid (2,4-difluoro-3-{5-[1-(1H-tetrazol-5-yl)-1H-pyrazol-4-yl]-1H-pyrrolo[2,3-b]pyridine-3-carbonyl}-phenyl)-amide | 514.5 |

TABLE I-continued

| Comp # | Structure | Name | MS |
|---|---|---|---|
| P-1009 | 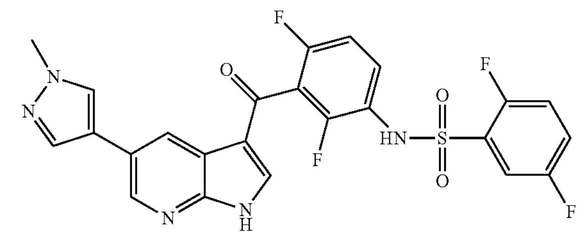 [SMILES: Cn1cc(-c2cnc3[nH]cc(C(=O)c4c(F)ccc(NS(=O)(=O)c5cc(F)ccc5F)c4F)c3c2)cn1] | N-{2,4-Difluoro-3-[5-(1-methyl-1H-pyrazol-4-yl)-1H-pyrrolo[2,3-b]pyridine-3-carbonyl]-phenyl}-2,5-difluoro-benzenesulfonamide | 530.0 |
| P-1010 | 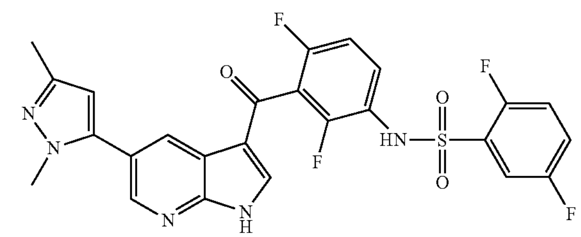 [SMILES: Cc1cc(-c2cnc3[nH]cc(C(=O)c4c(F)ccc(NS(=O)(=O)c5cc(F)ccc5F)c4F)c3c2)n(C)n1] | N-{3-[5-(2,5-Dimethyl-2H-pyrazol-3-yl)-1H-pyrrolo[2,3-b]pyridine-3-carbonyl]-2,4-difluoro-phenyl}-2,5-difluoro-benzenesulfonamide | 544.5 |
| P-1011 | 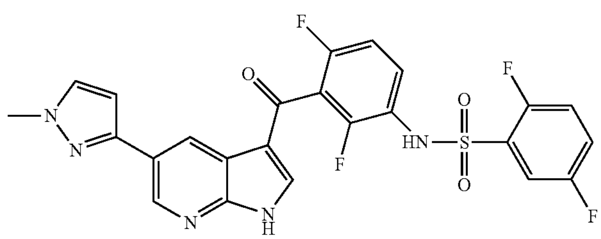 [SMILES: Cn1ccc(-c2cnc3[nH]cc(C(=O)c4c(F)ccc(NS(=O)(=O)c5cc(F)ccc5F)c4F)c3c2)n1] | N-{2,4-Difluoro-3-[5-(1-methyl-1H-pyrazol-3-yl)-1H-pyrrolo[2,3-b]pyridine-3-carbonyl]-phenyl}-2,5-difluoro-benzenesulfonamide | 530.0 |
| P-1012 | 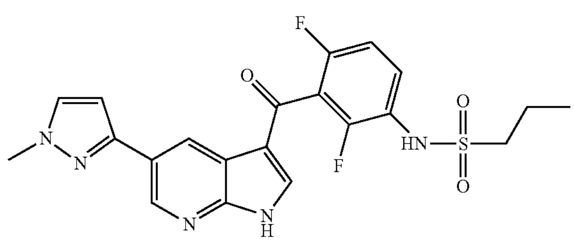 [SMILES: CCCS(=O)(=O)Nc1ccc(F)c(C(=O)c2c[nH]c3ncc(-c4ccn(C)n4)cc23)c1F] | Propane-1-sulfonic acid {2,4-difluoro-3-[5-(1-methyl-1H-pyrazol-3-yl)-1H-pyrrolo[2,3-b]pyridine-3-carbonyl]-phenyl}-amide | |
| P-1013 | 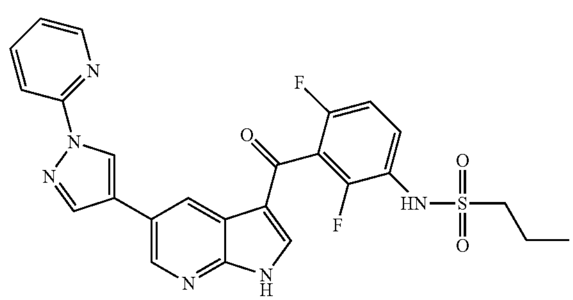 [SMILES: CCCS(=O)(=O)Nc1ccc(F)c(C(=O)c2c[nH]c3ncc(-c4cnn(-c5ccccn5)c4)cc23)c1F] | Propane-1-sulfonic acid {2,4-difluoro-3-[5-(1-pyridin-2-yl-1H-pyrazol-4-yl)-1H-pyrrolo[2,3-b]pyridine-3-carbonyl]-phenyl}-amide | |
| P-1014 | 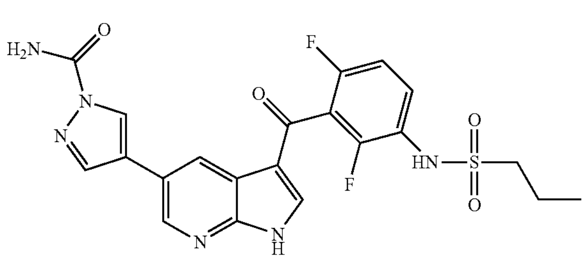 [SMILES: CCCS(=O)(=O)Nc1ccc(F)c(C(=O)c2c[nH]c3ncc(-c4cnn(C(N)=O)c4)cc23)c1F] | 4-{3-[2,6-Difluoro-3-(propane-1-sulfonylamino)-benzoyl]-1H-pyrrolo[2,3-b]pyridin-5-yl}-pyrazole-1-carboxylic acid amide | |

TABLE I-continued

| Comp # | Structure | Name | MS |
|---|---|---|---|
| P-1015 | 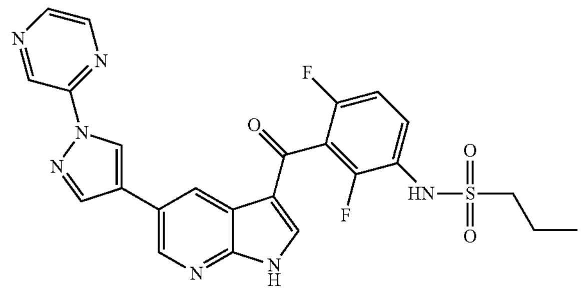 [SMILES: CCCS(=O)(=O)Nc1ccc(F)c(C(=O)c2c[nH]c3ncc(-c4cnn(-c5cnccn5)c4)cc23)c1F] | Propane-1-sulfonic acid {2,4-difluoro-3-[5-(1-pyrazin-2-yl)-1H-pyrazol-4-yl)-1H-pyrrolo[2,3-b]pyridine-3-carbonyl]-phenyl}-amide | 524.5 |
| P-1016 | 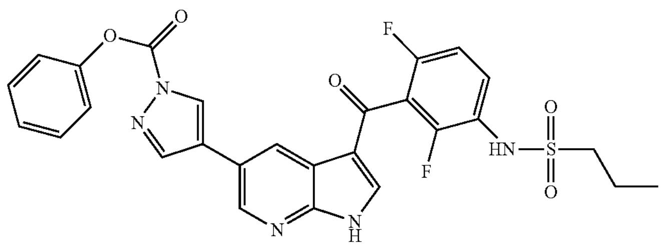 [SMILES: CCCS(=O)(=O)Nc1ccc(F)c(C(=O)c2c[nH]c3ncc(-c4cnn(C(=O)Oc5ccccc5)c4)cc23)c1F] | 4-{3-[2,6-Difluoro-3-(propane-1-sulfonylamino)-benzoyl]-1H-pyrrolo[2,3-b]pyridin-5-yl}-pyrazole-1-carboxylic acid phenyl ester 09-AB9332 | |
| P-1100 | 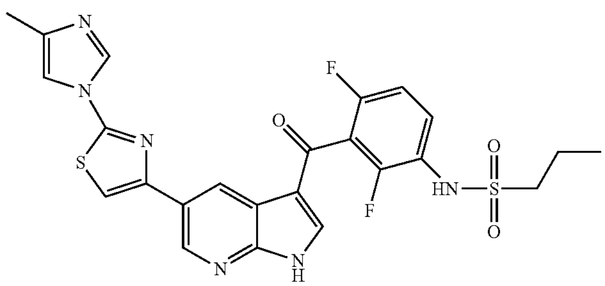 [SMILES: CCCS(=O)(=O)Nc1ccc(F)c(C(=O)c2c[nH]c3ncc(-c4csc(-n5cnc(C)c5)n4)cc23)c1F] | Propane-1-sulfonic acid (2,4-difluoro-3-{5-[2-(4-methyl-imidazol-1-yl)-thiazol-4-yl]-1H-pyrrolo[2,3-b]pyridine-3-carbonyl}-phenyl)-amide | 543.5 |
| P-1101 | 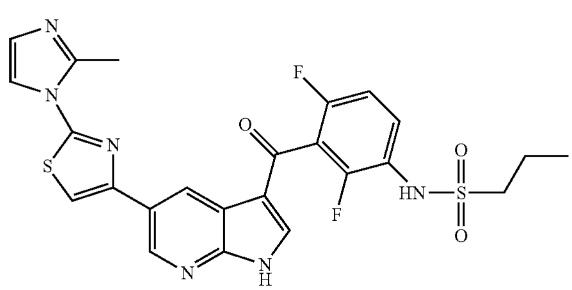 [SMILES: CCCS(=O)(=O)Nc1ccc(F)c(C(=O)c2c[nH]c3ncc(-c4csc(-n5ccnc5C)n4)cc23)c1F] | Propane-1-sulfonic acid (2,4-difluoro-3-{5-[2-(2-methyl-imidazol-1-yl)-thiazol-4-yl]-1H-pyrrolo[2,3-b]pyridine-3-carbonyl}-phenyl)-amide | 543.5 |
| P-1102 | 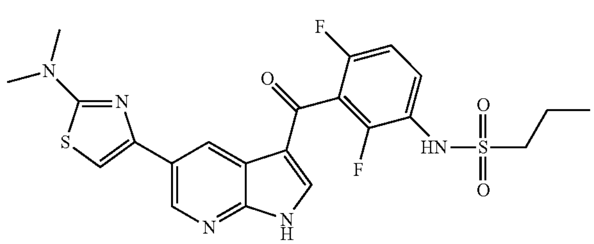 [SMILES: CCCS(=O)(=O)Nc1ccc(F)c(C(=O)c2c[nH]c3ncc(-c4csc(N(C)C)n4)cc23)c1F] | Propane-1-sulfonic acid {3-[5-(2-dimethylamino-thiazol-4-yl)-1H-pyrrolo[2,3-b]pyridine-3-carbonyl]-2,4-difluoro-phenyl}-amide | 506.0 |

TABLE I-continued

| Comp # | Structure | Name | MS |
|---|---|---|---|
| P-1103 | 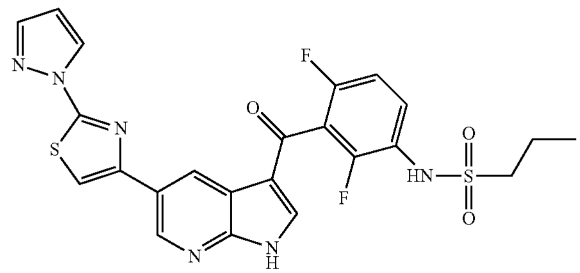 [SMILES: CCCS(=O)(=O)Nc1ccc(F)c(C(=O)c2c[nH]c3ncc(-c4csc(-n5cccn5)n4)cc23)c1F] | Propane-1-sulfonic acid {2,4-difluoro-3-[5-(2-pyrazol-1-yl-thiazol-4-yl)-1H-pyrrolo[2,3-b]pyridine-3-carbonyl]-phenyl}-amide | 529.0 |
| P-1104 | 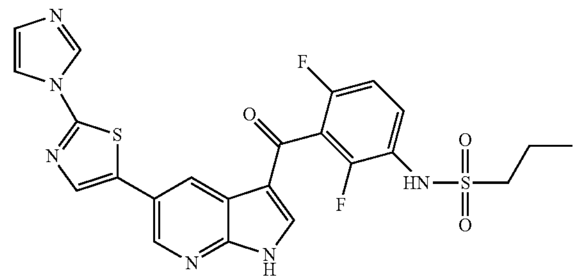 [SMILES: CCCS(=O)(=O)Nc1ccc(F)c(C(=O)c2c[nH]c3ncc(-c4cnc(-n5ccnc5)s4)cc23)c1F] | Propane-1-sulfonic acid {2,4-difluoro-3-[5-(2-imidazol-1-yl-thiazol-5-yl)-1H-pyrrolo[2,3-b]pyridine-3-carbonyl]-phenyl}-amide | 529.0 |
| P-1105 | 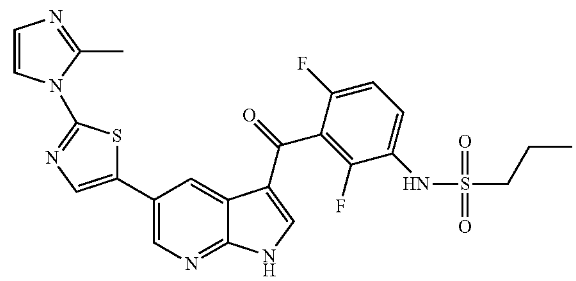 [SMILES: CCCS(=O)(=O)Nc1ccc(F)c(C(=O)c2c[nH]c3ncc(-c4cnc(-n5ccnc5C)s4)cc23)c1F] | Propane-1-sulfonic acid (2,4-difluoro-3-{5-[2-(2-methyl-imidazol-1-yl)-thiazol-5-yl]-1H-pyrrolo[2,3-b]pyridine-3-carbonyl}-phenyl)-amide | 543.5 |
| P-1106 | 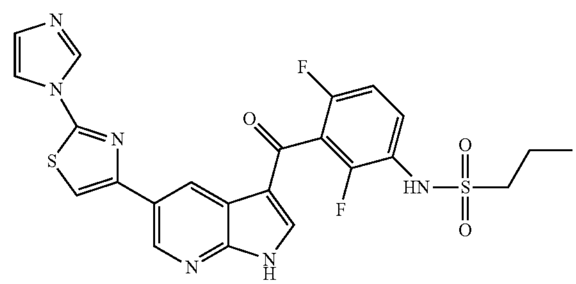 [SMILES: CCCS(=O)(=O)Nc1ccc(F)c(C(=O)c2c[nH]c3ncc(-c4csc(-n5ccnc5)n4)cc23)c1F] | Propane-1-sulfonic acid {2,4-difluoro-3-[5-(2-imidazol-1-yl-thiazol-4-yl)-1H-pyrrolo[2,3-b]pyridine-3-carbonyl]-phenyl}-amide | 529.0 |
| P-1107 | 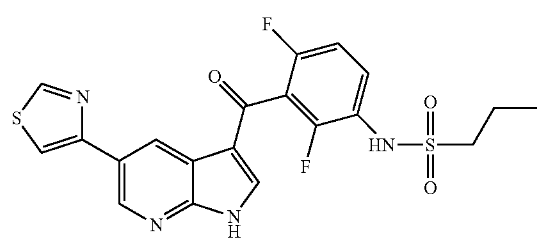 [SMILES: CCCS(=O)(=O)Nc1ccc(F)c(C(=O)c2c[nH]c3ncc(-c4cscn4)cc23)c1F] | Propane-1-sulfonic acid [2,4-difluoro-3-(5-thiazol-4-yl-1H-pyrrolo[2,3-b]pyridine-3-carbonyl)-phenyl]-amide | |
| P-1108 | 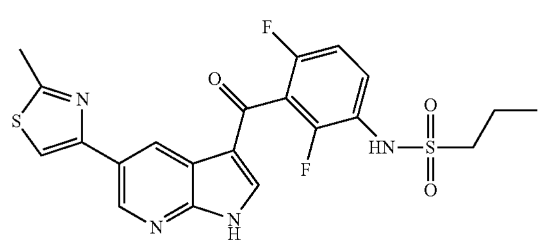 [SMILES: CCCS(=O)(=O)Nc1ccc(F)c(C(=O)c2c[nH]c3ncc(-c4csc(C)n4)cc23)c1F] | Propane-1-sulfonic acid {2,4-difluoro-3-[5-(2-methyl-thiazol-4-yl)-1H-pyrrolo[2,3-b]pyridine-3-carbonyl]-phenyl}-amide | |

| Comp # | Structure | Name | MS |
|---|---|---|---|
| P-1109 | 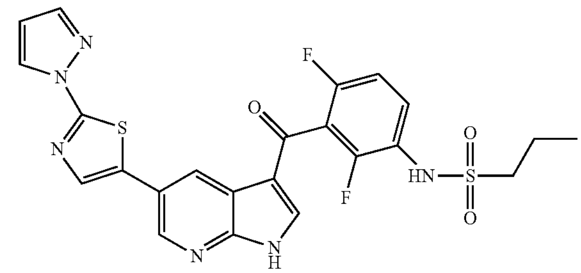 [SMILES: CCCS(=O)(=O)Nc1ccc(F)c(C(=O)c2c[nH]c3ncc(-c4cnc(-n5cccn5)s4)cc23)c1F] | Propane-1-sulfonic acid {2,4-difluoro-3-[5-(2-pyrazol-1-yl-thiazol-5-yl)-1H-pyrrolo[2,3-b]pyridine-3-carbonyl]-phenyl} amide | 529.0 |
| P-1110 | 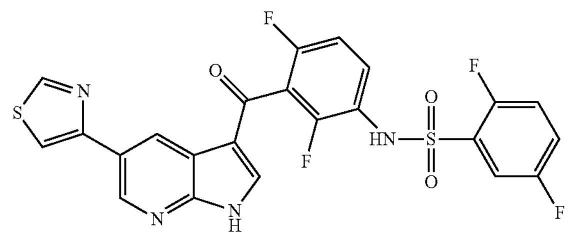 [SMILES: O=C(c1c(F)ccc(NS(=O)(=O)c2cc(F)ccc2F)c1F)c1c[nH]c2ncc(-c3cscn3)cc12] | N-[2,4-Difluoro-3-(5-thiazol-4-yl-1H-pyrrolo[2,3-b]pyridine-3-carbonyl)-phenyl]-2,5-difluoro-benzenesulfonamide | |
| P-1111 | 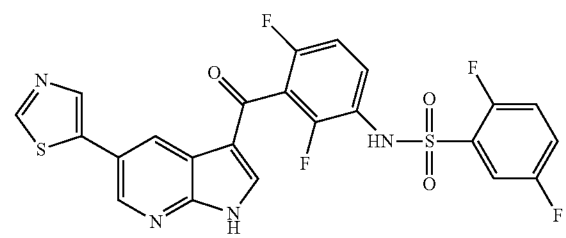 | N-[2,4-Difluoro-3-(5-thiazol-5-yl-1H-pyrrolo[2,3-b]pyridine-3-carbonyl)-phenyl]-2,5-difluoro-benzenesulfonamide | |
| P-1112 | 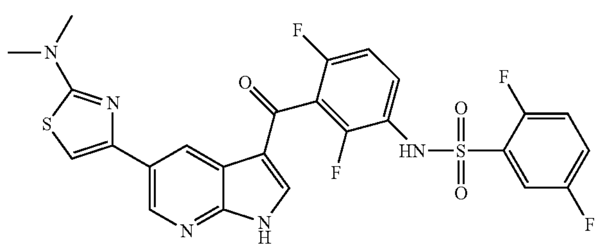 [SMILES: CN(C)c1nc(-c2cnc3[nH]cc(C(=O)c4c(F)ccc(NS(=O)(=O)c5cc(F)ccc5F)c4F)c3c2)cs1] | N-{3-[5-(2-Dimethylamino-thiazol-4-yl)-1H-pyrrolo[2,3-b]pyridine-3-carbonyl]-2,4-difluoro-phenyl}-2,5-difluoro-benzenesulfonamide | |
| P-1113 | 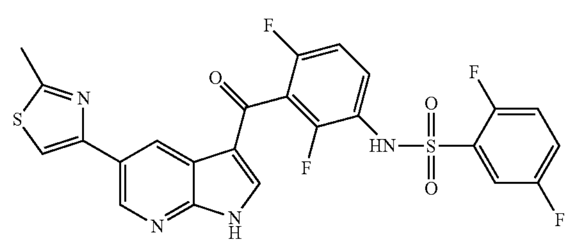 [SMILES: Cc1nc(-c2cnc3[nH]cc(C(=O)c4c(F)ccc(NS(=O)(=O)c5cc(F)ccc5F)c4F)c3c2)cs1] | N-{2,4-Difluoro-3-[5-(2-methyl-thiazol-4-yl)-1H-pyrrolo[2,3-b]pyridine-3-carbonyl]-phenyl}-2,5-difluoro-benzenesulfonamide | |
| P-1114 | 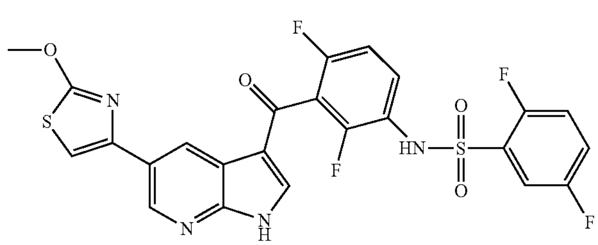 [SMILES: COc1nc(-c2cnc3[nH]cc(C(=O)c4c(F)ccc(NS(=O)(=O)c5cc(F)ccc5F)c4F)c3c2)cs1] | N-{2,4-Difluoro-3-[5-(2-methoxy-thiazol-4-yl)-1H-pyrrolo[2,3-b]pyridine-3-carbonyl]-phenyl}-2,5-difluoro-benzenesulfonamide | |

TABLE I-continued

| Comp # | Structure | Name | MS |
|---|---|---|---|
| P-1115 | 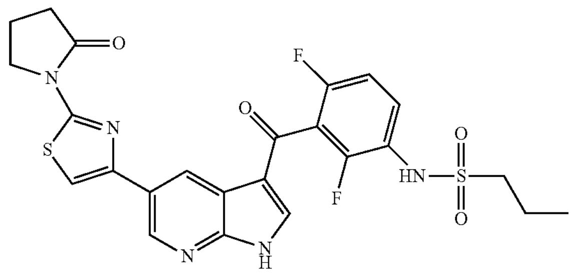 [SMILES: CCCS(=O)(=O)Nc1ccc(F)c(C(=O)c2c[nH]c3ncc(-c4csc(N5CCCC5=O)n4)cc23)c1F] | Propane-1-sulfonic acid (2,4-difluoro-3-{5-[2-(2-oxo-pyrrolidin-1-yl)-thiazol-4-yl]-1H-pyrrolo[2,3-b]pyridine-3-carbonyl}-phenyl)-amide | |
| P-1116 | 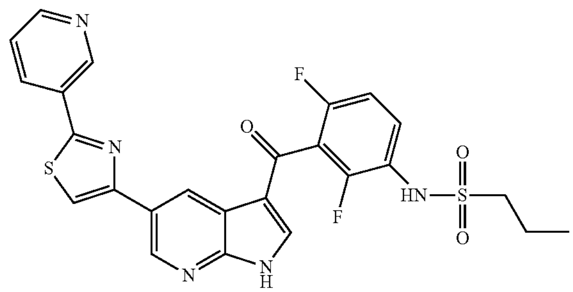 [SMILES: CCCS(=O)(=O)Nc1ccc(F)c(C(=O)c2c[nH]c3ncc(-c4csc(-c5cccnc5)n4)cc23)c1F] | Propane-1-sulfonic acid {2,4-difluoro-3-[5-(2-pyridin-3-yl-thiazol-4-yl)-1H-pyrrolo[2,3-b]pyridine-3-carbonyl]-phenyl}-amide | 540.5 |
| P-1117 | 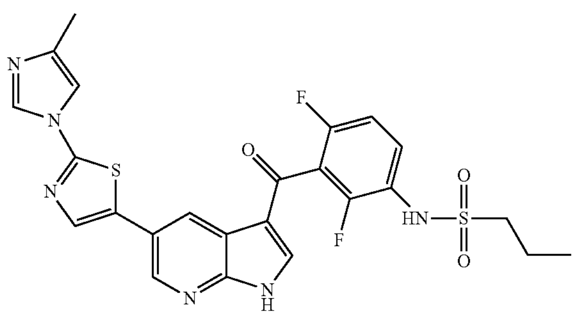 [SMILES: CCCS(=O)(=O)Nc1ccc(F)c(C(=O)c2c[nH]c3ncc(-c4cnc(-n5cnc(C)c5)s4)cc23)c1F] | Propane-1-sulfonic acid (2,4-difluoro-3-{5-[2-(4-methyl-imidazol-1-yl)-thiazol-5-yl]-1H-pyrrolo[2,3-b]pyridine-3-carbonyl}-phenyl)-amide | |
| P-1200 | 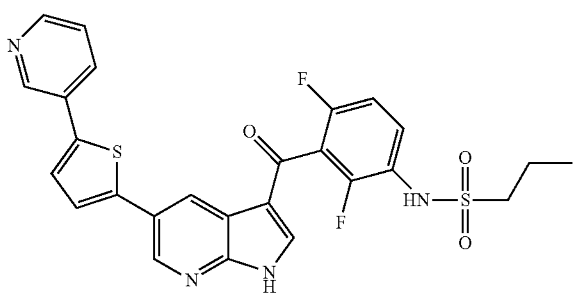 [SMILES: CCCS(=O)(=O)Nc1ccc(F)c(C(=O)c2c[nH]c3ncc(-c4ccc(-c5cccnc5)s4)cc23)c1F] | Propane-1-sulfonic acid {2,4-difluoro-3-[5-(5-pyridin-3-yl-thiophen-2-yl)-1H-pyrrolo[2,3-b]pyridine-3-carbonyl]-phenyl}-amide | 539.5 |
| P-1201 | 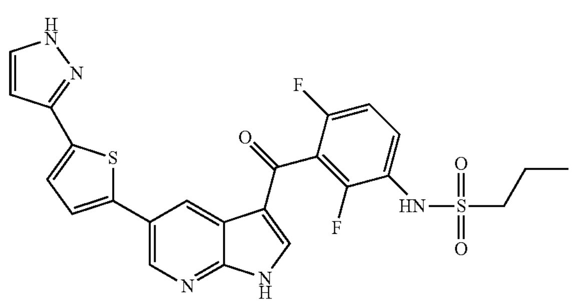 [SMILES: CCCS(=O)(=O)Nc1ccc(F)c(C(=O)c2c[nH]c3ncc(-c4ccc(-c5cc[nH]n5)s4)cc23)c1F] | Propane-1-sulfonic acid (2,4-difluoro-3-{5-[5-(1H-pyrazol-3-yl)-thiophen-2-yl]-1H-pyrrolo[2,3-b]pyridine-3-carbonyl}-phenyl)-amide | 528.0 |

TABLE I-continued

| Comp # | Name | MS |
|---|---|---|
| P-1202 | 5-{3-[2,6-Difluoro-3-(propane-1-sulfonylamino)-benzoyl]-1H-pyrrolo[2,3-b]pyridin-5-yl}-thiophene-2-sulfonic acid amide | 541.0 |
| P-1203 | Propane-1-sulfonic acid (2,4-difluoro-3-{5-[5-(5-methyl-[1,2,4]oxadiazol-3-yl)-thiophen-2-yl]-1H-pyrrolo[2,3-b]pyridine-3-carbonyl}-phenyl)-amide | 544.0 |
| P-1204 | Propane-1-sulfonic acid {2,4-difluoro-3-[5-(5-thiazol-2-yl-thiophen-2-yl)-1H-pyrrolo[2,3-b]pyridine-3-carbonyl]-phenyl}-amide | |
| P-1205 | Propane-1-sulfonic acid (2,4-difluoro-3-{5-[5-(1H-pyrazol-3-yl)-thiophen-2-yl]-1H-pyrrolo[2,3-b]pyridine-3-carbonyl}-phenyl)-amide | |
| P-1300 | N-[2,4-Difluoro-3-(5-oxazol-5-yl-1H-pyrrolo[2,3-b]pyridine-3-carbonyl)-phenyl]-2,5-difluoro-benzenesulfonamide | 517.5 |
| P-1401 | Propane-1-sulfonic acid [2,4-difluoro-3-(5-pyridin-2-yl-1H-pyrrolo[2,3-b]pyridine-3-carbonyl)-phenyl]-amide | 457.5 |

TABLE I-continued

| Comp # | Structure | Name | MS |
|---|---|---|---|
| P-1402 | 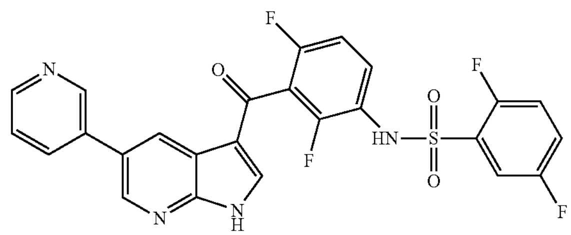 [SMILES: O=C(c1c(F)ccc(NS(=O)(=O)c2cc(F)ccc2F)c1F)c1c[nH]c2ncc(-c3cccnc3)cc12] | N-[2,4-Difluoro-3-(5-pyridin-3-yl-1H-pyrrolo[2,3-b]pyridine-3-carbonyl)-phenyl]-2,5-difluoro-benzenesulfonamide | 527.5 |
| P-1403 | 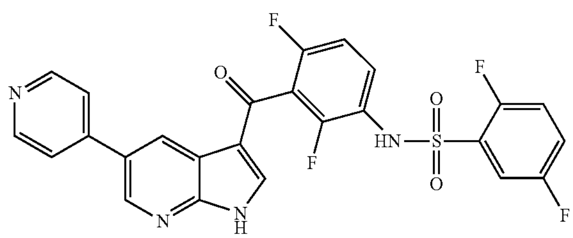 [SMILES: O=C(c1c(F)ccc(NS(=O)(=O)c2cc(F)ccc2F)c1F)c1c[nH]c2ncc(-c3ccncc3)cc12] | N-[2,4-Difluoro-3-(5-pyridin-4-yl-1H-pyrrolo[2,3-b]pyridine-3-carbonyl)-phenyl]-2,5-difluoro-benzenesulfonamide | 527.5 |
| P-1404 | 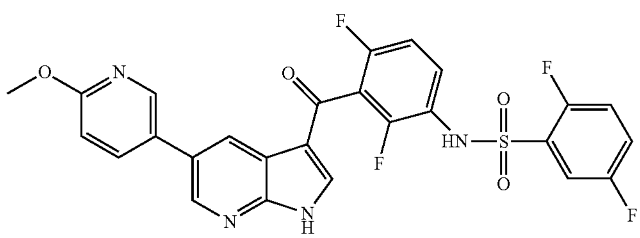 | N-{2,4-Difluoro-3-[5-(6-methoxy-pyridin-3-yl)-1H-pyrrolo[2,3-b]pyridine-3-carbonyl]-phenyl}-2,5-difluoro-benzenesulfonamide | 557.0 |
| P-1405 | 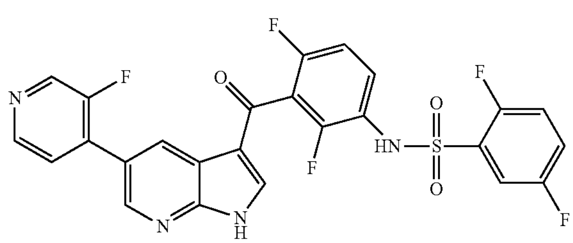 [SMILES: O=C(c1c(F)ccc(NS(=O)(=O)c2cc(F)ccc2F)c1F)c1c[nH]c2ncc(-c3ccncc3F)cc12] | N-{2,4-Difluoro-3-[5-(3-fluoro-pyridin-4-yl)-1H-pyrrolo[2,3-b]pyridine-3-carbonyl]-phenyl}-2,5-difluoro-benzenesulfonamide | 545.0 |
| P-1406 | 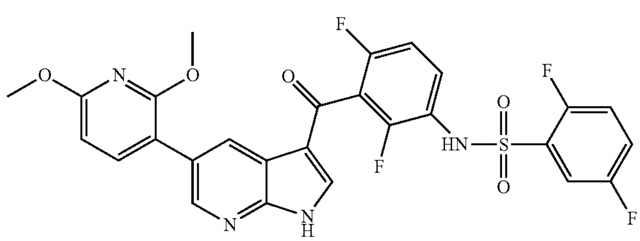 | N-{3-[5-(2,6-Dimethoxy-pyridin-3-yl)-1H-pyrrolo[2,3-b]pyridine-3-carbonyl]-2,4-difluoro-phenyl}-2,5-difluoro-benzenesulfonamide | 587.0 |
| P-1407 | 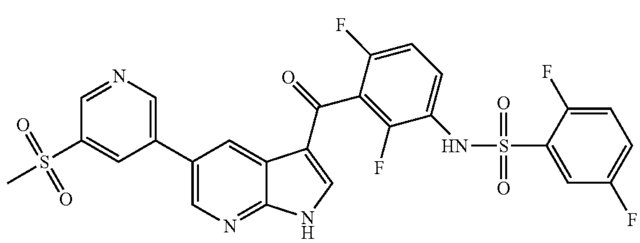 [SMILES: CS(=O)(=O)c1cncc(-c2cnc3[nH]cc(C(=O)c4c(F)ccc(NS(=O)(=O)c5cc(F)ccc5F)c4F)c3c2)c1] | N-{2,4-Difluoro-3-[5-(5-methanesulfonyl-pyridin-3-yl)-1H-pyrrolo[2,3-b]pyridine-3-carbonyl]-phenyl}-2,5-difluoro-benzenesulfonamide | 605.5 |

TABLE I-continued

| Comp # | Structure | Name | MS |
|---|---|---|---|
| P-1408 | 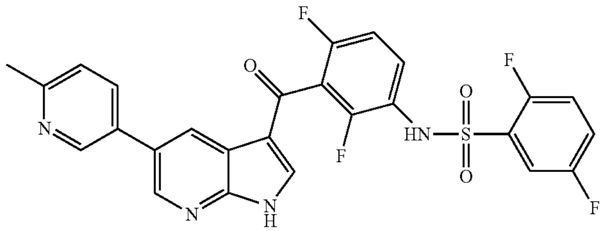 [SMILES: Cc1ccc(-c2cnc3[nH]cc(C(=O)c4c(F)ccc(NS(=O)(=O)c5cc(F)ccc5F)c4F)c3c2)cn1] | N-{2,4-Difluoro-3-[5-(6-methyl-pyridin-3-yl)-1H-pyrrolo[2,3-b]pyridine-3-carbonyl]-phenyl}-2,5-difluoro-benzenesulfonamide | 541.0 |
| P-1409 | 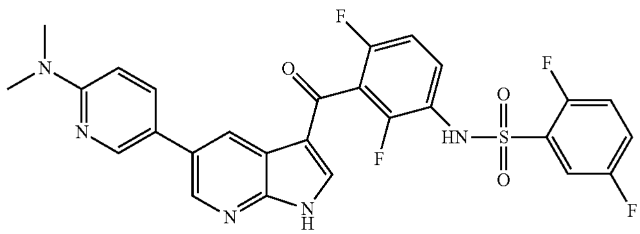 [SMILES: CN(C)c1ccc(-c2cnc3[nH]cc(C(=O)c4c(F)ccc(NS(=O)(=O)c5cc(F)ccc5F)c4F)c3c2)cn1] | N-{3-[5-(6-Dimethylamino-pyridin-3-yl)-1H-pyrrolo[2,3-b]pyridine-3-carbonyl]-2,4-difluoro-phenyl}-2,5-difluoro-benzenesulfonamide | 570.5 |
| P-1411 | 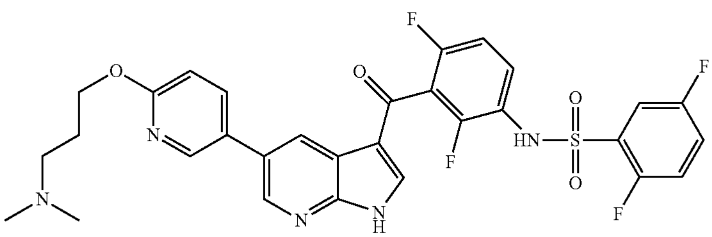 | N-(3-{5-[6-(3-Dimethylamino-propoxy)-pyridin-3-yl]-1H-pyrrolo[2,3-b]pyridine-3-carbonyl}-2,4-difluoro-phenyl)-2,5-difluoro-benzenesulfonamide | 628.0 |
| P-1500 | 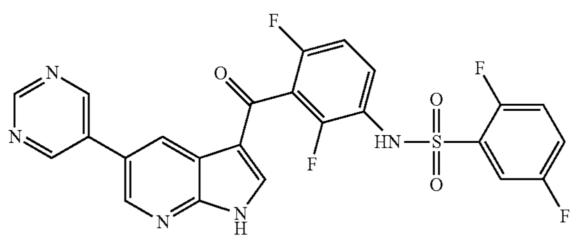 | N-[2,4-Difluoro-3-(5-pyrimidin-5-yl-1H-pyrrolo[2,3-b]pyridine-3-carbonyl)-phenyl]-2,5-difluoro-benzenesulfonamide | 528.0 |
| P-1501 | 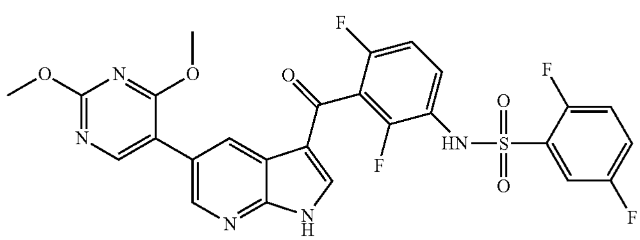 [SMILES: COc1ncc(-c2cnc3[nH]cc(C(=O)c4c(F)ccc(NS(=O)(=O)c5cc(F)ccc5F)c4F)c3c2)c(OC)n1] | N-{3-[5-(2,4-Dimethoxy-pyrimidin-5-yl)-1H-pyrrolo[2,3-b]pyridine-3-carbonyl]-2,4-difluoro-phenyl}-2,5-difluoro-benzenesulfonamide | 588.0 |
| P-1502 | 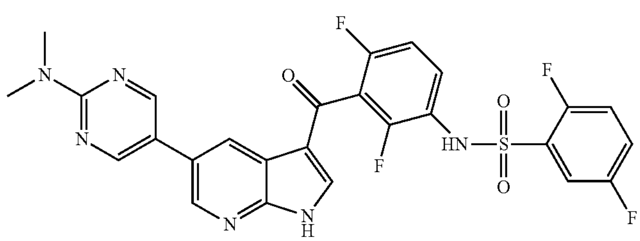 | N-{3-[5-(2-Dimethylamino-pyrimidin-5-yl)-1H-pyrrolo[2,3-b]pyridine-3-carbonyl]-2,4-difluoro-phenyl}-2,5-difluoro-benzenesulfonamide | 571.5 |

TABLE I-continued

| Comp # | Structure | Name | MS |
|---|---|---|---|
| P-1503 | 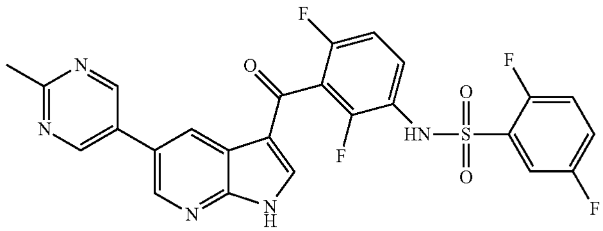 | N-{2,4-Difluoro-3-[5-(2-methyl-pyrimidin-5-yl)-1H-pyrrolo[2,3-b]pyridine-3-carbonyl]-phenyl}-2,5-difluoro-benzenesulfonamide | 542.5 |
| P-1504 | 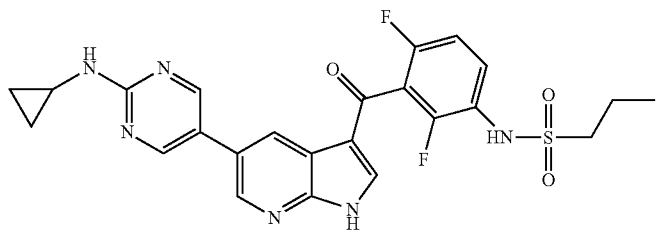 [SMILES: CCCS(=O)(=O)Nc1ccc(F)c(C(=O)c2c[nH]c3ncc(-c4cnc(NC5CC5)nc4)cc23)c1F] | Propane-1-sulfonic acid {3-[5-(2-cyclopropylamino-pyrimidin-5-yl)-1H-pyrrolo[2,3-b]pyridine-3-carbonyl]-2,4-difluoro-phenyl}-amide | 513.5 |
| P-1505 | 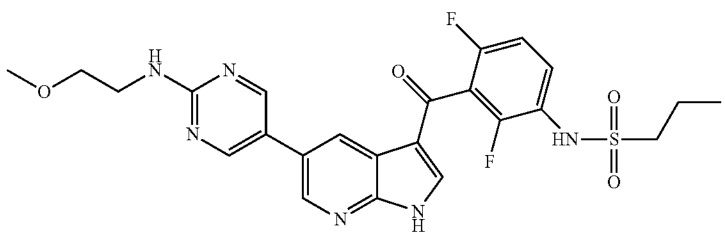 [SMILES: CCCS(=O)(=O)Nc1ccc(F)c(C(=O)c2c[nH]c3ncc(-c4cnc(NCCOC)nc4)cc23)c1F] | Propane-1-sulfonic acid (2,4-difluoro-3-{5-[2-(2-methoxy-ethylamino)-pyrimidin-5-yl]-1H-pyrrolo[2,3-b]pyridine-3-carbonyl}-phenyl)-amide | 531.5 |
| P-1506 | 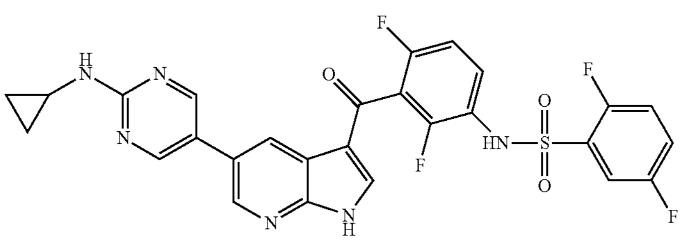 [SMILES: O=C(c1c(F)ccc(NS(=O)(=O)c2cc(F)ccc2F)c1F)c1c[nH]c2ncc(-c3cnc(NC4CC4)nc3)cc12] | N-{3-[5-(2-Cyclopropylamino-pyrimidin-5-yl)-1H-pyrrolo[2,3-b]pyridine-3-carbonyl]-2,4-difluoro-phenyl}-2,5-difluoro-benzenesulfonamide | 583.0 |
| P-1507 | 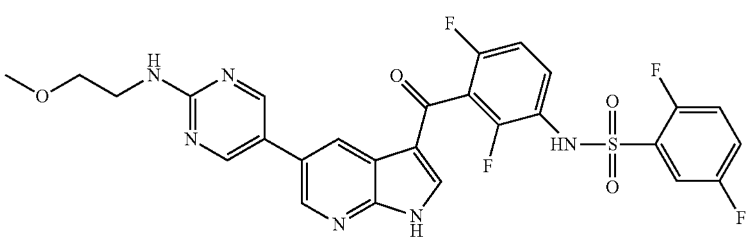 [SMILES: COCCNc1ncc(-c2cnc3[nH]cc(C(=O)c4c(F)ccc(NS(=O)(=O)c5cc(F)ccc5F)c4F)c3c2)cn1] | N-(2,4-Difluoro-3-{5-[2-(2-methoxy-ethylamino)-pyrimidin-5-yl]-1H-pyrrolo[2,3-b]pyridine-3-carbonyl}-phenyl)-2,5-difluoro-benzenesulfonamide | 601.5 |
| P-1508 | 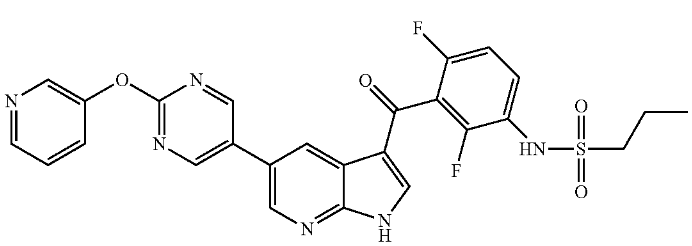 [SMILES: CCCS(=O)(=O)Nc1ccc(F)c(C(=O)c2c[nH]c3ncc(-c4cnc(Oc5cccnc5)nc4)cc23)c1F] | Propane-1-sulfonic acid (2,4-difluoro-3-{5-[2-(pyridin-3-yloxy)-pyrimidin-5-yl]-1H-pyrrolo[2,3-b]pyridine-3-carbonyl}-phenyl)-amide | |

| Comp # | Structure | Name | MS |
|---|---|---|---|
| P-1509 | 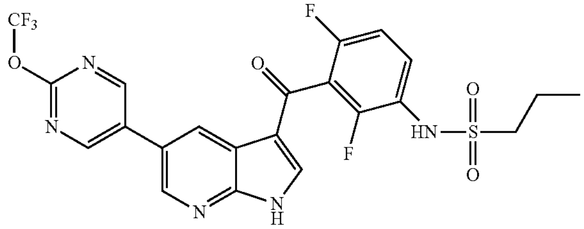 [SMILES: CCCS(=O)(=O)Nc1ccc(F)c(C(=O)c2c[nH]c3ncc(-c4cnc(OC(F)(F)F)nc4)cc23)c1F] | Propane-1-sulfonic acid {2,4-difluoro-3-[5-(2-trifluoromethoxy-pyrimidin-5-yl)-1H-pyrrolo[2,3-b]pyridine-3-carbonyl]-phenyl}-amide | |
| P-1510 | 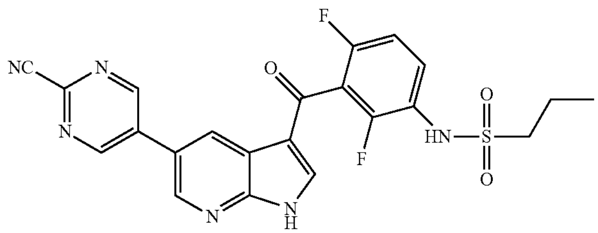 [SMILES: CCCS(=O)(=O)Nc1ccc(F)c(C(=O)c2c[nH]c3ncc(-c4cnc(C#N)nc4)cc23)c1F] | Propane-1-sulfonic acid {3-[5-(2-cyano-pyrimidin-5-yl)-1H-pyrrolo[2,3-b]pyridine-3-carbonyl]-2,4-difluoro-phenyl}-amide | |
| P-1511 | 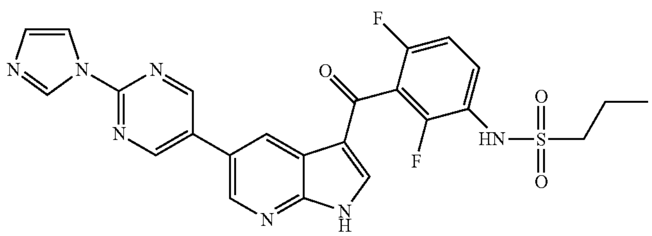 [SMILES: CCCS(=O)(=O)Nc1ccc(F)c(C(=O)c2c[nH]c3ncc(-c4cnc(-n5ccnc5)nc4)cc23)c1F] | Propane-1-sulfonic acid {2,4-difluoro-3-[5-(2-imidazol-1-yl-pyrimidin-5-yl)-1H-pyrrolo[2,3-b]pyridine-3-carbonyl]-phenyl}-amide | 524.5 |
| P-1512 | 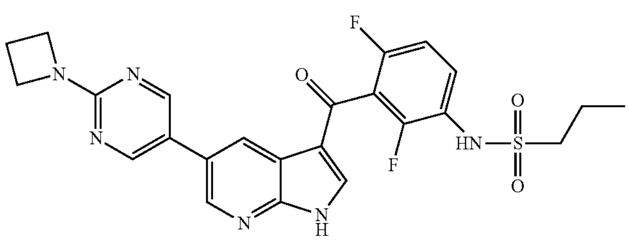 [SMILES: CCCS(=O)(=O)Nc1ccc(F)c(C(=O)c2c[nH]c3ncc(-c4cnc(N5CCC5)nc4)cc23)c1F] | Propane-1-sulfonic acid {3-[5-(2-azetidin-1-yl-pyrimidin-5-yl)-1H-pyrrolo[2,3-b]pyridine-3-carbonyl]-2,4-difluoro-phenyl}-amide | 513.5 |
| P-1513 | 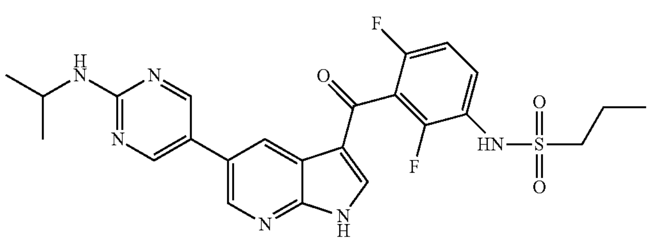 [SMILES: CCCS(=O)(=O)Nc1ccc(F)c(C(=O)c2c[nH]c3ncc(-c4cnc(NC(C)C)nc4)cc23)c1F] | Propane-1-sulfonic acid {2,4-difluoro-3-[5-(2-isopropylamino-pyrimidin-5-yl)-1H-pyrrolo[2,3-b]pyridine-3-carbonyl]-phenyl}-amide | |
| P-1514 | 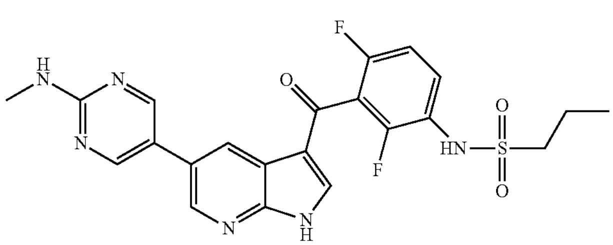 [SMILES: CCCS(=O)(=O)Nc1ccc(F)c(C(=O)c2c[nH]c3ncc(-c4cnc(NC)nc4)cc23)c1F] | Propane-1-sulfonic acid {2,4-difluoro-3-[5-(2-methylamino-pyrimidin-5-yl)-1H-pyrrolo[2,3-b]pyridine-3-carbonyl]-phenyl}-amide | 487.5 |

TABLE I-continued

| Comp # | Structure | Name | MS |
|---|---|---|---|
| P-1515 | 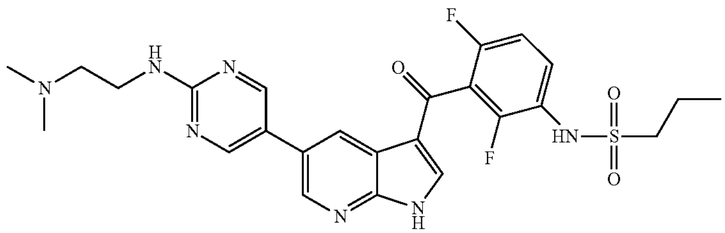 [SMILES: CCCS(=O)(=O)Nc1ccc(F)c(C(=O)c2c[nH]c3ncc(-c4cnc(NCCN(C)C)nc4)cc23)c1F] | Propane-1-sulfonic acid (3-{5-[2-(2-dimethylamino-ethylamino)-pyrimidin-5-yl]-1H-pyrrolo[2,3-b]pyridine-3-carbonyl}-2,4-difluoro-phenyl)-amide | 544.5 |
| P-1516 | 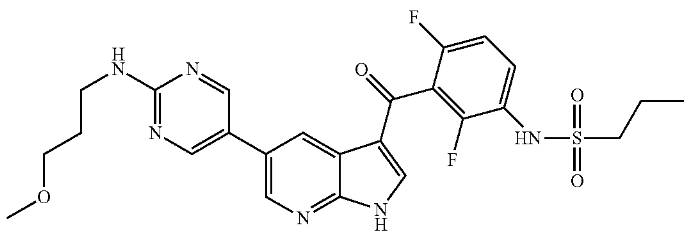 [SMILES: CCCS(=O)(=O)Nc1ccc(F)c(C(=O)c2c[nH]c3ncc(-c4cnc(NCCCOC)nc4)cc23)c1F] | Propane-1-sulfonic acid (2,4-difluoro-3-{5-[2-(3-methoxy-propylamino)-pyrimidin-5-yl]-1H-pyrrolo[2,3-b]pyridine-3-carbonyl}-phenyl)-amide | 545.5 |
| P-1517 | 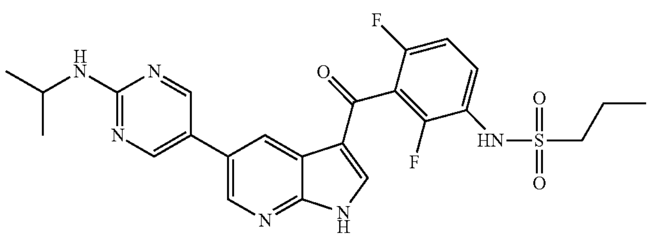 [SMILES: CCCS(=O)(=O)Nc1ccc(F)c(C(=O)c2c[nH]c3ncc(-c4cnc(NC(C)C)nc4)cc23)c1F] | Propane-1-sulfonic acid {2,4-difluoro-3-[5-(2-isopropylamino-pyrimidin-5-yl)-1H-pyrrolo[2,3-b]pyridine-3-carbonyl]-phenyl}-amide | 515.5 |
| P-1518 | 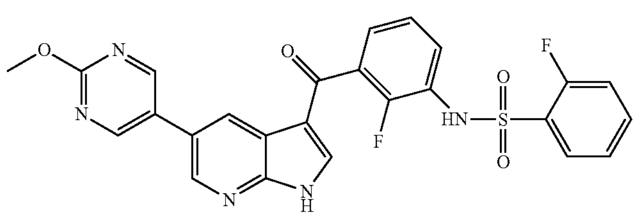 [SMILES: COc1ncc(-c2cnc3[nH]cc(C(=O)c4cccc(NS(=O)(=O)c5ccccc5F)c4F)c3c2)cn1] | 2-Fluoro-N-{2-fluoro-3-[5-(2-methoxy-pyrimidin-5-yl)-1H-pyrrolo[2,3-b]pyridine-3-carbonyl]-phenyl}-benzenesulfonamide | 521.95 |
| P-1519 | 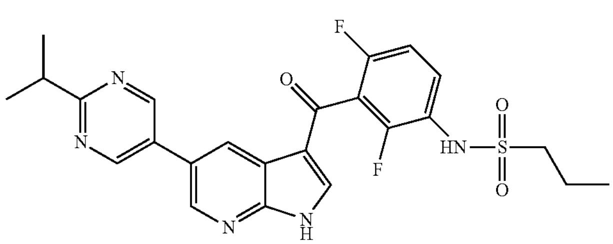 [SMILES: CCCS(=O)(=O)Nc1ccc(F)c(C(=O)c2c[nH]c3ncc(-c4cnc(C(C)C)nc4)cc23)c1F] | Propane-1-sulfonic acid {2,4-difluoro-3-[5-(2-isopropyl-pyrimidin-5-yl)-1H-pyrrolo[2,3-b]pyridine-3-carbonyl]-phenyl}-amide | 500.0 |
| P-1520 | 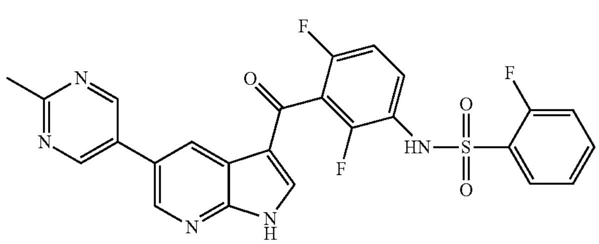 [SMILES: Cc1ncc(-c2cnc3[nH]cc(C(=O)c4c(F)ccc(NS(=O)(=O)c5ccccc5F)c4F)c3c2)cn1] | N-{2,4-Difluoro-3-[5-(2-methyl-pyrimidin-5-yl)-1H-pyrrolo[2,3-b]pyridine-3-carbonyl]-phenyl}-2-fluoro-benzenesulfonamide | |

TABLE I-continued

| Comp # | Name | MS |
|---|---|---|
| P-1521 | N-{2,4-Difluoro-3-[5-(2-isopropyl-pyrimidin-5-yl)-1H-pyrrolo[2,3-b]pyridine-3-carbonyl]-phenyl}-2,5-difluoro-benzenesulfonamide | 570.0 |
| P-1600 | Propane-1-sulfonic acid (2,4-difluoro-3-{5-[5-(2-oxo-2H-pyridin-1-yl)-pyrazin-2-yl]-1H-pyrrolo[2,3-b]pyridine-3-carbonyl}-phenyl)-amide | 551.5 |
| P-1601 | Propane-1-sulfonic acid {2,4-difluoro-3-[5-(5-pyrazol-1-yl-pyrazin-2-yl)-1H-pyrrolo[2,3-b]pyridine-3-carbonyl]-phenyl}-amide | 524.5 |
| P-1602 | Propane-1-sulfonic acid {2,4-difluoro-3-[5-(5-imidazol-1-yl-pyrazin-2-yl)-1H-pyrrolo[2,3-b]pyridine-3-carbonyl]-phenyl}-amide | 524.5 |
| P-1603 | Propane-1-sulfonic acid {3-[5-(5-amino-pyrazin-2-yl)-1H-pyrrolo[2,3-b]pyridine-3-carbonyl]-2,4-difluoro-phenyl}-amide | 473.0 |
| P-1700 | 2-Chloro-5-{3-[2,6-difluoro-3-(propane-1-sulfonylamino)-benzoyl]-1H-pyrrolo[2,3-b]pyridin-5-yl}-benzamide | 532.9 |

TABLE I-continued

| Comp # | Structure | Name | MS |
|---|---|---|---|
| P-1701 | 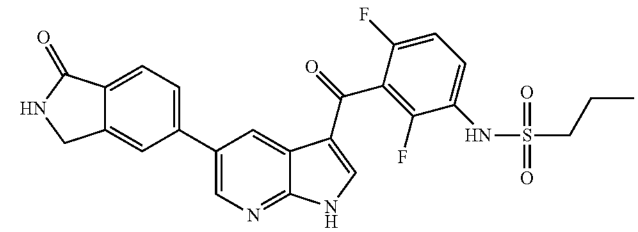 [SMILES: CCCS(=O)(=O)Nc1ccc(F)c(C(=O)c2c[nH]c3ncc(-c4ccc5c(c4)CNC5=O)cc23)c1F] | Propane-1-sulfonic acid {2,4-difluoro-3-[5-(1-oxo-2,3-dihydro-1H-isoindol-5-yl)-1H-pyrrolo[2,3-b]pyridine-3-carbonyl]-phenyl}-amide | 511.5 |
| P-1702 | 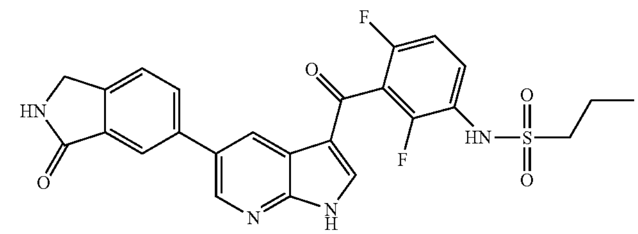 [SMILES: CCCS(=O)(=O)Nc1ccc(F)c(C(=O)c2c[nH]c3ncc(-c4ccc5c(c4)C(=O)NC5)cc23)c1F] | Propane-1-sulfonic acid {2,4-difluoro-3-[5-(3-oxo-2,3-dihydro-1H-isoindol-5-yl)-1H-pyrrolo[2,3-b]pyridine-3-carbonyl]-phenyl}-amide | 511.5 |
| P-1703 | 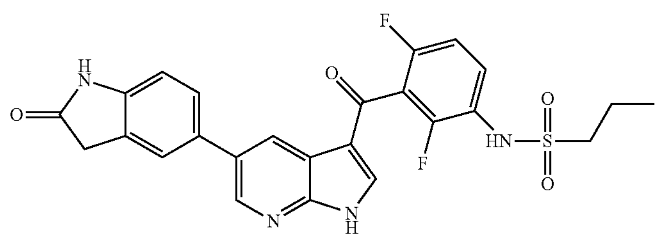 [SMILES: CCCS(=O)(=O)Nc1ccc(F)c(C(=O)c2c[nH]c3ncc(-c4ccc5c(c4)CC(=O)N5)cc23)c1F] | Propane-1-sulfonic acid {2,4-difluoro-3-[5-(2-oxo-2,3-dihydro-1H-indol-5-yl)-1H-pyrrolo[2,3-b]pyridine-3-carbonyl]-phenyl}-amide | 511.5 |
| P-1704 | 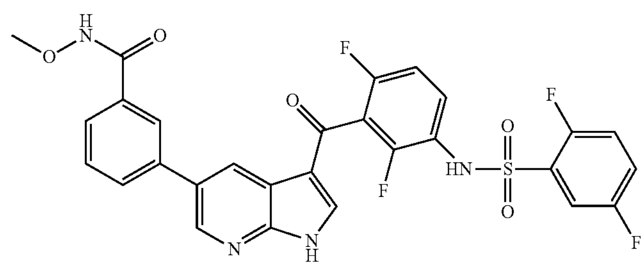 [SMILES: CONC(=O)c1cccc(-c2cnc3[nH]cc(C(=O)c4c(F)ccc(NS(=O)(=O)c5cc(F)ccc5F)c4F)c3c2)c1] | 3-{3-[3-(2,5-Difluoro-benzenesulfonylamino)-2,6-difluoro-benzoyl]-1H-pyrrolo[2,3-b]pyridin-5-yl}-N-methoxy-benzamide | 599.5 |
| P-1705 | 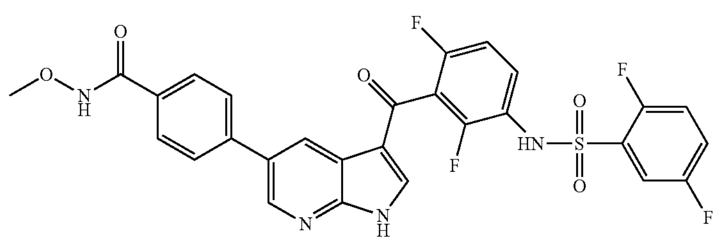 [SMILES: CONC(=O)c1ccc(-c2cnc3[nH]cc(C(=O)c4c(F)ccc(NS(=O)(=O)c5cc(F)ccc5F)c4F)c3c2)cc1] | 4-{3-[3-(2,5-Difluoro-benzenesulfonylamino)-2,6-difluoro-benzoyl]-1H-pyrrolo[2,3-b]pyridin-5-yl}-N-methoxy-benzamide | 599.5 |
| P-1706 | 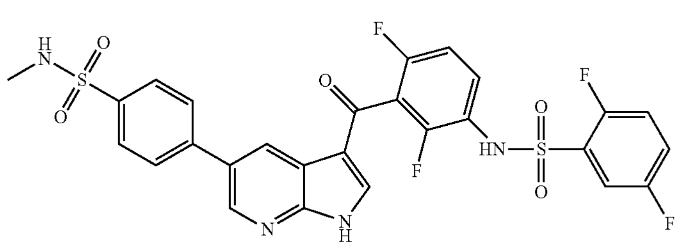 [SMILES: CNS(=O)(=O)c1ccc(-c2cnc3[nH]cc(C(=O)c4c(F)ccc(NS(=O)(=O)c5cc(F)ccc5F)c4F)c3c2)cc1] | N-{2,4-Difluoro-3-[5-(4-methylsulfamoyl-phenyl)-1H-pyrrolo[2,3-b]pyridine-3-carbonyl]-phenyl}-2,5-difluoro-benzenesulfonamide | 619.5 |

TABLE I-continued

| Comp # | Structure | Name | MS |
|---|---|---|---|
| P-1707 | 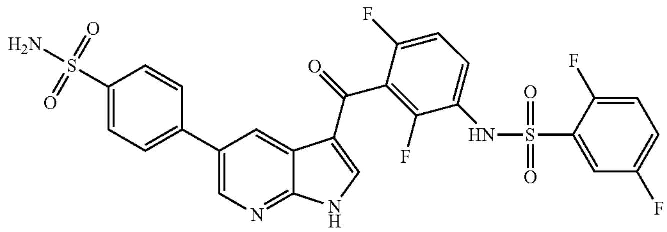 [SMILES: NS(=O)(=O)c1ccc(-c2cnc3[nH]cc(C(=O)c4c(F)ccc(NS(=O)(=O)c5cc(F)ccc5F)c4F)c3c2)cc1] | N-{2,4-Difluoro-3-[5-(4-sulfamoyl-phenyl)-1H-pyrrolo[2,3-b]pyridine-3-carbonyl]-phenyl}-2,5-difluoro-benzenesulfonamide | 605.5 |
| P-1901 | 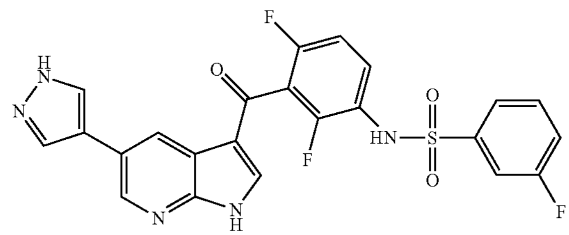 [SMILES: O=C(c1c(F)ccc(NS(=O)(=O)c2cccc(F)c2)c1F)c1c[nH]c2ncc(-c3cn[nH]c3)cc12] | N-[2,4-difluoro-3-[5-(1H-pyrazol-4-yl)-1H-pyrrolo[2,3-b]pyridine-3-carbonyl]phenyl]-3-fluoro-benzenesulfonamide | |
| P-1902 | 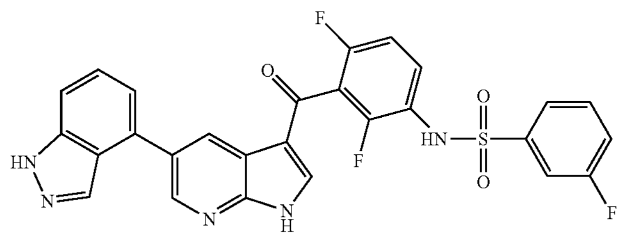 [SMILES: O=C(c1c(F)ccc(NS(=O)(=O)c2cccc(F)c2)c1F)c1c[nH]c2ncc(-c3cccc4[nH]ncc34)cc12] | N-[2,4-difluoro-3-[5-(1H-indazol-4-yl)-1H-pyrrolo[2,3-b]pyridine-3-carbonyl]phenyl]-3-fluoro-benzenesulfonamide | |
| P-1903 | 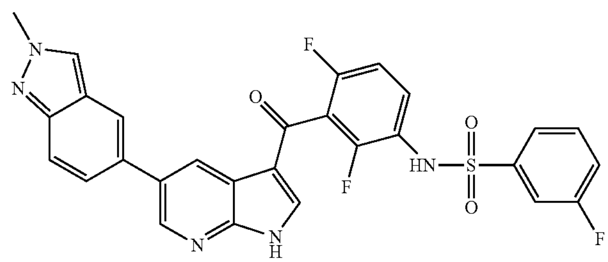 [SMILES: Cn1cc2cc(-c3cnc4[nH]cc(C(=O)c5c(F)ccc(NS(=O)(=O)c6cccc(F)c6)c5F)c4c3)ccc2n1] | N-[2,4-difluoro-3-[5-(2-methylindazol-5-yl)-1H-pyrrolo[2,3-b]pyridine-3-carbonyl]phenyl]-3-fluoro-benzenesulfonamide | |
| P-1904 | 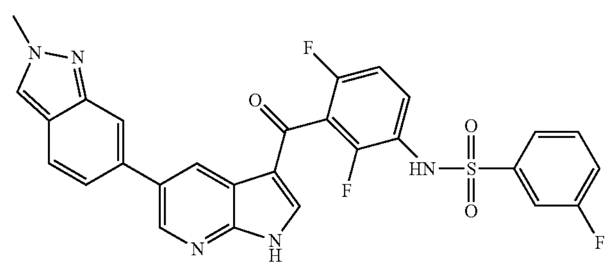 [SMILES: Cn1cc2ccc(-c3cnc4[nH]cc(C(=O)c5c(F)ccc(NS(=O)(=O)c6cccc(F)c6)c5F)c4c3)cc2n1] | N-[2,4-difluoro-3-[5-(2-methylindazol-6-yl)-1H-pyrrolo[2,3-b]pyridine-3-carbonyl]phenyl]-3-fluoro-benzenesulfonamide | |
| P-1905 | 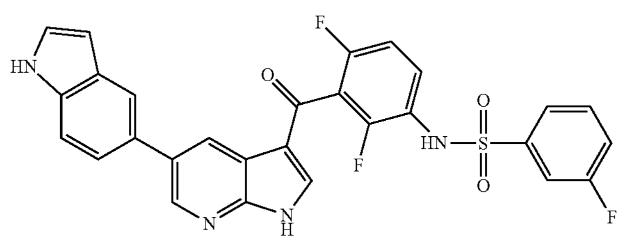 [SMILES: O=C(c1c(F)ccc(NS(=O)(=O)c2cccc(F)c2)c1F)c1c[nH]c2ncc(-c3ccc4[nH]ccc4c3)cc12] | N-[2,4-difluoro-3-[5-(1H-indol-5-yl)-1H-pyrrolo[2,3-b]pyridine-3-carbonyl]phenyl]-3-fluoro-benzenesulfonamide | |

TABLE I-continued

| Comp # | Structure | Name | MS |
|---|---|---|---|
| P-1906 | 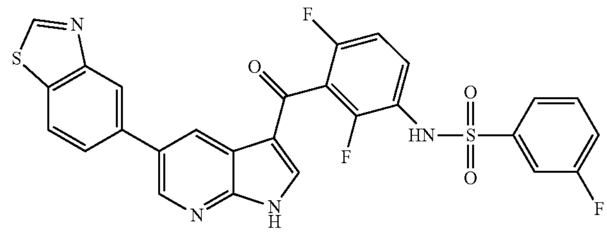 [SMILES: O=C(c1c(F)ccc(NS(=O)(=O)c2cccc(F)c2)c1F)c1c[nH]c2ncc(-c3ccc4scnc4c3)cc12] | N-[3-[5-(1,3-benzothiazol-5-yl)-1H-pyrrolo[2,3-b]pyridine-3-carbonyl]-2,4-difluoro-phenyl]-3-fluoro-benzenesulfonamide | |
| P-1907 | 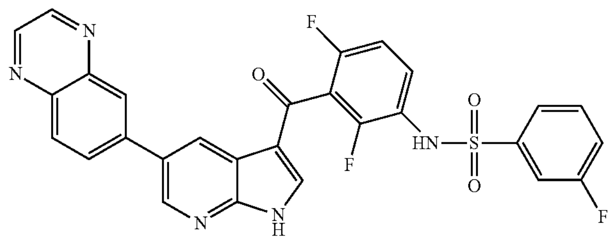 [SMILES: O=C(c1c(F)ccc(NS(=O)(=O)c2cccc(F)c2)c1F)c1c[nH]c2ncc(-c3ccc4nccnc4c3)cc12] | N-[2,4-difluoro-3-(5-quinoxalin-6-yl-1H-pyrrolo[2,3-b]pyridine-3-carbonyl)phenyl]-3-fluoro-benzenesulfonamide | |
| P-1908 | 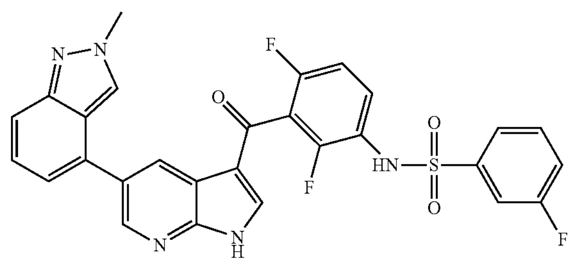 [SMILES: Cn1cc2c(-c3cnc4[nH]cc(C(=O)c5c(F)ccc(NS(=O)(=O)c6cccc(F)c6)c5F)c4c3)cccc2n1] | N-[2,4-difluoro-3-[5-(2-methylindazol-4-yl)-1H-pyrrolo[2,3-b]pyridine-3-carbonyl]phenyl]-3-fluoro-benzenesulfonamide | |
| P-1909 | 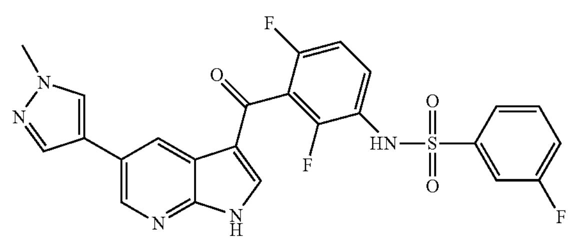 [SMILES: Cn1cc(-c2cnc3[nH]cc(C(=O)c4c(F)ccc(NS(=O)(=O)c5cccc(F)c5)c4F)c3c2)cn1] | N-[2,4-difluoro-3-[5-(1-methylpyrazol-4-yl)-1H-pyrrolo[2,3-b]pyridine-3-carbonyl]phenyl]-3-fluoro-benzenesulfonamide | |
| P-1910 | 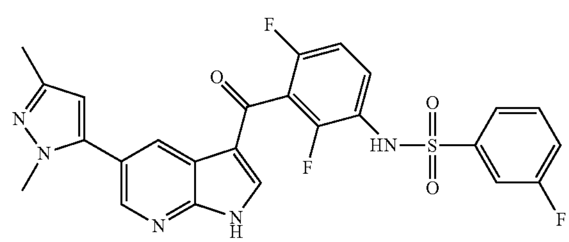 [SMILES: Cc1cc(-c2cnc3[nH]cc(C(=O)c4c(F)ccc(NS(=O)(=O)c5cccc(F)c5)c4F)c3c2)n(C)n1] | N-[3-[5-(2,5-dimethylpyrazol-3-yl)-1H-pyrrolo[2,3-b]pyridine-3-carbonyl]-2,4-difluoro-phenyl]-3-fluoro-benzenesulfonamide | |
| P-1911 | 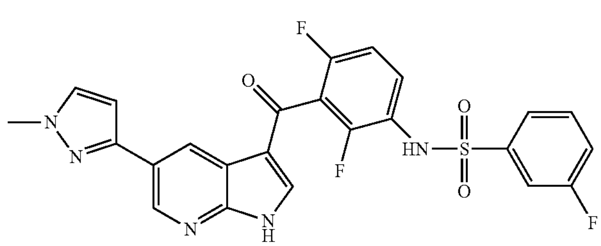 [SMILES: Cn1ccc(-c2cnc3[nH]cc(C(=O)c4c(F)ccc(NS(=O)(=O)c5cccc(F)c5)c4F)c3c2)n1] | N-[2,4-difluoro-3-[5-(1-methylpyrazol-3-yl)-1H-pyrrolo[2,3-b]pyridine-3-carbonyl]phenyl]-3-fluoro-benzenesulfonamide | |

TABLE I-continued

| Comp # | Structure | Name | MS |
|---|---|---|---|
| P-1912 | 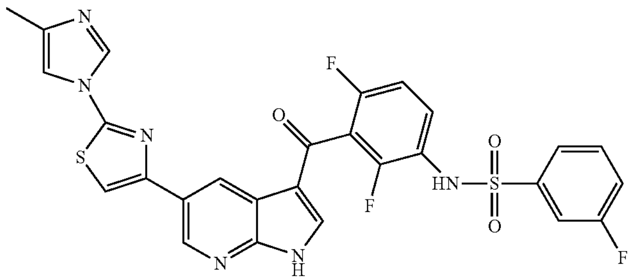 [SMILES: Cc1cn(-c2nc(-c3cnc4[nH]cc(C(=O)c5c(F)ccc(NS(=O)(=O)c6cccc(F)c6)c5F)c4c3)cs2)cn1] | N-[2,4-difluoro-3-[5-[2-(4-methylimidazol-1-yl)thiazol-4-yl]-1H-pyrrolo[2,3-b]pyridine-3-carbonyl]phenyl]-3-fluoro-benzenesulfonamide | |
| P-1913 | 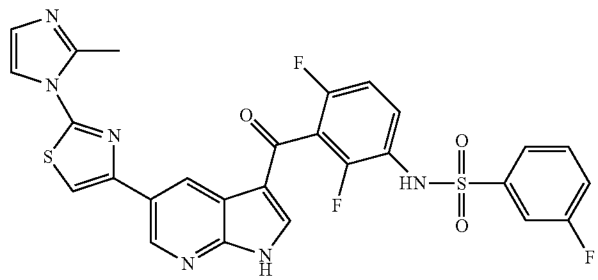 [SMILES: Cc1nccn1-c1nc(-c2cnc3[nH]cc(C(=O)c4c(F)ccc(NS(=O)(=O)c5cccc(F)c5)c4F)c3c2)cs1] | N-[2,4-difluoro-3-[5-[2-(2-methylimidazol-1-yl)thiazol-4-yl]-1H-pyrrolo[2,3-b]pyridine-3-carbonyl]phenyl]-3-fluoro-benzenesulfonamide | |
| P-1914 | 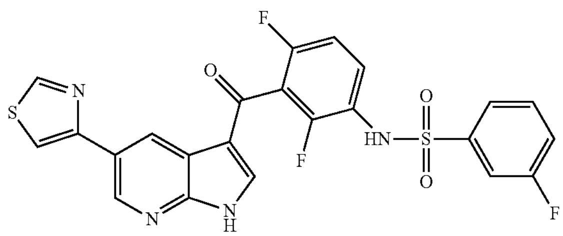 [SMILES: O=C(c1c(F)ccc(NS(=O)(=O)c2cccc(F)c2)c1F)c1c[nH]c2ncc(-c3cscn3)cc12] | N-[2,4-difluoro-3-(5-thiazol-4-yl-1H-pyrrolo[2,3-b]pyridine-3-carbonyl)phenyl]-3-fluoro-benzenesulfonamide | |
| P-1915 | 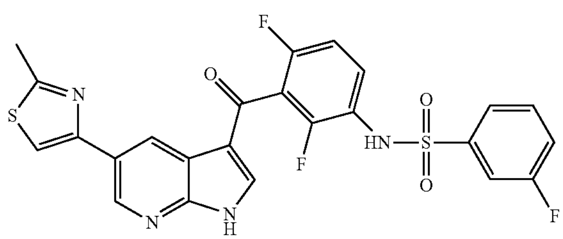 [SMILES: Cc1nc(-c2cnc3[nH]cc(C(=O)c4c(F)ccc(NS(=O)(=O)c5cccc(F)c5)c4F)c3c2)cs1] | N-[2,4-difluoro-3-[5-(2-methylthiazol-4-yl)-1H-pyrrolo[2,3-b]pyridine-3-carbonyl]phenyl]-3-fluoro-benzenesulfonamide | |
| P-1916 | 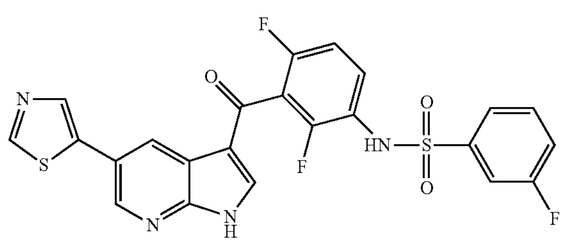 [SMILES: O=C(c1c(F)ccc(NS(=O)(=O)c2cccc(F)c2)c1F)c1c[nH]c2ncc(-c3cncs3)cc12] | N-[2,4-difluoro-3-(5-thiazol-5-yl-1H-pyrrolo[2,3-b]pyridine-3-carbonyl)phenyl]-3-fluoro-benzenesulfonamide | |
| P-1917 | 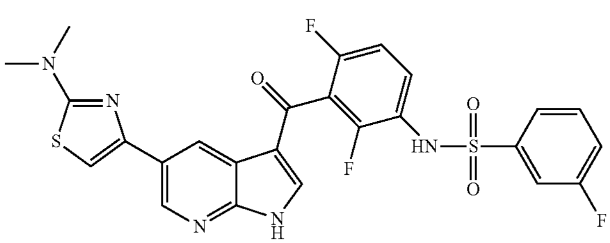 [SMILES: CN(C)c1nc(-c2cnc3[nH]cc(C(=O)c4c(F)ccc(NS(=O)(=O)c5cccc(F)c5)c4F)c3c2)cs1] | N-[3-[5-(2-dimethylaminothiazol-4-yl)-1H-pyrrolo[2,3-b]pyridine-3-carbonyl]-2,4-difluoro-phenyl]-3-fluoro-benzenesulfonamide | |

TABLE I-continued

| Comp # | Structure | Name | MS |
|---|---|---|---|
| P-1918 | 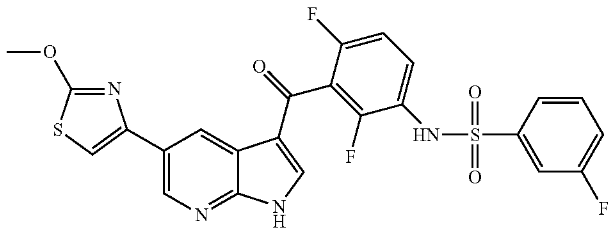 [SMILES: COc1nc(-c2cnc3[nH]cc(C(=O)c4c(F)ccc(NS(=O)(=O)c5cccc(F)c5)c4F)c3c2)cs1] | N-[2,4-difluoro-3-[5-(2-methoxythiazol-4-yl)-1H-pyrrolo[2,3-b]pyridine-3-carbonyl]phenyl]-3-fluoro-benzenesulfonamide | |
| P-1919 | 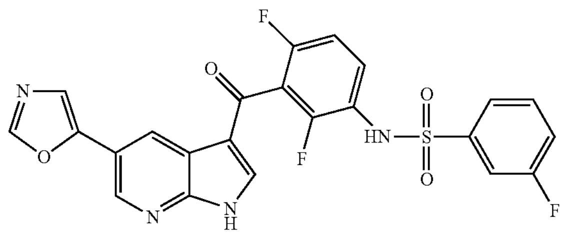 | N-[2,4-difluoro-3-(5-oxazol-5-yl-1H-pyrrolo[2,3-b]pyridine-3-carbonyl)phenyl]-3-fluoro-benzenesulfonamide | |
| P-1920 | 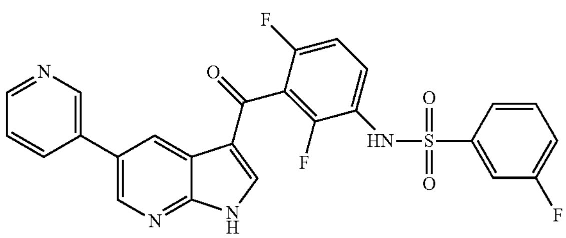 [SMILES: O=C(c1c(F)ccc(NS(=O)(=O)c2cccc(F)c2)c1F)c1c[nH]c2ncc(-c3cccnc3)cc12] | N-[2,4-difluoro-3-[5-(3-pyridyl)-1H-pyrrolo[2,3-b]pyridine-3-carbonyl]phenyl]-3-fluoro-benzenesulfonamide | |
| P-1921 | 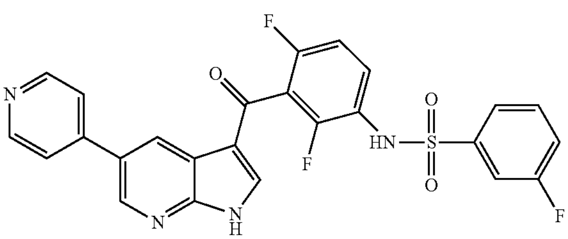 | N-[2,4-difluoro-3-[5-(4-pyridyl)-1H-pyrrolo[2,3-b]pyridine-3-carbonyl]phenyl]-3-fluoro-benzenesulfonamide | |
| P-1922 | 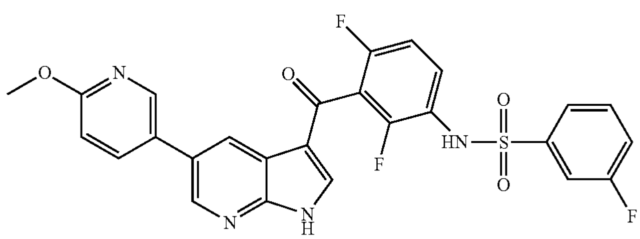 [SMILES: COc1ccc(-c2cnc3[nH]cc(C(=O)c4c(F)ccc(NS(=O)(=O)c5cccc(F)c5)c4F)c3c2)cn1] | N-[2,4-difluoro-3-[5-(6-methoxy-3-pyridyl)-1H-pyrrolo[2,3-b]pyridine-3-carbonyl]phenyl]-3-fluoro-benzenesulfonamide | |
| P-1923 | 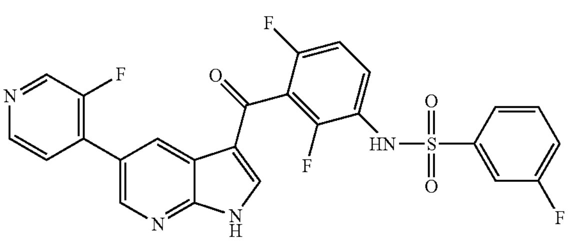 [SMILES: O=C(c1c(F)ccc(NS(=O)(=O)c2cccc(F)c2)c1F)c1c[nH]c2ncc(-c3ccncc3F)cc12] | N-[2,4-difluoro-3-[5-(3-fluoro-4-pyridyl)-1H-pyrrolo[2,3-b]pyridine-3-carbonyl]phenyl]-3-fluoro-benzenesulfonamide | |

TABLE I-continued

| Comp # | Structure | Name | MS |
|---|---|---|---|
| P-1924 | 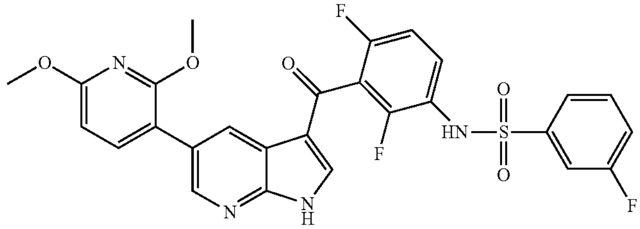 | N-[3-[5-(2,6-dimethoxy-3-pyridyl)-1H-pyrrolo[2,3-b]pyridine-3-carbonyl]-2,4-difluoro-phenyl]-3-fluoro-benzenesulfonamide | |
| P-1925 | 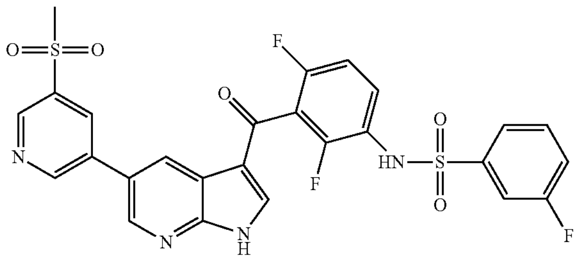 [SMILES: CS(=O)(=O)c1cncc(-c2cnc3[nH]cc(C(=O)c4c(F)ccc(NS(=O)(=O)c5cccc(F)c5)c4F)c3c2)c1] | N-[2,4-difluoro-3-[5-(5-methylsulfonyl-3-pyridyl)-1H-pyrrolo[2,3-b]pyridine-3-carbonyl]phenyl]-3-fluoro-benzenesulfonamide | |
| P-1926 | 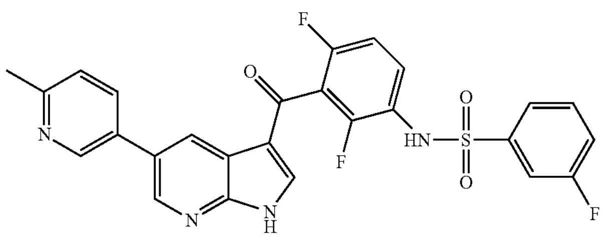 [SMILES: Cc1ccc(-c2cnc3[nH]cc(C(=O)c4c(F)ccc(NS(=O)(=O)c5cccc(F)c5)c4F)c3c2)cn1] | N-[2,4-difluoro-3-[5-(6-methyl-3-pyridyl)-1H-pyrrolo[2,3-b]pyridine-3-carbonyl]phenyl]-3-fluoro-benzenesulfonamide | |
| P-1927 | 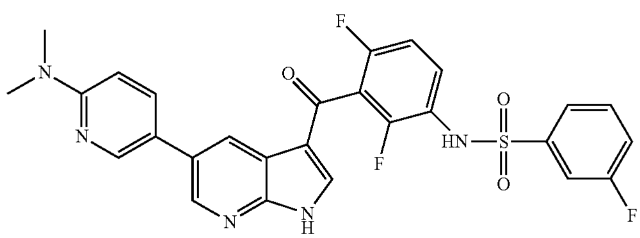 | N-[3-[5-(6-dimethylamino-3-pyridyl)-1H-pyrrolo[2,3-b]pyridine-3-carbonyl]-2,4-difluoro-phenyl]-3-fluoro-benzenesulfonamide | |
| P-1928 | 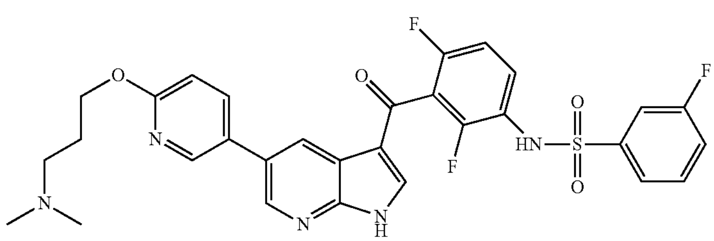 [SMILES: CN(C)CCCOc1ccc(-c2cnc3[nH]cc(C(=O)c4c(F)ccc(NS(=O)(=O)c5cccc(F)c5)c4F)c3c2)cn1] | N-[3-[5-[6-(3-dimethylaminopropoxy)-3-pyridyl]-1H-pyrrolo[2,3-b]pyridine-3-carbonyl]-2,4-difluoro-phenyl]-3-fluoro-benzenesulfonamide | |
| P-1929 | 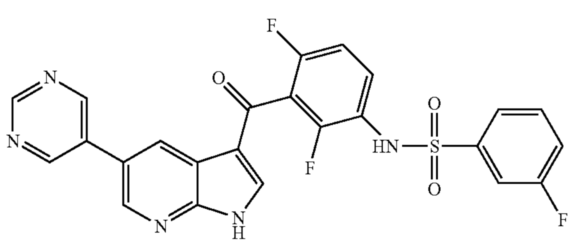 [SMILES: O=C(c1c(F)ccc(NS(=O)(=O)c2cccc(F)c2)c1F)c1c[nH]c2ncc(-c3cncnc3)cc12] | N-[2,4-difluoro-3-(5-pyrimidin-5-yl-1H-pyrrolo[2,3-b]pyridine-3-carbonyl)phenyl]-3-fluoro-benzenesulfonamide | |

TABLE I-continued

| Comp # | Structure | Name | MS |
|---|---|---|---|
| P-1930 | 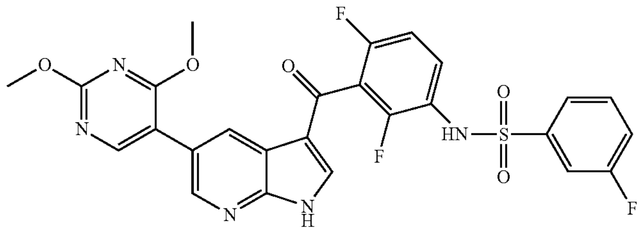 [SMILES: COc1ncc(-c2cnc3[nH]cc(C(=O)c4c(F)ccc(NS(=O)(=O)c5cccc(F)c5)c4F)c3c2)c(OC)n1] | N-[3-[5-(2,4-dimethoxypyrimidin-5-yl)-1H-pyrrolo[2,3-b]pyridine-3-carbonyl]-2,4-difluoro-phenyl]-3-fluoro-benzenesulfonamide | |
| P-1931 | 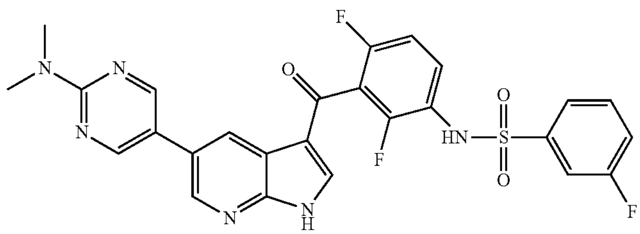 | N-[3-[5-(2-dimethylaminopyrimidin-5-yl)-1H-pyrrolo[2,3-b]pyridine-3-carbonyl]-2,4-difluoro-phenyl]-3-fluoro-benzenesulfonamide | |
| P-1932 | 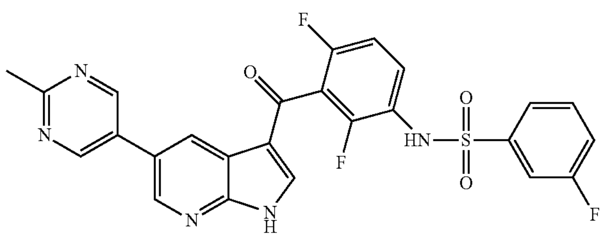 | N-[2,4-difluoro-3-[5-(2-methylpyrimidin-5-yl)-1H-pyrrolo[2,3-b]pyridine-3-carbonyl]phenyl]-3-fluoro-benzenesulfonamide | |
| P-1933 | 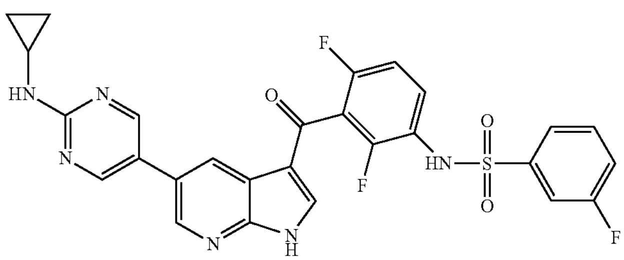 [SMILES: O=C(c1c(F)ccc(NS(=O)(=O)c2cccc(F)c2)c1F)c1c[nH]c2ncc(-c3cnc(NC4CC4)nc3)cc12] | N-[3-[5-[2-(cyclopropylamino)pyrimidin-5-yl]-1H-pyrrolo[2,3-b]pyridine-3-carbonyl]-2,4-difluoro-phenyl]-3-fluoro-benzenesulfonamide | |
| P-1934 | 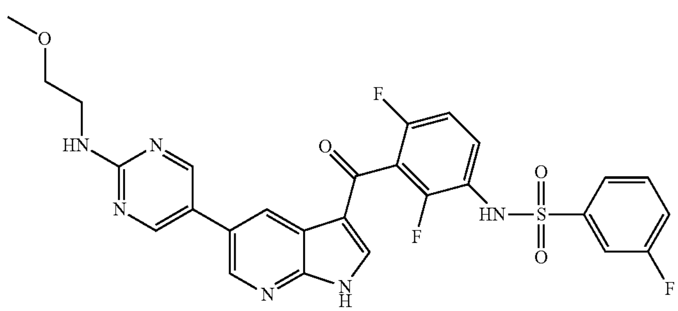 [SMILES: COCCNc1ncc(-c2cnc3[nH]cc(C(=O)c4c(F)ccc(NS(=O)(=O)c5cccc(F)c5)c4F)c3c2)cn1] | N-[2,4-difluoro-3-[5-[2-(2-methoxyethylamino)pyrimidin-5-yl]-1H-pyrrolo[2,3-b]pyridine-3-carbonyl]phenyl]-3-fluoro-benzenesulfonamide | |
| P-1935 | 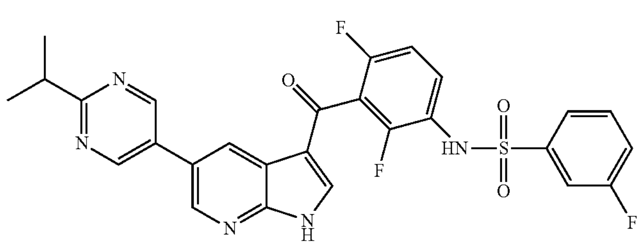 [SMILES: CC(C)c1ncc(-c2cnc3[nH]cc(C(=O)c4c(F)ccc(NS(=O)(=O)c5cccc(F)c5)c4F)c3c2)cn1] | N-[2,4-difluoro-3-[5-(2-isopropylpyrimidin-5-yl)-1H-pyrrolo[2,3-b]pyridine-3-carbonyl]phenyl]-3-fluoro-benzenesulfonamide | |

TABLE I-continued

| Comp # | Structure | Name | MS |
|---|---|---|---|
| P-1936 | 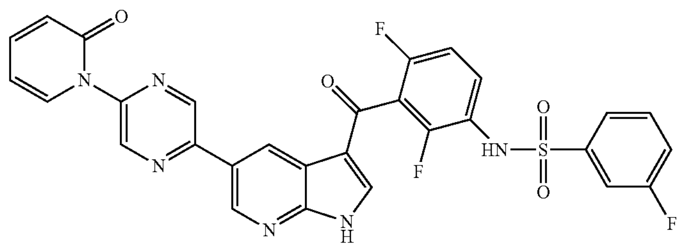 [SMILES: O=C(c1c(F)ccc(NS(=O)(=O)c2cccc(F)c2)c1F)c1c[nH]c2ncc(-c3cnc(-n4ccccc4=O)cn3)cc12] | N-[2,4-difluoro-3-[5-[5-(2-oxo-1-pyridyl)pyrazin-2-yl]-1H-pyrrolo[2,3-b]pyridine-3-carbonyl]phenyl]-3-fluoro-benzenesulfonamide | |
| P-1937 | 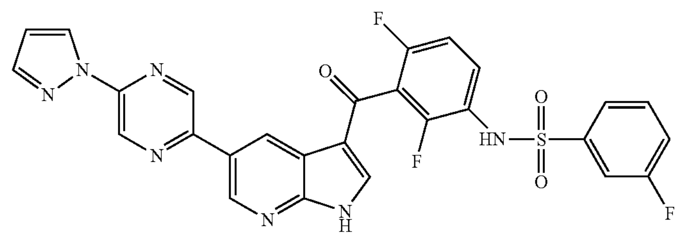 [SMILES: O=C(c1c(F)ccc(NS(=O)(=O)c2cccc(F)c2)c1F)c1c[nH]c2ncc(-c3cnc(-n4cccn4)cn3)cc12] | N-[2,4-difluoro-3-[5-(5-pyrazol-1-ylpyrazin-2-yl)-1H-pyrrolo[2,3-b]pyridine-3-carbonyl]phenyl]-3-fluoro-benzenesulfonamide | |
| P-1938 | 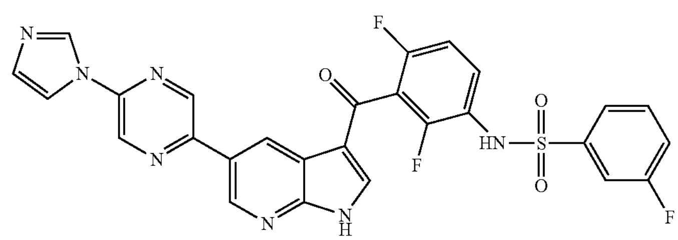 [SMILES: O=C(c1c(F)ccc(NS(=O)(=O)c2cccc(F)c2)c1F)c1c[nH]c2ncc(-c3cnc(-n4ccnc4)cn3)cc12] | N-[2,4-difluoro-3-[5-(5-imidazol-1-ylpyrazin-2-yl)-1H-pyrrolo[2,3-b]pyridine-3-carbonyl]phenyl]-3-fluoro-benzenesulfonamide | |
| P-1939 | 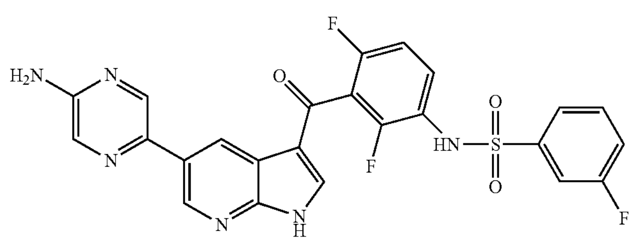 [SMILES: Nc1cnc(-c2cnc3[nH]cc(C(=O)c4c(F)ccc(NS(=O)(=O)c5cccc(F)c5)c4F)c3c2)cn1] | N-[3-[5-(5-aminopyrazin-2-yl)-1H-pyrrolo[2,3-b]pyridine-3-carbonyl]-2,4-difluoro-phenyl]-3-fluoro-benzenesulfonamide | |
| P-1940 | 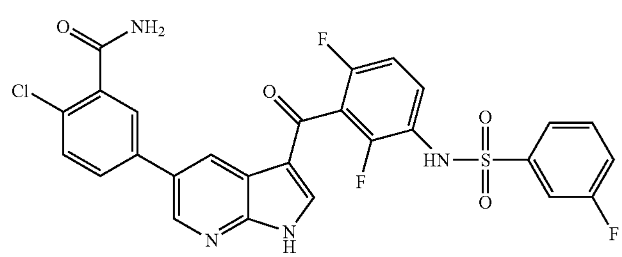 [SMILES: NC(=O)c1cc(-c2cnc3[nH]cc(C(=O)c4c(F)ccc(NS(=O)(=O)c5cccc(F)c5)c4F)c3c2)ccc1Cl] | 2-chloro-5-[3-[2,6-difluoro-3-[(3-fluorophenyl)sulfonylamino]benzoyl]-1H-pyrrolo[2,3-b]pyridin-5-yl]benzamide | |
| P-1941 | 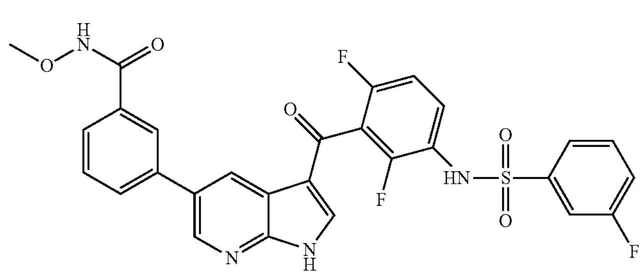 [SMILES: CONC(=O)c1cccc(-c2cnc3[nH]cc(C(=O)c4c(F)ccc(NS(=O)(=O)c5cccc(F)c5)c4F)c3c2)c1] | 3-[3-[2,6-difluoro-3-[(3-fluorophenyl)sulfonylamino]benzoyl]-1H-pyrrolo[2,3-b]pyridin-5-yl]-N-methoxy-benzamide | |

TABLE I-continued

| Comp # | Structure | Name | MS |
|---|---|---|---|
| P-1942 | 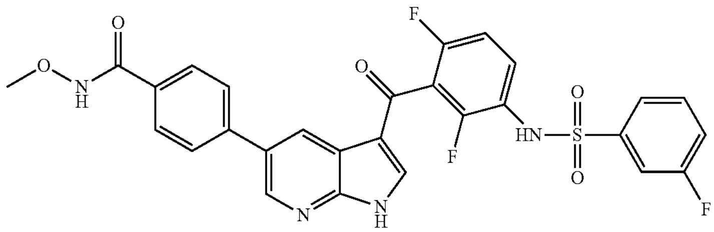 [SMILES: CONC(=O)c1ccc(-c2cnc3[nH]cc(C(=O)c4c(F)ccc(NS(=O)(=O)c5cccc(F)c5)c4F)c3c2)cc1] | 4-[3-[2,6-difluoro-3-[(3-fluorophenyl)sulfonylamino]benzoyl]-1H-pyrrolo[2,3-b]pyridin-5-yl]-N-methoxy-benzamide | |
| P-1943 | 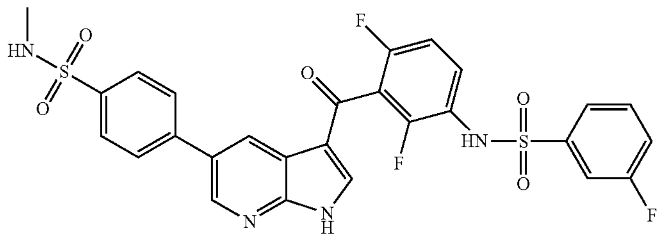 [SMILES: CNS(=O)(=O)c1ccc(-c2cnc3[nH]cc(C(=O)c4c(F)ccc(NS(=O)(=O)c5cccc(F)c5)c4F)c3c2)cc1] | N-[2,4-difluoro-3-[5-[4-(methylsulfamoyl)phenyl]-1H-pyrrolo[2,3-b]pyridine-3-carbonyl]phenyl]-3-fluoro-benzenesulfonamide | |
| P-1944 | 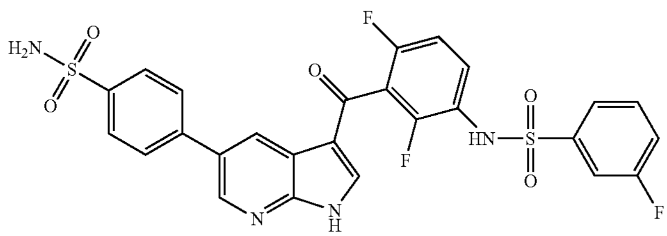 [SMILES: NS(=O)(=O)c1ccc(-c2cnc3[nH]cc(C(=O)c4c(F)ccc(NS(=O)(=O)c5cccc(F)c5)c4F)c3c2)cc1] | N-[2,4-difluoro-3-[5-(4-sulfamoylphenyl)-1H-pyrrolo[2,3-b]pyridine-3-carbonyl]phenyl]-3-fluoro-benzenesulfonamide | |
| P-1945 | 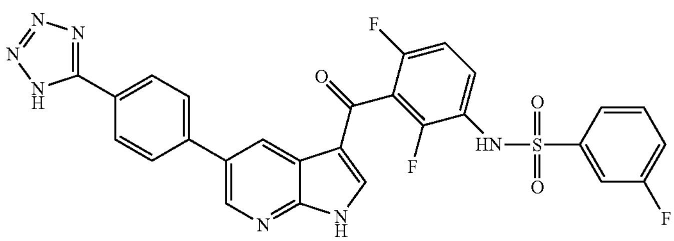 [SMILES: O=C(c1c(F)ccc(NS(=O)(=O)c2cccc(F)c2)c1F)c1c[nH]c2ncc(-c3ccc(-c4nnn[nH]4)cc3)cc12] | N-[2,4-difluoro-3-[5-[4-(1H-tetrazol-5-yl)phenyl]-1H-pyrrolo[2,3-b]pyridine-3-carbonyl]phenyl]-3-fluoro-benzenesulfonamide | |
| P-1946 | 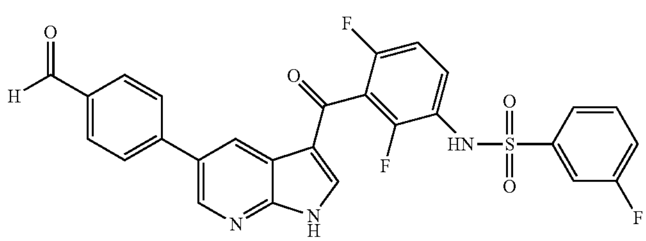 [SMILES: O=Cc1ccc(-c2cnc3[nH]cc(C(=O)c4c(F)ccc(NS(=O)(=O)c5cccc(F)c5)c4F)c3c2)cc1] | N-[2,4-difluoro-3-[5-(4-formylphenyl)-1H-pyrrolo[2,3-b]pyridine-3-carbonyl]phenyl]-3-fluoro-benzenesulfonamide | |
| P-1947 | 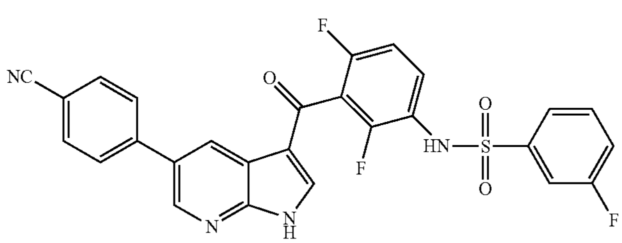 [SMILES: N#Cc1ccc(-c2cnc3[nH]cc(C(=O)c4c(F)ccc(NS(=O)(=O)c5cccc(F)c5)c4F)c3c2)cc1] | N-[3-[5-(4-cyanophenyl)-1H-pyrrolo[2,3-b]pyridine-3-carbonyl]-2,4-difluoro-phenyl]-3-fluoro-benzenesulfonamide | |

TABLE I-continued

| Comp # | Structure | Name | MS |
|---|---|---|---|
| P-1948 | 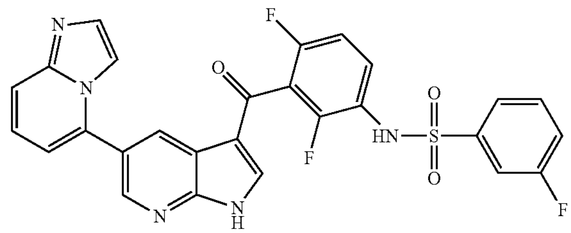 [SMILES: O=C(c1c(F)ccc(NS(=O)(=O)c2cccc(F)c2)c1F)c1c[nH]c2ncc(-c3cccc4nccn34)cc12] | N-[2,4-difluoro-3-(5-imidazo[1,2-a]pyridin-5-yl-1H-pyrrolo[2,3-b]pyridine-3-carbonyl)phenyl]-3-fluoro-benzenesulfonamide | |
| P-1949 | 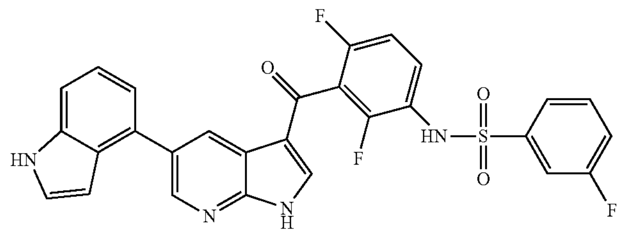 [SMILES: O=C(c1c(F)ccc(NS(=O)(=O)c2cccc(F)c2)c1F)c1c[nH]c2ncc(-c3cccc4[nH]ccc34)cc12] | N-[2,4-difluoro-3-[5-(1H-indol-4-yl)-1H-pyrrolo[2,3-b]pyridine-3-carbonyl]phenyl]-3-fluoro-benzenesulfonamide | |
| P-1950 | 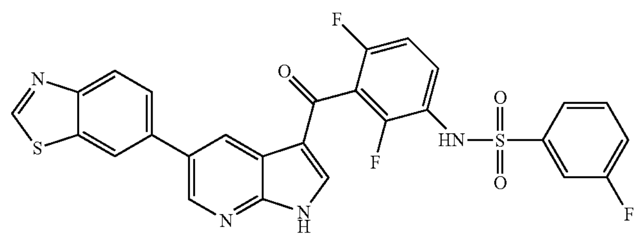 [SMILES: O=C(c1c(F)ccc(NS(=O)(=O)c2cccc(F)c2)c1F)c1c[nH]c2ncc(-c3ccc4ncsc4c3)cc12] | N-[3-[5-(1,3-benzothiazol-6-yl)-1H-pyrrolo[2,3-b]pyridine-3-carbonyl]-2,4-difluoro-phenyl]-3-fluoro-benzenesulfonamide | |
| P-1951 | 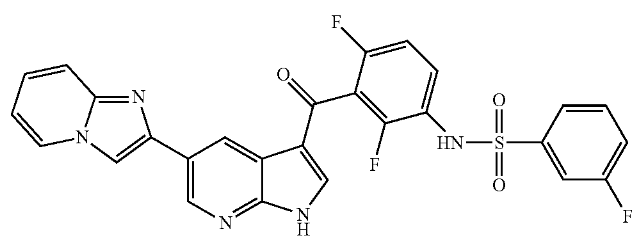 [SMILES: O=C(c1c(F)ccc(NS(=O)(=O)c2cccc(F)c2)c1F)c1c[nH]c2ncc(-c3cn4ccccc4n3)cc12] | N-[2,4-difluoro-3-(5-imidazo[1,2-a]pyridin-2-yl-1H-pyrrolo[2,3-b]pyridine-3-carbonyl)phenyl]-3-fluoro-benzenesulfonamide | |
| P-1952 | 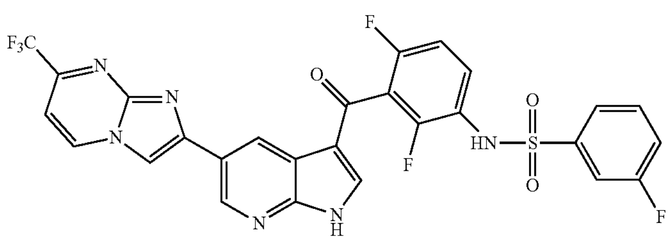 [SMILES: O=C(c1c(F)ccc(NS(=O)(=O)c2cccc(F)c2)c1F)c1c[nH]c2ncc(-c3cn4ccc(C(F)(F)F)nc4n3)cc12] | N-[2,4-difluoro-3-[5-[7-(trifluoromethyl)imidazo[1,2-a]pyrimidin-2-yl]-1H-pyrrolo[2,3-b]pyridine-3-carbonyl]phenyl]-3-fluoro-benzenesulfonamide | |
| P-1953 | 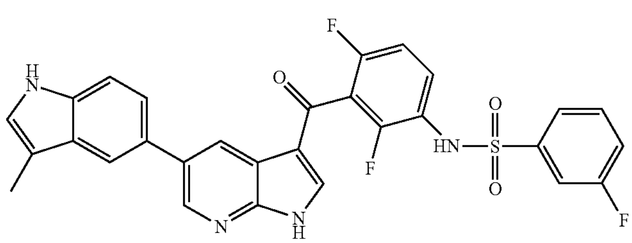 [SMILES: Cc1c[nH]c2ccc(-c3cnc4[nH]cc(C(=O)c5c(F)ccc(NS(=O)(=O)c6cccc(F)c6)c5F)c4c3)cc12] | N-[2,4-difluoro-3-[5-(3-methyl-1H-indol-5-yl)-1H-pyrrolo[2,3-b]pyridine-3-carbonyl]phenyl]-3-fluoro-benzenesulfonamide | |

TABLE I-continued

| Comp # | Structure | Name | MS |
|---|---|---|---|
| P-1954 | 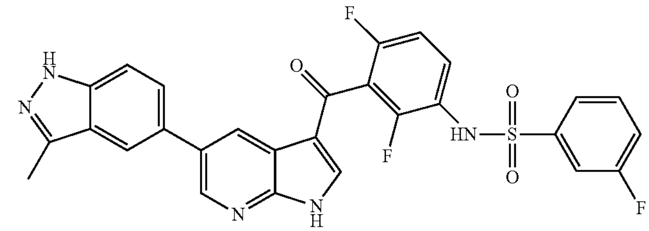 [SMILES: Cc1n[nH]c2ccc(-c3cnc4[nH]cc(C(=O)c5c(F)ccc(NS(=O)(=O)c6cccc(F)c6)c5F)c4c3)cc12] | N-[2,4-difluoro-3-[5-(3-methyl-1H-indazol-5-yl)-1H-pyrrolo[2,3-b]pyridine-3-carbonyl]phenyl]-3-fluoro-benzenesulfonamide | |
| P-1955 | 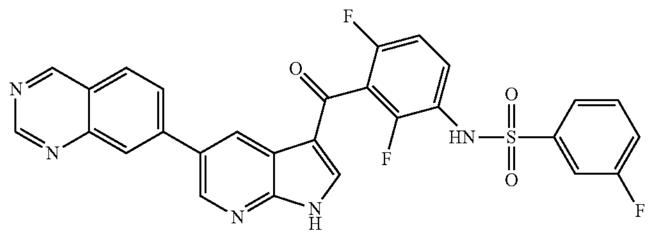 [SMILES: O=C(c1c(F)ccc(NS(=O)(=O)c2cccc(F)c2)c1F)c1c[nH]c2ncc(-c3ccc4cncnc4c3)cc12] | N-[2,4-difluoro-3-(5-quinazolin-7-yl-1H-pyrrolo[2,3-b]pyridine-3-carbonyl)phenyl]-3-fluoro-benzenesulfonamide | |
| P-1956 | 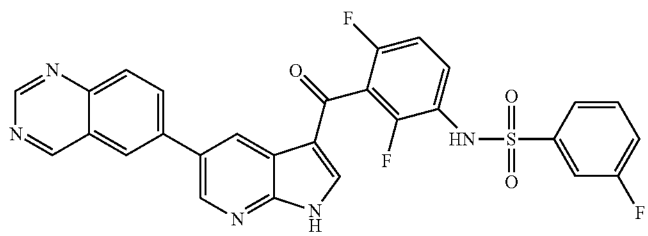 [SMILES: O=C(c1c(F)ccc(NS(=O)(=O)c2cccc(F)c2)c1F)c1c[nH]c2ncc(-c3ccc4ncncc4c3)cc12] | N-[2,4-difluoro-3-(5-quinazolin-6-yl-1H-pyrrolo[2,3-b]pyridine-3-carbonyl)phenyl]-3-fluoro-benzenesulfonamide | |
| P-1957 | 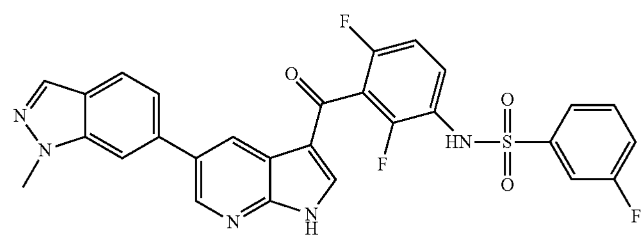 [SMILES: Cn1ncc2ccc(-c3cnc4[nH]cc(C(=O)c5c(F)ccc(NS(=O)(=O)c6cccc(F)c6)c5F)c4c3)cc21] | N-[2,4-difluoro-3-[5-(1-methylindazol-6-yl)-1H-pyrrolo[2,3-b]pyridine-3-carbonyl]phenyl]-3-fluoro-benzenesulfonamide | |
| P-1958 | 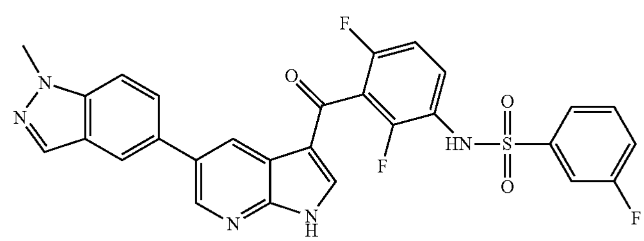 [SMILES: Cn1ncc2cc(-c3cnc4[nH]cc(C(=O)c5c(F)ccc(NS(=O)(=O)c6cccc(F)c6)c5F)c4c3)ccc21] | N-[2,4-difluoro-3-[5-(1-methylindazol-5-yl)-1H-pyrrolo[2,3-b]pyridine-3-carbonyl]phenyl]-3-fluoro-benzenesulfonamide | |
| P-1959 | 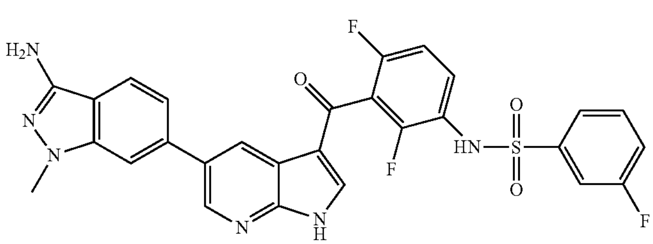 [SMILES: Cn1nc(N)c2ccc(-c3cnc4[nH]cc(C(=O)c5c(F)ccc(NS(=O)(=O)c6cccc(F)c6)c5F)c4c3)cc21] | N-[3-[5-(3-amino-1-methyl-indazol-6-yl)-1H-pyrrolo[2,3-b]pyridine-3-carbonyl]-2,4-difluoro-phenyl]-3-fluoro-benzenesulfonamide | |

TABLE I-continued

| Comp # | Structure | Name | MS |
|---|---|---|---|
| P-1960 | 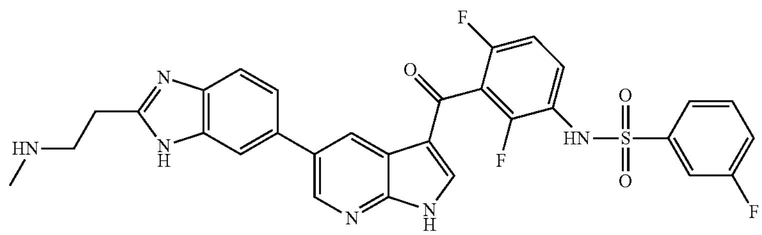 [SMILES: CNCCc1nc2ccc(-c3cnc4[nH]cc(C(=O)c5c(F)ccc(NS(=O)(=O)c6cccc(F)c6)c5F)c4c3)cc2[nH]1] | N-[2,4-difluoro-3-[5-[2-(2-methylaminoethyl)-3H-benzimidazol-5-yl]-1H-pyrrolo[2,3-b]pyridine-3-carbonyl]phenyl]-3-fluoro-benzenesulfonamide | |
| P-1961 | 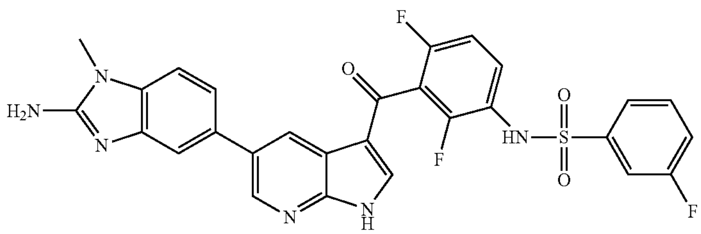 [SMILES: Cn1c(N)nc2cc(-c3cnc4[nH]cc(C(=O)c5c(F)ccc(NS(=O)(=O)c6cccc(F)c6)c5F)c4c3)ccc21] | N-[3-[5-(2-amino-1-methyl-benzimidazol-5-yl)-1H-pyrrolo[2,3-b]pyridine-3-carbonyl]-2,4-difluoro-phenyl]-3-fluoro-benzenesulfonamide | |
| P-1962 | 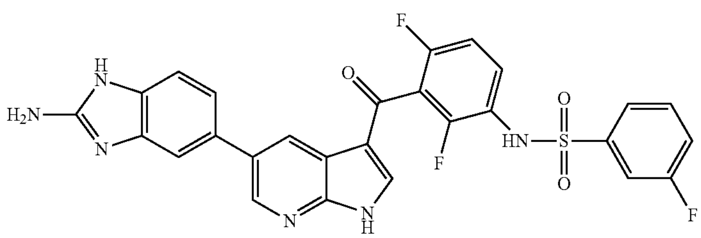 [SMILES: Nc1nc2cc(-c3cnc4[nH]cc(C(=O)c5c(F)ccc(NS(=O)(=O)c6cccc(F)c6)c5F)c4c3)ccc2[nH]1] | N-[3-[5-(2-amino-1H-benzimidazol-5-yl)-1H-pyrrolo[2,3-b]pyridine-3-carbonyl]-2,4-difluoro-phenyl]-3-fluoro-benzenesulfonamide | |
| P-1963 | 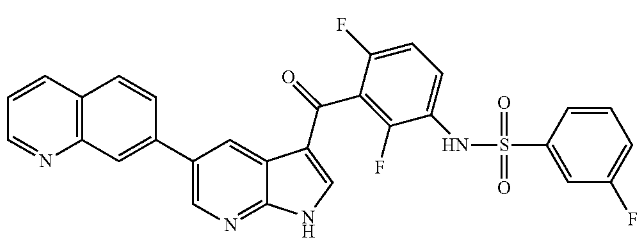 [SMILES: O=C(c1c(F)ccc(NS(=O)(=O)c2cccc(F)c2)c1F)c1c[nH]c2ncc(-c3ccc4cccnc4c3)cc12] | N-[2,4-difluoro-3-[5-(7-quinolyl)-1H-pyrrolo[2,3-b]pyridine-3-carbonyl]phenyl]-3-fluoro-benzenesulfonamide | |
| P-1964 | 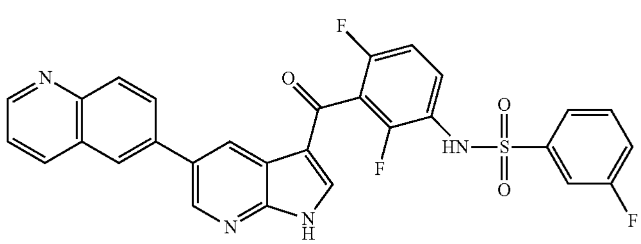 [SMILES: O=C(c1c(F)ccc(NS(=O)(=O)c2cccc(F)c2)c1F)c1c[nH]c2ncc(-c3ccc4ncccc4c3)cc12] | N-[2,4-difluoro-3-[5-(6-quinolyl)-1H-pyrrolo[2,3-b]pyridine-3-carbonyl]phenyl]-3-fluoro-benzenesulfonamide | |
| P-1965 | 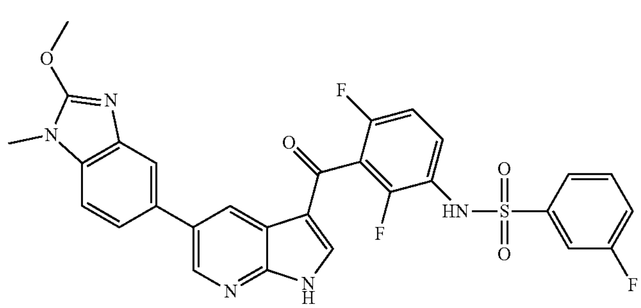 [SMILES: COc1nc2cc(-c3cnc4[nH]cc(C(=O)c5c(F)ccc(NS(=O)(=O)c6cccc(F)c6)c5F)c4c3)ccc2n1C] | N-[2,4-difluoro-3-[5-(2-methoxy-1-methyl-benzimidazol-5-yl)-1H-pyrrolo[2,3-b]pyridine-3-carbonyl]phenyl]-3-fluoro-benzenesulfonamide | |

TABLE I-continued

| Comp # | Structure | Name | MS |
|---|---|---|---|
| P-1966 | 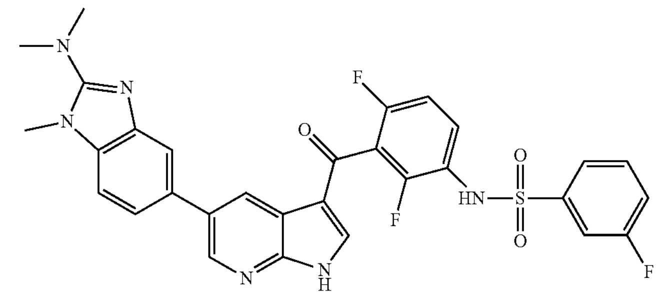 [SMILES: CN(C)c1nc2cc(-c3cnc4[nH]cc(C(=O)c5c(F)ccc(NS(=O)(=O)c6cccc(F)c6)c5F)c4c3)ccc2n1C] | N-[3-[5-(2-dimethylamino-1-methyl-benzimidazol-5-yl)-1H-pyrrolo[2,3-b]pyridine-3-carbonyl]-2,4-difluoro-phenyl]-3-fluoro-benzenesulfonamide | |
| P-1967 | 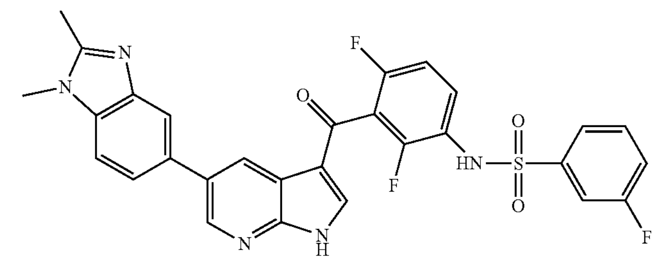 [SMILES: Cc1nc2cc(-c3cnc4[nH]cc(C(=O)c5c(F)ccc(NS(=O)(=O)c6cccc(F)c6)c5F)c4c3)ccc2n1C] | N-[3-[5-(1,2-dimethylbenzimidazol-5-yl)-1H-pyrrolo[2,3-b]pyridine-3-carbonyl]-2,4-difluoro-phenyl]-3-fluoro-benzenesulfonamide | |
| P-1968 | 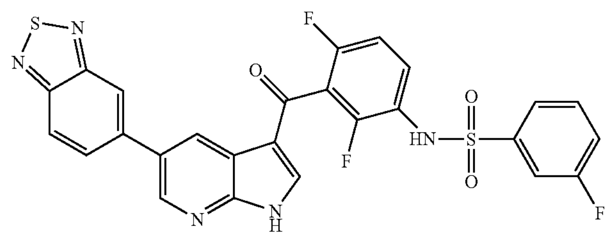 [SMILES: O=C(c1c(F)ccc(NS(=O)(=O)c2cccc(F)c2)c1F)c1c[nH]c2ncc(-c3ccc4nsnc4c3)cc12] | N-[3-[5-(2,1,3-benzothiadiazol-6-yl)-1H-pyrrolo[2,3-b]pyridine-3-carbonyl]-2,4-difluoro-phenyl]-3-fluoro-benzenesulfonamide | |
| P-1969 | 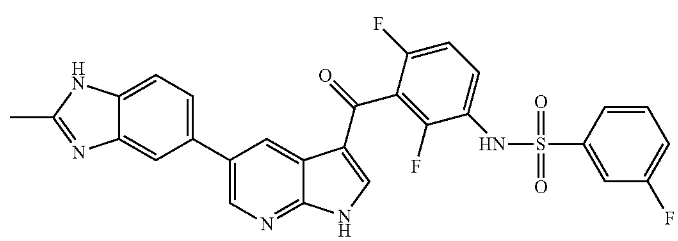 [SMILES: Cc1nc2cc(-c3cnc4[nH]cc(C(=O)c5c(F)ccc(NS(=O)(=O)c6cccc(F)c6)c5F)c4c3)ccc2[nH]1] | N-[2,4-difluoro-3-[5-(2-methyl-1H-benzimidazol-5-yl)-1H-pyrrolo[2,3-b]pyridine-3-carbonyl]phenyl]-3-fluoro-benzenesulfonamide | |
| P-1970 | 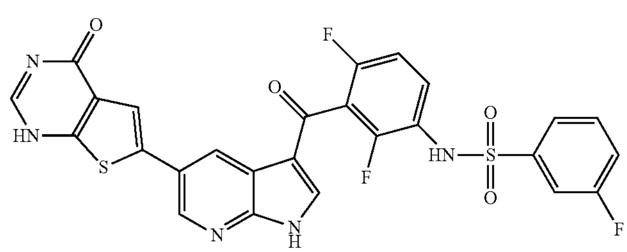 [SMILES: O=C(c1c(F)ccc(NS(=O)(=O)c2cccc(F)c2)c1F)c1c[nH]c2ncc(-c3cc4c(=O)nc[nH]c4s3)cc12] | N-[2,4-difluoro-3-[5-(4-oxo-1H-thieno[2,3-d]pyrimidin-6-yl)-1H-pyrrolo[2,3-b]pyridine-3-carbonyl]phenyl]-3-fluoro-benzenesulfonamide | |
| P-1971 | 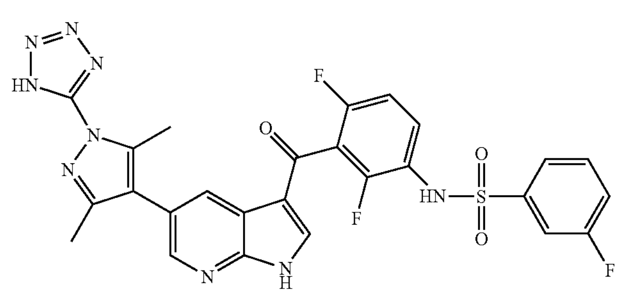 [SMILES: Cc1nn(-c2nnn[nH]2)c(C)c1-c1cnc2[nH]cc(C(=O)c3c(F)ccc(NS(=O)(=O)c4cccc(F)c4)c3F)c2c1] | N-[3-[5-[3,5-dimethyl-1-(1H-tetrazol-5-yl)pyrazol-4-yl]-1H-pyrrolo[2,3-b]pyridine-3-carbonyl]-2,4-difluoro-phenyl]-3-fluoro-benzenesulfonamide | |

TABLE I-continued

| Comp # | Structure | Name | MS |
|---|---|---|---|
| P-1972 | 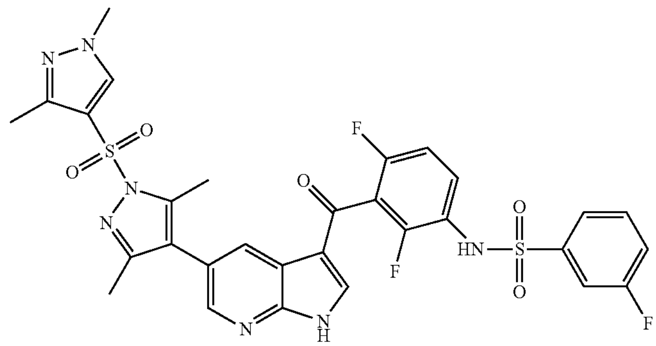 [SMILES: Cc1nn(C)cc1S(=O)(=O)n1nc(C)c(-c2cnc3[nH]cc(C(=O)c4c(F)ccc(NS(=O)(=O)c5cccc(F)c5)c4F)c3c2)c1C] | N-[3-[5-[1-(1,3-dimethylpyrazol-4-yl)sulfonyl-3,5-dimethyl-pyrazol-4-yl]-1H-pyrrolo[2,3-b]pyridine-3-carbonyl]-2,4-difluoro-phenyl]-3-fluoro-benzenesulfonamide | |
| P-1973 | 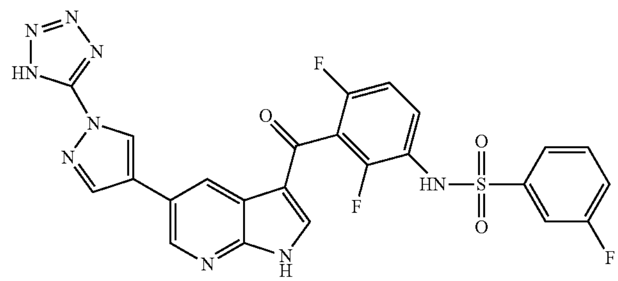 [SMILES: O=C(c1c(F)ccc(NS(=O)(=O)c2cccc(F)c2)c1F)c1c[nH]c2ncc(-c3cnn(-c4nnn[nH]4)c3)cc12] | N-[2,4-difluoro-3-[5-[1-(1H-tetrazol-5-yl)pyrazol-4-yl]-1H-pyrrolo[2,3-b]pyridine-3-carbonyl]phenyl]-3-fluoro-benzenesulfonamide | |
| P-1974 | 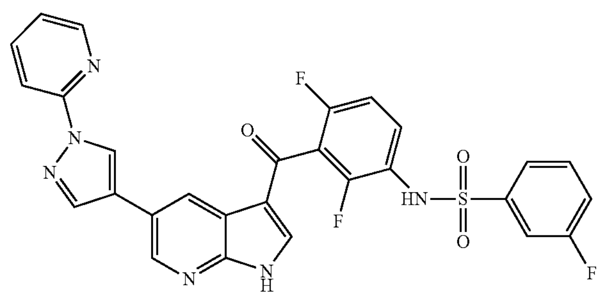 [SMILES: O=C(c1c(F)ccc(NS(=O)(=O)c2cccc(F)c2)c1F)c1c[nH]c2ncc(-c3cnn(-c4ccccn4)c3)cc12] | N-[2,4-difluoro-3-[5-[1-(2-pyridyl)pyrazol-4-yl]-1H-pyrrolo[2,3-b]pyridine-3-carbonyl]phenyl]-3-fluoro-benzenesulfonamide | |
| P-1975 | 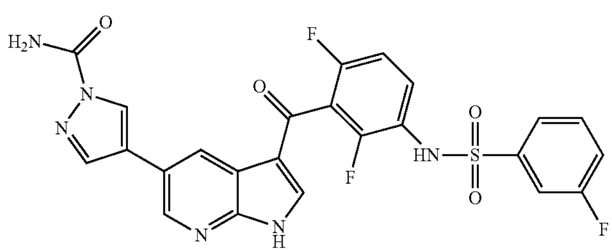 [SMILES: NC(=O)n1cc(-c2cnc3[nH]cc(C(=O)c4c(F)ccc(NS(=O)(=O)c5cccc(F)c5)c4F)c3c2)cn1] | 4-[3-[2,6-difluoro-3-[(3-fluorophenyl)sulfonylamino]benzoyl]-1H-pyrrolo[2,3-b]pyridin-5-yl]pyrazole-1-carboxamide | |
| P-1976 | 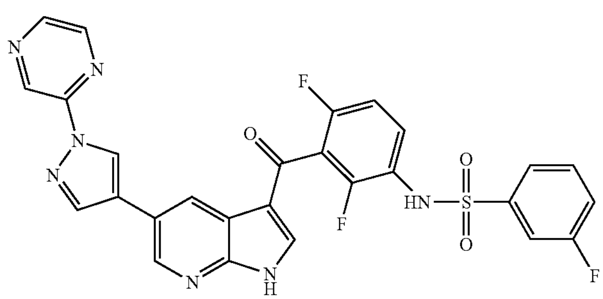 [SMILES: O=C(c1c(F)ccc(NS(=O)(=O)c2cccc(F)c2)c1F)c1c[nH]c2ncc(-c3cnn(-c4cnccn4)c3)cc12] | N-[2,4-difluoro-3-[5-(1-pyrazin-2-ylpyrazol-4-yl)-1H-pyrrolo[2,3-b]pyridine-3-carbonyl]phenyl]-3-fluoro-benzenesulfonamide | |

TABLE I-continued

| Comp # | Structure | Name | MS |
|---|---|---|---|
| P-1977 | 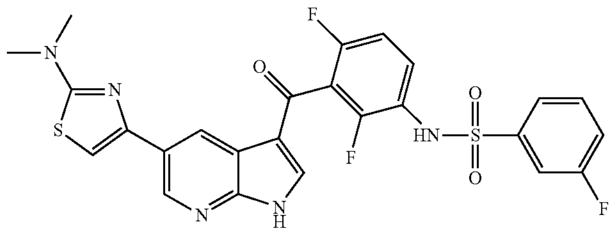 [SMILES: CN(C)c1nc(-c2cnc3[nH]cc(C(=O)c4c(F)ccc(NS(=O)(=O)c5cccc(F)c5)c4F)c3c2)cs1] | N-[3-[5-(2-dimethylaminothiazol-4-yl)-1H-pyrrolo[2,3-b]pyridine-3-carbonyl]-2,4-difluoro-phenyl]-3-fluoro-benzenesulfonamide | |
| P-1978 | 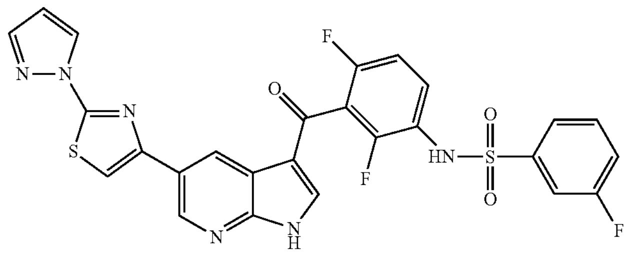 [SMILES: O=C(c1c(F)ccc(NS(=O)(=O)c2cccc(F)c2)c1F)c1c[nH]c2ncc(-c3csc(-n4cccn4)n3)cc12] | N-[2,4-difluoro-3-[5-(2-pyrazol-1-ylthiazol-4-yl)-1H-pyrrolo[2,3-b]pyridine-3-carbonyl]phenyl]-3-fluoro-benzenesulfonamide | |
| P-1979 | 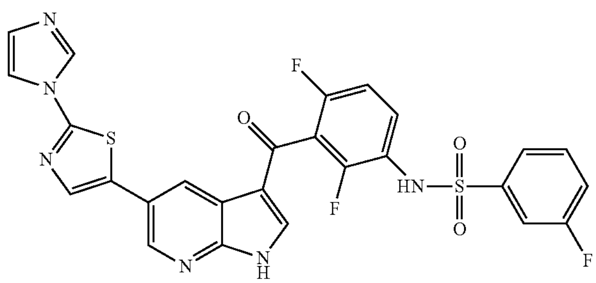 [SMILES: O=C(c1c(F)ccc(NS(=O)(=O)c2cccc(F)c2)c1F)c1c[nH]c2ncc(-c3cnc(-n4ccnc4)s3)cc12] | N-[2,4-difluoro-3-[5-(2-imidazol-1-ylthiazol-5-yl)-1H-pyrrolo[2,3-b]pyridine-3-carbonyl]phenyl]-3-fluoro-benzenesulfonamide | |
| P-1980 | 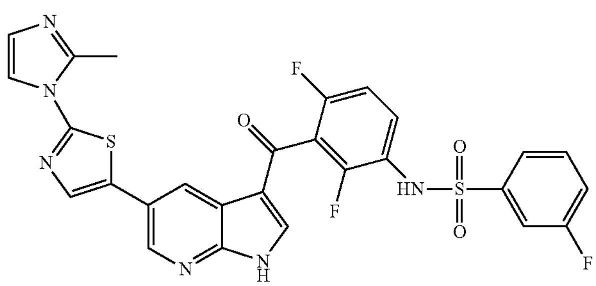 [SMILES: Cc1nccn1-c1ncc(-c2cnc3[nH]cc(C(=O)c4c(F)ccc(NS(=O)(=O)c5cccc(F)c5)c4F)c3c2)s1] | N-[2,4-difluoro-3-[5-[2-(2-methylimidazol-1-yl)thiazol-5-yl]-1H-pyrrolo[2,3-b]pyridine-3-carbonyl]phenyl]-3-fluoro-benzenesulfonamide | |
| P-1981 | 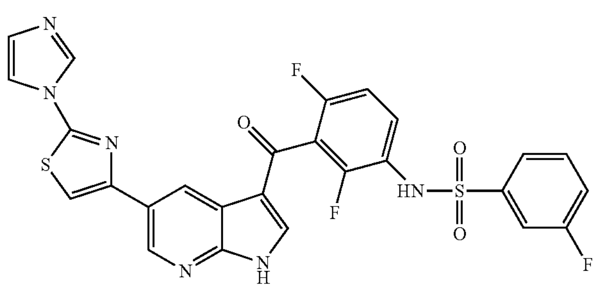 [SMILES: O=C(c1c(F)ccc(NS(=O)(=O)c2cccc(F)c2)c1F)c1c[nH]c2ncc(-c3csc(-n4ccnc4)n3)cc12] | N-[2,4-difluoro-3-[5-(2-imidazol-1-ylthiazol-4-yl)-1H-pyrrolo[2,3-b]pyridine-3-carbonyl]phenyl]-3-fluoro-benzenesulfonamide | |

| Comp # | Structure | Name | MS |
|---|---|---|---|
| P-1982 | 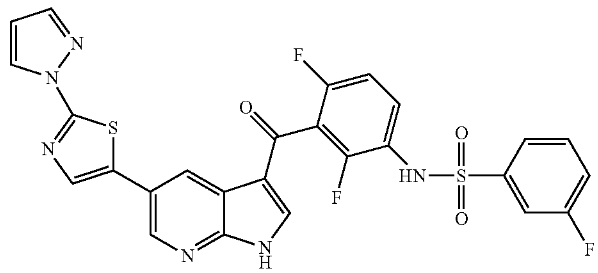 [SMILES: O=C(c1c(F)ccc(NS(=O)(=O)c2cccc(F)c2)c1F)c1c[nH]c2ncc(-c3cnc(-n4cccn4)s3)cc12] | N-[2,4-difluoro-3-[5-(2-pyrazol-1-yl thiazol-5-yl)-1H-pyrrolo[2,3-b]pyridine-3-carbonyl]phenyl]-3-fluoro-benzenesulfonamide | |
| P-1983 | 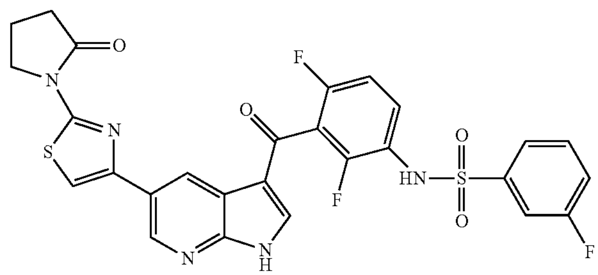 [SMILES: O=C(c1c(F)ccc(NS(=O)(=O)c2cccc(F)c2)c1F)c1c[nH]c2ncc(-c3csc(N4CCCC4=O)n3)cc12] | N-[2,4-difluoro-3-[5-[2-(2-oxopyrrolidin-1-yl)thiazol-4-yl]-1H-pyrrolo[2,3-b]pyridine-3-carbonyl]phenyl]-3-fluoro-benzenesulfonamide | |
| P-1984 | 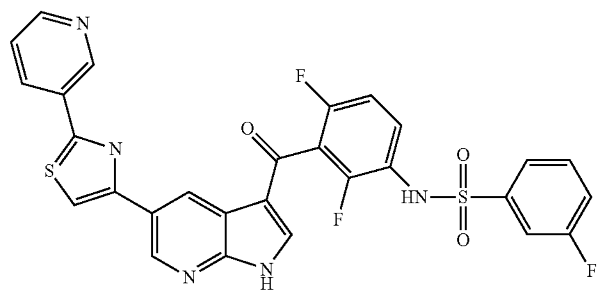 | N-[2,4-difluoro-3-[5-[2-(3-pyridyl)thiazol-4-yl]-1H-pyrrolo[2,3-b]pyridine-3-carbonyl]phenyl]-3-fluoro-benzenesulfonamide | |
| P-1985 | 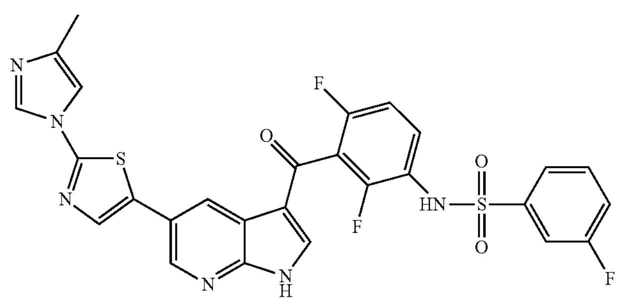 [SMILES: Cc1cn(-c2ncc(-c3cnc4[nH]cc(C(=O)c5c(F)ccc(NS(=O)(=O)c6cccc(F)c6)c5F)c4c3)s2)cn1] | N-[2,4-difluoro-3-[5-[2-(4-methylimidazol-1-yl)thiazol-5-yl]-1H-pyrrolo[2,3-b]pyridine-3-carbonyl]phenyl]-3-fluoro-benzenesulfonamide | |
| P-1986 | 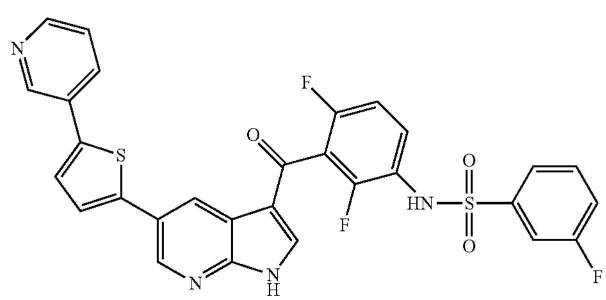 [SMILES: O=C(c1c(F)ccc(NS(=O)(=O)c2cccc(F)c2)c1F)c1c[nH]c2ncc(-c3ccc(-c4cccnc4)s3)cc12] | N-[2,4-difluoro-3-[5-[5-(3-pyridyl)-2-thienyl]-1H-pyrrolo[2,3-b]pyridine-3-carbonyl]phenyl]-3-fluoro-benzenesulfonamide | |

TABLE I-continued

| Comp # | Structure | Name | MS |
|---|---|---|---|
| P-1987 | 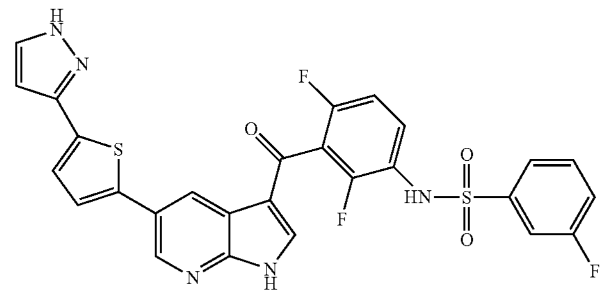 [SMILES: O=C(c1c(F)ccc(NS(=O)(=O)c2cccc(F)c2)c1F)c1c[nH]c2ncc(-c3ccc(-c4cc[nH]n4)s3)cc12] | N-[2,4-difluoro-3-[5-[5-(1H-pyrazol-3-yl)-2-thienyl]-1H-pyrrolo[2,3-b]pyridine-3-carbonyl]phenyl]-3-fluoro-benzenesulfonamide | |
| P-1988 | 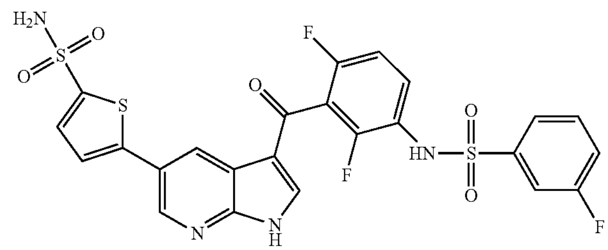 [SMILES: NS(=O)(=O)c1ccc(-c2cnc3[nH]cc(C(=O)c4c(F)ccc(NS(=O)(=O)c5cccc(F)c5)c4F)c3c2)s1] | 5-[3-[2,6-difluoro-3-[(3-fluorophenyl)sulfonylamino]benzoyl]-1H-pyrrolo[2,3-b]pyridin-5-yl]thiophene-2-sulfonamide | |
| P-1989 | 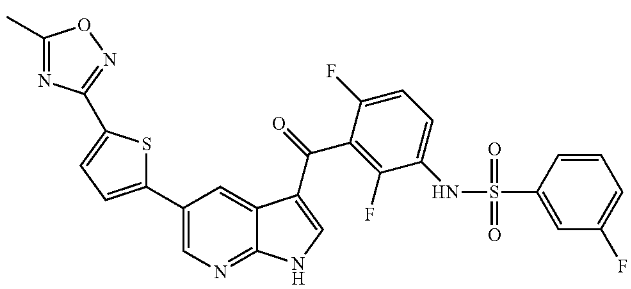 [SMILES: Cc1nc(-c2ccc(-c3cnc4[nH]cc(C(=O)c5c(F)ccc(NS(=O)(=O)c6cccc(F)c6)c5F)c4c3)s2)no1] | N-[2,4-difluoro-3-[5-[5-(5-methyl-1,2,4-oxadiazol-3-yl)-2-thienyl]-1H-pyrrolo[2,3-b]pyridine-3-carbonyl]phenyl]-3-fluoro-benzenesulfonamide | |
| P-1990 | 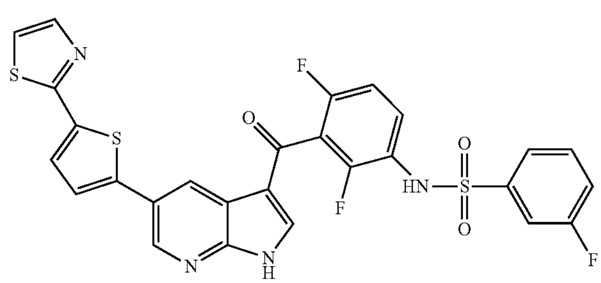 [SMILES: O=C(c1c(F)ccc(NS(=O)(=O)c2cccc(F)c2)c1F)c1c[nH]c2ncc(-c3ccc(-c4nccs4)s3)cc12] | N-[2,4-difluoro-3-[5-(5-thiazol-2-yl-2-thienyl)-1H-pyrrolo[2,3-b]pyridine-3-carbonyl]phenyl]-3-fluoro-benzenesulfonamide | |
| P-1991 | 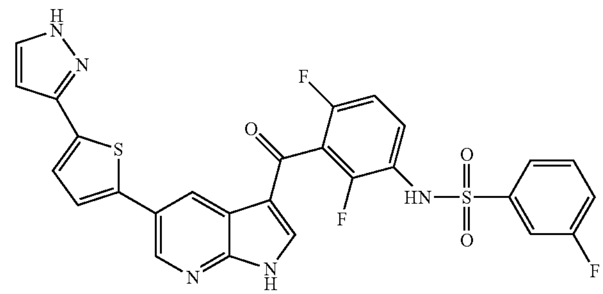 [SMILES: O=C(c1c(F)ccc(NS(=O)(=O)c2cccc(F)c2)c1F)c1c[nH]c2ncc(-c3ccc(-c4cc[nH]n4)s3)cc12] | N-[2,4-difluoro-3-[5-[5-(1H-pyrazol-3-yl)-2-thienyl]-1H-pyrrolo[2,3-b]pyridine-3-carbonyl]phenyl]-3-fluoro-benzenesulfonamide | |

TABLE I-continued

| Comp # | Structure | Name | MS |
|---|---|---|---|
| P-1992 | 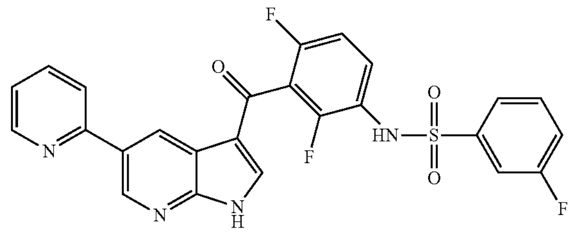 [SMILES: O=C(c1c(F)ccc(NS(=O)(=O)c2cccc(F)c2)c1F)c1c[nH]c2ncc(-c3ccccn3)cc12] | N-[2,4-difluoro-3-[5-(2-pyridyl)-1H-pyrrolo[2,3-b]pyridine-3-carbonyl]phenyl]-3-fluoro-benzenesulfonamide | |
| P-1993 | 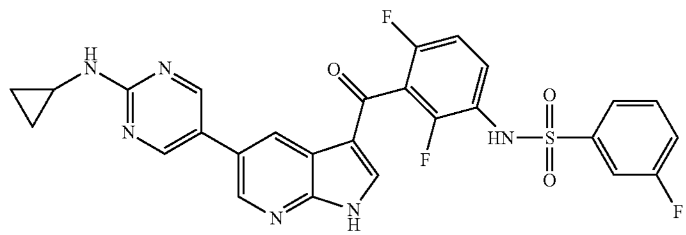 [SMILES: O=C(c1c(F)ccc(NS(=O)(=O)c2cccc(F)c2)c1F)c1c[nH]c2ncc(-c3cnc(NC4CC4)nc3)cc12] | N-[3-[5-[2-(cyclopropylamino)pyrimidin-5-yl]-1H-pyrrolo[2,3-b]pyridine-3-carbonyl]-2,4-difluoro-phenyl]-3-fluoro-benzenesulfonamide | |
| P-1994 | 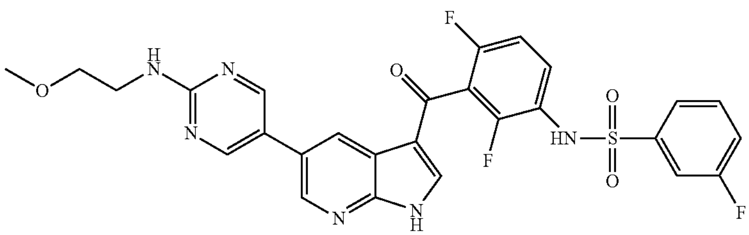 [SMILES: COCCNc1ncc(-c2cnc3[nH]cc(C(=O)c4c(F)ccc(NS(=O)(=O)c5cccc(F)c5)c4F)c3c2)cn1] | N-[2,4-difluoro-3-[5-[2-(2-methoxyethylamino)pyrimidin-5-yl]-1H-pyrrolo[2,3-b]pyridine-3-carbonyl]phenyl]-3-fluoro-benzenesulfonamide | |
| P-1995 | 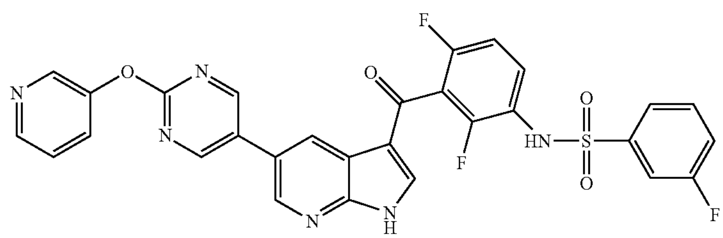 [SMILES: O=C(c1c(F)ccc(NS(=O)(=O)c2cccc(F)c2)c1F)c1c[nH]c2ncc(-c3cnc(Oc4cccnc4)nc3)cc12] | N-[2,4-difluoro-3-[5-[2-(3-pyridyloxy)pyrimidin-5-yl]-1H-pyrrolo[2,3-b]pyridine-3-carbonyl]phenyl]-3-fluoro-benzenesulfonamide | |
| P-1996 | 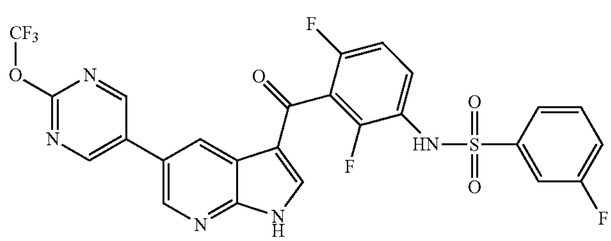 [SMILES: O=C(c1c(F)ccc(NS(=O)(=O)c2cccc(F)c2)c1F)c1c[nH]c2ncc(-c3cnc(OC(F)(F)F)nc3)cc12] | N-[2,4-difluoro-3-[5-[2-(trifluoromethoxy)pyrimidin-5-yl]-1H-pyrrolo[2,3-b]pyridine-3-carbonyl]phenyl]-3-fluoro-benzenesulfonamide | |
| P-1997 | 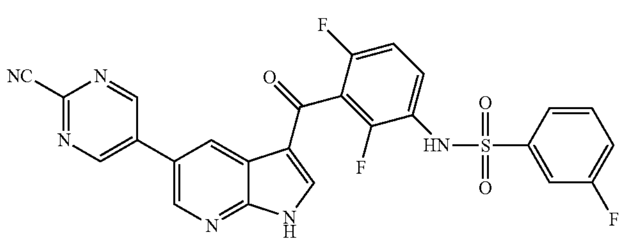 [SMILES: N#Cc1ncc(-c2cnc3[nH]cc(C(=O)c4c(F)ccc(NS(=O)(=O)c5cccc(F)c5)c4F)c3c2)cn1] | N-[3-[5-(2-cyanopyrimidin-5-yl)-1H-pyrrolo[2,3-b]pyridine-3-carbonyl]-2,4-difluoro-phenyl]-3-fluoro-benzenesulfonamide | |

| Comp # | Structure | Name | MS |
|---|---|---|---|
| P-1998 | 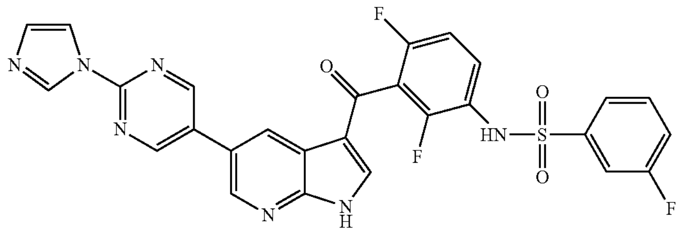 [SMILES: O=C(c1c(F)ccc(NS(=O)(=O)c2cccc(F)c2)c1F)c1c[nH]c2ncc(-c3cnc(-n4ccnc4)nc3)cc12] | N-[2,4-difluoro-3-[5-(2-imidazol-1-ylpyrimidin-5-yl)-1H-pyrrolo[2,3-b]pyridine-3-carbonyl]phenyl]-3-fluoro-benzenesulfonamide | |
| P-1999 | 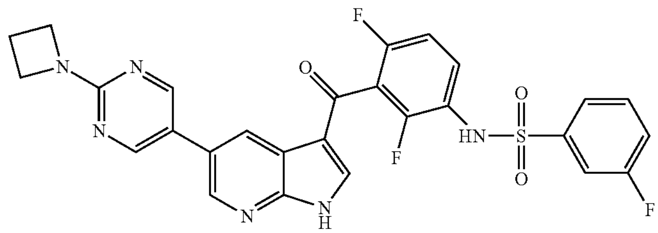 [SMILES: O=C(c1c(F)ccc(NS(=O)(=O)c2cccc(F)c2)c1F)c1c[nH]c2ncc(-c3cnc(N4CCC4)nc3)cc12] | N-[3-[5-[2-(azetidin-1-yl)pyrimidin-5-yl]-1H-pyrrolo[2,3-b]pyridine-3-carbonyl]-2,4-difluoro-phenyl]-3-fluoro-benzenesulfonamide | |
| P-2000 | 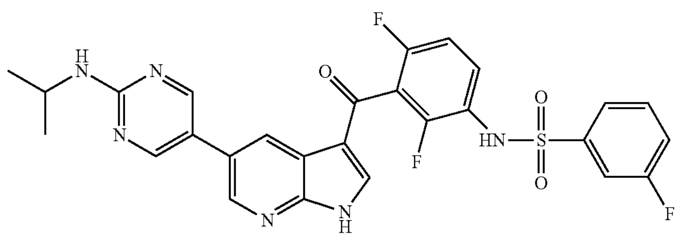 [SMILES: CC(C)Nc1ncc(-c2cnc3[nH]cc(C(=O)c4c(F)ccc(NS(=O)(=O)c5cccc(F)c5)c4F)c3c2)cn1] | N-[2,4-difluoro-3-[5-[2-(isopropylamino)pyrimidin-5-yl]-1H-pyrrolo[2,3-b]pyridine-3-carbonyl]phenyl]-3-fluoro-benzenesulfonamide | |
| P-2001 | 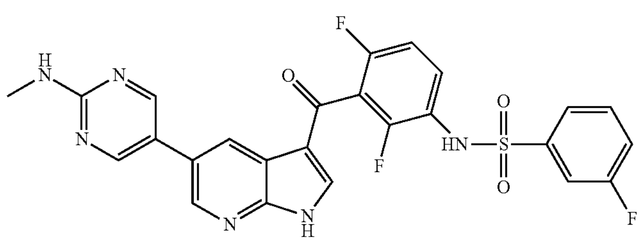 [SMILES: CNc1ncc(-c2cnc3[nH]cc(C(=O)c4c(F)ccc(NS(=O)(=O)c5cccc(F)c5)c4F)c3c2)cn1] | N-[2,4-difluoro-3-[5-(2-methylaminopyrimidin-5-yl)-1H-pyrrolo[2,3-b]pyridine-3-carbonyl]phenyl]-3-fluoro-benzenesulfonamide | |
| P-2002 | 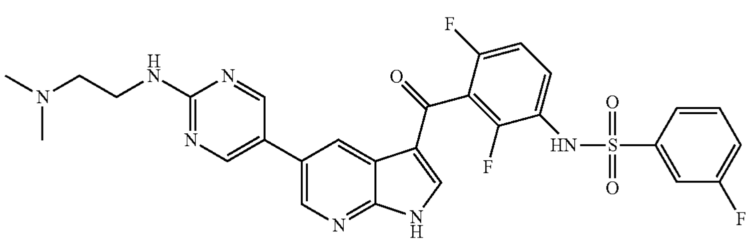 [SMILES: CN(C)CCNc1ncc(-c2cnc3[nH]cc(C(=O)c4c(F)ccc(NS(=O)(=O)c5cccc(F)c5)c4F)c3c2)cn1] | N-[3-[5-[2-(2-dimethylaminoethylamino)pyrimidin-5-yl]-1H-pyrrolo[2,3-b]pyridine-3-carbonyl]-2,4-difluoro-phenyl]-3-fluoro-benzenesulfonamide | |
| P-2003 | 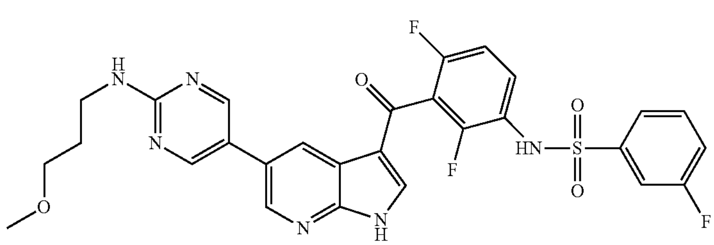 [SMILES: COCCCNc1ncc(-c2cnc3[nH]cc(C(=O)c4c(F)ccc(NS(=O)(=O)c5cccc(F)c5)c4F)c3c2)cn1] | N-[2,4-difluoro-3-[5-[2-(3-methoxypropylamino)pyrimidin-5-yl]-1H-pyrrolo[2,3-b]pyridine-3-carbonyl]phenyl]-3-fluoro-benzenesulfonamide | |

TABLE I-continued

| Comp # | Structure | Name | MS |
|---|---|---|---|
| P-2004 | 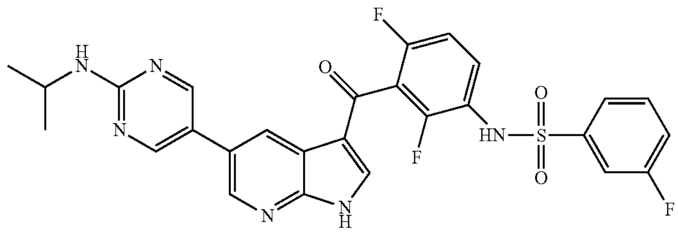 [SMILES: CC(C)Nc1ncc(-c2cnc3[nH]cc(C(=O)c4c(F)ccc(NS(=O)(=O)c5cccc(F)c5)c4F)c3c2)cn1] | N-[2,4-difluoro-3-[5-[2-(isopropylamino)pyrimidin-5-yl]-1H-pyrrolo[2,3-b]pyridine-3-carbonyl]phenyl]-3-fluoro-benzenesulfonamide | |
| P-2005 | 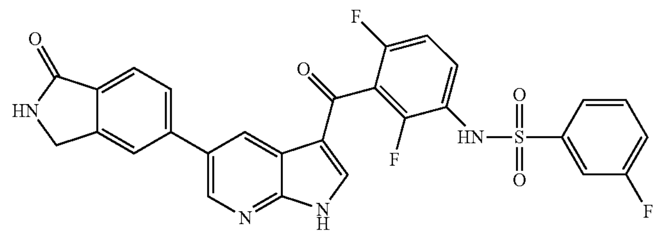 [SMILES: O=C1NCc2cc(-c3cnc4[nH]cc(C(=O)c5c(F)ccc(NS(=O)(=O)c6cccc(F)c6)c5F)c4c3)ccc21] | N-[2,4-difluoro-3-[5-(1-oxoisoindolin-5-yl)-1H-pyrrolo[2,3-b]pyridine-3-carbonyl]phenyl]-3-fluoro-benzenesulfonamide | |
| P-2006 | 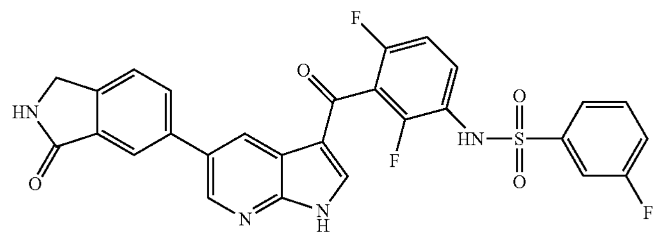 [SMILES: O=C1NCc2ccc(-c3cnc4[nH]cc(C(=O)c5c(F)ccc(NS(=O)(=O)c6cccc(F)c6)c5F)c4c3)cc21] | N-[2,4-difluoro-3-[5-(3-oxoisoindolin-5-yl)-1H-pyrrolo[2,3-b]pyridine-3-carbonyl]phenyl]-3-fluoro-benzenesulfonamide | |
| P-2007 | 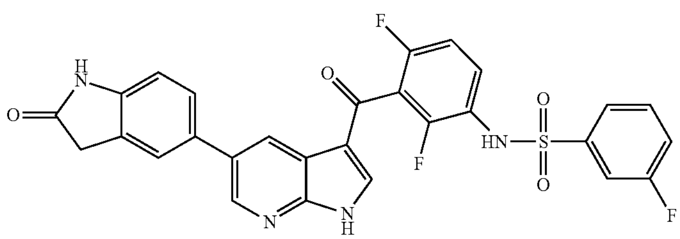 [SMILES: O=C1Cc2cc(-c3cnc4[nH]cc(C(=O)c5c(F)ccc(NS(=O)(=O)c6cccc(F)c6)c5F)c4c3)ccc2N1] | N-[2,4-difluoro-3-[5-(2-oxoindolin-5-yl)-1H-pyrrolo[2,3-b]pyridine-3-carbonyl]phenyl]-3-fluoro-benzenesulfonamide | |

In one embodiment of compounds contemplated herein, the compound is selected from the group consisting of:

Propane-1-sulfonic acid {2,4-difluoro-3-[5-(1H-indazol-5-yl)-1H-pyrrolo[2,3-b]pyridine-3-carbonyl]-phenyl}-amide (P-0001), N-{2,4-Difluoro-3-[5-(1H-indazol-5-yl)-1H-pyrrolo[2,3-b]pyridine-3-carbonyl]-phenyl}-2,5-difluoro-benzenesulfonamide (P-0002), 5-{3-[3-(2,5-Difluoro-benzenesulfonylamino)-2,6-difluoro-benzoyl]-1H-pyrrolo[2,3-b]pyridin-5-yl}-indazole-1-carboxylic acid methylamide (P-0003), N-{3-[1-Acetyl-5-(1-acetyl-1H-indazol-5-yl)-1H-pyrrolo[2,3-b]pyridine-3-carbonyl]-2,4-difluoro-phenyl}-2,5-difluoro-benzenesulfonamide (P-0004), N-{3-[5-(1-Acetyl-1H-indazol-5-yl)-1H-pyrrolo[2,3-b]pyridine-3-carbonyl]-2,4-difluoro-phenyl}-2,5-difluoro-benzenesulfonamide (P-0005), N-Acetyl-N-{3-[1-acetyl-5-(1-acetyl-1H-indazol-5-yl)-1H-pyrrolo[2,3-b]pyridine-3-carbonyl]-2,4-difluoro-phenyl}-2,5-difluoro-benzenesulfonamide (P-0006), Propane-1-sulfonic acid {2,4-difluoro-3-[5-(1H-pyrazolo[3,4-b]pyridin-5-yl)-1H-pyrrolo[2,3-b]pyridine-3-carbonyl]-phenyl}-amide (P-0008), Propane-1-sulfonic acid {2,4-difluoro-3-[5-(1H-indazol-4-yl)-1H-pyrrolo[2,3-b]pyridine-3-carbonyl]-phenyl}-amide (P-0009), Propane-1-sulfonic acid {2,4-difluoro-3-[5-(2-methyl-2H-indazol-5-yl)-1H-pyrrolo[2,3-b]pyridine-3-carbonyl]-phenyl}-amide (P-0010), Propane-1-sulfonic acid {2,4-difluoro-3-[5-(2-methyl-2H-indazol-6-yl)-1H-pyrrolo[2,3-b]pyridine-3-carbonyl]-phenyl}-amide (P-0011), Propane-1-sulfonic acid {2,4-difluoro-3-[5-(1H-indol-5-yl)-1H-pyrrolo[2,3-b]pyridine-3-carbonyl]-phenyl}-amide (P-0012), Propane-1-sulfonic acid [3-(5-benzothiazol-5-yl-1H-pyrrolo[2,3-b]pyridine-3-carbonyl)-2,4-difluoro-phenyl]-amide (P-0013), Propane-1-sulfonic acid [2,4-difluoro-3-(5-quinoxalin-6-yl-1H-pyrrolo[2,3-b]pyridine-3-carbonyl)-phenyl]-amide (P-0014), Propane-1-sulfonic acid {2,4-difluoro-3-[5-(2-methyl-2H-indazol-4-yl)-1H-pyrrolo[2,3-b]pyridine-3-carbonyl]-phenyl}-amide (P-0015), Propane-1-sulfonic acid {2,4-difluoro-3-[5-(1-methanesulfonyl-1H-indazol-5-yl)-1H-pyrrolo[2,3-b]pyridine-3-carbonyl]-phenyl}-amide (P-0016), Propane-1-sulfonic acid {3-[1-(2,6-dichloro-benzoyl)-5-(1H-indol-5-yl)-1H-pyrrolo[2,3-b]pyridine-3-carbonyl]-2,4-difluoro-phenyl}-amide (P-0017), Propane-1-sulfonic acid [2,4-difluoro-3-(5-imidazo[1,2-a]pyridin-5-yl-1H-pyrrolo[2,3-b]pyridine-3-carbonyl)-phenyl]-amide (P-0018), Propane-1-sulfonic acid {2,4-difluoro-3-[5-(1H-indol-4-yl)-1H-pyrrolo[2,3-b]pyridine-3-carbonyl]-phenyl}-amide (P-0019), Propane-1-sulfonic acid [3-(5-benzothiazol-6-yl-1H-pyrrolo[2,3-b]pyridine-3-carbonyl)-2,4-difluoro-phenyl]-amide (P-0020), Propane-1-sulfonic acid [2,4-difluoro-3-(5-imidazo[1,2-a]pyridin-2-yl-1H-pyrrolo[2,3-b]pyridine-3-carbonyl)-phenyl]-amide (P-0021), Propane-1-sulfonic acid {2,4-difluoro-3-[5-(7-trifluoromethyl-imidazo[1,2-a]pyrimidin-2-yl)-1H-pyrrolo[2,3-b]pyridine-3-carbonyl]-phenyl}-amide (P-0022), Propane-1-sulfonic acid {2,4-difluoro-3-[5-(3-methyl-1H-indol-5-yl)-1H-pyrrolo[2,3-b]pyridine-3-carbonyl]-phenyl}-amide (P-0023), Propane-1-sulfonic acid {2,4-difluoro-3-[5-(3-methyl-1H-indazol-5-yl)-1H-pyrrolo[2,3-b]pyridine-3-carbonyl]-phenyl}-amide (P-0024), Propane-1-sulfonic acid [2,4-difluoro-3-(5-quinazolin-7-yl-1H-pyrrolo[2,3-b]pyridine-3-carbonyl)-phenyl]-amide (P-0025), Propane-1-sulfonic acid [2,4-difluoro-3-(5-quinazolin-6-yl-1H-pyrrolo[2,3-b]pyridine-3-carbonyl)-phenyl]-amide (P-0026), Propane-1-sulfonic acid {2,4-difluoro-3-[5-(1-methyl-1H-indazol-6-yl)-1H-pyrrolo[2,3-b]pyridine-3-carbonyl]-phenyl}-amide (P-0027), Propane-1-sulfonic acid {2,4-difluoro-3-[5-(1-methyl-1H-indazol-5-yl)-1H-pyrrolo[2,3-b]pyridine-3-carbonyl]-phenyl}-amide (P-0028), Propane-1-sulfonic acid {3-[5-(3-amino-1-methyl-1H-indazol-6-yl)-1H-pyrrolo[2,3-b]pyridine-3-carbonyl]-2,4-difluoro-phenyl}-amide (P-0029), Propane-1-sulfonic acid (2,4-difluoro-3-{5-[2-(2-methylamino-ethyl)-3H-benzoimidazol-5-yl]-1H-pyrrolo[2,3-b]pyridine-3-carbonyl}-phenyl)-amide (P-0030), Propane-1-sulfonic acid {3-[5-(2-amino-1-methyl-1H-benzoimidazol-5-yl)-1H-pyrrolo[2,3-b]pyridine-3-carbonyl]-2,4-difluoro-phenyl}-amide (P-0031), Propane-1-sulfonic acid {3-[5-(2-amino-1H-benzoimidazol-5-yl)-1H-pyrrolo[2,3-b]pyridine-3-carbonyl]-2,4-difluoro-phenyl}-amide (P-0032), Propane-1-sulfonic acid [2,4-difluoro-3-(5-quinolin-7-yl-1H-pyrrolo[2,3-b]pyridine-3-carbonyl)-phenyl]-amide (P-0033), Propane-1-sulfonic acid [2,4-difluoro-3-(5-quinolin-6-yl-1H-pyrrolo[2,3-b]pyridine-3-carbonyl)-phenyl]-amide (P-0034), Propane-1-sulfonic acid {2,4-difluoro-3-[5-(2-methoxy-1-methyl-1H-benzoimidazol-5-yl)-1H-pyrrolo[2,3-b]pyridine-3-carbonyl]-phenyl}-amide (P-0035), Propane-1-sulfonic acid {3-[5-(2-dimethylamino-1-methyl-1H-benzoimidazol-5-yl)-1H-pyrrolo[2,3-b]pyridine-3-carbonyl]-2,4-difluoro-phenyl}-amide (P-0036), Propane-1-sulfonic acid {3-[5-(1,2-dimethyl-1H-benzoimidazol-5-yl)-1H-pyrrolo[2,3-b]pyridine-3-carbonyl]-2,4-difluoro-phenyl}-amide (P-0037), Propane-1-sulfonic acid [3-(5-benzo[1,2,5]thiadiazol-5-yl-1H-pyrrolo[2,3-b]pyridine-3-carbonyl)-2,4-difluoro-phenyl]-amide (P-0038), Propane-1-sulfonic acid {2,4-difluoro-3-[5-(2-methyl-1H-benzoimidazol-5-yl)-1H-pyrrolo[2,3-b]pyridine-3-carbonyl]-phenyl}-amide (P-0039), Propane-1-sulfonic acid (2,4-difluoro-3-{5-[2-(4-methyl-imidazol-1-yl)-thiazol-4-yl]-1H-pyrrolo[2,3-b]pyridine-3-carbonyl}-phenyl)-amide (P-1100), Propane-1-sulfonic acid (2,4-difluoro-3-{5-[2-(2-methyl-imidazol-1-yl)-thiazol-4-yl]-1H-pyrrolo[2,3-b]pyridine-3-carbonyl}-phenyl)-amide (P-1101), Propane-1-sulfonic acid {3-[5-(2-dimethylamino-thiazol-4-yl)-1H-pyrrolo[2,3-b]pyridine-3-carbonyl]-2,4-difluoro-phenyl}-amide (P-1102), Propane-1-sulfonic acid {2,4-difluoro-3-[5-(2-pyrazol-1-yl-thiazol-4-yl)-1H-pyrrolo[2,3-b]pyridine-3-carbonyl]-phenyl}-amide (P-1103), Propane-1-sulfonic acid {2,4-difluoro-3-[5-(2-imidazol-1-yl-thiazol-5-yl)-1H-pyrrolo[2,3-b]pyridine-3-carbonyl]-phenyl}-amide (P-1104), Propane-1-sulfonic acid (2,4-difluoro-3-{5-[2-(2-methyl-imidazol-1-yl)-thiazol-5-yl]-1H-pyrrolo[2,3-b]pyridine-3-carbonyl}-phenyl)-amide (P-1105), Propane-1-sulfonic acid {2,4-difluoro-3-[5-(2-imidazol-1-yl-thiazol-4-yl)-1H-pyrrolo[2,3-b]pyridine-3-carbonyl]-phenyl}-amide (P-1106), Propane-1-sulfonic acid [2,4-difluoro-3-(5-thiazol-4-yl-1H-pyrrolo[2,3-b]pyridine-3-carbonyl)-phenyl]-amide (P-1107), Propane-1-sulfonic acid {2,4-difluoro-3-[5-(2-methyl-thiazol-4-yl)-1H-pyrrolo[2,3-b]pyridine-3-carbonyl]-phenyl}-amide (P-1108), Propane-1-sulfonic acid {2,4-difluoro-3-[5-(2-pyrazol-1-yl-thiazol-5-yl)-1H-pyrrolo[2,3-b]pyridine-3-carbonyl]-phenyl}-amide (P-1109), N-[2,4-Difluoro-3-(5-thiazol-4-yl-1H-pyrrolo[2,3-b]pyridine-3-carbonyl)-phenyl]-2,5-difluoro-benzenesulfonamide (P-1110), N-[2,4-Difluoro-3-(5-thiazol-5-yl-1H-pyrrolo[2,3-b]pyridine-3-carbonyl)-phenyl]-2,5-difluoro-benzenesulfonamide (P-1111), N-{3-[5-(2-Dimethylamino-thiazol-4-yl)-1H-pyrrolo[2,3-b]pyridine-3-carbonyl]-2,4-difluoro-phenyl}-2,5-difluoro-benzenesulfonamide (P-1112), N-{2,4-Difluoro-3-[5-(2-methyl-thiazol-4-yl)-1H-pyrrolo[2,3-b]pyridine-3-carbonyl]-phenyl}-2,5-difluoro-benzenesulfonamide (P-1113), N-{2,4-Difluoro-3-[5-(2-methoxy-thiazol-4-yl)-1H-pyrrolo[2,3-b]pyridine-3-carbonyl]-phenyl}-2,5-difluoro-benzenesulfonamide (P-1114), Propane-1-sulfonic acid (2,4-difluoro-3-{5-[2-(2-oxo-pyrrolidin-1-yl)-thiazol-4-yl]-1H-pyrrolo[2,3-b]pyridine-3-carbonyl}-phenyl)-amide (P-1115), Propane-1-sulfonic acid {2,4-difluoro-3-[5-(2-pyridin-3-yl-thiazol-4-yl)-1H-pyrrolo[2,3-b]pyridine-3-carbonyl]-phenyl}-amide (P-1116), Propane-1-sulfonic acid (2,4-difluoro-3-{5-[2-(4-methyl-imidazol-1-yl)-thiazol-5-yl]-1H-pyrrolo[2,3-b]pyridine-3-carbonyl}-phenyl)-amide (P-1117), Propane-1-sulfonic acid {2,4-difluoro-3-[5-(5-pyridin-3-yl-thiophen-2-yl)-1H-pyrrolo[2,3-b]pyridine-3-carbonyl]-phenyl}-amide (P-1200), Propane-1-sulfonic acid (2,4-difluoro-3-{5-[5-(1H-pyrazol-3-yl)-thiophen-2-yl]-1H-pyrrolo[2,3-b]pyridine-3-carbonyl}-phenyl)-amide (P-1201), 5-{3-[2,6-Difluoro-3-(propane-1-sulfonylamino)-benzoyl]-1H-pyrrolo[2,3-b]pyridin-5-yl}-thiophene-2-sulfonic acid amide (P-1202), Propane-1-sulfonic acid (2,4-difluoro-3-{5-[5-(5-methyl-[1,2,4]oxadiazol-3-yl)-thiophen-2-yl]-1H-pyrrolo[2,3-b]pyridine-3-carbonyl}-phenyl)-amide (P-1203),
Propane-1-sulfonic acid {2,4-difluoro-3-[5-(5-thiazol-2-yl-thiophen-2-yl)-1H-pyrrolo[2,3-b]pyridine-3-carbonyl}-phenyl]-amide (P-1204),
Propane-1-sulfonic acid (2,4-difluoro-3-{5-[5-(1H-pyrazol-3-yl)-thiophen-2-yl]-1H-pyrrolo[2,3-b]pyridine-3-carbonyl}-phenyl)-amide (P-1205),
N-[2,4-Difluoro-3-(5-oxazol-5-yl-1H-pyrrolo[2,3-b]pyridine-3-carbonyl)-phenyl]-2,5-difluoro-benzenesulfonamide (P-1300),
Propane-1-sulfonic acid (2,4-difluoro-3-{5-[5-(2-oxo-2H-pyridin-1-yl)-pyrazin-2-yl]-1H-pyrrolo[2,3-b]pyridine-3-carbonyl}-phenyl)-amide (P-1600),
Propane-1-sulfonic acid {2,4-difluoro-3-[5-(5-pyrazol-1-yl-pyrazin-2-yl)-1H-pyrrolo[2,3-b]pyridine-3-carbonyl]-phenyl}-amide (P-1601),
Propane-1-sulfonic acid {2,4-difluoro-3-[5-(5-imidazol-1-yl-pyrazin-2-yl)-1H-pyrrolo[2,3-b]pyridine-3-carbonyl]-phenyl}-amide (P-1602),
Propane-1-sulfonic acid {3-[5-(5-amino-pyrazin-2-yl)-1H-pyrrolo[2,3-b]pyridine-3-carbonyl]-2,4-difluoro-phenyl}-amide (P-1603), and
any pharmaceutically acceptable salt thereof.

In one embodiment of compounds contemplated herein, the compound is selected from the group consisting of:
Propane-1-sulfonic acid {2,4-difluoro-3-[5-(1H-pyrazolo[3,4-b]pyridin-5-yl)-1H-pyrrolo[2,3-b]pyridine-3-carbonyl]-phenyl}-amide (P-0008),
Propane-1-sulfonic acid {2,4-difluoro-3-[5-(2-methyl-2H-indazol-5-yl)-1H-pyrrolo[2,3-b]pyridine-3-carbonyl]-phenyl}-amide (P-0010),
Propane-1-sulfonic acid {2,4-difluoro-3-[5-(2-methyl-2H-indazol-6-yl)-1H-pyrrolo[2,3-b]pyridine-3-carbonyl]-phenyl}-amide (P-0011),
Propane-1-sulfonic acid {2,4-difluoro-3-[5-(1H-indol-5-yl)-1H-pyrrolo[2,3-b]pyridine-3-carbonyl]-phenyl}-amide (P-0012),
Propane-1-sulfonic acid [3-(5-benzothiazol-5-yl-1H-pyrrolo[2,3-b]pyridine-3-carbonyl)-2,4-difluoro-phenyl]-amide (P-0013),
Propane-1-sulfonic acid [2,4-difluoro-3-(5-quinoxalin-6-yl-1H-pyrrolo[2,3-b]pyridine-3-carbonyl)-phenyl]-amide (P-0014),
Propane-1-sulfonic acid [3-(5-benzothiazol-6-yl-1H-pyrrolo[2,3-b]pyridine-3-carbonyl)-2,4-difluoro-phenyl]-amide (P-0020),
Propane-1-sulfonic acid [2,4-difluoro-3-(5-imidazo[1,2-a]pyridin-2-yl-1H-pyrrolo[2,3-b]pyridine-3-carbonyl)-phenyl]-amide (P-0021),
Propane-1-sulfonic acid {2,4-difluoro-3-[5-(3-methyl-1H-indol-5-yl)-1H-pyrrolo[2,3-b]pyridine-3-carbonyl]-phenyl}-amide (P-0023),
Propane-1-sulfonic acid {2,4-difluoro-3-[5-(3-methyl-1H-indazol-5-yl)-1H-pyrrolo[2,3-b]pyridine-3-carbonyl]-phenyl}-amide (P-0024),
Propane-1-sulfonic acid [2,4-difluoro-3-(5-quinazolin-7-yl-1H-pyrrolo[2,3-b]pyridine-3-carbonyl)-phenyl]-amide (P-0025),
Propane-1-sulfonic acid [2,4-difluoro-3-(5-quinazolin-6-yl-1H-pyrrolo[2,3-b]pyridine-3-carbonyl)-phenyl]-amide (P-0026),
Propane-1-sulfonic acid (2,4-difluoro-3-{5-[2-(4-methyl-imidazol-1-yl)-thiazol-4-yl]-1H-pyrrolo[2,3-b]pyridine-3-carbonyl}-phenyl)-amide (P-1100),
Propane-1-sulfonic acid (2,4-difluoro-3-{5-[2-(2-methyl-imidazol-1-yl)-thiazol-4-yl]-1H-pyrrolo[2,3-b]pyridine-3-carbonyl}-phenyl)-amide (P-1101),
Propane-1-sulfonic acid {2,4-difluoro-3-[5-(2-pyrazol-1-yl-thiazol-4-yl)-1H-pyrrolo[2,3-b]pyridine-3-carbonyl]-phenyl}-amide (P-1103),
Propane-1-sulfonic acid {2,4-difluoro-3-[5-(2-imidazol-1-yl-thiazol-5-yl)-1H-pyrrolo[2,3-b]pyridine-3-carbonyl]-phenyl}-amide (P-1104),
Propane-1-sulfonic acid (2,4-difluoro-3-{5-[2-(2-methyl-imidazol-1-yl)-thiazol-5-yl]-1H-pyrrolo[2,3-b]pyridine-3-carbonyl}-phenyl)-amide (P-1105),
Propane-1-sulfonic acid {2,4-difluoro-3-[5-(2-imidazol-1-yl-thiazol-4-yl)-1H-pyrrolo[2,3-b]pyridine-3-carbonyl]-phenyl}-amide (P-1106),
Propane-1-sulfonic acid {2,4-difluoro-3-[5-(2-pyrazol-1-yl-thiazol-5-yl)-1H-pyrrolo[2,3-b]pyridine-3-carbonyl]-phenyl}-amide (P-1109),
Propane-1-sulfonic acid {2,4-difluoro-3-[5-(5-pyridin-3-yl-thiophen-2-yl)-1H-pyrrolo[2,3-b]pyridine-3-carbonyl]-phenyl}-amide (P-1200),
Propane-1-sulfonic acid (2,4-difluoro-3-{5-[5-(1H-pyrazol-3-yl)-thiophen-2-yl]-1H-pyrrolo[2,3-b]pyridine-3-carbonyl}-phenyl)-amide (P-1201),
5-{3-[2,6-Difluoro-3-(propane-1-sulfonylamino)-benzoyl]-1H-pyrrolo[2,3-b]pyridin-5-yl}-thiophene-2-sulfonic acid amide (P-1202),
N-[2,4-Difluoro-3-(5-oxazol-5-yl-1H-pyrrolo[2,3-b]pyridine-3-carbonyl)-phenyl]-2,5-difluoro-benzenesulfonamide (P-1300), and
any pharmaceutically acceptable salt thereof.

In one embodiment of compounds contemplated herein, the compound is selected from the group consisting of:
Propane-1-sulfonic acid {2,4-difluoro-3-[5-(1H-indazol-5-yl)-1H-pyrrolo[2,3-b]pyridine-3-carbonyl]-phenyl}-amide (P-0001),
N-{2,4-Difluoro-3-[5-(1H-indazol-5-yl)-1H-pyrrolo[2,3-b]pyridine-3-carbonyl]-phenyl}-2,5-difluoro-benzenesulfonamide (P-0002),
5-{3-[3-(2,5-Difluoro-benzenesulfonylamino)-2,6-difluoro-benzoyl]-1H-pyrrolo[2,3-b]pyridin-5-yl}-indazole-1-carboxylic acid methylamide (P-0003),
N-{3-[1-Acetyl-5-(1-acetyl-1H-indazol-5-yl)-1H-pyrrolo[2,3-b]pyridine-3-carbonyl]-2,4-difluoro-phenyl}-2,5-difluoro-benzenesulfonamide (P-0004),
N-{3-[5-(1-Acetyl-1H-indazol-5-yl)-1H-pyrrolo[2,3-b]pyridine-3-carbonyl]-2,4-difluoro-phenyl}-2,5-difluoro-benzenesulfonamide (P-0005),
N-Acetyl-N-{3-[1-acetyl-5-(1-acetyl-1H-indazol-5-yl)-1H-pyrrolo[2,3-b]pyridine-3-carbonyl]-2,4-difluoro-phenyl}-2,5-difluoro-benzenesulfonamide (P-0006),
Propane-1-sulfonic acid {3-[5-(1-acetyl-1H-indazol-5-yl)-1H-pyrrolo[2,3-b]pyridine-3-carbonyl]-2,4-difluoro-phenyl}-amide (P-0007),
Propane-1-sulfonic acid {2,4-difluoro-3-[5-(1H-pyrazolo[3,4-b]pyridin-5-yl)-1H-pyrrolo[2,3-b]pyridine-3-carbonyl]-phenyl}-amide (P-0008),
Propane-1-sulfonic acid {2,4-difluoro-3-[5-(2-methyl-2H-indazol-5-yl)-1H-pyrrolo[2,3-b]pyridine-3-carbonyl]-phenyl}-amide (P-0010),
Propane-1-sulfonic acid {2,4-difluoro-3-[5-(2-methyl-2H-indazol-6-yl)-1H-pyrrolo[2,3-b]pyridine-3-carbonyl]-phenyl}-amide (P-0011),
Propane-1-sulfonic acid {2,4-difluoro-3-[5-(1H-indol-5-yl)-1H-pyrrolo[2,3-b]pyridine-3-carbonyl]-phenyl}-amide (P-0012), Propane-1-sulfonic acid [3-(5-benzothiazol-5-yl-1H-pyrrolo[2,3-b]pyridine-3-carbonyl)-2,4-difluoro-phenyl]-amide (P-0013), Propane-1-sulfonic acid [2,4-difluoro-3-(5-quinoxalin-6-yl-1H-pyrrolo[2,3-b]pyridine-3-carbonyl)-phenyl]-amide (P-0014), Propane-1-sulfonic acid {2,4-difluoro-3-[5-(2-methyl-2H-indazol-4-yl)-1H-pyrrolo[2,3-b]pyridine-3-carbonyl]-phenyl}-amide (P-0015), Propane-1-sulfonic acid {2,4-difluoro-3-[5-(1-methanesulfonyl-1H-indazol-5-yl)-1H-pyrrolo[2,3-b]pyridine-3-carbonyl]-phenyl}-amide (P-0016), Propane-1-sulfonic acid [2,4-difluoro-3-(5-imidazo[1,2-a]pyridin-5-yl-1H-pyrrolo[2,3-b]pyridine-3-carbonyl)-phenyl]-amide (P-0018), Propane-1-sulfonic acid {2,4-difluoro-3-[5-(1H-indol-4-yl)-1H-pyrrolo[2,3-b]pyridine-3-carbonyl]-phenyl}-amide (P-0019), Propane-1-sulfonic acid [3-(5-benzothiazol-6-yl-1H-pyrrolo[2,3-b]pyridine-3-carbonyl)-2,4-difluoro-phenyl]-amide (P-0020), Propane-1-sulfonic acid [2,4-difluoro-3-(5-imidazo[1,2-a]pyridin-2-yl-1H-pyrrolo[2,3-b]pyridine-3-carbonyl)-phenyl]-amide (P-0021), Propane-1-sulfonic acid {2,4-difluoro-3-[5-(7-trifluoromethyl-imidazo[1,2-a]pyrimidin-2-yl)-1H-pyrrolo[2,3-b]pyridine-3-carbonyl]-phenyl}-amide (P-0022), Propane-1-sulfonic acid {2,4-difluoro-3-[5-(3-methyl-1H-indol-5-yl)-1H-pyrrolo[2,3-b]pyridine-3-carbonyl]-phenyl}-amide (P-0023), Propane-1-sulfonic acid {2,4-difluoro-3-[5-(3-methyl-1H-indazol-5-yl)-1H-pyrrolo[2,3-b]pyridine-3-carbonyl]-phenyl}-amide (P-0024), Propane-1-sulfonic acid [2,4-difluoro-3-(5-quinazolin-7-yl-1H-pyrrolo[2,3-b]pyridine-3-carbonyl)-phenyl]-amide (P-0025), Propane-1-sulfonic acid [2,4-difluoro-3-(5-quinazolin-6-yl-1H-pyrrolo[2,3-b]pyridine-3-carbonyl)-phenyl]-amide (P-0026), Propane-1-sulfonic acid {2,4-difluoro-3-[5-(1-methyl-1H-indazol-6-yl)-1H-pyrrolo[2,3-b]pyridine-3-carbonyl]-phenyl}-amide (P-0027), Propane-1-sulfonic acid {2,4-difluoro-3-[5-(1-methyl-1H-indazol-5-yl)-1H-pyrrolo[2,3-b]pyridine-3-carbonyl]-phenyl}-amide (P-0028), Propane-1-sulfonic acid {3-[5-(3-amino-1-methyl-1H-indazol-6-yl)-1H-pyrrolo[2,3-b]pyridine-3-carbonyl]-2,4-difluoro-phenyl}-amide (P-0029), Propane-1-sulfonic acid (2,4-difluoro-3-{5-[2-(2-methyl-amino-ethyl)-3H-benzoimidazol-5-yl]-1H-pyrrolo[2,3-b]pyridine-3-carbonyl}-phenyl)-amide (P-0030), Propane-1-sulfonic acid {3-[5-(2-amino-1-methyl-1H-benzoimidazol-5-yl)-1H-pyrrolo[2,3-b]pyridine-3-carbonyl]-2,4-difluoro-phenyl}-amide (P-0031), Propane-1-sulfonic acid {3-[5-(2-amino-1H-benzoimidazol-5-yl)-1H-pyrrolo[2,3-b]pyridine-3-carbonyl]-2,4-difluoro-phenyl}-amide (P-0032), Propane-1-sulfonic acid [2,4-difluoro-3-(5-quinolin-7-yl-1H-pyrrolo[2,3-b]pyridine-3-carbonyl)-phenyl]-amide (P-0033), Propane-1-sulfonic acid [2,4-difluoro-3-(5-quinolin-6-yl-1H-pyrrolo[2,3-b]pyridine-3-carbonyl)-phenyl]-amide (P-0034), Propane-1-sulfonic acid {2,4-difluoro-3-[5-(2-methoxy-1-methyl-1H-benzoimidazol-5-yl)-1H-pyrrolo[2,3-b]pyridine-3-carbonyl]-phenyl}-amide (P-0035), Propane-1-sulfonic acid {3-[5-(2-dimethylamino-1-methyl-1H-benzoimidazol-5-yl)-1H-pyrrolo[2,3-b]pyridine-3-carbonyl]-2,4-difluoro-phenyl}-amide (P-0036), Propane-1-sulfonic acid {3-[5-(1,2-dimethyl-1H-benzoimidazol-5-yl)-1H-pyrrolo[2,3-b]pyridine-3-carbonyl]-2,4-difluoro-phenyl}-amide (P-0037), Propane-1-sulfonic acid [3-(5-benzo[1,2,5]thiadiazol-5-yl-1H-pyrrolo[2,3-b]pyridine-3-carbonyl)-2,4-difluoro-phenyl]-amide (P-0038), and any pharmaceutically acceptable salt thereof.

In one embodiment of compounds contemplated herein, the compound is selected from the group consisting of:

Propane-1-sulfonic acid (2,4-difluoro-3-{5-[2-(4-methyl-imidazol-1-yl)-thiazol-4-yl]-1H-pyrrolo[2,3-b]pyridine-3-carbonyl}-phenyl)-amide (P-1100), Propane-1-sulfonic acid (2,4-difluoro-3-{5-[2-(2-methyl-imidazol-1-yl)-thiazol-4-yl]-1H-pyrrolo[2,3-b]pyridine-3-carbonyl}-phenyl)-amide (P-1101), Propane-1-sulfonic acid {3-[5-(2-dimethylamino-thiazol-4-yl)-1H-pyrrolo[2,3-b]pyridine-3-carbonyl]-2,4-difluoro-phenyl}-amide (P-1102), Propane-1-sulfonic acid {2,4-difluoro-3-[5-(2-pyrazol-1-yl-thiazol-4-yl)-1H-pyrrolo[2,3-b]pyridine-3-carbonyl]-phenyl}-amide (P-1103), Propane-1-sulfonic acid {2,4-difluoro-3-[5-(2-imidazol-1-yl-thiazol-5-yl)-1H-pyrrolo[2,3-b]pyridine-3-carbonyl]-phenyl}-amide (P-1104), Propane-1-sulfonic acid (2,4-difluoro-3-{5-[2-(2-methyl-imidazol-1-yl)-thiazol-5-yl]-1H-pyrrolo[2,3-b]pyridine-3-carbonyl}-phenyl)-amide (P-1105), Propane-1-sulfonic acid {2,4-difluoro-3-[5-(2-imidazol-1-yl-thiazol-4-yl)-1H-pyrrolo[2,3-b]pyridine-3-carbonyl]-phenyl}-amide (P-1106), Propane-1-sulfonic acid [2,4-difluoro-3-(5-thiazol-4-yl-1H-pyrrolo[2,3-b]pyridine-3-carbonyl)-phenyl]-amide (P-1107), Propane-1-sulfonic acid {2,4-difluoro-3-[5-(2-methyl-thiazol-4-yl)-1H-pyrrolo[2,3-b]pyridine-3-carbonyl]-phenyl}-amide (P-1108), Propane-1-sulfonic acid {2,4-difluoro-3-[5-(2-pyrazol-1-yl-thiazol-5-yl)-1H-pyrrolo[2,3-b]pyridine-3-carbonyl]-phenyl}-amide (P-1109), N-[2,4-Difluoro-3-(5-thiazol-4-yl-1H-pyrrolo[2,3-b]pyridine-3-carbonyl)-phenyl]-2,5-difluoro-benzenesulfonamide (P-1110), N-[2,4-Difluoro-3-(5-thiazol-5-yl-1H-pyrrolo[2,3-b]pyridine-3-carbonyl)-phenyl]-2,5-difluoro-benzenesulfonamide (P-1111), N-{3-[5-(2-Dimethylamino-thiazol-4-yl)-1H-pyrrolo[2,3-b]pyridine-3-carbonyl]-2,4-difluoro-phenyl}-2,5-difluoro-benzenesulfonamide (P-1112), N-{2,4-Difluoro-3-[5-(2-methyl-thiazol-4-yl)-1H-pyrrolo[2,3-b]pyridine-3-carbonyl]-phenyl}-2,5-difluoro-benzenesulfonamide (P-1113), N-{2,4-Difluoro-3-[5-(2-methoxy-thiazol-4-yl)-1H-pyrrolo[2,3-b]pyridine-3-carbonyl]-phenyl}-2,5-difluoro-benzenesulfonamide (P-1114), Propane-1-sulfonic acid (2,4-difluoro-3-{5-[2-(2-oxo-pyrrolidin-1-yl)-thiazol-4-yl]-1H-pyrrolo[2,3-b]pyridine-3-carbonyl}-phenyl)-amide (P-1115), Propane-1-sulfonic acid {2,4-difluoro-3-[5-(2-pyridin-3-yl-thiazol-4-yl)-1H-pyrrolo[2,3-b]pyridine-3-carbonyl]-phenyl}-amide (P-1116), Propane-1-sulfonic acid (2,4-difluoro-3-{5-[2-(4-methyl-imidazol-1-yl)-thiazol-5-yl]-1H-pyrrolo[2,3-b]pyridine-3-carbonyl}-phenyl)-amide (P-1117), and any pharmaceutically acceptable salt thereof.

In one embodiment of compounds contemplated herein, the compound is selected from the group consisting of:

Propane-1-sulfonic acid {2,4-difluoro-3-[5-(5-pyridin-3-yl-thiophen-2-yl)-1H-pyrrolo[2,3-b]pyridine-3-carbonyl]-phenyl}-amide (P-1200), Propane-1-sulfonic acid (2,4-difluoro-3-{5-[5-(1H-pyrazol-3-yl)-thiophen-2-yl]-1H-pyrrolo[2,3-b]pyridine-3-carbonyl}-phenyl)-amide (P-1201), 5-{3-[2,6-Difluoro-3-(propane-1-sulfonylamino)-benzoyl]-1H-pyrrolo[2,3-b]pyridin-5-yl}-thiophene-2-sulfonic acid amide (P-1202), Propane-1-sulfonic acid (2,4-difluoro-3-{5-[5-(5-methyl-[1,2,4]oxadiazol-3-yl)-thiophen-2-yl]-1H-pyrrolo[2,3-b]pyridine-3-carbonyl}-phenyl)-amide (P-1203), Propane-1-sulfonic acid {2,4-difluoro-3-[5-(5-thiazol-2-yl-thiophen-2-yl)-1H-pyrrolo[2,3-b]pyridine-3-carbonyl]-phenyl}-amide (P-1204), Propane-1-sulfonic acid (2,4-difluoro-3-{5-[5-(1H-pyrazol-3-yl)-thiophen-2-yl]-1H-pyrrolo[2,3-b]pyridine-3-carbonyl}-phenyl)-amide (P-1205), and any pharmaceutically acceptable salt thereof.

In one embodiment of compounds contemplated herein, the compound is selected from the group consisting of:

Propane-1-sulfonic acid (2,4-difluoro-3-{5-[5-(2-oxo-2H-pyridin-1-yl)-pyrazin-2-yl]-1H-pyrrolo[2,3-b]pyridine-3-carbonyl}-phenyl)-amide (P-1600), Propane-1-sulfonic acid {2,4-difluoro-3-[5-(5-pyrazol-1-yl-pyrazin-2-yl)-1H-pyrrolo[2,3-b]pyridine-3-carbonyl]-phenyl}-amide (P-1601), Propane-1-sulfonic acid {2,4-difluoro-3-[5-(5-imidazol-1-yl-pyrazin-2-yl)-1H-pyrrolo[2,3-b]pyridine-3-carbonyl]-phenyl}-amide (P-1602), Propane-1-sulfonic acid {3-[5-(5-amino-pyrazin-2-yl)-1H-pyrrolo[2,3-b]pyridine-3-carbonyl]-2,4-difluoro-phenyl}-amide (P-1603), and any pharmaceutically acceptable salt thereof.

In a second aspect, compounds are provided, wherein the compound is selected from the group consisting of:

4-(4-{3-[2,6-Difluoro-3-(propane-1-sulfonylamino)-benzoyl]-1H-pyrrolo[2,3-b]pyridin-5-yl}-pyrazol-1-yl)-piperidine-1-carboxylic acid tert-butyl ester (P-1001), Propane-1-sulfonic acid {2,4-difluoro-3-[5-(1-piperidin-4-yl-1H-pyrazol-4-yl)-1H-pyrrolo[2,3-b]pyridine-3-carbonyl]-phenyl}-amide (P-1002), 4-(4-{3-[2,6-Difluoro-3-(4-trifluoromethyl-benzenesulfonylamino)-benzoyl]-1H-pyrrolo[2,3-b]pyridin-5-yl}-pyrazol-1-yl)-piperidine-1-carboxylic acid tert-butyl ester (P-1003), N-{2,4-Difluoro-3-[5-(1-piperidin-4-yl-1H-pyrazol-4-yl)-1H-pyrrolo[2,3-b]pyridine-3-carbonyl]-phenyl}-4-trifluoromethyl-benzenesulfonamide (P-1004), Propane-1-sulfonic acid {2,4-difluoro-3-[5-(1-pyrimidin-2-yl-1H-pyrazol-4-yl)-1H-pyrrolo[2,3-b]pyridine-3-carbonyl]phenyl}-amide (P-1005), Propane-1-sulfonic acid (3-{5-[3,5-dimethyl-1-(1H-tetrazol-5-yl)-1H-pyrazol-4-yl]-1H-pyrrolo[2,3-b]pyridine-3-carbonyl}-2,4-difluoro-phenyl)-amide (P-1006), Propane-1-sulfonic acid (3-{5-[1-(1,3-dimethyl-1H-pyrazole-4-sulfonyl)-3,5-dimethyl-1H-pyrazol-4-yl]-1H-pyrrolo[2,3-b]pyridine-3-carbonyl}-2,4-difluoro-phenyl)-amide (P-1007), Propane-1-sulfonic acid (2,4-difluoro-3-{5-[1-(1H-tetrazol-5-yl)-1H-pyrazol-4-yl]-1H-pyrrolo[2,3-b]pyridine-3-carbonyl}-phenyl)-amide (P-1008), N-{2,4-Difluoro-3-[5-(1-methyl-1H-pyrazol-4-yl)-1H-pyrrolo[2,3-b]pyridine-3-carbonyl]-phenyl}-2,5-difluoro-benzenesulfonamide (P-1009), N-{3-[5-(2,5-Dimethyl-2H-pyrazol-3-yl)-1H-pyrrolo[2,3-b]pyridine-3-carbonyl]-2,4-difluoro-phenyl}-2,5-difluoro-benzenesulfonamide (P-1010), N-{2,4-Difluoro-3-[5-(1-methyl-1H-pyrazol-3-yl)-1H-pyrrolo[2,3-b]pyridine-3-carbonyl]-phenyl}-2,5-difluoro-benzenesulfonamide (P-1011), Propane-1-sulfonic acid {2,4-difluoro-3-[5-(1-methyl-1H-pyrazol-3-yl)-1H-pyrrolo[2,3-b]pyridine-3-carbonyl]-phenyl}-amide (P-1012), Propane-1-sulfonic acid {2,4-difluoro-3-[5-(1-pyridin-2-yl-1H-pyrazol-4-yl)-1H-pyrrolo[2,3-b]pyridine-3-carbonyl]-phenyl}-amide (P-1013), 4-{3-[2,6-Difluoro-3-(propane-1-sulfonylamino)-benzoyl]-1H-pyrrolo[2,3-b]pyridin-5-yl}-pyrazole-1-carboxylic acid amide (P-1014), Propane-1-sulfonic acid {2,4-difluoro-3-[5-(1-pyrazin-2-yl-1H-pyrazol-4-yl)-1H-pyrrolo[2,3-b]pyridine-3-carbonyl]-phenyl}-amide (P-1015), 4-{3-[2,6-Difluoro-3-(propane-1-sulfonylamino)-benzoyl]-1H-pyrrolo[2,3-b]pyridin-5-yl}-pyrazole-1-carboxylic acid phenyl ester (P-1016), Propane-1-sulfonic acid [2,4-difluoro-3-(5-pyridin-2-yl-1H-pyrrolo[2,3-b]pyridine-3-carbonyl)-phenyl]-amide (P-1401), N-[2,4-Difluoro-3-(5-pyridin-3-yl-1H-pyrrolo[2,3-b]pyridine-3-carbonyl)-phenyl]-2,5-difluoro-benzenesulfonamide (P-1402), N-[2,4-Difluoro-3-(5-pyridin-4-yl-1H-pyrrolo[2,3-b]pyridine-3-carbonyl)-phenyl]-2,5-difluoro-benzenesulfonamide (P-1403), N-{2,4-Difluoro-3-[5-(6-methoxy-pyridin-3-yl)-1H-pyrrolo[2,3-b]pyridine-3-carbonyl]-phenyl}-2,5-difluoro-benzenesulfonamide (P-1404), N-{2,4-Difluoro-3-[5-(3-fluoro-pyridin-4-yl)-1H-pyrrolo[2,3-b]pyridine-3-carbonyl]-phenyl}-2,5-difluoro-benzenesulfonamide (P-1405), N-{3-[5-(2,6-Dimethoxy-pyridin-3-yl)-1H-pyrrolo[2,3-b]pyridine-3-carbonyl]-2,4-difluoro-phenyl}-2,5-difluoro-benzenesulfonamide (P-1406), N-{2,4-Difluoro-3-[5-(5-methanesulfonyl-pyridin-3-yl)-1H-pyrrolo[2,3-b]pyridine-3-carbonyl]-phenyl}-2,5-difluoro-benzenesulfonamide (P-1407), N-{2,4-Difluoro-3-[5-(6-methyl-pyridin-3-yl)-1H-pyrrolo[2,3-b]pyridine-3-carbonyl]-phenyl}-2,5-difluoro-benzenesulfonamide (P-1408), N-{3-[5-(6-Dimethylamino-pyridin-3-yl)-1H-pyrrolo[2,3-b]pyridine-3-carbonyl]-2,4-difluoro-phenyl}-2,5-difluoro-benzenesulfonamide (P-1409), N-(3-{5-[6-(3-Dimethylamino-propoxy)-pyridin-3-yl]-1H-pyrrolo[2,3-b]pyridine-3-carbonyl}-2,4-difluoro-phenyl)-2,5-difluoro-benzenesulfonamide (P-1411), N-[2,4-Difluoro-3-(5-pyrimidin-5-yl-1H-pyrrolo[2,3-b]pyridine-3-carbonyl)-phenyl]-2,5-difluoro-benzenesulfonamide (P-1500), N-{3-[5-(2,4-Dimethoxy-pyrimidin-5-yl)-1H-pyrrolo[2,3-b]pyridine-3-carbonyl]-2,4-difluoro-phenyl}-2,5-difluoro-benzenesulfonamide (P-1501), N-{3-[5-(2-Dimethylamino-pyrimidin-5-yl)-1H-pyrrolo[2,3-b]pyridine-3-carbonyl]-2,4-difluoro-phenyl}-2,5-difluoro-benzenesulfonamide (P-1502), N-{2,4-Difluoro-3-[5-(2-methyl-pyrimidin-5-yl)-1H-pyrrolo[2,3-b]pyridine-3-carbonyl]-phenyl}-2,5-difluoro-benzenesulfonamide (P-1503), Propane-1-sulfonic acid {3-[5-(2-cyclopropylamino-pyrimidin-5-yl)-1H-pyrrolo[2,3-b]pyridine-3-carbonyl]-2,4-difluoro-phenyl}-amide (P-1504), Propane-1-sulfonic acid (2,4-difluoro-3-{5-[2-(2-methoxy-ethylamino)-pyrimidin-5-yl]-1H-pyrrolo[2,3-b]pyridine-3-carbonyl}-phenyl)-amide (P-1505), N-{3-[5-(2-Cyclopropylamino-pyrimidin-5-yl)-1H-pyrrolo[2,3-b]pyridine-3-carbonyl]-2,4-difluoro-phenyl}-2,5-difluoro-benzenesulfonamide (P-1506), N-(2,4-Difluoro-3-{5-[2-(2-methoxy-ethylamino)-pyrimidin-5-yl]-1H-pyrrolo[2,3-b]pyridine-3-carbonyl}-phenyl)-2,5-difluoro-benzenesulfonamide (P-1507), Propane-1-sulfonic acid (2,4-difluoro-3-{5-[2-(pyridin-3-yloxy)-pyrimidin-5-yl]-1H-pyrrolo[2,3-b]pyridine-3-carbonyl}-phenyl)-amide (P-1508), Propane-1-sulfonic acid {2,4-difluoro-3-[5-(2-tri fluoromethoxy-pyrimidin-5-yl)-1H-pyrrolo[2,3-b]pyridine-3-carbonyl]-phenyl}-amide (P-1509), Propane-1-sulfonic acid {3-[5-(2-cyano-pyrimidin-5-yl)-1H-pyrrolo[2,3-b]pyridine-3-carbonyl]-2,4-difluoro-phenyl}-amide (P-1510), Propane-1-sulfonic acid {2,4-difluoro-3-[5-(2-imidazol-1-yl-pyrimidin-5-yl)-1H-pyrrolo[2,3-b]pyridine-3-carbonyl]-phenyl}-amide (P-1511), Propane-1-sulfonic acid {3-[5-(2-azetidin-1-yl-pyrimidin-5-yl)-1H-pyrrolo[2,3-b]pyridine-3-carbonyl]-2,4-difluoro-phenyl}-amide (P-1512), Propane-1-sulfonic acid {2,4-difluoro-3-[5-(2-isopropylamino-pyrimidin-5-yl)-1H-pyrrolo[2,3-b]pyridine-3-carbonyl]-phenyl}-amide (P-1513), Propane-1-sulfonic acid {2,4-difluoro-3-[5-(2-methylamino-pyrimidin-5-yl)-1H-pyrrolo[2,3-b]pyridine-3-carbonyl]-phenyl}-amide (P-1514), Propane-1-sulfonic acid (3-{5-[2-(2-dimethylamino-ethylamino)-pyrimidin-5-yl]-1H-pyrrolo[2,3-b]pyridine-3-carbonyl}-2,4-difluoro-phenyl)-amide (P-1515), Propane-1-sulfonic acid (2,4-difluoro-3-{5-[2-(3-methoxy-propylamino)-pyrimidin-5-yl]-1H-pyrrolo[2,3-b]pyridine-3-carbonyl}-phenyl)-amide (P-1516), Propane-1-sulfonic acid {2,4-difluoro-3-[5-(2-isopropylamino-pyrimidin-5-yl)-1H-pyrrolo[2,3-b]pyridine-3-carbonyl]-phenyl}-amide (P-1517), 2-Fluoro-N-{2-fluoro-3-[5-(2-methoxy-pyrimidin-5-yl)-1H-pyrrolo[2,3-b]pyridine-3-carbonyl]-phenyl}-benzenesulfonamide (P-1518), Propane-1-sulfonic acid {2,4-difluoro-3-[5-(2-isopropyl-pyrimidin-5-yl)-1H-pyrrolo[2,3-b]pyridine-3-carbonyl]-phenyl}-amide (P-1519), N-{2,4-Difluoro-3-[5-(2-methyl-pyrimidin-5-yl)-1H-pyrrolo[2,3-b]pyridine-3-carbonyl]-phenyl}-2-fluoro-benzenesulfonamide (P-1520), N-{2,4-Difluoro-3-[5-(2-isopropyl-pyrimidin-5-yl)-1H-pyrrolo[2,3-b]pyridine-3-carbonyl]-phenyl}-2,5-difluoro-benzenesulfonamide (P-1521), 2-Chloro-5-{3-[2,6-difluoro-3-(propane-1-sulfonylamino)-benzoyl]-1H-pyrrolo[2,3-b]pyridin-5-yl}-benzamide (P-1700), Propane-1-sulfonic acid {2,4-difluoro-3-[5-(1-oxo-2,3-dihydro-1H-isoindol-5-yl)-1H-pyrrolo[2,3-b]pyridine-3-carbonyl]-phenyl}-amide (P-1701), Propane-1-sulfonic acid {2,4-difluoro-3-[5-(3-oxo-2,3-dihydro-1H-isoindol-5-yl)-1H-pyrrolo[2,3-b]pyridine-3-carbonyl]-phenyl}-amide (P-1702), Propane-1-sulfonic acid {2,4-difluoro-3-[5-(2-oxo-2,3-dihydro-1H-indol-5-yl)-1H-pyrrolo[2,3-b]pyridine-3-carbonyl]-phenyl}-amide (P-1703), 3-{3-[3-(2,5-Difluoro-benzenesulfonylamino)-2,6-difluoro-benzoyl]-1H-pyrrolo[2,3-b]pyridin-5-yl}-N-methoxy-benzamide (P-1704), 4-{3-[3-(2,5-Difluoro-benzenesulfonylamino)-2,6-difluoro-benzoyl]-1,4-pyrrolo[2,3-b]pyridin-5-yl}-N-methoxy-benzamide (P-1705), N-{2,4-Difluoro-3-[5-(4-methylsulfamoyl-phenyl)-1H-pyrrolo[2,3-b]pyridine-3-carbonyl]-phenyl}-2,5-difluoro-benzenesulfonamide (P-1706), N-{2,4-Difluoro-3-[5-(4-sulfamoyl-phenyl)-1H-pyrrolo[2,3-b]pyridine-3-carbonyl]-phenyl}-2,5-difluoro-benzenesulfonamide (P-1707), N-{3-[2,6-Difluoro-3-(propane-1-sulfonylamino)-benzoyl]-1H-pyrrolo[2,3-b]pyridin-5-yl}-nicotinamide (P-1800), 3-[2,6-Difluoro-3-(propane-1-sulfonylamino)-benzoyl]-1H-pyrrolo[2,3-b]pyridine-5-carboxylic acid pyridin-3-ylamide (P-1801), 5-Methyl-2,3-dihydro-isoxazole-3-carboxylic acid {3-[2,6-difluoro-3-(propane-1-sulfonylamino)-benzoyl]-1H-pyrrolo[2,3-b]pyridin-5-yl}-amide (P-1802), and any pharmaceutically acceptable salt thereof.

In one embodiment of the second aspect, the compound is selected from the group consisting of:

4-(4-{3-[2,6-Difluoro-3-(propane-1-sulfonylamino)-benzoyl]-1H-pyrrolo[2,3-b]pyridin-5-yl}-pyrazol-1-yl)-piperidine-1-carboxylic acid tert-butyl ester (P-1001), Propane-1-sulfonic acid {2,4-difluoro-3-[5-(1-piperidin-4-yl-1H-pyrazol-4-yl)-1H-pyrrolo[2,3-b]pyridine-3-carbonyl]-phenyl}-amide (P-1002), Propane-1-sulfonic acid {2,4-difluoro-3-[5-(1-pyrimidin-2-yl-1H-pyrazol-4-yl)-1H-pyrrolo[2,3-b]pyridine-3-carbonyl]-phenyl}-amide (P-1005), N-{2,4-Difluoro-3-[5-(1-methyl-1H-pyrazol-4-yl)-1H-pyrrolo[2,3-b]pyridine-3-carbonyl]-phenyl}-2,5-difluoro-benzenesulfonamide (P-1009), Propane-1-sulfonic acid [2,4-difluoro-3-(5-pyridin-2-yl-1H-pyrrolo[2,3-b]pyridine-3-carbonyl)-phenyl]-amide (P-1401), N-[2,4-Difluoro-3-(5-pyridin-3-yl-1H-pyrrolo[2,3-b]pyridine-3-carbonyl)-phenyl]-2,5-difluoro-benzenesulfonamide (P-1402), N-[2,4-Difluoro-3-(5-pyridin-4-yl-1H-pyrrolo[2,3-b]pyridine-3-carbonyl)-phenyl]-2,5-difluoro-benzenesulfonamide (P-1403), N-{2,4-Difluoro-3-[5-(6-methoxy-pyridin-3-yl)-1H-pyrrolo[2,3-b]pyridine-3-carbonyl]-phenyl}-2,5-difluoro-benzenesulfonamide (P-1404), N-{2,4-Difluoro-3-[5-(5-methanesulfonyl-pyridin-3-yl)-1H-pyrrolo[2,3-b]pyridine-3-carbonyl]-phenyl}-2,5-difluoro-benzenesulfonamide (P-1407), N-{2,4-Difluoro-3-[5-(6-methyl-pyridin-3-yl)-1H-pyrrolo[2,3-b]pyridine-3-carbonyl]-phenyl}-2,5-difluoro-benzenesulfonamide (P-1408), N-{3-[5-(6-Dimethylamino-pyridin-3-yl)-1H-pyrrolo[2,3-b]pyridine-3-carbonyl]-2,4-difluoro-phenyl}-2,5-difluoro-benzenesulfonamide (P-1409), N-(3-{5-[6-(3-Dimethylamino-propoxy)-pyridin-3-yl]-1H-pyrrolo[2,3-b]pyridine-3-carbonyl}-2,4-difluoro-phenyl)-2,5-difluoro-benzenesulfonamide (P-1411), N-[2,4-Difluoro-3-(5-pyrimidin-5-yl-1H-pyrrolo[2,3-b]pyridine-3-carbonyl)-phenyl]-2,5-difluoro-benzenesulfonamide (P-1500), N-{3-[5-(2-Dimethylamino-pyrimidin-5-yl)-1H-pyrrolo[2,3-b]pyridine-3-carbonyl]-2,4-difluoro-phenyl}-2,5-difluoro-benzenesulfonamide (P-1502), N-{2,4-Difluoro-3-[5-(2-methyl-pyrimidin-5-yl)-1H-pyrrolo[2,3-b]pyridine-3-carbonyl]-phenyl}-2,5-difluoro-benzenesulfonamide (P-1503), 2-Chloro-5-{3-[2,6-difluoro-3-(propane-1-sulfonylamino)-benzoyl]-1H-pyrrolo[2,3-b]pyridin-5-yl}-benzamide (P-1700),
Propane-1-sulfonic acid {2,4-difluoro-3-[5-(3-oxo-2,3-dihydro-1H-isoindol-5-yl)-1H-pyrrolo[2,3-b]pyridine-3-carbonyl]-phenyl}-amide (P-1702),
Propane-1-sulfonic acid {2,4-difluoro-3-[5-(2-oxo-2,3-dihydro-1H-indol-5-yl)-1H-pyrrolo[2,3-b]pyridine-3-carbonyl]-phenyl}-amide (P-1703),
3-{3-[3-(2,5-Difluoro-benzenesulfonylamino)-2,6-difluoro-benzoyl]-1H-pyrrolo[2,3-b]pyridin-5-yl}-N-methoxy-benzamide (P-1704),
4-{3-[3-(2,5-Difluoro-benzenesulfonylamino)-2,6-difluoro-benzoyl]-1H-pyrrolo[2,3-b]pyridin-5-yl}-N-methoxy-benzamide (P-1705),
N-{2,4-Difluoro-3-[5-(4-methylsulfamoyl-phenyl)-1H-pyrrolo[2,3-b]pyridine-3-carbonyl]-phenyl}-2,5-difluoro-benzenesulfonamide (P-1706),
N-{2,4-Difluoro-3-[5-(4-sulfamoyl-phenyl)-1H-pyrrolo[2,3-b]pyridine-3-carbonyl]-phenyl}-2,5-difluoro-benzenesulfonamide (P-1707), and
any pharmaceutically acceptable salt thereof.

In one embodiment of the second aspect, the compound is selected from the group consisting of:
4-(4-{3-[2,6-Difluoro-3-(propane-1-sulfonylamino)-benzoyl]-1H-pyrrolo[2,3-b]pyridin-5-yl}-pyrazol-1-yl)-piperidine-1-carboxylic acid tert-butyl ester (P-1001),
Propane-1-sulfonic acid {2,4-difluoro-3-[5-(1-piperidin-4-yl-1H-pyrazol-4-yl)-1H-pyrrolo[2,3-b]pyridine-3-carbonyl]-phenyl}-amide (P-1002),
N-{2,4-Difluoro-3-[5-(1-piperidin-4-yl-1H-pyrazol-4-yl)-1H-pyrrolo[2,3-b]pyridine-3-carbonyl]-phenyl}-4-trifluoromethyl-benzenesulfonamide (P-1004),
Propane-1-sulfonic acid {2,4-difluoro-3-[5-(1-pyrimidin-2-yl-1H-pyrazol-4-yl)-1H-pyrrolo[2,3-b]pyridine-3-carbonyl]-phenyl}-amide (P-1005),
Propane-1-sulfonic acid (3-{5-[3,5-dimethyl-1-(1H-tetrazol-5-yl)-1H-pyrazol-4-yl]-1H-pyrrolo[2,3-b]pyridine-3-carbonyl}-2,4-difluoro-phenyl)-amide (P-1006),
Propane-1-sulfonic acid (3-{5-[1-(1,3-dimethyl-1H-pyrazole-4-sulfonyl)-3,5-dimethyl-1H-pyrazol-4-yl]-1H-pyrrolo[2,3-b]pyridine-3-carbonyl}-2,4-difluoro-phenyl)-amide (P-1007),
Propane-1-sulfonic acid (2,4-difluoro-3-{5-[1-(1H-tetrazol-5-yl)-1H-pyrazol-4-yl]-1H-pyrrolo[2,3-b]pyridine-3-carbonyl}-phenyl)-amide (P-1008),
N-{2,4-Difluoro-3-[5-(1-methyl-1H-pyrazol-4-yl)-1H-pyrrolo[2,3-b]pyridine-3-carbonyl]-phenyl}-2,5-difluoro-benzenesulfonamide (P-1009),
N-{3-[5-(2,5-Dimethyl-2H-pyrazol-3-yl)-1H-pyrrolo[2,3-b]pyridine-3-carbonyl]-2,4-difluoro-phenyl}-2,5-difluoro-benzenesulfonamide (P-1010),
N-{2,4-Difluoro-3-[5-(1-methyl-1H-pyrazol-3-yl)-1H-pyrrolo[2,3-b]pyridine-3-carbonyl]-phenyl}-2,5-difluoro-benzenesulfonamide (P-1011),
Propane-1-sulfonic acid {2,4-difluoro-3-[5-(1-methyl-1H-pyrazol-3-yl)-1H-pyrrolo[2,3-b]pyridine-3-carbonyl]-phenyl}-amide (P-1012),
Propane-1-sulfonic acid {2,4-difluoro-3-[5-(1-pyridin-2-yl-1H-pyrazol-4-yl)-1H-pyrrolo[2,3-b]pyridine-3-carbonyl]-phenyl}-amide (P-1013),
4-{3-[2,6-Difluoro-3-(propane-1-sulfonylamino)-benzoyl]-1H-pyrrolo[2,3-b]pyridin-5-yl}-pyrazole-1-carboxylic acid amide (P-1014), and
any pharmaceutically acceptable salt thereof.

In one embodiment of the second aspect, the compound is selected from the group consisting of:
Propane-1-sulfonic acid [2,4-difluoro-3-(5-pyridin-2-yl-1H-pyrrolo[2,3-b]pyridine-3-carbonyl)-phenyl]-amide (P-1401),
N-[2,4-Difluoro-3-(5-pyridin-3-yl-1H-pyrrolo[2,3-b]pyridine-3-carbonyl)-phenyl]-2,5-difluoro-benzenesulfonamide (P-1402),
N-[2,4-Difluoro-3-(5-pyridin-4-yl-1H-pyrrolo[2,3-b]pyridine-3-carbonyl)-phenyl]-2,5-difluoro-benzenesulfonamide (P-1403),
N-{2,4-Difluoro-3-[5-(6-methoxy-pyridin-3-yl)-1H-pyrrolo[2,3-b]pyridine-3-carbonyl]-phenyl}-2,5-difluoro-benzenesulfonamide (P-1404),
N-{2,4-Difluoro-3-[5-(3-fluoro-pyridin-4-yl)-1H-pyrrolo[2,3-b]pyridine-3-carbonyl]-phenyl}-2,5-difluoro-benzenesulfonamide (P-1405),
N-{3-[5-(2,6-Dimethoxy-pyridin-3-yl)-1H-pyrrolo[2,3-b]pyridine-3-carbonyl]-2,4-difluoro-phenyl}-2,5-difluoro-benzenesulfonamide (P-1406),
N-{2,4-Difluoro-3-[5-(5-methanesulfonyl-pyridin-3-yl)-1H-pyrrolo[2,3-b]pyridine-3-carbonyl]-phenyl}-2,5-difluoro-benzenesulfonamide (P-1407),
N-{2,4-Difluoro-3-[5-(6-methyl-pyridin-3-yl)-1H-pyrrolo[2,3-b]pyridine-3-carbonyl]-phenyl}-2,5-difluoro-benzenesulfonamide (P-1408),
N-{3-[5-(6-Dimethylamino-pyridin-3-yl)-1H-pyrrolo[2,3-b]pyridine-3-carbonyl]-2,4-difluoro-phenyl}-2,5-difluoro-benzenesulfonamide (P-1409),
N-(3-{5-[6-(3-Dimethylamino-propoxy)-pyridin-3-yl]-1H-pyrrolo[2,3-b]pyridine-3-carbonyl}-2,4-difluoro-phenyl)-2,5-difluoro-benzenesulfonamide (P-1411), and
any pharmaceutically acceptable salt thereof.

In one embodiment of the second aspect, the compound is selected from the group consisting of:
N-[2,4-Difluoro-3-(5-pyrimidin-5-yl-1H-pyrrolo[2,3-b]pyridine-3-carbonyl)-phenyl]-2,5-difluoro-benzenesulfonamide (P-1500),
N-{3-[5-(2,4-Dimethoxy-pyrimidin-5-yl)-1H-pyrrolo[2,3-b]pyridine-3-carbonyl]-2,4-difluoro-phenyl}-2,5-difluoro-benzenesulfonamide (P-1501),
N-{3-[5-(2-Dimethylamino-pyrimidin-5-yl)-1H-pyrrolo[2,3-b]pyridine-3-carbonyl]-2,4-difluoro-phenyl}-2,5-difluoro-benzenesulfonamide (P-1502),
N-{2,4-Difluoro-3-[5-(2-methyl-pyrimidin-5-yl)-1H-pyrrolo[2,3-b]pyridine-3-carbonyl]-phenyl}-2,5-difluoro-benzenesulfonamide (P-1503),
Propane-1-sulfonic acid {3-[5-(2-cyclopropylamino-pyrimidin-5-yl)-1H-pyrrolo[2,3-b]pyridine-3-carbonyl]-2,4-difluoro-phenyl}-amide (P-1504),
Propane-1-sulfonic acid (2,4-difluoro-3-{5-[2-(2-methoxy-ethylamino)-pyrimidin-5-yl]-1H-pyrrolo[2,3-b]pyridine-3-carbonyl}-phenyl)-amide (P-1505),
N-{3-[5-(2-Cyclopropylamino-pyrimidin-5-yl)-1H-pyrrolo[2,3-b]pyridine-3-carbonyl]-2,4-difluoro-phenyl}-2,5-difluoro-benzenesulfonamide (P-1506),
N-(2,4-Difluoro-3-{5-[2-(2-methoxy-ethylamino)-pyrimidin-5-yl]-1H-pyrrolo[2,3-b]pyridine-3-carbonyl}-phenyl)-2,5-difluoro-benzenesulfonamide (P-1507),
Propane-1-sulfonic acid (2,4-difluoro-3-{5-[2-(pyridin-3-yloxy)-pyrimidin-5-yl]-1H-pyrrolo[2,3-b]pyridine-3-carbonyl}-phenyl)-amide (P-1508),
Propane-1-sulfonic acid {2,4-difluoro-3-[5-(2-trifluoromethoxy-pyrimidin-5-yl)-1H-pyrrolo[2,3-b]pyridine-3-carbonyl]-phenyl}-amide (P-1509),
Propane-1-sulfonic acid {3-[5-(2-cyano-pyrimidin-5-yl)-1H-pyrrolo[2,3-b]pyridine-3-carbonyl]-2,4-difluoro-phenyl}-amide (P-1510), Propane-1-sulfonic acid {2,4-difluoro-3-[5-(2-imidazol-1-yl-pyrimidin-5-yl)-1H-pyrrolo[2,3-b]pyridine-3-carbonyl]-phenyl}-amide (P-1511),
Propane-1-sulfonic acid {3-[5-(2-azetidin-1-yl-pyrimidin-5-yl)-1H-pyrrolo[2,3-b]pyridine-3-carbonyl]-2,4-difluoro-phenyl}-amide (P-1512),
Propane-1-sulfonic acid {2,4-difluoro-3-[5-(2-isopropylamino-pyrimidin-5-yl)-1H-pyrrolo[2,3-b]pyridine-3-carbonyl]-phenyl}-amide (P-1513),
Propane-1-sulfonic acid {2,4-difluoro-3-[5-(2-methylamino-pyrimidin-5-yl)-1H-pyrrolo[2,3-b]pyridine-3-carbonyl]-phenyl}-amide (P-1514),
Propane-1-sulfonic acid (3-{5-[2-(2-dimethylamino-ethylamino)-pyrimidin-5-yl]-1H-pyrrolo[2,3-b]pyridine-3-carbonyl}-2,4-difluoro-phenyl)-amide (P-1515),
Propane-1-sulfonic acid (2,4-difluoro-3-{5-[2-(3-methoxy-propylamino)-pyrimidin-5-yl]-1H-pyrrolo[2,3-b]pyridine-3-carbonyl}-phenyl)-amide (P-1516),
Propane-1-sulfonic acid {2,4-difluoro-3-[5-(2-isopropylamino-pyrimidin-5-yl)-1H-pyrrolo[2,3-b]pyridine-3-carbonyl]-phenyl}-amide (P-1517),
2-Fluoro-N-{2-fluoro-3-[5-(2-methoxy-pyrimidin-5-yl)-1H-pyrrolo[2,3-b]pyridine-3-carbonyl]-phenyl}-benzenesulfonamide (P-1518),
Propane-1-sulfonic acid {2,4-difluoro-3-[5-(2-isopropyl-pyrimidin-5-yl)-1H-pyrrolo[2,3-b]pyridine-3-carbonyl]-phenyl}-amide (P-1519),
N-{2,4-Difluoro-3-[5-(2-methyl-pyrimidin-5-yl)-1H-pyrrolo[2,3-b]pyridine-3-carbonyl]-phenyl}-2-fluoro-benzenesulfonamide (P-1520),
N-{2,4-Difluoro-3-[5-(2-isopropyl-pyrimidin-5-yl)-1H-pyrrolo[2,3-b]pyridine-3-carbonyl]-phenyl}-2,5-difluoro-benzenesulfonamide (P-1521), and
any pharmaceutically acceptable salt thereof.

In one embodiment of the second aspect, the compound is selected from the group consisting of:
2-Chloro-5-{3-[2,6-difluoro-3-(propane-1-sulfonylamino)-benzoyl]-1H-pyrrolo[2,3-b]pyridin-5-yl}-benzamide (P-1700),
Propane-1-sulfonic acid {2,4-difluoro-3-[5-(1-oxo-2,3-dihydro-1H-isoindol-5-yl)-1H-pyrrolo[2,3-b]pyridine-3-carbonyl]-phenyl}-amide (P-1701),
Propane-1-sulfonic acid {2,4-difluoro-3-[5-(3-oxo-2,3-dihydro-1H-isoindol-5-yl)-1H-pyrrolo[2,3-b]pyridine-3-carbonyl]-phenyl}-amide (P-1702),
Propane-1-sulfonic acid {2,4-difluoro-3-[5-(2-oxo-2,3-dihydro-1H-indol-5-yl)-1H-pyrrolo[2,3-b]pyridine-3-carbonyl]-phenyl}-amide (P-1703),
3-{3-[3-(2,5-Difluoro-benzenesulfonylamino)-2,6-difluoro-benzoyl]-1H-pyrrolo[2,3-b]pyridin-5-yl}-N-methoxy-benzamide (P-1704),
4-{3-[3-(2,5-Difluoro-benzenesulfonylamino)-2,6-difluoro-benzoyl]-1H-pyrrolo[2,3-b]pyridin-5-yl}-N-methoxy-benzamide (P-1705),
N-{2,4-Difluoro-3-[5-(4-methylsulfamoyl-phenyl)-1H-pyrrolo[2,3-b]pyridine-3-carbonyl]-phenyl}-2,5-difluoro-benzenesulfonamide (P-1706),
N-{2,4-Difluoro-3-[5-(4-sulfamoyl-phenyl)-1H-pyrrolo[2,3-b]pyridine-3-carbonyl]-phenyl}-2,5-difluoro-benzenesulfonamide (P-1707), and
any pharmaceutically acceptable salt thereof.

In one embodiment of the second aspect, the compound is selected from the group consisting of:
3-[2,6-Difluoro-3-(propane-1-sulfonylamino)-benzoyl]-1H-pyrrolo[2,3-b]pyridine-5-carboxylic acid pyridin-3-ylamide (P-1801),
5-Methyl-2,3-dihydro-isoxazole-3-carboxylic acid {3-[2,6-difluoro-3-(propane-1-sulfonylamino)-benzoyl]-1H-pyrrolo[2,3-b]pyridin-5-yl}-amide (P-1802), and
any pharmaceutically acceptable salt thereof.

In one embodiment of the second aspect, the compound is selected from the group consisting of:
N-{2,4-Difluoro-3-[5-(1-methyl-1H-pyrazol-4-yl)-1H-pyrrolo[2,3-b]pyridine-3-carbonyl]-phenyl}-2,5-difluoro-benzenesulfonamide (P-1009),
N-{3-[5-(2,5-Dimethyl-2H-pyrazol-3-yl)-1H-pyrrolo[2,3-b]pyridine-3-carbonyl]-2,4-difluoro-phenyl}-2,5-difluoro-benzenesulfonamide (P-1010),
N-{2,4-Difluoro-3-[5-(1-methyl-1H-pyrazol-3-yl)-1H-pyrrolo[2,3-b]pyridine-3-carbonyl]-phenyl}-2,5-difluoro-benzenesulfonamide (P-1011),
Propane-1-sulfonic acid [2,4-difluoro-3-(5-pyridin-2-yl-1H-pyrrolo[2,3-b]pyridine-3-carbonyl)-phenyl]-amide (P-1401),
N-[2,4-Difluoro-3-(5-pyridin-3-yl-1H-pyrrolo[2,3-b]pyridine-3-carbonyl)-phenyl]-2,5-difluoro-benzenesulfonamide (P-1402),
N-[2,4-Difluoro-3-(5-pyridin-4-yl-1H-pyrrolo[2,3-b]pyridine-3-carbonyl)-phenyl]-2,5-difluoro-benzenesulfonamide (P-1403),
N-{2,4-Difluoro-3-[5-(6-methoxy-pyridin-3-yl)-1H-pyrrolo[2,3-b]pyridine-3-carbonyl]-phenyl}-2,5-difluoro-benzenesulfonamide (P-1404),
N-{2,4-Difluoro-3-[5-(3-fluoro-pyridin-4-yl)-1H-pyrrolo[2,3-b]pyridine-3-carbonyl]-phenyl}-2,5-difluoro-benzenesulfonamide (P-1405),
N-{3-[5-(2,6-Dimethoxy-pyridin-3-yl)-1H-pyrrolo[2,3-b]pyridine-3-carbonyl]-2,4-difluoro-phenyl}-2,5-difluoro-benzenesulfonamide (P-1406),
N-{2,4-Difluoro-3-[5-(5-methanesulfonyl-pyridin-3-yl)-1H-pyrrolo[2,3-b]pyridine-3-carbonyl]-phenyl}-2,5-difluoro-benzenesulfonamide (P-1407),
N-{2,4-Difluoro-3-[5-(6-methyl-pyridin-3-yl)-1H-pyrrolo[2,3-b]pyridine-3-carbonyl]-phenyl}-2,5-difluoro-benzenesulfonamide (P-1408),
N-{3-[5-(6-Dimethylamino-pyridin-3-yl)-1H-pyrrolo[2,3-b]pyridine-3-carbonyl]-2,4-difluoro-phenyl}-2,5-difluoro-benzenesulfonamide (P-1409),
N-(3-{5-[6-(3-Dimethylamino-propoxy)-pyridin-3-yl]-1H-pyrrolo[2,3-b]pyridine-3-carbonyl}-2,4-difluoro-phenyl)-2,5-difluoro-benzenesulfonamide (P-1411),
N-[2,4-Difluoro-3-(5-pyrimidin-5-yl-1H-pyrrolo[2,3-b]pyridine-3-carbonyl)-phenyl]-2,5-difluoro-benzenesulfonamide (P-1500),
N-{3-[5-(2,4-Dimethoxy-pyrimidin-5-yl)-1H-pyrrolo[2,3-b]pyridine-3-carbonyl]-2,4-difluoro-phenyl}-2,5-difluoro-benzenesulfonamide (P-1501),
N-{3-[5-(2-Dimethylamino-pyrimidin-5-yl)-1H-pyrrolo[2,3-b]pyridine-3-carbonyl]-2,4-difluoro-phenyl}-2,5-difluoro-benzenesulfonamide (P-1502),
N-{2,4-Difluoro-3-[5-(2-methyl-pyrimidin-5-yl)-1H-pyrrolo[2,3-b]pyridine-3-carbonyl]-phenyl}-2,5-difluoro-benzenesulfonamide (P-1503),
N-{3-[5-(2-Cyclopropylamino-pyrimidin-5-yl)-1H-pyrrolo[2,3-b]pyridine-3-carbonyl]-2,4-difluoro-phenyl}-2,5-difluoro-benzenesulfonamide (P-1506),
N-(2,4-Difluoro-3-{5-[2-(2-methoxy-ethylamino)-pyrimidin-5-yl]-1H-pyrrolo[2,3-b]pyridine-3-carbonyl}-phenyl)-2,5-difluoro-benzenesulfonamide (P-1507),
2-Fluoro-N-{2-fluoro-3-[5-(2-methoxy-pyrimidin-5-yl)-1H-pyrrolo[2,3-b]pyridine-3-carbonyl]-phenyl}-benzenesulfonamide (P-1518), N-{2,4-Difluoro-3-[5-(2-methyl-pyrimidin-5-yl)-1H-pyrrolo[2,3-b]pyridine-3-carbonyl]-phenyl}-2-fluoro-benzenesulfonamide (P-1520), N-{2,4-Difluoro-3-[5-(2-isopropyl-pyrimidin-5-yl)-1H-pyrrolo[2,3-b]pyridine-3-carbonyl]-phenyl}-2,5-difluoro-benzenesulfonamide (P-1521), 3-{3-[3-(2,5-Difluoro-benzenesulfonylamino)-2,6-difluoro-benzoyl]-1H-pyrrolo[2,3-b]pyridin-5-yl}-N-methoxy-benzamide (P-1704), 4-{3-[3-(2,5-Difluoro-benzenesulfonylamino)-2,6-difluoro-benzoyl]-1H-pyrrolo[2,3-b]pyridin-5-yl}-N-methoxy-benzamide (P-1705), N-{2,4-Difluoro-3-[5-(4-methylsulfamoyl-phenyl)-1H-pyrrolo[2,3-b]pyridine-3-carbonyl]-phenyl}-2,5-difluoro-benzenesulfonamide (P-1706), N-{2,4-Difluoro-3-[5-(4-sulfamoyl-phenyl)-1H-pyrrolo[2,3-b]pyridine-3-carbonyl]-phenyl}-2,5-difluoro-benzenesulfonamide (P-1707), and any pharmaceutically acceptable salt thereof.

In another aspect, compounds are provided, wherein the compound is selected from the group consisting of:

N-[2,4-difluoro-3-[5-(1H-pyrazol-4-yl)-1H-pyrrolo[2,3-b]pyridine-3-carbonyl]phenyl]-3-fluoro-benzenesulfonamide (P-1901), N-[2,4-difluoro-3-[5-(1H-indazol-4-yl)-1H-pyrrolo[2,3-b]pyridine-3-carbonyl]phenyl]-3-fluoro-benzenesulfonamide (P-1902), N-[2,4-difluoro-3-[5-(2-methylindazol-5-yl)-1H-pyrrolo[2,3-b]pyridine-3-carbonyl]phenyl]-3-fluoro-benzenesulfonamide (P-1903), N-[2,4-difluoro-3-[5-(2-methylindazol-6-yl)-1H-pyrrolo[2,3-b]pyridine-3-carbonyl]phenyl]-3-fluoro-benzenesulfonamide (P-1904), N-[2,4-difluoro-3-[5-(1H-indol-5-yl)-1H-pyrrolo[2,3-b]pyridine-3-carbonyl]phenyl]-3-fluoro-benzenesulfonamide (P-1905), N-[3-[5-(1,3-benzothiazol-5-yl)-1H-pyrrolo[2,3-b]pyridine-3-carbonyl]-2,4-difluoro-phenyl]-3-fluoro-benzenesulfonamide (P-1906), N-[2,4-difluoro-3-(5-quinoxalin-6-yl-1H-pyrrolo[2,3-b]pyridine-3-carbonyl)phenyl]-3-fluoro-benzenesulfonamide (P-1907), N-[2,4-difluoro-3-[5-(2-methylindazol-4-yl)-1H-pyrrolo[2,3-b]pyridine-3-carbonyl]phenyl]-3-fluoro-benzenesulfonamide (P-1908), N-[2,4-difluoro-3-[5-(1-methylpyrazol-4-yl)-1H-pyrrolo[2,3-b]pyridine-3-carbonyl]phenyl]-3-fluoro-benzenesulfonamide (P-1909), N-[3-[5-(2,5-dimethylpyrazol-3-yl)-1H-pyrrolo[2,3-b]pyridine-3-carbonyl]-2,4-difluoro-phenyl]-3-fluoro-benzenesulfonamide (P-1910), N-[2,4-difluoro-3-[5-(1-methylpyrazol-3-yl)-1H-pyrrolo[2,3-b]pyridine-3-carbonyl]phenyl]-3-fluoro-benzenesulfonamide (P-1911), N-[2,4-difluoro-3-[5-[2-(4-methylimidazol-1-yl)thiazol-4-yl]-1H-pyrrolo[2,3-b]pyridine-3-carbonyl]phenyl]-3-fluoro-benzenesulfonamide (P-1912), N-[2,4-difluoro-3-[5-[2-(2-methylimidazol-1-yl)thiazol-4-yl]-1H-pyrrolo[2,3-b]pyridine-3-carbonyl]phenyl]-3-fluoro-benzenesulfonamide (P-1913), N-[2,4-difluoro-3-(5-thiazol-4-yl-1H-pyrrolo[2,3-b]pyridine-3-carbonyl)phenyl]-3-fluoro-benzenesulfonamide (P-1914), N-[2,4-difluoro-3-[5-(2-methylthiazol-4-yl)-1H-pyrrolo[2,3-b]pyridine-3-carbonyl]phenyl]-3-fluoro-benzenesulfonamide (P-1915), N-[2,4-difluoro-3-(5-thiazol-5-yl-1H-pyrrolo[2,3-b]pyridine-3-carbonyl)phenyl]-3-fluoro-benzenesulfonamide (P-1916), N-[3-[5-(2-dimethylaminothiazol-4-yl)-1H-pyrrolo[2,3-b]pyridine-3-carbonyl]-2,4-difluoro-phenyl]-3-fluoro-benzenesulfonamide (P-1917), N-[2,4-difluoro-3-[5-(2-methoxythiazol-4-yl)-1H-pyrrolo[2,3-b]pyridine-3-carbonyl]phenyl]-3-fluoro-benzenesulfonamide (P-1918), N-[2,4-difluoro-3-(5-oxazol-5-yl-1H-pyrrolo[2,3-b]pyridine-3-carbonyl)phenyl]-3-fluoro-benzenesulfonamide (P-1919), N-[2,4-difluoro-3-[5-(3-pyridyl)-1H-pyrrolo[2,3-b]pyridine-3-carbonyl]phenyl]-3-fluoro-benzenesulfonamide (P-1920), N-[2,4-difluoro-3-[5-(4-pyridyl)-1H-pyrrolo[2,3-b]pyridine-3-carbonyl]phenyl]-3-fluoro-benzenesulfonamide (P-1921), N-[2,4-difluoro-3-[5-(6-methoxy-3-pyridyl)-1H-pyrrolo[2,3-b]pyridine-3-carbonyl]phenyl]-3-fluoro-benzenesulfonamide (P-1922), N-[2,4-difluoro-3-[5-(3-fluoro-4-pyridyl)-1H-pyrrolo[2,3-b]pyridine-3-carbonyl]phenyl]-3-fluoro-benzenesulfonamide (P-1923), N-[3-[5-(2,6-dimethoxy-3-pyridyl)-1H-pyrrolo[2,3-b]pyridine-3-carbonyl]-2,4-difluoro-phenyl]-3-fluoro-benzenesulfonamide (P-1924), N-[2,4-difluoro-3-[5-(5-methylsulfonyl-3-pyridyl)-1H-pyrrolo[2,3-b]pyridine-3-carbonyl]phenyl]-3-fluoro-benzenesulfonamide (P-1925), N-[2,4-difluoro-3-[5-(6-methyl-3-pyridyl)-1H-pyrrolo[2,3-b]pyridine-3-carbonyl]phenyl]-3-fluoro-benzenesulfonamide (P-1926), N-[3-[5-(6-dimethylamino-3-pyridyl)-1H-pyrrolo[2,3-b]pyridine-3-carbonyl]-2,4-difluoro-phenyl]-3-fluoro-benzenesulfonamide (P-1927), N-[3-[5-(6-(3-dimethylaminopropoxy)-3-pyridyl)-1H-pyrrolo[2,3-b]pyridine-3-carbonyl]-2,4-difluoro-phenyl]-3-fluoro-benzenesulfonamide (P-1928), N-[2,4-difluoro-3-(5-pyrimidin-5-yl-1H-pyrrolo[2,3-b]pyridine-3-carbonyl)phenyl]-3-fluoro-benzenesulfonamide (P-1929), N-[3-[5-(2,4-dimethoxypyrimidin-5-yl)-1H-pyrrolo[2,3-b]pyridine-3-carbonyl]-2,4-difluoro-phenyl]-3-fluoro-benzenesulfonamide (P-1930), N-[3-[5-(2-dimethylaminopyrimidin-5-yl)-1H-pyrrolo[2,3-b]pyridine-3-carbonyl]-2,4-difluoro-phenyl]-3-fluoro-benzenesulfonamide (P-1931), N-[2,4-difluoro-3-[5-(2-methylpyrimidin-5-yl)-1H-pyrrolo[2,3-b]pyridine-3-carbonyl]phenyl]-3-fluoro-benzenesulfonamide (P-1932), N-[3-[5-[2-(cyclopropylamino)pyrimidin-5-yl]-1H-pyrrolo[2,3-b]pyridine-3-carbonyl]-2,4-difluoro-phenyl]-3-fluoro-benzenesulfonamide (P-1933), N-[2,4-difluoro-3-[5-[2-(2-methoxyethylamino)pyrimidin-5-yl]-1H-pyrrolo[2,3-b]pyridine-3-carbonyl]phenyl]-3-fluoro-benzenesulfonamide (P-1934), N-[2,4-difluoro-3-[5-(2-isopropylpyrimidin-5-yl)-1H-pyrrolo[2,3-b]pyridine-3-carbonyl]phenyl]-3-fluoro-benzenesulfonamide (P-1935), N-[2,4-difluoro-3-[5-[5-(2-oxo-1-pyridyl)pyrazin-2-yl]-1H-pyrrolo[2,3-b]pyridine-3-carbonyl]phenyl]-3-fluoro-benzenesulfonamide (P-1936), N-[2,4-difluoro-3-[5-(5-pyrazol-1-ylpyrazin-2-yl)-1H-pyrrolo[2,3-b]pyridine-3-carbonyl]phenyl]-3-fluoro-benzenesulfonamide (P-1937), N-[2,4-difluoro-3-[5-(5-imidazol-1-ylpyrazin-2-yl)-1H-pyrrolo[2,3-b]pyridine-3-carbonyl]phenyl]-3-fluoro-benzenesulfonamide (P-1938), N-[3-[5-(5-aminopyrazin-2-yl)-1H-pyrrolo[2,3-b]pyridine-3-carbonyl]-2,4-difluoro-phenyl]-3-fluoro-benzenesulfonamide (P-1939), 2-chloro-5-[3-[2,6-difluoro-3-[(3-fluorophenyl)sulfonylamino]benzoyl]-1H-pyrrolo[2,3-b]pyridin-5-yl]benzamide (P-1940), 3-[3-[2,6-difluoro-3-[(3-fluorophenyl)sulfonylamino]benzoyl]-1H-pyrrolo[2,3-b]pyridin-5-yl]-N-methoxy-benzamide (P-1941), 4-[3-[2,6-difluoro-3-[(3-fluorophenyl)sulfonylamino]benzoyl]-1H-pyrrolo[2,3-b]pyridin-5-yl]-N-methoxy-benzamide (P-1942), N-[2,4-difluoro-3-[5-[4-(methylsulfamoyl)phenyl]-1H-pyrrolo[2,3-b]pyridine-3-carbonyl]phenyl]-3-fluoro-benzenesulfonamide (P-1943), N-[2,4-difluoro-3-[5-(4-sulfamoylphenyl)-1H-pyrrolo[2,3-b]pyridine-3-carbonyl]phenyl]-3-fluoro-benzenesulfonamide (P-1944), N-[2,4-difluoro-3-[5-[4-(1H-tetrazol-5-yl)phenyl]-1H-pyrrolo[2,3-b]pyridine-3-carbonyl]phenyl]-3-fluoro-benzenesulfonamide (P-1945), N-[2,4-difluoro-3-[5-(4-formylphenyl)-1H-pyrrolo[2,3-b]pyridine-3-carbonyl]phenyl]-3-fluoro-benzenesulfonamide (P-1946), N-[3-[5-(4-cyanophenyl)-1H-pyrrolo[2,3-b]pyridine-3-carbonyl]-2,4-difluoro-phenyl]-3-fluoro-benzenesulfonamide (P-1947), N-[2,4-difluoro-3-(5-imidazo[1,2-a]pyridin-5-yl-1H-pyrrolo[2,3-b]pyridine-3-carbonyl)phenyl]-3-fluoro-benzenesulfonamide (P-1948), N-[2,4-difluoro-3-[5-(1H-indol-4-yl)-1H-pyrrolo[2,3-b]pyridine-3-carbonyl]phenyl]-3-fluoro-benzenesulfonamide (P-1949), N-[3-[5-(1,3-benzothiazol-6-yl)-1H-pyrrolo[2,3-b]pyridine-3-carbonyl]-2,4-difluoro-phenyl]-3-fluoro-benzenesulfonamide (P-1950), N-[2,4-difluoro-3-(5-imidazo[1,2-a]pyridin-2-yl-1H-pyrrolo[2,3-b]pyridine-3-carbonyl)phenyl]-3-fluoro-benzenesulfonamide (P-1951), N-[2,4-difluoro-3-[5-[7-(trifluoromethyl)imidazo[1,2-a]pyrimidin-2-yl]-1H-pyrrolo[2,3-b]pyridine-3-carbonyl]phenyl]-3-fluoro-benzenesulfonamide (P-1952), N-[2,4-difluoro-3-[5-(3-methyl-1H-indol-5-yl)-1H-pyrrolo[2,3-b]pyridine-3-carbonyl]phenyl]-3-fluoro-benzenesulfonamide (P-1953), N-[2,4-difluoro-3-[5-(3-methyl-1H-indazol-5-yl)-1H-pyrrolo[2,3-b]pyridine-3-carbonyl]phenyl]-3-fluoro-benzenesulfonamide (P-1954), N-[2,4-difluoro-3-(5-quinazolin-7-yl-1H-pyrrolo[2,3-b]pyridine-3-carbonyl)phenyl]-3-fluoro-benzenesulfonamide (P-1955), N-[2,4-difluoro-3-(5-quinazolin-6-yl-1H-pyrrolo[2,3-b]pyridine-3-carbonyl)phenyl]-3-fluoro-benzenesulfonamide (P-1956), N-[2,4-difluoro-3-[5-(1-methylindazol-6-yl)-1H-pyrrolo[2,3-b]pyridine-3-carbonyl]phenyl]-3-fluoro-benzenesulfonamide (P-1957), N-[2,4-difluoro-3-[5-(1-methylindazol-5-yl)-1H-pyrrolo[2,3-b]pyridine-3-carbonyl]phenyl]-3-fluoro-benzenesulfonamide (P-1958), N-[3-[5-(3-amino-1-methyl-indazol-6-yl)-1H-pyrrolo[2,3-b]pyridine-3-carbonyl]-2,4-difluoro-phenyl]-3-fluoro-benzenesulfonamide (P-1959), N-[2,4-difluoro-3-[5-[2-(2-methylaminoethyl)-3H-benzimidazol-5-yl]-1H-pyrrolo[2,3-b]pyridine-3-carbonyl]phenyl]-3-fluoro-benzenesulfonamide (P-1960), N-[3-[5-(2-amino-1-methyl-benzimidazol-5-yl)-1H-pyrrolo[2,3-b]pyridine-3-carbonyl]-2,4-difluoro-phenyl]-3-fluoro-benzenesulfonamide (P-1961), N-[3-[5-(2-amino-1H-benzimidazol-5-yl)-1H-pyrrolo[2,3-b]pyridine-3-carbonyl]-2,4-difluoro-phenyl]-3-fluoro-benzenesulfonamide (P-1962), N-[2,4-difluoro-3-[5-(7-quinolyl)-1H-pyrrolo[2,3-b]pyridine-3-carbonyl]phenyl]-3-fluoro-benzenesulfonamide (P-1963), N-[2,4-difluoro-3-[5-(6-quinolyl)-1H-pyrrolo[2,3-b]pyridine-3-carbonyl]phenyl]-3-fluoro-benzenesulfonamide (P-1964), N-[2,4-difluoro-3-[5-(2-methoxy-1-methyl-benzimidazol-5-yl)-1H-pyrrolo[2,3-b]pyridine-3-carbonyl]phenyl]-3-fluoro-benzenesulfonamide (P-1965), N-[3-[5-(2-dimethylamino-1-methyl-benzimidazol-5-yl)-1H-pyrrolo[2,3-b]pyridine-3-carbonyl]-2,4-difluoro-phenyl]-3-fluoro-benzenesulfonamide (P-1966), N-[3-[5-(1,2-dimethylbenzimidazol-5-yl)-1H-pyrrolo[2,3-b]pyridine-3-carbonyl]-2,4-difluoro-phenyl]-3-fluoro-benzenesulfonamide (P-1967), N-[3-[5-(2,1,3-benzothiadiazol-6-yl)-1H-pyrrolo[2,3-b]pyridine-3-carbonyl]-2,4-difluoro-phenyl]-3-fluoro-benzenesulfonamide (P-1968), N-[2,4-difluoro-3-[5-(2-methyl-1H-benzimidazol-5-yl)-1H-pyrrolo[2,3-b]pyridine-3-carbonyl]phenyl]-3-fluoro-benzenesulfonamide (P-1969), N-[2,4-difluoro-3-[5-(4-oxo-1H-thieno[2,3-d]pyrimidin-6-yl)-1H-pyrrolo[2,3-b]pyridine-3-carbonyl]phenyl]-3-fluoro-benzenesulfonamide (P-1970), N-[3-[5-[3,5-dimethyl-1-(1H-tetrazol-5-yl)pyrazol-4-yl]-1H-pyrrolo[2,3-b]pyridine-3-carbonyl]-2,4-difluoro-phenyl]-3-fluoro-benzenesulfonamide (P-1971), N-[3-[5-[1-(1,3-dimethylpyrazol-4-yl)sulfonyl-3,5-dimethyl-pyrazol-4-yl]-1H-pyrrolo[2,3-b]pyridine-3-carbonyl]-2,4-difluoro-phenyl]-3-fluoro-benzenesulfonamide (P-1972), N-[2,4-difluoro-3-[5-[1-(1H-tetrazol-5-yl)pyrazol-4-yl]-1H-pyrrolo[2,3-b]pyridine-3-carbonyl]phenyl]-3-fluoro-benzenesulfonamide (P-1973), N-[2,4-difluoro-3-[5-[1-(2-pyridyl)pyrazol-4-yl]-1H-pyrrolo[2,3-b]pyridine-3-carbonyl]phenyl]-3-fluoro-benzenesulfonamide (P-1974), 4-[3-[2,6-difluoro-3-[(3-fluorophenyl)sulfonylamino]benzoyl]-1H-pyrrolo[2,3-b]pyridin-5-yl]pyrazole-1-carboxamide (P-1975), N-[2,4-difluoro-3-[5-(1-pyrazin-2-ylpyrazol-4-yl)-1H-pyrrolo[2,3-b]pyridine-3-carbonyl]phenyl]-3-fluoro-benzenesulfonamide (P-1976), N-[3-[5-(2-dimethylaminothiazol-4-yl)-1H-pyrrolo[2,3-b]pyridine-3-carbonyl]-2,4-difluoro-phenyl]-3-fluoro-benzenesulfonamide (P-1977), N-[2,4-difluoro-3-[5-(2-pyrazol-1-ylthiazol-4-yl)-1H-pyrrolo[2,3-b]pyridine-3-carbonyl]phenyl]-3-fluoro-benzenesulfonamide (P-1978), N-[2,4-difluoro-3-[5-(2-imidazol-1-ylthiazol-5-yl)-1H-pyrrolo[2,3-b]pyridine-3-carbonyl]phenyl]-3-fluoro-benzenesulfonamide (P-1979), N-[2,4-difluoro-3-[5-[2-(2-methylimidazol-1-yl)thiazol-5-yl]-1H-pyrrolo[2,3-b]pyridine-3-carbonyl]phenyl]-3-fluoro-benzenesulfonamide (P-1980), N-[2,4-difluoro-3-[5-(2-imidazol-1-ylthiazol-4-yl)-1H-pyrrolo[2,3-b]pyridine-3-carbonyl]phenyl]-3-fluoro-benzenesulfonamide (P-1981), N-[2,4-difluoro-3-[5-(2-pyrazol-1-ylthiazol-5-yl)-1H-pyrrolo[2,3-b]pyridine-3-carbonyl]phenyl]-3-fluoro-benzenesulfonamide (P-1982),
N-[2,4-difluoro-3-[5-[2-(2-oxopyrrolidin-1-yl)thiazol-4-yl]-1H-pyrrolo[2,3-b]pyridine-3-carbonyl]phenyl]-3-fluoro-benzenesulfonamide (P-1983),
N-[2,4-difluoro-3-[5-[2-(3-pyridyl)thiazol-4-yl]-1H-pyrrolo[2,3-b]pyridine-3-carbonyl]phenyl]-3-fluoro-benzenesulfonamide (P-1984),
N-[2,4-difluoro-3-[5-[2-(4-methylimidazol-1-yl)thiazol-5-yl]-1H-pyrrolo[2,3-b]pyridine-3-carbonyl]phenyl]-3-fluoro-benzenesulfonamide (P-1985),
N-[2,4-difluoro-3-[5-[5-(3-pyridyl)-2-thienyl]-1H-pyrrolo[2,3-b]pyridine-3-carbonyl]phenyl]-3-fluoro-benzenesulfonamide (P-1986),
N-[2,4-difluoro-3-[5-[5-(1H-pyrazol-3-yl)-2-thienyl]-1H-pyrrolo[2,3-b]pyridine-3-carbonyl]phenyl]-3-fluoro-benzenesulfonamide (P-1987),
5-[3-[2,6-difluoro-3-[(3-fluorophenyl)sulfonylamino]benzoyl]-1H-pyrrolo[2,3-b]pyridin-5-yl]thiophene-2-sulfonamide (P-1988),
N-[2,4-difluoro-3-[5-[5-(5-methyl-1,2,4-oxadiazol-3-yl)-2-thienyl]-1H-pyrrolo[2,3-b]pyridine-3-carbonyl]phenyl]-3-fluoro-benzenesulfonamide (P-1989),
N-[2,4-difluoro-3-[5-(5-thiazol-2-yl-2-thienyl)-1H-pyrrolo[2,3-b]pyridine-3-carbonyl]phenyl]-3-fluoro-benzenesulfonamide (P-1990),
N-[2,4-difluoro-3-[5-[5-(1H-pyrazol-3-yl)-2-thienyl]-1H-pyrrolo[2,3-b]pyridine-3-carbonyl]phenyl]-3-fluoro-benzenesulfonamide (P-1991),
N-[2,4-difluoro-3-[5-(2-pyridyl)-1H-pyrrolo[2,3-b]pyridine-3-carbonyl]phenyl]-3-fluoro-benzenesulfonamide (P-1992),
N-[3-[5-[2-(cyclopropylamino)pyrimidin-5-yl]-1H-pyrrolo[2,3-b]pyridine-3-carbonyl]-2,4-difluoro-phenyl]-3-fluoro-benzenesulfonamide (P-1993),
N-[2,4-difluoro-3-[5-[2-(2-methoxyethylamino)pyrimidin-5-yl]-1H-pyrrolo[2,3-b]pyridine-3-carbonyl]phenyl]-3-fluoro-benzenesulfonamide (P-1994),
N-[2,4-difluoro-3-[5-[2-(3-pyridyloxy)pyrimidin-5-yl]-1H-pyrrolo[2,3-b]pyridine-3-carbonyl]phenyl]-3-fluoro-benzenesulfonamide (P-1995),
N-[2,4-difluoro-3-[5-[2-(trifluoromethoxy)pyrimidin-5-yl]-1H-pyrrolo[2,3-b]pyridine-3-carbonyl]phenyl]-3-fluoro-benzenesulfonamide (P-1996),
N-[3-[5-(2-cyanopyrimidin-5-yl)-1H-pyrrolo[2,3-b]pyridine-3-carbonyl]-2,4-difluoro-phenyl]-3-fluoro-benzenesulfonamide (P-1997),
N-[2,4-difluoro-3-[5-(2-imidazol-1-ylpyrimidin-5-yl)-1H-pyrrolo[2,3-b]pyridine-3-carbonyl]phenyl]-3-fluoro-benzenesulfonamide (P-1998),
N-[3-[5-[2-(azetidin-1-yl)pyrimidin-5-yl]-1H-pyrrolo[2,3-b]pyridine-3-carbonyl]-2,4-difluoro-phenyl]-3-fluoro-benzenesulfonamide (P-1999),
N-[2,4-difluoro-3-[5-[2-(isopropylamino)pyrimidin-5-yl]-1H-pyrrolo[2,3-b]pyridine-3-carbonyl]phenyl]-3-fluoro-benzenesulfonamide (P-2000),
N-[2,4-difluoro-3-[5-(2-methylaminopyrimidin-5-yl)-1H-pyrrolo[2,3-b]pyridine-3-carbonyl]phenyl]-3-fluoro-benzenesulfonamide (P-2001),
N-[3-[5-[2-(2-dimethylaminoethylamino)pyrimidin-5-yl]-1H-pyrrolo[2,3-b]pyridine-3-carbonyl]-2,4-difluoro-phenyl]-3-fluoro-benzenesulfonamide (P-2002),
N-[2,4-difluoro-3-[5-[2-(3-methoxypropylamino)pyrimidin-5-yl]-1H-pyrrolo[2,3-b]pyridine-3-carbonyl]phenyl]-3-fluoro-benzenesulfonamide (P-2003),
N-[2,4-difluoro-3-[5-[2-(isopropylamino)pyrimidin-5-yl]-1H-pyrrolo[2,3-b]pyridine-3-carbonyl]phenyl]-3-fluoro-benzenesulfonamide (P-2004),
N-[2,4-difluoro-3-[5-(1-oxoisoindolin-5-yl)-1H-pyrrolo[2,3-b]pyridine-3-carbonyl]phenyl]-3-fluoro-benzenesulfonamide (P-2005),
N-[2,4-difluoro-3-[5-(3-oxoisoindolin-5-yl)-1H-pyrrolo[2,3-b]pyridine-3-carbonyl]phenyl]-3-fluoro-benzenesulfonamide (P-2006),
N-[2,4-difluoro-3-[5-(2-oxoindolin-5-yl)-1H-pyrrolo[2,3-b]pyridine-3-carbonyl]phenyl]-3-fluoro-benzenesulfonamide (P-2007), and
any pharmaceutically acceptable salt thereof.

In one embodiment of any of the above aspects and embodiments, the compound includes any prodrug thereof.

In one embodiment of any of the above aspects and embodiments, the compound includes any tautomer thereof.

In one embodiment of any of the above aspects and embodiments, the compound includes any stereoisomer thereof.

In one embodiment of any of the above aspects and embodiments, the compound includes any pharmaceutically acceptable formulation thereof.

In one embodiment of any of the above aspects and embodiments, the compound includes any conjugate thereof.

In one embodiment of any of the above aspects and embodiments, the compound includes any derivative thereof.

In one embodiment of any of the above aspects and embodiments, the compound includes any form thereof.

In reference to compounds described herein, unless clearly indicated to the contrary, specification of a compound or group of compounds includes salts of such compound(s) (including pharmaceutically acceptable salts), formulations of such compound(s) (including pharmaceutically acceptable formulations), conjugates thereof, derivatives thereof, forms thereof, prodrugs thereof, and all stereoisomers thereof. In reference to compositions, kits, methods of use, etc. of compounds as described herein, i.e. compounds of the invention, it is understood (unless indicated otherwise) that a compound as described herein includes compounds of Formulae I-XX, including all sub-embodiments thereof, and compounds as listed in the second aspect above, including all sub-embodiments thereof.

In a third aspect, methods are provided for treating any Raf protein kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In a fourth aspect, methods are provided for treating any B-Raf protein kinase mediated disease or condition, including any B-Raf mutant kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In a fifth aspect, methods are provided for treating any B-Raf V600E mutant protein kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In a sixth aspect, methods are provided for treating any c-Raf-1 protein kinase mediated disease or condition, including any c-Raf-1 mutant kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In a seventh aspect, a compound as described herein is a Raf kinase inhibitor and has an $IC_{50}$ of less than 500 nM, less than 100 nM, less than 50 nM, less than 20 nM, less than 10 nM, less than 5 nM, or less than 1 nM as determined in a generally accepted Raf kinase activity assay. In some embodiments, a compound as described herein will have an $IC_{50}$ of less than 500 nM, less than 100 nM, less than 50 nM, less than 20 nM, less than 10 nM, less than 5 nM, or less than 1 nM with respect to B-Raf, c-Raf-1, or B-Raf V600E mutant. In some embodiments, a compound as described herein will selectively inhibit one or more Raf kinases relative to one or more other non-Raf kinases.

In an eighth aspect, a compound as described herein is a pan Raf inhibitor, i.e. inhibits each of B-Raf V600E mutant kinase, B-Raf kinase and c-Raf-1 kinase, with an $IC_{50}$ of less than 100 nM, less than 50 nM, less than 20 nM, less than 10 nM, less than 5 nM, or less than 1 nM as determined in each of a generally accepted B-Raf V600E mutant kinase activity assay, B-Raf kinase activity assay, and c-Raf-1 kinase activity assay. In some embodiments, the compounds are approximately equipotent on each of B-Raf V600E, B-Raf and c-Raf-1, i.e. the ratio of $IC_{50}$ for any of B-Raf V600E, B-Raf and c-Raf-1 divided by the $IC_{50}$ for any other of B-Raf V600E, B-Raf and c-Raf-1 (e.g. B-Raf $IC_{50}$ divided by B-Raf V600E $IC_{50}$) is in the range of 10 to 0.1, also 5 to 0.2. In some embodiments, the compound is selective relative to other protein kinases, such that the ratio of $IC_{50}$ for another kinase assessed comparably, divided by the $IC_{50}$ for any of B-Raf V600E, B-Raf and c-Raf-1 is >10, also >20, also >30, also >40, also >50, also >60, also >70, also >80, also >90, also >100, wherein the other protein kinase includes, but is not limited to CSK, Insulin receptor kinase, AMPK, PDGFR or VEGFR. In one embodiment, the pan Raf inhibitor is a compound selected from the group consisting of:

Propane-1-sulfonic acid {2,4-difluoro-3-[5-(1H-pyrazolo[3,4-b]pyridin-5-yl)-1H-pyrrolo[2,3-b]pyridine-3-carbonyl]-phenyl}-amide (P-0008),
Propane-1-sulfonic acid {2,4-difluoro-3-[5-(2-methyl-2H-indazol-5-yl)-1H-pyrrolo[2,3-b]pyridine-3-carbonyl]-phenyl}-amide (P-0010),
Propane-1-sulfonic acid {2,4-difluoro-3-[5-(2-methyl-2H-indazol-6-yl)-1H-pyrrolo[2,3-b]pyridine-3-carbonyl]-phenyl}-amide (P-0011),
Propane-1-sulfonic acid {2,4-difluoro-3-[5-(1H-indol-5-yl)-1H-pyrrolo[2,3-b]pyridine-3-carbonyl]-phenyl}-amide (P-0012),
Propane-1-sulfonic acid [3-(5-benzothiazol-5-yl-1H-pyrrolo[2,3-b]pyridine-3-carbonyl)-2,4-difluoro-phenyl]-amide (P-0013),
Propane-1-sulfonic acid [2,4-difluoro-3-(5-quinoxalin-6-yl-1H-pyrrolo[2,3-b]pyridine-3-carbonyl)-phenyl]-amide (P-0014),
Propane-1-sulfonic acid [3-(5-benzothiazol-6-yl-1H-pyrrolo[2,3-b]pyridine-3-carbonyl)-2,4-difluoro-phenyl]-amide (P-0020),
Propane-1-sulfonic acid [2,4-difluoro-3-(5-imidazo[1,2-a]pyridin-2-yl-1H-pyrrolo[2,3-b]pyridine-3-carbonyl)-phenyl]-amide (P-0021),
Propane-1-sulfonic acid {2,4-difluoro-3-[5-(3-methyl-1H-indol-5-yl)-1H-pyrrolo[2,3-b]pyridine-3-carbonyl]-phenyl}-amide (P-0023),
Propane-1-sulfonic acid {2,4-difluoro-3-[5-(3-methyl-1H-indazol-5-yl)-1H-pyrrolo[2,3-b]pyridine-3-carbonyl]-phenyl}-amide (P-0024),
Propane-1-sulfonic acid [2,4-difluoro-3-(5-quinazolin-7-yl-1H-pyrrolo[2,3-b]pyridine-3-carbonyl)-phenyl]-amide (P-0025),
Propane-1-sulfonic acid [2,4-difluoro-3-(5-quinazolin-6-yl-1H-pyrrolo[2,3-b]pyridine-3-carbonyl)-phenyl]-amide (P-0026),
Propane-1-sulfonic acid (2,4-difluoro-3-{5-[2-(4-methyl-imidazol-1-yl)-thiazol-4-yl]-1H-pyrrolo[2,3-b]pyridine-3-carbonyl}-phenyl)-amide (P-1100),
Propane-1-sulfonic acid (2,4-difluoro-3-{5-[2-(2-methyl-imidazol-1-yl)-thiazol-4-yl]-1H-pyrrolo[2,3-b]pyridine-3-carbonyl}-phenyl)-amide (P-1101),
Propane-1-sulfonic acid {2,4-difluoro-3-[5-(2-pyrazol-1-yl-thiazol-4-yl)-1H-pyrrolo[2,3-b]pyridine-3-carbonyl]-phenyl}-amide (P-1103),
Propane-1-sulfonic acid {2,4-difluoro-3-[5-(2-imidazol-1-yl-thiazol-5-yl)-1H-pyrrolo[2,3-b]pyridine-3-carbonyl]-phenyl}-amide (P-1104),
Propane-1-sulfonic acid (2,4-difluoro-3-{5-[2-(2-methyl-imidazol-1-yl)-thiazol-5-yl]-1H-pyrrolo[2,3-b]pyridine-3-carbonyl}-phenyl)-amide (P-1105),
Propane-1-sulfonic acid {2,4-difluoro-3-[5-(2-imidazol-1-yl-thiazol-4-yl)-1H-pyrrolo[2,3-b]pyridine-3-carbonyl]-phenyl}-amide (P-1106),
Propane-1-sulfonic acid {2,4-difluoro-3-[5-(2-pyrazol-1-yl-thiazol-5-yl)-1H-pyrrolo[2,3-b]pyridine-3-carbonyl]-phenyl}-amide (P-1109),
Propane-1-sulfonic acid {2,4-difluoro-3-[5-(5-pyridin-3-yl-thiophen-2-yl)-1H-pyrrolo[2,3-b]pyridine-3-carbonyl]-phenyl}-amide (P-1200),
Propane-1-sulfonic acid (2,4-difluoro-3-{5-[5-(1H-pyrazol-3-yl)-thiophen-2-yl]-1H-pyrrolo[2,3-b]pyridine-3-carbonyl}-phenyl)-amide (P-1201),
5-{3-[2,6-Difluoro-3-(propane-1-sulfonylamino)-benzoyl]-1H-pyrrolo[2,3-b]pyridin-5-yl}-thiophene-2-sulfonic acid amide (P-1202),
N-[2,4-Difluoro-3-(5-oxazol-5-yl-1H-pyrrolo[2,3-b]pyridine-3-carbonyl)-phenyl]-2,5-difluoro-benzenesulfonamide (P-1300),
4-(4-{3-[2,6-Difluoro-3-(propane-1-sulfonylamino)-benzoyl]-1H-pyrrolo[2,3-b]pyridin-5-yl}-pyrazol-1-yl)-piperidine-1-carboxylic acid tert-butyl ester (P-1001),
Propane-1-sulfonic acid {2,4-difluoro-3-[5-(1-piperidin-4-yl-1H-pyrazol-4-yl)-1H-pyrrolo[2,3-b]pyridine-3-carbonyl]-phenyl}-amide (P-1002),
Propane-1-sulfonic acid {2,4-difluoro-3-[5-(1-pyrimidin-2-yl-1H-pyrazol-4-yl)-1H-pyrrolo[2,3-b]pyridine-3-carbonyl]-phenyl}-amide (P-1005),
N-{2,4-Difluoro-3-[5-(1-methyl-1H-pyrazol-4-yl)-1H-pyrrolo[2,3-b]pyridine-3-carbonyl]-phenyl}-2,5-difluoro-benzenesulfonamide (P-1009), Propane-1-sulfonic acid [2,4-difluoro-3-(5-pyridin-2-yl-1H-pyrrolo[2,3-b]pyridine-3-carbonyl)-phenyl]-amide (P-1401),
N-[2,4-Difluoro-3-(5-pyridin-3-yl-1H-pyrrolo[2,3-b]pyridine-3-carbonyl)-phenyl]-2,5-difluoro, benzenesulfonamide (P-1402),
N-[2,4-Difluoro-3-(5-pyridin-4-yl-1H-pyrrolo[2,3-b]pyridine-3-carbonyl)-phenyl]-2,5-difluoro-benzenesulfonamide (P-1403),
N-{2,4-Difluoro-3-[5-(6-methoxy-pyridin-3-yl)-1H-pyrrolo[2,3-b]pyridine-3-carbonyl]-phenyl}-2,5-difluoro-benzenesulfonamide (P-1404),
N-{2,4-Difluoro-3-[5-(5-methanesulfonyl-pyridin-3-yl)-1H-pyrrolo[2,3-b]pyridine-3-carbonyl]-phenyl}-2,5-difluoro-benzenesulfonamide (P-1407),
N-{2,4-Difluoro-3-[5-(6-methyl-pyridin-3-yl)-1H-pyrrolo[2,3-b]pyridine-3-carbonyl]-phenyl}-2,5-difluoro-benzenesulfonamide (P-1408),
N-{3-[5-(6-Dimethylamino-pyridin-3-yl)-1H-pyrrolo[2,3-b]pyridine-3-carbonyl]-2,4-difluoro-phenyl}-2,5-difluoro-benzenesulfonamide (P-1409),
N-[2,4-Difluoro-3-(5-pyrimidin-5-yl-1H-pyrrolo[2,3-b]pyridine-3-carbonyl)-phenyl]-2,5-difluoro-benzenesulfonamide (P-1500),
N-{3-[5-(2-Dimethylamino-pyrimidin-5-yl)-1H-pyrrolo[2,3-b]pyridine-3-carbonyl]-2,4-difluoro-phenyl}-2,5-difluoro-benzenesulfonamide (P-1502),
N-{2,4-Difluoro-3-[5-(2-methyl-pyrimidin-5-yl)-1H-pyrrolo[2,3-b]pyridine-3-carbonyl]-phenyl}-2,5-difluoro-benzenesulfonamide (P-1503),
2-Chloro-5-{3-[2,6-difluoro-3-(propane-1-sulfonylamino)-benzoyl]-1H-pyrrolo[2,3-b]pyridin-5-yl}-benzamide (P-1700),
Propane-1-sulfonic acid {2,4-difluoro-3-[5-(3-oxo-2,3-dihydro-1H-isoindol-5-yl)-1H-pyrrolo[2,3-b]pyridine-3-carbonyl]-phenyl}-amide (P-1702),
Propane-1-sulfonic acid {2,4-difluoro-3-[5-(2-oxo-2,3-dihydro-1H-indol-5-yl)-1H-pyrrolo[2,3-b]pyridine-3-carbonyl]-phenyl}-amide (P-1703),
3-{3-[3-(2,5-Difluoro-benzenesulfonylamino)-2,6-difluoro-benzoyl]-1H-pyrrolo[2,3-b]pyridin-5-yl}-N-methoxy-benzamide (P-1704),
4-{3-[3-(2,5-Difluoro-benzenesulfonylamino)-2,6-difluoro-benzoyl]-1H-pyrrolo[2,3-b]pyridin-5-yl}-N-methoxy-benzamide (P-1705),
N-{2,4-Difluoro-3-[5-(4-methylsulfamoyl-phenyl)-1H-pyrrolo[2,3-b]pyridine-3-carbonyl]-phenyl}-2,5-difluoro-benzenesulfonamide (P-1706),
N-{2,4-Difluoro-3-[5-(4-sulfamoyl-phenyl)-1H-pyrrolo[2,3-b]pyridine-3-carbonyl]-phenyl}-2,5-difluoro-benzenesulfonamide (P-1707), and
any salt, prodrug, tautomer, or stereoisomer thereof.

In a ninth aspect, compositions are provided that include a therapeutically effective amount of any one or more compound(s) as described herein and at least one pharmaceutically acceptable carrier, excipient, and/or diluent, including combinations of any two or more compounds as described herein. The composition can further include a plurality of different pharmacologically active compounds, which can include a plurality of compounds as described herein. In certain embodiments, the composition can include any one or more compound(s) as described herein along with one or more compounds that are therapeutically effective for the same disease indication. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In a tenth aspect, the invention provides methods for treating a disease or condition mediated by one or more Raf kinases (including A-Raf, B-Raf, and c-Raf-1 kinases), including mutations thereof, in a subject in need thereof by administering to the subject an effective amount of a composition including any one or more compound(s) as described herein. In one embodiment, the invention provides methods for treating a disease or condition mediated by one or more Raf kinases, including mutations thereof, by administering to the subject an effective amount of a composition including any one or more compound(s) as described herein in combination with one or more other suitable therapies for treating the disease.

In an eleventh aspect, the invention provides methods for treating a disease or condition mediated by B-Raf kinase, including any mutations thereof, in a subject in need thereof by administering to the subject an effective amount of a composition including any one or more compound(s) as described herein. In one embodiment, the invention provides methods for treating a disease or condition mediated by B-Raf kinase, including any mutations thereof, by administering to the subject an effective amount of a composition including any one or more compound(s) as described herein in combination with one or more other suitable therapies for treating the disease.

In a twelfth aspect, the invention provides methods for treating a disease or condition mediated by B-Raf V600E mutant kinase, in a subject in need thereof by administering to the subject an effective amount of a composition including any one or more compound(s) as described herein. In one embodiment, the invention provides methods for treating a disease or condition mediated by B-Raf V600E mutant kinase, by administering to the subject an effective amount of a composition including any one or more compound(s) as described herein in combination with one or more other suitable therapies for treating the disease. In one embodiment, the invention provides methods for treating a cancer mediated by B-Raf V600E mutant by administering to the subject an effective amount of a composition including any one or more compound(s) as described herein. In one embodiment, the invention provides methods for treating a cancer mediated by B-Raf V600E mutant by administering to the subject an effective amount of a composition including any one or more compound(s) as described herein in combination with one or more suitable anticancer therapies, such as one or more chemotherapeutic drugs.

In a thirteenth aspect, the invention provides methods for treating a disease or condition mediated by c-Raf-1 kinase, including any mutations thereof, in a subject in need thereof by administering to the subject an effective amount of a composition including any one or more compound(s) as described herein. In one embodiment, the invention provides methods for treating a disease or condition mediated by c-Raf-1 kinase, including any mutations thereof, by administering to the subject an effective amount of a composition including any one or more compound(s) as described herein in combination with one or more other suitable therapies for treating the disease.

In a fourteenth aspect, the invention provides a method of treating a cancer in a subject in need thereof by administering to the subject an effective amount of a composition including any one or more compound(s) as described herein. In one embodiment, the invention provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or α particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

In a fifteenth aspect, the invention provides a method of treating a cancer in a subject in need thereof by administering to the subject an effective amount of a composition including any one or more compound(s) as described herein in combination with one or more suitable chemotherapeutic agents. In one embodiment, the one or more suitable chemotherapeutic agents is selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90 Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib). Preferably, the method of treating a cancer involves administering to the subject an effective amount of a composition including any one or more compound(s) as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib.

In a sixteenth aspect, the invention provides a method of treating a disease or condition in a subject in need thereof, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug. The compound can be alone or can be part of a composition. In one embodiment, the invention provides a method of treating a disease or condition in a subject, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug in combination with one or more other suitable therapies for the disease or condition.

In a seventeenth aspect, the invention provides kits that include a compound or composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the invention kit may include written instructions for use and/or other indication that the compound or composition is suitable or approved for administration to a mammal, e.g., a human, for a Raf protein kinase-mediated disease or condition; and the compound or composition may be packaged in unit dose or single dose form, e.g., single dose pills, capsules, or the like.

In aspects and embodiments involving treatment of a disease or condition with any one or more compound(s) as described herein, the invention provides methods for treating an A-Raf-mediated, B-Raf-mediated and/or c-Raf-1-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal A-Raf, B-Raf, and/or c-Raf-1 activity (e.g. kinase activity). In some embodiments, invention methods may involve administering to the subject suffering from or at risk of an A-Raf-mediated, B-Raf-mediated and/or c-Raf-1-mediated disease or condition an effective amount of any one or more Raf inhibitor(s) as described herein. In one embodiment, the A-Raf-mediated, B-Raf-mediated, and/or c-Raf-1-mediated disease is selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy); inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma, sarcoma, liver cancer, biliary tract cancer, cholangiocarcinoma, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, pheochromocytoma, acute pain, chronic pain, and polycystic kidney disease. In a preferred embodiment, the disease or condition is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain, and polycystic kidney disease.

In aspects and embodiments involving treatment of a disease or condition with any one or more compound(s) as described herein, the invention provides methods for treating a c-Raf-1-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal c-Raf-1 activity (e.g. kinase activity). In one embodiment, the c-Raf-1-mediated disease is selected from the group consisting of polycystic kidney disease, acute pain, and chronic pain.

In aspects and embodiments involving treatment of a disease or condition with any one or more compound(s) as described herein, the invention provides methods for treating a B-Raf V600E mutant-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal B-Raf V600E mutant activity (e.g. kinase activity). In one embodiment, the B-Raf V600E mutant-mediated disease is a cancer, preferably a cancer selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma.

In aspects and embodiments involving treatment of a disease or condition with any one or more compound(s) as described herein, the invention provides methods for treating a cancer in a subject in need thereof (e.g. a mammal such as a human, other primates, sports animals, animals of commercial interest such as cattle, farm animals such as horses, or pets such as dogs and cats). In some embodiments, invention methods may involve administering to the subject suffering from or at risk of a cancer an effective amount of any one or more pan Raf inhibitor(s) as described herein, wherein the cancer is selected from the group consisting of melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma.

In an eighteenth aspect, any one or more compound(s) as described herein can be used in the preparation of a medicament for the treatment of an A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (facio-cutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma sarcoma, liver cancer, biliary tract cancer, cholangiocarcinoma, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, pheochromocytoma, pain, and polycystic kidney disease. In a preferred embodiment, the disease or condition is selected from the group consisting of melanoma, glioma, glioblastoma multiforme, pilocytic astrocytoma colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain, and polycystic kidney disease.

In a nineteenth aspect, any one or more pan Raf inhibitor(s) as described herein can be used in the preparation of a medicament for the treatment of a cancer selected from the group consisting of melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma.

In various aspects and embodiments, a compound as disclosed herein (including any compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Table I, or any other compounds specifically disclosed herein) or any compounds recited in claims 1-27 is a pan Raf inhibitor. In various aspects and embodiments, a compound as disclosed herein (including any compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Table I, or any other compounds specifically disclosed herein) is a Ras activity inhibitor. In some embodiments, a compound as disclosed herein (including any compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Table I, or any other compounds specifically disclosed herein) is both a pan Raf inhibitor and a Ras activity inhibitor. In certain embodiments, a compound as disclosed herein (including any compounds of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XIX, Formula XX, Table I, or any other compounds specifically disclosed herein) is a pan Raf inhibitor having an $IC_{50}$ of less than 500 nM in activity assays for each of B-Raf, c-Raf-1 and B-Raf V600E protein kinases and is a Ras activity inhibitor that inhibits proliferation of a mutant Ras cell line with an $IC_{50}$ of less than 1 µM.

In another aspect, the invention provides a method for preparing a compound of Formula I

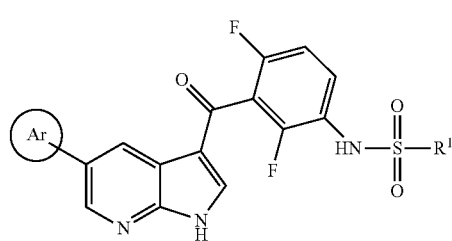

The method includes contacting a compound of Formula Ia:

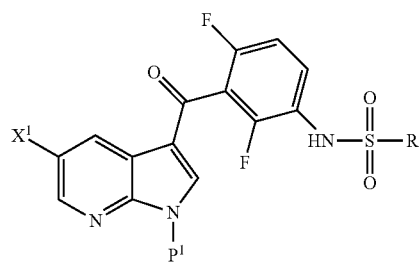

with a compound of Formula Ib:

under conditions sufficient to form the compound of Formula I, wherein $X^1$ is a halogen, such as Cl, Br or I; $P^1$ is a protecting group;

is a boronic acid or ester and Q is a boronic acid or ester residue. Ar is as defined in any of the embodiments descried herein for compounds of Formulas I-XX, Table I or any other compounds specifically disclosed herein or any compounds recited in claims 1-27 and in the Examples below. Exemplary Q includes, but is not limited to —$B(OH)_2$ or

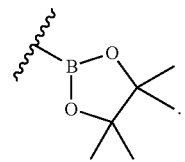 [SMILES: *B1OC(C)(C)C(C)(C)O1]

In some embodiments, the reaction is performed in the presence of a palladium complex, such as 1,1'-bis(diphenylphosphino)ferrocene]dichloropalladium(II). In some embodiments, protecting group $P^1$ is t-butoxycarbonyl, 2,6-dichlorophenylcarbonyl or phenylsulfonyl.

Additional aspects and embodiments will be apparent from the following Detailed Description of the Invention and from the claims.

DETAILED DESCRIPTION OF THE INVENTION

As used herein the following definitions apply unless clearly indicated otherwise:

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^{1}$H, $^{2}$H, $^{3}$H; carbon includes for example $^{11}$C, $^{12}$C, $^{13}$C, $^{14}$C; oxygen includes for example $^{16}$O, $^{17}$O, $^{18}$O; nitrogen includes for example $^{13}$N, $^{14}$N, $^{15}$N; sulfur includes for example $^{32}$S, $^{33}$S, $^{34}$S, $^{35}$S, $^{36}$S, $^{37}$S, $^{38}$S; fluoro includes for example $^{17}$F, $^{18}$F, $^{19}$F; chloro includes for example $^{35}$Cl, $^{36}$Cl, $^{37}$Cl, $^{38}$Cl, $^{39}$Cl; and the like.

"Halogen" refer to all halogens, that is, chloro (Cl), fluoro (F), bromo (Br), or iodo (I).

"Hydroxyl" or "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched lower alkyl group is chemically feasible and attached at any available point to provide a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. A lower alkyl may be independently substituted as described herein, unless indicated otherwise, with one or more, preferably 1, 2, 3, 4 or 5, also 1, 2, or 3 substituents, wherein the substituents are as indicated. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. It is understood that any such substitutions, or substitution of lower alkyl on another moiety are chemically feasible and attached at any available atom to provide a stable compound.

"Cycloalkyl" refers to saturated or unsaturated, non-aromatic monocyclic carbon ring systems of 3-10, also 3-8, more preferably 3-6, ring members per ring, such as cyclopropyl, cyclopentyl, cyclohexyl, cycloheptyl, and the like. A "substituted cycloalkyl" is a cycloalkyl that is independently substituted, unless indicated otherwise, with one or more, preferably 1, 2, 3, 4 or 5, also 1, 2, or 3 substituents, wherein the substituents are as indicated. It is understood that substitutions on cycloalkyl, or substitutions of cycloalkyl on another moiety are chemically feasible and attached at any available atom to provide a stable compound.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholine, tetrahydrofuranyl, dihydropyridinyl, piperidinyl, pyrrolidinyl, pyrrolidonyl, piperazinyl, dihydrobenzofuryl, and dihydroindolyl. A "substituted heterocycloalkyl" is a heterocycloalkyl that is independently substituted, unless indicated otherwise, with one or more, preferably 1, 2, 3, 4 or 5, also 1, 2, or 3 substituents, wherein the substituents are as indicated. It is understood that substitutions on heterocycloalkyl, or substitutions of heterocycloalkyl on another moiety are chemically feasible and attached at any available atom to provide a stable compound.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. A "substituted aryl" is an aryl that is independently substituted, unless indicated otherwise, with one or more, preferably 1, 2, 3, 4 or 5, also 1, 2, or 3 substituents, wherein the substituents are as indicated. It is understood that substitutions on aryl, or substitutions of aryl on another moiety are chemically feasible and attached at any available atom to provide a stable compound.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is provided. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A "substituted heteroaryl" is a heteroaryl that is independently substituted, unless indicated otherwise, with one or more, preferably 1, 2, 3, 4 or 5, also 1, 2, or 3 substituents, wherein the substituents are as indicated. It is understood that substitutions on heteroaryl, or substitutions of heteroaryl on another moiety are chemically feasible and attached at any available atom to provide a stable compound.

"Lower alkoxy" denotes the group —OR$^a$, where R$^a$ is lower alkyl. "Substituted lower alkoxy" denotes lower alkoxy in which R$^a$ is lower alkyl substituted with one or more substituents as indicated herein. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. It is understood that substitutions on alkoxy, or alkoxy substitution of other moieties are chemically feasible and attached at any available atom to provide a stable compound.

"Lower alkylthio" denotes the group —SR$^b$, where R$^b$ is lower alkyl. "Substituted lower alkylthio" denotes lower alkylthio in which R$^b$ is lower alkyl substituted with one or more substituents as indicated herein. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. It is understood that substitutions on alkylthio, or alkylthio substitution of other moieties are chemically feasible and attached at any available atom to provide a stable compound.

"Mono-alkylamino" denotes the group —NHR$^c$ where R$^c$ is lower alkyl. "Di-alkylamino" denotes the group —NR$^c$R$^d$, where R$^c$ and R$^d$ are independently lower alkyl. "Cycloalkylamino" denotes the group —NR$^e$R$^f$, where R$^e$ and R$^f$ combine with the nitrogen to form a 5-7 membered heterocycloalkyl, where the heterocycloalkyl may contain an additional heteroatom within the ring, such as O, N, or S, and may also be further substituted with lower alkyl. Examples of 5-7 membered heterocycloalkyl include, but are not limited to, piperidine, piperazine, 4-methylpiperazine, morpholine, and thiomorpholine. It is understood that when mono-alkylamino, di-alkylamino, or cycloalkylamino are substituents on other moieties, these are chemically feasible and attached at any available atom to provide a stable compound.

As used herein "Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), CURRENT PROTOCOLS IN NUCLEIC ACID CHEMISTRY, John Wiley and Sons, New York, Volume 1, 2000).

As used herein, the terms "treat", "treating", "therapy", "therapies", and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

As used herein, the term "Raf protein kinase mediated disease or condition" refers to a disease or condition in which the biological function of a Raf protein kinase (also referred to as Raf kinase, or Raf), including any of A-Raf protein kinase, B-Raf protein kinase or c-Raf-1 protein kinase, or any mutation thereof, affects the development, course, and/or symptoms of the disease or condition, and/or in which modulation of Raf alters the development, course, and/or symptoms of the disease or condition. The Raf mediated disease or condition includes a disease or condition for which Raf modulation provides a therapeutic benefit, e.g. wherein treatment with Raf inhibitor(s), including one or more compound(s) described herein, provides a therapeutic benefit to the subject suffering from or at risk of the disease or condition.

As used herein, the term "A-Raf protein kinase mediated disease or condition," and the like refer to a disease or condition in which the biological function of an A-Raf protein kinase (also referred to as A-Raf kinase, or A-Raf), including any mutations thereof, affects the development, course, and/or symptoms of the disease or condition, and/or in which modulation of A-Raf alters the development, course, and/or symptoms of the disease or condition. The A-Raf mediated disease or condition includes a disease or condition for which A-Raf inhibition provides a therapeutic benefit, e.g. wherein treatment with a compound that inhibits A-Raf, including one or more compound(s) described herein, provides a therapeutic benefit to the subject suffering from or at risk of the disease or condition.

As used herein, the term "B-Raf protein kinase mediated disease or condition," and the like refer to a disease or condition in which the biological function of a B-Raf protein kinase (also referred to as B-Raf kinase, or B-Raf), including any mutations thereof, affects the development, course, and/or symptoms of the disease or condition, and/or in which modulation of B-Raf alters the development, course, and/or symptoms of the disease or condition. The B-Raf mediated disease or condition includes a disease or condition for which B-Raf inhibition provides a therapeutic benefit, e.g. wherein treatment with a compound that inhibits B-Raf, including one or more compound(s) described herein, provides a therapeutic benefit to the subject suffering from or at risk of the disease or condition.

As used herein, the term "B-Raf V600E mutant protein kinase mediated disease or condition," and the like refer to a disease or condition in which the biological function of B-Raf V600E mutant protein kinase (also referred to as B-Raf V600E kinase, or B-Raf V600E) affects the development, course, and/or symptoms of the disease or condition; and/or in which modulation of B-Raf V600E alters the development, course, and/or symptoms of the disease or condition. The B-Raf V600E mediated disease or condition includes a disease or condition for which B-Raf V600E inhibition provides a therapeutic benefit, e.g. wherein treatment with a compound that inhibits B-Raf V600E, including one or more compound(s) described herein, provides a therapeutic benefit to the subject suffering from or at risk of the disease or condition.

As used herein, the term "c-Raf-1 protein kinase mediated disease or condition," and the like refer to a disease or condition in which the biological function of a c-Raf-1 protein kinase (also referred to as c-Raf-1 kinase, or c-Raf-1), including any mutations thereof, affects the development, course, and/or symptoms of the disease or condition, and/or in which modulation of c-Raf-1 alters the development, course, and/or symptoms of the disease or condition. The c-Raf-1 mediated disease or condition includes a disease or condition for which c-Raf-1 inhibition provides a therapeutic benefit, e.g. wherein treatment with a compound that inhibits c-Raf-1, including one or more compound(s) described herein, provides a therapeutic benefit to the subject suffering from or at risk of the disease or condition.

As used herein, the term "Raf inhibitor" refers to a compound that inhibits at least one of A-Raf, B-Raf, c-Raf-1, or any mutations thereof, i.e. a compound having an $IC_{50}$ of less than 500 nM, less than 100 nM, less than 50 nM, less than 20 nM, less than 10 nM, less than 5 nM, or less than 1 nM as determined in a generally accepted Raf kinase activity assay. Such compounds are preferably, but not necessarily, selective with respect to other protein kinases, i.e. when compared to another protein kinase, the $IC_{50}$ for the other kinase divided by the $IC_{50}$ for the Raf kinase is >10, also >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR.

As used herein, the term "pan Raf inhibitor" refers to a compound that inhibits at least each of B-Raf, c-Raf-1 and B-Raf V600E protein kinases, i.e. a compound having an $IC_{50}$ of less than 100 nM, less than 50 nM, less than 20 nM, less than 10 nM, less than 5 nM, or less than 1 nM as determined in a generally accepted B-Raf kinase activity assay, and having an $IC_{50}$ of less than 500 nM, less than 100 nM, less than 50 nM, less than 20 nM, less than 10 nM, less than 5 nM, or less than 1 nM as determined in a comparable generally accepted c-Raf-1 kinase activity assay, and having an $IC_{50}$ of less than 500 nM, less than 100 nM, less than 50 nM, less than 20 nM, less than 10 nM, less than 5 nM, or less than 1 nM as determined in a comparable generally accepted B-Raf V600E kinase activity assay. The pan Raf inhibitor may be, but is not necessarily, approximately equipotent on each of B-Raf, c-Raf-1 and B-Raf V600E. Compounds are considered approximately equipotent on each of B-Raf V600E, B-Raf and c-Raf-1 if the ratio of $IC_{50}$ for any of B-Raf V600E, B-Raf and c-Raf-1 divided by the $IC_{50}$ for any other of B-Raf V600E, B-Raf and c-Raf-1 (e.g. B-Raf $IC_{50}$ divided by B-Raf V600E $IC_{50}$) is in the range of 10 to 0.1, also 5 to 0.2. Such compounds are preferably, but not necessarily, selective with respect to other protein kinases, i.e. when compared to another protein kinase, the $IC_{50}$ for the other kinase divided by the $IC_{50}$ for any of B-Raf, c-Raf-1 or B-Raf V600E is >10, also >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a pan Raf inhibitor may be used to treat any B-Raf, c-Raf-1 or B-Raf V600E kinase mediated disease or condition, the inhibition of each of B-Raf, c-Raf-1 and B-Raf V600E provides beneficial effects in treating cancers, in particular cancers having a Ras pathway mutation, including, but not limited to, melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma. Such compounds are also beneficial in treating B-Raf V600E mediated cancers that become resistant to B-Raf V600E selective inhibitors.

As used herein, the term "Ras activity inhibitor" refers to a compound that inhibits proliferation of a mutant Ras cell line; i.e., a compound that inhibits proliferation of a mutant Ras cell line with an $IC_{50}$ of less than 1 µM, less than 100 nM, less than 50 nM, less than 20 nM, less than 10 nM, less than 5 nM, or less than 1 nM. In some embodiments, a Ras activity inhibitor inhibits proliferation of a mutant Ras cell line with an $IC_{50}$ of less than 1 µM. In some embodiments, a Ras activity inhibitor inhibits proliferation of a mutant Ras cell line with an $IC_{50}$ of less than 100 nM. In some embodiments, a Ras activity inhibitor inhibits proliferation of a mutant Ras cell line with an $IC_{50}$ of less than 50 nM. In some embodiments, a Ras activity inhibitor inhibits proliferation of a mutant Ras cell line with an $IC_{50}$ of less than 20 nM. In some embodiments, a Ras activity inhibitor inhibits proliferation of a mutant Ras cell line with an $IC_{50}$ of less than 10 nM. In some embodiments, a Ras activity inhibitor inhibits proliferation of a mutant Ras cell line with an $IC_{50}$ of less than 5 nM. In some embodiments, a Ras activity inhibitor inhibits proliferation of a mutant Ras cell line with an $IC_{50}$ of less than 1 nM. In some embodiments the mutant Ras cell line is a N-Ras mutant cell line, a K-Ras mutant cell line, or a H-Ras mutant cell line. In various embodiments a Ras activity inhibitor inhibits proliferation of a mutant N-Ras cell line with an $IC_{50}$ of less than 1 µM, less than 100 nM, less than 50 nM, less than 20 nM, less than 10 nM, less than 5 nM, or less than 1 nM. In some embodiments, a Ras activity inhibitor inhibits proliferation of a N-Ras mutant cell line with an $IC_{50}$ of less than 1 µM. In some embodiments, a Ras activity inhibitor inhibits proliferation of a N-Ras mutant cell line with an $IC_{50}$ of less than 100 nM. In some embodiments, a Ras activity inhibitor inhibits proliferation of a N-Ras mutant cell line with an $IC_{50}$ of less than 50 nM. In some embodiments, a Ras activity inhibitor inhibits proliferation of a N-Ras mutant cell line with an $IC_{50}$ of less than 20 nM. In some embodiments, a Ras activity inhibitor inhibits proliferation of a N-Ras mutant cell line with an $IC_{50}$ of less than 10 nM. In some embodiments, a Ras activity inhibitor inhibits proliferation of a N-Ras mutant cell line with an $IC_{50}$ of less than 5 nM. In some embodiments, a Ras activity inhibitor inhibits proliferation of a N-Ras mutant cell line with an $IC_{50}$ of less than 1 nM. In certain embodiments, the N-Ras mutant cell line is one or more cell lines selected from the group consisting of M244, M202, M207, SK-MEL-2, IPC-298, S'117, M296, SK-MEL-30, SK-MEL-173, and HL-60. In some embodiments, the N-Ras mutant cell line is one or more cell lines selected from the group consisting of M244, M202, M207, SK-MEL-2, SK-MEL-173, and IPC298. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 1 µM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 100 nM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 50 nM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 20 nM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 10 nM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 5 nM. In some embodiments, a Ras activity inhibitor inhibits proliferation of a mutant Ras cell line selected from the group consisting of M244, M202, M207, SK-MEL-2, SK-MEL-173, and IPC298 with an $IC_{50}$ of less than 1 nM. In some embodiments, a Ras activity inhibitor inhibits proliferation of IPC298 cells with an $IC_{50}$ of less than 1 µM. In some embodiments, a Ras activity inhibitor inhibits proliferation of IPC298 cells with an $IC_{50}$ of less than 100 nM. In some embodiments, a Ras activity inhibitor inhibits proliferation of IPC298 cells with an $IC_{50}$ of less than 50 nM. In some embodiments, a Ras activity inhibitor inhibits proliferation of IPC298 cells with an $IC_{50}$ of less than 20 nM. In some embodiments, a Ras activity inhibitor inhibits proliferation of IPC298 cells with an $IC_{50}$ of less than 10 nM. In some embodiments, a Ras activity inhibitor inhibits proliferation of IPC298 cells with an $IC_{50}$ of less than 5 nM. In some embodiments, a Ras activity inhibitor inhibits proliferation of IPC298 cells with an $IC_{50}$ of less than 1 nM.

As used herein, the term "solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "substantially crystalline" material embraces material which has greater than about 90% crystallinity; and "crystalline" material embraces material which has greater than about 98% crystallinity.

As used herein, the term "substantially amorphous" material embraces material which has no more than about 10% crystallinity; and "amorphous" material embraces material which has no more than about 2% crystallinity.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. In one aspect of the present invention, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailability. Such a mixture may provide both rapid and extended exposure to the active compound.

As used herein, the term "complex" refers to a combination of a pharmaceutically active compound and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may also be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "stoichiometry" refers to the molar ratio of a combination of two or more components, for example, the molar ratio of acid or base to compound that form an amorphous complex. For example, a 1:1 mixture of acid or base with compound (i.e. 1 mole acid or base per mole of compound) resulting in an amorphous solid form has a 1:1 stoichiometry.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

As used herein, the term "biopharmaceutical properties" refers to the pharmacokinetic action of a compound or complex of the present invention, including the dissolution, absorption and distribution of the compound on administration to a subject. As such, certain solid forms of compounds of the invention, such as amorphous complexes of compounds of the invention, are intended to provide improved dissolution and absorption of the active compound, which is typically reflected in improved $C_{max}$ (i.e. the maximum achieved concentration in the plasma after administration of the drug) and improved AUC (i.e. area under the curve of drug plasma concentration vs. time after administration of the drug).

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the term "modulating" or "modulate" refers to an effect of altering a biological activity (i.e. increasing or decreasing the activity), especially a biological activity associated with a particular biomolecule such as a protein kinase. For example, an inhibitor of a particular biomolecule modulates the activity of that biomolecule, e.g., an enzyme, by decreasing the activity of the biomolecule, such as an enzyme. Such activity is typically indicated in terms of an inhibitory concentration ($IC_{50}$) of the compound for an inhibitor with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal chord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gallbladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Specific target protein kinases contemplated by the present invention are described in the art, including, without limitation, protein kinases as described in U.S. patent application Ser. No. 11/473,347 (see also, PCT publication WO2007002433), the disclosure of which is hereby incorporated by reference as it relates to such kinase targets, as well as the following:

A-Raf: Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RBD (i.e., Ras binding domain) and phorbol-ester/DAG-type zinc finger domain and is involved in the transduction of mitogenic signals from the cell membrane to the nucleus. A-Raf inhibitors may be useful in treating neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf: Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS→Raf→MEK→ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAF inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat Genet. 2006, 38(3):294-6).

Many cancers associated with dysregulation of the RAS-RAF-ERK pathway, such as cancers having B-Raf V600E mutations or NRAS mutations, may be treated with Raf kinase inhibitors, such as the Pan Raf kinase inhibitors as described herein. The ability of these compounds to inhibit multiple Raf kinase targets, including c-Raf-1, B-Raf, and B-Raf V600E, provides additional benefits for inhibiting activating mutations in this pathway, with such cancers less likely to develop resistance to such inhibitors as they are targeting several points in the pathway. Pan Raf kinase inhibitors as described herein may be useful in treating a variety of cancers, including, but not limited to, melanoma, glioma, glioblastoma mulitforme, pilocytic astrocytoma, carcinoma (e.g. gastrointestinal, liver, biliary tract, bile duct (cholangiocarcinoma), colorectal, lung, brain, bladder, gallbladder, breast, pancreatic, thyroid, kidney, ovarian, adrenocortical, prostate), gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma. See McDermott et al., PNAS, 2007, 104(50): 19936-19941; and Jaiswal et al., PLoS One, 2009, 4(5):e5717.

c-Raf-1: Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. c-Raf-1 is also implicated as an important mediator of tumor angiogenesis (Hood, J. D. et al., 2002, Science 296, 2404). c-Raf-1 inhibitors may also be useful for the treatment of acute myeloid leukemia and myelodysplastic syndromes (Crump, Curr Pharm Des 2002, 8(25):2243-8). c-Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2):139-42).

Raf inhibitors (A-Raf and/or B-Raf and/or c-Raf-1) may be useful in treating A-Raf-mediated, B-Raf-mediated or c-Raf-1-mediated diseases or conditions selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, brain, bladder, gallbladder, breast, pancreatic, thyroid, renal, ovarian, adrenocortical, prostate), lymphoma (e.g. histiocytic lymphoma) neurofibromatosis, acute myeloid leukemia, myelodysplastic syndrome, leukemia, chronic myelomonocytic leukemia, childhood, acute lymphoblastic leukemia, plasma cell leukemia, multiple myeloma, tumor angiogenesis, gastrointestinal stromal tumors, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 1-position of the 1H-pyrrolo[2,3-b]pyridine ring, or the nitrogen of the sulfonamide group of compounds as described herein, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656, 838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such stereoisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds described herein can be in the form of pharmaceutically acceptable salts, or can be formulated as pharmaceutically acceptable salts. Contemplated pharmaceutically acceptable salt forms include, without limitation, mono, bis, tris, tetrakis. and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the invention may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1, 6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfate, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see Remington's Pharmaceutical Sciences, 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the invention are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the invention with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

Formulations and Administration

The methods and compounds will typically be used in therapy for human subjects. However, they may also be used to treat similar or identical indications in other animal subjects. Compounds described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: The Science and Practice of Pharmacy, 21$^{st}$ edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular. intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery; along with a compound described herein administered within a short time or longer time before or after the other therapy or procedure. In some embodiments, the present invention provides for delivery of a compound described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

In addition to the disclosures herein, the following non-limiting embodiments are contemplated herein:

1. A compound having the chemical structure of Formula I,

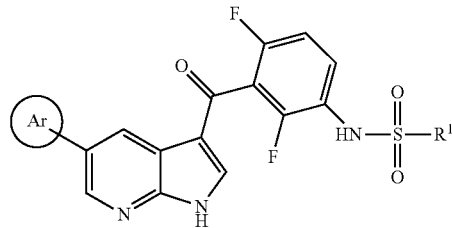

Formula I or any pharmaceutically acceptable salt thereof,
wherein:
$R^1$ is n-propyl, 4-trifluoromethyl-phenyl, 2-fluoro-phenyl, 3-fluoro-phenyl, or 2,5-difluoro-phenyl;
Ar is selected from the group consisting of bicyclic heteroaryl optionally independently substituted with one or more $R^2$, thiophenyl optionally independently substituted with one or more $R^3$, thiazolyl optionally independently substituted with one or more $R^4$, oxazolyl optionally independently substituted with one or more $R^5$, pyrazolyl optionally independently substituted with one or more $R^6$, pyridyl optionally independently substituted with one or more $R^7$, pyrimidinyl optionally independently substituted with one or more $R^8$, phenyl substituted with one or more $R^9$, and pyrazinyl optionally independently substituted with one or more $R^{10}$;
each $R^2$ is independently selected from the group consisting of —CN, —NO$_2$, —C(O)—$R^{11}$, —S(O)$_2$—$R^{12}$, —O—$R^{13}$, —N($R^{14}$)—$R^{15}$, fluoro, chloro, lower alkyl, lower alkylthio, fluoro substituted lower alkylthio, cycloalkylamino, and heterocycloalkylamino, wherein lower alkyl is optionally independently substituted with one or more fluoro, lower alkoxy, mono-alkylamino, di-alkylamino, cycloalkylamino, or heterocycloalkylamino;
each $R^3$ is independently selected from the group consisting of —CN, —OH, —NH$_2$, —NO$_2$, —C(O)—$R^{11}$, —S(O)$_2$—$R^{12}$, fluoro, chloro, lower alkyl, fluoro substituted lower alkyl, lower alkoxy, fluoro substituted lower alkoxy, lower alkylthio, fluoro substituted lower alkylthio, mono-alkylamino, di-alkylamino, cycloalkylamino, cycloalkyl, heterocycloalkyl, phenyl, and heteroaryl, wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;
each $R^4$ is independently selected from the group consisting of —CN, —OH, —NH$_2$, —NO$_2$, —C(O)—$R^{11}$, —S(O)$_2$—$R^{12}$, fluoro, chloro, lower alkyl, fluoro substituted lower alkyl, lower alkoxy, fluoro substituted lower alkoxy, lower alkylthio, fluoro substituted lower alkylthio, mono-alkylamino, di-alkylamino, cycloalkylamino, cycloalkyl, heterocycloalkyl, phenyl, and heteroaryl, wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;
each $R^5$ is independently selected from the group consisting of —CN, —OH, —NH$_2$, —NO$_2$, —C(O)—$R^{11}$, —S(O)$_2$—$R^{12}$, fluoro, chloro, lower alkyl, fluoro substituted lower alkyl, lower alkoxy, fluoro substituted lower alkoxy, lower alkylthio, fluoro substituted lower alkylthio, mono-alkylamino, di-alkylamino, cycloalkyl, cycloalkylamino, heterocycloalkyl, phenyl, and heteroaryl, wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^6$ is independently selected from the group consisting of —CN, —C(O)—$R^{11}$, fluoro, chloro, and lower alkyl, wherein lower alkyl is optionally independently substituted with one or more fluoro, lower alkoxy, mono-alkylamino, di-alkylamino, cycloalkylamino, or heterocycloalkylamino;

each $R^7$ is independently selected from the group consisting of —C(O)—$R^{11}$, —S(O)$_2$—$R^{12}$, —C(O)—N(H)—O—$R^{16}$, —O—$R^{13}$, —N($R^{14}$)—$R^{15}$, fluoro, chloro, lower alkyl, lower alkylthio, fluoro substituted lower alkylthio, cycloalkyl, heterocycloalkyl, phenyl, and heteroaryl, wherein lower alkyl is optionally independently substituted with one or more fluoro, lower alkoxy, mono-alkylamino, di-alkylamino, cycloalkylamino, and heterocycloalkylamino, and wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^8$ is independently selected from the group consisting of —C(O)—$R^{11}$, —S(O)$_2$—$R^{12}$, —C(O)—N(H)—O—$R^{16}$, —O—$R^{13}$, —N($R^{14}$)—$R^{15}$, fluoro, chloro, lower alkyl, lower alkylthio, fluoro substituted lower alkylthio, cycloalkyl, heterocycloalkyl, phenyl, and heteroaryl, wherein lower alkyl is optionally independently substituted with one or more fluoro, lower alkoxy, mono-alkylamino, di-alkylamino, cycloalkylamino, or heterocycloalkylamino, and wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^9$ is independently selected from the group consisting of —CN, —NO$_2$, —C(O)—$R^{11}$, —S(O)$_2$—$R^{12}$, —C(O)—N(H)—O—$R^{16}$, —O—$R^{13}$, —N($R^{14}$)—$R^{15}$, fluoro, chloro, lower alkyl, lower alkylthio, fluoro substituted lower alkylthio, cycloalkyl, heterocycloalkyl, phenyl, and heteroaryl, wherein lower alkyl is optionally independently substituted with one or more fluoro, lower alkoxy, mono-alkylamino, di-alkylamino, cycloalkylamino, or heterocycloalkylamino, and wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^{10}$ is independently selected from the group consisting of —CN, —NO$_2$, —C(O)—$R^{11}$, —S(O)$_2$—$R^{12}$, —C(O)—N(H)—O—$R^{16}$, —O—$R^{13}$, —N($R^{14}$)—$R^{15}$, fluoro, chloro, lower alkyl, lower alkylthio, fluoro substituted lower alkylthio, cycloalkyl, heterocycloalkyl, phenyl, and heteroaryl, wherein lower alkyl is optionally independently substituted with one or more fluoro, lower alkoxy, mono-alkylamino, di-alkylamino, cycloalkylamino, or heterocycloalkylamino, and wherein cycloalkyl, heterocycloalkyl, phenyl and heteroaryl are optionally independently substituted with one or more lower alkyl, fluoro substituted lower alkyl, lower alkoxy, fluoro substituted lower alkoxy, lower alkylthio, or fluoro substituted lower alkylthio;

each $R^{11}$ is independently selected from the group consisting of lower alkyl, —O$R^{13}$, —NH$_2$, mono-alkylamino, di-alkylamino, cycloalkylamino, and heterocycloalkylamino;

each $R^{12}$ is independently selected from the group consisting of —NH$_2$, lower alkyl, mono-alkylamino, di-alkylamino, cycloalkylamino, and heterocycloalkylamino;

each $R^{13}$ is independently hydrogen or lower alkyl, wherein lower alkyl is optionally substituted with one or more fluoro, or, when $R^{13}$ is $C_{2-6}$ alkyl, $R^{13}$ is optionally independently substituted with lower alkoxy, mono-alkylamino, di-alkylamino, cycloalkylamino, or heterocycloalkylamino; and each $R^{14}$, $R^{15}$ and $R^{16}$ is independently hydrogen, lower alkyl, or cycloalkyl, wherein lower alkyl is optionally substituted with one or more fluoro, or, when $R^{14}$, $R^{15}$ or $R^{16}$ is $C_{2-6}$ alkyl, $R^{14}$, $R^{15}$ and $R^{16}$ are independently substituted with lower alkoxy, mono-alkylamino, di-alkylamino, cycloalkylamino, or heterocycloalkylamino.

2. A composition comprising a pharmaceutically acceptable carrier; and a compound according to Embodiment 1.

3. A kit comprising a compound according to Embodiment 1 or a composition according to Embodiment 2.

4. The compound of Embodiment 1, wherein Ar is selected from the group consisting of

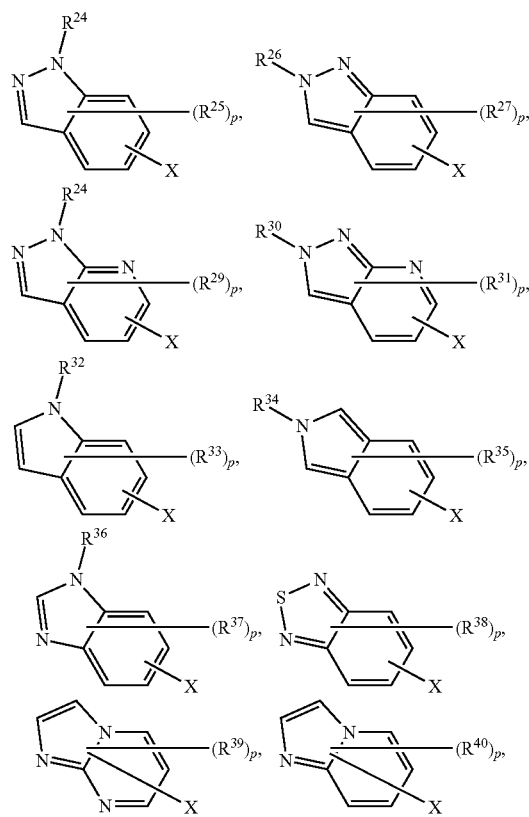

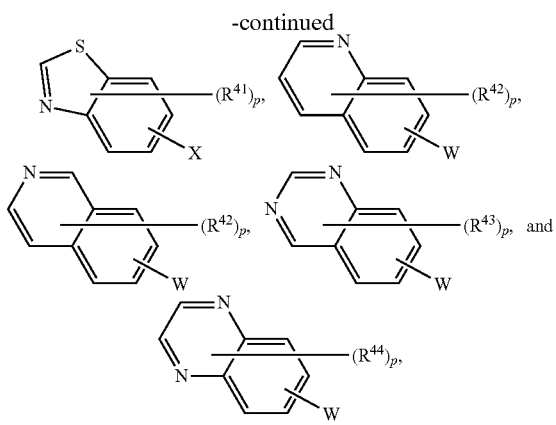

wherein:
W represents the point of attachment to the 5-position of the pyrrolo[2,3-b]pyridine ring of Formula I, wherein W is attached at any available position of the 6-membered phenyl ring portion of Ar;
X represents the point of attachment to the 5-position of the pyrrolo[2,3-b]pyridine ring of Formula I, wherein X is attached at any available position of the 6-membered ring portion of Ar;
Y represents the point of attachment to the 5-position of the pyrrolo[2,3-b]pyridine ring of Formula I, wherein Y is attached at any available position of the bicyclic ring of Ar;
$R^{24}$, $R^{26}$, $R^{28}$, $R^{30}$, $R^{32}$, $R^{34}$, and $R^{36}$ are selected from the group consisting of hydrogen, —C(O)—$R^{45}$, —S(O)$_2$—$R^{46}$, and lower alkyl, wherein lower alkyl is optionally independently substituted with one or more fluoro, or, when $R^{24}$, $R^{26}$, $R^{28}$, $R^{30}$, $R^{32}$, $R^{34}$, and/or $R^{36}$ is $C_{2-6}$, alkyl, $R^{24}$, $R^{26}$, $R^{28}$, $R^{30}$, $R^{32}$, $R^{34}$, and $R^{36}$ are each optionally independently substituted with one, or more lower alkoxy, mono-alkylamino, di-alkylamino or cycloalkylamino;
each $R^{25}$, $R^{27}$, $R^{29}$, $R^{31}$, $R^{33}$, $R^{35}$, $R^{37}$, $R^{38}$, $R^{39}$, $R^{40}$, $R^{41}$, $R^{42}$, $R^{43}$, and $R^{44}$, are independently selected from the group consisting of —CN, —C(O)—$R^{45}$, —S(O)$_2$—$R^{46}$, —O—$R^{47}$, —N($R^{48}$)—$R^{49}$, fluoro, chloro, lower alkyl, and cycloalkylamino, and are attached at any available position of the bicyclic ring of Ar, wherein lower alkyl is optionally independently substituted with one or more fluoro, lower alkoxy, mono-alkylamino, di-alkylamino or cycloalkylamino; each $R^{45}$ and $R^{46}$ are independently selected from the group consisting of —O—$R^{47}$, —N($R^{48}$)—$R^{49}$, lower alkyl, mono-alkylamino, di-alkylamino, and cycloalkylamino;
each $R^{47}$ is independently hydrogen or lower alkyl, wherein lower alkyl is optionally independently substituted with one or more fluoro, or, when $R^{47}$ is $C_{2-6}$, alkyl, $R^{47}$ is optionally substituted with one or more lower alkoxy, mono-alkylamino, di-alkylamino or cycloalkylamino;
each $R^{48}$ and $R^{49}$ are independently selected from the group consisting of hydrogen, lower alkyl, or cycloalkyl, wherein lower alkyl is optionally independently substituted with lower alkoxy, mono-alkylamino, di-alkylamino, or cycloalkylamino; and
p is 0, 1, 2 or 3.

5. A composition comprising a pharmaceutically acceptable carrier; and a compound according to Embodiment 4.

6. A kit comprising a compound according to Embodiment 4 or a composition according to Embodiment 5.

7. The compound of Embodiment 1, wherein Ar is selected from the group consisting of

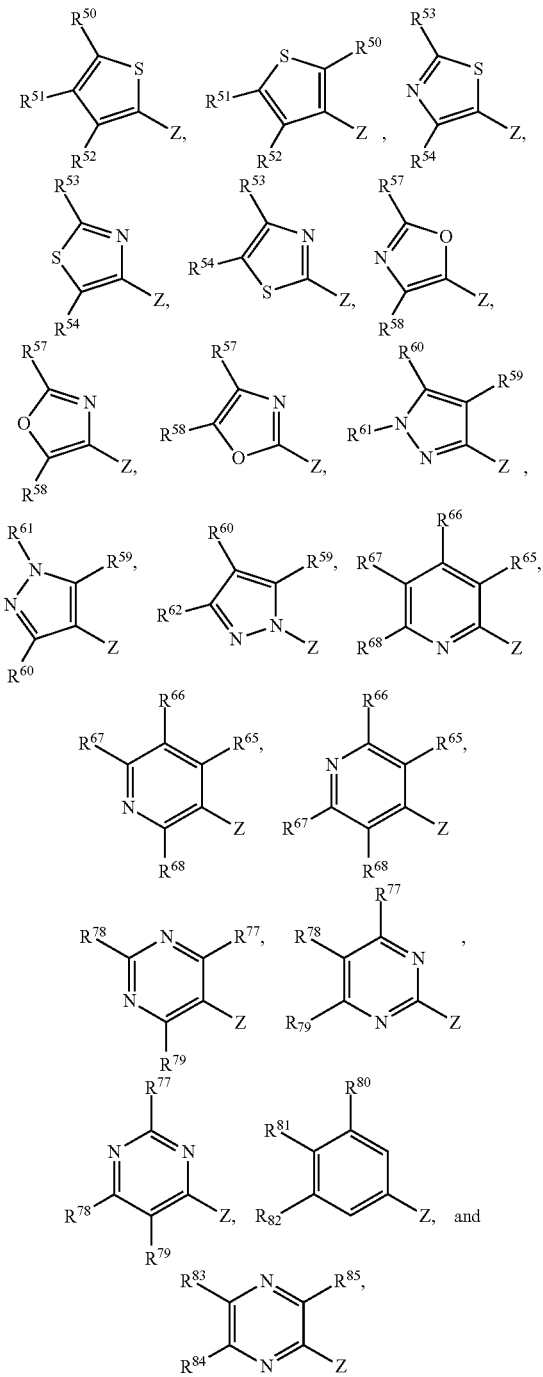

wherein:
Z represents the point of attachment to the 5-position of the pyrrolo[2,3-b]pyridine ring of Formula I;
$R^{50}$, $R^{51}$ and $R^{52}$ are independently selected from hydrogen or the $R^3$ substituents;
$R^{53}$ and $R^{54}$ are independently selected from hydrogen or the $R^4$ substituents;

$R^{57}$ and $R^{58}$ are independently selected from hydrogen or the $R^5$ substituents;

$R^{59}$, $R^{69}$ and $R^{62}$ are independently selected from hydrogen or the $R^6$ substituents; $R^{61}$ is selected from the group consisting of hydrogen, —C(O)—$R^{45}$, —S(O)$_2$—$R^{46}$, and lower alkyl optionally substituted with one or more fluoro, or, when one or more of $R^{59}$, $R^{60}$ and $R^{62}$ is C$_{2-6}$, alkyl, $R^{59}$, $R^{69}$ and/or $R^{62}$ are optionally independently substituted with one or more lower alkoxy, mono-alkylamino, di-alkylamino or cycloalkylamino;

$R^{65}$, $R^{66}$, $R^{67}$ and $R^{68}$ are independently selected from hydrogen or the $R^7$ substituents;

$R^{77}$, $R^{78}$ and $R^{79}$ are independently selected from hydrogen or the $R^8$ substituents;

$R^{80}$, $R^{81}$ and $R^{82}$ are independently selected from hydrogen or the $R^9$ substituents, and $R^{83}$, $R^{84}$ and $R^{85}$ are independently selected from hydrogen or the $R^{10}$ substituents.

8. A composition comprising a pharmaceutically acceptable carrier; and a compound according to Embodiment 7.

9. A kit comprising a compound according to Embodiment 7 or a composition according to Embodiment 8.

10. A compound selected from the group consisting of:

4-(4-{3-[2,6-Difluoro-3-(propane-1-sulfonylamino)-benzoyl]-1H-pyrrolo[2,3-b]pyridin-5-yl}-pyrazol-1-yl)-piperidine-1-carboxylic acid tert-butyl ester (P-1001), Propane-1-sulfonic acid {2,4-difluoro-3-[5-(1-piperidin-4-yl-1H-pyrazol-4-yl)-1H-pyrrolo[2,3-b]pyridine-3-carbonyl]-phenyl}-amide (P-1002), 4-(4-{3-[2,6-Difluoro-3-(4-trifluoromethyl-benzenesulfonylamino)-benzoyl]-1H-pyrrolo[2,3-b]pyridin-5-yl}-pyrazol-1-yl)-piperidine-1-carboxylic acid tert-butyl ester (P-1003), N-{2,4-Difluoro-3-[5-(1-piperidin-4-yl-1H-pyrazol-4-yl)-1H-pyrrolo[2,3-b]pyridine-3-carbonyl]-phenyl}-4-trifluoromethyl-benzenesulfonamide (P-1004), Propane-1-sulfonic acid {2,4-difluoro-3-[5-(1-pyrimidin-2-yl-1H-pyrazol-4-yl)-1H-pyrrolo[2,3-b]pyridine-3-carbonyl]-phenyl}-amide (P-1005), Propane-1-sulfonic acid (3-{5-[3,5-dimethyl-1-(1H-tetrazol-5-yl)-1H-pyrazol-4-yl]-1H-pyrrolo[2,3-b]pyridine-3-carbonyl}-2,4-difluoro-phenyl)-amide (P-1006), Propane-1-sulfonic acid (3-{5-[1-(1,3-dimethyl-1H-pyrazole-4-sulfonyl)-3,5-dimethyl-1H-pyrazol-4-yl]-1H-pyrrolo[2,3-b]pyridine-3-carbonyl}-2,4-difluoro-phenyl)-amide (P-1007), Propane-1-sulfonic acid (2,4-difluoro-3-{5-[1-(1H-tetrazol-5-yl)-1H-pyrazol-4-yl]-1H-pyrrolo[2,3-b]pyridine-3-carbonyl}-phenyl)-amide (P-1008), N-{2,4-Difluoro-3-[5-(1-methyl-1H-pyrazol-4-yl)-1H-pyrrolo[2,3-b]pyridine-3-carbonyl]-phenyl}-2,5-difluoro-benzenesulfonamide (P-1009), N-{3-[5-(2,5-Dimethyl-2H-pyrazol-3-yl)-1H-pyrrolo[2,3-b]pyridine-3-carbonyl]-2,4-difluoro-phenyl}-2,5-difluoro-benzenesulfonamide (P-1010), N-{2,4-Difluoro-3-[5-(1-methyl-1H-pyrazol-3-yl)-1H-pyrrolo[2,3-b]pyridine-3-carbonyl]-phenyl}-2,5-difluoro-benzenesulfonamide (P-1011), Propane-1-sulfonic acid {2,4-difluoro-3-[5-(1-methyl-1H-pyrazol-3-yl)-1H-pyrrolo[2,3-b]pyridine-3-carbonyl]-phenyl}-amide (P-1012), Propane-1-sulfonic acid {2,4-difluoro-3-[5-(1-pyridin-2-yl-1H-pyrazol-4-yl)-1H-pyrrolo[2,3-b]pyridine-3-carbonyl]phenyl}-amide (P-1013), 4-{3-[2,6-Difluoro-3-(propane-1-sulfonylamino)-benzoyl]-1H-pyrrolo[2,3-b]pyridin-5-yl}-pyrazole-1-carboxylic acid amide (P-1014), Propane-1-sulfonic acid [2,4-difluoro-3-(5-pyridin-2-yl-1H-pyrrolo[2,3-b]pyridine-3-carbonyl)-phenyl]-amide (P-1401), N-[2,4-Difluoro-3-(5-pyridin-3-yl-1H-pyrrolo[2,3-b]pyridine-3-carbonyl)-phenyl]-2,5-difluoro-benzenesulfonamide (P-1402), N-[2,4-Difluoro-3-(5-pyridin-4-yl-1H-pyrrolo[2,3-b]pyridine-3-carbonyl)-phenyl]-2,5-difluoro-benzenesulfonamide (P-1403), N-{2,4-Difluoro-3-[5-(6-methoxy-pyridin-3-yl)-1H-pyrrolo[2,3-b]pyridine-3-carbonyl]-phenyl}-2,5-difluoro-benzenesulfonamide (P-1404), N-{2,4-Difluoro-3-[5-(3-fluoro-pyridin-4-yl)-1H-pyrrolo[2,3-b]pyridine-3-carbonyl]-phenyl}-2,5-difluoro-benzenesulfonamide (P-1405), N-{3-[5-(2,6-Dimethoxy-pyridin-3-yl)-1H-pyrrolo[2,3-b]pyridine-3-carbonyl]-2,4-difluoro-phenyl}-2,5-difluoro-benzenesulfonamide (P-1406), N-{2,4-Difluoro-3-[5-(5-methanesulfonyl-pyridin-3-yl)-1H-pyrrolo[2,3-b]pyridine-3-carbonyl]-phenyl}-2,5-difluoro-benzenesulfonamide (P-1407), N-{2,4-Difluoro-3-[5-(6-methyl-pyridin-3-yl)-1H-pyrrolo[2,3-b]pyridine-3-carbonyl]-phenyl}-2,5-difluoro-benzenesulfonamide (P-1408), N-{3-[5-(6-Dimethylamino-pyridin-3-yl)-1H-pyrrolo[2,3-b]pyridine-3-carbonyl]-2,4-difluoro-phenyl}-2,5-difluoro-benzenesulfonamide (P-1409), N-[2,4-Difluoro-3-(5-pyrimidin-5-yl-1H-pyrrolo[2,3-b]pyridine-3-carbonyl)-phenyl]-2,5-difluoro-benzenesulfonamide (P-1500), N-{3-[5-(2,4-Dimethoxy-pyrimidin-5-yl)-1H-pyrrolo[2,3-b]pyridine-3-carbonyl]-2,4-difluoro-phenyl}-2,5-difluoro-benzenesulfonamide (P-1501), N-{3-[5-(2-Dimethylamino-pyrimidin-5-yl)-1H-pyrrolo[2,3-b]pyridine-3-carbonyl]-2,4-difluoro-phenyl}-2,5-difluoro-benzenesulfonamide (P-1502), N-{2,4-Difluoro-3-[5-(2-methyl-pyrimidin-5-yl)-1H-pyrrolo[2,3-b]pyridine-3-carbonyl]-phenyl}-2,5-difluoro-benzenesulfonamide (P-1503), Propane-1-sulfonic acid {3-[5-(2-cyclopropylamino-pyrimidin-5-yl)-1H-pyrrolo[2,3-b]pyridine-3-carbonyl]-2,4-difluoro-phenyl}-amide (P-1504), Propane-1-sulfonic acid (2,4-difluoro-3-{5-[2-(2-methoxy-ethylamino)-pyrimidin-5-yl]-1H-pyrrolo[2,3-b]pyridine-3-carbonyl}-phenyl)-amide (P-1505), N-{3-[5-(2-Cyclopropylamino-pyrimidin-5-yl)-1H-pyrrolo[2,3-b]pyridine-3-carbonyl]-2,4-difluoro-phenyl}-2,5-difluoro-benzenesulfonamide (P-1506), N-(2,4-Difluoro-3-{5-[2-(2-methoxy-ethylamino)-pyrimidin-5-yl]-1H-pyrrolo[2,3-b]pyridine-3-carbonyl}-phenyl)-2,5-difluoro-benzenesulfonamide (P-1507), Propane-1-sulfonic acid (2,4-difluoro-3-{5-[2-(pyridin-3-yloxy)-pyrimidin-5-yl]-1H-pyrrolo[2,3-b]pyridine-3-carbonyl}-phenyl)-amide (P-1508), Propane-1-sulfonic acid {2,4-difluoro-3-[5-(2-trifluoromethoxy-pyrimidin-5-yl)-1H-pyrrolo[2,3-b]pyridine-3-carbonyl]-phenyl}-amide (P-1509), Propane-1-sulfonic acid {3-[5-(2-cyano-pyrimidin-5-yl)-1H-pyrrolo[2,3-b]pyridine-3-carbonyl]-2,4-difluoro-phenyl}-amide (P-1510), Propane-1-sulfonic acid {2,4-difluoro-3-[5-(2-imidazol-1-yl-pyrimidin-5-yl)-1H-pyrrolo[2,3-b]pyridine-3-carbonyl]-phenyl}-amide (P-1511), Propane-1-sulfonic acid {3-[5-(2-azetidin-1-yl-pyrimidin-5-yl)-1H-pyrrolo[2,3-b]pyridine-3-carbonyl]-2,4-difluoro-phenyl}-amide (P-1512), Propane-1-sulfonic acid {2,4-difluoro-3-[5-(2-isopropylamino-pyrimidin-5-yl)-1H-pyrrolo[2,3-b]pyridine-3-carbonyl]-phenyl}-amide (P-1513), Propane-1-sulfonic acid {2,4-difluoro-3-[5-(2-methylamino-pyrimidin-5-yl)-1H-pyrrolo[2,3-b]pyridine-3-carbonyl]-phenyl}-amide (P-1514), Propane-1-sulfonic acid (3-{5-[2-(2-dimethylamino-ethyl-amino)-pyrimidin-5-yl]-1H-pyrrolo[2,3-b]pyridine-3-carbonyl}-2,4-difluoro-phenyl)-amide (P-1515), Propane-1-sulfonic acid (2,4-difluoro-3-{5-[2-(3-methoxy-propylamino)-pyrimidin-5-yl]-1H-pyrrolo[2,3-b]pyridine-3-carbonyl}-phenyl)-amide (P-1516), 2-Chloro-5-{3-[2,6-difluoro-3-(propane-1-sulfonylamino)-benzoyl]-1H-pyrrolo[2,3-b]pyridin-5-yl}-benzamide (P-1700), Propane-1-sulfonic acid {2,4-difluoro-3-[5-(1-oxo-2,3-dihydro-1H-isoindol-5-yl)-1H-pyrrolo[2,3-b]pyridine-3-carbonyl]-phenyl}-amide (P-1701), Propane-1-sulfonic acid {2,4-difluoro-3-[5-(3-oxo-2,3-dihydro-1H-isoindol-5-yl)-1H-pyrrolo[2,3-b]pyridine-3-carbonyl]-phenyl}-amide (P-1702), Propane-1-sulfonic acid {2,4-difluoro-3-[5-(2-oxo-2,3-dihydro-1H-indol-5-yl)-1H-pyrrolo[2,3-b]pyridine-3-carbonyl]-phenyl}-amide (P-1703), 3-{3-[3-(2,5-Difluoro-benzenesulfonylamino)-2,6-difluoro-benzoyl]-1H-pyrrolo[2,3-b]pyridin-5-yl}-N-methoxy-benzamide (P-1704), 4-{3-[3-(2,5-Difluoro-benzenesulfonylamino)-2,6-difluoro-benzoyl]-1H-pyrrolo[2,3-b]pyridin-5-yl}-N-methoxy-benzamide (P-1705), N-{2,4-Difluoro-3-[5-(4-methylsulfamoyl-phenyl)-1H-pyrrolo[2,3-b]pyridine-3-carbonyl]-phenyl}-2,5-difluoro-benzenesulfonamide (P-1706), N-{2,4-Difluoro-3-[5-(4-sulfamoyl-phenyl)-1H-pyrrolo[2,3-b]pyridine-3-carbonyl]-phenyl}-2,5-difluoro-benzenesulfonamide (P-1707), N-{3-[2,6-Difluoro-3-(propane-1-sulfonylamino)-benzoyl]-1H-pyrrolo[2,3-b]pyridin-5-yl}-nicotinamide (P-1800), 3-[2,6-Difluoro-3-(propane-1-sulfonylamino)-benzoyl]-1H-pyrrolo[2,3-b]pyridine-5-carboxylic acid pyridin-3-ylamide (P-1801), 5-Methyl-2,3-dihydro-isoxazole-3-carboxylic acid {3-[2,6-difluoro-3-(propane-1-sulfonylamino)-benzoyl]-1H-pyrrolo[2,3-b]pyridin-5-yl}-amide (P-1802), and any pharmaceutically acceptable salt thereof.

11. A composition comprising a pharmaceutically acceptable carrier; and a compound according to Embodiment 10.

12. A kit comprising a compound according to Embodiment 10 or a composition according to Embodiment 11.

13. The compound according to Embodiment 1, wherein the compound is a pan Raf inhibitor selected from the group consisting of:

Propane-1-sulfonic acid {2,4-difluoro-3-[5-(1H-pyrazolo[3,4-b]pyridin-5-yl)-1H-pyrrolo[2,3-b]pyridine-3-carbonyl]-phenyl}-amide (P-0008), Propane-1-sulfonic acid {2,4-difluoro-3-[5-(2-methyl-2H-indazol-5-yl)-1H-pyrrolo[2,3-b]pyridine-3-carbonyl]-phenyl}-amide (P-0010), Propane-1-sulfonic acid {2,4-difluoro-3-[5-(2-methyl-2H-indazol-6-yl)-1H-pyrrolo[2,3-b]pyridine-3-carbonyl]-phenyl}-amide (P-0011), Propane-1-sulfonic acid {2,4-difluoro-3-[5-(1H-indol-5-yl)-1H-pyrrolo[2,3-b]pyridine-3-carbonyl]-phenyl}-amide (P-0012), Propane-1-sulfonic acid [3-(5-benzothiazol-5-yl-1H-pyrrolo[2,3-b]pyridine-3-carbonyl)-2,4-difluoro-phenyl]-amide (P-0013), Propane-1-sulfonic acid [2,4-difluoro-3-(5-quinoxalin-6-yl-1H-pyrrolo[2,3-b]pyridine-3-carbonyl)-phenyl]-amide (P-0014), Propane-1-sulfonic acid [3-(5-benzothiazol-6-yl-1H-pyrrolo[2,3-b]pyridine-3-carbonyl)-2,4-difluoro-phenyl]-amide (P-0020), Propane-1-sulfonic acid [2,4-difluoro-3-(5-imidazo[1,2-a]pyridin-2-yl-1H-pyrrolo[2,3-b]pyridine-3-carbonyl)-phenyl]-amide (P-0021), Propane-1-sulfonic acid {2,4-difluoro-3-[5-(3-methyl-1H-indol-5-yl)-1H-pyrrolo[2,3-b]pyridine-3-carbonyl]-phenyl}-amide (P-0023), Propane-1-sulfonic acid {2,4-difluoro-3-[5-(3-methyl-1H-indazol-5-yl)-1H-pyrrolo[2,3-b]pyridine-3-carbonyl]-phenyl}-amide (P-0024), Propane-1-sulfonic acid [2,4-difluoro-3-(5-quinazolin-7-yl-1H-pyrrolo[2,3-b]pyridine-3-carbonyl)-phenyl]-amide (P-0025), Propane-1-sulfonic acid [2,4-difluoro-3-(5-quinazolin-6-yl-1H-pyrrolo[2,3-b]pyridine-3-carbonyl)-phenyl]-amide (P-0026), Propane-1-sulfonic acid (2,4-difluoro-3-{5-[2-(4-methyl-imidazol-1-yl)-thiazol-4-yl]-1H-pyrrolo[2,3-b]pyridine-3-carbonyl}-phenyl)-amide (P-1100), Propane-1-sulfonic acid (2,4-difluoro-3-{5-[2-(2-methyl-imidazol-1-yl)-thiazol-4-yl]-1H-pyrrolo[2,3-b]pyridine-3-carbonyl}-phenyl)-amide (P-1101), Propane-1-sulfonic acid {2,4-difluoro-3-[5-(2-pyrazol-1-yl-thiazol-4-yl)-1H-pyrrolo[2,3-b]pyridine-3-carbonyl]-phenyl}-amide (P-1103), Propane-1-sulfonic acid {2,4-difluoro-3-[5-(2-imidazol-1-yl-thiazol-5-yl)-1H-pyrrolo[2,3-b]pyridine-3-carbonyl]-phenyl}-amide (P-1104), Propane-1-sulfonic acid (2,4-difluoro-3-{5-[2-(2-methyl-imidazol-1-yl)-thiazol-5-yl]-1H-pyrrolo[2,3-b]pyridine-3-carbonyl}-phenyl)-amide (P-1105), Propane-1-sulfonic acid {2,4-difluoro-3-[5-(2-imidazol-1-yl-thiazol-4-yl)-1H-pyrrolo[2,3-b]pyridine-3-carbonyl]-phenyl}-amide (P-1106), Propane-1-sulfonic acid {2,4-difluoro-3-[5-(2-pyrazol-1-yl-thiazol-5-yl)-1H-pyrrolo[2,3-b]pyridine-3-carbonyl]-phenyl}-amide (P-1109), Propane-1-sulfonic acid {2,4-difluoro-3-[5-(5-pyridin-3-yl-thiophen-2-yl)-1H-pyrrolo[2,3-b]pyridine-3-carbonyl]-phenyl}-amide (P-1200), Propane-1-sulfonic acid (2,4-difluoro-3-{5-[5-(1H-pyrazol-3-yl)-thiophen-2-yl]-1H-pyrrolo[2,3-b]pyridine-3-carbonyl}-phenyl)-amide (P-1201), 5-{3-[2,6-Difluoro-3-(propane-1-sulfonylamino)-benzoyl]-1H-pyrrolo[2,3-b]pyridin-5-yl}-thiophene-2-sulfonic acid amide (P-1202), N-[2,4-Difluoro-3-(5-oxazol-5-yl-1H-pyrrolo[2,3-b]pyridine-3-carbonyl)-phenyl]-2,5-difluoro-benzenesulfonamide (P-1300), 4-(4-{3-[2,6-Difluoro-3-(propane-1-sulfonylamino)-benzoyl]-1H-pyrrolo[2,3-b]pyridin-5-yl}-pyrazol-1-yl)-piperidine-1-carboxylic acid tert-butyl ester (P-1001), Propane-1-sulfonic acid {2,4-difluoro-3-[5-(1-piperidin-4-yl-1H-pyrazol-4-yl)-1H-pyrrolo[2,3-b]pyridine-3-carbonyl]-phenyl}-amide (P-1002), Propane-1-sulfonic acid {2,4-difluoro-3-[5-(1-pyrimidin-2-yl-1H-pyrazol-4-yl)-1H-pyrrolo[2,3-b]pyridine-3-carbonyl]-phenyl}-amide (P-1005), N-{2,4-Difluoro-3-[5-(1-methyl-1H-pyrazol-4-yl)-1H-pyrrolo[2,3-b]pyridine-3-carbonyl]-phenyl}-2,5-difluoro-benzenesulfonamide (P-1009), Propane-1-sulfonic acid [2,4-difluoro-3-(5-pyridin-2-yl-1H-pyrrolo[2,3-b]pyridine-3-carbonyl)-phenyl]-amide (P-1401), N-[2,4-Difluoro-3-(5-pyridin-3-yl-1H-pyrrolo[2,3-b]pyridine-3-carbonyl)-phenyl]-2,5-difluoro-benzenesulfonamide (P-1402), N-[2,4-Difluoro-3-(5-pyridin-4-yl-1H-pyrrolo[2,3-b]pyridine-3-carbonyl)-phenyl]-2,5-difluoro-benzenesulfonamide (P-1403), N-{2,4-Difluoro-3-[5-(6-methoxy-pyridin-3-yl)-1H-pyrrolo[2,3-b]pyridine-3-carbonyl]-phenyl}-2,5-difluoro-benzenesulfonamide (P-1404), N-{2,4-Difluoro-3-[5-(5-methanesulfonyl-pyridin-3-yl)-1H-pyrrolo[2,3-b]pyridine-3-carbonyl]-phenyl}-2,5-difluoro-benzenesulfonamide (P-1407), N-{2,4-Difluoro-3-[5-(6-methyl-pyridin-3-yl)-1H-pyrrolo[2,3-b]pyridine-3-carbonyl]-phenyl}-2,5-difluoro-benzenesulfonamide (P-1408), N-{3-[5-(6-Dimethylamino-pyridin-3-yl)-1H-pyrrolo[2,3-b]pyridine-3-carbonyl]-2,4-difluoro-phenyl}-2,5-difluoro-benzenesulfonamide (P-1409), N-[2,4-Difluoro-3-(5-pyrimidin-5-yl-1H-pyrrolo[2,3-b]pyridine-3-carbonyl)-phenyl]-2,5-difluoro-benzenesulfonamide (P-1500), N-{3-[5-(2-Dimethylamino-pyrimidin-5-yl)-1H-pyrrolo[2,3-b]pyridine-3-carbonyl]-2,4-difluoro-phenyl}-2,5-difluoro-benzenesulfonamide (P-1502), N-{2,4-Difluoro-3-[5-(2-methyl-pyrimidin-5-yl)-1H-pyrrolo[2,3-b]pyridine-3-carbonyl]-phenyl}-2,5-difluoro-benzenesulfonamide (P-1503), 2-Chloro-5-{3-[2,6-difluoro-3-(propane-1-sulfonylamino)-benzoyl]-1H-pyrrolo[2,3-b]pyridin-5-yl}-benzamide (P-1700), Propane-1-sulfonic acid {2,4-difluoro-3-[5-(3-oxo-2,3-dihydro-1H-isoindol-5-yl)-1H-pyrrolo[2,3-b]pyridine-3-carbonyl]-phenyl}-amide (P-1702), Propane-1-sulfonic acid {2,4-difluoro-3-[5-(2-oxo-2,3-dihydro-1H-indol-5-yl)-1H-pyrrolo[2,3-b]pyridine-3-carbonyl]-phenyl}-amide (P-1703), 3-{3-[3-(2,5-Difluoro-benzenesulfonylamino)-2,6-difluoro-benzoyl]-1H-pyrrolo[2,3-b]pyridin-5-yl}-N-methoxy-benzamide (P-1704), 4-{3-[3-(2,5-Difluoro-benzenesulfonylamino)-2,6-difluoro-benzoyl]-1H-pyrrolo[2,3-b]pyridin-5-yl}-N-methoxy-benzamide (P-1705), N-{2,4-Difluoro-3-[5-(4-methylsulfamoyl-phenyl)-1H-pyrrolo[2,3-b]pyridine-3-carbonyl]-phenyl}-2,5-difluoro-benzenesulfonamide (P-1706), N-{2,4-Difluoro-3-[5-(4-sulfamoyl-phenyl)-1H-pyrrolo[2,3-b]pyridine-3-carbonyl]-phenyl}-2,5-difluoro-benzenesulfonamide (P-1707), and any pharmaceutically acceptable salt thereof.

14. A composition comprising a pharmaceutically acceptable carrier; and a compound according to Embodiment 13.

15. A kit comprising a compound according to Embodiment 13.

16. A kit comprising a composition according to Embodiment 14.

17. A method for treating one or more indications selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, testicular cancer, and cholangiocarcinoma in a subject in need thereof, said method comprising administering to said subject an effective amount of a compound according to any one of Embodiments 1, 4, 7, 10 or 13, or a compound listed on Table I.

18. Use of a compound according to any one of Embodiments 1, 4, 7, 10 or 13, or a compound listed on Table 1 for the preparation of a medicament for treating one or more indications selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, testicular cancer, and cholangiocarcinoma in a subject in need thereof.

19. A compound according to any one of Embodiments 1, 4, 7, 10 or 13, or a compound listed on Table I for the treatment of one or more indications selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, testicular cancer, and cholangiocarcinoma in a subject in need thereof.

20. A method for treating melanoma in a subject in need thereof, said method comprising administering to said subject an effective amount of a compound according to any one of Embodiments 1, 4, 7, 10 or 13, or a compound listed on Table I.

21. Use of a compound according to any one of Embodiments 1, 4, 7, 10 or 13, or a compound listed on Table I for the preparation of a medicament for treating melanoma in a subject in need thereof.

22. A compound according to any one of Embodiments 1, 4, 7, 10 or 13, or a compound listed on Table I for the treatment melanoma in a subject in need thereof.

23. A method for treating glioma in a subject in need thereof, said method comprising administering to said subject an effective amount of a compound according to any one of Embodiments 1, 4, 7, 10 or 13, or a compound listed on Table I.

24. Use of a compound according to any one of Embodiments 1, 4, 7, 10 or 13, or a compound listed on Table I for the preparation of a medicament for treating glioma in a subject in need thereof.

25. A compound according to any one of Embodiments 1, 4, 7, 10 or 13, or a compound listed on Table I for glioma in a subject in need thereof.

26. A method for treating glioblastoma multiforme in a subject in need thereof, said method comprising administering to said subject an effective amount of a compound according to any one of Embodiments 1, 4, 7, 10 or 13, or a compound listed on Table I.

27. Use of a compound according to any one of Embodiments 1, 4, 7, 10 or 13, or a compound listed on Table I for the preparation of a medicament for treating glioblastoma multiforme in a subject in need thereof.

28. A compound according to any one of Embodiments 1, 4, 7, 10 or 13, or a compound listed on Table I for the treatment of glioblastoma multiforme in a subject in need thereof.

29. A method for treating pilocytic astrocytoma, said method comprising administering to said subject an effective amount of a compound according to any one of Embodiments 1, 4, 7, 10 or 13, or a compound listed on Table I.

30. Use of a compound according to any one of Embodiments 1, 4, 7, 10 or 13, or a compound listed on Table I for the preparation of a medicament for treating pilocytic astrocytoma in a subject in need thereof.

31. A compound according to any one of Embodiments 1, 4, 7, 10 or 13, or a compound listed on Table I for the treatment of pilocytic astrocytoma in a subject in need thereof.

32. A method for treating colorectal cancer comprising administering to said subject an effective amount of a compound according to any one of Embodiments 1, 4, 7, 10 or 13, or a compound listed on Table I.

33. Use of a compound according to any one of Embodiments 1, 4, 7, 10 or 13, or a compound listed on Table I for the preparation of a medicament for treating colorectal cancer in a subject in need thereof.

34. A compound according to any one of Embodiments 1, 4, 7, 10 or 13, or a compound listed on Table I for the treatment of colorectal cancer in a subject in need thereof.

35. A method for treating thyroid cancer in a subject in need thereof, said method comprising administering to said subject an effective amount of a compound according to any one of Embodiments 1, 4, 7, 10 or 13, or a compound listed on Table I.

36. Use of a compound according to any one of Embodiments 1, 4, 7, 10 or 13, or a compound listed on Table I for the preparation of a medicament for treating thyroid cancer in a subject in need thereof.

37. A compound according to any one of Embodiments 1, 4, 7, 10 or 13, or a compound listed on Table I for the treatment of thyroid cancer in a subject in need thereof.

38. A method for treating, lung cancer in a subject in need thereof, said method comprising administering to said subject an effective amount of a compound according to any one of Embodiments 1, 4, 7, 10 or 13, or a compound listed on Table I.

39. Use of a compound according to any one of Embodiments 1, 4, 7, 10 or 13, or a compound listed on Table I for the preparation of a medicament for treating lung cancer in a subject in need thereof.

40. A compound according to any one of Embodiments 1, 4, 7, 10 or 13, or a compound listed on Table I for the treatment of lung cancer in a subject in need thereof.

41. A method for treating ovarian cancer in a subject in need thereof, said method comprising administering to said subject an effective amount of a compound according to any one of Embodiments 1, 4, 7, 10 or 13, or a compound listed on Table I.

42. Use of a compound according to any one of Embodiments 1, 4, 7, 10 or 13, or a compound listed on Table I for the preparation of a medicament for treating ovarian cancer in a subject in need thereof.

43. A compound according to any one of Embodiments 1, 4, 7, 10 or 13, or a compound listed on Table I for the treatment of ovarian cancer in a subject in need thereof.

44. A method for treating prostate cancer in a subject in need thereof, said method comprising administering to said subject an effective amount of a compound according to any one of Embodiments 1, 4, 7, 10 or 13, or a compound listed on Table I.

45. Use of a compound according to any one of Embodiments 1, 4, 7, 10 or 13, or a compound listed on Table I for the preparation of a medicament for treating prostate cancer in a subject in need thereof.

46. A compound according to any one of Embodiments 1, 4, 7, 10 or 13, or a compound listed on Table I for the treatment of prostate cancer in a subject in need thereof.

47. A method for treating liver cancer in a subject in need thereof, said method comprising administering to said subject an effective amount of a compound according to any one of Embodiments 1, 4, 7, 10 or 13, or a compound listed on Table I.

48. Use of a compound according to any one of Embodiments 1, 4, 7, 10 or 13, or a compound listed on Table I for the preparation of a medicament for treating liver cancer in a subject in need thereof.

49. A compound according to any one of Embodiments 1, 4, 7, 10 or 13, or a compound listed on Table I for the treatment of liver cancer in a subject in need thereof.

50. A method for treating gallbladder cancer in a subject in need thereof, said method comprising administering to said subject an effective amount of a compound according to any one of Embodiments 1, 4, 7, 10 or 13, or a compound listed on Table I.

51. Use of a compound according to any one of Embodiments 1, 4, 7, 10 or 13, or a compound listed on Table I for the preparation of a medicament for treating gallbladder cancer in a subject in need thereof.

52. A compound according to any one of Embodiments 1, 4, 7, 10 or 13, or a compound listed on Table I for the treatment of gallbladder cancer in a subject in need thereof.

53. A method for treating gastrointestinal stromal tumors in a subject in need thereof, said method comprising administering to said subject an effective amount of a compound according to any one of Embodiments 1, 4, 7, 10 or 13, or a compound listed on Table I.

54. Use of a compound according to any one of Embodiments 1, 4, 7, 10 or 13, or a compound listed on Table I for the preparation of a medicament for treating gastrointestinal stromal tumors in a subject in need thereof.

55. A compound according to any one of Embodiments 1, 4, 7, 10 or 13, or a compound listed on Table I for the treatment of gastrointestinal stromal tumors in a subject in need thereof.

56. A method for treating biliary tract cancer in a subject in need thereof, said method comprising administering to said subject an effective amount of a compound according to any one of Embodiments 1, 4, 7, 10 or 13, or a compound listed on Table I.

57. Use of a compound according to any one of Embodiments 1, 4, 7, 10 or 13, or a compound listed on Table I for the preparation of a medicament for treating biliary tract cancer in a subject in need thereof.

58. A compound according to any one of Embodiments 1, 4, 7, 10 or 13, or a compound listed on Table I for the treatment of biliary tract cancer in a subject in need thereof.

59. A method for treating cholangiocarcinoma in a subject in need thereof, said method comprising administering to said subject an effective amount of a compound according to any one of Embodiments 1, 4, 7, 10 or 13, or a compound listed on Table I.

60. Use of a compound according to any one of Embodiments 1, 4, 7, 10 or 13, or a compound listed on Table I for the preparation of a medicament for treating cholangiocarcinoma in a subject in need thereof.

61. A compound according to any one of Embodiments 1, 4, 7, 10 or 13, or a compound listed on Table I for the treatment of cholangiocarcinoma in a subject in need thereof.

62. A method for treating one or more indications selected from the group consisting of acute pain, chronic pain, and polycystic kidney disease in a subject in need thereof, said method comprising administering to said subject an effective amount of a compound according to any one of Embodiments 1, 4, 7, 10 or 13, or a compound listed on Table I.

63. Use of a compound according to any one of Embodiments 1, 4, 7, 10 or 13, or a compound listed on Table I for the preparation of a medicament for treating one or more indications selected from the group consisting of acute pain, chronic pain, and polycystic kidney disease in a subject in need thereof.

64. A compound according to any one of Embodiments 1, 4, 7, 10 or 13, or a compound listed on Table I for the treatment of one or more indications selected from the group consisting of acute pain, chronic pain, and polycystic kidney disease in a subject in need thereof.

65. A method for treating acute pain in a subject in need thereof, said method comprising administering to said subject an effective amount of a compound according to any one of Embodiments 1, 4, 7, 10 or 13, or a compound listed on Table I.

66. Use of a compound according to any one of Embodiments 1, 4, 7, 10 or 13, or a compound listed on Table I for the preparation of a medicament for treating acute pain in a subject in need thereof.

67. A compound according to any one of Embodiments 1, 4, 7, 10 or 13, or a compound listed on Table I for the treatment of acute pain in a subject in need thereof.

68. A method for treating chronic pain in a subject in need thereof, said method comprising administering to said subject an effective amount of a compound according to any one of Embodiments 1, 4, 7, 10 or 13, or a compound listed on Table I.

69. Use of a compound according to any one of Embodiments 1, 4, 7, 10 or 13, or a compound listed on Table I for the preparation of a medicament for treating chronic pain in a subject in need thereof.

70. A compound according to any one of Embodiments 1, 4, 7, 10 or 13, or a compound listed on Table I for the treatment of chronic pain in a subject in need thereof.

71. A method for treating polycystic kidney disease in a subject in need thereof, said method comprising administering to said subject an effective amount of a compound according to any one of Embodiments 1, 4, 7, 10 or 13, or a compound listed on Table I.

72. Use of a compound according to any one of Embodiments 1, 4, 7, 10 or 13, or a compound listed on Table I for the preparation of a medicament for treating polycystic kidney disease in a subject in need thereof.

73. A compound according to any one of Embodiments 1, 4, 7, 10 or 13, or a compound listed on Table I for the treatment of polycystic kidney disease in a subject in need thereof.

74. A method for treating one or more indications selected from the group consisting of multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency) in a subject in need thereof, said method comprising administering to said subject an effective amount of a compound according to any one of Embodiments 1, 4, 7, 10 or 13, or a compound listed on Table I.

75. Use of a compound according to any one of Embodiments 1, 4, 7, 10 or 13, or a compound listed on Table I for the preparation of a medicament for treating one or more indications selected from the group consisting of multi-infarct dementia, head injury, spinal cord injury, Alzheimer's disease (AD), Parkinson's disease, seizures and epilepsy; neoplastic diseases including, but not limited to, melanoma. glioma, glioblastoma multiforme, pilocytic astrocytoma sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease. nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal. Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency) in a subject in need thereof.

76. A compound according to any one of Embodiments 1, 4, 7, 10 or 13, or a compound listed on Table I for the treatment of one or more indications selected from the group consisting of multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi-'s sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency) in a subject in need thereof.

77. A method for treating testicular cancer in a subject in need thereof, said method comprising administering to said subject an effective amount of a compound according to any one of Embodiments 1, 4, 7, 10 or 13, or a compound listed on Table I.

78. Use of a compound according to any one of Embodiments 1, 4, 7, 10 or 13, or a compound listed on Table I for the preparation of a medicament for treating testicular cancer in a subject in need thereof.

79. A compound according to any one of Embodiments 1, 4, 7, 10 or 13, or a compound listed on Table I for the treatment of testicular cancer in a subject in need thereof.

80. A method for treating Noonan's syndrome in a subject in need thereof, said method comprising administering to said subject an effective amount of a compound according to any one of Embodiments 1, 4, 7, 10 or 13, or a compound listed on Table I.

81. Use of a compound according to any one of Embodiments 1, 4, 7, 10 or 13, or a compound listed on Table I for the preparation of a medicament for treating Noonan's syndrome in a subject in need thereof.

82. A compound according to any one of Embodiments 1, 4, 7, 10 or 13, or a compound listed on Table I for the treatment of Noonan's syndrome in a subject in need thereof.

83. A method for treating cardio-faciocutaneous syndrome (CFC) in a subject in need thereof, said method comprising administering to said subject an effective amount of a compound according to any one of Embodiments 1, 4, 7, 10 or 13, or a compound listed on Table I.

84. Use of a compound according to any one of Embodiments 1, 4, 7, 10 or 13, or a compound listed on Table I for the preparation of a medicament for treating cardio-faciocutaneous syndrome (CFC) in a subject in need thereof.

85. A compound according to any one of Embodiments 1, 4, 7, 10 or 13, or a compound listed on Table I for the treatment of cardio-faciocutaneous syndrome (CFC) in a subject in need thereof.

86. A compound according to any one of Embodiments 1, 4, 7, 10 or 13, or a compound listed on Table I wherein said compound is a pan Raf inhibitor.

87. A compound according to any one of Embodiments 1, 4, 7, 10 or 13, or a compound listed on Table I wherein said compound is a Ras activity inhibitor.

88. A compound according to any one of Embodiments 1, 4, 7, 10 or 13, or a compound listed on Table I wherein said compound is a pan Raf inhibitor and a Ras activity inhibitor.

89. A compound or composition according to any one of the preceeding Embodiments, wherein said compound inhibits proliferation of a mutant Ras cell line with an $IC_{50}$ of less than 1 µM.

90. A compound or composition according to any one of the preceeding Embodiments, wherein said compound inhibits proliferation of a mutant Ras cell line with an $IC_{50}$ of less than 100 nM.

91. A compound or composition according to any one of the preceeding Embodiments, wherein said compound inhibits proliferation of a mutant Ras cell line with an $IC_{50}$ of less than 20 nM.

92. A compound or composition according to any one of the preceeding Embodiments, wherein said compound inhibits proliferation of a mutant Ras cell line with an $IC_{50}$ of less than 1 nM.

93. A compound or composition according to any one of the preceeding Embodiments, wherein said compound inhibits proliferation of a mutant Ras cell line with an $IC_{50}$ of less than 1 µM and wherein said compound is a pan Raf inhibitor having an $IC_{50}$ of less than 500 nM in activity assays for each of B-Raf, c-Raf-1 and B-Raf V600E protein kinases.

94. A compound or composition according to any one of the preceeding Embodiments, wherein said compound inhibits proliferation of a mutant Ras cell line with an $IC_{50}$ of less than 100 nM and wherein said compound is a pan Raf inhibitor having an $IC_{50}$ of less than 500 nM in activity assays for each of B-Raf, c-Raf-1 and B-Raf V600E protein kinases.

95. A compound or composition according to any one of the preceeding Embodiments, wherein said compound inhibits proliferation of a mutant Ras cell line with an $IC_{50}$ of less than 20 nM and wherein said compound is a pan Raf inhibitor having an $IC_{50}$ of less than 500 nM in activity assays for each of B-Raf, c-Raf-1 and B-Raf V600E protein kinases.

96. A compound or composition according to any one of the preceeding Embodiments, wherein said compound inhibits proliferation of a mutant Ras cell line with an $IC_{50}$ of less than 1 nM and wherein said compound is a pan Raf inhibitor having an $IC_{50}$ of less than 500 nM in activity assays for each of B-Raf, c-Raf-1 and B-Raf V600E protein kinases.

97. A compound or composition according to any one of the preceeding Embodiments, wherein said compound inhibits proliferation of a N-Ras mutant cell line with an $IC_{50}$ of less than 1 µM.

98. A compound or composition according to any one of the preceeding Embodiments, wherein said compound inhibits proliferation of a N-Ras mutant cell line with an $IC_{50}$ of less than 100 nM.

99. A compound or composition according to any one of the preceeding Embodiments, wherein said compound inhibits proliferation of a N-Ras mutant cell line with an $IC_{50}$ of less than 20 nM.

100. A compound or composition according to any one of the preceeding Embodiments, wherein said compound inhibits proliferation of a N-Ras mutant cell line with an $IC_{50}$ of less than 1 nM.

101. A compound or composition according to any one of the preceeding Embodiments, wherein said compound inhibits proliferation of a N-Ras mutant cell line with an $IC_{50}$ of less than 1 µM and wherein said compound is a pan Raf inhibitor having an $IC_{50}$ of less than 500 nM in activity assays for each of B-Raf, c-Raf-1 and B-Raf V600E protein kinases.

102. A compound or composition according to any one of the preceeding Embodiments, wherein said compound inhibits proliferation of a N-Ras mutant cell line with an $IC_{50}$ of less than 100 nM and wherein said compound is a pan Raf inhibitor having an $IC_{50}$ of less than 500 nM in activity assays for each of B-Raf, c-Raf-1 and B-Raf V600E protein kinases.

103. A compound or composition according to any one of the preceeding Embodiments, wherein said compound inhibits proliferation of a N-Ras mutant cell line with an $IC_{50}$ of less than 20 nM and wherein said compound is a pan Raf inhibitor having an $IC_{50}$ of less than 500 nM in activity assays for each of B-Raf, c-Raf-1 and B-Raf V600E protein kinases.

104. A compound or composition according to any one of the preceeding Embodiments, wherein said compound inhibits proliferation of a N-Ras mutant cell line with an $IC_{50}$ of less than 1 nM and wherein said compound is a pan Raf inhibitor having an $IC_{50}$ of less than 500 nM in activity assays for each of B-Raf, c-Raf-1 and B-Raf V600E protein kinases.

105. A compound or composition according to any one of the preceeding Embodiments, wherein said compound inhibits proliferation of a mutant Ras cell line selected from the group consisting of M244, M202, M207, SK-MEL-2, SK-MEL-173, and IPC298 with an $IC_{50}$ of less than 1 μM.

106. A compound or composition according to any one of the preceeding Embodiments, wherein said compound inhibits proliferation of a mutant Ras cell line selected from the group consisting of M244, M202, M207, SK-MEL-2, SK-MEL-173, and IPC298 with an $IC_{50}$ of less than 100 nM.

107. A compound or composition according to any one of the preceeding Embodiments, wherein said compound inhibits proliferation of a mutant Ras cell line selected from the group consisting of M244, M202, M207, SK-MEL-2, SK-MEL-173, and IPC298 with an $IC_{50}$ of less than 20 nM.

108. A compound or composition according to any one of the preceeding Embodiments, wherein said compound inhibits proliferation of a mutant Ras cell line selected from the group consisting of M244, M202, M207, SK-MEL-2, SK-MEL-173, and IPC298 with an $IC_{50}$ of less than 1 nM.

109. A compound or composition according to any one of the preceeding Embodiments, wherein said compound inhibits proliferation of a mutant Ras cell line selected from the group consisting of M244, M202, M207, SK-MEL-2, SK-MEL-173, and IPC298 with an $IC_{50}$ of less than 1 μM and wherein said compound is a pan Raf inhibitor having an $IC_{50}$ of less than 500 nM in activity assays for each of B-Raf, c-Raf-1 and B-Raf V600E protein kinases.

110. A compound or composition according to any one of the preceeding Embodiments, wherein said compound inhibits proliferation of a mutant Ras cell line selected from the group consisting of M244, M202, M207, SK-MEL-2, SK-MEL-173, and IPC298 with an $IC_{50}$ of less than 100 nM and wherein said compound is a pan Raf inhibitor having an $IC_{50}$ of less than 500 nM in activity assays for each of B-Raf, c-Raf-1 and B-Raf V600E protein kinases.

111. A compound or composition according to any one of the preceeding Embodiments, wherein said compound inhibits proliferation of a mutant Ras cell line selected from the group consisting of M244, M202, M207, SK-MEL-2, SK-MEL-173, and IPC298 with an $IC_{50}$ of less than 20 nM and wherein said compound is a pan Raf inhibitor having an $IC_{50}$ of less than 500 nM in activity assays for each of B-Raf, c-Raf-1 and B-Raf V600E protein kinases.

112. A compound or composition according to any one of the preceeding Embodiments, wherein said compound inhibits proliferation of a mutant Ras cell line selected from the group consisting of M244, M202, M207, SK-MEL-2, SK-MEL-173, and IPC298 with an $IC_{50}$ of less than 1 nM and wherein said compound is a pan Raf inhibitor having an $IC_{50}$ of less than 500 nM in activity assays for each of B-Raf, c-Raf-1 and B-Raf V600E protein kinases.

113. A compound or composition according to any one of the preceeding Embodiments, wherein said compound inhibits proliferation of IPC298 cells with an $IC_{50}$ of less than 1 μM.

114. A compound or composition according to any one of the preceeding Embodiments, wherein said compound inhibits proliferation of IPC298 cells with an $IC_{50}$ of less than 100 nM.

115. A compound or composition according to any one of the preceeding Embodiments, wherein said compound inhibits proliferation of IPC298 cells with an $IC_{50}$ of less than 20 nM.

116. A compound or composition according to any one of the preceeding Embodiments, wherein said compound inhibits proliferation of IPC298 cells with an $IC_{50}$ of less than 1 nM.

117. A compound or composition according to any one of the preceeding Embodiments, wherein said compound inhibits proliferation of IPC298 cells with an $IC_{50}$ of less than 1 μM and wherein said compound is a pan Raf inhibitor having an $IC_{50}$ of less than 500 nM in activity assays for each of B-Raf, c-Raf-1 and B-Raf V600E protein kinases.

118. A compound or composition according to any one of the preceeding Embodiments, wherein said compound inhibits proliferation of IPC298 cells with an $IC_{50}$ of less than 100 nM and wherein said compound is a pan Raf inhibitor having an $IC_{50}$ of less than 500 nM in activity assays for each of B-Raf, c-Raf-1 and B-Raf V600E protein kinases.

119. A compound or composition according to any one of the preceeding Embodiments, wherein said compound inhibits proliferation of IPC298 cells with an $IC_{50}$ of less than 20 nM and wherein said compound is a pan Raf inhibitor having an $IC_{50}$ of less than 500 nM in activity assays for each of B-Raf, c-Raf-1 and B-Raf V600E protein kinases.

120. A compound or composition according to any one of the preceeding Embodiments, wherein said compound inhibits proliferation of IPC298 cells with an $IC_{50}$ of less than 1 nM and wherein said compound is a pan Raf inhibitor having an $IC_{50}$ of less than 500 nM in activity assays for each of B-Raf, c-Raf-1 and B-Raf V600E protein kinases.

121. A method for treating a subject suffering from or at risk of a disease or condition, comprising administering to the subject in need thereof an effective amount of a compound according to any one of Embodiments 1, 4, 7, 10 or 13, wherein the disease or condition is selected from the group consisting of melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma.

122. A compound according to any one of Embodiments 1, 4, 7, 10 or 13 for the treatment of a disease or condition selected from the group consisting of melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma.

123. Use of a compound according to any one of Embodiments 1, 4, 7, 10 or 13 or a composition according to any one of Embodiments 2, 5, 8, 11 or 14 in the preparation of a medicament for the treatment of a disease or condition selected from the group consisting of melanoma, glioma, glioblastoma, pilocytic astrocytoma, liver cancer, biliary tract cancer, cholangiocarcinoma, colorectal cancer, lung cancer, bladder cancer, gallbladder cancer, breast cancer, pancreatic cancer, thyroid cancer, kidney cancer, ovarian cancer, adrenocortical cancer, prostate cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma.

EXAMPLES

Examples related to the present invention are described below. In most cases, alternative techniques can be used. The examples are intended to be illustrative and are not limiting or restrictive to the scope of the invention. For example, where additional compounds are prepared following a protocol of a Scheme for a particular compound, it is understood that conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. In some examples, the mass spectrometry result indicated for a compound may have more than one value due to the isotope distribution of an atom in the molecule, such as a compound having a bromo or chloro substituent.

Unless specifically indicated otherwise, the Formula enumeration and R group enumeration used in the following examples is not related to such enumeration in other sections of this application. The reagents and solvents used in these examples can be readily substituted with appropriate alternatives as are known in the art and isolation of products is readily achieved by methods known in the art, including, but not limited to, extraction, crystallization, and chromatographic methods.

Ring numbering for the 1H-pyrrolo[2,3-b]pyridine in the following Examples is as follows:

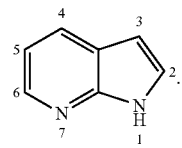

Example 1

Synthesis of propane-1-sulfonic acid {2,4-difluoro-3-[5-(1H-indazol-5-yl)-1H-pyrrolo[2,3-b]pyridine-3-carbonyl]-phenyl}-amide P-0001

Propane-1-sulfonic acid {2,4-difluoro-3-[5-(1H-indazol-5-yl)-1H-pyrrolo[2,3-b]pyridine-3-carbonyl]-phenyl}-amide P-0001 is prepared in eight steps from 2,4-difluorophenylamine 1 as shown in Scheme 1.

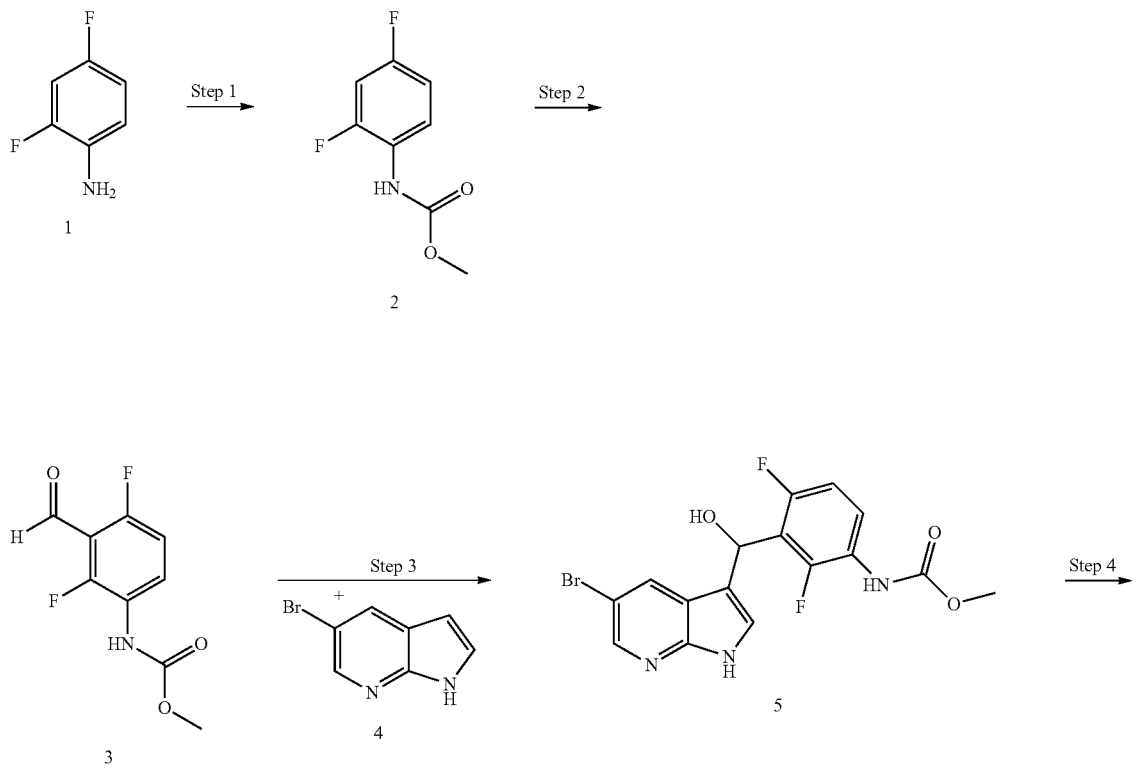

Scheme 1

-continued
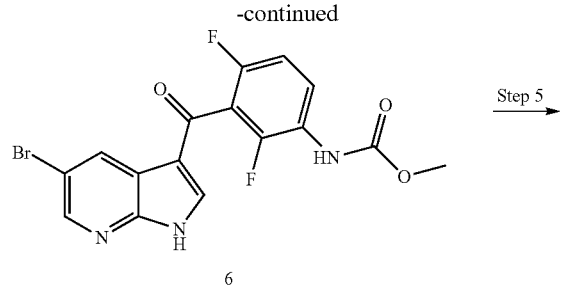
6
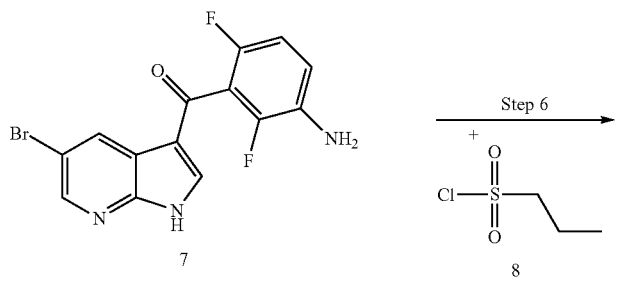
7 + 8 →Step 6
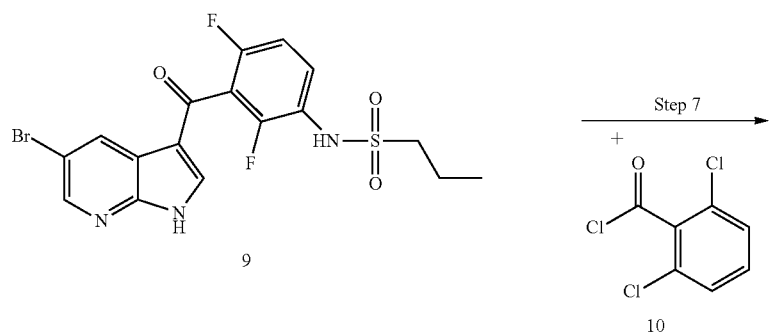
9 + 10 →Step 7
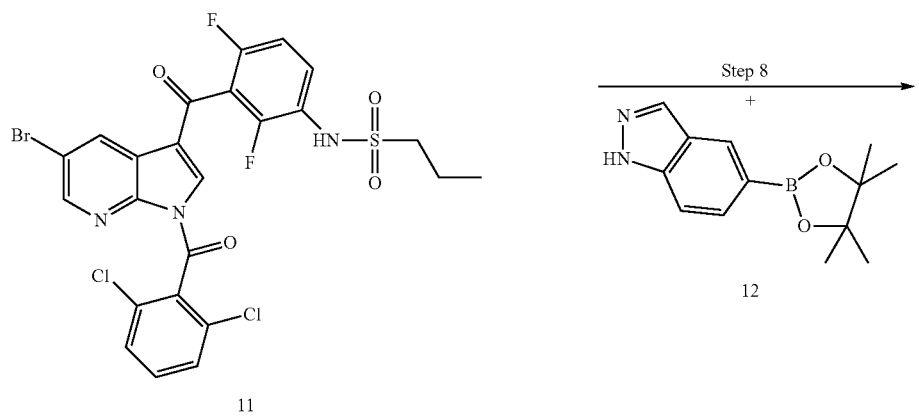
11 + 12 →Step 8
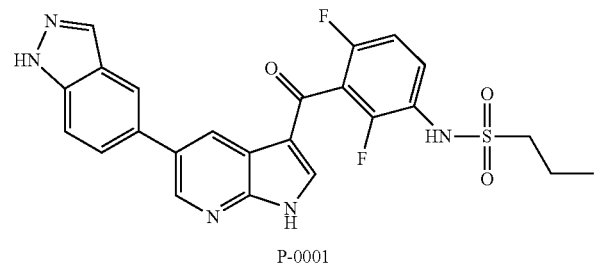
P-0001

Step 1—Preparation of (2,4-Difluoro-Phenyl)-Carbamic Acid Methyl Ester (2)

Into a reaction flask under nitrogen, 2,4-difluoro-phenylamine (1, 50.00 g, 390 mmol) is combined with 550 mL of anhydrous dichloromethane and anhydrous pyridine (61.27 g, 770 mmol). Methyl chloroformate (43.92 g, 460 mmol) is added dropwise while cooling to maintain the temperature in the range of 20-30° C. The reaction is stirred overnight, then concentrated under vacuum. The resulting material is diluted with 250 mL of water, adjusted to pH 2 with 2M hydrochloric acid, and extracted with 3×250 mL of ethyl acetate. The organic layers are combined, dried over magnesium sulfate, filtered and the filtrate concentrated under vacuum. The resulting material is slurried from hexane and the resulting solid is collected by filtration and dried to provide the desired compound (2, 71.06 g, 98%).

Step 2—Preparation of (2,4-difluoro-3-formyl-phenyl)-carbamic acid methyl ester (3)

Into a reaction flask under nitrogen, diisopropylamine (24.87 g, 250 mmol) is combined with 160 mL of anhydrous tetrahydrofuran and the solution is cooled to −78° C. n-Butyllithium (154 mL, 1.6 M in hexanes, 250 mmol) is added dropwise, maintaining the temperature below −70° C. After stirring at −78° C. for 1 hour, (2,4-difluoro-phenyl)-carbamic acid methyl ester (2, 20.00 g, 110 mmol) in 40 mL of tetrahydrofuran is added dropwise, maintaining the temperature below −70° C. The reaction is stirred at −78° C. for 1 hour, then warmed to room temperature and stirred for 1 minute. The reaction is poured into 250 mL of water, the pH is adjusted to 1 with addition of 2M hydrochloric acid, and the mixture is extracted with 3×250 mL of ethyl acetate. The organic layers are combined, dried over magnesium sulfate, filtered and the filtrate concentrated under vacuum. The resulting material is slurried in hexane and the resulting solid is collected by filtration and dried to provide the desired compound (3, 19.38 g, 84%).

Step 3—Preparation of {3-[(5-bromo-1H-pyrrolo[2,3-b]pyridin-3-yl)-hydroxy-methyl]-2,4-difluoro-phenyl}-carbamic acid methyl ester (5)

Into a reaction flask under nitrogen, 5-bromo-1H-pyrrolo[2,3-b]pyridine (4, 1.00 g, 5.08 mmol) is combined with (2,4-difluoro-3-formyl-phenyl)-carbamic acid methyl ester (3, 1.09 g, 5.08 mmol), 10 mL of methanol and potassium hydroxide (0.41 g, 7.31 mmol). The reaction is stirred at room temperature overnight, then diluted with 30 mL of water and extracted with 1×50 mL, then 2×30 mL of ethyl acetate. The organic layers are combined, dried over magnesium sulfate, filtered and the filtrate concentrated under vacuum. The resulting material is purified by silica gel column chromatography, eluting with a gradient of ethyl acetate:hexane. Appropriate fractions are combined and concentrated under vacuum to provide the desired compound (5, 1.91 g, 91%).

Step 4—Preparation of [3-(5-bromo-1H-pyrrolo[2,3-b]pyridine-3-carbonyl)-2,4-difluoro-phenyl]-carbamic acid methyl ester (6)

Into a reaction flask, {3-[(5-bromo-1H-pyrrolo[2,3-b]pyridin-3-yl)-hydroxy-methyl]-2,4-difluoro-phenyl}-carbamic acid methyl ester (5, 1.91 g, 4.63 mmol) is combined with 10 mL of tetrahydrofuran and Dess-Martin periodinane (2.36 g, 5.56 mmol). The reaction is stirred at room temperature for 2 hours, then diluted with 50 mL of 1M aqueous potassium carbonate and 50 mL of 1M aqueous sodium thiosulfate and extracted with 3×30 mL of ethyl acetate. The organic layers are combined, dried over magnesium sulfate, filtered and the filtrate concentrated under vacuum to provide the desired compound (6, 1.91 g).

Step 5—Preparation of (3-amino-2,6-difluoro-phenyl)-(5-bromo-1H-pyrrolo[2,3-b]pyridin-3-yl)-methanone (7)

Into a reaction flask under nitrogen, [3-(5-bromo-1H-pyrrolo[2,3-b]pyridine-3-carbonyl)-2,4-difluoro-phenyl]-carbamic acid methyl ester (6, 15.00 g, 36.6 mmol) is combined with 300 mL of anhydrous acetonitrile and trimethylsilyl iodide (21.95 g, 109.7 mmol). The reaction is stirred at room temperature overnight, then diluted with 500 mL of ethyl acetate and washed with 2×500 mL of 10% aqueous sodium thiosulfate. The aqueous layers are combined and back extracted with 1×500 mL of ethyl acetate. The organic layers are combined and washed with 1×500 mL of saturated aqueous sodium bicarbonate, dried over magnesium sulfate, filtered and the filtrate concentrated under vacuum to provide the desired compound (7, 13.34 g).

Step 6—Preparation of propane-1-sulfonic acid [3-(5-bromo-1H-pyrrolo[2,3-b]pyridine-3-carbonyl)-2,4-difluoro-phenyl]-amide (9)

Into a reaction flask under nitrogen, (3-amino-2,6-difluoro-phenyl)-(5-bromo-1H-pyrrolo[2,3-b]pyridin-3-yl)-methanone (7, 13.00 g, 36.9 mmol) is combined with 150 mL of dichloromethane and anhydrous pyridine (5.84 g, 73.8 mmol), and propane-1-sulfonyl chloride (8, 6.05 g, 42.5 mmol) is added. The reaction is stirred at room temperature overnight, and additional pyridine (1.46 g, 18.5 mmol) and propane-1-sulfonyl chloride (1.51 g, 10.6 mmol) are added. The reaction is stirred at room temperature another 3 hours, then diluted with 500 mL of water and extracted 3×250 mL with dichloromethane. The organic layers are combined and washed with 250 mL of brine, dried over magnesium sulfate, filtered and the filtrate concentrated under vacuum. The resulting material is purified by silica gel column chromatography, eluting with a gradient of ethyl acetate:hexane. Appropriate fractions are combined and concentrated under vacuum to provide the desired compound (9, 8.41 g, 50%).

Step 7—Preparation of propane-1-sulfonic acid {3-[5-bromo-1-(2,6-dichloro-benzoyl)-1H-pyrrolo[2,3-b]pyridine-3-carbonyl]-2,4-difluoro-phenyl}-amide (II)

Into a reaction flask under nitrogen, propane-1-sulfonic acid [3-(5-bromo-1H-pyrrolo[2,3-b]pyridine-3-carbonyl)-2,4-difluoro-phenyl]-amide (9, 8.40 g, 18.3 mmol) is combined with 100 mL of toluene, 4-dimethylaminopyridine (447 mg, 3.7 mmol), diisopropylethylamine (4.74 g, 36.7 mmol) and 2,6-dichloro-benzoyl chloride (10, 4.34 g, 20.7 mmol). The reaction is stirred at room temperature overnight, then diluted with 300 mL of dichloromethane and washed with 200 mL of saturated aqueous sodium bicarbonate, then 200 mL of brine. The organic layer is dried over magnesium sulfate, filtered and the filtrate concentrated under vacuum. The resulting material is purified by silica gel column chromatography, eluting with a gradient of ethyl acetate:hexane. Appropriate fractions are combined to provide crude material that is further purified with additional chromatography, eluting with 1:1 hexane:dichloromethane up to 100% dichloromethane. Appropriate fractions are combined and concentrated under vacuum to provide the desired compound (11, 4.15 g, 36%).

Step 8 Preparation of propane-1-sulfonic acid {2,4-difluoro-3-[5-(1H-indazol-5-yl)-1H-pyrrolo[2,3-b]pyridine-3-carbonyl]-phenyl}-amide (P-0001)

Into a microwave vial, propane-1-sulfonic acid {3-[5-bromo-1-(2,6-dichloro-benzoyl)-1H-pyrrolo[2,3-b]pyridine-3-carbonyl]-2,4-difluoro-phenyl}-amide (11, 0.100 g, 0.158 mmol), 5-(4,4,5,5-tetramethyl-[1,3,2]dioxaborolan-2-yl)-1H-indazole (12, 0.080 g, 0.33 mmol) and 1,1'-bis(diphenylphosphino)ferrocene]dichloropalladium(II) (0.07 g, 0.086 mmol, 1:1 complex with dichloromethane) are combined with 2.0 mL of toluene and 2.0 mL of ethanol. The mixture is stirred for 5 minutes, then potassium carbonate (0.475 mL, 1.0 M aqueous) is added and the reaction heated at 110° C. for 60 minutes in a microwave, followed by 140° C. for 45 minutes. The reaction is added to silica and the solvents are removed under vacuum. The resulting material is purified by silica gel column chromatography, eluting with a gradient of ethyl acetate (with 2% acetic acid):hexanes. Appropriate fractions are combined and concentrated under vacuum, then washed with acetonitrile to provide the desired compound (P-0001). MS (ESI) [M+H$^+$]$^+$=496.0.

N-{3-[5-Bromo-1-(2,6-dichloro-benzoyl)-1H-pyrrolo[2,3-b]pyridine-3-carbonyl]-2,4-difluoro-phenyl}-2,5-difluoro-benzenesulfonamide 13,

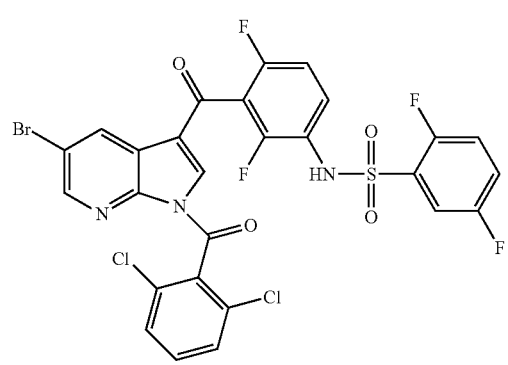

is prepared following the protocol of Scheme 1, steps 1-7, replacing propane-1-sulfonyl chloride 8 with 2,5-difluoro-benzenesulfonyl chloride in step 6.

Propane-1-sulfonic acid {3-[1-(2,6-dichloro-benzoyl)-5-(1H-indol-5-yl)-1H-pyrrolo[2,3-b]pyridine-3-carbonyl]-2,4-difluoro-phenyl}-amide P-0017 is prepared similarly to the protocol of Scheme 1 using the following step 8a.

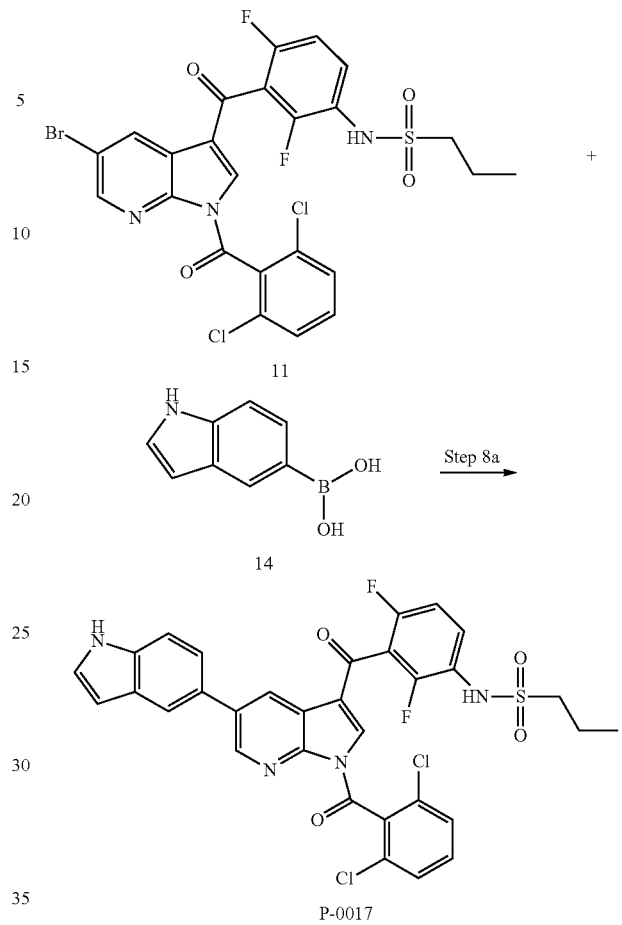

Step 8a—Preparation of propane-1-sulfonic acid {3-[1-(2,6-dichloro-benzoyl)-5-(1H-indol-5-yl)-1H-pyrrolo[2,3-b]pyridine-3-carbonyl]-2,4-difluoro-phenyl}-amide (P-0017)

Propane-1-sulfonic acid {3-[5-bromo-1-(2,6-dichloro-benzoyl)-1H-pyrrolo[2,3-b]pyridine-3-carbonyl]-2,4-difluoro-phenyl}-amide (11, 113 mg, 0.18 mmol) and 1H-indole-5-boronic acid (14, 44 mg, 0.27 mmol) are dissolved in 4 mL of tetrahydrofuran, then 2 mL of 1M aqueous potassium carbonate and 1,1'-bis(diphenylphosphino)ferrocene]dichloropalladium(II) (6.5 mg, 0.018 mmol, 10%) are added. The reaction mixture is heated at 70° C. overnight. The reaction is neutralized with acetic acid and diluted with ethyl acetate and water. The organic layer is washed with brine, dried over magnesium sulfate, filtered and the filtrate concentrated under vacuum. The resulting material is dissolved in 1 mL of dimethylformamide and purified by HPLC using a C8 column, eluting with water/acetonitrile and 0.1% trifluoroacetic acid, 40-85% acetonitrile at 15 mL per minute. Appropriate fractions are combined and concentrated under vacuum to provide the desired compound. MS (ESI)=[M+H$^+$]$^+$=669.5. This compound is a prodrug of P-0012, or can be further reacted to remove the dichlorobenzoyl protecting group to provide P-0012.

Propane-1-sulfonic acid {2,4-difluoro-3-[5-(1H-indazol-5-yl)-1H-pyrrolo[2,3-b]pyridine-3-carbonyl]-phenyl}-amide P-0001 is further reacted according to the following step 9 to provide propane-1-sulfonic acid {3-[5-(1-acetyl-1H-indazol-5-yl)-1H-pyrrolo[2,3-b]pyridine-3-carbonyl]-2,4-difluoro-phenyl}-amide P-0007.

amide P-0001 is alternatively further reacted according to the following step 9a to provide propane-1-sulfonic acid {2,4-difluoro-3-[5-(1-methanesulfonyl-1H-indazol-5-yl)-1H-pyrrolo[2,3-b]pyridine-3-carbonyl]-phenyl}-amide P-0016.

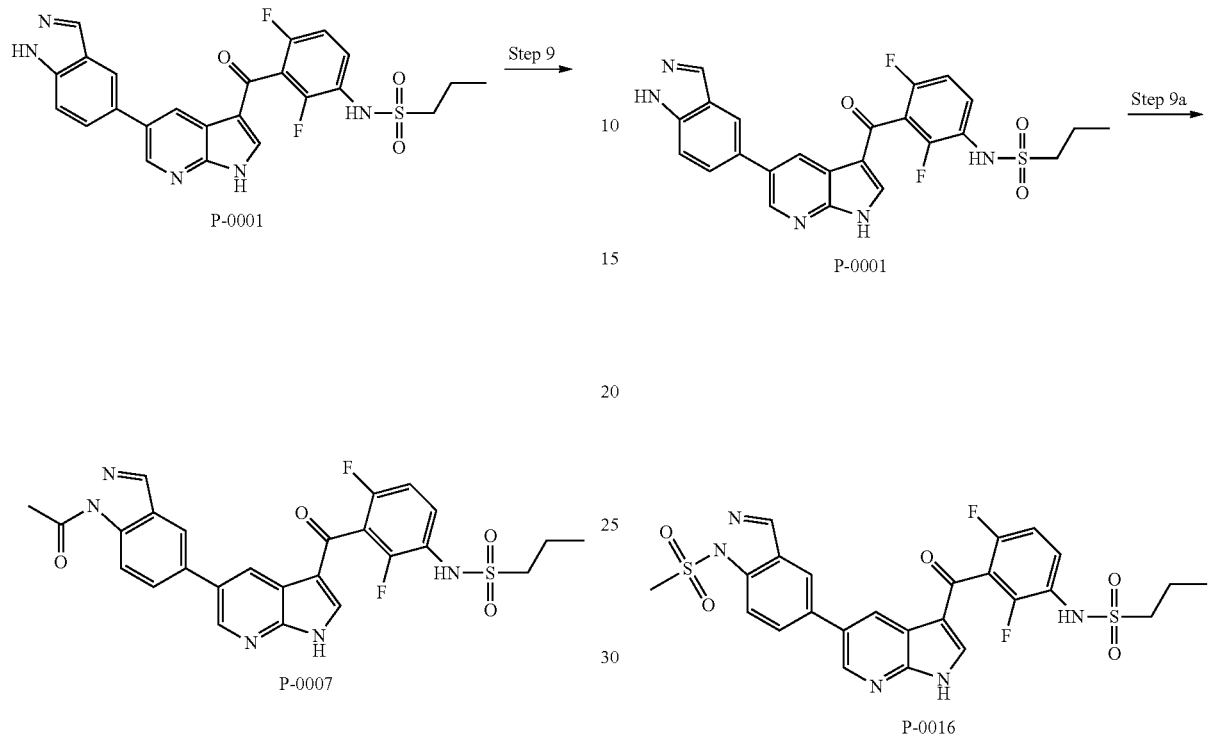

Step 9—Preparation of propane-1-sulfonic acid {3-[5-(1-acetyl-1H-indazol-5-yl)-1H-pyrrolo[2,3-b]pyridine-3-carbonyl]-2,4-difluoro-phenyl}-amide (P-0007)

Into a round bottom flask, propane-1-sulfonic acid {2,4-difluoro-3-[5-(1H-indazol-5-yl)-1H-pyrrolo[2,3-b]pyridine-3-carbonyl]-phenyl}-amide (P-0001, 0.020 g, 0.040 mmol) is combined with acetic anhydride (0.023 mL, 0.24 mmol) and 4 mL of acetonitrile. The reaction is stirred at room temperature for 3 hours, then concentrated under vacuum, combined with water and extracted with ethyl acetate. The organic layer is dried over sodium sulfate, filtered and the filtrate concentrated under vacuum. The resulting material is purified by silica gel column chromatography, eluting with a gradient of 20-100% ethyl acetate (with 2% acetic acid) in hexanes. Appropriate fractions are combined and concentrated under vacuum, and the resulting solid is further washed with a mixture of ethyl acetate:hexanes to provide the desired compound. MS (ESI) [M+H$^+$]$^+$=538.0.

Propane-1-sulfonic acid {2,4-difluoro-3-[5-(1H-indazol-5-yl)-1H-pyrrolo[2,3-b]pyridine-3-carbonyl]-phenyl}-

Step 9a—Preparation of propane-1-sulfonic acid {2,4-difluoro-3-[5-(1-methanesulfonyl-1H-indazol-5-yl)-1H-pyrrolo[2,3-b]pyridine-3-carbonyl]-phenyl}-amide (P-0016)

Into a round bottom flask, propane-1-sulfonic acid {2,4-difluoro-3-[5-(1H-indazol-5-yl)-1H-pyrrolo[2,3-b]pyridine-3-carbonyl]-phenyl}-amide (P-0001, 0.015 g, 0.030 mmol) is dissolved in 3.0 mL of pyridine and methanesulfonyl chloride (50 µL, 0.6 mmol) is added. The reaction is stirred at room temperature for 1 hour, then concentrated under vacuum, then twice redissolved in toluene and concentrated under vacuum. The resulting solid is added to water and 1N hydrochloric acid and extracted with ethyl acetate. The organic layer is dried with sodium sulfate, filtered and the filtrate concentrated under vacuum. The resulting material is purified by reverse phase HPLC. MS (ESI) [M+H$^+$]$^+$=574.5.

2-Fluoro-N-{2-fluoro-3-[5-(2-methoxy-pyrimidin-5-yl)-1H-pyrrolo[2,3-b]pyridine-3-carbonyl]-phenyl}-benzenesulfonamide P-1518 is prepared in six steps from 2-fluoro-3-nitro-benzaldehyde 15 according to the following Scheme 1a.

Scheme 1a

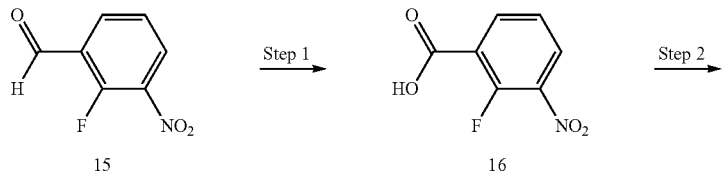

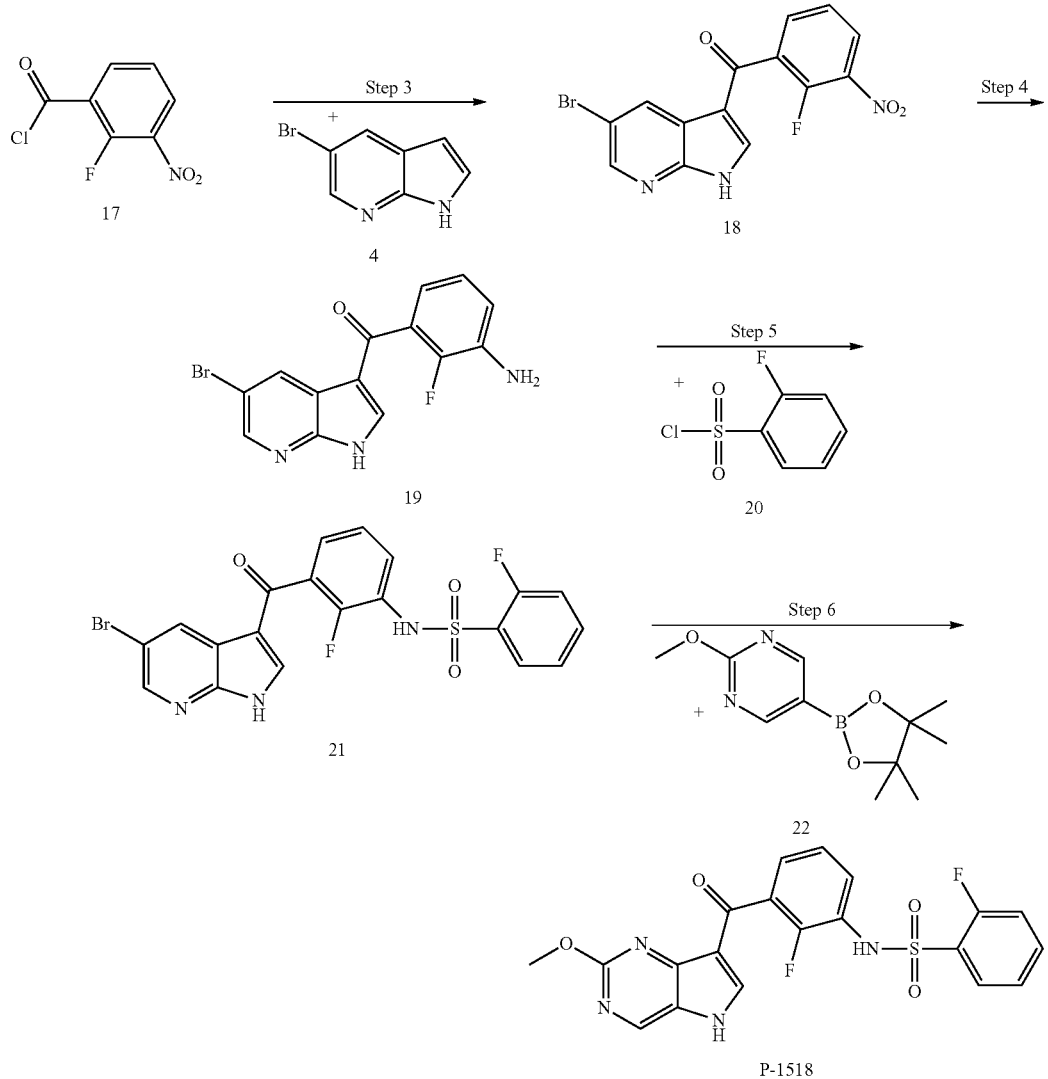

Step 1—Preparation of 2-fluoro-3-nitro-benzoic acid (16)

In a round bottom flask, 2-fluoro-3-nitro-benzaldehyde (15, 1.02 g, 6.03 mmol) is combined with sodium chlorite (1.26 g, 11.15 mmol), 60 mL of 1,4-dioxane, 20 mL of water, and sulfamic acid (4.47 g, 46.0 mmol) and the reaction is stirred at room temperature for 30 minutes. The mixture is poured into water and extracted with ethyl acetate. The organic layer is washed with water, then brine, dried over magnesium sulfate, filtered and the filtrate is concentrated under vacuum. The resulting material is purified on column chromatography, eluting with methanol and dichloromethane. Appropriate fractions are combined and concentrated under vacuum, then suspended in dichloromethane. The resulting solid is collected by filtration to provide the desired compound (16, 151 mg). MS (ESI)[M−H$^+$]$^-$=184.4.

Step 2—Preparation of 2-fluoro-3-nitro-benzoyl chloride (17)

2-Fluoro-3-nitro-benzoic acid (16, 0.497 g, 2.68 mmol) is combined with thionyl chloride (3 mL, 40.0 mmol) and N,N-dimethylformamide (20 µL, 0.2 mmol) and the reaction is heated at 80° C. overnight. The reaction is concentrated under vacuum, suspended in toluene and concentrated under vacuum twice, and dried to provide the desired compound as a white solid (17, 0.535 g).

Step 3—Preparation of (5-bromo-1H-pyrrolo[2,3-b]pyridin-3-yl)-(2-fluoro-3-nitro-phenyl)-methanone (18)

5-Bromo-1H-pyrrolo[2,3-b]pyridine (4, 0.525 g, 2.66 mmol) is combined with aluminum trichloride (2.05 g, 15.4 mmol) and 10 mL of nitromethane. 2-Fluoro-3-nitro-benzoyl chloride (17, 0.521 g, 2.56 mmol) in 5 mL of nitromethane is added and the reaction is heated at 45° C. for 6 hours. The reaction is quenched by slowly adding 5 mL of methanol. The resulting precipitate is collected by filtration and combined with ethyl acetate, water and celite, then stirred for 30 minutes and filtered. The organic layer is isolated and washed with water, then brine, dried over magnesium sulfate, filtered and the filtrate is concentrated under vacuum to provide the desired compound (18, 151 mg). MS (ESI) [M−H$^+$]$^-$=362.4 and 364.4.

Step 4—Preparation of (3-amino-2-fluoro-phenyl)-(5-bromo-1H-pyrrolo[2,3-b]pyridin-3-yl)-methanone (19)

To (5-bromo-1H-pyrrolo[2,3-b]pyridin-3-yl)-(2-fluoro-3-nitro-phenyl)-methanone (18, 2.27 g, 6.23 mmol) in 200 mL of tetrahydrofuran and 200 mL of ethyl acetate, stannous chloride, dehydrate (4.85 g, 2.15 mmol) is added. The reaction is heated at 60° C. for 3 days, then 300 mL of water and 200 mL of ethyl acetate are added. The mixture is treated with celite and filtered. Brine is added, the organic layer is separated, dried over magnesium sulfate, filtered and the filtrate is concentrated under vacuum. The resulting material is purified by silica gel column chromatography, eluting with ethyl acetate and hexane. Appropriate fractions are combined and concentrated under vacuum to provide the desired compound (19, 972 mg).

Step 5—Preparation of N-[3-(5-bromo-1H-pyrrolo[2,3-b]pyridine-3-carbonyl)-2-fluoro-phenyl]-2-fluoro-benzenesulfonamide (21)

To (3-amino-2-fluoro-phenyl)-(5-bromo-1H-pyrrolo[2,3-b]pyridin-3-yl)-methanone (19, 53 mg, 0.159 mmol) in 0.63 mL of tetrahydrofuran, pyridine (0.115 mL, 1.43 mmol) is added, followed by 2-fluorobenzenesulfonyl chloride (20, 46 mg, 0.238 mmol) and the reaction is stirred at room temperature for 48 hours. Hydrochloric acid (1M aqueous) is added to adjust the mixture to pH 4, and the mixture is extracted with ethyl acetate. The organic layer is washed with brine, dried over sodium sulfate, filtered and the filtrate is concentrated under vacuum. The resulting material is purified by silica gel column chromatography, eluting with ethyl acetate and dichloromethane. Appropriate fractions are combined and concentrated under vacuum to provide the desired compound (21, 56 mg).

Step 6—Preparation of 2-fluoro-N-{2-fluoro-3-[5-(2-methoxy-pyrimidin-5-yl)-1H-pyrrolo[2,3-b]pyridine-3-carbonyl]phenyl}-benzenesulfonamide (P-1518)

In a microwave vial, N-[3-(5-bromo-1H-pyrrolo[2,3-b]pyridine-3-carbonyl)-2-fluoro-phenyl]-2-fluoro-benzenesulfonamide (21, 100 mg, 0.203 mmol), 2-methoxy-5-(4,4,5,5-tetramethyl-[1,3,2]dioxaborolan-2-yl)-pyrimidine (22, 72 mg, 0.305 mmol) and tetrakis-(triphenylphosphine) palladium(0) (10 mg) are combined with potassium carbonate (0.609 mL, 1M aqueous, 0.609 mmol) and 0.6 mL of acetonitrile. The reaction mixture is heated in a microwave at 160° C. for 15 minutes. The mixture is filtered through celite, and the celite is washed with water and ethyl acetate. The aqueous layer is separated from the filtrate and extracted with ethyl acetate. The organic portions are combined and washed with brine, then dried over sodium sulfate, filtered and the filtrate concentrated under vacuum. The resulting material is purified by silica gel column chromatography, eluting with methanol and dichloromethane. Appropriate fractions are combined and concentrated under vacuum to provide the desired compound (P-1518, 27 mg). MS (ESI) [M+H⁺]⁺=521.95.

Propane-1-sulfonic acid {2,4-difluoro-3-[5-(1H-pyrazol-4-yl)-1H-pyrrolo[2,3-b]pyridine-3-carbonyl]-phenyl}-amide 23 is prepared according to Scheme 1a, replacing N-[3-(5-bromo-1H-pyrrolo[2,3-b]pyridine-3-carbonyl)-2-fluoro-phenyl]-2-fluoro-benzenesulfonamide 21 with propane-1-sulfonic acid [3-(5-bromo-1H-pyrrolo[2,3-b]pyridine-3-carbonyl)-2,4-difluoro-phenyl]-amide and replacing 2-methoxy-5-(4,4,5,5-tetramethyl-[1,3,2]dioxaborolan-2-yl)-pyrimidine 22 with 1H-pyrazole-4-carboxylic acid. Propane-1-sulfonic acid {2,4-difluoro-3-[5-(1H-pyrazol-4-yl)-1H-pyrrolo[2,3-b]pyridine-3-carbonyl]-phenyl}-amide 23 is further reacted according to Scheme 1b to provide 4-{3-[2,6-difluoro-3-(propane-1-sulfonylamino)-benzoyl]-1H-pyrrolo[2,3-b]pyridin-5-yl}-pyrazole-1-carboxylic acid phenyl ester P-1016.

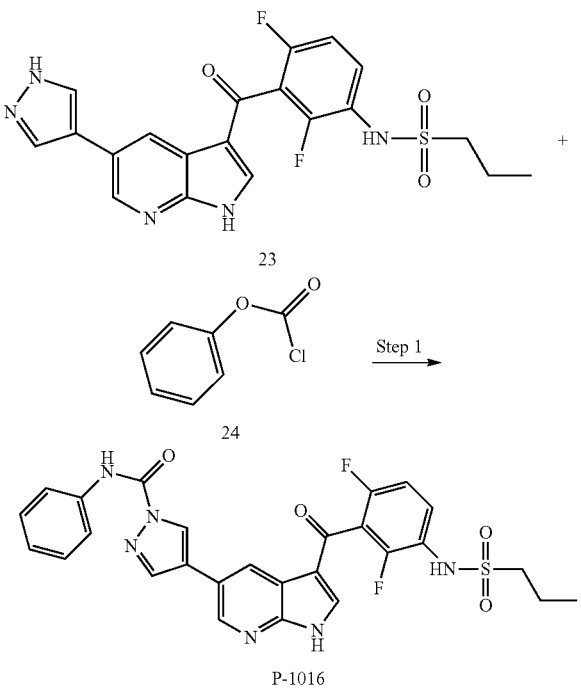

Scheme 1b

Step 1—Preparation of 4-{3-[2,6-difluoro-3-(propane-1-sulfonylamino)-benzoyl]-1H-pyrrolo[2,3-b]pyridin-5-yl}-pyrazole-1-carboxylic acid phenyl ester (P-1016)

In a reaction vial, propane-1-sulfonic acid {2,4-difluoro-3-[5-(1H-pyrazol-4-yl)-1H-pyrrolo[2,3-b]pyridine-3-carbonyl]-phenyl}-amide (23, 7 mg, 0.02 mmol) is dissolved in 0.05 mL of acetonitrile and potassium carbonate (4 mg, 0.03 mmol) and carbonochloridic acid, phenyl ester (24, 0.0025 mL, 0.02 mmol) are added and the reaction is stirred at room temperature overnight. The reaction is concentrated under vacuum and the resulting material is purified by reverse phase HPLC to provide the desired compound (P-1016, 0.7 mg).

Additional compounds are prepared similarly to the protocol of Scheme 1 step 8 or Scheme 1a step 6. The reactions are performed using a suitable boronic acid or boronic acid ester in place of 12 or 22 and optionally replacing 11 or 21 with a suitable 5-halo-1H-pyrrolo[2,3-b]pyridine in step 8 or Scheme 1a. The following compounds are prepared following this procedure:

Propane-1-sulfonic acid {2,4-difluoro-3-[5-(1H-pyrazol-4-yl)-1H-pyrrolo[2,3-b]pyridine-3-carbonyl]-phenyl}-amide (17), Propane-1-sulfonic acid {2,4-difluoro-3-[5-(1H-indazol-4-yl)-1H-pyrrolo[2,3-b]pyridine-3-carbonyl]-phenyl}-amide (P-0009),
Propane-1-sulfonic acid {2,4-difluoro-3-[5-(2-methyl-2H-indazol-5-yl)-1H-pyrrolo[2,3-b]pyridine-3-carbonyl]-phenyl}-amide (P-0010),
Propane-1-sulfonic acid {2,4-difluoro-3-[5-(2-methyl-2H-indazol-6-yl)-1H-pyrrolo[2,3-b]pyridine-3-carbonyl]-phenyl}-amide (P-0011),
Propane-1-sulfonic acid {2,4-difluoro-3-[5-(1H-indol-5-yl)-1H-pyrrolo[2,3-b]pyridine-3-carbonyl]-phenyl}-amide (P-0012),
propane-1-sulfonic acid [3-(5-benzothiazol-5-yl-1H-pyrrolo[2,3-b]pyridine-3-carbonyl)-2,4-difluoro-phenyl]-amide (P-0013),
Propane-1-sulfonic acid [2,4-difluoro-3-(5-quinoxalin-6-yl-1H-pyrrolo[2,3-b]pyridine-3-carbonyl)-phenyl]-amide (P-0014),
Propane-1-sulfonic acid {2,4-difluoro-3-[5-(2-methyl-2H-indazol-4-yl)-1H-pyrrolo[2,3-b]pyridine-3-carbonyl]-phenyl}-amide (P-0015),
N-{2,4-Difluoro-3-[5-(1-methyl-1H-pyrazol-4-yl)-1H-pyrrolo[2,3-b]pyridine-3-carbonyl]-phenyl}-2,5-difluoro-benzenesulfonamide (P-1009),
N-{3-[5-(2,5-Dimethyl-2H-pyrazol-3-yl)-1H-pyrrolo[2,3-b]pyridine-3-carbonyl]-2,4-difluoro-phenyl}-2,5-difluoro-benzenesulfonamide (P-1010),
N-{2,4-Difluoro-3-[5-(1-methyl-1H-pyrazol-3-yl)-1H-pyrrolo[2,3-b]pyridine-3-carbonyl]-phenyl}-2,5-difluoro-benzenesulfonamide (P-1011),
Propane-1-sulfonic acid {2,4-difluoro-3-[5-(1-methyl-1H-pyrazol-3-yl)-1H-pyrrolo[2,3-b]pyridine-3-carbonyl]-phenyl}-amide (P-1012),
Propane-1-sulfonic acid (2,4-difluoro-3-{5-[2-(4-methyl-imidazol-1-yl)-thiazol-4-yl]-1H-pyrrolo[2,3-b]pyridine-3-carbonyl}-phenyl)-amide (P-1100),
Propane-1-sulfonic acid (2,4-difluoro-3-{5-[2-(2-methyl-imidazol-1-yl)-thiazol-4-yl]-1H-pyrrolo[2,3-b]pyridine-3-carbonyl}-phenyl)-amide (P-1101),
Propane-1-sulfonic acid [2,4-difluoro-3-(5-thiazol-4-yl-1H-pyrrolo[2,3-b]pyridine-3-carbonyl)-phenyl]-amide (P-1107),
Propane-1-sulfonic acid {2,4-difluoro-3-[5-(2-methyl-thiazol-4-yl)-1H-pyrrolo[2,3-b]pyridine-3-carbonyl]-phenyl}-amide (P-1108),
N-[2,4-Difluoro-3-(5-thiazol-4-yl-1H-pyrrolo[2,3-b]pyridine-3-carbonyl)-phenyl]-2,5-difluoro-benzenesulfonamide (P-1110),
N-[2,4-Difluoro-3-(5-thiazol-5-yl-1H-pyrrolo[2,3-b]pyridine-3-carbonyl)-phenyl]-2,5-difluoro-benzenesulfonamide (P-1111),
N-{3-[5-(2-Dimethylamino-thiazol-4-yl)-1H-pyrrolo[2,3-b]pyridine-3-carbonyl]-2,4-difluoro-phenyl}-2,5-difluoro-benzenesulfonamide (P-1112),
N-{2,4-Difluoro-3-[5-(2-methyl-thiazol-4-yl)-1H-pyrrolo[2,3-b]pyridine-3-carbonyl]-phenyl}-2,5-difluoro-benzenesulfonamide (P-1113),
N-{2,4-Difluoro-3-[5-(2-methoxy-thiazol-4-yl)-1H-pyrrolo[2,3-b]pyridine-3-carbonyl]-phenyl}-2,5-difluoro-benzenesulfonamide (P-1114),
N-[2,4-Difluoro-3-(5-oxazol-5-yl-1H-pyrrolo[2,3-b]pyridine-3-carbonyl)-phenyl]-2,5-difluoro-benzenesulfonamide (P-1300),
N-[2,4-Difluoro-3-(5-pyridin-3-yl-1H-pyrrolo[2,3-b]pyridine-3-carbonyl)-phenyl]-2,5-difluoro-benzenesulfonamide (P-1402),
N-[2,4-Difluoro-3-(5-pyridin-4-yl-1H-pyrrolo[2,3-b]pyridine-3-carbonyl)-phenyl]-2,5-difluoro-benzenesulfonamide (P-1403),
N-{2,4-Difluoro-3-[5-(6-methoxy-pyridin-3-yl)-1H-pyrrolo[2,3-b]pyridine-3-carbonyl]-phenyl}-2,5-difluoro-benzenesulfonamide (P-1404),
N-{2,4-Difluoro-3-[5-(3-fluoro-pyridin-4-yl)-1H-pyrrolo[2,3-b]pyridine-3-carbonyl]-phenyl}-2,5-difluoro-benzenesulfonamide (P-1405),
N-{3-[5-(2,6-Dimethoxy-pyridin-3-yl)-1H-pyrrolo[2,3-b]pyridine-3-carbonyl]-2,4-difluoro-phenyl}-2,5-difluoro-benzenesulfonamide (P-1406),
N-{2,4-Difluoro-3-[5-(5-methanesulfonyl-pyridin-3-yl)-1H-pyrrolo[2,3-b]pyridine-3-carbonyl]-phenyl}-2,5-difluoro-benzenesulfonamide (P-1407),
N-{2,4-Difluoro-3-[5-(6-methyl-pyridin-3-yl)-1H-pyrrolo[2,3-b]pyridine-3-carbonyl]-phenyl}-2,5-difluoro-benzenesulfonamide (P-1408),
N-{3-[5-(6-Dimethylamino-pyridin-3-yl)-1H-pyrrolo[2,3-b]pyridine-3-carbonyl]-2,4-difluoro-phenyl}-2,5-difluoro-benzenesulfonamide (P-1409),
N-(3-{5-[6-(3-Dimethylamino-propoxy)-pyridin-3-yl]-1H-pyrrolo[2,3-b]pyridine-3-carbonyl}-2,4-difluoro-phenyl)-2,5-difluoro-benzenesulfonamide (P-1411),
N-[2,4-Difluoro-3-(5-pyrimidin-5-yl-1H-pyrrolo[2,3-b]pyridine-3-carbonyl)-phenyl]-2,5-difluoro-benzenesulfonamide (P-1500),
N-{3-[5-(2,4-Dimethoxy-pyrimidin-5-yl)-1H-pyrrolo[2,3-b]pyridine-3-carbonyl]-2,4-difluoro-phenyl}-2,5-difluoro-benzenesulfonamide (P-1501),
N-{3-[5-(2-Dimethylamino-pyrimidin-5-yl)-1H-pyrrolo[2,3-b]pyridine-3-carbonyl]-2,4-difluoro-phenyl}-2,5-difluoro-benzenesulfonamide (P-1502),
N-{2,4-Difluoro-3-[5-(2-methyl-pyrimidin-5-yl)-1H-pyrrolo[2,3-b]pyridine-3-carbonyl]-phenyl}-2,5-difluoro-benzenesulfonamide (P-1503),
Propane-1-sulfonic acid {3-[5-(2-cyclopropylamino-pyrimidin-5-yl)-1H-pyrrolo[2,3-b]pyridine-3-carbonyl]-2,4-difluoro-phenyl}-amide (P-1504),
Propane-1-sulfonic acid (2,4-difluoro-3-{5-[2-(2-methoxy-ethylamino)-pyrimidin-5-yl]-1H-pyrrolo[2,3-b]pyridine-3-carbonyl}-phenyl)-amide (P-1505),
N-{3-[5-(2-Cyclopropylamino-pyrimidin-5-yl)-1H-pyrrolo[2,3-b]pyridine-3-carbonyl]-2,4-difluoro-phenyl}-2,5-difluoro-benzenesulfonamide (P-1506),
N-(2,4-Difluoro-3-{5-[2-(2-methoxy-ethylamino)-pyrimidin-5-yl]-1H-pyrrolo[2,3-b]pyridine-3-carbonyl}-phenyl)-2,5-difluoro-benzenesulfonamide (P-1507),
Propane-1-sulfonic acid {2,4-difluoro-3-[5-(2-isopropyl-pyrimidin-5-yl)-1H-pyrrolo[2,3-b]pyridine-3-carbonyl]-phenyl}-amide (P-1519),
N-{2,4-Difluoro-3-[5-(2-isopropyl-pyrimidin-5-yl)-1H-pyrrolo[2,3-b]pyridine-3-carbonyl]-phenyl}-2,5-difluoro-benzenesulfonamide (P-1521),
N-[2,4-difluoro-3-[5-(2-methoxypyrimidin-5-yl)-1H-pyrrolo[2,3-b]pyridine-3-carbonyl]-phenyl]-3-fluoro-benzenesulfonamide (P-1522),
2-fluoro-N-[2-fluoro-3-[5-(2-methoxypyrimidin-5-yl)-1H-pyrrolo[2,3-b]pyridine-3-carbonyl]phenyl]benzenesulfonamide (P-1523),
Propane-1-sulfonic acid (2,4-difluoro-3-{5-[5-(2-oxo-2H-pyridin-1-yl)-pyrazin-2-yl]-1H-pyrrolo[2,3-b]pyridine-3-carbonyl}-phenyl)-amide (P-1600),
Propane-1-sulfonic acid {2,4-difluoro-3-[5-(5-pyrazol-1-yl-pyrazin-2-yl)-1H-pyrrolo[2,3-b]pyridine-3-carbonyl]-phenyl}-amide (P-1601), Propane-1-sulfonic acid {2,4-difluoro-3-[5-(5-imidazol-1-yl-pyrazin-2-yl)-1H-pyrrolo[2,3-b]pyridine-3-carbonyl]-phenyl}-amide (P-1602), Propane-1-sulfonic acid {3-[5-(5-amino-pyrazin-2-yl)-1H-pyrrolo[2,3-b]pyridine-3-carbonyl]-2,4-difluoro-phenyl}-amide (P-1603), 2-Chloro-5-{3-[2,6-difluoro-3-(propane-1-sulfonylamino)-benzoyl]-1H-pyrrolo[2,3-b]pyridin-5-yl}-benzamide (P-1700), 3-{3-[3-(2,5-Difluoro-benzenesulfonylamino)-2,6-difluoro-benzoyl]-1H-pyrrolo[2,3-b]pyridin-5-yl}-N-methoxy-benzamide (P-1704), 4-{3-[3-(2,5-Difluoro-benzenesulfonylamino)-2,6-difluoro-benzoyl]-1H-pyrrolo[2,3-b]pyridin-5-yl}-N-methoxy-benzamide (P-1705), N-{2,4-Difluoro-3-[5-(4-methylsulfamoyl-phenyl)-1H-pyrrolo[2,3-b]pyridine-3-carbonyl]-phenyl}-2,5-difluoro-benzenesulfonamide (P-1706), N-{2,4-Difluoro-3-[5-(4-sulfamoyl-phenyl)-1H-pyrrolo[2,3-b]pyridine-3-carbonyl]-phenyl}-2,5-difluoro-benzenesulfonamide (P-1707), Propane-1-sulfonic acid (2,4-difluoro-3-{5-[4-(1H-tetrazol-5-yl)-phenyl]-1H-pyrrolo[2,3-b]pyridine-3-carbonyl}-phenyl)-amide (P-1709), Propane-1-sulfonic acid {2,4-difluoro-3-[5-(4-formyl-phenyl)-1H-pyrrolo[2,3-b]pyridine-3-carbonyl]-phenyl}-amide (P-1710), Propane-1-sulfonic acid {3-[5-(4-cyano-phenyl)-1H-pyrrolo[2,3-b]pyridine-3-carbonyl]-2,4-difluoro-phenyl}-amide (P-1711), N-[2,4-difluoro-3-[5-(1H-pyrazol-4-yl)-1H-pyrrolo[2,3-b]pyridine-3-carbonyl]phenyl]-3-fluoro-benzenesulfonamide (P-1901), N-[2,4-difluoro-3-[5-(1H-indazol-4-yl)-1H-pyrrolo[2,3-b]pyridine-3-carbonyl]phenyl]-3-fluoro-benzenesulfonamide (P-1902), N-[2,4-difluoro-3-[5-(2-methylindazol-5-yl)-1H-pyrrolo[2,3-b]pyridine-3-carbonyl]phenyl]-3-fluoro-benzenesulfonamide (P-1903), N-[2,4-difluoro-3-[5-(2-methylindazol-6-yl)-1H-pyrrolo[2,3-b]pyridine-3-carbonyl]phenyl]-3-fluoro-benzenesulfonamide (P-1904), N-[2,4-difluoro-3-[5-(1H-indol-5-yl)-1H-pyrrolo[2,3-b]pyridine-3-carbonyl]phenyl]-3-fluoro-benzenesulfonamide (P-1905), N-[3-[5-(1,3-benzothiazol-5-yl)-1H-pyrrolo[2,3-b]pyridine-3-carbonyl]-2,4-difluoro-phenyl]-3-fluoro-benzenesulfonamide (P-1906), N-[2,4-difluoro-3-(5-quinoxalin-6-yl-1H-pyrrolo[2,3-b]pyridine-3-carbonyl)phenyl]-3-fluoro-benzenesulfonamide (P-1907), N-[2,4-difluoro-3-[5-(2-methylindazol-4-yl)-1H-pyrrolo[2,3-b]pyridine-3-carbonyl]phenyl]-3-fluoro-benzenesulfonamide (P-1908), N-[2,4-difluoro-3-[5-(1-methylpyrazol-4-yl)-1H-pyrrolo[2,3-b]pyridine-3-carbonyl]phenyl]-3-fluoro-benzenesulfonamide (P-1909), N-[3-[5-(2,5-dimethylpyrazol-3-yl)-1H-pyrrolo[2,3-b]pyridine-3-carbonyl]-2,4-difluoro-phenyl]-3-fluoro-benzenesulfonamide (P-1910), N-[2,4-difluoro-3-[5-(1-methylpyrazol-3-yl)-1H-pyrrolo[2,3-b]pyridine-3-carbonyl]phenyl]-3-fluoro-benzenesulfonamide (P-1911), N-[2,4-difluoro-3-[5-[2-(4-methylimidazol-1-yl)thiazol-4-yl]-1H-pyrrolo[2,3-b]pyridine-3-carbonyl]phenyl]-3-fluoro-benzenesulfonamide (P-1912), N-[2,4-difluoro-3-[5-[2-(2-methylimidazol-1-yl)thiazol-4-yl]-1H-pyrrolo[2,3-b]pyridine-3-carbonyl]phenyl]-3-fluoro-benzenesulfonamide (P-1913), N-[2,4-difluoro-3-(5-thiazol-4-yl-1H-pyrrolo[2,3-b]pyridine-3-carbonyl)phenyl]-3-fluoro-benzenesulfonamide (P-1914), N-[2,4-difluoro-3-[5-(2-methylthiazol-4-yl)-1H-pyrrolo[2,3-b]pyridine-3-carbonyl]phenyl]-3-fluoro-benzenesulfonamide (P-1915), N-[2,4-difluoro-3-(5-thiazol-5-yl-1H-pyrrolo[2,3-b]pyridine-3-carbonyl)phenyl]-3-fluoro-benzenesulfonamide (P-1916), N-[3-[5-(2-dimethylaminothiazol-4-yl)-1H-pyrrolo[2,3-b]pyridine-3-carbonyl]-2,4-difluoro-phenyl]-3-fluoro-benzenesulfonamide (P-1917), N-[2,4-difluoro-3-[5-(2-methoxythiazol-4-yl)-1H-pyrrolo[2,3-b]pyridine-3-carbonyl]phenyl]-3-fluoro-benzenesulfonamide (P-1918), N-[2,4-difluoro-3-(5-oxazol-5-yl-1H-pyrrolo[2,3-b]pyridine-3-carbonyl)phenyl]-3-fluoro-benzenesulfonamide (P-1919), N-[2,4-difluoro-3-[5-(3-pyridyl)-1H-pyrrolo[2,3-b]pyridine-3-carbonyl]phenyl]-3-fluoro-benzenesulfonamide (P-1920), N-[2,4-difluoro-3-[5-(4-pyridyl)-1H-pyrrolo[2,3-b]pyridine-3-carbonyl]phenyl]-3-fluoro-benzenesulfonamide (P-1921), N-[2,4-difluoro-3-[5-(6-methoxy-3-pyridyl)-1H-pyrrolo[2,3-b]pyridine-3-carbonyl]phenyl]-3-fluoro-benzenesulfonamide (P-1922), N-[2,4-difluoro-3-[5-(3-fluoro-4-pyridyl)-1H-pyrrolo[2,3-b]pyridine-3-carbonyl]phenyl]-3-fluoro-benzenesulfonamide (P-1923), N-[3-[5-(2,6-dimethoxy-3-pyridyl)-1H-pyrrolo[2,3-b]pyridine-3-carbonyl]-2,4-difluoro-phenyl]-3-fluoro-benzenesulfonamide (P-1924), N-[2,4-difluoro-3-[5-(5-methylsulfonyl-3-pyridyl)-1H-pyrrolo[2,3-b]pyridine-3-carbonyl]phenyl]-3-fluoro-benzenesulfonamide (P-1925), N-[2,4-difluoro-3-[5-(6-methyl-3-pyridyl)-1H-pyrrolo[2,3-b]pyridine-3-carbonyl]phenyl]-3-fluoro-benzenesulfonamide (P-1926), N-[3-[5-(6-dimethylamino-3-pyridyl)-1H-pyrrolo[2,3-b]pyridine-3-carbonyl]-2,4-difluoro-phenyl]-3-fluoro-benzenesulfonamide (P-1927), N-[3-[5-[6-(3-dimethylaminopropoxy)-3-pyridyl]-1H-pyrrolo[2,3-b]pyridine-3-carbonyl]-2,4-difluoro-phenyl]-3-fluoro-benzenesulfonamide (P-1928), N-[2,4-difluoro-3-(5-pyrimidin-5-yl-1H-pyrrolo[2,3-b]pyridine-3-carbonyl)phenyl]-3-fluoro-benzenesulfonamide (P-1929), N-[3-[5-(2,4-dimethoxypyrimidin-5-yl)-1H-pyrrolo[2,3-b]pyridine-3-carbonyl]-2,4-difluoro-phenyl]-3-fluoro-benzenesulfonamide (P-1930), N-[3-[5-(2-dimethylaminopyrimidin-5-yl)-1H-pyrrolo[2,3-b]pyridine-3-carbonyl]-2,4-difluoro-phenyl]-3-fluoro-benzenesulfonamide (P-1931), N-[2,4-difluoro-3-[5-(2-methylpyrimidin-5-yl)-1H-pyrrolo[2,3-b]pyridine-3-carbonyl]phenyl]-3-fluoro-benzenesulfonamide (P-1932), N-[3-[5-[2-(cyclopropylamino)pyrimidin-5-yl]-1H-pyrrolo[2,3-b]pyridine-3-carbonyl]-2,4-difluoro-phenyl]-3-fluoro-benzenesulfonamide (P-1933), N-[2,4-difluoro-3-[5-[2-(2-methoxyethylamino)pyrimidin-5-yl]-1H-pyrrolo[2,3-b]pyridine-3-carbonyl]phenyl]-3-fluoro-benzenesulfonamide (P-1934), N-[2,4-difluoro-3-[5-(2-isopropylpyrimidin-5-yl)-1H-pyrrolo[2,3-b]pyridine-3-carbonyl]phenyl]-3-fluoro-benzenesulfonamide (P-1935), N-[2,4-difluoro-3-[5-[5-(2-oxo-1-pyridyl)pyrazin-2-yl]-1H-pyrrolo[2,3-b]pyridine-3-carbonyl]phenyl]-3-fluoro-benzenesulfonamide (P-1936), N-[2,4-difluoro-3-[5-(5-pyrazol-1-ylpyrazin-2-yl)-1H-pyrrolo[2,3-b]pyridine-3-carbonyl]phenyl]-3-fluoro-benzenesulfonamide (P-1937), N-[2,4-difluoro-3-[5-(5-imidazol-1-ylpyrazin-2-yl)-1H-pyrrolo[2,3-b]pyridine-3-carbonyl]phenyl]-3-fluoro-benzenesulfonamide (P-1938), N-[3-[5-(5-aminopyrazin-2-yl)-1H-pyrrolo[2,3-b]pyridine-3-carbonyl]-2,4-difluoro-phenyl]-3-fluoro-benzenesulfonamide (P-1939), 2-chloro-5-[3-[2,6-difluoro-3-[(3-fluorophenyl)sulfonylamino]benzoyl]-1H-pyrrolo[2,3-b]pyridin-5-yl]benzamide (P-1940), 3-[3-[2,6-difluoro-3-[(3-fluorophenyl)sulfonylamino]benzoyl]-1H-pyrrolo[2,3-b]pyridin-5-yl]-N-methoxy-benzamide (P-1941), 4-[3-[2,6-difluoro-3-[(3-fluorophenyl)sulfonylamino]benzoyl]-1H-pyrrolo[2,3-b]pyridin-5-yl]-N-methoxy-benzamide (P-1942), N-[2,4-difluoro-3-[5-[4-(methylsulfamoyl)phenyl]-1H-pyrrolo[2,3-b]pyridine-3-carbonyl]phenyl]-3-fluoro-benzenesulfonamide (P-1943), N-[2,4-difluoro-3-[5-(4-sulfamoylphenyl)-1H-pyrrolo[2,3-b]pyridine-3-carbonyl]phenyl]-3-fluoro-benzenesulfonamide (P-1944), N-[2,4-difluoro-3-[5-[4-(1H-tetrazol-5-yl)phenyl]-1H-pyrrolo[2,3-b]pyridine-3-carbonyl]phenyl]-3-fluoro-benzenesulfonamide (P-1945), N-[2,4-difluoro-3-[5-(4-formylphenyl)-1H-pyrrolo[2,3-b]pyridine-3-carbonyl]phenyl]-3-fluoro-benzenesulfonamide (P-1946), N-[3-[5-(4-cyanophenyl)-1H-pyrrolo[2,3-b]pyridine-3-carbonyl]-2,4-difluoro-phenyl]-3-fluoro-benzenesulfonamide (P-1947), and any pharmaceutically acceptable salt thereof.

The following table indicates the boronic acid/ester (column 2) and 1H-pyrrolo[2,3-b]pyridine (column 3) used to afford the desired compound (column 4). The compound number is provided in column 1, and the observed mass is in column 5.

| Comp. number | Boronic acid/ester | 5-Br-1H-pyrrolo[2,3-b]pyridine |
|---|---|---|
| 17 | 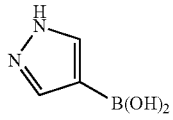 | 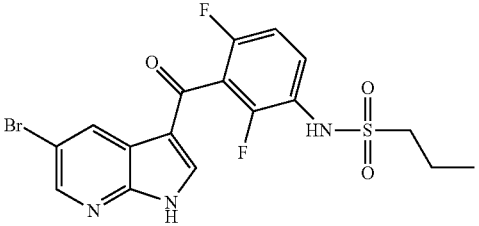 [SMILES: CCCS(=O)(=O)Nc1ccc(F)c(C(=O)c2c[nH]c3ncc(Br)cc23)c1F] |
| P-0009 | 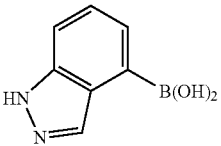 [SMILES: OB(O)c1cccc2[nH]ncc12] | 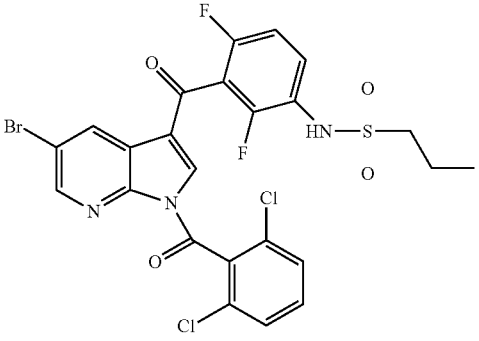 |
| P-0010 | 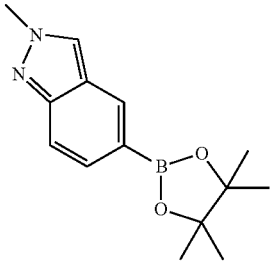 | 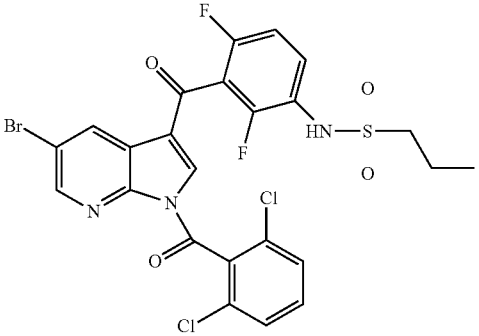 |

-continued
P-0011 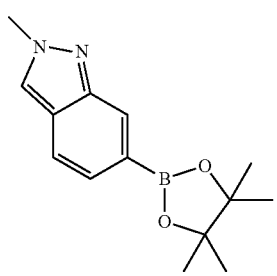 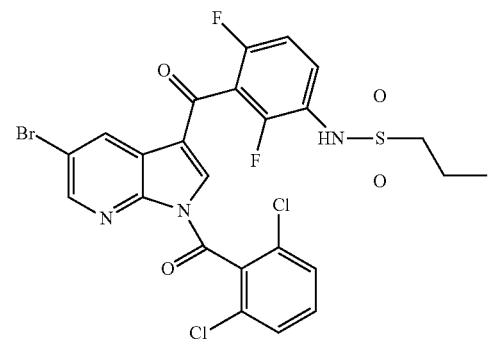
P-0012 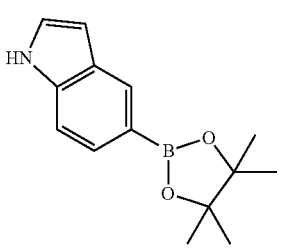 [SMILES: CC1(C)OB(c2ccc3[nH]ccc3c2)OC1(C)C] 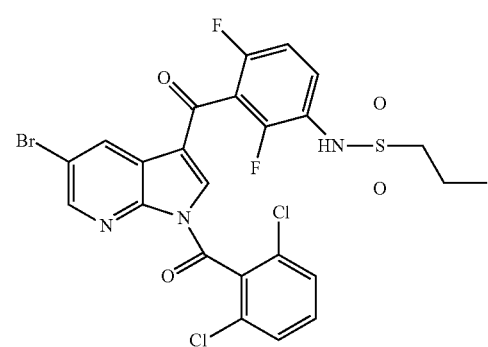
P-0013 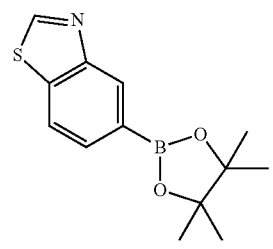 [SMILES: CC1(C)OB(c2ccc3scnc3c2)OC1(C)C] 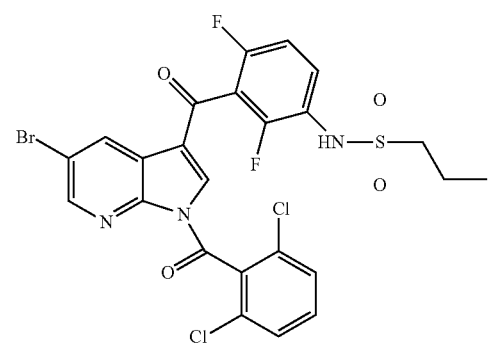
P-0014 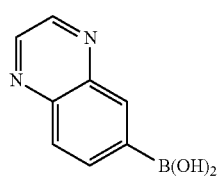 [SMILES: OB(O)c1ccc2nccnc2c1] 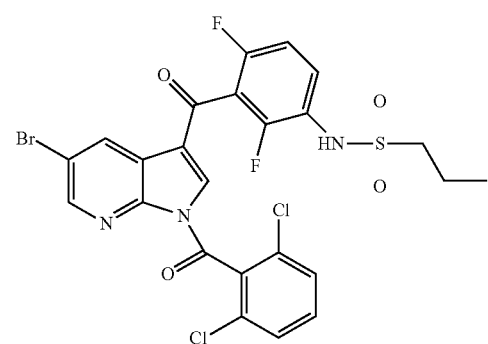

| | | |
|---|---|---|
| P-0015 | 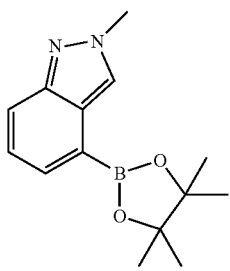 [SMILES: Cn1cc2c(B3OC(C)(C)C(C)(C)O3)cccc2n1] | 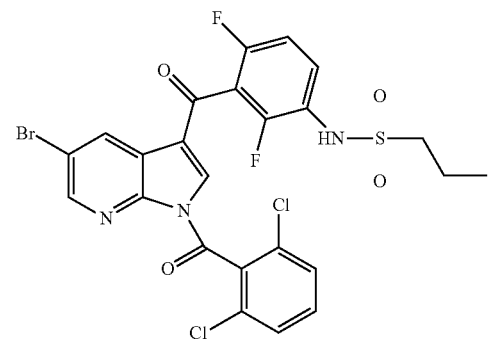 |
| P-1009 | 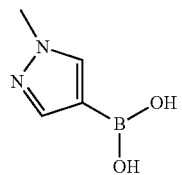 | 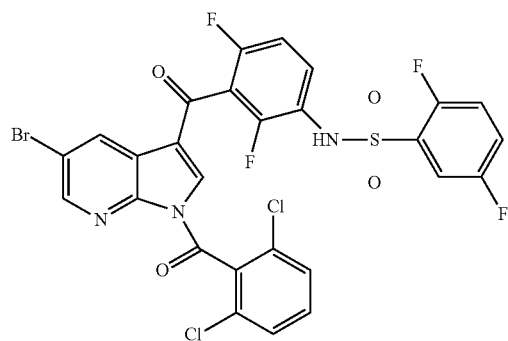 |
| P-1010 | 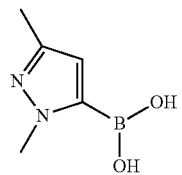 | 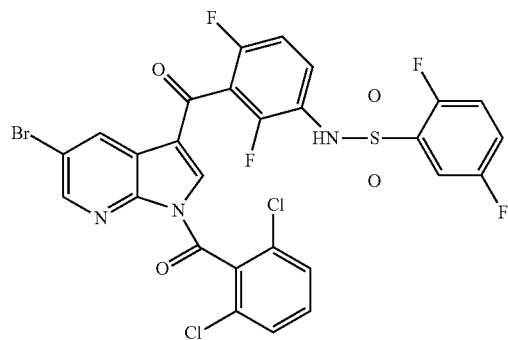 |
| P-1011 | 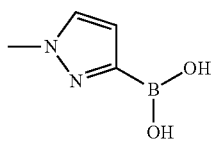 | 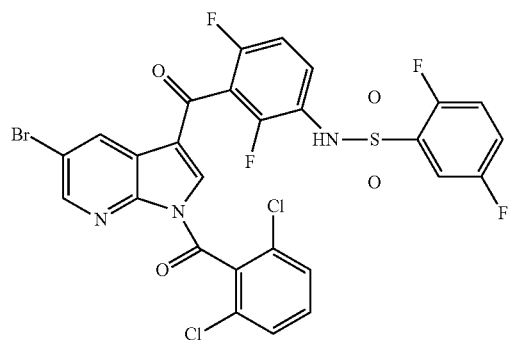 |

| P-1012 | 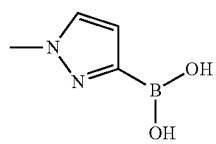 | 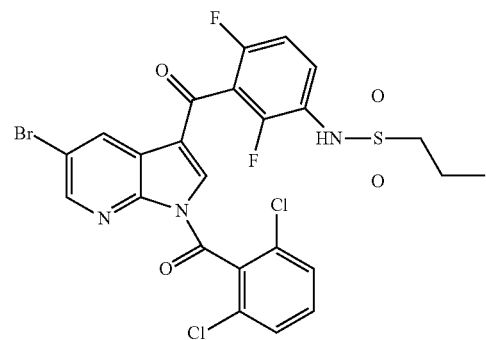 |
| --- | --- | --- |
| P-1100 | 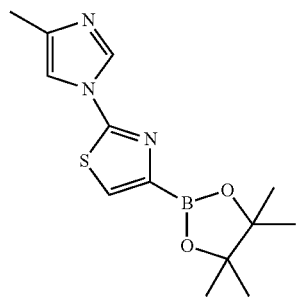 | 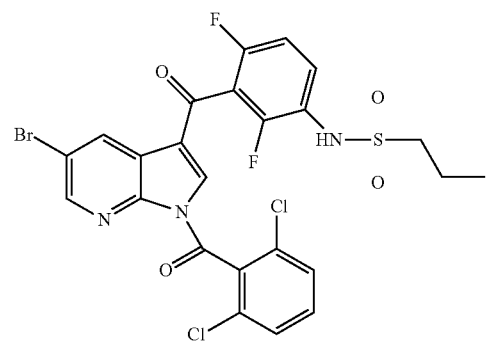 |
| P-1101 | 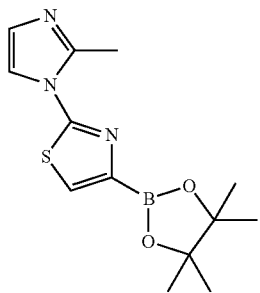 [SMILES: Cc1nccn1-c1nc(B2OC(C)(C)C(C)(C)O2)cs1] | 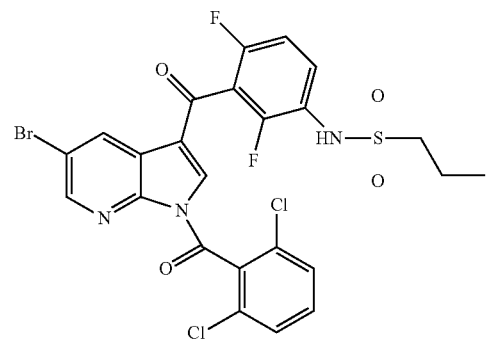 |
| P-1107 | 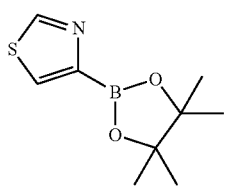 | 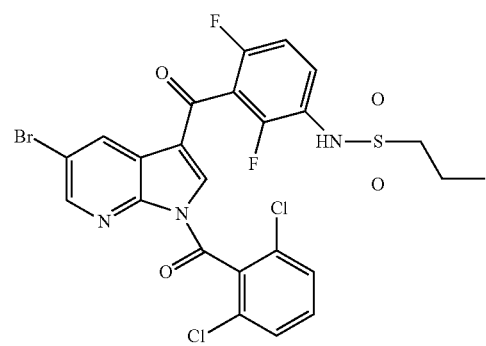 |

-continued
P-1108 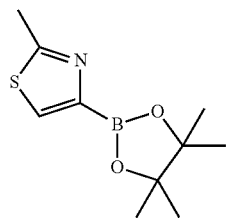 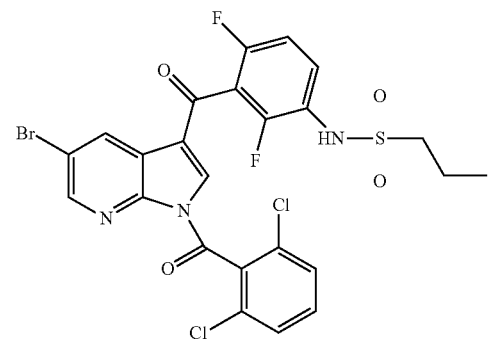
P-1110 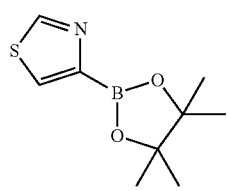 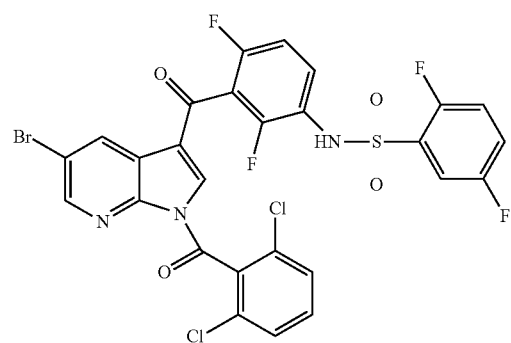
P-1111 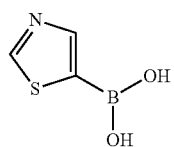 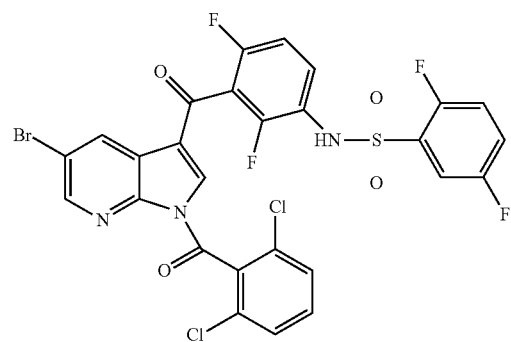
P-1112 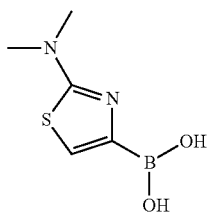 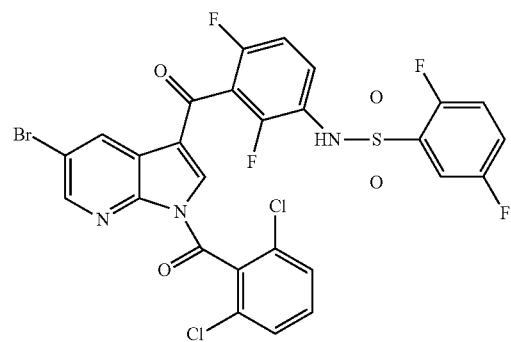

| | | |
|---|---|---|
| P-1113 | 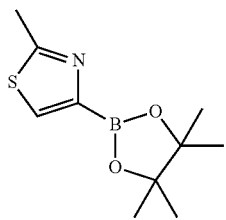 | 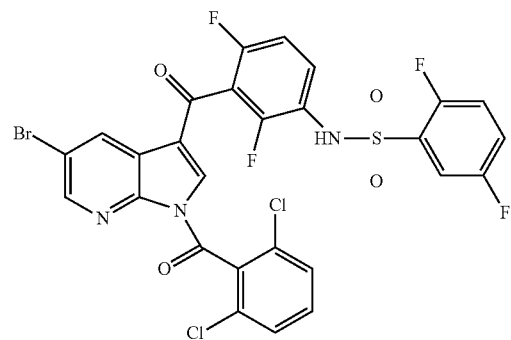 |
| P-1114 | 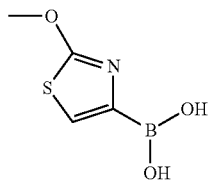 | 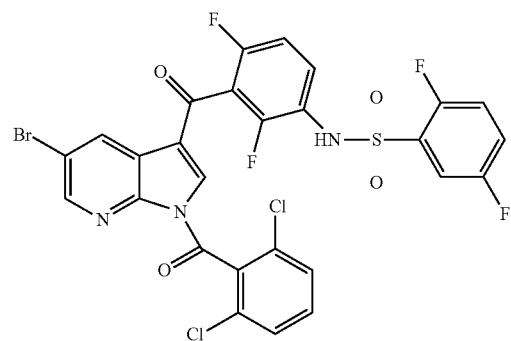 |
| P-1300 | 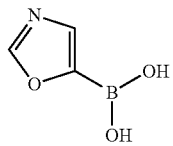 | 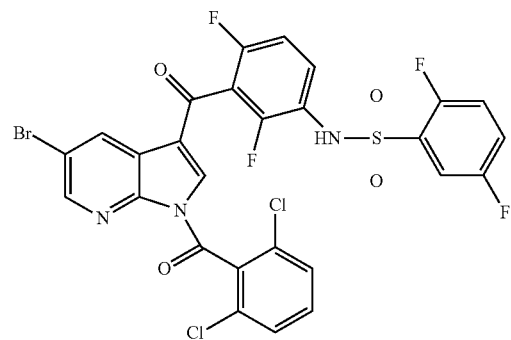 |
| P-1402 | 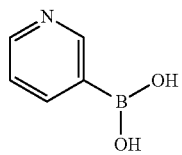 | 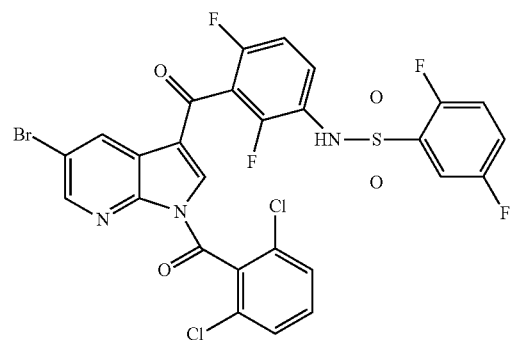 |

-continued
P-1403 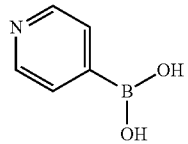 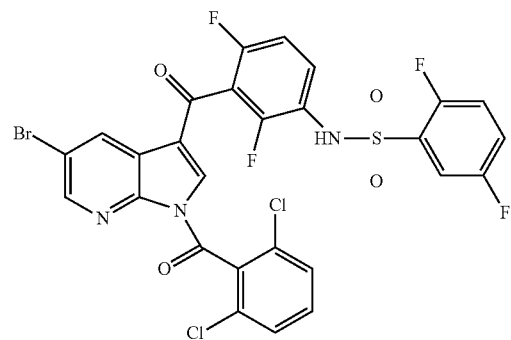
P-1404 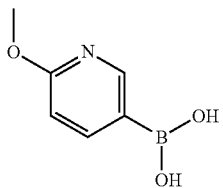 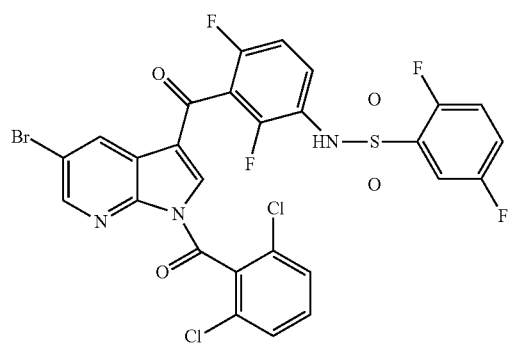
P-1405 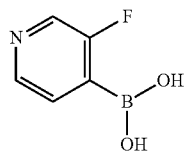 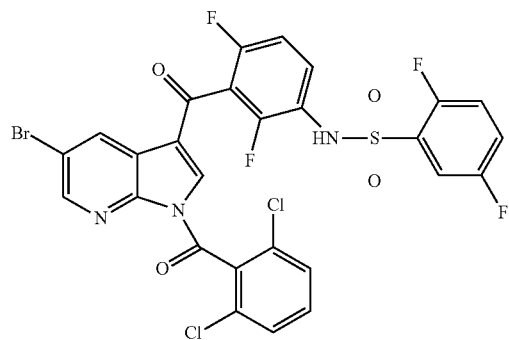
P-1406 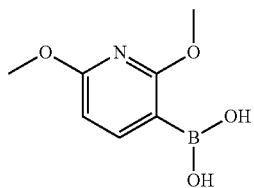 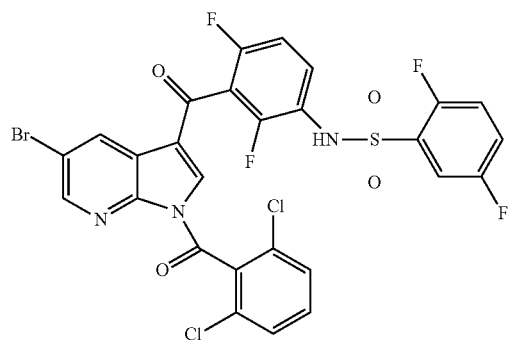

-continued
P-1407 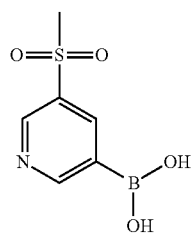 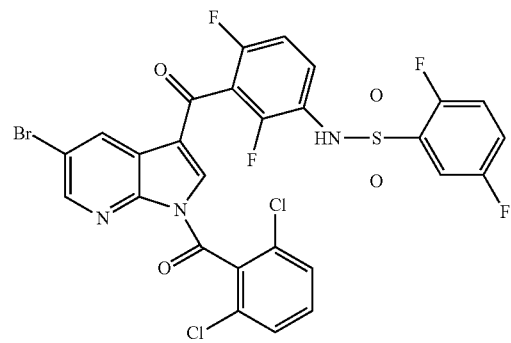
P-1408 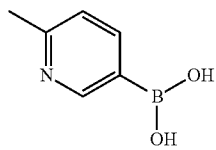 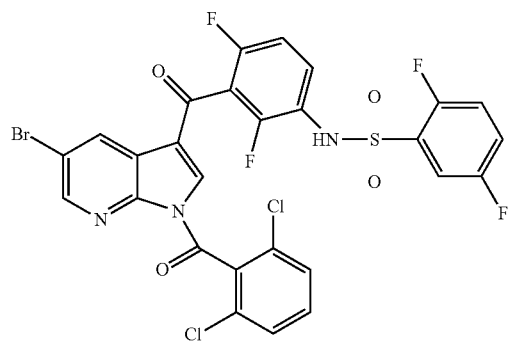
P-1409 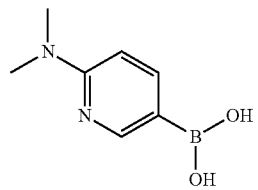 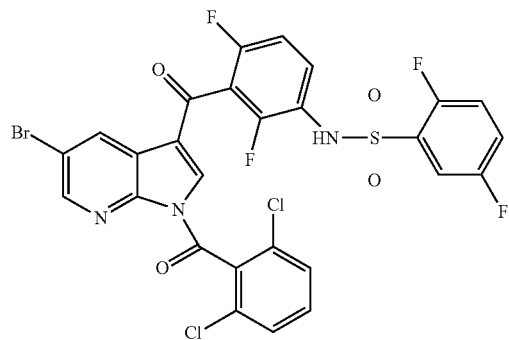
P-1411 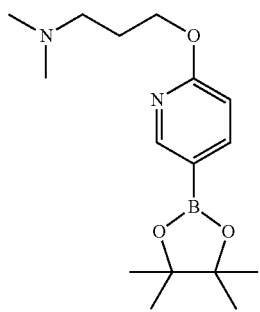 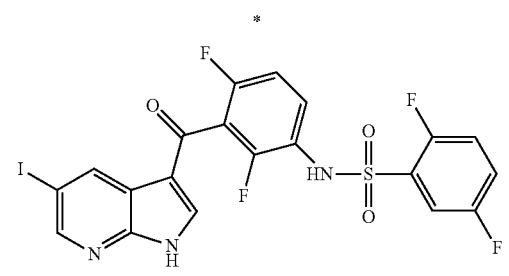 [SMILES: O=C(c1c(F)ccc(NS(=O)(=O)c2cc(F)ccc2F)c1F)c1c[nH]c2ncc(I)cc12]

-continued
P-1500 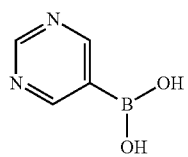 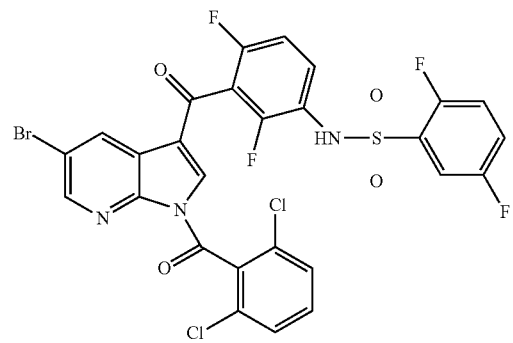
P-1501 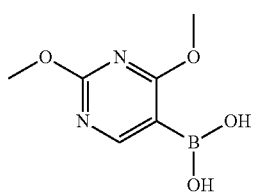 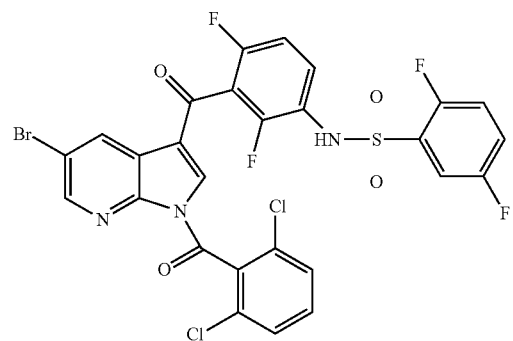
P-1502 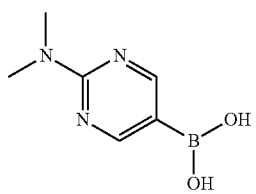 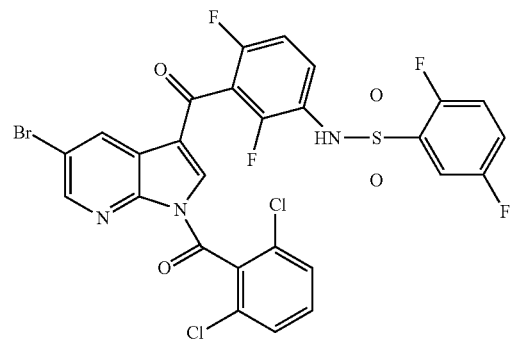
P-1503 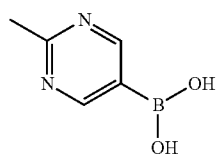 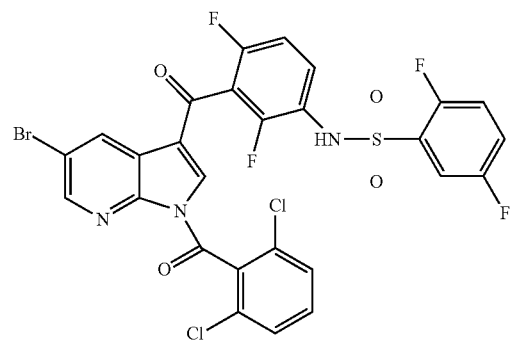

| | | |
|---|---|---|
| P-1504 | 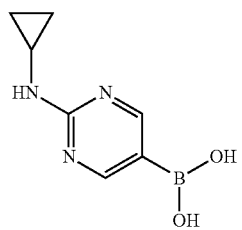 [SMILES: OB(O)c1cnc(NC2CC2)nc1] | 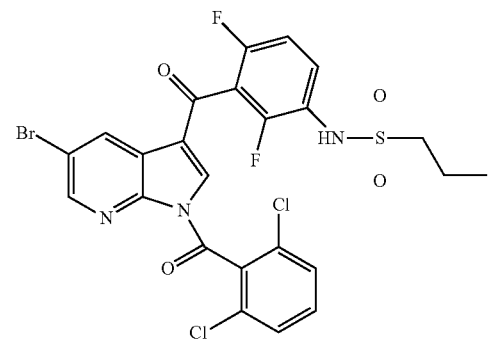 |
| P-1505 | 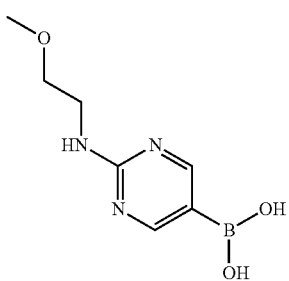 | 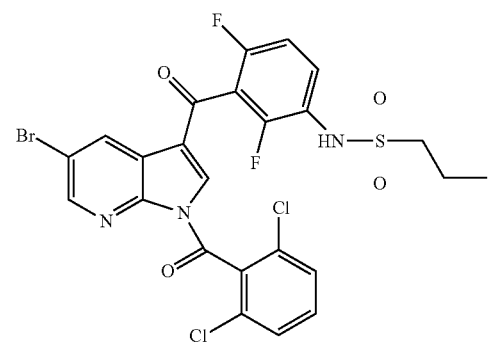 |
| P-1506 | 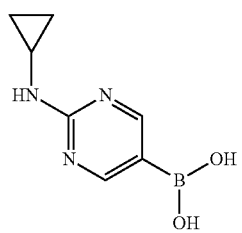 [SMILES: OB(O)c1cnc(NC2CC2)nc1] | 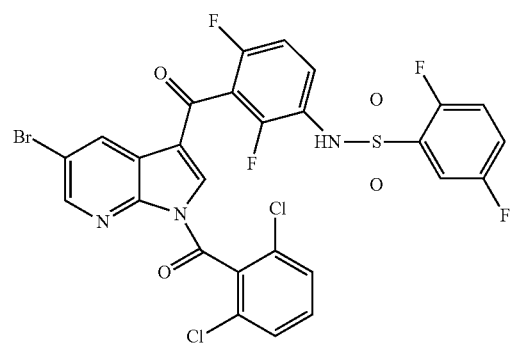 |
| P-1507 | 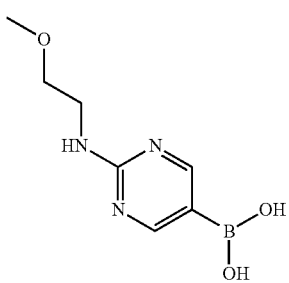 | 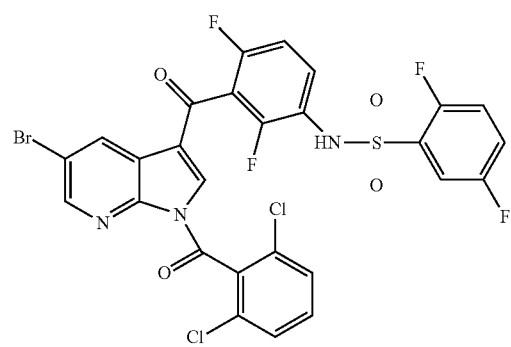 |
| P-1519 | 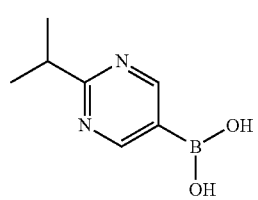 | 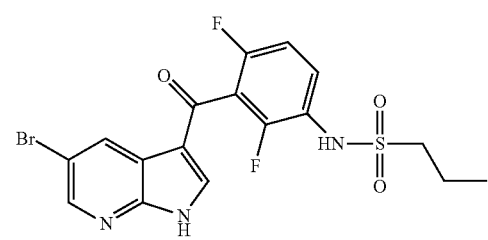 [SMILES: CCCS(=O)(=O)Nc1ccc(F)c(C(=O)c2c[nH]c3ncc(Br)cc23)c1F] |

| | | |
|---|---|---|
| P-1521 | 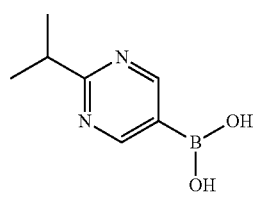 | 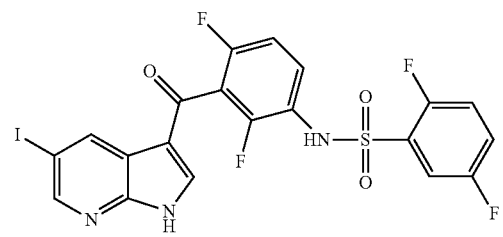 [SMILES: O=C(c1c(F)ccc(NS(=O)(=O)c2cc(F)ccc2F)c1F)c1c[nH]c2ncc(I)cc12] |
| P-1522 | 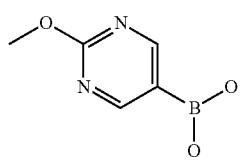 | 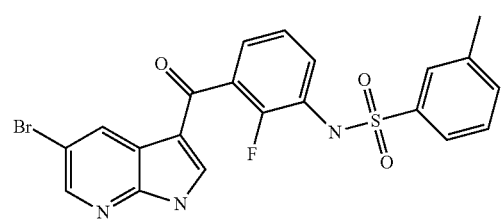 [SMILES: Cc1cccc(S(=O)(=O)Nc2cccc(C(=O)c3c[nH]c4ncc(Br)cc34)c2F)c1] |
| P-1523 | 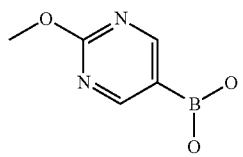 | 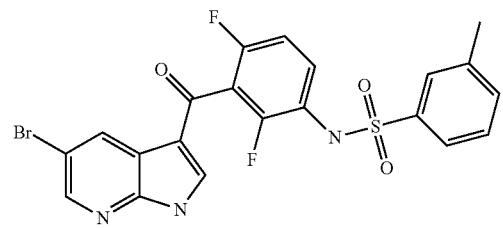 [SMILES: Cc1cccc(S(=O)(=O)Nc2ccc(F)c(C(=O)c3c[nH]c4ncc(Br)cc34)c2F)c1] |
| P-1600 | 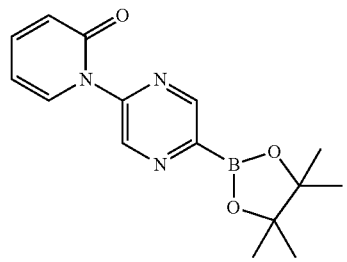 [SMILES: CC1(C)OB(c2cnc(-n3ccccc3=O)cn2)OC1(C)C] | 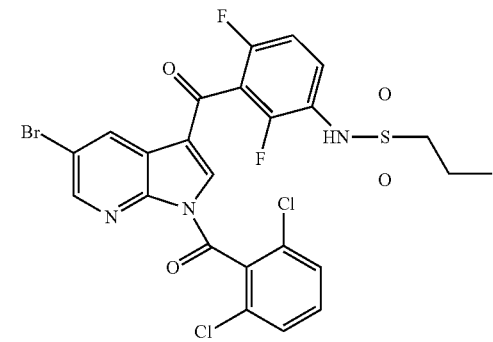 |
| P-1601 | 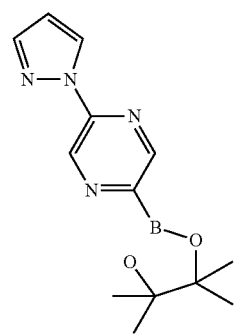 | 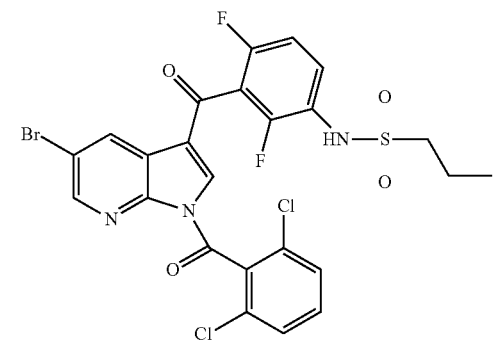 |

-continued
P-1602 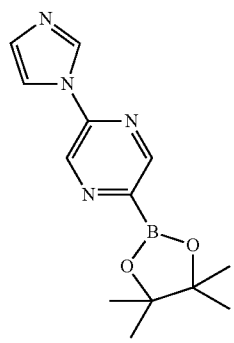 [SMILES: CC1(C)OB(c2cnc(-n3ccnc3)cn2)OC1(C)C] 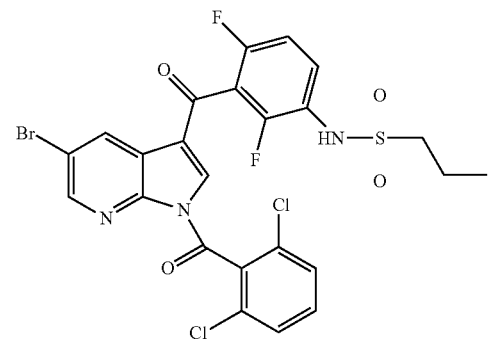
P-1603 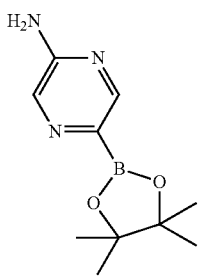 [SMILES: CC1(C)OB(c2cnc(N)cn2)OC1(C)C] 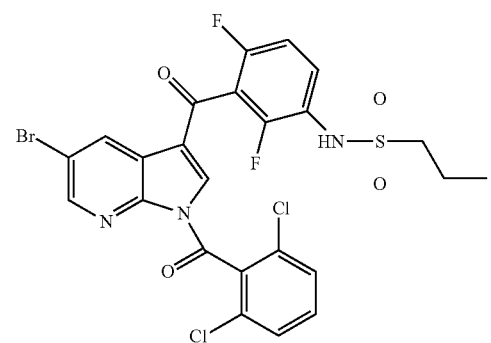
P-1700 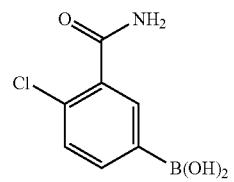 [SMILES: NC(=O)c1cc(B(O)O)ccc1Cl] 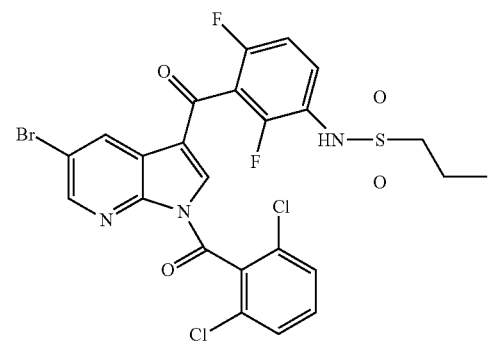
P-1704 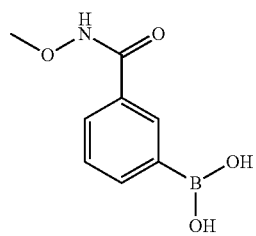 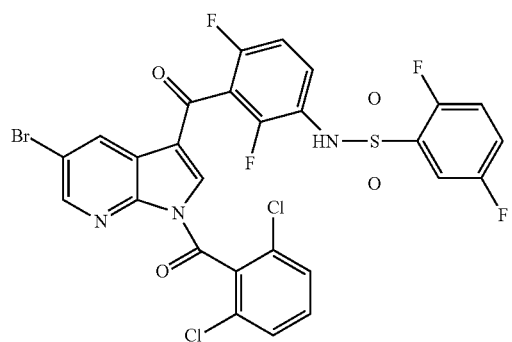

-continued
P-1705 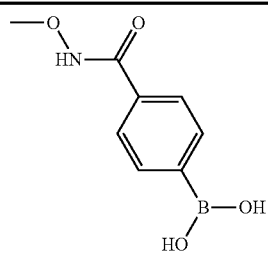 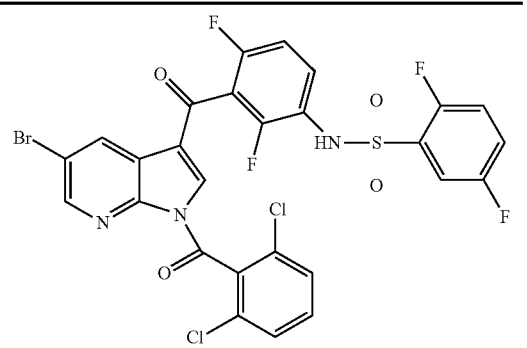
P-1706 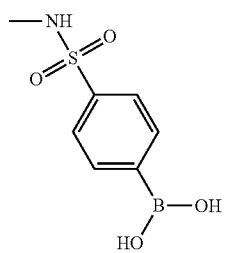 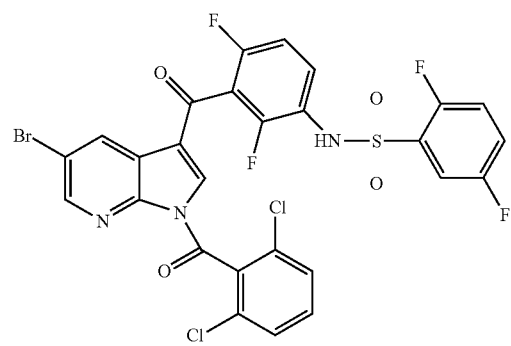
P-1707 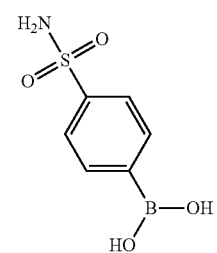 [SMILES: NS(=O)(=O)c1ccc(B(O)O)cc1] 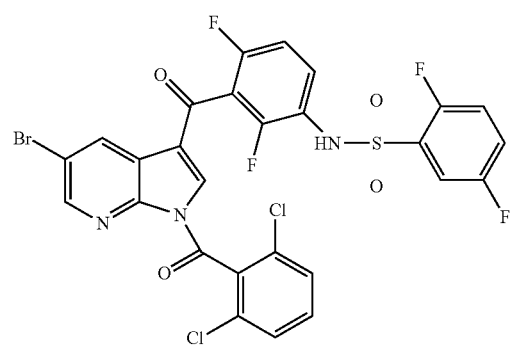
P-1709 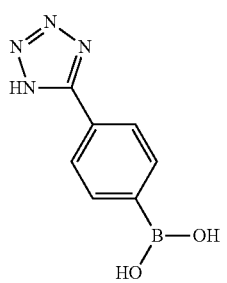 [SMILES: OB(O)c1ccc(-c2nnn[nH]2)cc1] 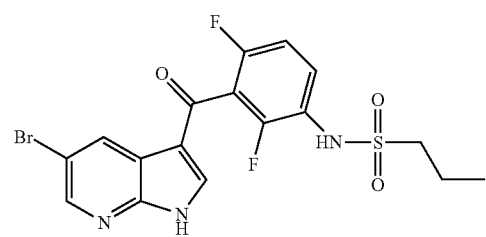 [SMILES: CCCS(=O)(=O)Nc1ccc(F)c(C(=O)c2c[nH]c3ncc(Br)cc23)c1F]
P-1710 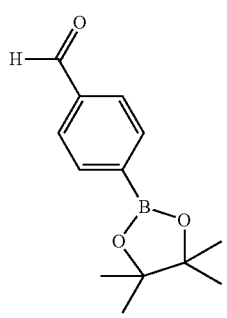 [SMILES: CC1(C)OB(c2ccc(C=O)cc2)OC1(C)C] 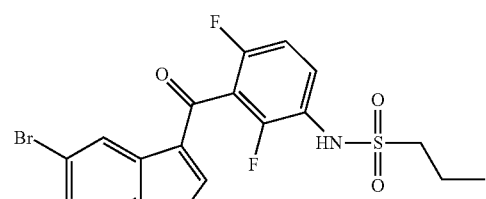

-continued
P-1711 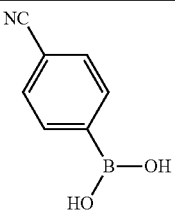 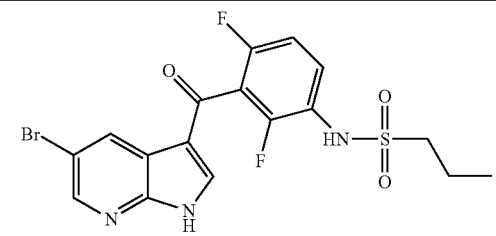
P-1901 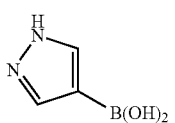 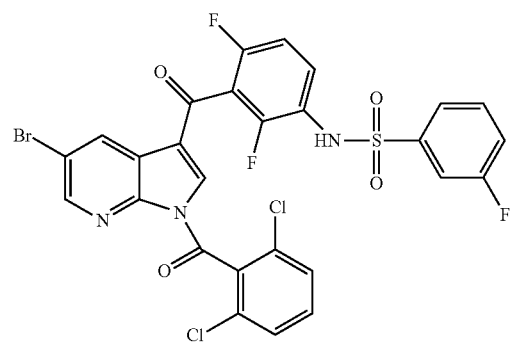 [SMILES: O=C(c1c(F)ccc(NS(=O)(=O)c2cccc(F)c2)c1F)c1cn(C(=O)c2c(Cl)cccc2Cl)c2ncc(Br)cc12]
P-1902 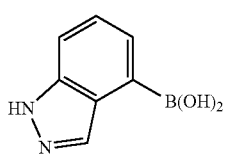 [SMILES: OB(O)c1cccc2[nH]ncc12] 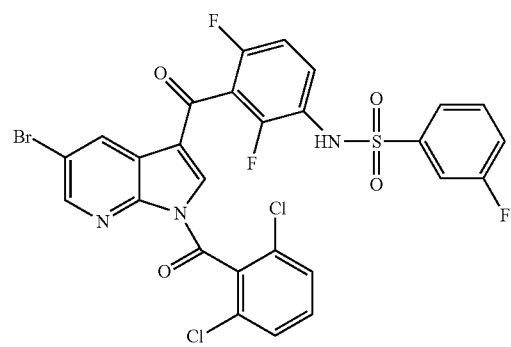 [SMILES: O=C(c1c(F)ccc(NS(=O)(=O)c2cccc(F)c2)c1F)c1cn(C(=O)c2c(Cl)cccc2Cl)c2ncc(Br)cc12]
P-1903 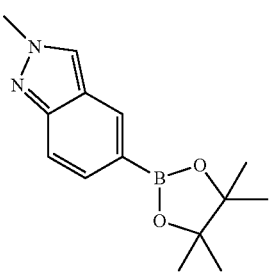 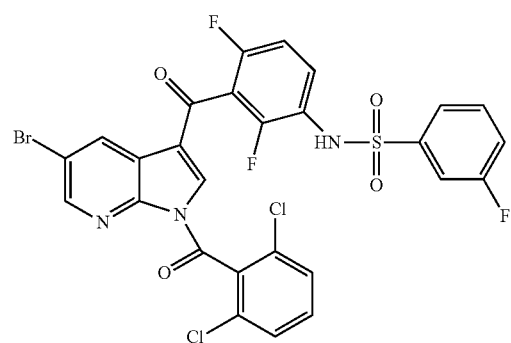 [SMILES: O=C(c1c(F)ccc(NS(=O)(=O)c2cccc(F)c2)c1F)c1cn(C(=O)c2c(Cl)cccc2Cl)c2ncc(Br)cc12]
P-1904 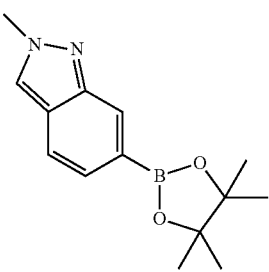 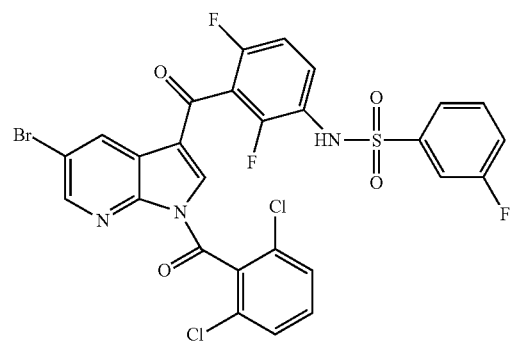 [SMILES: O=C(c1c(F)ccc(NS(=O)(=O)c2cccc(F)c2)c1F)c1cn(C(=O)c2c(Cl)cccc2Cl)c2ncc(Br)cc12]

P-1905 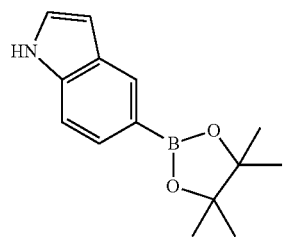 [SMILES: CC1(C)OB(c2ccc3[nH]ccc3c2)OC1(C)C] 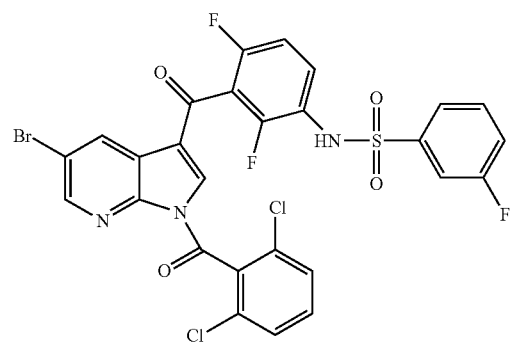 [SMILES: O=C(c1c(F)ccc(NS(=O)(=O)c2cccc(F)c2)c1F)c1cn(C(=O)c2c(Cl)cccc2Cl)c2ncc(Br)cc12]
P-1906 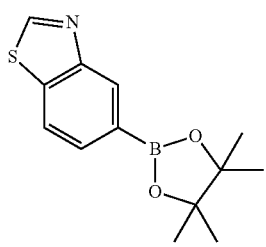 [SMILES: CC1(C)OB(c2ccc3scnc3c2)OC1(C)C] 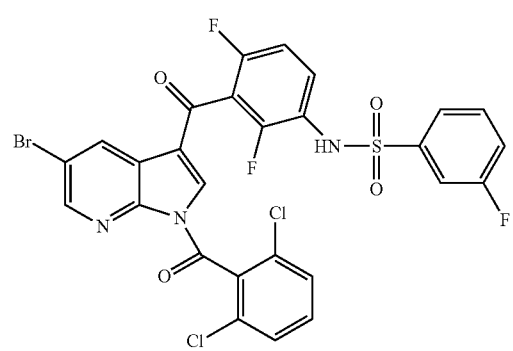 [SMILES: O=C(c1c(F)ccc(NS(=O)(=O)c2cccc(F)c2)c1F)c1cn(C(=O)c2c(Cl)cccc2Cl)c2ncc(Br)cc12]
P-1907 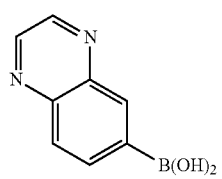 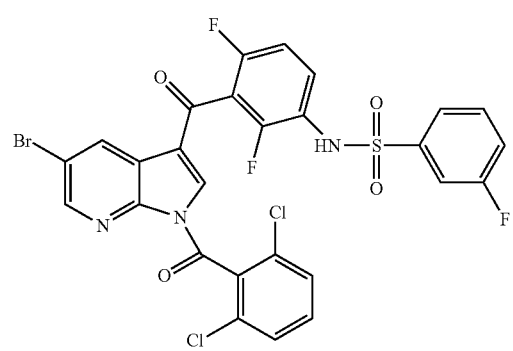 [SMILES: O=C(c1c(F)ccc(NS(=O)(=O)c2cccc(F)c2)c1F)c1cn(C(=O)c2c(Cl)cccc2Cl)c2ncc(Br)cc12]
P-1908 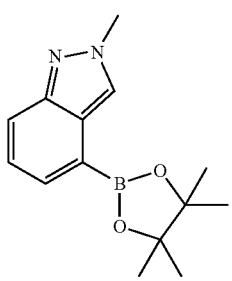 [SMILES: Cn1cc2c(B3OC(C)(C)C(C)(C)O3)cccc2n1] 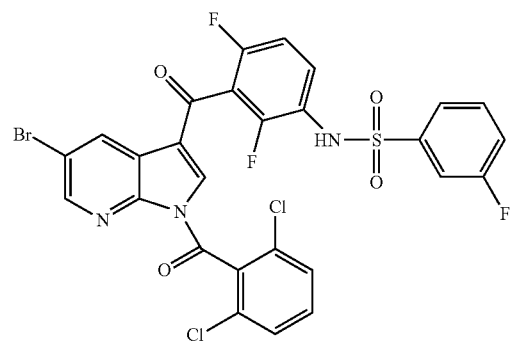 [SMILES: O=C(c1c(F)ccc(NS(=O)(=O)c2cccc(F)c2)c1F)c1cn(C(=O)c2c(Cl)cccc2Cl)c2ncc(Br)cc12]

-continued
P-1909 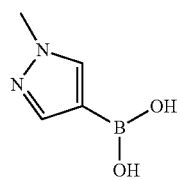 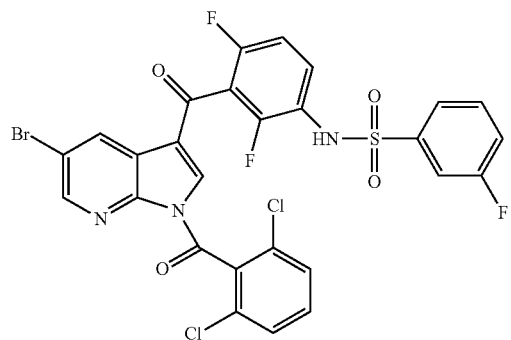 [SMILES: O=C(c1c(F)ccc(NS(=O)(=O)c2cccc(F)c2)c1F)c1cn(C(=O)c2c(Cl)cccc2Cl)c2ncc(Br)cc12]
P-1910 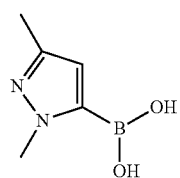 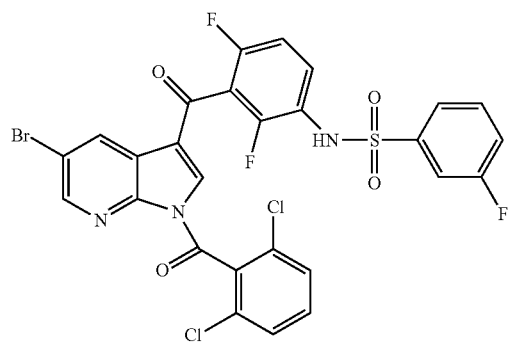 [SMILES: O=C(c1c(F)ccc(NS(=O)(=O)c2cccc(F)c2)c1F)c1cn(C(=O)c2c(Cl)cccc2Cl)c2ncc(Br)cc12]
P-1911 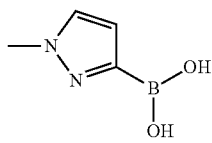 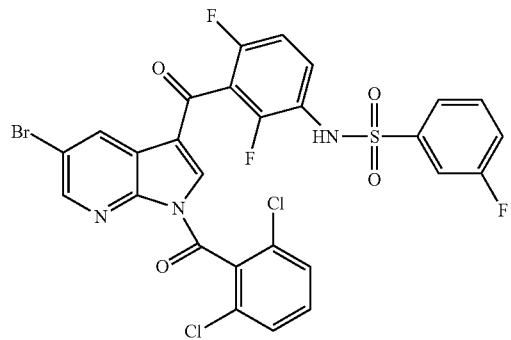 [SMILES: O=C(c1c(F)ccc(NS(=O)(=O)c2cccc(F)c2)c1F)c1cn(C(=O)c2c(Cl)cccc2Cl)c2ncc(Br)cc12]
P-1912 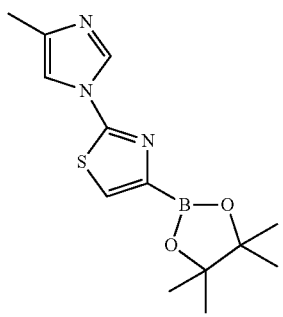 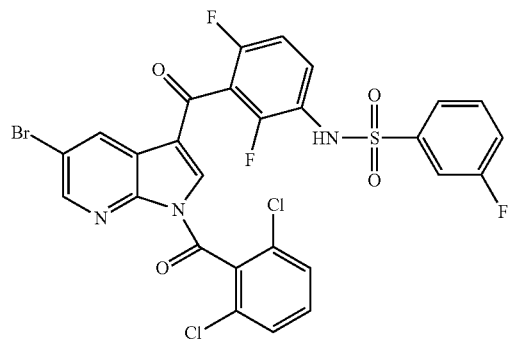 [SMILES: O=C(c1c(F)ccc(NS(=O)(=O)c2cccc(F)c2)c1F)c1cn(C(=O)c2c(Cl)cccc2Cl)c2ncc(Br)cc12]

P-1913 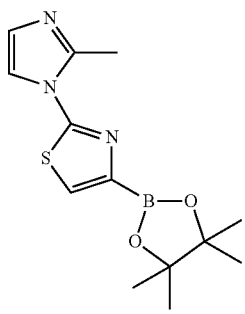 [SMILES: Cc1nccn1-c1nc(B2OC(C)(C)C(C)(C)O2)cs1] 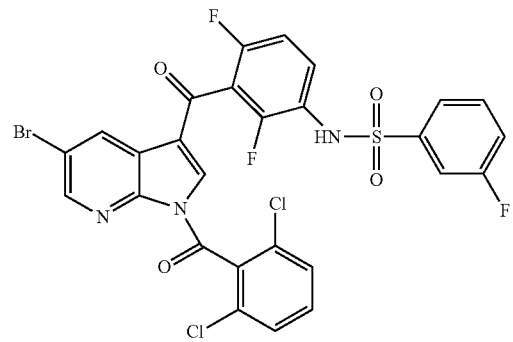 [SMILES: O=C(c1c(F)ccc(NS(=O)(=O)c2cccc(F)c2)c1F)c1cn(C(=O)c2c(Cl)cccc2Cl)c2ncc(Br)cc12]
P-1914 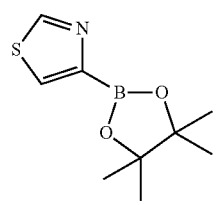 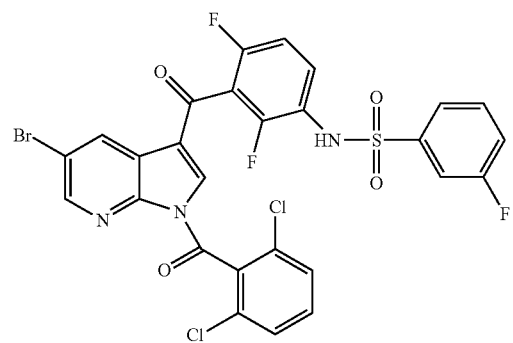 [SMILES: O=C(c1c(F)ccc(NS(=O)(=O)c2cccc(F)c2)c1F)c1cn(C(=O)c2c(Cl)cccc2Cl)c2ncc(Br)cc12]
P-1915 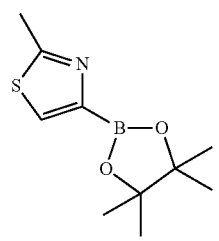 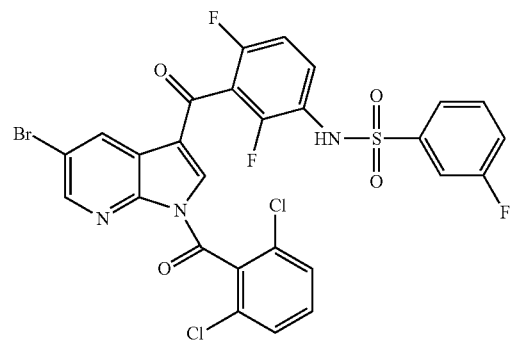 [SMILES: O=C(c1c(F)ccc(NS(=O)(=O)c2cccc(F)c2)c1F)c1cn(C(=O)c2c(Cl)cccc2Cl)c2ncc(Br)cc12]
P-1916 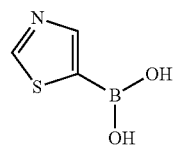 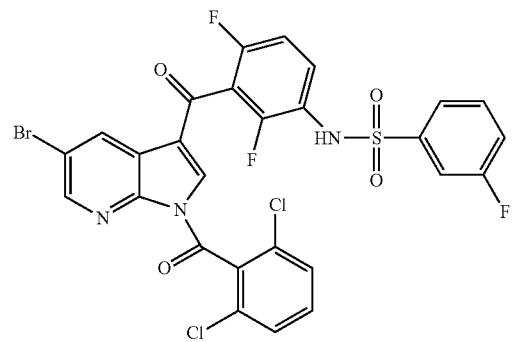 [SMILES: O=C(c1c(F)ccc(NS(=O)(=O)c2cccc(F)c2)c1F)c1cn(C(=O)c2c(Cl)cccc2Cl)c2ncc(Br)cc12]

-continued
| | | |
|---|---|---|
| P-1917 | 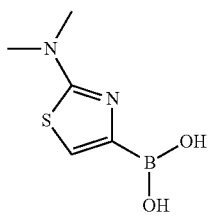 | 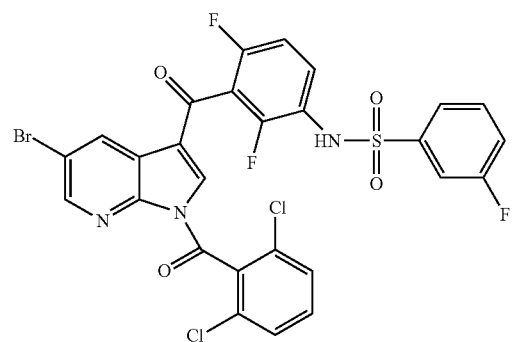 [SMILES: O=C(c1c(F)ccc(NS(=O)(=O)c2cccc(F)c2)c1F)c1cn(C(=O)c2c(Cl)cccc2Cl)c2ncc(Br)cc12] |
| P-1918 | 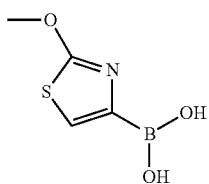 | 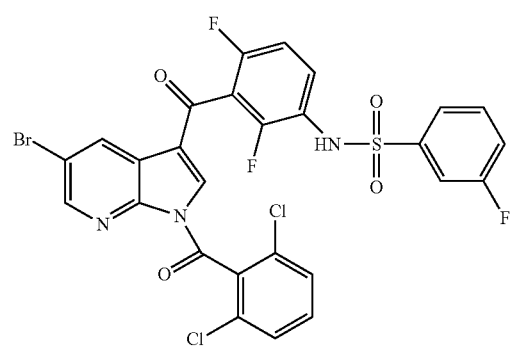 [SMILES: O=C(c1c(F)ccc(NS(=O)(=O)c2cccc(F)c2)c1F)c1cn(C(=O)c2c(Cl)cccc2Cl)c2ncc(Br)cc12] |
| P-1919 | 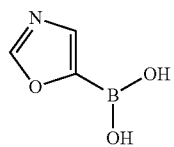 | 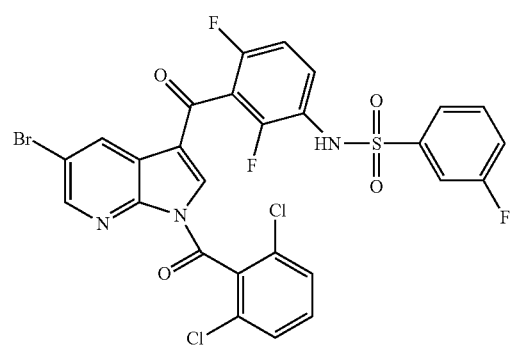 [SMILES: O=C(c1c(F)ccc(NS(=O)(=O)c2cccc(F)c2)c1F)c1cn(C(=O)c2c(Cl)cccc2Cl)c2ncc(Br)cc12] |
| P-1920 | 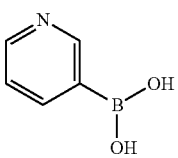 | 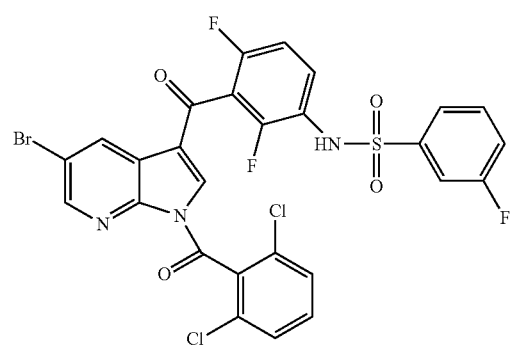 [SMILES: O=C(c1c(F)ccc(NS(=O)(=O)c2cccc(F)c2)c1F)c1cn(C(=O)c2c(Cl)cccc2Cl)c2ncc(Br)cc12] |

| | | |
|---|---|---|
| P-1921 | 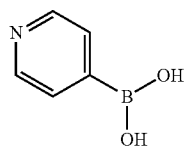 | 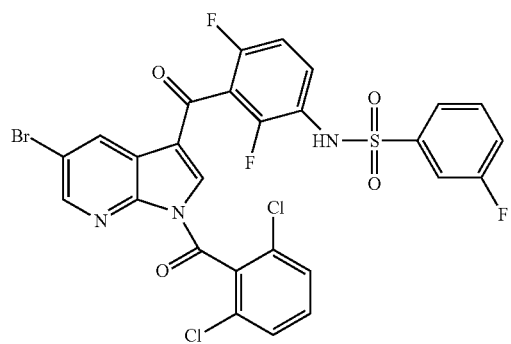 [SMILES: O=C(c1c(F)ccc(NS(=O)(=O)c2cccc(F)c2)c1F)c1cn(C(=O)c2c(Cl)cccc2Cl)c2ncc(Br)cc12] |
| P-1922 | 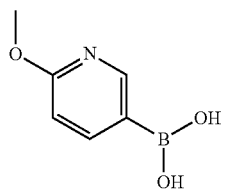 | 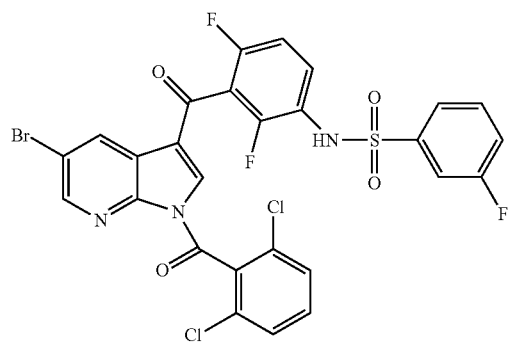 [SMILES: O=C(c1c(F)ccc(NS(=O)(=O)c2cccc(F)c2)c1F)c1cn(C(=O)c2c(Cl)cccc2Cl)c2ncc(Br)cc12] |
| P-1923 | 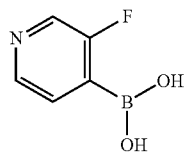 | 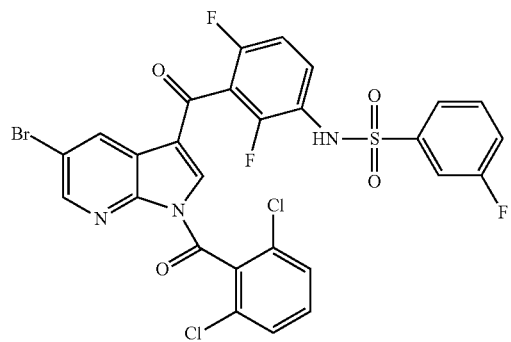 [SMILES: O=C(c1c(F)ccc(NS(=O)(=O)c2cccc(F)c2)c1F)c1cn(C(=O)c2c(Cl)cccc2Cl)c2ncc(Br)cc12] |
| P-1924 | 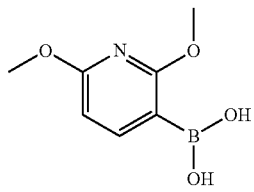 | 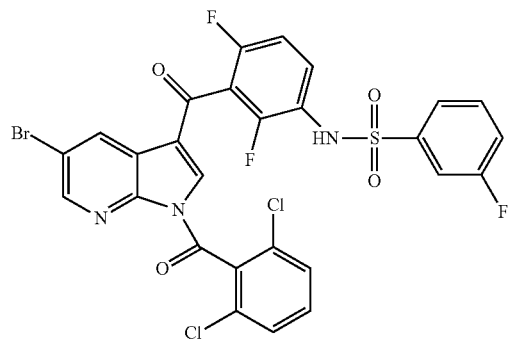 [SMILES: O=C(c1c(F)ccc(NS(=O)(=O)c2cccc(F)c2)c1F)c1cn(C(=O)c2c(Cl)cccc2Cl)c2ncc(Br)cc12] |

P-1925 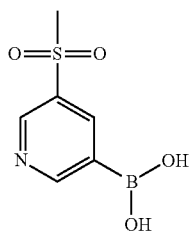 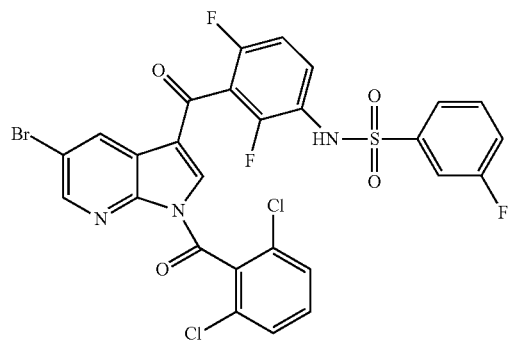 [SMILES: O=C(c1c(F)ccc(NS(=O)(=O)c2cccc(F)c2)c1F)c1cn(C(=O)c2c(Cl)cccc2Cl)c2ncc(Br)cc12]
P-1926 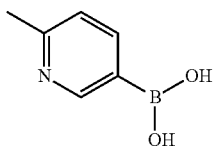 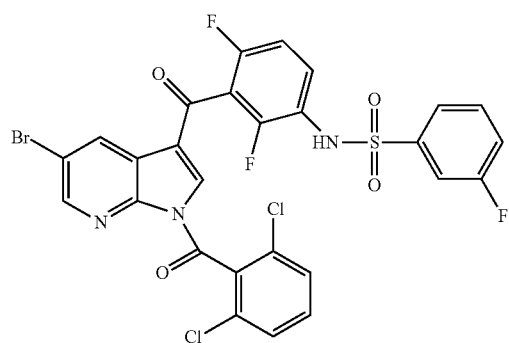 [SMILES: O=C(c1c(F)ccc(NS(=O)(=O)c2cccc(F)c2)c1F)c1cn(C(=O)c2c(Cl)cccc2Cl)c2ncc(Br)cc12]
P-1927 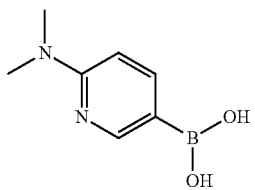 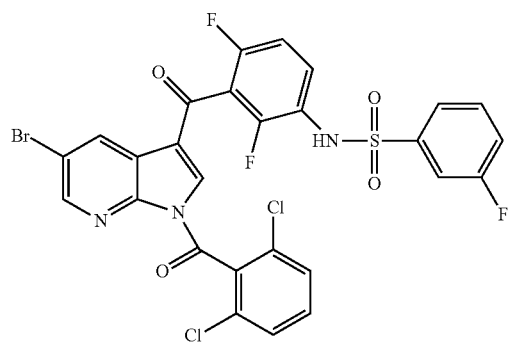 [SMILES: O=C(c1c(F)ccc(NS(=O)(=O)c2cccc(F)c2)c1F)c1cn(C(=O)c2c(Cl)cccc2Cl)c2ncc(Br)cc12]
P-1928 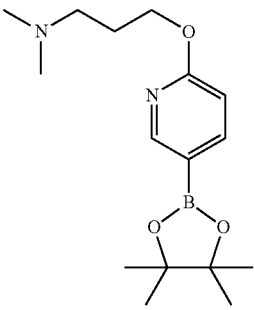 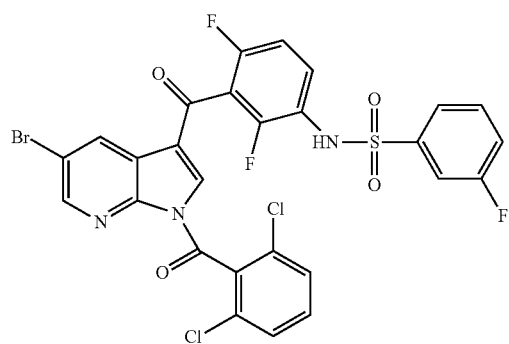 [SMILES: O=C(c1c(F)ccc(NS(=O)(=O)c2cccc(F)c2)c1F)c1cn(C(=O)c2c(Cl)cccc2Cl)c2ncc(Br)cc12]

US 9,440,969 B2
-continued
P-1929 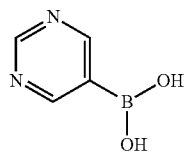 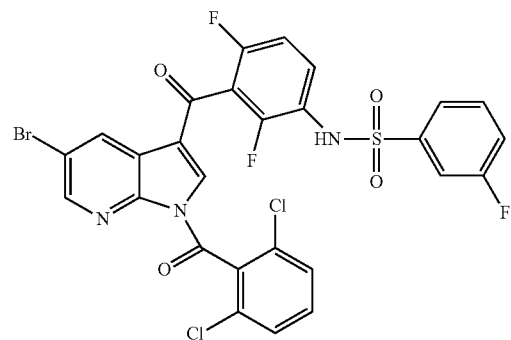 [SMILES: O=C(c1c(F)ccc(NS(=O)(=O)c2cccc(F)c2)c1F)c1cn(C(=O)c2c(Cl)cccc2Cl)c2ncc(Br)cc12]
P-1930 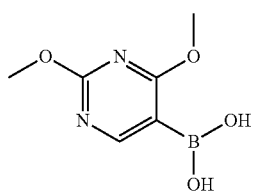 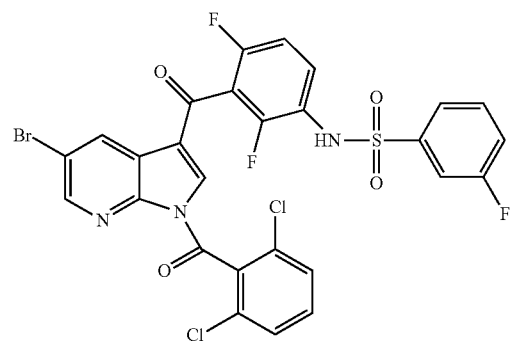 [SMILES: O=C(c1c(F)ccc(NS(=O)(=O)c2cccc(F)c2)c1F)c1cn(C(=O)c2c(Cl)cccc2Cl)c2ncc(Br)cc12]
P-1931 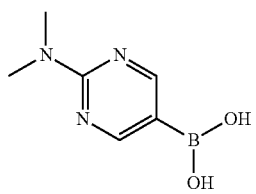 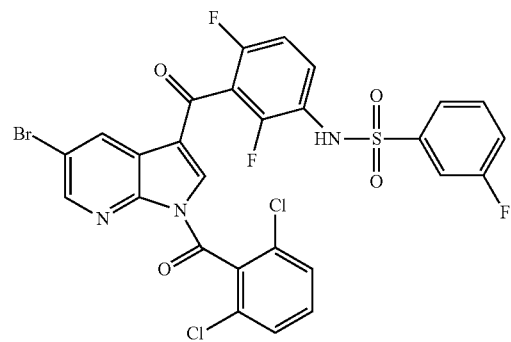 [SMILES: O=C(c1c(F)ccc(NS(=O)(=O)c2cccc(F)c2)c1F)c1cn(C(=O)c2c(Cl)cccc2Cl)c2ncc(Br)cc12]
P-1932  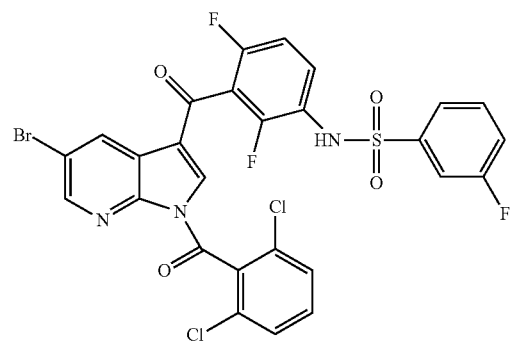 [SMILES: O=C(c1c(F)ccc(NS(=O)(=O)c2cccc(F)c2)c1F)c1cn(C(=O)c2c(Cl)cccc2Cl)c2ncc(Br)cc12]

P-1933 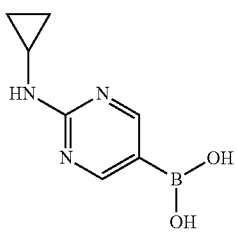 [SMILES: OB(O)c1cnc(NC2CC2)nc1] 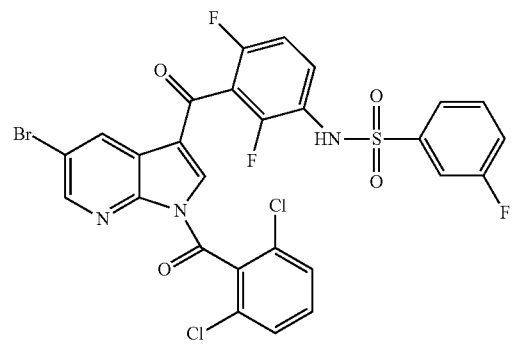 [SMILES: O=C(c1c(F)ccc(NS(=O)(=O)c2cccc(F)c2)c1F)c1cn(C(=O)c2c(Cl)cccc2Cl)c2ncc(Br)cc12]
P-1934 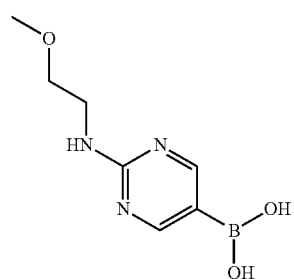 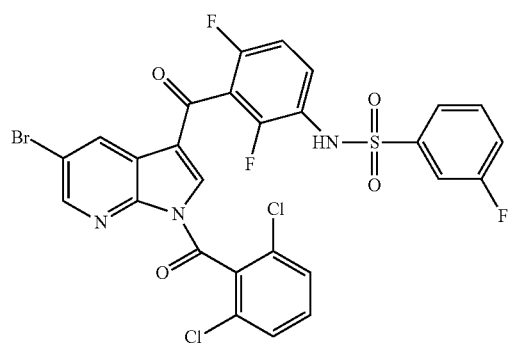 [SMILES: O=C(c1c(F)ccc(NS(=O)(=O)c2cccc(F)c2)c1F)c1cn(C(=O)c2c(Cl)cccc2Cl)c2ncc(Br)cc12]
P-1935 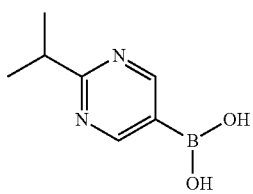 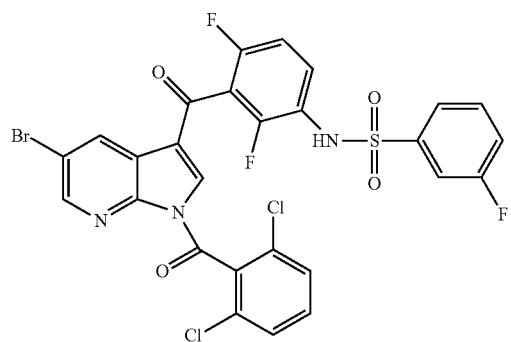 [SMILES: O=C(c1c(F)ccc(NS(=O)(=O)c2cccc(F)c2)c1F)c1cn(C(=O)c2c(Cl)cccc2Cl)c2ncc(Br)cc12]
P-1936 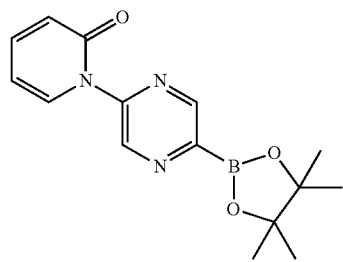 [SMILES: CC1(C)OB(c2cnc(-n3ccccc3=O)cn2)OC1(C)C] 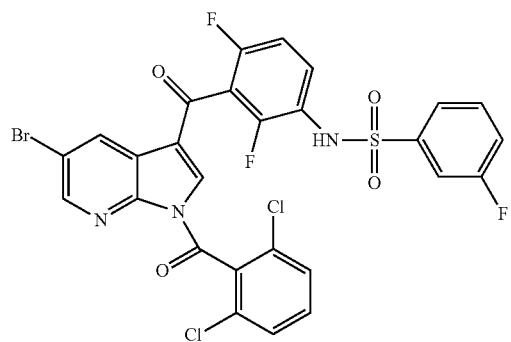 [SMILES: O=C(c1c(F)ccc(NS(=O)(=O)c2cccc(F)c2)c1F)c1cn(C(=O)c2c(Cl)cccc2Cl)c2ncc(Br)cc12]

| | | |
|---|---|---|
| P-1937 | 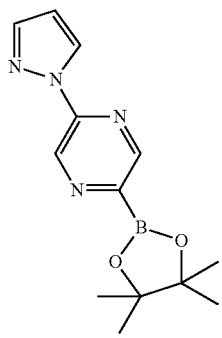 [SMILES: CC1(C)OB(c2cnc(-n3cccn3)cn2)OC1(C)C] | 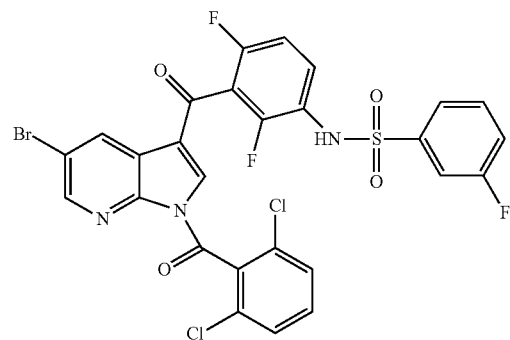 [SMILES: O=C(c1c(F)ccc(NS(=O)(=O)c2cccc(F)c2)c1F)c1cn(C(=O)c2c(Cl)cccc2Cl)c2ncc(Br)cc12] |
| P-1938 | 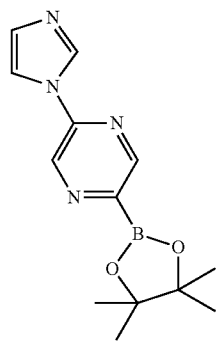 [SMILES: CC1(C)OB(c2cnc(-n3ccnc3)cn2)OC1(C)C] | 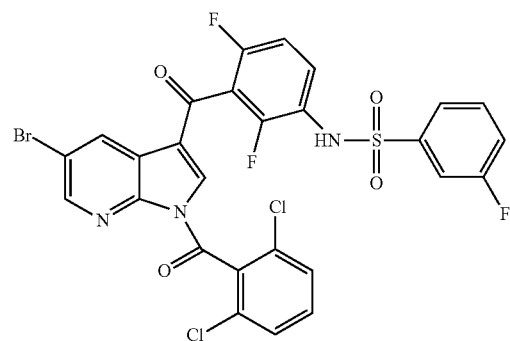 [SMILES: O=C(c1c(F)ccc(NS(=O)(=O)c2cccc(F)c2)c1F)c1cn(C(=O)c2c(Cl)cccc2Cl)c2ncc(Br)cc12] |
| P-1939 | 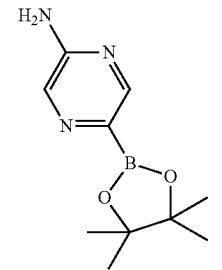 [SMILES: CC1(C)OB(c2cnc(N)cn2)OC1(C)C] | 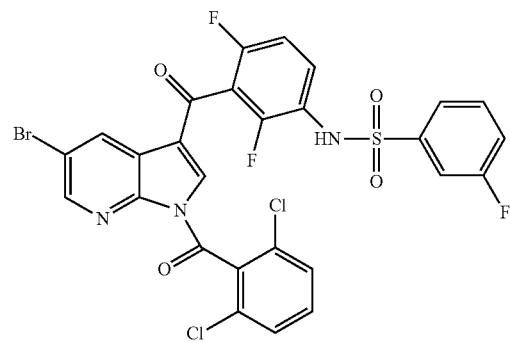 [SMILES: O=C(c1c(F)ccc(NS(=O)(=O)c2cccc(F)c2)c1F)c1cn(C(=O)c2c(Cl)cccc2Cl)c2ncc(Br)cc12] |
| P-1940 | 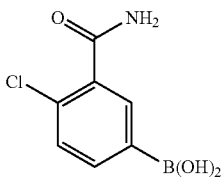 [SMILES: NC(=O)c1cc(B(O)O)ccc1Cl] | 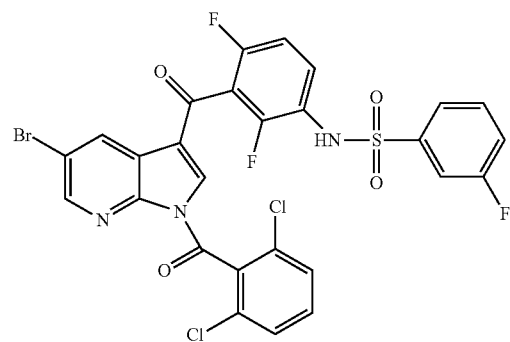 [SMILES: O=C(c1c(F)ccc(NS(=O)(=O)c2cccc(F)c2)c1F)c1cn(C(=O)c2c(Cl)cccc2Cl)c2ncc(Br)cc12] |

P-1941 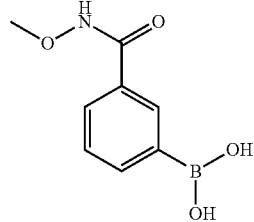 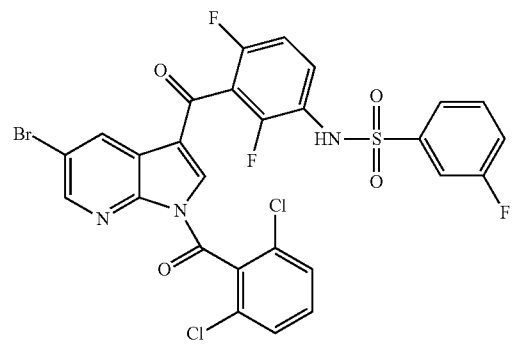 [SMILES: O=C(c1c(F)ccc(NS(=O)(=O)c2cccc(F)c2)c1F)c1cn(C(=O)c2c(Cl)cccc2Cl)c2ncc(Br)cc12]
P-1942 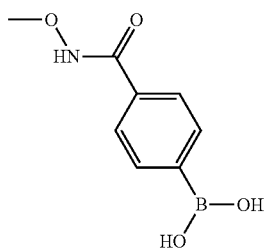 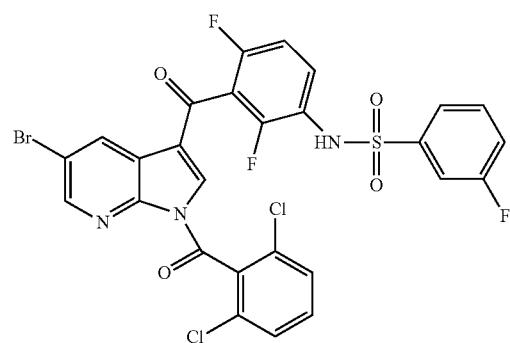 [SMILES: O=C(c1c(F)ccc(NS(=O)(=O)c2cccc(F)c2)c1F)c1cn(C(=O)c2c(Cl)cccc2Cl)c2ncc(Br)cc12]
P-1943 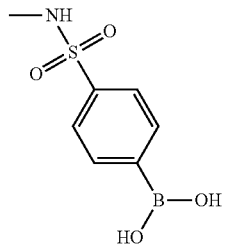 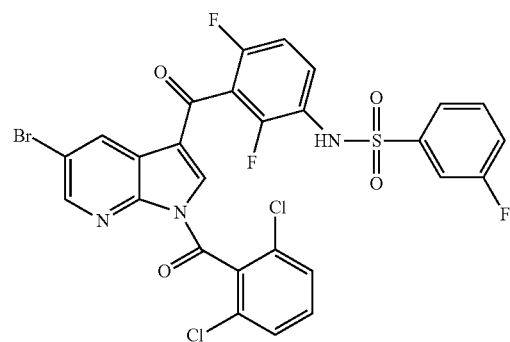 [SMILES: O=C(c1c(F)ccc(NS(=O)(=O)c2cccc(F)c2)c1F)c1cn(C(=O)c2c(Cl)cccc2Cl)c2ncc(Br)cc12]
P-1944 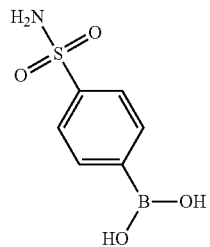 [SMILES: NS(=O)(=O)c1ccc(B(O)O)cc1] 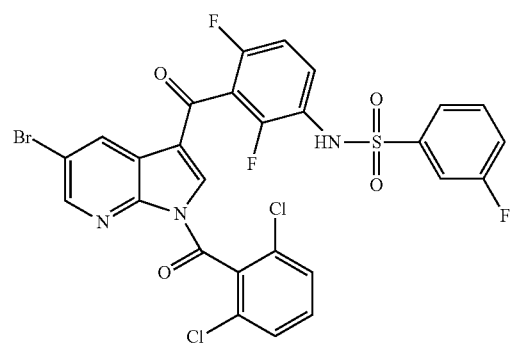 [SMILES: O=C(c1c(F)ccc(NS(=O)(=O)c2cccc(F)c2)c1F)c1cn(C(=O)c2c(Cl)cccc2Cl)c2ncc(Br)cc12]

-continued
P-1945 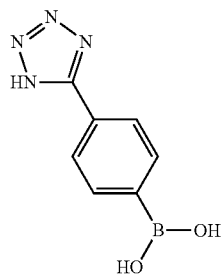 [SMILES: OB(O)c1ccc(-c2nnn[nH]2)cc1] 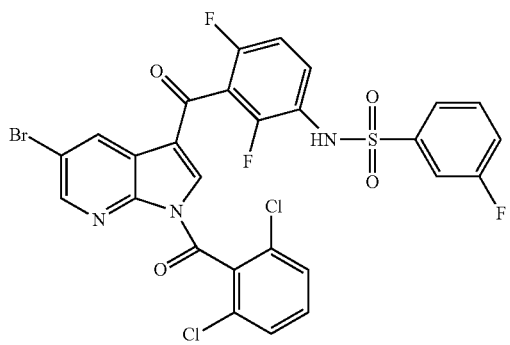 [SMILES: O=C(c1c(F)ccc(NS(=O)(=O)c2cccc(F)c2)c1F)c1cn(C(=O)c2c(Cl)cccc2Cl)c2ncc(Br)cc12]
P-1946 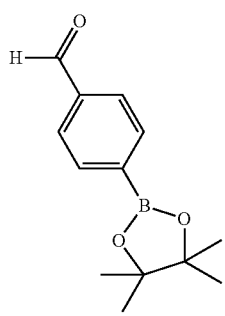 [SMILES: CC1(C)OB(c2ccc(C=O)cc2)OC1(C)C] 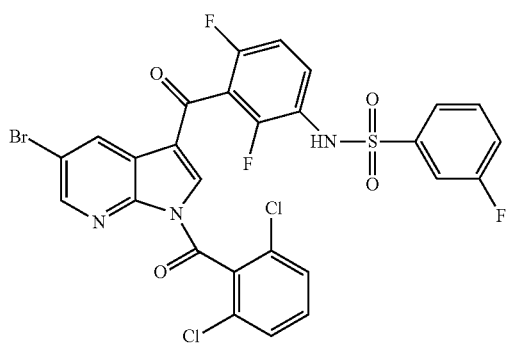 [SMILES: O=C(c1c(F)ccc(NS(=O)(=O)c2cccc(F)c2)c1F)c1cn(C(=O)c2c(Cl)cccc2Cl)c2ncc(Br)cc12]
P-1947 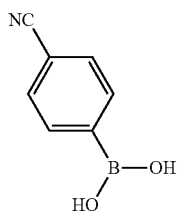 [SMILES: N#Cc1ccc(B(O)O)cc1] 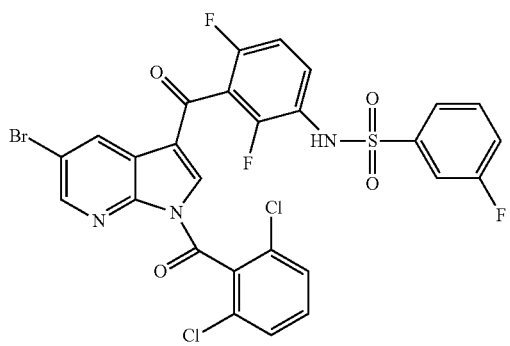 [SMILES: O=C(c1c(F)ccc(NS(=O)(=O)c2cccc(F)c2)c1F)c1cn(C(=O)c2c(Cl)cccc2Cl)c2ncc(Br)cc12]
| Comp. number | Compound | MS (ESI) [M + H$^+$]$^+$ |
|---|---|---|
| 17 | 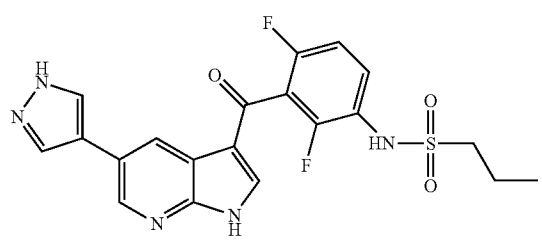 [SMILES: CCCS(=O)(=O)Nc1ccc(F)c(C(=O)c2c[nH]c3ncc(-c4cn[nH]c4)cc23)c1F] | 446.0 |
| P-0009 | 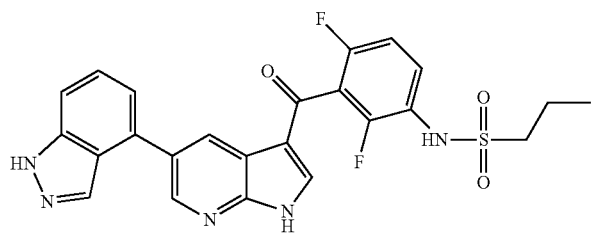 [SMILES: CCCS(=O)(=O)Nc1ccc(F)c(C(=O)c2c[nH]c3ncc(-c4cccc5[nH]ncc45)cc23)c1F] | 496.5 |

| | | |
|---|---|---|
| P-0010 | 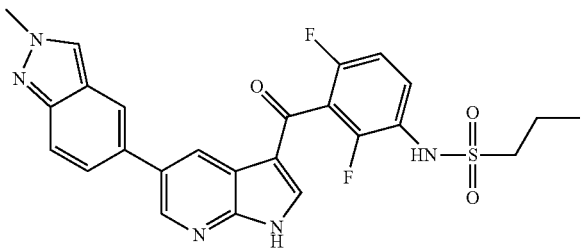 [SMILES: CCCS(=O)(=O)Nc1ccc(F)c(C(=O)c2c[nH]c3ncc(-c4ccc5nn(C)cc5c4)cc23)c1F] | 510.5 |
| P-0011 | 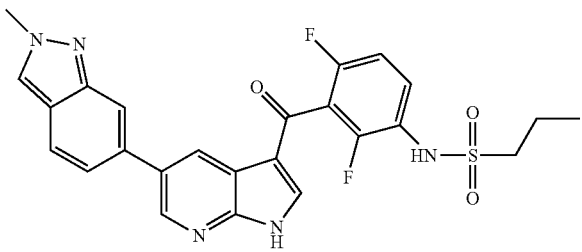 [SMILES: CCCS(=O)(=O)Nc1ccc(F)c(C(=O)c2c[nH]c3ncc(-c4ccc5cn(C)nc5c4)cc23)c1F] | 510.5 |
| P-0012 | 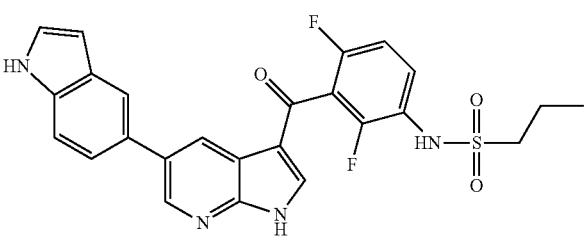 | 495.5 |
| P-0013 | 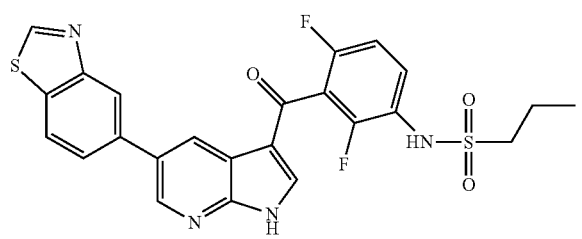 [SMILES: CCCS(=O)(=O)Nc1ccc(F)c(C(=O)c2c[nH]c3ncc(-c4ccc5scnc5c4)cc23)c1F] | 513.5 |
| P-0014 | 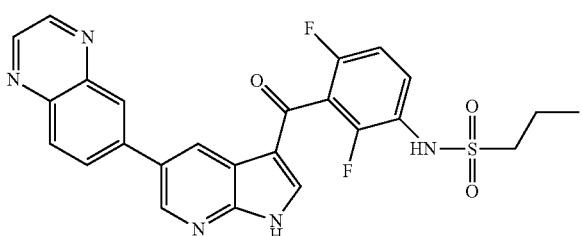 | 508.0 |
| P-0015 | 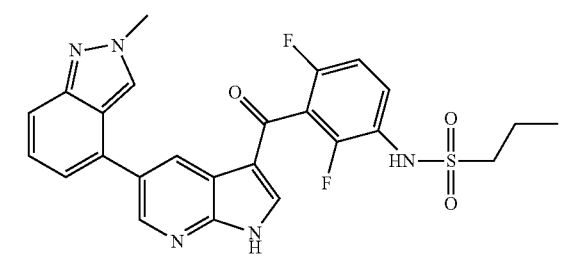 [SMILES: CCCS(=O)(=O)Nc1ccc(F)c(C(=O)c2c[nH]c3ncc(-c4cccc5nn(C)cc45)cc23)c1F] | 510.5 |

| | | |
|---|---|---|
| P-1009 | 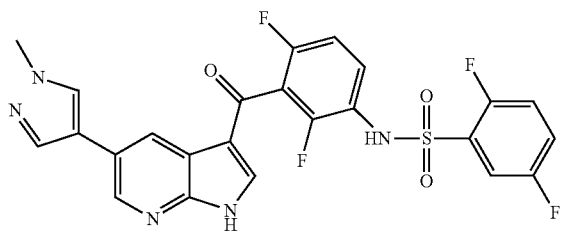 [SMILES: CN/C=C(\C=N)c1cnc2[nH]cc(C(=O)c3c(F)ccc(NS(=O)(=O)c4cc(F)ccc4F)c3F)c2c1] | 530.0 |
| P-1010 | 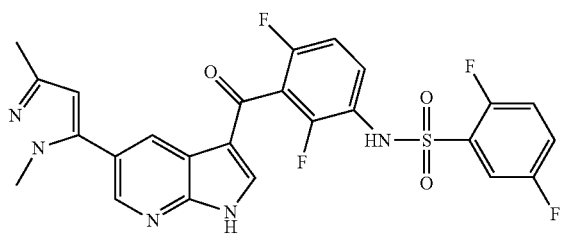 [SMILES: CN/C(=C\C(C)=N)c1cnc2[nH]cc(C(=O)c3c(F)ccc(NS(=O)(=O)c4cc(F)ccc4F)c3F)c2c1] | 544.5 |
| P-1011 | 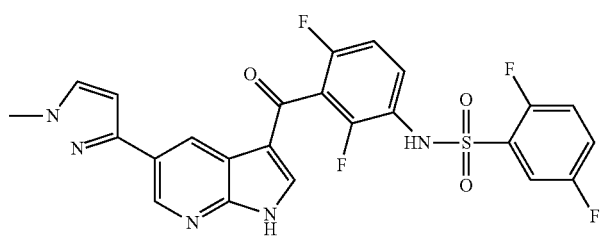 [SMILES: CN/C=C\C(=N)c1cnc2[nH]cc(C(=O)c3c(F)ccc(NS(=O)(=O)c4cc(F)ccc4F)c3F)c2c1] | 530.0 |
| P-1012 | 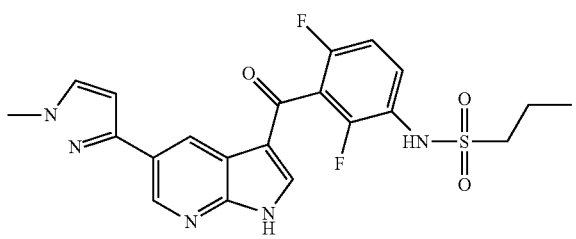 [SMILES: CCCS(=O)(=O)Nc1ccc(F)c(C(=O)c2c[nH]c3ncc(C(=N)/C=C\NC)cc23)c1F] | |
| P-1100 | 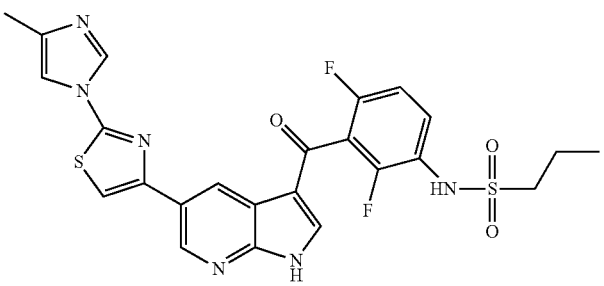 [SMILES: CCCS(=O)(=O)Nc1ccc(F)c(C(=O)c2c[nH]c3ncc(-c4csc(-n5cnc(C)c5)n4)cc23)c1F] | 543.5 |
| P-1101 | 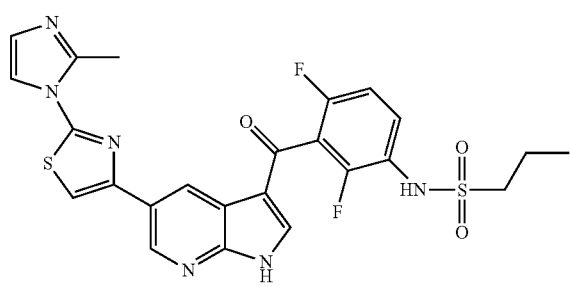 [SMILES: CCCS(=O)(=O)Nc1ccc(F)c(C(=O)c2c[nH]c3ncc(-c4csc(-n5ccnc5C)n4)cc23)c1F] | 543.5 |

P-1107 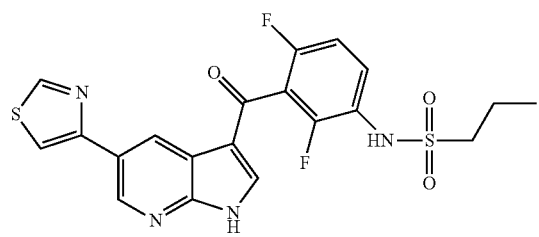 [SMILES: CCCS(=O)(=O)Nc1ccc(F)c(C(=O)c2c[nH]c3ncc(-c4cscn4)cc23)c1F]
P-1108 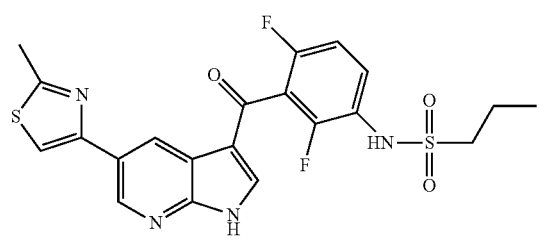 [SMILES: CCCS(=O)(=O)Nc1ccc(F)c(C(=O)c2c[nH]c3ncc(-c4csc(C)n4)cc23)c1F]
P-1110 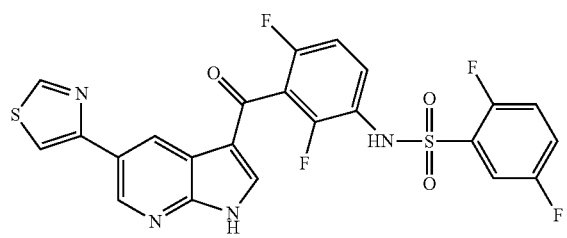 [SMILES: O=C(c1c(F)ccc(NS(=O)(=O)c2cc(F)ccc2F)c1F)c1c[nH]c2ncc(-c3cscn3)cc12]
P-1111 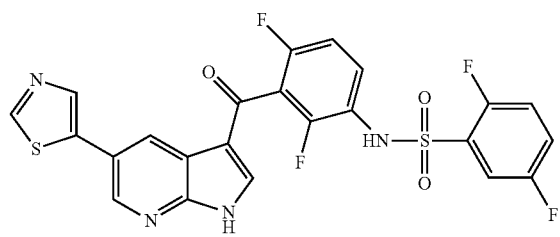
P-1112 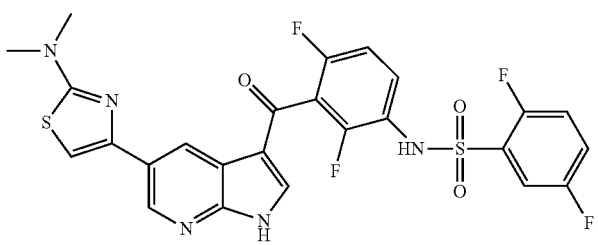 [SMILES: CN(C)c1nc(-c2cnc3[nH]cc(C(=O)c4c(F)ccc(NS(=O)(=O)c5cc(F)ccc5F)c4F)c3c2)cs1]
P-1113 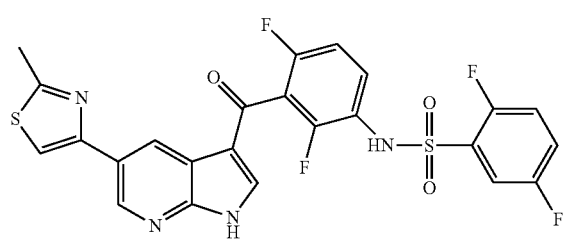 [SMILES: Cc1nc(-c2cnc3[nH]cc(C(=O)c4c(F)ccc(NS(=O)(=O)c5cc(F)ccc5F)c4F)c3c2)cs1]

-continued
P-1114 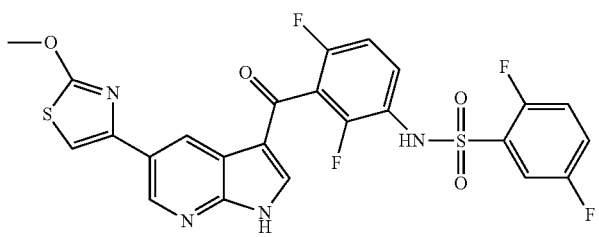 [SMILES: COc1nc(-c2cnc3[nH]cc(C(=O)c4c(F)ccc(NS(=O)(=O)c5cc(F)ccc5F)c4F)c3c2)cs1]
P-1300 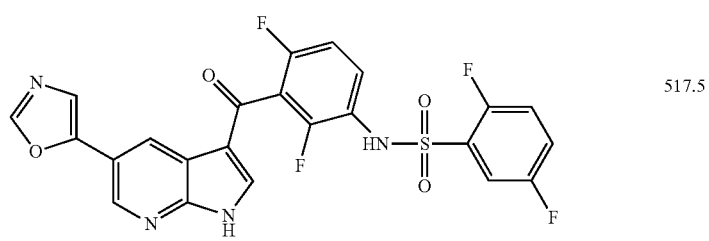 517.5
P-1402 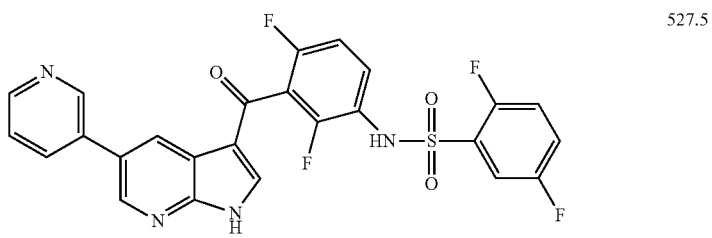 527.5
P-1403 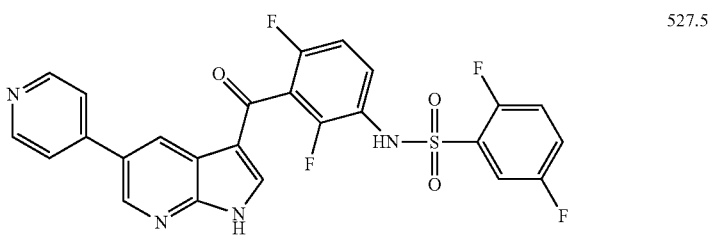 527.5
P-1404 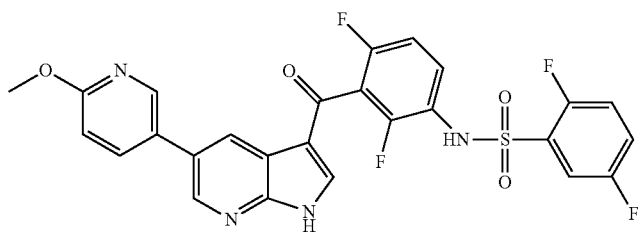 [SMILES: COc1ccc(-c2cnc3[nH]cc(C(=O)c4c(F)ccc(NS(=O)(=O)c5cc(F)ccc5F)c4F)c3c2)cn1] 557.0
P-1405 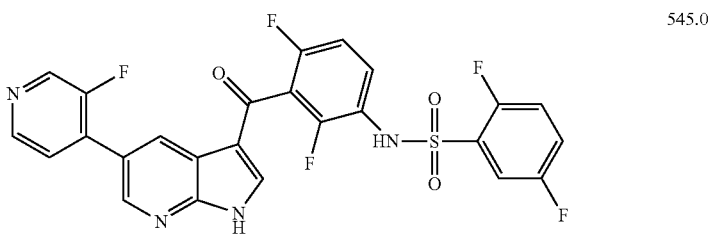 545.0

| | | |
|---|---|---|
| P-1406 | 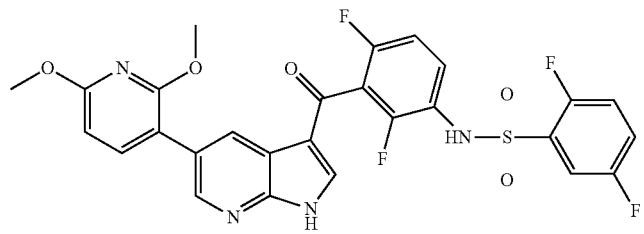 | 587.0 |
| P-1407 | 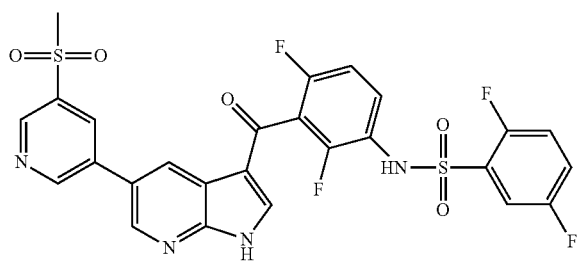 [SMILES: CS(=O)(=O)c1cncc(-c2cnc3[nH]cc(C(=O)c4c(F)ccc(NS(=O)(=O)c5cc(F)ccc5F)c4F)c3c2)c1] | 605.5 |
| P-1408 | 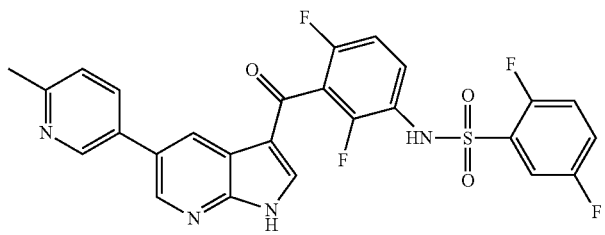 [SMILES: Cc1ccc(-c2cnc3[nH]cc(C(=O)c4c(F)ccc(NS(=O)(=O)c5cc(F)ccc5F)c4F)c3c2)cn1] | 541.0 |
| P-1409 | 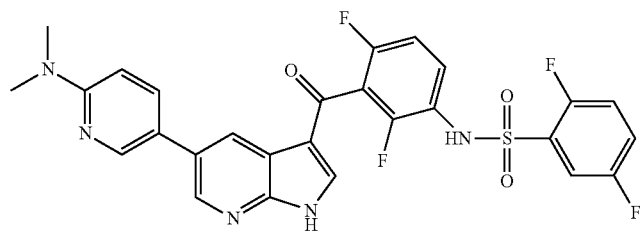 [SMILES: CN(C)c1ccc(-c2cnc3[nH]cc(C(=O)c4c(F)ccc(NS(=O)(=O)c5cc(F)ccc5F)c4F)c3c2)cn1] | 570.5 |
| P-1411 | 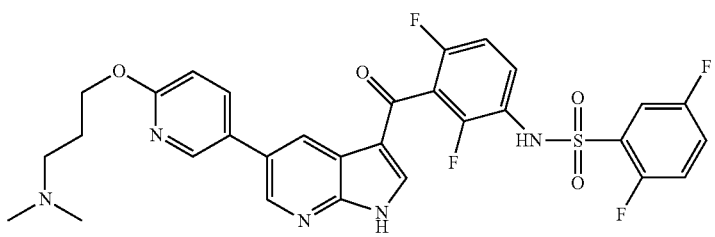 [SMILES: CN(C)CCCOc1ccc(-c2cnc3[nH]cc(C(=O)c4c(F)ccc(NS(=O)(=O)c5cc(F)ccc5F)c4F)c3c2)cn1] | 628.0 |
| P-1500 | 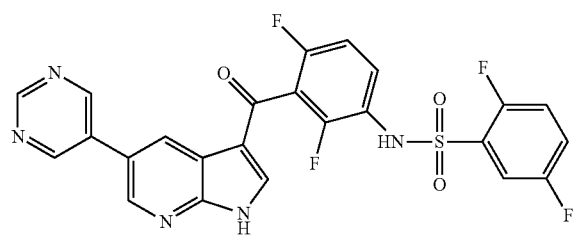 [SMILES: O=C(c1c(F)ccc(NS(=O)(=O)c2cc(F)ccc2F)c1F)c1c[nH]c2ncc(-c3cncnc3)cc12] | 528.0 |

| | | |
|---|---|---|
| P-1501 | 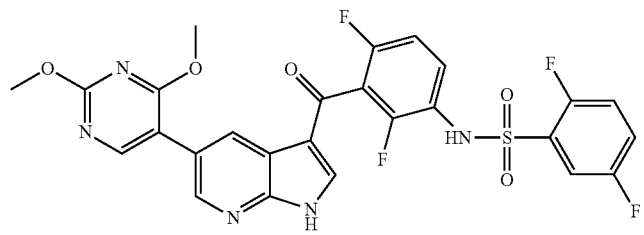 [SMILES: COc1ncc(-c2cnc3[nH]cc(C(=O)c4c(F)ccc(NS(=O)(=O)c5cc(F)ccc5F)c4F)c3c2)c(OC)n1] | 588.0 |
| P-1502 | 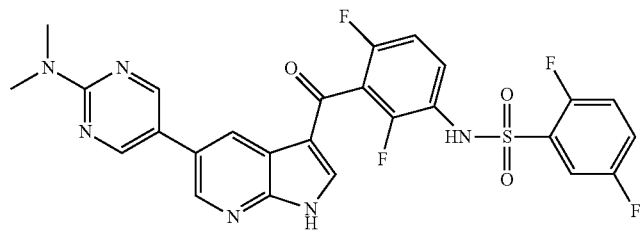 | 571.5 |
| P-1503 | 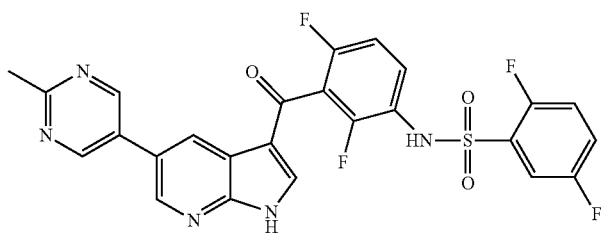 | 542.5 |
| P-1504 | 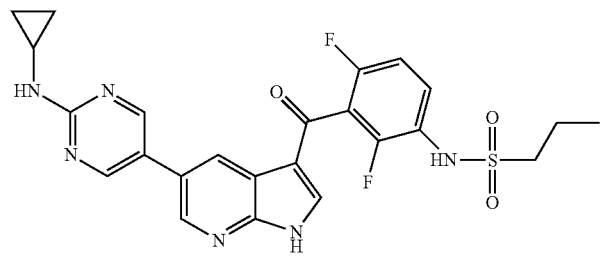 [SMILES: CCCS(=O)(=O)Nc1ccc(F)c(C(=O)c2c[nH]c3ncc(-c4cnc(NC5CC5)nc4)cc23)c1F] | |
| P-1505 | 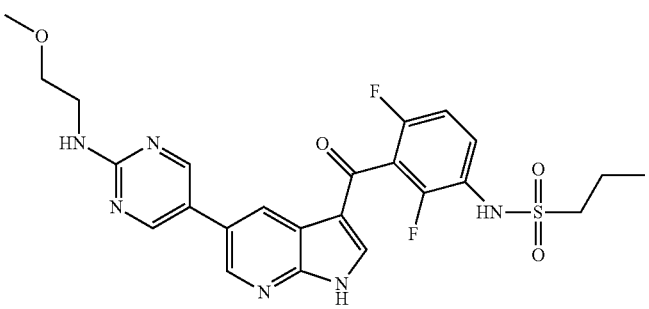 [SMILES: CCCS(=O)(=O)Nc1ccc(F)c(C(=O)c2c[nH]c3ncc(-c4cnc(NCCOC)nc4)cc23)c1F] | |
| P-1506 | 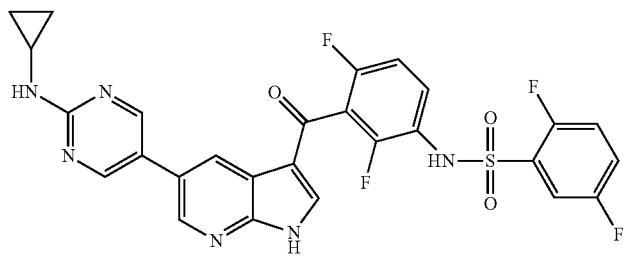 [SMILES: O=C(c1c(F)ccc(NS(=O)(=O)c2cc(F)ccc2F)c1F)c1c[nH]c2ncc(-c3cnc(NC4CC4)nc3)cc12] | 583.0 |

| | | |
|---|---|---|
| P-1507 | 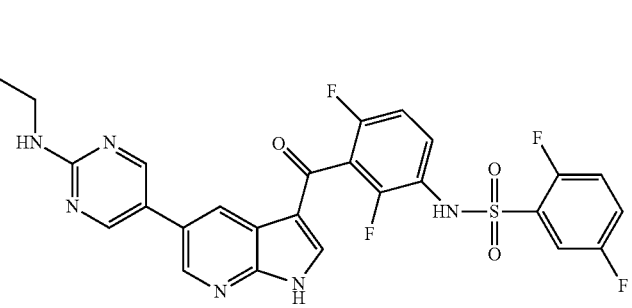 | 601.5 |
| P-1519 | 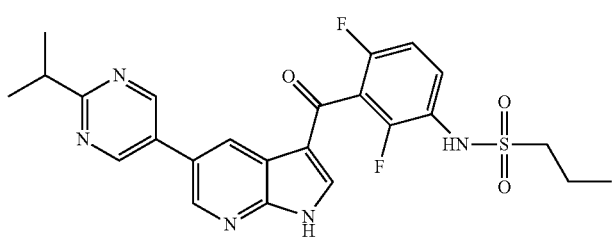 [SMILES: CCCS(=O)(=O)Nc1ccc(F)c(C(=O)c2c[nH]c3ncc(-c4cnc(C(C)C)nc4)cc23)c1F] | 500.0 |
| P-1521 | 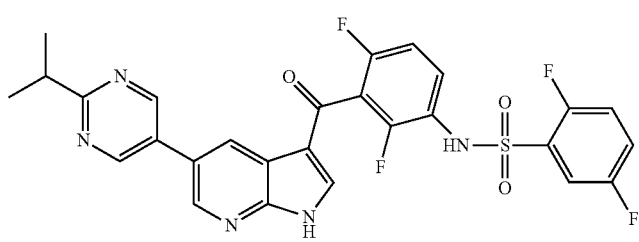 [SMILES: CC(C)c1ncc(-c2cnc3[nH]cc(C(=O)c4c(F)ccc(NS(=O)(=O)c5cc(F)ccc5F)c4F)c3c2)cn1] | 570.0 |
| P-1522 | 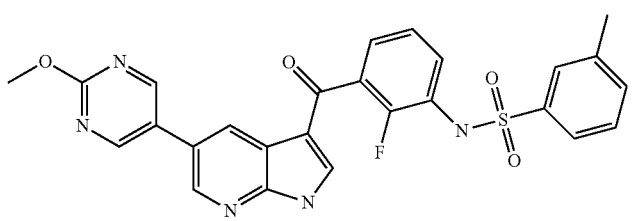 [SMILES: COc1ncc(-c2cnc3[nH]cc(C(=O)c4cccc(NS(=O)(=O)c5cccc(C)c5)c4F)c3c2)cn1] | |
| P-1523 | 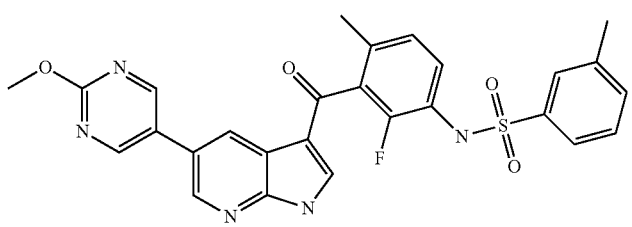 [SMILES: COc1ncc(-c2cnc3[nH]cc(C(=O)c4c(C)ccc(NS(=O)(=O)c5cccc(C)c5)c4F)c3c2)cn1] | |
| P-1600 | 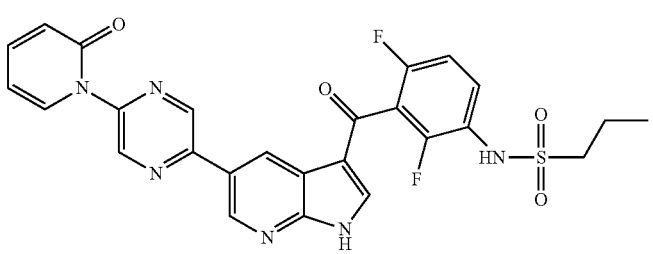 [SMILES: CCCS(=O)(=O)Nc1ccc(F)c(C(=O)c2c[nH]c3ncc(-c4cnc(-n5ccccc5=O)cn4)cc23)c1F] | 551.5 |

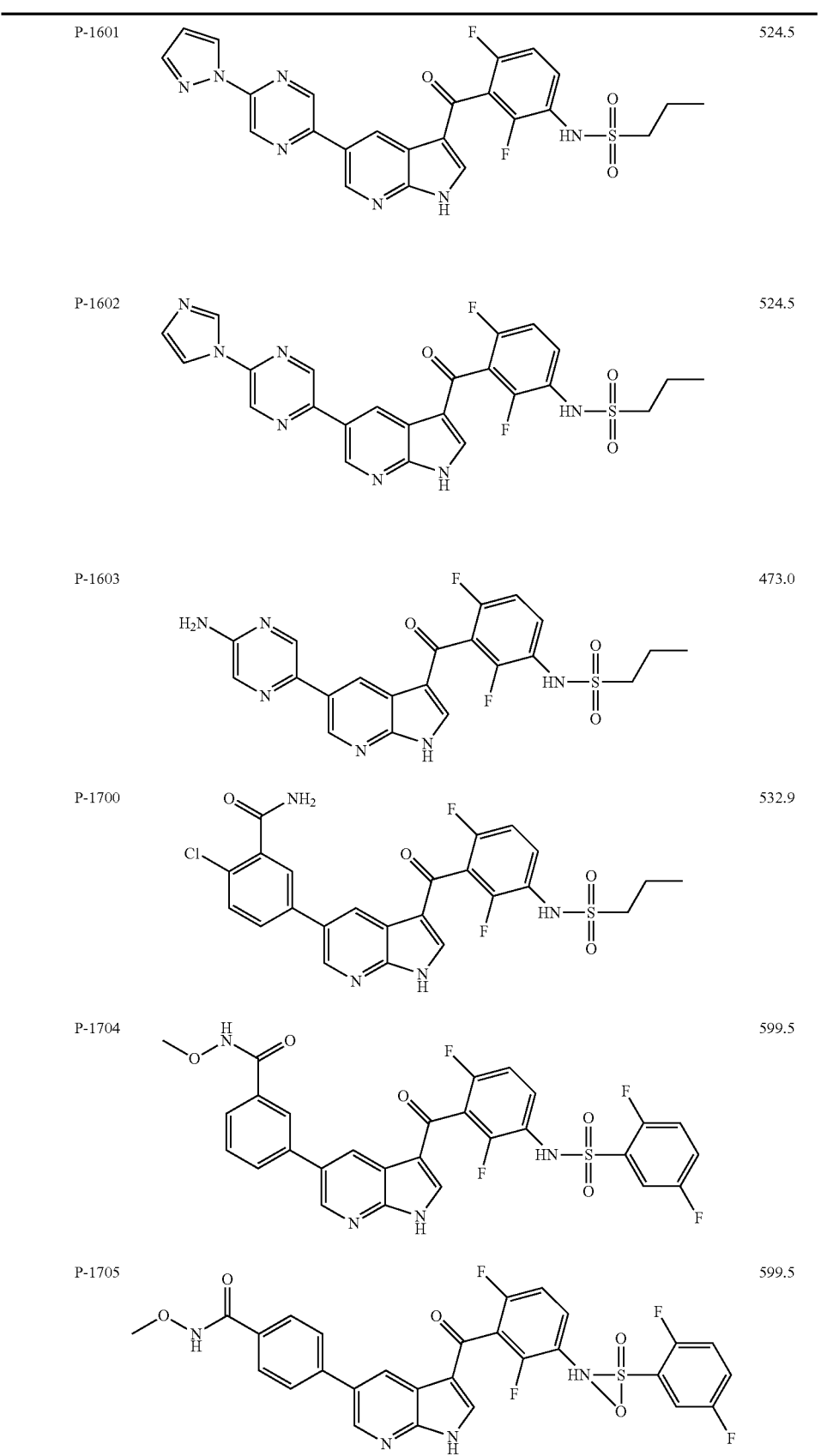

| | | |
|---|---|---|
| P-1706 | 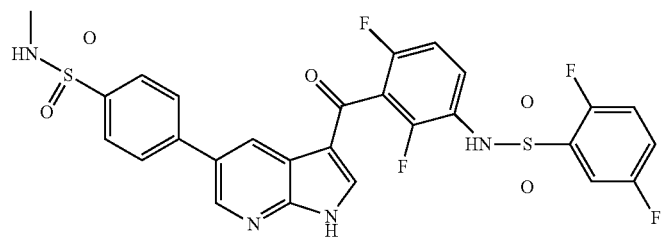 | 619.5 |
| P-1707 | 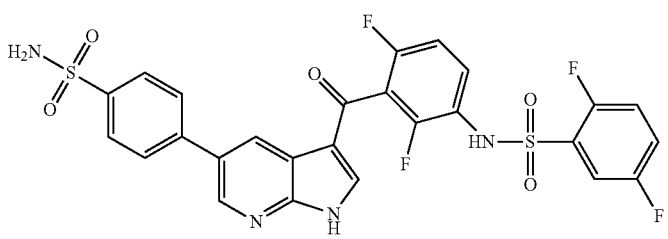 | 605.5 |
| P-1709 | 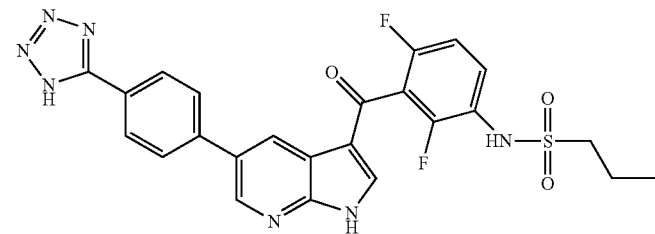 [SMILES: CCCS(=O)(=O)Nc1ccc(F)c(C(=O)c2c[nH]c3ncc(-c4ccc(-c5nnn[nH]5)cc4)cc23)c1F] | 523.95 |
| P-1710 | 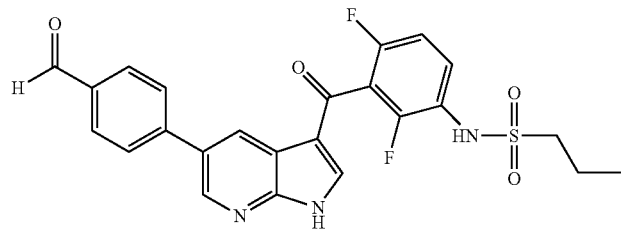 [SMILES: CCCS(=O)(=O)Nc1ccc(F)c(C(=O)c2c[nH]c3ncc(-c4ccc(C=O)cc4)cc23)c1F] | 482.05 [M − H⁺]⁻ |
| P-1711 | 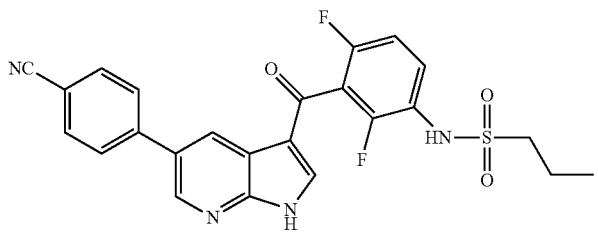 [SMILES: CCCS(=O)(=O)Nc1ccc(F)c(C(=O)c2c[nH]c3ncc(-c4ccc(C#N)cc4)cc23)c1F] | 480.95 |
| P-1901 | 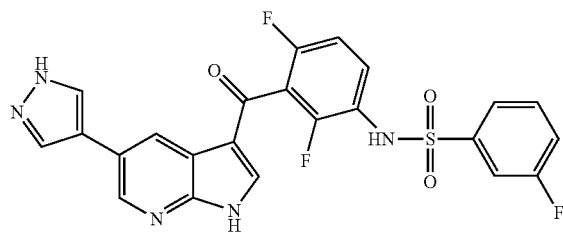 [SMILES: O=C(c1c(F)ccc(NS(=O)(=O)c2cccc(F)c2)c1F)c1c[nH]c2ncc(-c3cn[nH]c3)cc12] | |

P-1902 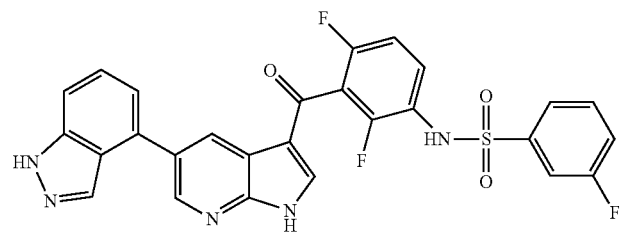 [SMILES: O=C(c1c(F)ccc(NS(=O)(=O)c2cccc(F)c2)c1F)c1c[nH]c2ncc(-c3cccc4[nH]ncc34)cc12]
P-1903 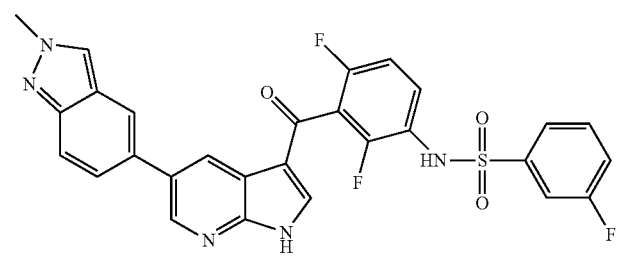 [SMILES: Cn1cc2cc(-c3cnc4[nH]cc(C(=O)c5c(F)ccc(NS(=O)(=O)c6cccc(F)c6)c5F)c4c3)ccc2n1]
P-1904 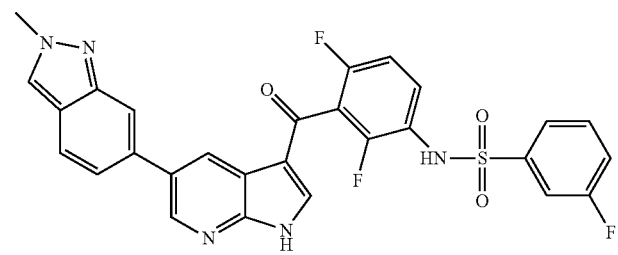 [SMILES: Cn1cc2ccc(-c3cnc4[nH]cc(C(=O)c5c(F)ccc(NS(=O)(=O)c6cccc(F)c6)c5F)c4c3)cc2n1]
P-1905 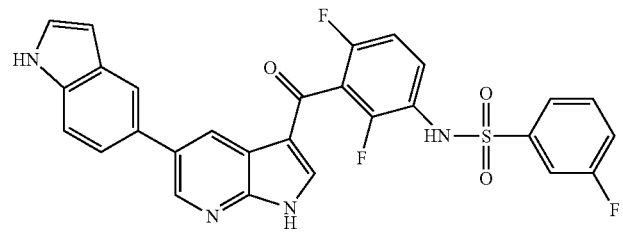 [SMILES: O=C(c1c(F)ccc(NS(=O)(=O)c2cccc(F)c2)c1F)c1c[nH]c2ncc(-c3ccc4[nH]ccc4c3)cc12]
P-1906 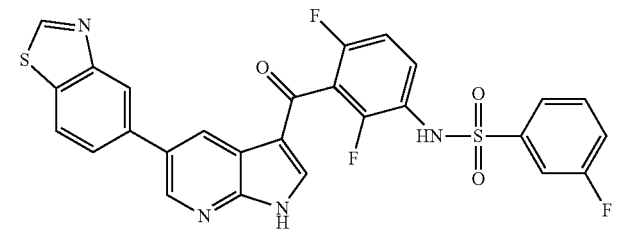 [SMILES: O=C(c1c(F)ccc(NS(=O)(=O)c2cccc(F)c2)c1F)c1c[nH]c2ncc(-c3ccc4scnc4c3)cc12]
P-1907 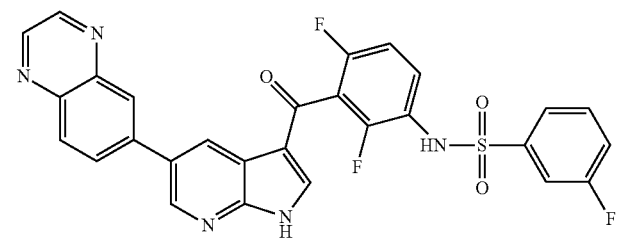 [SMILES: O=C(c1c(F)ccc(NS(=O)(=O)c2cccc(F)c2)c1F)c1c[nH]c2ncc(-c3ccc4nccnc4c3)cc12]

P-1908 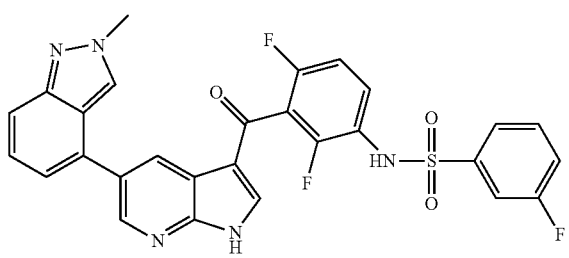 [SMILES: Cn1cc2c(-c3cnc4[nH]cc(C(=O)c5c(F)ccc(NS(=O)(=O)c6cccc(F)c6)c5F)c4c3)cccc2n1]
P-1909 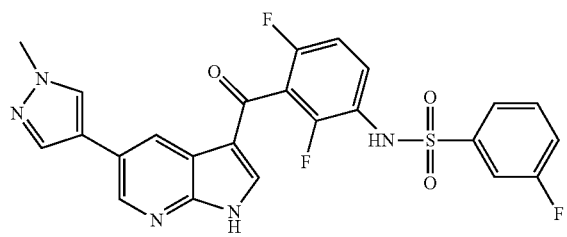 [SMILES: Cn1cc(-c2cnc3[nH]cc(C(=O)c4c(F)ccc(NS(=O)(=O)c5cccc(F)c5)c4F)c3c2)cn1]
P-1910 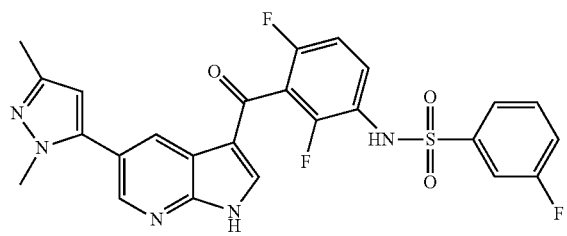
P-1911 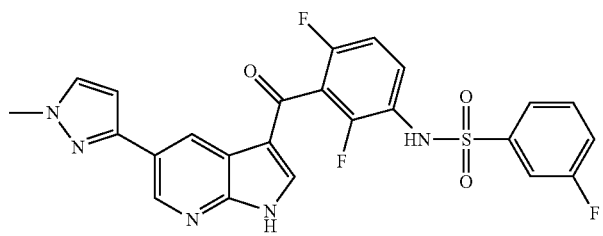 [SMILES: Cn1ccc(-c2cnc3[nH]cc(C(=O)c4c(F)ccc(NS(=O)(=O)c5cccc(F)c5)c4F)c3c2)n1]
P-1912 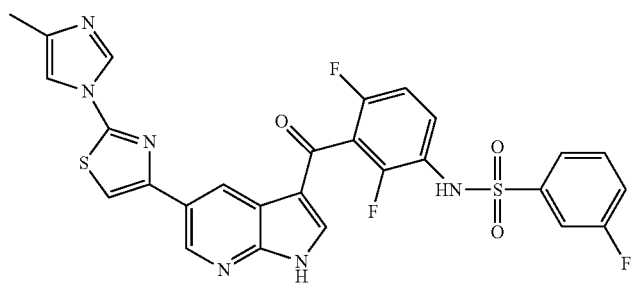 [SMILES: Cc1cn(-c2nc(-c3cnc4[nH]cc(C(=O)c5c(F)ccc(NS(=O)(=O)c6cccc(F)c6)c5F)c4c3)cs2)cn1]
P-1913 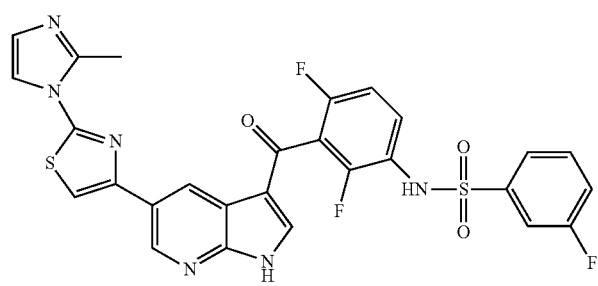

-continued
P-1914
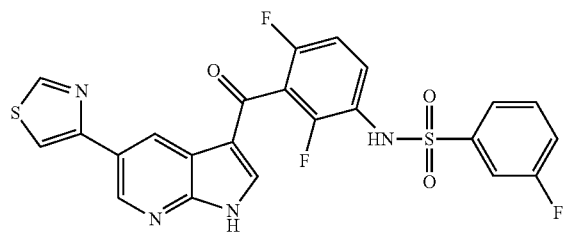 [SMILES: O=C(c1c(F)ccc(NS(=O)(=O)c2cccc(F)c2)c1F)c1c[nH]c2ncc(-c3cscn3)cc12]
P-1915
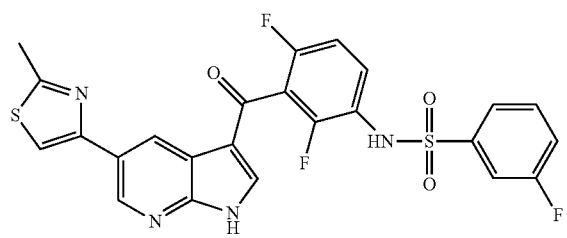 [SMILES: Cc1nc(-c2cnc3[nH]cc(C(=O)c4c(F)ccc(NS(=O)(=O)c5cccc(F)c5)c4F)c3c2)cs1]
P-1916
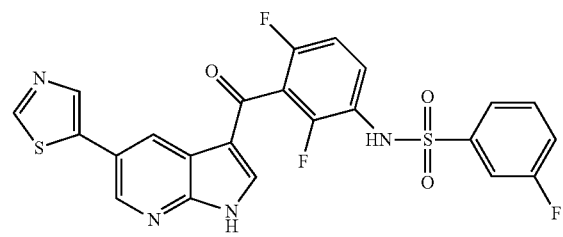
P-1917
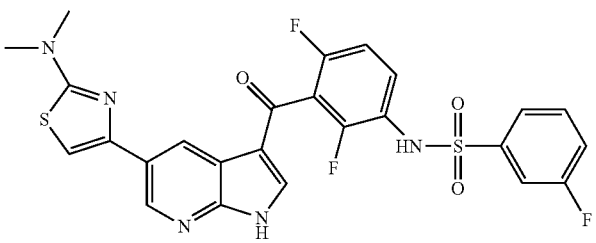 [SMILES: CN(C)c1nc(-c2cnc3[nH]cc(C(=O)c4c(F)ccc(NS(=O)(=O)c5cccc(F)c5)c4F)c3c2)cs1]
P-1918
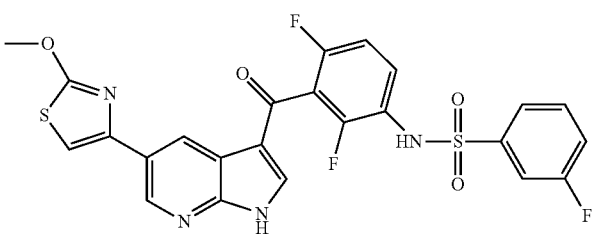 [SMILES: COc1nc(-c2cnc3[nH]cc(C(=O)c4c(F)ccc(NS(=O)(=O)c5cccc(F)c5)c4F)c3c2)cs1]
P-1919
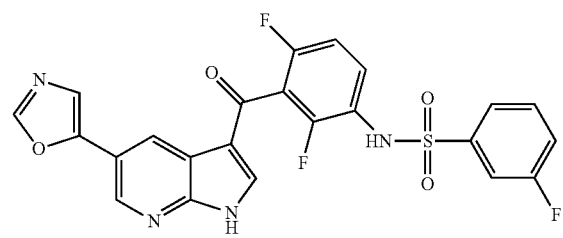 [SMILES: O=C(c1c(F)ccc(NS(=O)(=O)c2cccc(F)c2)c1F)c1c[nH]c2ncc(-c3cnco3)cc12]

P-1920
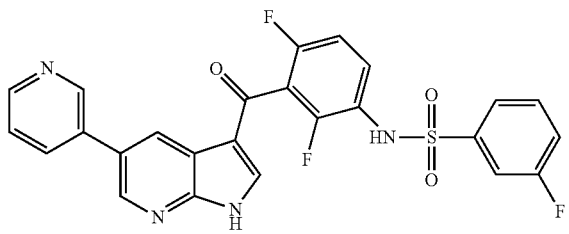 [SMILES: O=C(c1c(F)ccc(NS(=O)(=O)c2cccc(F)c2)c1F)c1c[nH]c2ncc(-c3cccnc3)cc12]
P-1921
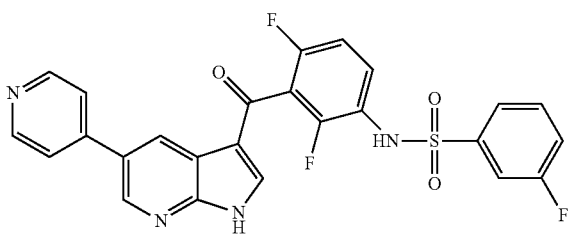
P-1922
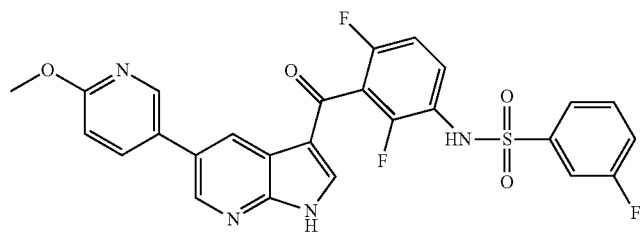 [SMILES: COc1ccc(-c2cnc3[nH]cc(C(=O)c4c(F)ccc(NS(=O)(=O)c5cccc(F)c5)c4F)c3c2)cn1]
P-1923
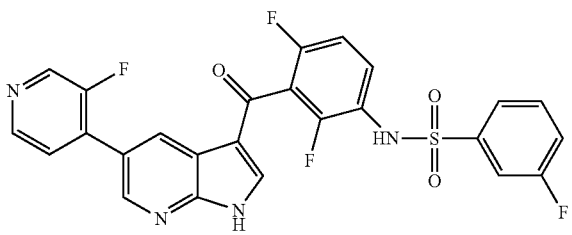 [SMILES: O=C(c1c(F)ccc(NS(=O)(=O)c2cccc(F)c2)c1F)c1c[nH]c2ncc(-c3ccncc3F)cc12]
P-1924
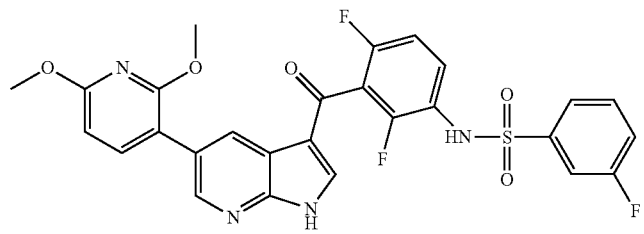
P-1925
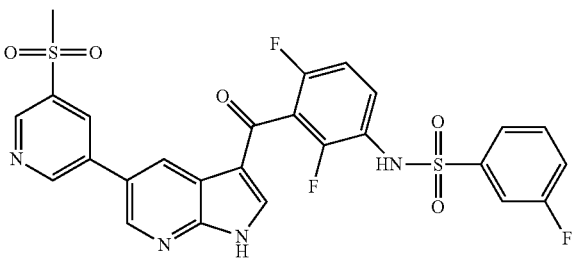 [SMILES: CS(=O)(=O)c1cncc(-c2cnc3[nH]cc(C(=O)c4c(F)ccc(NS(=O)(=O)c5cccc(F)c5)c4F)c3c2)c1]

-continued
P-1926
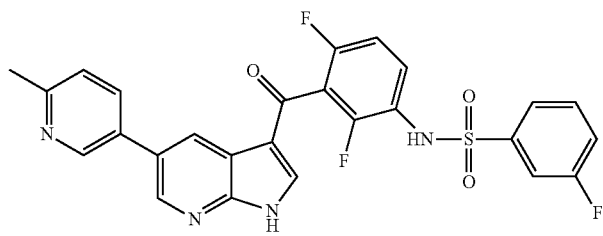 [SMILES: Cc1ccc(-c2cnc3[nH]cc(C(=O)c4c(F)ccc(NS(=O)(=O)c5cccc(F)c5)c4F)c3c2)cn1]
P-1927
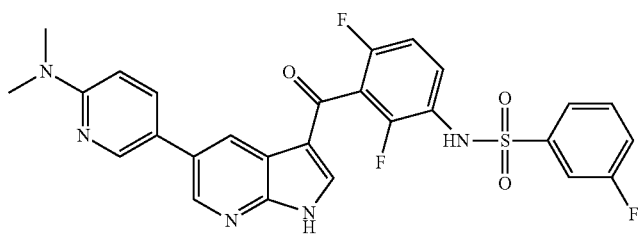 [SMILES: CN(C)c1ccc(-c2cnc3[nH]cc(C(=O)c4c(F)ccc(NS(=O)(=O)c5cccc(F)c5)c4F)c3c2)cn1]
P-1928
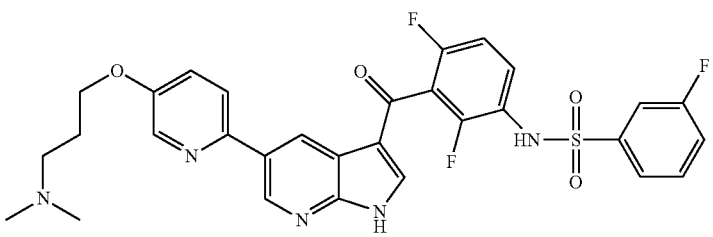 [SMILES: CN(C)CCCOc1ccc(-c2cnc3[nH]cc(C(=O)c4c(F)ccc(NS(=O)(=O)c5cccc(F)c5)c4F)c3c2)nc1]
P-1929
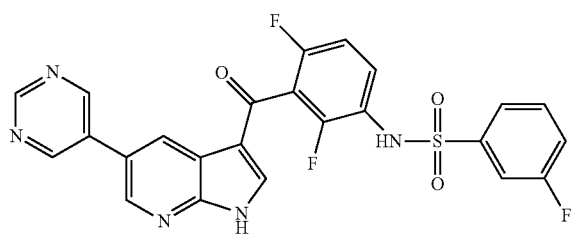 [SMILES: O=C(c1c(F)ccc(NS(=O)(=O)c2cccc(F)c2)c1F)c1c[nH]c2ncc(-c3cncnc3)cc12]
P-1930
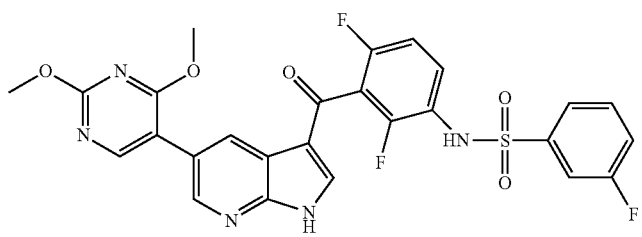 [SMILES: COc1ncc(-c2cnc3[nH]cc(C(=O)c4c(F)ccc(NS(=O)(=O)c5cccc(F)c5)c4F)c3c2)c(OC)n1]
P-1931
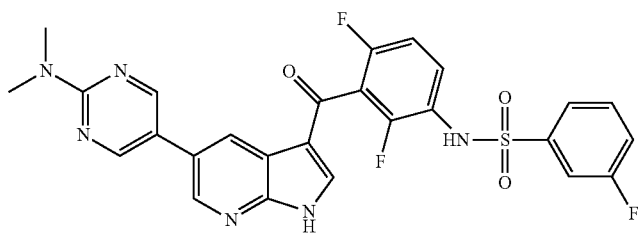

P-1932 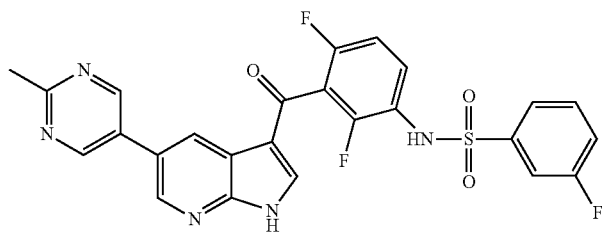 [SMILES: Cc1ncc(-c2cnc3[nH]cc(C(=O)c4c(F)ccc(NS(=O)(=O)c5cccc(F)c5)c4F)c3c2)cn1]
P-1933 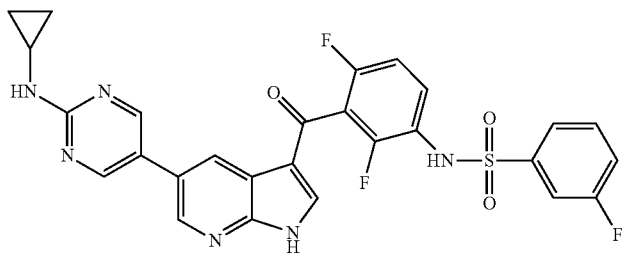 [SMILES: O=C(c1c(F)ccc(NS(=O)(=O)c2cccc(F)c2)c1F)c1c[nH]c2ncc(-c3cnc(NC4CC4)nc3)cc12]
P-1934 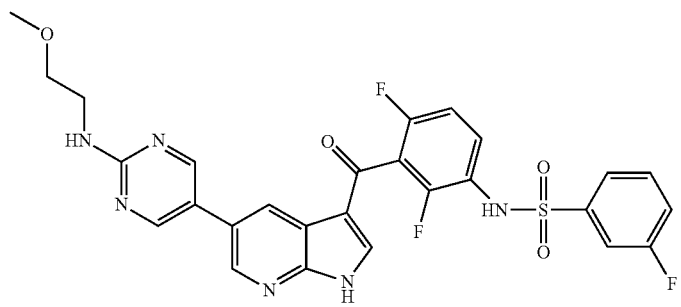 [SMILES: COCCNc1ncc(-c2cnc3[nH]cc(C(=O)c4c(F)ccc(NS(=O)(=O)c5cccc(F)c5)c4F)c3c2)cn1]
P-1935 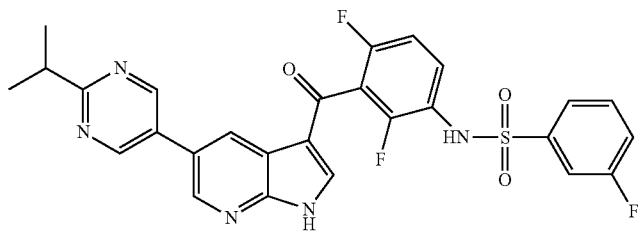
P-1936 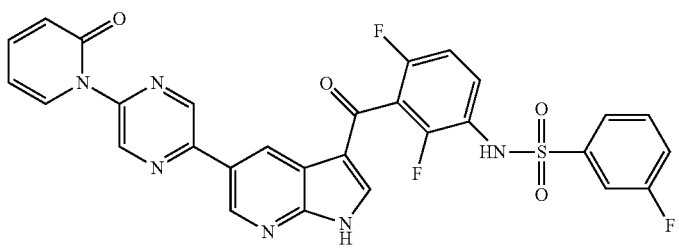 [SMILES: O=C(c1c(F)ccc(NS(=O)(=O)c2cccc(F)c2)c1F)c1c[nH]c2ncc(-c3cnc(-n4ccccc4=O)cn3)cc12]
P-1937 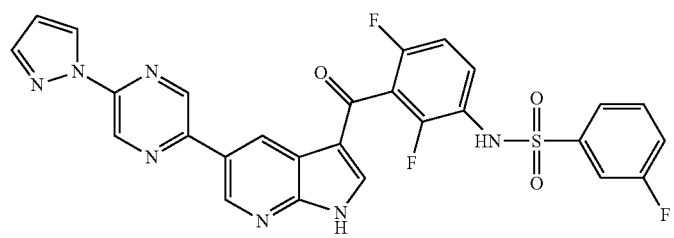 [SMILES: O=C(c1c(F)ccc(NS(=O)(=O)c2cccc(F)c2)c1F)c1c[nH]c2ncc(-c3cnc(-n4cccn4)cn3)cc12]

P-1938 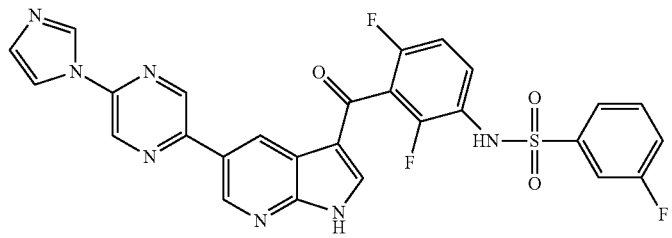 [SMILES: O=C(c1c(F)ccc(NS(=O)(=O)c2cccc(F)c2)c1F)c1c[nH]c2ncc(-c3cnc(-n4ccnc4)cn3)cc12]
P-1939 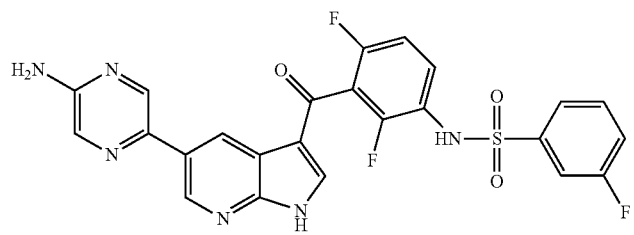 [SMILES: Nc1cnc(-c2cnc3[nH]cc(C(=O)c4c(F)ccc(NS(=O)(=O)c5cccc(F)c5)c4F)c3c2)cn1]
P-1940 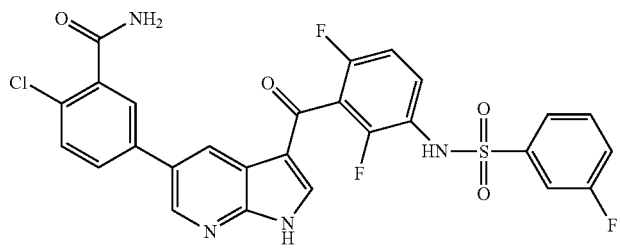 [SMILES: NC(=O)c1cc(-c2cnc3[nH]cc(C(=O)c4c(F)ccc(NS(=O)(=O)c5cccc(F)c5)c4F)c3c2)ccc1Cl]
P-1941 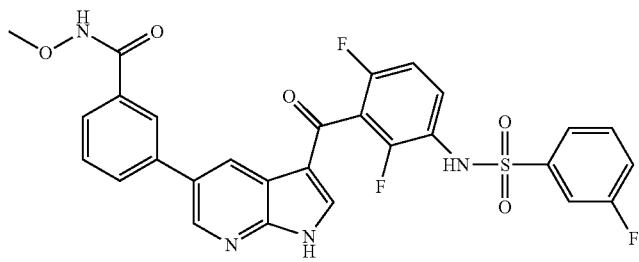 [SMILES: CONC(=O)c1cccc(-c2cnc3[nH]cc(C(=O)c4c(F)ccc(NS(=O)(=O)c5cccc(F)c5)c4F)c3c2)c1]
P-1942 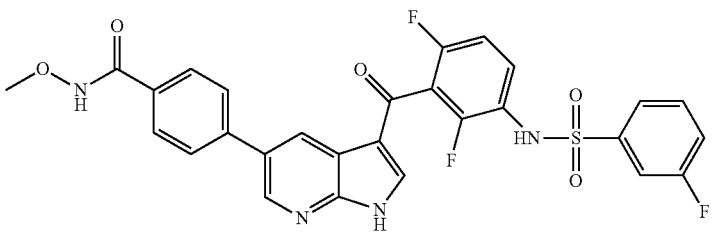 [SMILES: CONC(=O)c1ccc(-c2cnc3[nH]cc(C(=O)c4c(F)ccc(NS(=O)(=O)c5cccc(F)c5)c4F)c3c2)cc1]
P-1943 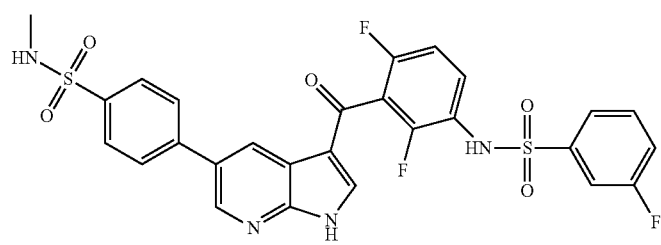 [SMILES: CNS(=O)(=O)c1ccc(-c2cnc3[nH]cc(C(=O)c4c(F)ccc(NS(=O)(=O)c5cccc(F)c5)c4F)c3c2)cc1]

P-1944
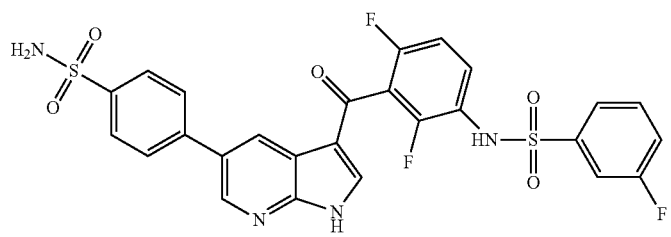 [SMILES: NS(=O)(=O)c1ccc(-c2cnc3[nH]cc(C(=O)c4c(F)ccc(NS(=O)(=O)c5cccc(F)c5)c4F)c3c2)cc1]
P-1945
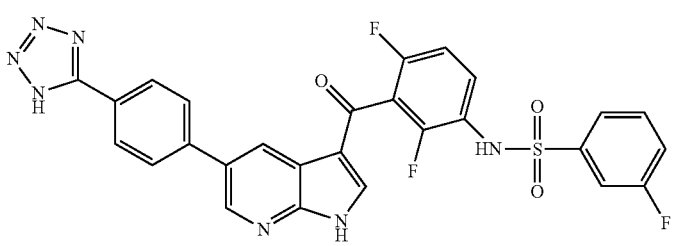 [SMILES: O=C(c1c(F)ccc(NS(=O)(=O)c2cccc(F)c2)c1F)c1c[nH]c2ncc(-c3ccc(-c4nnn[nH]4)cc3)cc12]
P-1946
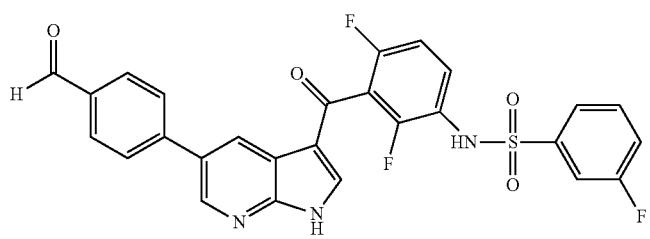 [SMILES: O=Cc1ccc(-c2cnc3[nH]cc(C(=O)c4c(F)ccc(NS(=O)(=O)c5cccc(F)c5)c4F)c3c2)cc1]
P-1947
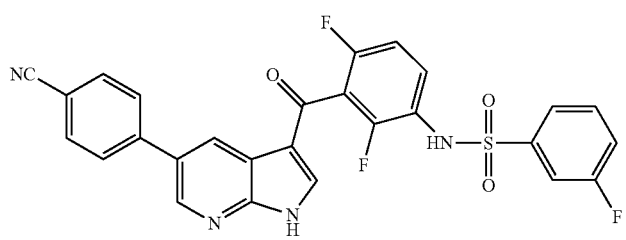 [SMILES: N#Cc1ccc(-c2cnc3[nH]cc(C(=O)c4c(F)ccc(NS(=O)(=O)c5cccc(F)c5)c4F)c3c2)cc1]
* Prepared according to Scheme 1a, where 2,6-difluoro-3-nitro-benzaldehyde is used in place of 2-fluoro-3-nitro-benzaldehyde 15 in step 1; 5-iodo-1H-pyrrolo[2,3-b]pyridine is used in place of 5-bromo-1H-pyrrolo[2,3-b]pyridine 4 in step 3; and 2,5-difluoro-benzenesulfonyl chloride is used in place of 2-fluorobenzenesulfonyl chloride 20 in step 5.

Example 2

Synthesis of N-{3-[5-(1-acetyl-1H-indazol-5-yl)-1H-pyrrolo[2,3-b]pyridine-3-carbonyl]-2,4-difluoro-phenyl}-2,5-difluoro-benzenesulfonamide P-0005

N-{3-[5-(1-acetyl-1H-indazol-5-yl)-1H-pyrrolo[2,3-b]pyridine-3-carbonyl]-2,4-difluoro-phenyl}-2,5-difluoro-benzenesulfonamide P-0005 is prepared in three steps from (3-amino-2,6-difluoro-phenyl)-(5-bromo-1H-pyrrolo[2,3-b]pyridin-3-yl)-methanone 7 and 2,5-difluoro-benzenesulfonyl chloride 15 as shown in Scheme 2.

Step 1—Preparation of N-[3-(5-bromo-1H-pyrrolo[2,3-b]pyridine-3-carbonyl)-2,4-difluoro-phenyl]-2,5-difluoro-benzenesulfonamide (26)

Into a reaction flask, (3-amino-2,6-difluoro-phenyl)-(5-bromo-1H-pyrrolo[2,3-b]pyridin-3-yl)-methanone (7, 140 mg, 0.40 mmol) is stirred in 3 mL of tetrahydrofuran and pyridine (0.3 mL, 4.0 mmol) is added, followed by 2,5-difluoro-benzenesulfonyl chloride (25, 127 mg, 0.596 mmol). The reaction is stirred at room temperature for 24 hours, then adjusted to pH 4 with addition of 1M aqueous hydrochloric acid and extracted with ethyl acetate. The

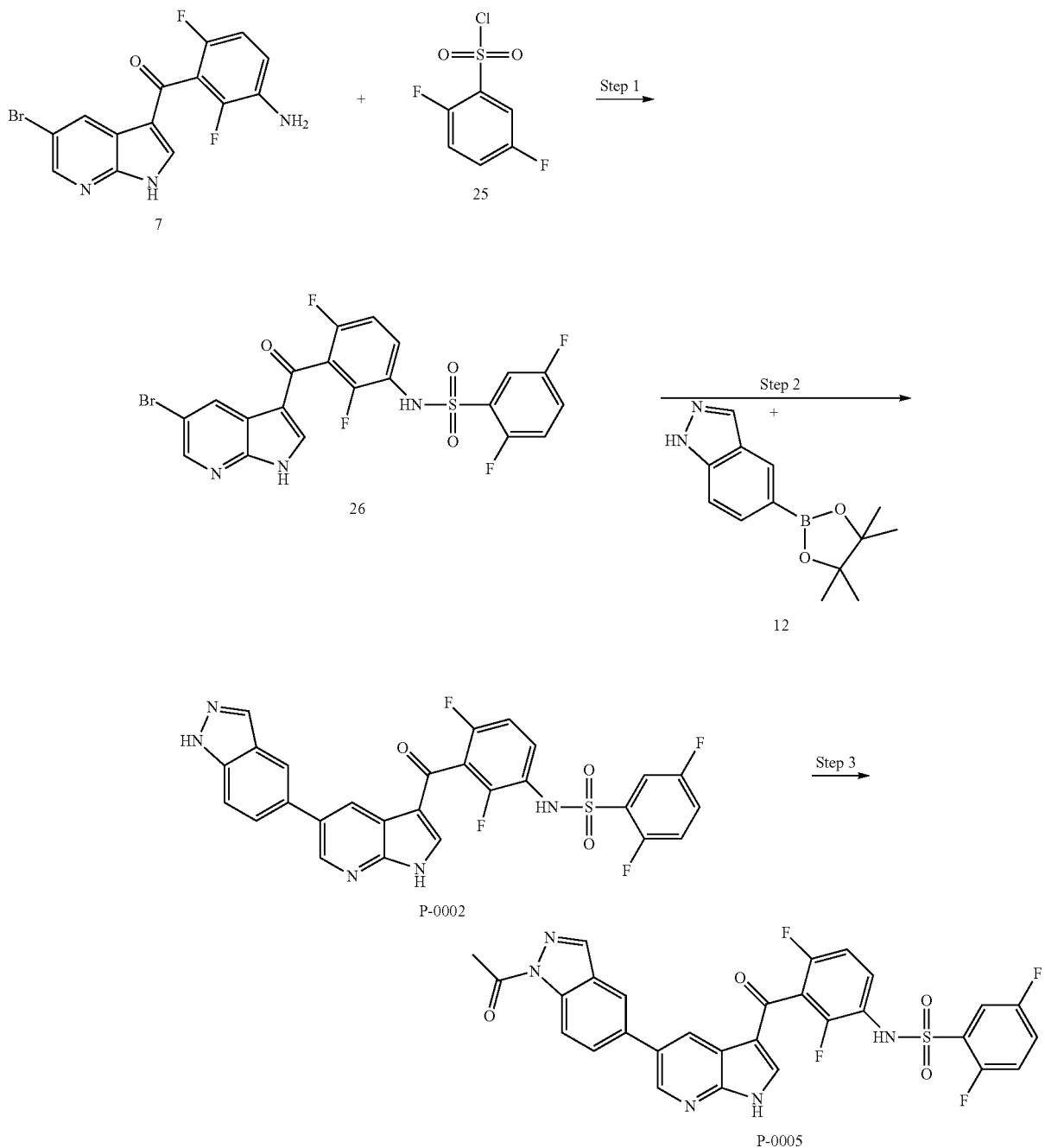

organic layer is washed with brine, dried with sodium sulfate, filtered and the filtrate concentrated under vacuum. The resulting material is purified by silica gel column chromatography to provide the desired compound (26, 190 mg, 90%).

Step 2—Preparation of N-{2,4-difluoro-3-[5-(1H-indazol-5-yl)-1H-pyrrolo[2,3-b]pyridine-3-carbonyl]-phenyl}-2,5-difluoro-benzenesulfonamide (P-0002)

Into a microwave vial, 5-(4,4,5,5-tetramethyl-[1,3,2]dioxaborolan-2-yl)-1H-indazole (12, 28 mg, 0.11 mmol) is combined with N-[3-(5-bromo-1H-pyrrolo[2,3-b]pyridine-3-carbonyl)-2,4-difluoro-phenyl]-2,5-difluoro-benzenesulfonamide (26, 50 mg, 0.09 mmol), tetrakis(triphenylphosphine)palladium(0) (2.2 mg, 0.0019 mmol), and potassium carbonate (1.0 mL, 1.0 M in water) in 3 mL of acetonitrile. The reaction is heated at 140° C. for 50 minutes in a microwave, the solvents removed under vacuum, and the residue purified by silica gel column chromatography, eluting with dichloromethane and methanol. Appropriate fractions are combined and concentrated under vacuum to provide the desired compound as a white solid (P-0002, 28 mg, 50%). MS (ESI) [M+H$^+$]$^+$=565.85.

Step 3—Preparation of N-{3-[5-(1-acetyl-1H-indazol-5-yl)-1H-pyrrolo[2,3-b]pyridine-3-carbonyl]-2,4-difluoro-phenyl}-2,5-difluoro-benzenesulfonamide (P-0005)

Into a reaction flask, a mixture of acetic anhydride (12 mg, 0.11 mmol) and N-{2,4-difluoro-3-[5-(1H-indazol-5-yl)-1H-pyrrolo[2,3-b]pyridine-3-carbonyl]-phenyl}-2,5-difluoro-benzenesulfonamide (P-0002, 22 mg, 0.031 mmol) is stirred at room temperature overnight, then diluted with water and ethyl acetate. The organic layer is washed with saturated sodium bicarbonate, then brine and dried over sodium sulfate, filtered and the filtrate concentrated under vacuum. The resulting material is purified by silica gel column chromatography, eluting with methanol and dichloromethane. Appropriate fractions are combined and concentrated under vacuum to provide the desired compound (P-0005, 3 mg, 20%). MS (ESI) [M+H$^+$]$^+$=607.8.

N-{3-[1-Acetyl-5-(1-acetyl-1H-indazol-5-yl)-1H-pyrrolo[2,3-b]pyridine-3-carbonyl]-2,4-difluoro-phenyl}-2,5-difluoro-benzenesulfonamide P-0004 and N-Acetyl-N-{3-[1-acetyl-5-(1-acetyl-1H-indazol-5-yl)-1H-pyrrolo[2,3-b]pyridine-3-carbonyl]-2,4-difluoro-phenyl}-2,5-difluoro-benzenesulfonamide P-0006,

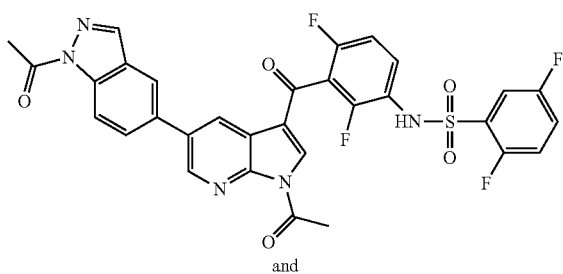
P-0004 and

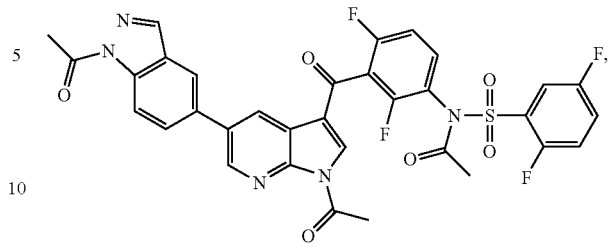
P-0006 are also isolated from step 3: MS (ESI) [M+H$^+$]$^+$=650.0 (P-0004) and 692.0 (P-0006).

N-{2,4-difluoro-3-[5-(1H-indazol-5-yl)-1H-pyrrolo[2,3-b]pyridine-3-carbonyl]-phenyl}-2,5-difluoro-benzenesulfonamide P-0002 is alternatively reacted according to the following step 3a to provide 5-{3-[3-(2,5-difluoro-benzenesulfonylamino)-2,6-difluoro-benzoyl]-1H-pyrrolo[2,3-b]pyridin-5-yl}-indazole-1-carboxylic acid methylamide P-0003.

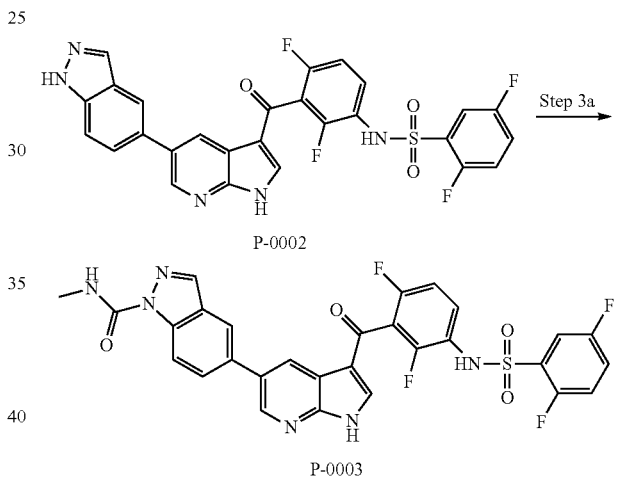

Step 3a—Preparation of 5-{3-[3-(2,5-difluoro-benzenesulfonylamino)-2,6-difluoro-benzoyl]-1H-pyrrolo[2,3-b]pyridin-5-yl}-indazole-1-carboxylic acid methylamide (P-0003)

Into a reaction flask, methyl isocyanate (6.5 mg, 0.11 mmol) is combined with N-{2,4-difluoro-3-[5-(1H-indazol-5-yl)-1H-pyrrolo[2,3-b]pyridine-3-carbonyl]-phenyl}-2,5-difluoro-benzenesulfonamide (P-0002, 22 mg, 0.031 mmol), tetrakis(triphenylphosphine)palladium(0) (2.2 mg, 0.0019 mmol), potassium carbonate (1.0 mL, 1.0 M in water) and 3 mL of acetonitrile. The reaction is heated at 140° C. for 50 minutes in a microwave, then diluted with water and ethyl acetate. The organic layer is washed with saturated sodium bicarbonate, then brine and dried over sodium sulfate, filtered and the filtrate concentrated under vacuum. The resulting material is purified by silica gel column chromatography, eluting with methanol and dichloromethane. Appropriate fractions are combined and concentrated under vacuum to provide the desired compound (P-0003, 14 mg, 72%). MS (ESI) [M+H$^+$]$^+$=623.

Example 3

Synthesis of propane-1-sulfonic acid {2,4-difluoro-3-[5-(1H-pyrazolo[3,4-b]pyridin-5-yl)-1H-pyrrolo[2,3-b]pyridine-3-carbonyl]-phenyl}-amide P-0008

Propane-1-sulfonic acid {2,4-difluoro-3-[5-(1H-pyrazolo[3,4-b]pyridin-5-yl)-1H-pyrrolo[2,3-b]pyridine-3-carbonyl]-phenyl}-amide P-0008 is prepared in three steps from 5-(4,4,5,5-tetramethyl-[1,3,2]dioxaborolan-2-yl)-1H-pyrrolo[2,3-b]pyridine 17 and propane-1-sulfonic acid (2,4-difluoro-3-formyl-phenyl)-amide 18 as shown in Scheme 3.

room temperature for 3 hours, with additional potassium hydroxide added up to 7 equivalents. The reaction is concentrated under vacuum, the solid added to water and extracted with ethyl acetate. The organic layer is dried over sodium sulfate, filtered and the filtrate concentrated under vacuum. The resulting material is purified by silica gel column chromatography, eluting with a gradient of 10-100% ethyl acetate (with 2.5% acetic acid) in hexanes. Appropriate fractions are combined and concentrated under vacuum to provide the desired compound. MS (ESI) $[M+H^+]^+=508.37$.

Scheme 3

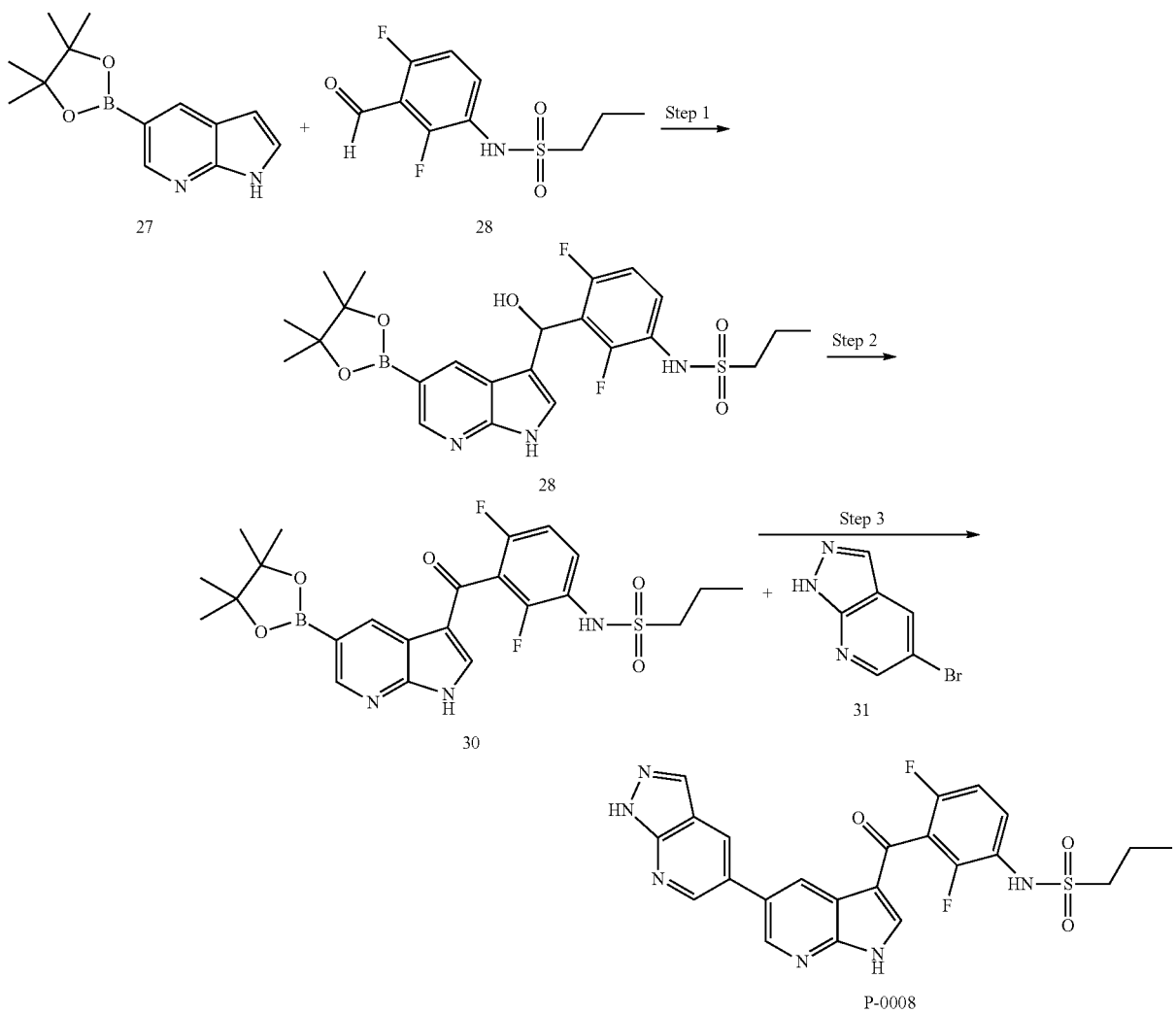

Step 1—Preparation of propane-1-sulfonic acid (2,4-difluoro-3-{hydroxy-[5-(4,4,5,5-tetramethyl-[1,3,2]dioxaborolan-2-yl)-1H-pyrrolo[2,3-b]pyridin-3-yl]-methyl}-phenyl)-amide (29)

In a round bottom flask, 5-(4,4,5,5-tetramethyl-[1,3,2]dioxaborolan-2-yl)-1H-pyrrolo[2,3-b]pyridine (27, 0.400 g, 1.64 mmol) is combined with 10 mL of methanol and potassium hydroxide (0.256 g, 4.56 mmol). Propane-1-sulfonic acid (2,4-difluoro-3-formyl-phenyl)-amide (28, 0.400 g, 1.52 mmol) is added and the reaction is stirred at

Step 2—Preparation of propane-1-sulfonic acid (2,4-difluoro-3-[5-(4,4,5,5-tetramethyl-[1,3,2]dioxaborolan-2-yl)-1H-pyrrolo[2,3-b]pyridine-3-carbonyl]-phenyl)-amide (30)

In a reaction flask, propane-1-sulfonic acid (2,4-difluoro-3-{hydroxy-[5-(4,4,5,5-tetramethyl-[1,3,2]dioxaborolan-2-yl)-1H-pyrrolo[2,3-b]pyridin-3-yl]-methyl}-phenyl)-amide (29, 0.155 g, 0.306 mmol) is combined with 10 mL of tetrahydrofuran and 3 mL of dichloromethane. Dess-Martin periodinane (0.648 g, 1.53 mmol) is added and the reaction is stirred at room temperature for 20 minutes. The reaction is mixed with 1N sodium thiosulfate, extracted with ethyl acetate and the organic layer dried and purified by silica gel column chromatography, eluting with a gradient of 20-100% ethyl acetate in hexanes. Appropriate fractions are combined and concentrated under vacuum to provide the desired compound. MS (ESI) [M+H$^+$]$^+$=506.29.

Step 3—Preparation of propane-1-sulfonic acid {2,4-difluoro-3-[5-(1H-pyrazolo[3,4-b]pyridin-5-yl)-1H-pyrrolo[2,3-b]pyridine-3-carbonyl]-phenyl}-amide (P-0008)

In a microwave vial, propane-1-sulfonic acid {2,4-difluoro-3-[5-(4,4,5,5-tetramethyl-[1,3,2]dioxaborolan-2-yl)-1H-pyrrolo[2,3-b]pyridine-3-carbonyl]-phenyl}-amide (30, 0.050 g, 0.099 mmol) is combined with 5-bromo-1H-pyrazolo[3,4-b]pyridine (31, 0.030 g, 0.15 mmol), 1 mL of tetrahydrofuran, 1 mL of acetonitrile, tetrakis(triphenylphosphine)palladium(0) (0.050 g, 0.043 mmol), and potassium carbonate (0.400 mL, 1.00 M in water). The reaction is heated at 145° C. for 45 minutes in a microwave, then extracted with ethyl acetate, and the organic layer is washed with water and brine. The organic layer is dried over sodium sulfate, filtered and the filtrate concentrated under vacuum. The resulting material is purified by silica gel column chromatography, eluting with a gradient of methanol:dichloromethane. Appropriate fractions are combined, concentrated under vacuum and the resulting solid is further washed with a mixture of ethyl acetate:hexane to provide the desired compound. MS (ESI) [M−H$^+$]$^−$=495.05.

Additional compounds, such as propane-1-sulfonic acid {2,4-difluoro-3-[5-(1-pyrimidin-2-yl-1H-pyrazol-4-yl)-1H-pyrrolo[2,3-b]pyridine-3-carbonyl]-phenyl}-amide P-1005, are prepared following the protocol of steps 3a and 4 of Scheme 3a (steps 1 and 2 are the same as Scheme 3).

Scheme 3a

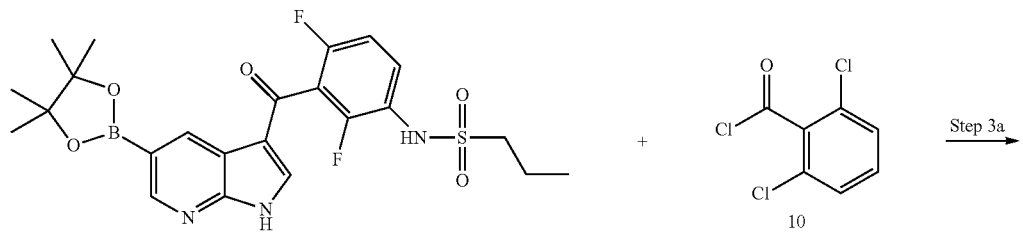

30

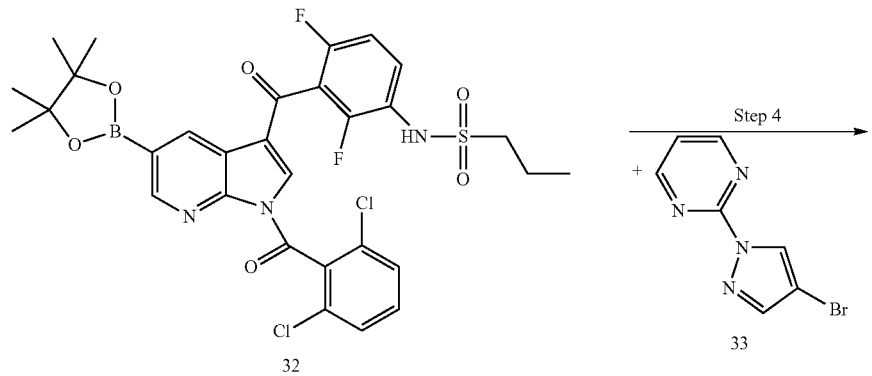

32

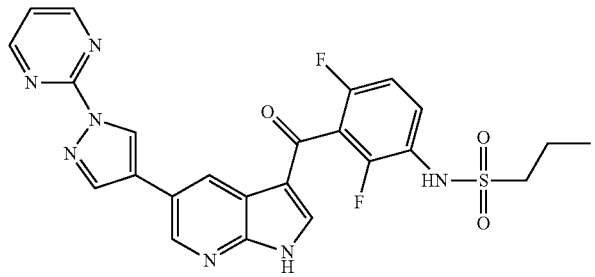

P-1005

Step 3—Preparation of propane-1-sulfonic acid {3-[1-(2,6-dichloro-benzoyl)-5-(4,4,5,5-tetramethyl-[1,3,2]dioxaborolan-2-yl)-1H-pyrrolo[2,3-b]pyridine-3-carbonyl]-2,4-difluoro-phenyl}-amide (32)

Propane-1-sulfonic acid {2,4-difluoro-3-[5-(4,4,5,5-tetramethyl-[1,3,2]dioxaborolan-2-yl)-1H-pyrrolo[2,3-b]pyridine-3-carbonyl]-phenyl}-amide (30, 2.1 g, 4.16 mmol), 21 mL of toluene, diisopropylamine (1.5 mL, 8.31 mmol), 4-dimethylaminopyridine (101 mg, 0.83 mmol) and 2,6-dichloro-benzoyl chloride (10, 0.7 mL, 4.78 mmol) are combined in a reaction flask under nitrogen. The reaction is stirred at room temperature for 17 hours, then diluted with 100 mL of ethyl acetate and extracted. The organic layer is washed sequentially with 40 mL of saturated aqueous sodium bicarbonate, 40 mL of water, and 40 mL of brine, then dried with sodium sulfate, filtered and the filtrate concentrated under vacuum. The resulting material is purified by silica gel column chromatography, eluting with a gradient of ethyl acetate and hexane. Appropriate fractions are combined and concentrated under vacuum and the resulting material is triturated with diethyl ether to provide the desired compound.

Step 4—Preparation of propane-1-sulfonic acid {2,4-difluoro-3-[5-(1-pyrimidin-2-yl-1H-pyrazol-4-yl)-1H-pyrrolo[2,3-b]pyridine-3-carbonyl]-phenyl}-amide (P-1005)

To a solution of propane-1-sulfonic acid {3-[1-(2,6-dichloro-benzoyl)-5-(4,4,5,5-tetramethyl-[1,3,2]dioxaborolan-2-yl)-1H-pyrrolo[2,3-b]pyridine-3-carbonyl]-2,4-difluoro-phenyl}-amide (32, 18 mg, 0.026 mmol) and 2-(4-bromo-pyrazol-1-yl)-pyrimidine (33, 4.95 mg, 0.022 mmol) in 800 μL of acetonitrile is added 400 μL of 1M aqueous potassium carbonate and approximately 1-2 mg of [1,1'-bis(diphenylphosphino)ferrocene]dichloro-palladium (II) (PdCl$_2$ dppf). The reaction mixture is microwave irradiated at 145° C. for 15 minutes, then neutralized with acetic acid, and extracted with 2×1 mL of ethyl acetate. The combined organic layer is concentrated under vacuum, the residue dissolved in 500 μL of dimethylsulfoxide and purified by HPLC using a C18 column, eluting with water/acetonitrile and 0.1% trifluoroacetic acid, 20-100% acetonitrile at 6 mL per minute. Appropriate fractions are combined and concentrated under vacuum to provide the desired compound. MS (ESI) [M+H]$^+$=524.5.

Additional compounds are prepared similarly to the protocol of Scheme 3 step 3, or Scheme 3a step 4. The reactions are performed substituting 5-bromo-1H-pyrazolo[3,4-b]pyridine 21 or 2-(4-bromo-pyrazol-1-yl)-pyrimidine 24 with an appropriate halogen (e.g. chloro-, bromo- or iodo-) substituted heteroaryl compound in step 3 or 4. The following compounds are prepared following this procedure:

Propane-1-sulfonic acid [2,4-difluoro-3-(5-imidazo[1,2-a]pyridin-5-yl-1H-pyrrolo[2,3-b]pyridine-3-carbonyl)-phenyl]-amide (P-0018), Propane-1-sulfonic acid {2,4-difluoro-3-[5-(1H-indol-4-yl)-1H-pyrrolo[2,3-b]pyridine-3-carbonyl]-phenyl}-amide (P-0019), Propane-1-sulfonic acid [3-(5-benzothiazol-6-yl-1H-pyrrolo[2,3-b]pyridine-3-carbonyl)-2,4-difluoro-phenyl]-amide (P-0020), Propane-1-sulfonic acid [2,4-difluoro-3-(5-imidazo[1,2-a]pyridin-2-yl-1H-pyrrolo[2,3-b]pyridine-3-carbonyl)-phenyl]-amide (P-0021), Propane-1-sulfonic acid {2,4-difluoro-3-[5-(7-trifluoromethyl-imidazo[1,2-a]pyrimidin-2-yl)-1H-pyrrolo[2,3-b]pyridine-3-carbonyl]-phenyl}-amide (P-0022), Propane-1-sulfonic acid {2,4-difluoro-3-[5-(3-methyl-1H-indol-5-yl)-1H-pyrrolo[2,3-b]pyridine-3-carbonyl]-phenyl}-amide (P-0023), Propane-1-sulfonic acid {2,4-difluoro-3-[5-(3-methyl-1H-indazol-5-yl)-1H-pyrrolo[2,3-b]pyridine-3-carbonyl]-phenyl}-amide (P-0024), Propane-1-sulfonic acid [2,4-difluoro-3-(5-quinazolin-7-yl-1H-pyrrolo[2,3-b]pyridine-3-carbonyl)-phenyl]-amide (P-0025), Propane-1-sulfonic acid [2,4-difluoro-3-(5-quinazolin-6-yl-1H-pyrrolo[2,3-b]pyridine-3-carbonyl)-phenyl]-amide (P-0026), Propane-1-sulfonic acid {2,4-difluoro-3-[5-(1-methyl-1H-indazol-6-yl)-1H-pyrrolo[2,3-b]pyridine-3-carbonyl]-phenyl}-amide (P-0027), Propane-1-sulfonic acid {2,4-difluoro-3-[5-(1-methyl-1H-indazol-5-yl)-1H-pyrrolo[2,3-b]pyridine-3-carbonyl]-phenyl}-amide (P-0028), Propane-1-sulfonic acid {3-[5-(3-amino-1-methyl-1H-indazol-6-yl)-1H-pyrrolo[2,3-b]pyridine-3-carbonyl]-2,4-difluoro-phenyl}-amide (P-0029), Propane-1-sulfonic acid (2,4-difluoro-3-{5-[2-(2-methylamino-ethyl)-3H-benzoimidazol-5-yl]-1H-pyrrolo[2,3-b]pyridine-3-carbonyl}-phenyl)-amide (P-0030), Propane-1-sulfonic acid {3-[5-(2-amino-1-methyl-1H-benzoimidazol-5-yl)-1H-pyrrolo[2,3-b]pyridine-3-carbonyl]-2,4-difluoro-phenyl}-amide (P-0031), Propane-1-sulfonic acid {3-[5-(2-amino-1H-benzoimidazol-5-yl)-1H-pyrrolo[2,3-b]pyridine-3-carbonyl]-2,4-difluoro-phenyl}-amide (P-0032), Propane-1-sulfonic acid [2,4-difluoro-3-(5-quinolin-7-yl-1H-pyrrolo[2,3-b]pyridine-3-carbonyl)-phenyl]-amide (P-0033), Propane-1-sulfonic acid [2,4-difluoro-3-(5-quinolin-6-yl-1H-pyrrolo[2,3-b]pyridine-3-carbonyl)-phenyl]-amide (P-0034), Propane-1-sulfonic acid {2,4-difluoro-3-[5-(2-methoxy-1-methyl-1H-benzoimidazol-5-yl)-1H-pyrrolo[2,3-b]pyridine-3-carbonyl]-phenyl}-amide (P-0035), Propane-1-sulfonic acid {3-[5-(2-dimethylamino-1-methyl-1H-benzoimidazol-5-yl)-1H-pyrrolo[2,3-b]pyridine-3-carbonyl]-2,4-difluoro-phenyl}-amide (P-0036), Propane-1-sulfonic acid {3-[5-(1,2-dimethyl-1H-benzoimidazol-5-yl)-1H-pyrrolo[2,3-b]pyridine-3-carbonyl]-2,4-difluoro-phenyl}-amide (P-0037), Propane-1-sulfonic acid [3-(5-benzo[1,2,5]thiadiazol-5-yl-1H-pyrrolo[2,3-b]pyridine-3-carbonyl)-2,4-difluoro-phenyl]-amide (P-0038), Propane-1-sulfonic acid {2,4-difluoro-3-[5-(2-methyl-1H-benzoimidazol-5-yl)-1H-pyrrolo[2,3-b]pyridine-3-carbonyl]-phenyl}-amide (P-0039), Propane-1-sulfonic acid {2,4-difluoro-3-[5-(4-oxo-1,4-dihydro-thieno[2,3-d]pyrimidin-6-yl)-1H-pyrrolo[2,3-b]pyridine-3-carbonyl]-phenyl}-amide (P-0044), Propane-1-sulfonic acid (3-{5-[3,5-dimethyl-1-(1H-tetrazol-5-yl)-1H-pyrazol-4-yl]-1H-pyrrolo[2,3-b]pyridine-3-carbonyl}-2,4-difluoro-phenyl)-amide (P-1006), Propane-1-sulfonic acid (3-{5-[1-(1,3-dimethyl-1H-pyrazole-4-sulfonyl)-3,5-dimethyl-1H-pyrazol-4-yl]-1H-pyrrolo[2,3-b]pyridine-3-carbonyl}-2,4-difluoro-phenyl)-amide (P-1007), Propane-1-sulfonic acid (2,4-difluoro-3-{5-[1-(1H-tetrazol-5-yl)-1H-pyrazol-4-yl]-1H-pyrrolo[2,3-b]pyridine-3-carbonyl}-phenyl)-amide (P-1008), Propane-1-sulfonic acid {2,4-difluoro-3-[5-(1-pyridin-2-yl-1H-pyrazol-4-yl)-1H-pyrrolo[2,3-b]pyridine-3-carbonyl]-phenyl}-amide (P-1013), 4-{3-[2,6-Difluoro-3-(propane-1-sulfonylamino)-benzoyl]-1H-pyrrolo[2,3-b]pyridin-5-yl}-pyrazole-1-carboxylic acid amide (P-1014), Propane-1-sulfonic acid {2,4-difluoro-3-[5-(1-pyrazin-2-yl-1H-pyrazol-4-yl)-1H-pyrrolo[2,3-b]pyridine-3-carbonyl]-phenyl}-amide (P-1015), Propane-1-sulfonic acid {3-[5-(2-dimethylamino-thiazol-4-yl)-1H-pyrrolo[2,3-b]pyridine-3-carbonyl]-2,4-difluoro-phenyl}-amide (P-1102), Propane-1-sulfonic acid {2,4-difluoro-3-[5-(2-pyrazol-1-yl-thiazol-4-yl)-1H-pyrrolo[2,3-b]pyridine-3-carbonyl]-phenyl}-amide (P-1103), Propane-1-sulfonic acid {2,4-difluoro-3-[5-(2-imidazol-1-yl-thiazol-5-yl)-1H-pyrrolo[2,3-b]pyridine-3-carbonyl]-phenyl}-amide (P-1104), Propane-1-sulfonic acid (2,4-difluoro-3-{5-[2-(2-methyl-imidazol-1-yl)-thiazol-5-yl]-1H-pyrrolo[2,3-b]pyridine-3-carbonyl}-phenyl)-amide (P-1105), Propane-1-sulfonic acid {2,4-difluoro-3-[5-(2-imidazol-1-yl-thiazol-4-yl)-1H-pyrrolo[2,3-b]pyridine-3-carbonyl]-phenyl}-amide (P-1106), Propane-1-sulfonic acid {2,4-difluoro-3-[5-(2-pyrazol-1-yl-thiazol-5-yl)-1H-pyrrolo[2,3-b]pyridine-3-carbonyl]-phenyl}-amide (P-1109), Propane-1-sulfonic acid (2,4-difluoro-3-{5-[2-(2-oxo-pyrrolidin-1-yl)-thiazol-4-yl]-1H-pyrrolo[2,3-b]pyridine-3-carbonyl}-phenyl)-amide (P-1115), Propane-1-sulfonic acid {2,4-difluoro-3-[5-(2-pyridin-3-yl-thiazol-4-yl)-1H-pyrrolo[2,3-b]pyridine-3-carbonyl]-phenyl}-amide (P-1116), Propane-1-sulfonic acid (2,4-difluoro-3-{5-[2-(4-methyl-imidazol-1-yl)-thiazol-5-yl]-1H-pyrrolo[2,3-b]pyridine-3-carbonyl}-phenyl)-amide (P-1117), Propane-1-sulfonic acid {2,4-difluoro-3-[5-(5-pyridin-3-yl-thiophen-2-yl)-1H-pyrrolo[2,3-b]pyridine-3-carbonyl]-phenyl}-amide (P-1200), Propane-1-sulfonic acid (2,4-difluoro-3-{5-[5-(1H-pyrazol-3-yl)-thiophen-2-yl]-1H-pyrrolo[2,3-b]pyridine-3-carbonyl}-phenyl)-amide (P-1201), 5-{3-[2,6-Difluoro-3-(propane-1-sulfonylamino)-benzoyl]-1H-pyrrolo[2,3-b]pyridin-5-yl}-thiophene-2-sulfonic acid amide (P-1202), Propane-1-sulfonic acid (2,4-difluoro-3-{5-[5-(5-methyl-[1,2,4]oxadiazol-3-yl)-thiophen-2-yl]-1H-pyrrolo[2,3-b]pyridine-3-carbonyl}-phenyl)-amide (P-1203), Propane-1-sulfonic acid {2,4-difluoro-3-[5-(5-thiazol-2-yl-thiophen-2-yl)-1H-pyrrolo[2,3-b]pyridine-3-carbonyl]-phenyl}-amide (P-1204), Propane-1-sulfonic acid (2,4-difluoro-3-{5-[5-(1H-pyrazol-3-yl)-thiophen-2-yl]-1H-pyrrolo[2,3-b]pyridine-3-carbonyl}-phenyl)-amide (P-1205), Propane-1-sulfonic acid [2,4-difluoro-3-(5-pyridin-2-yl-1H-pyrrolo[2,3-b]pyridine-3-carbonyl)-phenyl]-amide (P-1401), Propane-1-sulfonic acid {3-[5-(2-cyclopropylamino-pyrimidin-5-yl)-1H-pyrrolo[2,3-b]pyridine-3-carbonyl]-2,4-difluoro-phenyl}-amide (P-1504), Propane-1-sulfonic acid (2,4-difluoro-3-{5-[2-(2-methoxy-ethylamino)-pyrimidin-5-yl]-1H-pyrrolo[2,3-b]pyridine-3-carbonyl}-phenyl)-amide (P-1505), Propane-1-sulfonic acid (2,4-difluoro-3-{5-[2-(pyridin-3-yloxy)-pyrimidin-5-yl]-1H-pyrrolo[2,3-b]pyridine-3-carbonyl}-phenyl)-amide (P-1508), Propane-1-sulfonic acid {2,4-difluoro-3-[5-(2-trifluoromethoxy-pyrimidin-5-yl)-1H-pyrrolo[2,3-b]pyridine-3-carbonyl]-phenyl}-amide (P-1509), Propane-1-sulfonic acid {3-[5-(2-cyano-pyrimidin-5-yl)-1H-pyrrolo[2,3-b]pyridine-3-carbonyl]-2,4-difluoro-phenyl}-amide (P-1510), Propane-1-sulfonic acid {2,4-difluoro-3-[5-(2-imidazol-1-yl-pyrimidin-5-yl)-1H-pyrrolo[2,3-b]pyridine-3-carbonyl]-phenyl}-amide (P-1511), Propane-1-sulfonic acid {3-[5-(2-azetidin-1-yl-pyrimidin-5-yl)-1H-pyrrolo[2,3-b]pyridine-3-carbonyl]-2,4-difluoro-phenyl}-amide (P-1512), Propane-1-sulfonic acid {2,4-difluoro-3-[5-(2-isopropylamino-pyrimidin-5-yl)-1H-pyrrolo[2,3-b]pyridine-3-carbonyl]-phenyl}-amide (P-1513), Propane-1-sulfonic acid {2,4-difluoro-3-[5-(2-methylamino-pyrimidin-5-yl)-1H-pyrrolo[2,3-b]pyridine-3-carbonyl]-phenyl}-amide (P-1514), Propane-1-sulfonic acid (3-{5-[2-(2-dimethylamino-ethylamino)-pyrimidin-5-yl]-1H-pyrrolo[2,3-b]pyridine-3-carbonyl}-2,4-difluoro-phenyl)-amide (P-1515), Propane-1-sulfonic acid (2,4-difluoro-3-{5-[2-(3-methoxy-propylamino)-pyrimidin-5-yl]-1H-pyrrolo[2,3-b]pyridine-3-carbonyl}-phenyl)-amide (P-1516), Propane-1-sulfonic acid {2,4-difluoro-3-[5-(2-isopropylamino-pyrimidin-5-yl)-1H-pyrrolo[2,3-b]pyridine-3-carbonyl]-phenyl}-amide (P-1517), Propane-1-sulfonic acid {2,4-difluoro-3-[5-(1-oxo-2,3-dihydro-1H-isoindol-5-yl)-1H-pyrrolo[2,3-b]pyridine-3-carbonyl]-phenyl}-amide (P-1701), Propane-1-sulfonic acid {2,4-difluoro-3-[5-(3-oxo-2,3-dihydro-1H-isoindol-5-yl)-1H-pyrrolo[2,3-b]pyridine-3-carbonyl]-phenyl}-amide (P-1702), Propane-1-sulfonic acid {2,4-difluoro-3-[5-(2-oxo-2,3-dihydro-1H-indol-5-yl)-1H-pyrrolo[2,3-b]pyridine-3-carbonyl]-phenyl}-amide (P-1703), N-[2,4-difluoro-3-(5-imidazo[1,2-a]pyridin-5-yl-1H-pyrrolo[2,3-b]pyridine-3-carbonyl)phenyl]-3-fluoro-benzenesulfonamide (P-1948), N-[2,4-difluoro-3-[5-(1H-indol-4-yl)-1H-pyrrolo[2,3-b]pyridine-3-carbonyl]phenyl]-3-fluoro-benzenesulfonamide (P-1949), N-[3-[5-(1,3-benzothiazol-6-yl)-1H-pyrrolo[2,3-b]pyridine-3-carbonyl]-2,4-difluoro-phenyl]-3-fluoro-benzenesulfonamide (P-1950), N-[2,4-difluoro-3-(5-imidazo[1,2-a]pyridin-2-yl-1H-pyrrolo[2,3-b]pyridine-3-carbonyl)phenyl]-3-fluoro-benzenesulfonamide (P-1951), N-[2,4-difluoro-3-[5-[7-(trifluoromethyl)imidazo[1,2-a]pyrimidin-2-yl]-1H-pyrrolo[2,3-b]pyridine-3-carbonyl]phenyl]-3-fluoro-benzenesulfonamide (P-1952), N-[2,4-difluoro-3-[5-(3-methyl-1H-indol-5-yl)-1H-pyrrolo[2,3-b]pyridine-3-carbonyl]phenyl]-3-fluoro-benzenesulfonamide (P-1953), N-[2,4-difluoro-3-[5-(3-methyl-1H-indazol-5-yl)-1H-pyrrolo[2,3-b]pyridine-3-carbonyl]phenyl]-3-fluoro-benzenesulfonamide (P-1954), N-[2,4-difluoro-3-(5-quinazolin-7-yl-1H-pyrrolo[2,3-b]pyridine-3-carbonyl)phenyl]-3-fluoro-benzenesulfonamide (P-1955), N-[2,4-difluoro-3-(5-quinazolin-6-yl-1H-pyrrolo[2,3-b]pyridine-3-carbonyl)phenyl]-3-fluoro-benzenesulfonamide (P-1956), N-[2,4-difluoro-3-[5-(1-methylindazol-6-yl)-1H-pyrrolo[2,3-b]pyridine-3-carbonyl]phenyl]-3-fluoro-benzenesulfonamide (P-1957), N-[2,4-difluoro-3-[5-(1-methylindazol-5-yl)-1H-pyrrolo[2,3-b]pyridine-3-carbonyl]phenyl]-3-fluoro-benzenesulfonamide (P-1958), N-[3-[5-(3-amino-1-methyl-indazol-6-yl)-1H-pyrrolo[2,3-b]pyridine-3-carbonyl]-2,4-difluoro-phenyl]-3-fluoro-benzenesulfonamide (P-1959), N-[2,4-difluoro-3-[5-[2-(2-methylaminoethyl)-3H-benzimidazol-5-yl]-1H-pyrrolo[2,3-b]pyridine-3-carbonyl]phenyl]-3-fluoro-benzenesulfonamide (P-1960), N-[3-[5-(2-amino-1-methyl-benzimidazol-5-yl)-1H-pyrrolo[2,3-b]pyridine-3-carbonyl]-2,4-difluoro-phenyl]-3-fluoro-benzenesulfonamide (P-1961), N-[3-[5-(2-amino-1H-benzimidazol-5-yl)-1H-pyrrolo[2,3-b]pyridine-3-carbonyl]-2,4-difluoro-phenyl]-3-fluoro-benzenesulfonamide (P-1962), N-[2,4-difluoro-3-[5-(7-quinolyl)-1H-pyrrolo[2,3-b]pyridine-3-carbonyl]phenyl]-3-fluoro-benzenesulfonamide (P-1963), N-[2,4-difluoro-3-[5-(6-quinolyl)-1H-pyrrolo[2,3-b]pyridine-3-carbonyl]phenyl]-3-fluoro-benzenesulfonamide (P-1964), N-[2,4-difluoro-3-[5-(2-methoxy-1-methyl-benzimidazol-5-yl)-1H-pyrrolo[2,3-b]pyridine-3-carbonyl]phenyl]-3-fluoro-benzenesulfonamide (P-1965), N-[3-[5-(2-dimethylamino-1-methyl-benzimidazol-5-yl)-1H-pyrrolo[2,3-b]pyridine-3-carbonyl]-2,4-difluoro-phenyl]-3-fluoro-benzenesulfonamide (P-1966), N-[3-[5-(1,2-dimethylbenzimidazol-5-yl)-1H-pyrrolo[2,3-b]pyridine-3-carbonyl]-2,4-difluoro-phenyl]-3-fluoro-benzenesulfonamide (P-1967), N-[3-[5-(2,1,3-benzothiadiazol-6-yl)-1H-pyrrolo[2,3-b]pyridine-3-carbonyl]-2,4-difluoro-phenyl]-3-fluoro-benzenesulfonamide (P-1968), N-[2,4-difluoro-3-[5-(2-methyl-1H-benzimidazol-5-yl)-1H-pyrrolo[2,3-b]pyridine-3-carbonyl]phenyl]-3-fluoro-benzenesulfonamide (P-1969), N-[2,4-difluoro-3-[5-(4-oxo-1H-thieno[2,3-d]pyrimidin-6-yl)-1H-pyrrolo[2,3-b]pyridine-3-carbonyl]phenyl]-3-fluoro-benzenesulfonamide (P-1970), N-[3-[5-[3,5-dimethyl-1-(1H-tetrazol-5-yl)pyrazol-4-yl]-1H-pyrrolo[2,3-b]pyridine-3-carbonyl]-2,4-difluoro-phenyl]-3-fluoro-benzenesulfonamide (P-1971), N-[3-[5-[1-(1,3-dimethylpyrazol-4-yl)sulfonyl-3,5-dimethyl-pyrazol-4-yl]-1H-pyrrolo[2,3-b]pyridine-3-carbonyl]-2,4-difluoro-phenyl]-3-fluoro-benzenesulfonamide (P-1972), N-[2,4-difluoro-3-[5-[1-(1H-tetrazol-5-yl)pyrazol-4-yl]-1H-pyrrolo[2,3-b]pyridine-3-carbonyl]phenyl]-3-fluoro-benzenesulfonamide (P-1973), N-[2,4-difluoro-3-[5-[1-(2-pyridyl)pyrazol-4-yl]-1H-pyrrolo[2,3-b]pyridine-3-carbonyl]phenyl]-3-fluoro-benzenesulfonamide (P-1974), 4-[3-[2,6-difluoro-3-[(3-fluorophenyl)sulfonylamino]benzoyl]-1H-pyrrolo[2,3-b]pyridin-5-yl]pyrazole-1-carboxamide (P-1975), N-[2,4-difluoro-3-[5-(1-pyrazin-2-ylpyrazol-4-yl)-1H-pyrrolo[2,3-b]pyridine-3-carbonyl]phenyl]-3-fluoro-benzenesulfonamide (P-1976), N-[3-[5-(2-dimethylaminothiazol-4-yl)-1H-pyrrolo[2,3-b]pyridine-3-carbonyl]-2,4-difluoro-phenyl]-3-fluoro-benzenesulfonamide (P-1977), N-[2,4-difluoro-3-[5-(2-pyrazol-1-ylthiazol-4-yl)-1H-pyrrolo[2,3-b]pyridine-3-carbonyl]phenyl]-3-fluoro-benzenesulfonamide (P-1978), N-[2,4-difluoro-3-[5-(2-imidazol-1-ylthiazol-5-yl)-1H-pyrrolo[2,3-b]pyridine-3-carbonyl]phenyl]-3-fluoro-benzenesulfonamide (P-1979), N-[2,4-difluoro-3-[5-[2-(2-methylimidazol-1-yl)thiazol-5-yl]-1H-pyrrolo[2,3-b]pyridine-3-carbonyl]phenyl]-3-fluoro-benzenesulfonamide (P-1980), N-[2,4-difluoro-3-[5-(2-imidazol-1-ylthiazol-4-yl)-1H-pyrrolo[2,3-b]pyridine-3-carbonyl]phenyl]-3-fluoro-benzenesulfonamide (P-1981), N-[2,4-difluoro-3-[5-(2-pyrazol-1-ylthiazol-5-yl)-1H-pyrrolo[2,3-b]pyridine-3-carbonyl]phenyl]-3-fluoro-benzenesulfonamide (P-1982), N-[2,4-difluoro-3-[5-[2-(2-oxopyrrolidin-1-yl)thiazol-4-yl]-1H-pyrrolo[2,3-b]pyridine-3-carbonyl]phenyl]-3-fluoro-benzenesulfonamide (P-1983), N-[2,4-difluoro-3-[5-[2-(3-pyridyl)thiazol-4-yl]-1H-pyrrolo[2,3-b]pyridine-3-carbonyl]phenyl]-3-fluoro-benzenesulfonamide (P-1984), N-[2,4-difluoro-3-[5-[2-(4-methylimidazol-1-yl)thiazol-5-yl]-1H-pyrrolo[2,3-b]pyridine-3-carbonyl]phenyl]-3-fluoro-benzenesulfonamide (P-1985), N-[2,4-difluoro-3-[5-[5-(3-pyridyl)-2-thienyl]-1H-pyrrolo[2,3-b]pyridine-3-carbonyl]phenyl]-3-fluoro-benzenesulfonamide (P-1986), N-[2,4-difluoro-3-[5-[5-(1H-pyrazol-3-yl)-2-thienyl]-1H-pyrrolo[2,3-b]pyridine-3-carbonyl]phenyl]-3-fluoro-benzenesulfonamide (P-1987), 5-[3-[2,6-difluoro-3-[(3-fluorophenyl)sulfonylamino]benzoyl]-1H-pyrrolo[2,3-b]pyridin-5-yl]thiophene-2-sulfonamide (P-1988), N-[2,4-difluoro-3-[5-[5-(5-methyl-1,2,4-oxadiazol-3-yl)-2-thienyl]-1H-pyrrolo[2,3-b]pyridine-3-carbonyl]phenyl]-3-fluoro-benzenesulfonamide (P-1989), N-[2,4-difluoro-3-[5-(5-thiazol-2-yl-2-thienyl)-1H-pyrrolo[2,3-b]pyridine-3-carbonyl]phenyl]-3-fluoro-benzenesulfonamide (P-1990), N-[2,4-difluoro-3-[5-[5-(1H-pyrazol-3-yl)-2-thienyl]-1H-pyrrolo[2,3-b]pyridine-3-carbonyl]phenyl]-3-fluoro-benzenesulfonamide (P-1991), N-[2,4-difluoro-3-[5-(2-pyridyl)-1H-pyrrolo[2,3-b]pyridine-3-carbonyl]phenyl]-3-fluoro-benzenesulfonamide (P-1992), N-[3-[5-[2-(cyclopropylamino)pyrimidin-5-yl]-1H-pyrrolo[2,3-b]pyridine-3-carbonyl]-2,4-difluoro-phenyl]-3-fluoro-benzenesulfonamide (P-1993), N-[2,4-difluoro-3-[5-[2-(2-methoxyethylamino)pyrimidin-5-yl]-1H-pyrrolo[2,3-b]pyridine-3-carbonyl]phenyl]-3-fluoro-benzenesulfonamide (P-1994), N-[2,4-difluoro-3-[5-[2-(3-pyridyloxy)pyrimidin-5-yl]-1H-pyrrolo[2,3-b]pyridine-3-carbonyl]phenyl]-3-fluoro-benzenesulfonamide (P-1995), N-[2,4-difluoro-3-[5-[2-(trifluoromethoxy)pyrimidin-5-yl]-1H-pyrrolo[2,3-b]pyridine-3-carbonyl]phenyl]-3-fluoro-benzenesulfonamide (P-1996), N-[3-[5-(2-cyanopyrimidin-5-yl)-1H-pyrrolo[2,3-b]pyridine-3-carbonyl]-2,4-difluoro-phenyl]-3-fluoro-benzenesulfonamide (P-1997), N-[2,4-difluoro-3-[5-(2-imidazol-1-ylpyrimidin-5-yl)-1H-pyrrolo[2,3-b]pyridine-3-carbonyl]phenyl]-3-fluoro-benzenesulfonamide (P-1998), N-[3-[5-[2-(azetidin-1-yl)pyrimidin-5-yl]-1H-pyrrolo[2,3-b]pyridine-3-carbonyl]-2,4-difluoro-phenyl]-3-fluoro-benzenesulfonamide (P-1999), N-[2,4-difluoro-3-[5-[2-(isopropylamino)pyrimidin-5-yl]-1H-pyrrolo[2,3-b]pyridine-3-carbonyl]phenyl]-3-fluoro-benzenesulfonamide (P-2000), N-[2,4-difluoro-3-[5-(2-methylaminopyrimidin-5-yl)-1H-pyrrolo[2,3-b]pyridine-3-carbonyl]phenyl]-3-fluoro-benzenesulfonamide (P-2001), N-[3-[5-[2-(2-dimethylaminoethylamino)pyrimidin-5-yl]-1H-pyrrolo[2,3-b]pyridine-3-carbonyl]-2,4-difluoro-phenyl]-3-fluoro-benzenesulfonamide (P-2002), N-[2,4-difluoro-3-[5-[2-(3-methoxypropylamino)pyrimidin-5-yl]-1H-pyrrolo[2,3-b]pyridine-3-carbonyl]phenyl]-3-fluoro-benzenesulfonamide (P-2003), N-[2,4-difluoro-3-[5-[2-(isopropylamino)pyrimidin-5-yl]-1H-pyrrolo[2,3-b]pyridine-3-carbonyl]phenyl]-3-fluoro-benzenesulfonamide (P-2004), N-[2,4-difluoro-3-[5-(1-oxoisoindolin-5-yl)-1H-pyrrolo[2,3-b]pyridine-3-carbonyl]phenyl]-3-fluoro-benzenesulfonamide (P-2005), N-[2,4-difluoro-3-[5-(3-oxoisoindolin-5-yl)-1H-pyrrolo[2,3-b]pyridine-3-carbonyl]phenyl]-3-fluoro-benzenesulfonamide (P-2006), N-[2,4-difluoro-3-[5-(2-oxoindolin-5-yl)-1H-pyrrolo[2,3-b]pyridine-3-carbonyl]phenyl]-3-fluoro-benzenesulfonamide (P-2007), and any pharmaceutically acceptable salt thereof.

The following table indicates the halo-heteroaryl compound (column 2) used to afford the desired compound (column 3). The compound number is provided in column 1, and the observed mass is in column 4.

| Compound number | halo-heteroaryl used in step 3 | Compound | MS (ESI) [M + H$^+$]$^+$ |
|---|---|---|---|
| P-0018 | 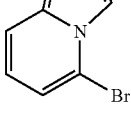 | 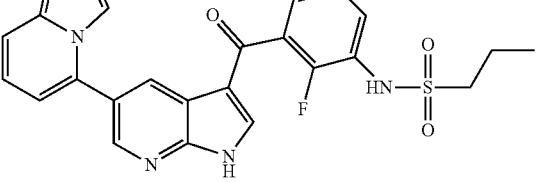 | 495.95 |
| P-0019 | 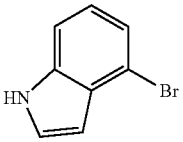 | 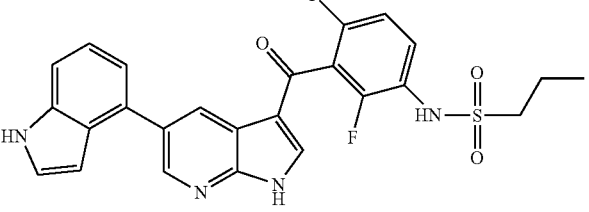 | 495.5 |
| P-0020 | 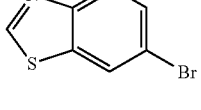 | 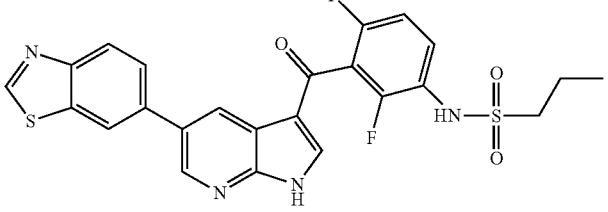 | 513.5 |
| P-0021 | 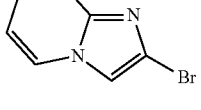 | 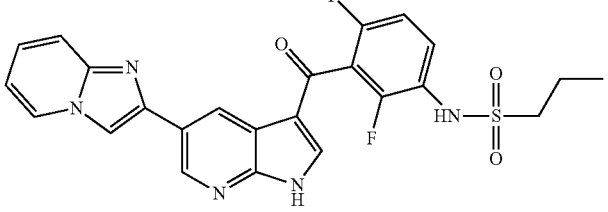 | 496.5 |
| P-0022 | 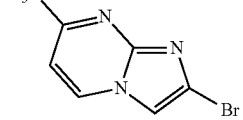 | 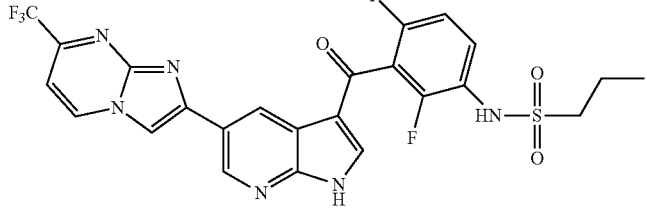 | 565.5 |

-continued

| Compound number | halo-heteroaryl used in step 3 | Compound | MS (ESI) [M + H⁺]⁺ |
|---|---|---|---|
| P-0023 | 5-bromo-3-methyl-1H-indole | | 509.5 |
| P-0024 | 5-bromo-3-methyl-1H-indazole | | 510.5 |
| P-0025 | 7-bromoquinazoline | | 526.5 |
| P-0026 | 6-bromoquinazoline | | 526.5 |
| P-0027 | 6-bromo-1-methyl-1H-indazole | | 510.5 |
| P-0028 | 5-bromo-1-methyl-1H-indazole | | 510.5 |

-continued

| Compound number | halo-heteroaryl used in step 3 | Compound | MS (ESI) [M + H⁺]⁺ |
|---|---|---|---|
| P-0029 | | | |
| P-0030 | | | |
| P-0031 | | | |
| P-0032 | | | |
| P-0033 | | | 507.0 |
| P-0034 | | | 507.0 |

-continued

| Compound number | halo-heteroaryl used in step 3 | Compound | MS (ESI) [M + H+]+ |
|---|---|---|---|
| P-0035 | | | |
| P-0036 | | | |
| P-0037 | | | |
| P-0038 | | | 514.0 |
| P-0039 | | | 510.0 |
| P-0044 | | | 530.0 |

-continued

| Compound number | halo-heteroaryl used in step 3 | Compound | MS (ESI) [M + H+]+ |
|---|---|---|---|
| P-1006 | | | 542.5 |
| P-1007 | | | 632.5 |
| P-1008 | | | 514.5 |
| P-1013 | | | |
| P-1014 | | | |

-continued

| Compound number | halo-heteroaryl used in step 3 | Compound | MS (ESI) [M + H+]+ |
|---|---|---|---|
| P-1015 | | | 524.5 |
| P-1102 | | | 506.0 |
| P-1103 | | | 529.0 |
| P-1104 | | | 529.0 |
| P-1105 | | | 543.5 |
| P-1106 | | | 529.0 |

-continued
| Compound number | halo-heteroaryl used in step 3 | Compound | MS (ESI) [M + H⁺]⁺ |
|---|---|---|---|
| P-1109 | 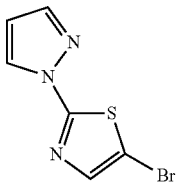 [SMILES: Brc1cnc(-n2cccn2)s1] | 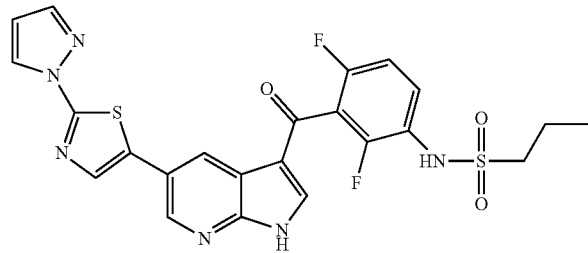 [SMILES: CCCS(=O)(=O)Nc1ccc(F)c(C(=O)c2c[nH]c3ncc(-c4cnc(-n5cccn5)s4)cc23)c1F] | 529.0 |
| P-1115 | 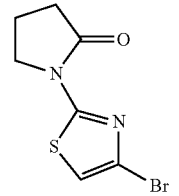 [SMILES: O=C1CCCN1c1nc(Br)cs1] | 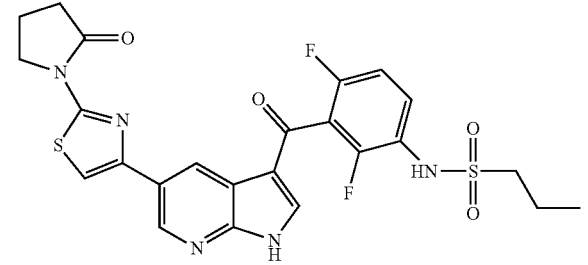 [SMILES: CCCS(=O)(=O)Nc1ccc(F)c(C(=O)c2c[nH]c3ncc(-c4csc(N5CCCC5=O)n4)cc23)c1F] | |
| P-1116 | 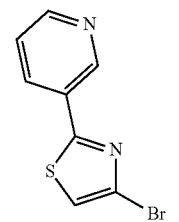 [SMILES: Brc1csc(-c2cccnc2)n1] | 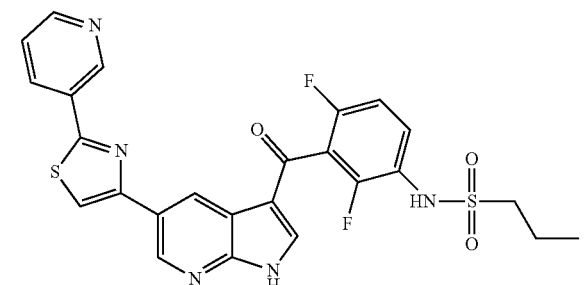 | 540.5 |
| P-1117 | 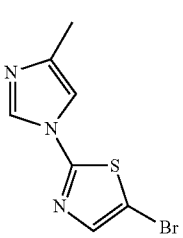 | 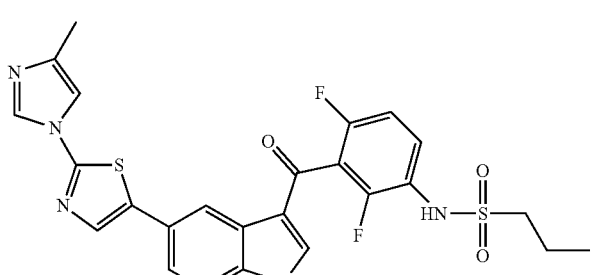 | |
| P-1200 | 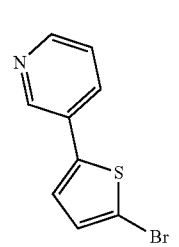 [SMILES: Brc1ccc(-c2cccnc2)s1] | 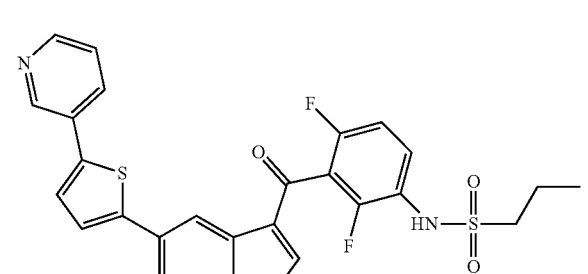 | 539.5 |

-continued
| Compound number | halo-heteroaryl used in step 3 | Compound | MS (ESI) [M + H+]+ |
|---|---|---|---|
| P-1201 | 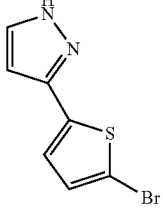 | 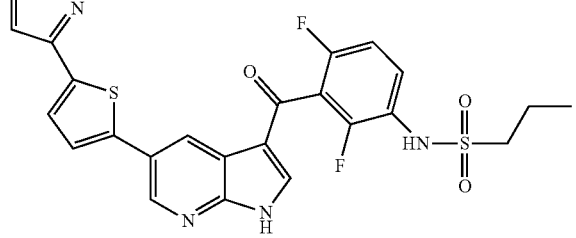 | 528.0 |
| P-1202 | 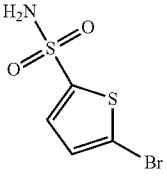 | 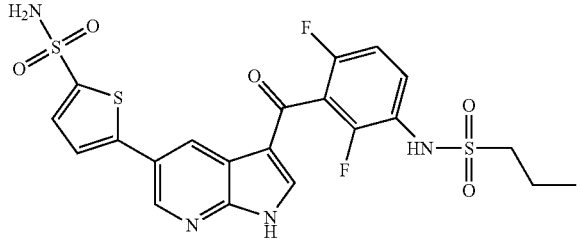 [SMILES: CCCS(=O)(=O)Nc1ccc(F)c(C(=O)c2c[nH]c3ncc(-c4ccc(S(N)(=O)=O)s4)cc23)c1F] | 541.0 |
| P-1203 | 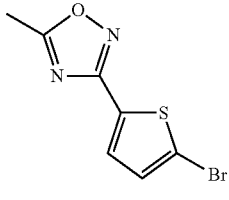 | 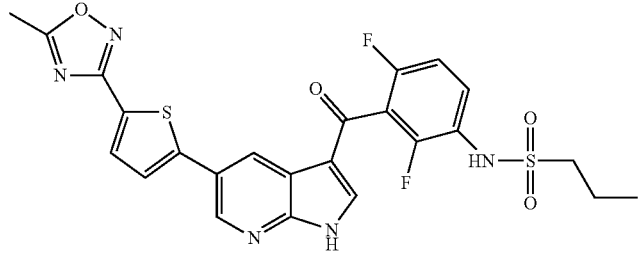 [SMILES: CCCS(=O)(=O)Nc1ccc(F)c(C(=O)c2c[nH]c3ncc(-c4ccc(-c5noc(C)n5)s4)cc23)c1F] | 544.0 |
| P-1204 |  | 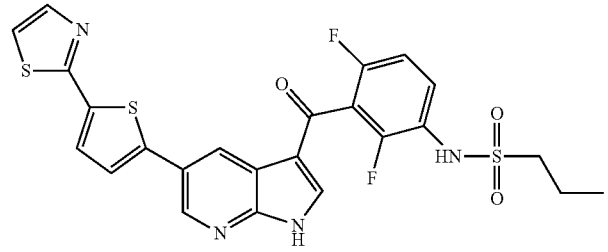 [SMILES: CCCS(=O)(=O)Nc1ccc(F)c(C(=O)c2c[nH]c3ncc(-c4ccc(-c5nccs5)s4)cc23)c1F] | |
| P-1205 | 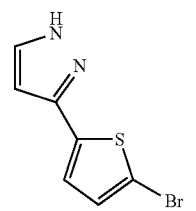 | 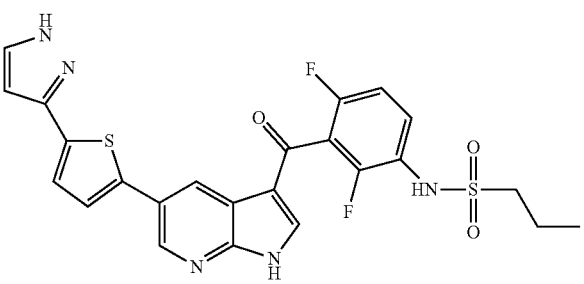 | |
| P-1401 | 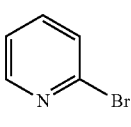 | 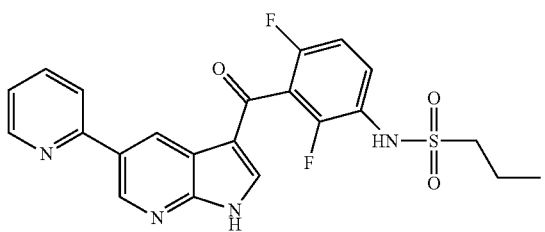 [SMILES: CCCS(=O)(=O)Nc1ccc(F)c(C(=O)c2c[nH]c3ncc(-c4ccccn4)cc23)c1F] | 457.5 |

-continued
| Compound number | halo-heteroaryl used in step 3 | Compound | MS (ESI) [M + H⁺]⁺ |
|---|---|---|---|
| P-1504 | 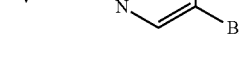 |  | 513.5 |
| P-1505 | 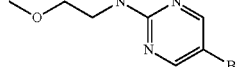 | 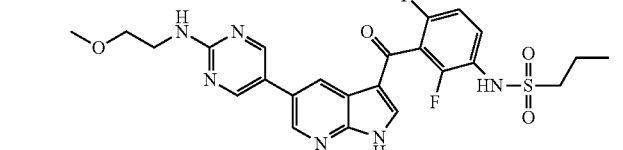 | 531.5 |
| P-1508 | 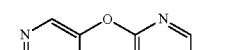 | 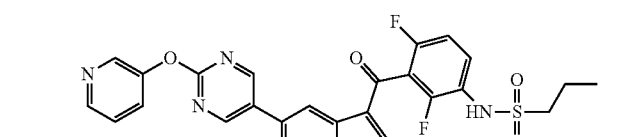 | |
| P-1509 |  | 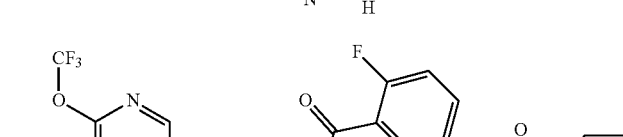 | |
| P-1510 |  | 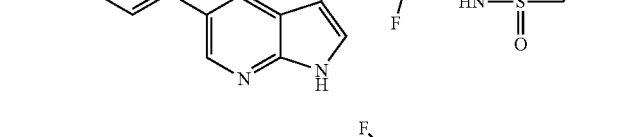 | |
| P-1511 | 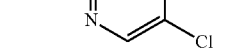 | 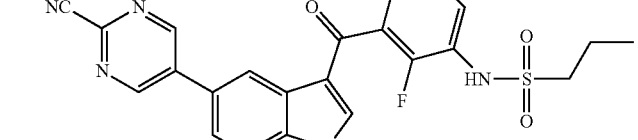 | 524.5 |
| P-1512 |  | 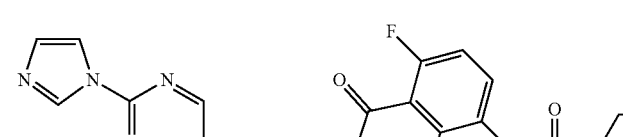 | 513.5 |

-continued

| Compound number | halo-heteroaryl used in step 3 | Compound | MS (ESI) [M + H⁺]⁺ |
|---|---|---|---|
| P-1513 | | | |
| P-1514 | | | 487.5 |
| P-1515 | | | 544.5 |
| P-1516 | | | 545.5 |
| P-1517 | | | 515.5 |
| P-1701 | | | 511.5 |
| P-1702 | | | 511.5 |

-continued

| Compound number | halo-heteroaryl used in step 3 | Compound | MS (ESI) [M + H⁺]⁺ |
|---|---|---|---|
| P-1703 | | | 511.5 |
| P-1948 | | | |
| P-1949 | | | |
| P-1950 | | | |
| P-1951 | | | |
| P-1952 | | | |

| Compound number | halo-heteroaryl used in step 3 | Compound | MS (ESI) [M + H+]+ |
|---|---|---|---|
| P-1953 | 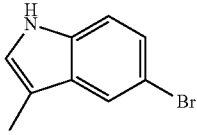 | 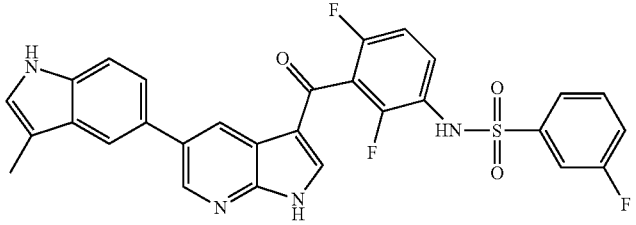 [SMILES: Cc1c[nH]c2ccc(-c3cnc4[nH]cc(C(=O)c5c(F)ccc(NS(=O)(=O)c6cccc(F)c6)c5F)c4c3)cc12] | |
| P-1954 | 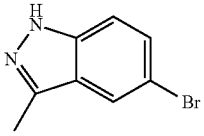 | 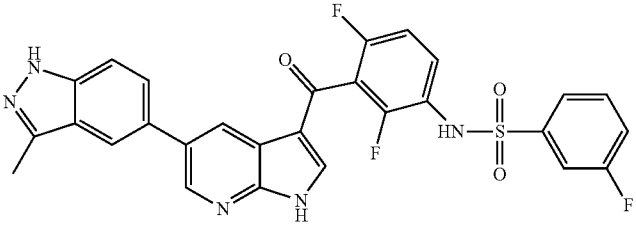 [SMILES: Cc1n[nH]c2ccc(-c3cnc4[nH]cc(C(=O)c5c(F)ccc(NS(=O)(=O)c6cccc(F)c6)c5F)c4c3)cc12] | |
| P-1955 | 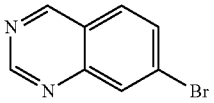 | 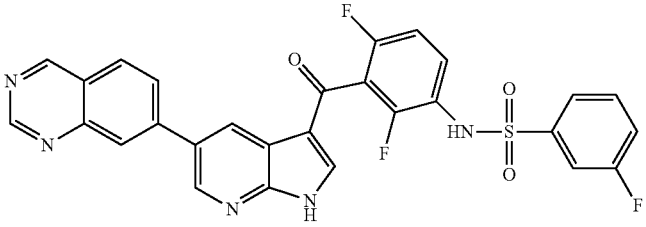 [SMILES: O=C(c1c(F)ccc(NS(=O)(=O)c2cccc(F)c2)c1F)c1c[nH]c2ncc(-c3ccc4cncnc4c3)cc12] | |
| P-1956 | 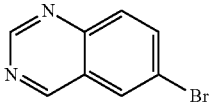 | 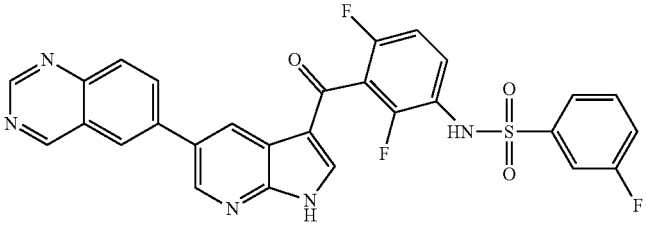 [SMILES: O=C(c1c(F)ccc(NS(=O)(=O)c2cccc(F)c2)c1F)c1c[nH]c2ncc(-c3ccc4ncncc4c3)cc12] | |
| P-1957 | 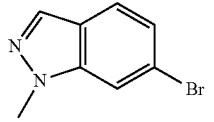 | 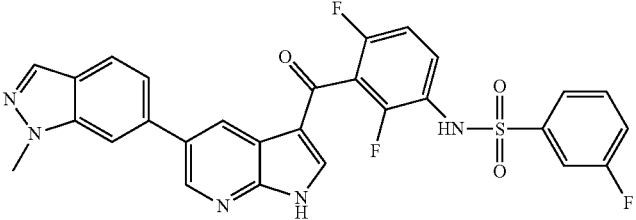 [SMILES: Cn1ncc2ccc(-c3cnc4[nH]cc(C(=O)c5c(F)ccc(NS(=O)(=O)c6cccc(F)c6)c5F)c4c3)cc21] | |
| P-1958 | 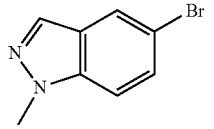 | 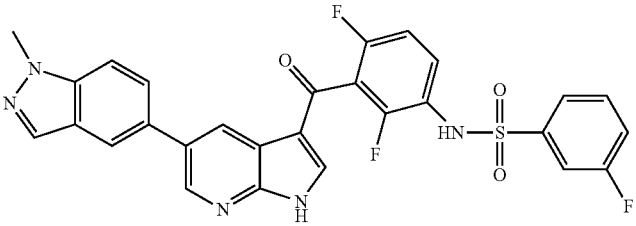 [SMILES: Cn1ncc2cc(-c3cnc4[nH]cc(C(=O)c5c(F)ccc(NS(=O)(=O)c6cccc(F)c6)c5F)c4c3)ccc21] | |

-continued

| Compound number | halo-heteroaryl used in step 3 | Compound | MS (ESI) [M + H+]+ |
|---|---|---|---|
| P-1959 | | | |
| P-1960 | | | |
| P-1961 | | | |
| P-1962 | | | |
| P-1963 | | | |
| P-1964 | | | |
| P-1965 | | | |

-continued

| Compound number | halo-heteroaryl used in step 3 | Compound | MS (ESI) [M + H+]+ |
|---|---|---|---|
| P-1966 | | | |
| P-1967 | | | |
| P-1968 | | | |
| P-1969 | | | |
| P-1970 | | | |
| P-1971 | | | |

-continued
| Compound number | halo-heteroaryl used in step 3 | Compound | MS (ESI) [M + H⁺]⁺ |
|---|---|---|---|
| P-1972 | 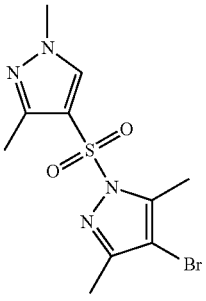 [SMILES: Cc1nn(C)cc1S(=O)(=O)n1nc(C)c(Br)c1C] | 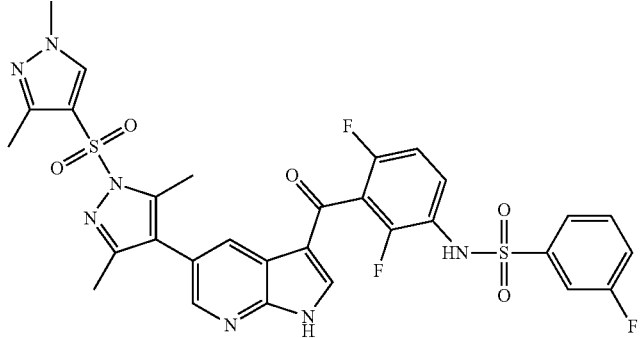 [SMILES: Cc1nn(C)cc1S(=O)(=O)n1nc(C)c(-c2cnc3[nH]cc(C(=O)c4c(F)ccc(NS(=O)(=O)c5cccc(F)c5)c4F)c3c2)c1C] | |
| P-1973 | 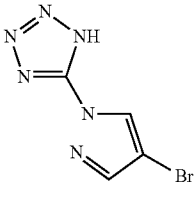 | 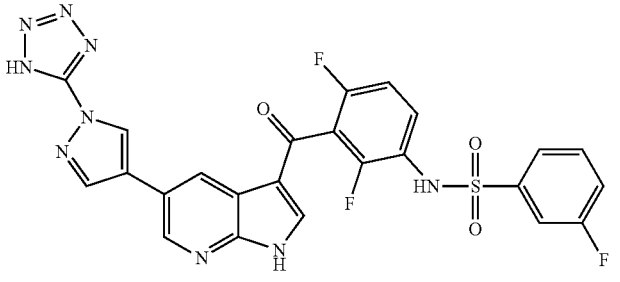 [SMILES: O=C(c1c(F)ccc(NS(=O)(=O)c2cccc(F)c2)c1F)c1c[nH]c2ncc(-c3cnn(-c4nnn[nH]4)c3)cc12] | |
| P-1974 | 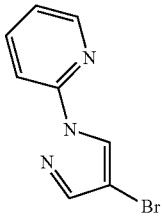 [SMILES: N=C/C(Br)=C\Nc1ccccn1] | 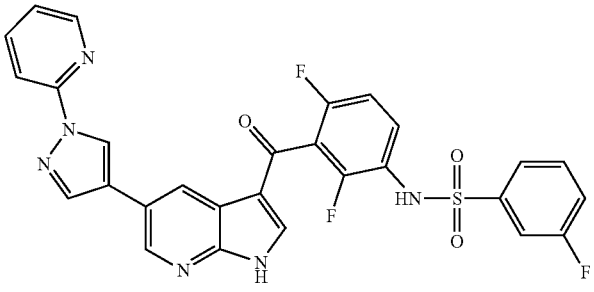 [SMILES: O=C(c1c(F)ccc(NS(=O)(=O)c2cccc(F)c2)c1F)c1c[nH]c2ncc(-c3cnn(-c4ccccn4)c3)cc12] | |
| P-1975 | 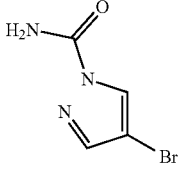 | 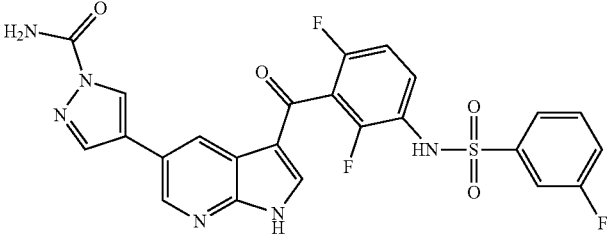 [SMILES: NC(=O)n1cc(-c2cnc3[nH]cc(C(=O)c4c(F)ccc(NS(=O)(=O)c5cccc(F)c5)c4F)c3c2)cn1] | |
| P-1976 | 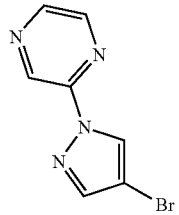 [SMILES: Brc1cnn(-c2cnccn2)c1] | 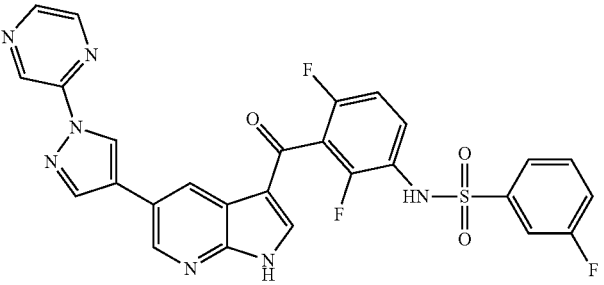 [SMILES: O=C(c1c(F)ccc(NS(=O)(=O)c2cccc(F)c2)c1F)c1c[nH]c2ncc(-c3cnn(-c4cnccn4)c3)cc12] | |

-continued
| Compound number | halo-heteroaryl used in step 3 | Compound | MS (ESI) [M + H+]+ |
|---|---|---|---|
| P-1977 | 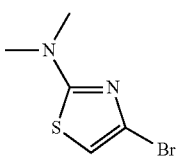 | 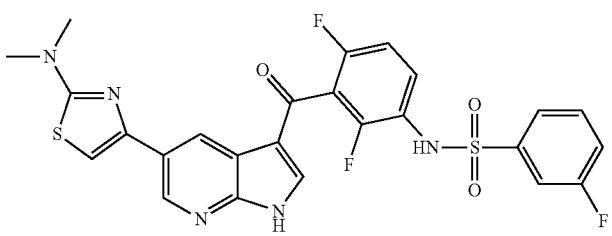 [SMILES: CN(C)c1nc(-c2cnc3[nH]cc(C(=O)c4c(F)ccc(NS(=O)(=O)c5cccc(F)c5)c4F)c3c2)cs1] | |
| P-1978 | 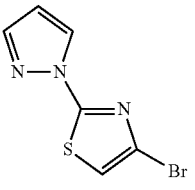 [SMILES: Brc1csc(-n2cccn2)n1] | 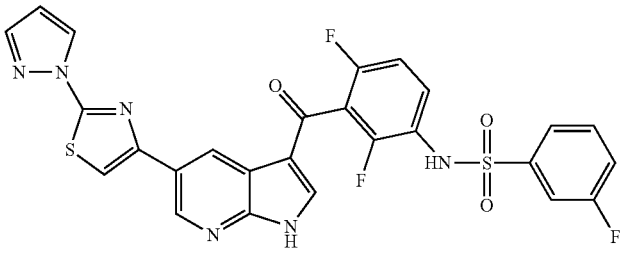 [SMILES: O=C(c1c(F)ccc(NS(=O)(=O)c2cccc(F)c2)c1F)c1c[nH]c2ncc(-c3csc(-n4cccn4)n3)cc12] | |
| P-1979 | 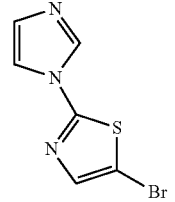 [SMILES: Brc1cnc(-n2ccnc2)s1] | 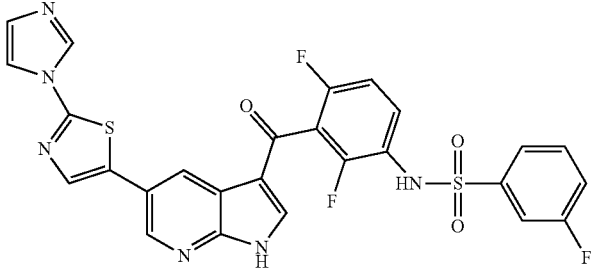 [SMILES: O=C(c1c(F)ccc(NS(=O)(=O)c2cccc(F)c2)c1F)c1c[nH]c2ncc(-c3cnc(-n4ccnc4)s3)cc12] | |
| P-1980 | 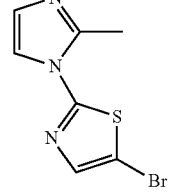 | 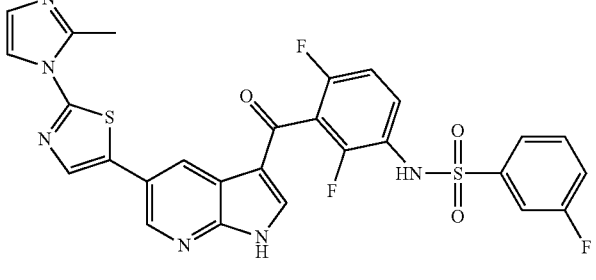 | |
| P-1981 | 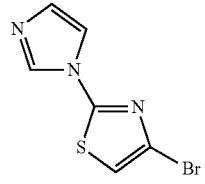 [SMILES: Brc1csc(-n2ccnc2)n1] | 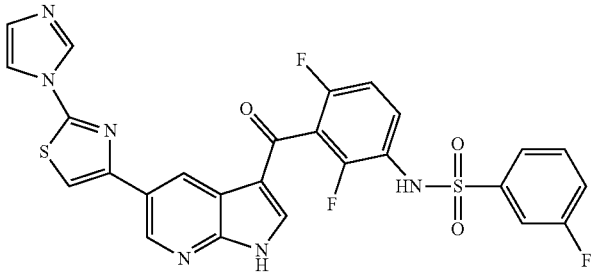 [SMILES: O=C(c1c(F)ccc(NS(=O)(=O)c2cccc(F)c2)c1F)c1c[nH]c2ncc(-c3csc(-n4ccnc4)n3)cc12] | |

-continued

| Compound number | halo-heteroaryl used in step 3 | Compound | MS (ESI) [M + H⁺]⁺ |
|---|---|---|---|
| P-1982 | | | |
| P-1983 | | | |
| P-1984 | | | |
| P-1985 | | | |
| P-1986 | | | |

-continued

| Compound number | halo-heteroaryl used in step 3 | Compound | MS (ESI) [M + H+]+ |
|---|---|---|---|
| P-1987 | | | |
| P-1988 | | | |
| P-1989 | | | |
| P-1990 | | | |
| P-1991 | | | |
| P-1992 | | | |

| Compound number | halo-heteroaryl used in step 3 | Compound | MS (ESI) [M + H⁺]⁺ |
|---|---|---|---|
| P-1993 | 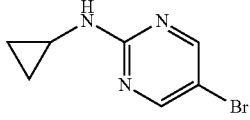 [SMILES: Brc1cnc(NC2CC2)nc1] | 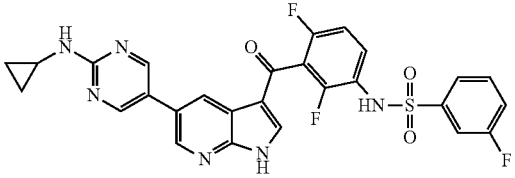 [SMILES: O=C(c1c(F)ccc(NS(=O)(=O)c2cccc(F)c2)c1F)c1c[nH]c2ncc(-c3cnc(NC4CC4)nc3)cc12] | |
| P-1994 | 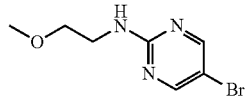 | 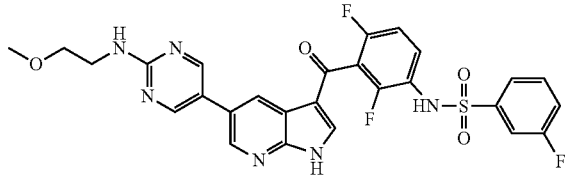 [SMILES: COCCNc1ncc(-c2cnc3[nH]cc(C(=O)c4c(F)ccc(NS(=O)(=O)c5cccc(F)c5)c4F)c3c2)cn1] | |
| P-1995 | 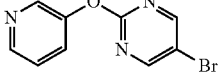 | 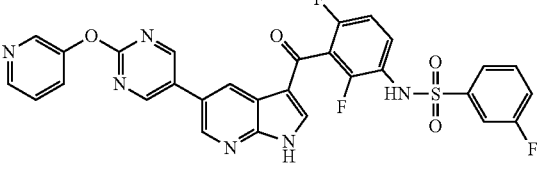 | |
| P-1996 | 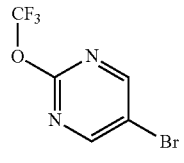 | 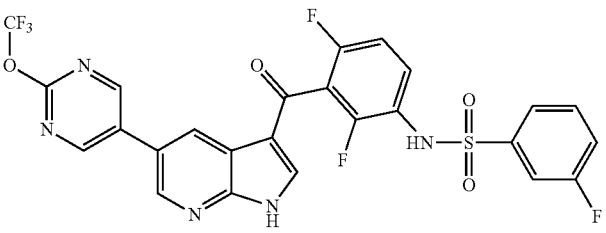 [SMILES: O=C(c1c(F)ccc(NS(=O)(=O)c2cccc(F)c2)c1F)c1c[nH]c2ncc(-c3cnc(OC(F)(F)F)nc3)cc12] | |
| P-1997 | 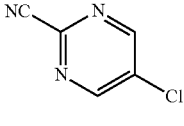 | 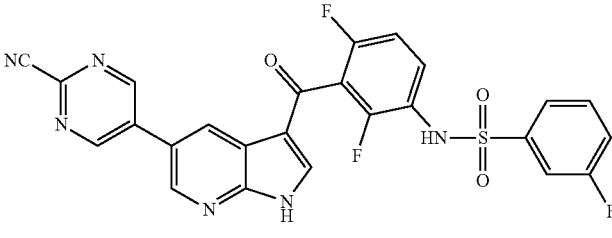 [SMILES: N#Cc1ncc(-c2cnc3[nH]cc(C(=O)c4c(F)ccc(NS(=O)(=O)c5cccc(F)c5)c4F)c3c2)cn1] | |
| P-1998 | 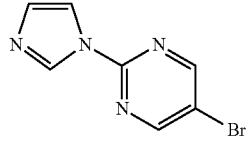 [SMILES: Brc1cnc(-n2ccnc2)nc1] |  | |
| P-1999 | 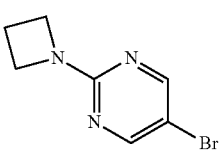 [SMILES: Brc1cnc(N2CCC2)nc1] | 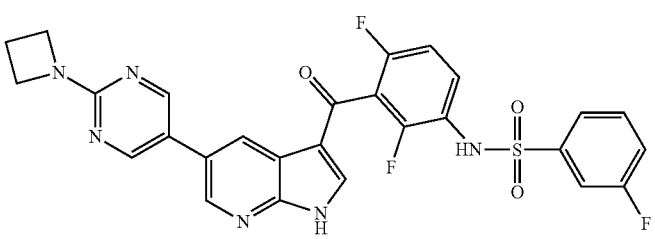 [SMILES: O=C(c1c(F)ccc(NS(=O)(=O)c2cccc(F)c2)c1F)c1c[nH]c2ncc(-c3cnc(N4CCC4)nc3)cc12] | |

-continued

| Compound number | halo-heteroaryl used in step 3 | Compound | MS (ESI) [M + H⁺]⁺ |
|---|---|---|---|
| P-2000 | | | |
| P-2001 | | | |
| P-2002 | | | |
| P-2003 | | | |
| P-2004 | | | |
| P-2005 | | | |
| P-2006 | | | |

| Compound number | halo-heteroaryl used in step 3 | Compound | MS (ESI) [M + H⁺]⁺ |
|---|---|---|---|
| P-2007 | 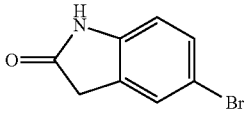 [SMILES: O=C1Cc2cc(Br)ccc2N1] | 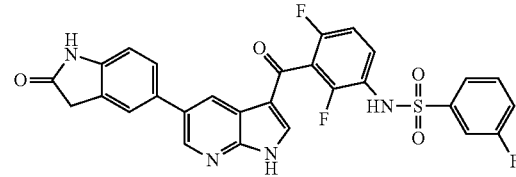 [SMILES: O=C1Cc2cc(-c3cnc4[nH]cc(C(=O)c5c(F)ccc(NS(=O)(=O)c6cccc(F)c6)c5F)c4c3)ccc2N1] | |

Example 4

Synthesis of propane-1-sulfonic acid {2,4-difluoro-3-[5-(1-piperidin-4-yl-1H-pyrazol-4-yl)-1H-pyrrolo[2,3-b]pyridine-3-carbonyl]-phenyl}-amide P-1002

Propane-1-sulfonic acid {2,4-difluoro-3-[5-(1-piperidin-4-yl-1H-pyrazol-4-yl)-1H-pyrrolo[2,3-b]pyridine-3-carbonyl]-phenyl}-amide P-1002 is prepared in two steps from propane-1-sulfonic acid [3-(5-bromo-1H-pyrrolo[2,3-b]pyridine-3-carbonyl)-2,4-difluoro-phenyl]-amide 9 and 4-[4-(4,4,5,5-tetramethyl-[1,3,2]dioxaborolan-2-yl)-pyrazol-1-yl]-piperidine-1-carboxylic acid tert-butyl ester 34 as shown in Scheme 4.

Scheme 4

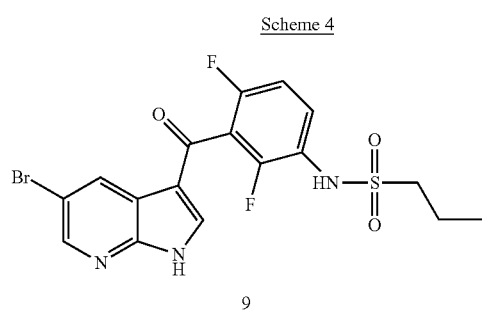

+

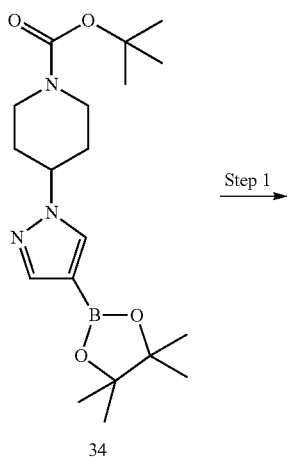

Step 1 →

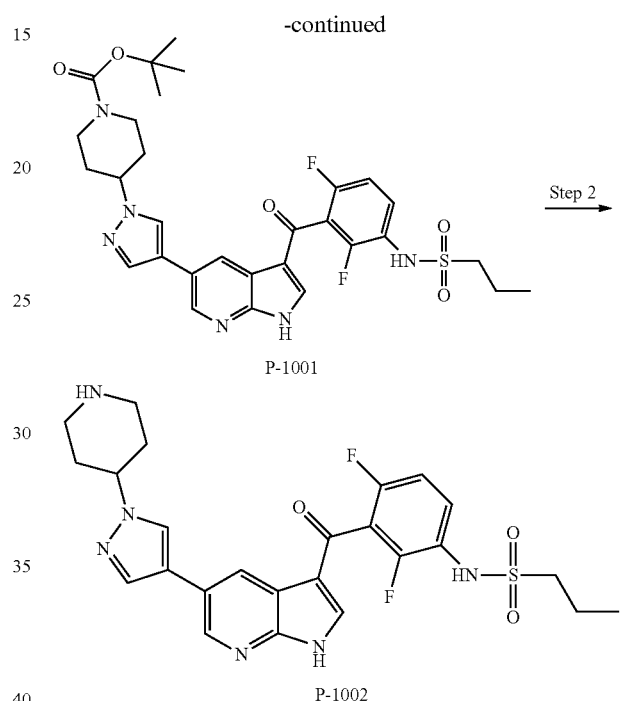

Step 1—Preparation of 4-(4-{3-[2,6-difluoro-3-(propane-1-sulfonylamino)-benzoyl]-1H-pyrrolo[2,3-b]pyridin-5-yl}-pyrazol-1-yl)-piperidine-1-carboxylic acid tert-butyl ester (P-1001)

In a 10 mL microwave vial, propane-1-sulfonic acid [3-(5-bromo-1H-pyrrolo[2,3-b]pyridine-3-carbonyl)-2,4-difluoro-phenyl]-amide (9, 51.0 mg, 0.111 mmol) and 4-[4-(4,4,5,5-tetramethyl-[1,3,2]dioxaborolan-2-yl)-pyrazol-1-yl]-piperidine-1-carboxylic acid tert-butyl ester (34, 84.2 mg, 0.223 mmol) are combined with 0.680 mL of acetonitrile and potassium carbonate (0.34 mL, 1.00 M in water). 1,1'-bis(diphenylphosphino)ferrocene]dichloropalladium (II) (8.3 mg, 0.011 mmol) is added and the mixture is heated at 160° C. in the microwave for 5 minutes, then diluted with water and extracted with ethyl acetate. The organic layer is washed with water, brine, and dried with magnesium sulfate, filtered and the filtrate concentrated under vacuum. The resulting material is purified by silica gel column chromatography, eluting with ethyl acetate and hexane. Appropriate fractions are combined and concentrated under vacuum to provide the desired compound (P-1001, 47 mg). MS (ESI) [M+H⁺]⁺=629.0.

Step 2—Preparation of propane-1-sulfonic acid (2,4-difluoro-3-[5-(1-piperidin-4-yl-1H-pyrazol-4-yl)-1H-pyrrolo[2,3-b]pyridine-3-carbonyl]-phenyl)-amide (P-1002)

In a reaction flask, 4-(4-{3-[2,6-difluoro-3-(propane-1-sulfonylamino)-benzoyl]-1H-pyrrolo[2,3-b]pyridin-5-yl}-pyrazol-1-yl)-piperidine-1-carboxylic acid tert-butyl ester (P-1001, 42.0 mg, 0.067 mmol) is dissolved in 9.0 mL of dichloromethane and 1.0 mL of trifluoroacetic acid and the reaction is stirred at room temperature for 2 hours. Aqueous saturated sodium bicarbonate is added and the mixture is extracted with ethyl acetate. The aqueous layer is frozen and lyophilized and the residue is suspended in tetrahydrofuran and sonicated. The mixture is filtered twice and the filtrate is concentrated under vacuum. The resulting material is purified by reverse phase HPLC, eluting with acetonitrile/water with 0.1% formic acid, 5-47.5% acetonitrile over 40 minutes. Appropriate fractions are combined and dried by lyophilization to provide the desired compound as a white solid (P-1002, 5.7 mg). MS (ESI) [M+H$^+$]$^+$=529.0.

4-(4-{3-[2,6-Difluoro-3-(4-trifluoromethyl-benzenesulfonylamino)-benzoyl]-1H-pyrrolo[2,3-b]pyridin-5-yl}-pyrazol-1-yl)-piperidine-1-carboxylic acid tert-butyl ester P-1003 and N-{2,4-Difluoro-3-[5-(1-piperidin-4-yl-1H-pyrazol-4-yl)-1H-pyrrolo[2,3-b]pyridine-3-carbonyl]-phenyl}-4-trifluoromethyl-benzenesulfonamide P-1004,

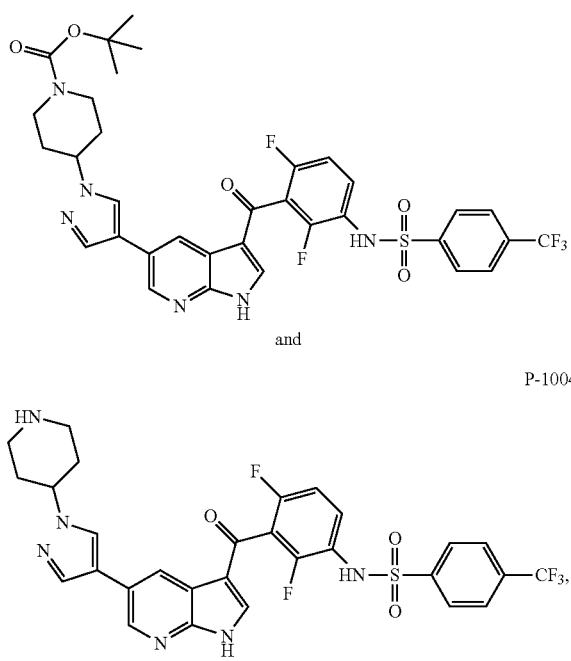

P-1003 and

P-1004 are made similarly to the protocol of Scheme 4, replacing propane-1-sulfonic acid [3-(5-bromo-1H-pyrrolo[2,3-b]pyridine-3-carbonyl)-2,4-difluoro-phenyl]-amide 9 with N-[3-(5-bromo-1H-pyrrolo[2,3-b]pyridine-3-carbonyl)-2,4-difluoro-phenyl]-4-trifluoromethyl-benzenesulfonamide in Step 1. P-1003 is isolated after step 1, MS (ESI) [M+H$^+$]$^+$=731.1. P-1004 is isolated after step 2, suspending in acetonitrile water instead of tetrahydrofuran, and the resulting precipitate is isolated and washed with water to provide the desired compound (P-1004, 121 mg). MS (ESI) [M+H$^+$]$^+$=631.0.

Example 5

Synthesis of N-{3-[2,6-difluoro-3-(propane-1-sulfonylamino)-benzoyl]-1H-pyrrolo[2,3-b]pyridin-5-yl}-nicotinamide P-1800

N-{3-[2,6-Difluoro-3-(propane-1-sulfonylamino)-benzoyl]-1H-pyrrolo[2,3-b]pyridin-5-yl}-nicotinamide P-1800 is prepared in two steps from 1H-pyrrolo[2,3-b]pyridin-5-ylamine 35 and nicotinoyl chloride 36 as shown in Scheme 5.

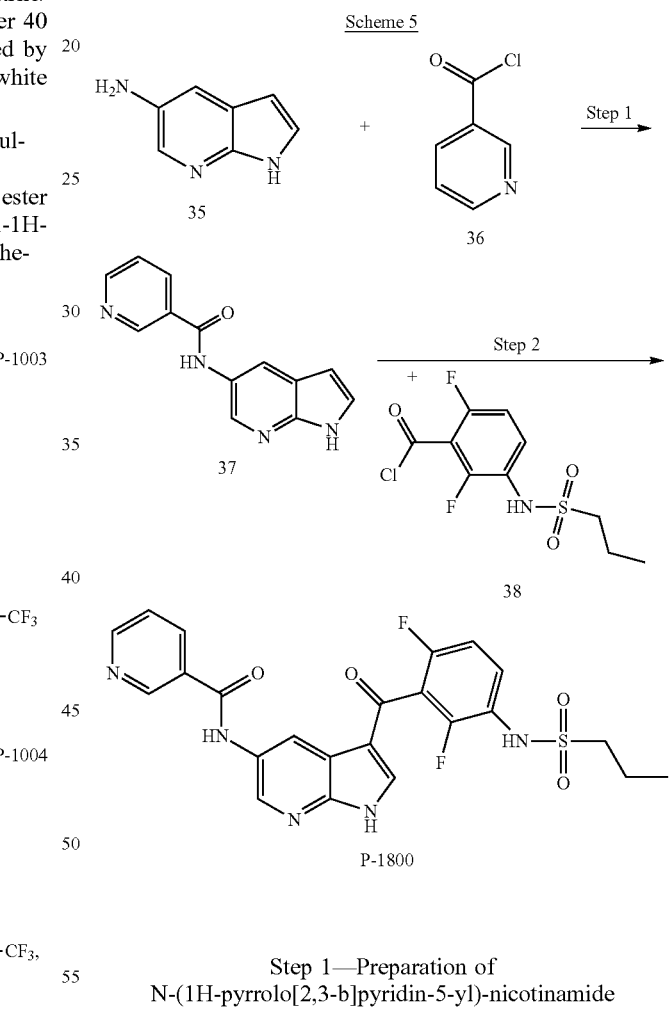

Step 1—Preparation of N-(1H-pyrrolo[2,3-b]pyridin-5-yl)-nicotinamide (37)

In a reaction vial, 1H-Pyrrolo[2,3-b]pyridin-5-ylamine (35, 0.1 g, 0.8 mmol) is dissolved in 7 mL of tetrahydrofuran and triethylamine (0.10 mL, 0.75 mmol) and nicotinoyl chloride (36, 0.16 g, 1.1 mmol) are added. The reaction is stirred at room temperature for 16 hours, then diluted with water and extracted 3× with ethyl acetate. The organic layers are combined and washed with brine, then dried over sodium sulfate, filtered and the filtrate concentrated under vacuum to provide the desired compound.

Step 2—Preparation of N-{3-[2,6-difluoro-3-(propane-1-sulfonylamino)-benzoyl]-1H-pyrrolo[2,3-b]pyridin-5-yl}-nicotinamide (P-1800)

In a reaction vial, N-(1H-pyrrolo[2,3-b]pyridin-5-yl)-nicotinamide (37, 0.050 g, 0.21 mmol) is dissolved in 2 mL of dichloromethane. Aluminum trichloride (0.1 g, 1 mmol) and 2,6-difluoro-3-(propane-1-sulfonylamino)-benzoyl chloride (38, 0.075 g, 0.25 mmol) are added in one portion, and the reaction is stirred at room temperature for 36 hours, then diluted with water and extracted 3× with ethyl acetate. The organic layers are combined and washed 2× with brine, dried over sodium sulfate, filtered and the filtrate concentrated under vacuum. The amide linked at the 5-position is lost, so half the material is mixed with 3 mL of triethylamine in 2 mL of tetrahydrofuran and nicotinoyl chloride (36, 0.036 g, 0.25 mmol) is added and stirred at room temperature overnight. The reaction is diluted with water and extracted 3× with ethyl acetate. The organic layers are combined and washed 2× with brine, dried over sodium sulfate, filtered and the filtrate concentrated under vacuum. The resulting material is further purified by reverse phase chromatography and the resulting material confirmed by LC-MS.

5-Methyl-2,3-dihydro-isoxazole-3-carboxylic acid {3-[2,6-difluoro-3-(propane-1-sulfonylamino)-benzoyl]-1H-pyrrolo[2,3-b]pyridin-5-yl}-amide P-1802 is prepared from the intermediate of the reaction from Scheme 5 step 2 that loses amide at the 5-position, according to the following step 2a.

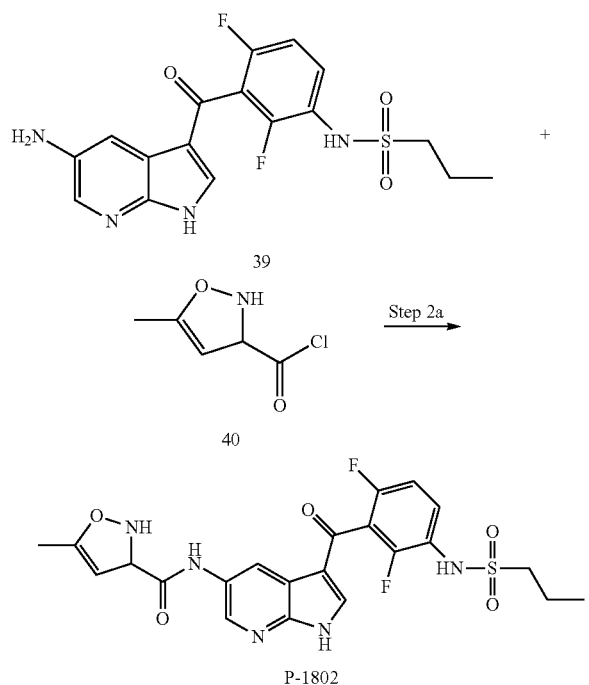

Step 2a—Preparation of 5-methyl-2,3-dihydro-isoxazole-3-carboxylic acid {3-[2,6-difluoro-3-(propane-1-sulfonylamino)-benzoyl]-1H-pyrrolo[2,3-b]pyridin-5-yl}-amide (P-1802)

In a reaction vial, propane-1-sulfonic acid [3-(5-amino-1H-pyrrolo[2,3-b]pyridine-3-carbonyl)-2,4-difluoro-phenyl]-amide (39, crude material e.g. from Scheme 5, step 2) is mixed with triethylamine (0.0363 mL, 0.26 mmol), 5-methyl-2,3-dihydro-isoxazole-3-carbonyl chloride (40, 45.4 mg, 0.312 mmol), 1 mL of tetrahydrofuran, and 1 mL of pyridine. The reaction is stirred at room temperature for 16 hours, then diluted with water, and extracted 3× with ethyl acetate. The combined organic layers are washed 2× with brine, dried with sodium sulfate, filtered and the filtrate concentrated under vacuum. The resulting material is further purified by reverse phase chromatography and the resulting material confirmed by LC-MS.

Example 6

Synthesis of 3-[2,6-difluoro-3-(propane-1-sulfonylamino)-benzoyl]-1H-pyrrolo[2,3-b]pyridine-5-carboxylic acid pyridin-3-ylamide P-1801

3-[2,6-Difluoro-3-(propane-1-sulfonylamino)-benzoyl]-1H-pyrrolo[2,3-b]pyridine-5-carboxylic acid pyridin-3-ylamide P-1801 is prepared in one step from 3-[2,6-difluoro-3-(propane-1-sulfonylamino)-benzoyl]-1H-pyrrolo[2,3-b]pyridine-5-carboxylic acid 41 and pyridin-3-ylamine 42 as shown in Scheme 6.

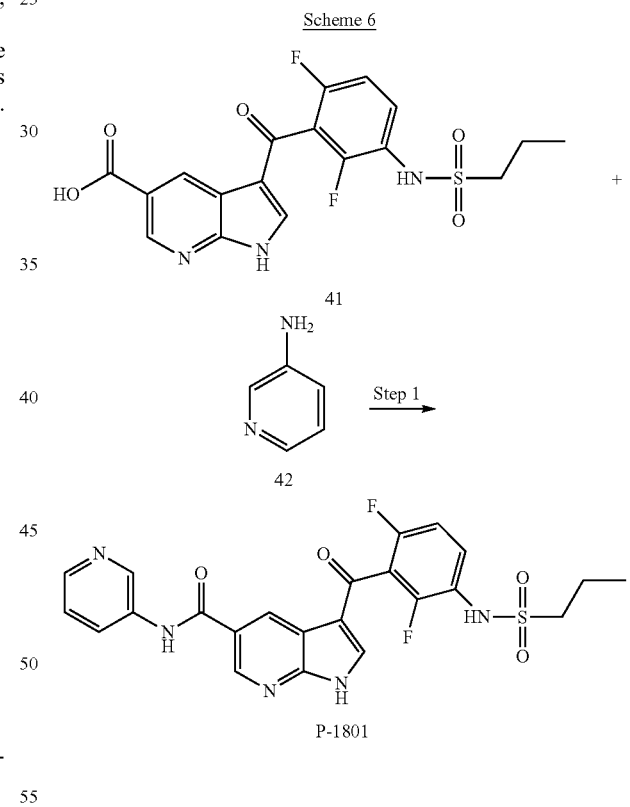

Step 1—Preparation of 3-[2,6-difluoro-3-(propane-1-sulfonylamino)-benzoyl]-1H-pyrrolo[2,3-b]pyridine-5-carboxylic acid pyridin-3-ylamide (P-1801)

In a reaction vial, 3-[2,6-difluoro-3-(propane-1-sulfonylamino)-benzoyl]-1H-pyrrolo[2,3-b]pyridine-5-carboxylic acid (41, 13 mg, 0.031 mmol) is dissolved in 0.5 mL of N,N-dimethylformamide and O-(benzotriazol-1-yl)-N,N,N',N'-tetramethyluronium hexafluorophosphate (17 mg, 0.046 mmol) is added followed by triethylamine (21 μL, 0.15 mmol). The mixture is stirred for 15 minutes, then pyridin-3-ylamine (42, 29 mg, 0.31 mmol) is added and the reaction is stirred at room temperature overnight. The reaction is diluted with water and ethyl acetate. The aqueous phase is separated and extracted with ethyl acetate. The organic layers are combined and dried with sodium sulfate, filtered and the filtrate concentrated under vacuum. The resulting material is purified by reverse phase chromatography to provide the desired compound. MS (ESI) [M+H$^+$]$^+$=500.0.

Example 7

Synthesis of N-{2,4-difluoro-3-[5-(2-methyl-pyrimidin-5-yl)-1H-pyrrolo[2,3-b]pyridine-3-carbonyl]-phenyl}-2-fluoro-benzenesulfonamide P-1520

N-{2,4-Difluoro-3-[5-(2-methyl-pyrimidin-5-yl)-1H-pyrrolo[2,3-b]pyridine-3-carbonyl]-phenyl}-2-fluoro-benzenesulfonamide P-1520 is prepared in five steps from 5-iodo-1H-pyrrolo[2,3-b]pyridine 43 and 2,6-difluoro-3-nitro-benzoyl chloride 44 as shown in Scheme 7.

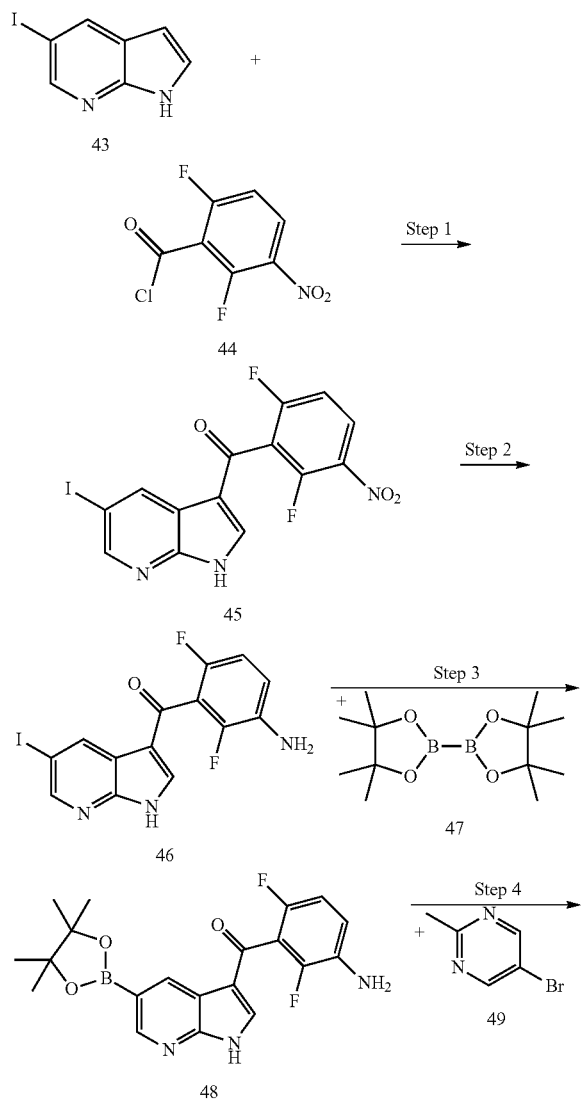

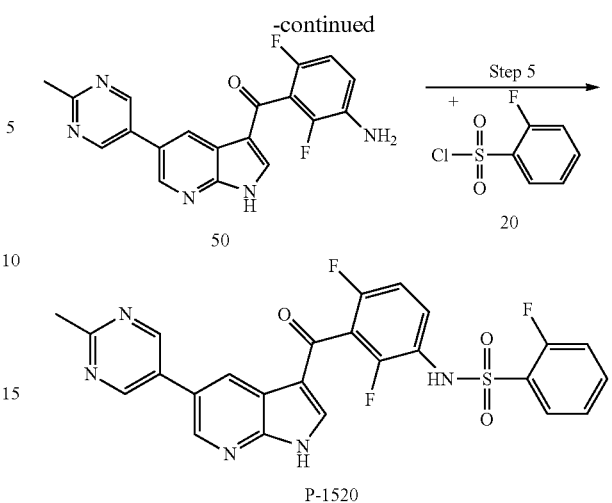

Step 1—Preparation of (2,6-difluoro-3-nitro-phenyl)-(5-iodo-1H-pyrrolo[2,3-b]pyridin-3-yl)-methanone (45)

In a reaction vial, 5-iodo-1H-pyrrolo[2,3-b]pyridine (43, 1.00 g, 4.10 mmol) is mixed with 22 mL of nitromethane and aluminum trichloride (3.28 g, 24.6 mmol) is added. The reaction is stirred at room temperature for 1 hour and 2,6-difluoro-3-nitro-benzoyl chloride (44, 1.36 g, 6.15 mmol) is added. The reaction is heated at 45° C. for 93 hours, then quenched with addition of methanol. The resulting precipitate is collected by filtration to provide the desired compound (45, 1.06 g).

Step 2—Preparation of (3-amino-2,6-difluoro-phenyl)-(5-iodo-1H-pyrrolo[2,3-b]pyridin-3-yl)-methanone (46)

In a reaction vial, (2,6-difluoro-3-nitro-phenyl)-(5-iodo-1H-pyrrolo[2,3-b]pyridin-3-yl)-methanone (45, 0.123 g, 0.287 mmol) is mixed with 5.0 mL of ethyl acetate and 5.0 mL of tetrahydrofuran. Stannous chloride, dehydrate (0.223 g, 0.989 mmol) is added and the reaction is heated at 60° C. for 24 hours. The reaction is poured into a mixture of 25 mL of water and 25 mL of saturated aqueous sodium bicarbonate and treated with celite, then filtered through a bed of celite. The celite is washed with ethyl acetate. The organic layer is separated and washed with brine, dried over sodium sulfate, filtered and the filtrate concentrated under vacuum. The resulting material is purified by silica gel column chromatography, eluting with ethyl acetate and dichloromethane. Appropriate fractions are combined and concentrated under vacuum to provide the desired compound (46, 0.100 g). MS (ESI) [M+H$^+$]$^+$=399.9.

Step 3—Preparation of (3-amino-2,6-difluoro-phenyl)-[5-(4,4,5,5-tetramethyl-[1,3,2]dioxaborolan-2-yl)-1H-pyrrolo[2,3-b]pyridin-3-yl]-methanone (48)

In a reaction vial, (3-amino-2,6-difluoro-phenyl)-(5-iodo-1H-pyrrolo[2,3-b]pyridin-3-yl)-methanone (46, 2 g, 5.01 mmol) and 4,4,5,5,4',4',5',5'-octamethyl-[2,2']bi[[1,3,2]dioxaborolanyl] (47, 1.527 g, 6.01 mmol) in 20.04 mL of dimethylformamide potassium acetate (1.475 g, 15.03 mmol) and [1,1'-bis(diphenylphosphino)ferrocene]dichloropalladium(II) (0.409 g, 0.501 mmol) are added and the mixture is heated at 100° C. overnight. After cooling, the reaction is poured into 20 volumes of water and diluted with ethyl acetate. The mixture is filtered through Celite and the organic layer is separated and concentrated under vacuum to provide a crude oil that slowly solidified upon standing. The solid is triturated with dichloromethane and filtered to provide ~400 mg of the desired compound. The filtrate is also purified by silica gel column chromatography eluting with 0-10% methanol in dichloromethane, then triturated from dichloromethane and combined with the first solid to give the desired compound as an off-white solid (48, 0.90 g, 2.255 mmol, 45.0% yield).

Step 4—Preparation of (3-amino-2,6-difluoro-phenyl)-[5-(2-methyl-pyrimidin-5-yl)-1H-pyrrolo[2,3-b]pyridin-3-yl]-methanone (50)

In a reaction vial, (3-amino-2,6-difluoro-phenyl)-[5-(4,4,5,5-tetramethyl-[1,3,2]dioxaborolan-2-yl)-1H-pyrrolo[2,3-b]pyridin-3-yl]-methanone is combined with (48, 0.850 g, 2.129 mmol), 5-bromo-2-methyl-pyrimidine (49, 0.737 g, 4.26 mmol), potassium carbonate (0.589 g, 4.26 mmol) and [1,1'-bis(diphenylphosphino)ferrocene]dichloropalladium (II) (0.174 g, 0.213 mmol) in 14.20 mL of dioxane and 7.10 mL of water (7.10 mL). The reaction is heated at 100° C. overnight. Upon cooling, the reaction mixture is partitioned between water/brine and ethyl acetate/tetrahydrofuran and then filtered through Celite. The organic layer is separated and concentrated under vacuum. The resulting residue is purified by silica gel column chromatography eluting with 0-10% methanol in dichloromethane to provide the desired compound as a tan solid (50, ~220 mg).

Step 5—Preparation of N-{2,4-difluoro-3-[5-(2-methyl-pyrimidin-5-yl)-1H-pyrrolo[2,3-b]pyridine-3-carbonyl]-phenyl}-2-fluoro-benzenesulfonamide (P-1520)

To (3-amino-2,6-difluoro-phenyl)-[5-(2-methyl-pyrimidin-5-yl)-1H-pyrrolo[2,3-b]pyridin-3-yl]-methanone (50, 0.220 g, 0.602 mmol) in 4.01 mL of tetrahydrofuran, 2-fluoro-benzenesulfonyl chloride (20, 0.352 g, 1.807 mmol) and pyridine (0.146 mL, 1.807 mmol) are added and the reaction is heated at 60° C. overnight. The reaction is partitioned between brine/water and ethyl acetate/tetrahydrofuran. The organic layer is separated and the solvent is removed under vacuum. The resulting residue is purified by silica gel column chromatography eluting with 0-10% methanol in dichloromethane, then triturated with ethyl acetate/heptane to provide the desired compound as a light tan solid (P-1520, 0.130 g, 0.248 mmol, 41.2% yield).

Example 8

Compound Properties

While the inhibitory activity of the compounds on any Raf kinase is important to their activity in treating of disease, the compounds described herein show favorable properties that provide advantages as a pharmaceutical as well. In addition to demonstrating kinase inhibitory activity against each of B-Raf, c-Raf-1 and B-Raf V600E in either biochemical or cell based assays, compounds may show favorable solubility, favorable pharmacokinetic properties, and low Cyp inhibition. The compounds are assessed in the following assays or similar assays available to one skilled in the art.

Assays for biochemical and cell based activity are known in the art, for example, as described in PCT publication WO 2007/002433, the disclosure of which is hereby incorporated by reference as it relates to such assays. For example, the biochemical activity $IC_{50}$ values are determined with respect to inhibition of B-Raf kinase activity, c-Raf-1 kinase activity, or B-Raf V600E kinase activity, where inhibition of phosphorylation of a peptide substrate is measured as a function of compound concentration. Compounds to be tested are diluted in dimethyl sulfoxide to a concentration of 0.1 mM. These are serially diluted 15 µL into 30 µL of dimethyl sulfoxide seven times in 96 well plates for a total of 8 dilution points, and for each dilution point 1 µL is added to a well of an assay plate. Plates are prepared such that each well in a 384 well plate contains 1 µL of compound in 10 µL, volume with 0.1 ng Raf enzyme (i.e. any of B-Raf, c-Raf-1 or B-Raf V600E, Upstate Biotechnology or prepared by methods known to one of skill in the art), 50 mM HEPES, pH 7.0, 50 mM NaCl, 2 mM $MgCl_2$, 1 mM $MnCl_2$, 0.01% Tween-20, 1 mM DTT, and 100 nM biotin-MEK1 as substrate. The reaction is started with addition of 10 µL of 200 µM ATP (i.e. final 100 µM ATP). After incubation of the kinase reaction for 45 minutes at room temperature, 5 µL/well of Stop Solution is added (25 mM Hepes pH 7.5, 100 mM EDTA, 0.01% BSA with donor beads (Streptavidin coated beads, Perkin Elmer), acceptor beads (Protein A coated, Perkin Elmer), and anti phosphor MEK1/2 antibody (CellSignal), each at final concentration 10 µg/mL). The plates are incubated for 3 hours at room temperature and read on Envision reader (Perkin Elmer). Phosphorylation of Mek1 results in binding of the anti-phosphor-MEK1/2 antibody and association of the donor and acceptor beads such that signal correlates with kinase activity. The signal vs. compound concentration is used to determine the $IC_{50}$.

Compounds are assessed in a variety of cell based assays. For example human cell lines with B-Raf V600E mutation (A375 melanoma, SKMEL3 melanoma, and COLO205 colon adenocarcinoma), as well as tumorigenic cell lines with wild-type B-RAF (SW620 colon adenocarcinoma) or with Ras mutations (SKMEL2 melanoma and IPC298 melanoma). Similar assays may be used to assess additional tumorigenic cell lines with Ras mutations, including, but not limited to, M202, M207, M243, M244, M296, S117, HCT116, HCT15, DLD1, MiaPaCa, A549, NCI-H23, NCI-H460, HOP62, MDA-MB231, Hs-578T, HL60, MOLT-4, and CCRF-CEM.

On day 1, cells are counted, then centrifuged in a conical tube for 5 minutes at 1000 rpm. The supernatant is removed and cells are re-suspended as follows:

SW620 (ATCC catalog #CCL-27): resuspend in Leibovitz's L-15 medium, 2 mM L-glutamine, 10% fetal bovine serum to $6 \times 10^4$ cells/mL.

A375 (ATCC catalog #CRL-1619): resuspend in Dulbecco's modified Eagle's medium, 4 mM L-glutamine, 4.5 g/L D-glucose, 10% fetal bovine serum to $6 \times 10^4$ cells/mL.

COLO205 (ATCC catalog #CCL-222): resuspend in RPMI 1640, 2 mM L-glutamine, 1.5 g/L sodium bicarbonate, 4.5 g/L D-glucose, 10 mM HEPES, 1.0 mM sodium pyruvate, 10% fetal bovine serum to $6 \times 10^4$ cells/mL.

SKMEL2 (ATCC catalog #HTB-68): resuspend in Minimum Eagle essential medium, 2 mM L-glutamine, 1.5 g/L sodium bicarbonate, 0.1 mM non-essential amino acids, 1.0 mM sodium pyruvate, 10% fetal bovine serum to $6 \times 10^4$ cells/mL.

SKMEL3 (ATCC catalog #HTB-69): resuspend in McCoy's 5A medium, 1.5 mM L-glutamine, 15% fetal bovine serum to $6\times10^4$ cells/mL.

IPC298 (DSMZ catalog #ACC 251): resuspend in RPMI 1640, 2 mM L-glutamine, 10% fetal bovine serum to $6\times10^4$ cells/mL.

The cells are plated, 50 µL in each well of a 96-well dish (Corning 3610) and incubated at 37° C. in 5% $CO_2$ overnight, cells plated to a final concentration of cells as follows:
SW620: 5,000 cells per well.
A375: 2,000 cells per well.
COLO205: 2,000 cells per well.
SKMEL2: 2,000 cells per well.
SKMEL3: 3,000 cells per well.
IPC298: 2,000 cells per well.

On day 2, compound at a maximum concentration of 5 mM is serially diluted 1:3 (e.g. 10 µL with 30 µL dimethyl sulfoxide) for a total of 8 point titration with DMSO as a control. A 1 µL aliquot of each dilution point and control is added to 249 µL growth media and 50 µL is added to a well containing cells, providing 10 µM compound at the maximum concentration point. The cells are incubated for 3 days at 37° C. in 5% $CO_2$.

On day 5, ATPlite 1 step Luminescence Assay System (Perkin Elmer #6016739) is brought to room temperature along with the cell cultures. ATPlite is added 25 µL to each well, shake for 2 minutes, and the cells are incubated at room temperature for 10 minutes, then luminescence is read on Safire reader. The measured luminescence correlates directly with cell number, such that the reading as a function of compound concentration is used to determine the $IC_{50}$ value.

It is understood that the results of these assays may vary as assay conditions are varied. Inhibition levels determined under the conditions described herein represent a relative activity for the compounds tested under the specific conditions employed. The cell based assays are likely to show variability due to the complexity of the system and the sensitivity thereof to any changes in the assay conditions. As such, some level of inhibition in the cell based assays is indicative of the compounds having some inhibitory activity for those cells, whereas lack of inhibition below the threshold of the highest concentration tested does not necessarily indicate that the compound has no inhibitory activity on the cells, only that under the conditions tested, no inhibition is observed. Results for compounds that are tested and show substantially no inhibition below the highest tested concentration are represented as "-" in the tables below. In some instances, the compounds were not tested in all of the assays, or assay results were not valid, as indicated by NA in the tables below.

The following table provides data indicating the B-Raf, B-Raf V600E and c-Raf-1 biochemical inhibitory activity and A375 and COLO205 cell growth inhibitory activity for exemplary compounds as described herein:

| Compound number | Biochemical activity ($IC_{50}$ µM) | | | Cell activity ($IC_{50}$ µM) | |
|---|---|---|---|---|---|
| | B-Raf | V600E | c-Raf-1 | A375 | COLO205 |
| P-0001 | <0.1 | <0.1 | <0.1 | <1 | <1 |
| P-0002 | <0.1 | <0.1 | <0.1 | | <1 |
| P-0003 | <0.1 | <0.1 | <0.1 | <1 | <1 |
| P-0004 | <0.1 | <0.1 | <0.1 | | <1 |
| P-0005 | <0.1 | <0.1 | <0.1 | | <1 |
| P-0006 | <0.1 | <0.1 | <0.1 | | <1 |
| P-0007 | <0.1 | <0.1 | ~0.1 | >1 | <1 |
| P-0008 | <0.1 | <0.1 | <0.1 | | <1 |
| P-0009 | <1 | <1 | <1 | | <1 |
| P-0010 | <0.1 | <0.1 | <0.1 | <1 | <1 |
| P-0011 | <0.1 | <0.1 | <0.1 | <1 | <1 |
| P-0012 | <0.1 | <0.1 | <0.1 | <1 | <1 |
| P-0013 | <0.1 | <0.1 | <0.1 | | <1 |
| P-0014 | <0.1 | <0.1 | <0.1 | | <1 |
| P-0015 | <0.1 | <0.1 | <0.1 | <1 | <1 |
| P-0016 | <0.1 | <0.1 | <0.1 | | <1 |
| P-0018 | <0.1 | <0.1 | <0.1 | | |
| P-0019 | <0.1 | <0.1 | <0.1 | | >1 |
| P-0020 | <0.1 | <0.1 | <0.1 | | <1 |
| P-0021 | <0.1 | <0.1 | <0.1 | | <1 |
| P-0022 | <0.1 | <0.1 | <0.1 | | >1 |
| P-0023 | <0.1 | <0.1 | <0.1 | | <1 |
| P-0024 | <0.1 | <0.1 | <0.1 | | <1 |
| P-0025 | <0.1 | <0.1 | <0.1 | | <1 |
| P-0026 | <0.1 | <0.1 | <0.1 | | |
| P-1001 | | | <0.1 | | |
| P-1002 | <0.1 | <0.1 | <0.1 | | <1 |
| P-1003 | <0.1 | <10 | | | |
| P-1004 | <0.1 | <0.1 | <0.1 | | >1 |
| P-1005 | <0.1 | <0.1 | <0.1 | | <1 |
| P-1006 | <0.1 | <0.1 | <0.1 | | |
| P-1007 | <0.1 | <0.1 | <0.1 | | |
| P-1008 | <0.1 | <0.1 | <0.1 | | >1 |
| P-1009 | <0.1 | <0.1 | <0.1 | | |
| P-1010 | <0.1 | <0.1 | <0.1 | | |
| P-1011 | <0.1 | <0.1 | <0.1 | | |
| P-1100 | <0.1 | <0.1 | <0.1 | | <1 |
| P-1101 | <0.1 | <0.1 | <0.1 | <1 | <1 |
| P-1102 | <0.1 | <0.1 | <0.1 | | >1 |
| P-1103 | <0.1 | <0.1 | <0.1 | | >1 |
| P-1104 | <0.1 | <0.1 | <0.1 | | <1 |
| P-1105 | <0.1 | <0.1 | <0.1 | | <1 |
| P-1106 | <0.1 | <0.1 | <0.1 | | >1 |
| P-1109 | <0.1 | <0.1 | <0.1 | | |
| P-1200 | <0.1 | <0.1 | <0.1 | | >1 |
| P-1201 | <0.1 | <0.1 | <0.1 | | <1 |
| P-1202 | <0.1 | <0.1 | <0.1 | | <1 |
| P-1203 | <0.1 | <0.1 | <0.1 | | >1 |
| P-1300 | <0.1 | <0.1 | <0.1 | | |
| P-1401 | <0.1 | <0.1 | <0.1 | | >1 |
| P-1402 | <0.1 | <0.1 | <0.1 | | |
| P-1403 | <0.1 | <0.1 | <0.1 | | |
| P-1404 | <0.1 | <0.1 | <0.1 | | |
| P-1405 | <0.1 | <0.1 | <0.1 | | |
| P-1406 | <0.1 | <0.1 | <0.1 | | |
| P-1407 | <0.1 | <0.1 | <0.1 | | |
| P-1408 | <0.1 | <0.1 | <0.1 | | |
| P-1409 | <0.1 | <0.1 | <0.1 | | |
| P-1500 | <0.1 | <0.1 | <0.1 | | |
| P-1501 | <0.1 | <0.1 | <0.1 | | |
| P-1502 | <0.1 | <0.1 | <0.1 | | |
| P-1503 | <0.1 | <0.1 | <0.1 | | |
| P-1600 | <0.1 | <0.1 | <0.1 | >1 | <1 |
| P-1601 | <0.1 | <0.1 | <0.1 | | <1 |
| P-1602 | <0.1 | <0.1 | <0.1 | | <1 |
| P-1603 | <0.1 | <0.1 | <0.1 | | <1 |
| P-1700 | <0.1 | <0.1 | <0.1 | | <1 |
| P-1701 | <0.1 | <0.1 | <0.1 | | <1 |
| P-1702 | <0.1 | <0.1 | <0.1 | | <1 |
| P-1703 | <0.1 | <0.1 | <0.1 | | <1 |
| P-1704 | <0.1 | <0.1 | <0.1 | | |
| P-1705 | <0.1 | <0.1 | <0.1 | | |
| P-1706 | <0.1 | <0.1 | <0.1 | | |
| P-1707 | <0.1 | <0.1 | <0.1 | | |
| P-1800 | <1 | <0.1 | <0.1 | | |
| P-1801 | <0.1 | <0.1 | <0.1 | | >1 |
| P-1802 | <1 | <0.1 | ~0.1 | | |

As an indication of relative solubility, the turbidity of compounds in aqueous solutions is assessed. To assess possible compound properties in different physiological compartments, such as stomach, intestine, and blood, a series of aqueous buffers with varying pH is used. Thus each compound is diluted into four different physiologically relevant buffers and solution turbidity is measured by spectrophotometry. The concentration of compound that demonstrates turbidity by forming enough insoluble suspension to raise the average optical density above 0.01 at three wavelengths (490, 535, and 650 nm) is used to define the limit of the compound solubility in that buffer.

Compounds are dissolved at a concentration of 25 mM in dimethyl sulfoxide, then serially diluted 1:1 into a 96 well plate, diluting 10 times in pure dimethyl sulfoxide, with the final well of each row a dimethyl sulfoxide blank. In an assay plate, 99 μL of appropriate buffer is added to each well, and 1 μL of each sample dilution is added to the buffer, achieving a range of final total concentrations in aqueous solutions having different pH. The buffers used are Simulated Gastric Fluid (SGF-pH 1.5) 0.5M NaCl, pH 1.5; Simulated Intestinal fluid (SIF-pH 4.5 and pH 6.8) 0.05M $NaH_2PO_4$, pH 4.5 and 6.8; and Hepes Buffer (HEPES-pH 7.4) 10 mM HEPES, 150 mM NaCl, pH 7.4. Control compounds pyrene, estriol and propranolol HCl are also assessed. Plates are spun and then mixed for 1 minute, and the absorbance is read using a Tecan Safire II to read wavelengths in the visible range (490, 535, and 650 nm) at four locations per well, reflecting the degree of turbidity present. The average optical density for each wavelength in each well is graphed vs. compound concentration, and the concentration at which the curve crosses a threshold O.D. of 0.01 for each wavelength is reported as the endpoint turbidity assay result. The average of the three wavelengths is used to compare turbidity of compounds. Compounds are considered to have low solubility if the threshold concentration is <31.3 μM, moderate solubility if the threshold concentration is 31.3 μM to 250 μM, and high solubility if the threshold concentration is >250 μM.

The following table indicates the relative solubility (L=low, M=moderate, H=high) based on turbidity threshold concentration at each pH for exemplary compounds according to the invention:

| Compound number | turbidity threshold (L, M, H) | | | |
|---|---|---|---|---|
| | 1.4 | 4.5 | 6.8 | 7.4 |
| P-0010 | L | L | L | L |
| P-0011 | L | L | M | L |
| P-0012 | L | L | L | L |
| P-0015 | L | L | L | L |
| P-0026 | L | L | L | L |
| P-0027 | L | L | L | L |
| P-0028 | L | L | L | L |
| P-0033 | L | L | L | L |
| P-1001 | M | L | M | L |
| P-1002 | M | M | L | M |
| P-1004 | L | L | L | L |
| P-1010 | M | L | L | M |
| P-1011 | L | L | M | M |
| P-1406 | L | L | L | L |
| P-1408 | M | L | L | L |
| P-1409 | L | L | L | L |
| P-1501 | L | L | L | L |
| P-1502 | L | L | L | L |
| P-1503 | L | L | L | M |
| P-1504 | L | M | M | M |
| P-1505 | L | L | L | M |
| P-1506 | L | L | L | L |
| P-1507 | L | L | L | L |
| P-1512 | L | L | L | L |
| P-1514 | L | L | M | L |
| P-1515 | L | M | M | M |
| P-1516 | L | L | L | L |
| P-1518 | L | L | L | L |
| P-1704 | L | L | L | L |
| P-1705 | M | L | L | L |

CYP (Cytochrome P450) enzymes are the major drug metabolizing enzymes present in the liver. The inhibition of CYP enzyme activity ($IC_{50}$) for each of CYP1A2, CYP2C19, CYP2C9, CYP2D6, CYP3A4(BFC) and CYP3A4(BQ) is determined for compounds, where inhibition of metabolism of a known substrate leads to a decrease in the fluorescence of the metabolized product. The fluorescence of the product is monitored as a function of compound concentration.

Compounds are dissolved in dimethyl sulfoxide to a concentration of 100 mM. These are diluted 1 μA, into 82 μL of acetonitrile. An 11 μL aliquot of this solution is then added to 204 μL of cofactor mix (1.3% NADPH Regeneration system Solution A, 1.04% NADPH Regeneration system Solution B from BD Biosciences, 5% acetonitrile and 0.05% dimethyl sulfoxide). These are then serially diluted 1:1 (160 μL to 160 μL co-factor mix) for a total of 10 points. A 10 μL aliquot of this final mixture is dispensed into 384 well assay plates and incubated for 10 minutes at 37° C. Enzyme and substrate mix (10 μL; 0.5 pmol CYP1A2/5 μM CEC; 1.0 pmol CYP2C9/75 μM MFC; 0.5 pmol CYP2C19/25 μM CEC; 1.5 pmol CYP2D6/1.5 μM AMMC; 1.0 pmol CYP3A4/50 μM BFC; or 1.0 pmol CYP3A4/40 μM BQ) is added to these assay plates. Assay plates are incubated at 37° C. (CYP1A2-15 min; CYP2C9-45 min; CYP2C19, 2D6 and 3A4-30 min) and read in a Tecan Safire 2 plate reader (CYP1A2, 2C19 and 3A4 409 ex/460 em; CYP2C9 and 2D6 409 ex/530 em). The signal versus compound concentration is used to determine the $IC_{50}$. The enzymes and substrates for this assay are obtained from BD Biosciences. While other factors are involved in determining CYP effects in vivo, compounds preferably have $IC_{50}$ values of >5 μM, more preferably $IC_{50}$ values of >10 μM.

The following table indicates the Cyp inhibition for exemplary compounds according to the invention:

| Compound number | Cyp $IC_{50}$ (μM) | | | | | |
|---|---|---|---|---|---|---|
| | 1A2 | 2C19 | 2C9 | 2D6 | 3A4(BFC) | 3A4(BQ) |
| P-0001 | >10 | <5 | <5 | >10 | >10 | |
| P-0002 | >10 | 5-10 | <5 | >10 | | |
| P-0003 | >10 | <5 | <5 | >10 | >10 | |
| P-0004 | >10 | <5 | <5 | >10 | >10 | |
| P-0005 | >10 | <5 | <5 | >10 | >10 | |
| P-0006 | 5-10 | 5-10 | <5 | >10 | >10 | |
| P-0007 | <5 | <5 | <5 | >10 | >10 | |
| P-0010 | >10 | >10 | >10 | >10 | >10 | >10 |
| P-0011 | <5 | >10 | 5-10 | >10 | >10 | >10 |
| P-0012 | >10 | <5 | 5-10 | >10 | 5-10 | >10 |
| P-0015 | >10 | >10 | 5-10 | >10 | >10 | >10 |
| P-0016 | >10 | >10 | >10 | >10 | >10 | |
| P-0020 | >10 | 5-10 | >10 | >10 | >10 | >10 |
| P-0023 | >10 | <5 | >10 | >10 | >10 | >10 |
| P-0025 | >10 | >10 | 5-10 | >10 | >10 | >10 |
| P-0033 | >10 | <5 | >10 | >10 | >10 | >10 |
| P-0034 | >10 | >10 | >10 | >10 | >10 | >10 |
| P-1001 | >10 | 5-10 | >10 | >10 | 5-10 | >10 |
| P-1002 | >10 | >10 | >10 | >10 | >10 | >10 |
| P-1004 | >10 | >10 | >10 | >10 | 5-10 | >10 |
| P-1101 | >10 | >10 | <5 | >10 | >10 | |

-continued

| Compound number | Cyp IC$_{50}$ (μM) | | | | | |
|---|---|---|---|---|---|---|
| | 1A2 | 2C19 | 2C9 | 2D6 | 3A4(BFC) | 3A4(BQ) |
| P-1404 | >10 | >10 | >10 | >10 | >10 | >10 |
| P-1408 | >10 | >10 | 5-10 | >10 | >10 | >10 |
| P-1503 | >10 | >10 | >10 | >10 | >10 | >10 |
| P-1506 | >10 | >10 | <5 | >10 | <5 | >10 |
| P-1518 | >10 | >10 | >10 | >10 | >10 | >10 |

Pharmacokinetic properties of compounds (including any solid forms or formulations thereof) are assessed in male Sprague Dawley rats or male Beagle dogs. Rats are dosed daily with compound either by IV injections via surgically implanted jugular catheters or by oral gavage (PO). Each compound is prepared as a 20 mg/mL stock solution in dimethyl sulfoxide, which is further diluted to provide the dosing stock at the desired concentration for the IV or PO formulations. For IV dosing, the dosing stock is diluted into a 1:1:8 mixture of Solutol®:ethanol:water. For PO dosing, the dosing stock is diluted into 1% methylcellulose. In a cassette format (or each compound, solid form thereof or formulation thereof is done individually), compounds are diluted to 0.5 mg/mL each for IV dosing and 0.4 mg/mL each for PO dosing and dosed at 1 mg/kg (2 mL/kg) or 2 mg/kg (5 mL/kg), respectively. For IV dosed animals, tail vein blood samples are collected with lithium heparin anticoagulant at 5, 15, 30, and 60 minutes and 4, 8, and 24 hours post dosing each day. For PO dosed animals, tail vein blood samples are collected with lithium heparin anticoagulant at 30 minutes, 1, 2, 4, 8 and 24 hours post dosing each day. Dogs are dosed daily by oral capsules in a suitable formulation at 50 mg/mL. Cephalic vein blood samples are collected with lithium heparin anticoagulant at 30 minutes, 1, 2, 4, 8 and 24 hours post dosing each day. All samples are processed to plasma and frozen for later analysis of each compound by LC/MS/MS. Plasma levels as a function of time are plotted to assess the AUC (ng*hr/mL). Compounds according to the present invention preferably show improved pharmacokinetic properties relative to previously described compounds, i.e. they have substantially higher values for one or more of AUC, Cmax and half-life relative to previously described compounds.

Example 9

Efficacy of Compounds in Combination with Standard-of-Care Chemotherapeutic Agents in Four Human Cancer Cell Lines Compounds of the invention, such as compounds of Formulae I-XX, in combination with a standard chemotherapeutic agent, such as 5-fluorouracil, carboplatin, dacarbazine, gefitinib, oxaliplatin, paclitaxel, SN-38, temozolomide, or vinblastine, can be assessed for their effectiveness in killing human tumor cells. Such assays are known in the art, for example, as described in U.S. patent application Ser. No. 11/473,347, the disclosure of which is hereby incorporated by reference as it relates to such assays.

Additional features of the complex can be used to demonstrate improved properties, such as comparison of the intrinsic dissolution rate of a similarly prepared substantially amorphous citrate complex or formulation thereof as compared to that of a crystalline form of the compound or similar formulation thereof in simulated gastric fluid (SGF) without enzyme and in simulated intestinal fluid (SIF). A pellet of test sample is dissolved in the appropriate fluid, and the UV absorbance as a function of time is measured at 254 nm (SGF) or 310 nm (SIF) and plotted.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound having the chemical structure of Formula I,

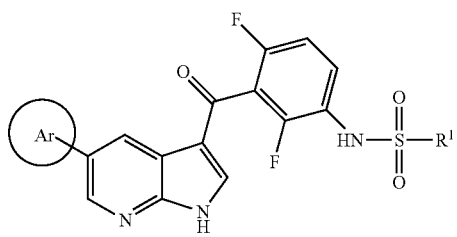

Formula I or a pharmaceutically acceptable salt or a tautomer or a stereoisomer thereof, wherein:

$R^1$ is aryl substituted with one or two trifluoromethyl, trifluoromethoxy, $C_{1-6}$ alkyl or halogen;

Ar is selected from the group consisting of:

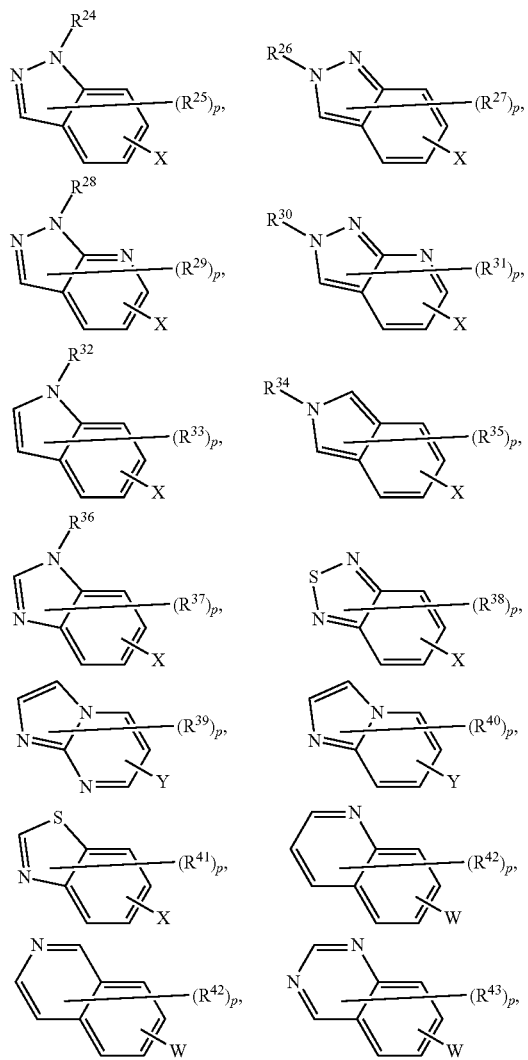

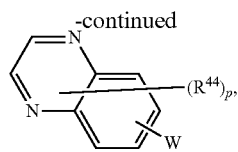

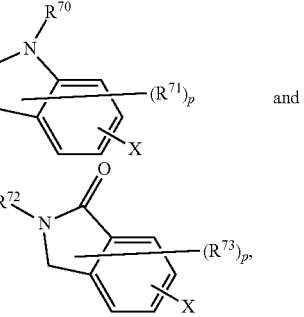

wherein:

W represents the point of attachment to the 5-position of the pyrrolo[2,3-b]pyridine ring of Formula I, wherein W is attached at any available position of the 6-membered phenyl ring portion of Ar;

X represents the point of attachment to the 5-position of the pyrrolo[2,3-b]pyridine ring of Formula I, wherein X is attached at any available position of the 6-membered ring portion of Ar;

Y represents the point of attachment to the 5-position of the pyrrolo[2,3-b]pyridine ring of Formula I, wherein Y is attached at any available position of the bicyclic ring of Ar;

$R^{24}$, $R^{26}$, $R^{28}$, $R^{30}$, $R^{32}$, $R^{34}$, $R^{36}$, $R^{70}$ and $R^{72}$ are selected from the group consisting of hydrogen, —C(O)—$R^{45}$, —S(O)$_2$—$R^{46}$, and $C_{1-6}$ alkyl, wherein $C_{1-6}$ alkyl is optionally independently substituted with one or more fluoro, or, when $R^{24}$, $R^{26}$, $R^{28}$, $R^{30}$, $R^{32}$, $R^{34}$, and/or $R^{36}$ is $C_{2-6}$alkyl, $R^{24}$, $R^{26}$, $R^{28}$, $R^{30}$, $R^{32}$, $R^{34}$, and $R^{36}$ are each optionally independently substituted with one or more $C_{1-6}$ alkoxy, mono-alkylamino, di-alkylamino or cycloalkylamino;

each $R^{25}$, $R^{27}$, $R^{29}$, $R^{31}$, $R^{33}$, $R^{35}$, $R^{37}$, $R^{38}$, $R^{39}$, $R^{40}$, $R^{41}$, $R^{42}$, $R^{43}$, $R^{44}$, $R^{71}$ and $R^{73}$ are independently selected from the group consisting of —CN, —C(O)—$R^{45}$, —S(O)$_2$—$R^{46}$, —O—$R^{47}$, —N($R^{48}$)—$R^{49}$, fluoro, chloro, $C_{1-6}$ alkyl, and cycloalkylamino, and are attached at any available position of the bicyclic ring of Ar, wherein $C_{1-6}$ alkyl is optionally independently substituted with one or more fluoro $C_{1-6}$ alkoxy, mono-alkylamino, di-alkylamino or cycloalkylamino;

each $R^{45}$ is independently selected from the group consisting of —O—$R^{47}$, —NH$_2$, $C_{1-6}$ alkyl, mono-alkylamino, di-alkylamino, and cycloalkylamino;

each $R^{46}$ are independently selected from the group consisting of —NH$_2$, $C_{1-6}$ alkyl, mono-alkylamino, di-alkylamino, and cycloalkylamino;

each $R^{47}$ is independently or $C_{1-6}$ hydrogen alkyl, wherein $C_{1-6}$ alkyl is optionally independently substituted with one or more fluoro, or, when $R^{47}$ is $C_{2-6}$ alkyl, $R^{47}$ is optionally substituted with one or more $C_{1-6}$ alkoxy, mono-alkylamino, di-alkylamino or cycloalkylamino;

each $R^{48}$ and $R^{49}$ are independently selected from the group consisting of hydrogen, $C_{1-6}$ alkyl, or cycloalkyl, wherein $C_{1-6}$ alkyl is optionally independently substituted with $C_{1-6}$ alkoxy, mono-alkylamino, di-alkylamino, or cycloalkylamino; and each p is independently 0, 1, 2 or 3.

2. The compound of claim 1, wherein Ar is:

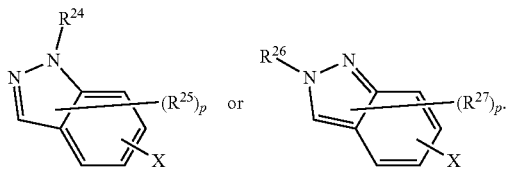

3. The compound of claim 2, wherein p is 0.

4. The compound of claim 2, wherein $R^{24}$ and $R^{26}$ are each independently selected from hydrogen, $C_{1-6}$ alkyl, $C_{1-6}$ alkyl carbamoyl, $C_{1-6}$ alkyl-C(=O)— or $C_{1-6}$ alkyl sulfonyl.

5. The compound of claim 2, wherein $R^{24}$ and $R^{26}$ are each independently selected from hydrogen, methyl, ethyl, propyl, acetyl, $CH_3NHC(=O)$—, methyl sulfonyl or ethyl sulfonyl.

6. The compound of claim 1, wherein Ar is:

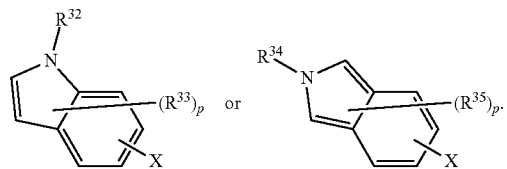

7. The compound of claim 1, wherein Ar is:

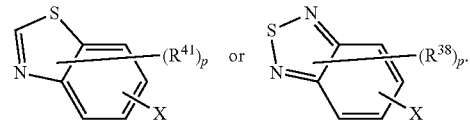

8. The compound of claim 1, wherein Ar is:

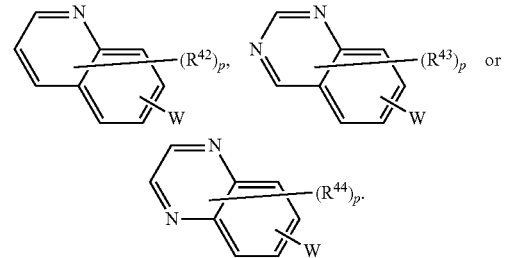

9. The compound of claim 1, wherein Ar is:

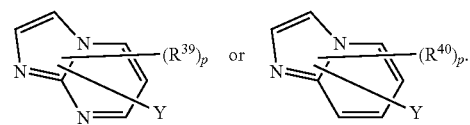

10. The compound of claim 1, wherein Ar is:

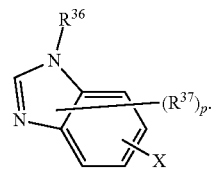

11. The compound of claim 1, wherein Ar is:

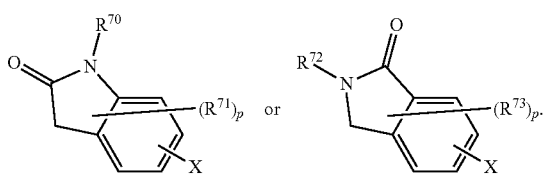

12. The compound of claim 1, wherein Ar is 1H-4-indazolyl, 1H-5-indazolyl, 1H-6-indazolyl, 1H-7-indazolyl, 1,3-benzothiazol-4yl, 1,3-benzothiazol-5yl, 1,3-benzothiazol-6yl, 1,3-benzothiazol-7yl, imidazo[1,2-a]pyridine-2-yl, imidazo[1,2-a]pyridine-3-yl, imidazo[1,2-a]pyridine-5-yl, imidazo[1,2-a]pyridine-6-yl, imidazo[1,2-a]pyridine-7-yl, imidazo[1,2-a]pyridine-8-yl, imidazo[1,2-a]pyrimidin-5-yl, imidazo[1,2-a]pyrimidin-6-yl, imidazo[1,2-a]pyrimidin-7-yl, imidazo[1,2-a]pyrimidin-8-yl, 1H-indol-5yl, 1H-indol-2yl, 1H-indol-3yl, 1H-indol-4yl, 1H-indol-6yl, 1H-indol-7yl, 3-methyl-1-H-indol-5-yl, quinazolin-2-yl, quinazolin-4-yl, quinazolin-5-yl, quinazolin-6-yl, quinazolin-7-yl, quinazolin-8-yl, benzimidazol-2-yl, benzimidazol-4-yl, benzimidazol-5-yl, quinolin-2-yl, quinolin-3-yl, quinolin-4-yl, quinolin-5-yl, quinolin-6-yl, quinolin-7-yl, quinolin-8-yl, 1-oxo-isoindolin-4-yl, 1-oxo-isoindolin-5-yl, 1-oxo-isoindolin-6-yl, 1-oxo-isoindolin-7-yl, 2-oxo-indolin-4-yl, 2-oxo-indolin-5-yl, 2-oxo-indolin-6-yl or 2-oxo-indolin-7-yl, each of which is optionally substituted with one to two members selected from methyl, amino, $CF_3$, $CF_3O$, $CH_3O$, acetyl, alkoxycarbonyl, t-butoxycarbonyl, dimethylamino, fluoro, chloro or methylaminoethyl.

13. The compound of claim 1, wherein Ar is 1H-4-indazolyl, 1H-5-indazolyl, 1H-6-indazolyl, 1H-7-indazolyl, 1-methyl-4-indazolyl, 1-methyl-5-indazolyl, 1-methyl-6-indazolyl, 1-methyl-7-indazolyl, 1-acetyl-4-indazolyl, 1-acetyl-5-indazolyl, 1-acetyl-6-indazolyl, 1-acetyl-7-indazolyl, 1-methylsulfonyl-4-indazolyl, 1-methylsulfonyl-5-indazolyl, 1-methylsulfonyl-6-indazolyl, 1-methylsulfonyl-7-indazolyl, 1-methyl-3-amino-6-indazolyl, 1,3-benzothiazol-4yl, 1,3-benzothiazol-5yl, 1,3-benzothiazol-6yl, 1,3-benzothiazol-7yl, imidazo[1,2-a]pyridine-2-yl, imidazo[1,2-a]pyridine-3-yl, imidazo[1,2-a]pyridine-5-yl, imidazo[1,2-a]pyridine-6-yl, imidazo[1,2-a]pyridine-7-yl, imidazo[1,2-a]pyridine-8-yl, 7-trifluoromethylimidazo[1,2-a]pyrimidin-2-yl, 7-trifluoromethylimidazo[1,2-a]pyrimidin-3-yl, imidazo[1,2-a]pyrimidin-5-yl, imidazo[1,2-a]pyrimidin-6-yl, imidazo[1,2-a]pyrimidin-7-yl, imidazo[1,2-a]pyrimidin-8-yl, 1H-indol-5yl, 1H-indol-2yl, 1H-indol-3yl, 1H-indol-4yl, 1H-indol-6yl, 1H-indol-7yl, 3-methyl-1-H-indol-5-yl, quinazolin-2-yl, quinazolin-4-yl, quinazolin-5-yl, quinazolin-6-yl, quinazolin-7-yl, quinazolin-8-yl, benzimidazol-2-yl, benzimidazol-4-yl, benzimidazol-5-yl, 1-methyl-2-aminobenzimidazol-5-yl, 1-methyl-2-aminobenzimidazol-4-yl, quinolin-2-yl, quinolin-3-yl, quinolin-4-yl, quinolin-5-yl, quinolin-6-yl, quinolin-7-yl, quinolin-8-yl, 1-oxo-isoindolin-4-yl, 1-oxo-isoindolin-5-yl, 1-oxo-isoindolin-6-yl, 1-oxo-isoindolin-7-yl, 2-oxo-indolin-4-yl, 2-oxo-indolin-5-yl, 2-oxo-indolin-6-yl or 2-oxo-indolin-7-yl.

14. The compound of claim 1, wherein $R^1$ is 2-trifluoromethyl-phenyl, 3-trifluoromethyl-phenyl, 4-trifluoromethyl-phenyl, 2-fluoro-phenyl, 3-fluoro-phenyl, 4-fluoro-phenyl, 2,3-difluoro-phenyl, 2,4-difluoro-phenyl, 2,6-difluoro-phenyl, 2,5-difluoro-phenyl, 3,4-difluoro-phenyl, 3,5-difluoro-phenyl or 3,6-difluoro-phenyl.

15. A compound selected from the group consisting of:
N-[2,4-difluoro-3-[5-(1H-indazol-4-yl)-1H-pyrrolo[2,3-b]pyridine-3-carbonyl]phenyl]-3-fluoro-benzenesulfonamide P-1902
N-[2,4-difluoro-3-[5-(2-methylindazol-5-yl)-1H-pyrrolo[2,3-b]pyridine-3-carbonyl]phenyl]-3-fluoro-benzenesulfonamide P-1903
N-[2,4-difluoro-3-[5-(2-methylindazol-6-yl)-1H-pyrrolo[2,3-b]pyridine-3-carbonyl]phenyl]-3-fluoro-benzenesulfonamide P-1904
N-[2,4-difluoro-3-[5-(1H-indol-5-yl)-1H-pyrrolo[2,3-b]pyridine-3-carbonyl]phenyl]-3-fluoro-benzenesulfonamide P-1905
N-[3-[5-(1,3-benzothiazol-5-yl)-1H-pyrrolo[2,3-b]pyridine-3-carbonyl]-2,4-difluoro-phenyl]-3-fluoro-benzenesulfonamide P-1906
N-[2,4-difluoro-3-(5-quinoxalin-6-yl-1H-pyrrolo[2,3-b]pyridine-3-carbonyl)phenyl]-3-fluoro-benzenesulfonamide P-1907
N-[2,4-difluoro-3-[5-(2-methylindazol-4-yl)-1H-pyrrolo[2,3-b]pyridine-3-carbonyl]phenyl]-3-fluoro-benzenesulfonamide P1908
N-[2,4-difluoro-3-(5-imidazo[1,2-a]pyridin-5-yl-1H-pyrrolo[2,3-b]pyridine-3-carbonyl)phenyl]-3-fluoro-benzenesulfonamide P1948
N-[2,4-difluoro-3-[5-(1H-indol-4-yl)-1H-pyrrolo[2,3-b]pyridine-3-carbonyl]phenyl]-3-fluoro-benzenesulfonamide P-1949
N-[3-[5-(1,3-benzothiazol-6-yl)-1H-pyrrolo[2,3-b]pyridine-3-carbonyl]-2,4-difluoro-phenyl]-3-fluoro-benzenesulfonamide P-1950
N-[2,4-difluoro-3-(5-imidazo[1,2-a]pyridin-2-yl-1H-pyrrolo[2,3-b]pyridine-3-carbonyl)phenyl]-3-fluoro-benzenesulfonamide P-1951
N-[2,4-difluoro-3-[5-[7-(trifluoromethyl)imidazo[1,2-a]pyrimidin-2-yl]-1H-pyrrolo[2,3-b]pyridine-3-carbonyl]phenyl]-3-fluoro-benzenesulfonamide P-1952
N-[2,4-difluoro-3-[5-(3-methyl-1H-indol-5-yl)-1H-pyrrolo[2,3-b]pyridine-3-carbonyl]phenyl]-3-fluoro-benzenesulfonamide P-1953
N-[2,4-difluoro-3-[5-(3-methyl-1H-indazol-5-yl)-1H-pyrrolo[2,3-b]pyridine-3-carbonyl]phenyl]-3-fluoro-benzenesulfonamide P-1954
N-[2,4-difluoro-3-(5-quinazolin-7-yl-1H-pyrrolo[2,3-b]pyridine-3-carbonyl)phenyl]-3-fluoro-benzenesulfonamide P-1955
N-[2,4-difluoro-3-(5-quinazolin-6-yl-1H-pyrrolo[2,3-b]pyridine-3-carbonyl)phenyl]-3-fluoro-benzenesulfonamide P-1956
N-[2,4-difluoro-3-[5-(1-methylindazol-6-yl)-1H-pyrrolo[2,3-b]pyridine-3-carbonyl]phenyl]-3-fluoro-benzenesulfonamide P-1957
N-[2,4-difluoro-3-[5-(1-methylindazol-5-yl)-1H-pyrrolo[2,3-b]pyridine-3-carbonyl]phenyl]-3-fluoro-benzenesulfonamide P-1958
N-[3-[5-(3-amino-1-methyl-indazol-6-yl)-1H-pyrrolo[2,3-b]pyridine-3-carbonyl]-2,4-difluoro-phenyl]-3-fluoro-benzenesulfonamide P-1959
N-[2,4-difluoro-3-[5-[2-(2-methylaminoethyl)-3H-benzimidazol-5-yl]-1H-pyrrolo[2,3-b]pyridine-3-carbonyl]phenyl]-3-fluoro-benzenesulfonamide P-1960
N-[3-[5-(2-amino-1-methyl-benzimidazol-5-yl)-1H-pyrrolo[2,3-b]pyridine-3-carbonyl]-2,4-difluoro-phenyl]-3-fluoro-benzenesulfonamide P-1961
N-[3-[5-(2-amino-1H-benzimidazol-5-yl)-1H-pyrrolo[2,3-b]pyridine-3-carbonyl]-2,4-difluoro-phenyl]-3-fluoro-benzenesulfonamide P-1962
N-[2,4-difluoro-3-[5-(7-quinolyl)-1H-pyrrolo[2,3-b]pyridine-3-carbonyl]phenyl]-3-fluoro-benzenesulfonamide P-1963
N-[2,4-difluoro-3-[5-(6-quinolyl)-1H-pyrrolo[2,3-b]pyridine-3-carbonyl]phenyl]-3-fluoro-benzenesulfonamide P-1964
N-[2,4-difluoro-3-[5-(2-methoxy-1-methyl-benzimidazol-5-yl)-1H-pyrrolo[2,3-b]pyridine-3-carbonyl]phenyl]-3-fluoro-benzenesulfonamide P-1965
N-[3-[5-(2-dimethylamino-1-methyl-benzimidazol-5-yl)-1H-pyrrolo[2,3-b]pyridine-3-carbonyl]-2,4-difluoro-phenyl]-3-fluoro-benzenesulfonamide P-1966
N-[3-[5-(1,2-dimethylbenzimidazol-5-yl)-1H-pyrrolo[2,3-b]pyridine-3-carbonyl]-2,4-difluoro-phenyl]-3-fluoro-benzenesulfonamide P-1967
N-[3-[5-(2,1,3-benzothiadiazol-6-yl)-1H-pyrrolo[2,3-b]pyridine-3-carbonyl]-2,4-difluoro-phenyl]-3-fluoro-benzenesulfonamide P-1968
N-[2,4-difluoro-3-[5-(2-methyl-1H-benzimidazol-5-yl)-1H-pyrrolo[2,3-b]pyridine-3-carbonyl]phenyl]-3-fluoro-benzenesulfonamide P-1969
and
N-[2,4-difluoro-3-[5-(4-oxo-1H-thieno[2,3-d]pyrimidin-6-yl)-1H-pyrrolo[2,3-b]pyridine-3-carbonyl]phenyl]-3-fluoro-benzenesulfonamide P-1970
or a pharmaceutically acceptable salt thereof.

16. A composition comprising a compound of claim 1 and a pharmaceutically acceptable carrier, diluent or excipient.

17. A method for preparing a compound of Formula I according to claim 1,

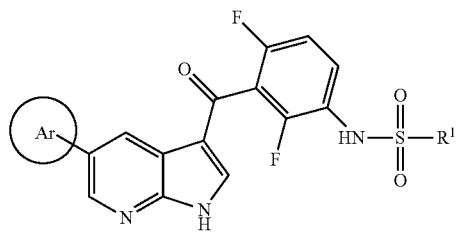

said method comprising:
contacting a compound of Formula Ia:

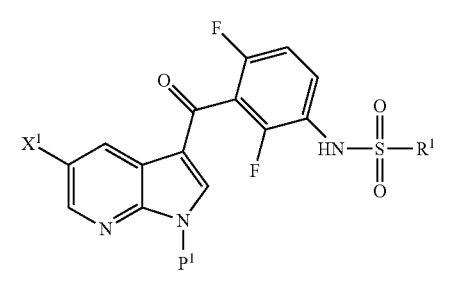

with a compound of Formula Ib:

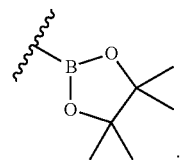 [SMILES: *B1OC(C)(C)C(C)(C)O1]

under conditions sufficient to form the compound of Formula I, wherein $X^1$ is halogen;
$P^1$ is an amino protecting group; and
Q is a boronic acid or ester residue.

18. The method claim 17, wherein $X^1$ is Br and Q is

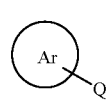

19. The method of claim 17, wherein the contacting comprises reacting a compound of formula Ia and a compound of formula Ib in the presence of a palladium complex.

* * * * *